(12) United States Patent
Wohlstadter et al.

(10) Patent No.: US 11,861,145 B2
(45) Date of Patent: *Jan. 2, 2024

(54) GRAPHICAL USER INTERFACE SYSTEM

(71) Applicant: METHODICAL MIND, LLC., Rockville, MD (US)

(72) Inventors: Jacob N. Wohlstadter, Potomac, MD (US); George Sigal, Rockville, MD (US); Edward J. S. Roques, Bethesda, MD (US); Louis W. Pang, Sandy Spring, MD (US); Pankaj Oberoi, Rockville, MD (US); Kin Ng, Monrovia, MD (US); Michael Vock, Loveland, OH (US)

(73) Assignee: METHODICAL MIND, LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/849,376

(22) Filed: Jun. 24, 2022

(65) Prior Publication Data

US 2023/0118183 A1 Apr. 20, 2023

Related U.S. Application Data

(63) Continuation of application No. 17/186,659, filed on Feb. 26, 2021, now Pat. No. 11,372,523, which is a (Continued)

(51) Int. Cl.
*G06F 3/048* (2013.01)
*G06F 3/0482* (2013.01)
(Continued)

(52) U.S. Cl.
CPC ........ *G06F 3/0482* (2013.01); *G06F 3/04845* (2013.01); *G16C 20/10* (2019.02)

(58) Field of Classification Search
None
See application file for complete search history.

(56) References Cited

U.S. PATENT DOCUMENTS 5,628,031 A 5/1997 Kikinis et al.
5,689,668 A 11/1997 Beaudet et al.
(Continued)

FOREIGN PATENT DOCUMENTS

CN 1555520 A 12/2004
CN 101071360 A 11/2007
(Continued)

OTHER PUBLICATIONS

Any reference or information that is not included with this Information Disclosure Statement can be found in U.S. Appl. No. 17/186,659, to which this application claims priority.
(Continued)

*Primary Examiner* — Hua Lu
(74) *Attorney, Agent, or Firm* — MEDLER FERRO WOODHOUSE & MILLS

(57) ABSTRACT

A method of interactively navigating a user through a path of menu choices on a user interface may include displaying a current menu of choices on a first portion of a user interface display. The user interface allows for selecting of a menu item from the current menu of choices and to drill down through levels of menu choices based on selecting a menu item from a prior level of menu choices. A second portion of the user interface display presents past selected and past unselected menu items of the drilled-down levels. The past unselected menu items are displayed as selectable options. The user interface allows for jumping to a different path of menu choices by selecting a past unselected menu item from a previously navigated menu level displayed on the second portion of the user interface display.

31 Claims, 173 Drawing Sheets

Related U.S. Application Data continuation of application No. 16/513,526, filed on Jul. 16, 2019, now Pat. No. 10,936,163.

(60) Provisional application No. 62/699,381, filed on Jul. 17, 2018.

(51) Int. Cl.
*G16C 20/10* (2019.01)
*G06F 3/04845* (2022.01)

(56) References Cited

U.S. PATENT DOCUMENTS

| | | | |
|---|---|---|---|
| 5,821,936 A * | 10/1998 | Shaffer | G06F 3/0482 715/810 |
| 5,995,106 A | 11/1999 | Naughton et al. | |
| 6,128,012 A | 10/2000 | Seidensticker et al. | |
| 6,701,525 B1 | 3/2004 | Neervoort et al. | |
| 7,246,329 B1 * | 7/2007 | Miura | G06F 3/0481 715/764 |
| 7,360,175 B2 * | 4/2008 | Gardner | G06F 3/0482 715/825 |
| 7,404,200 B1 | 7/2008 | Hailey et al. | |
| 7,418,670 B2 | 8/2008 | Goldsmith | |
| 7,461,077 B1 | 12/2008 | Greenwood | |
| 7,512,904 B2 * | 3/2009 | Matthews | G06F 3/0482 715/733 |
| 7,696,980 B1 | 4/2010 | Piot et al. | |
| 8,065,630 B1 | 11/2011 | Donoghue et al. | |
| 8,113,376 B2 | 2/2012 | Matsubara et al. | |
| 8,473,868 B1 | 6/2013 | Kauffman | |
| 8,904,286 B2 * | 12/2014 | Lee | G06F 3/0236 715/708 |
| 8,935,654 B2 | 1/2015 | Sengupta et al. | |
| 9,110,579 B2 | 8/2015 | Miyazaki | |
| 9,135,663 B1 | 9/2015 | Heiferman et al. | |
| 9,411,487 B2 | 8/2016 | Ording | |
| 9,436,346 B2 | 9/2016 | Kallio et al. | |
| 9,535,594 B1 | 1/2017 | Ruiz et al. | |
| 9,632,664 B2 * | 4/2017 | Foss | G06F 3/0481 |
| 9,727,209 B2 * | 8/2017 | Wang | G06F 3/0482 |
| 9,740,306 B1 | 8/2017 | Buchheit | |
| 9,740,381 B1 | 8/2017 | Chaudhri et al. | |
| 10,180,714 B1 | 1/2019 | Kin et al. | |
| 10,254,928 B1 | 4/2019 | Jesensky et al. | |
| 10,296,168 B2 | 5/2019 | Kaehler et al. | |
| 10,310,697 B2 * | 6/2019 | Roberts | H04N 21/47214 |
| 10,310,705 B2 | 6/2019 | Xing et al. | |
| 10,324,581 B2 | 6/2019 | Bi | |
| 10,366,434 B1 * | 7/2019 | Belousova | G06Q 50/12 |
| 10,860,174 B2 | 12/2020 | Konno | |
| 10,979,583 B2 | 4/2021 | Horiike | |
| 11,126,329 B2 | 9/2021 | Seto et al. | |
| 2002/0122072 A1 * | 9/2002 | Selker | G06F 3/0482 715/834 |
| 2002/0184397 A1 | 12/2002 | Cooper | |
| 2003/0004638 A1 | 1/2003 | Villers et al. | |
| 2003/0132911 A1 | 7/2003 | Narioka et al. | |
| 2004/0075693 A1 | 4/2004 | Moyer et al. | |
| 2004/0160463 A1 * | 8/2004 | Battles | G09G 5/003 715/814 |
| 2004/0190129 A1 | 9/2004 | Peter et al. | |
| 2005/0003870 A1 | 1/2005 | Nakano et al. | |
| 2005/0054381 A1 | 3/2005 | Lee et al. | |
| 2005/0160375 A1 | 7/2005 | Sciammarella et al. | |
| 2005/0275879 A1 * | 12/2005 | Ogasawara | G06F 40/106 358/1.18 |
| 2006/0092177 A1 | 5/2006 | Blasko | |
| 2006/0121939 A1 | 6/2006 | Anwar et al. | |
| 2006/0123360 A1 | 6/2006 | Anwar et al. | |
| 2006/0271867 A1 | 11/2006 | Wang et al. | |
| 2007/0184546 A1 * | 8/2007 | Farrelly | G01N 35/04 435/303.1 |
| 2007/0234202 A1 | 10/2007 | Lyness | |
| 2007/0254688 A1 | 11/2007 | Griffin et al. | |
| 2007/0254708 A1 | 11/2007 | Griffin et al. | |
| 2008/0005700 A1 | 1/2008 | Morikawa | |
| 2008/0216005 A1 | 9/2008 | Bamba et al. | |
| 2008/0281471 A1 * | 11/2008 | Smith | B01L 3/502792 422/50 |
| 2009/0013254 A1 * | 1/2009 | Walker | G06F 3/167 715/727 |
| 2009/0019397 A1 * | 1/2009 | Buffet | G06F 3/0482 715/837 |
| 2009/0172597 A1 | 7/2009 | Mercer | |
| 2009/0199122 A1 * | 8/2009 | Deutsch | G06F 9/445 715/771 |
| 2009/0228832 A1 * | 9/2009 | Cheng | G06F 3/0236 715/810 |
| 2009/0307188 A1 | 12/2009 | Oldham et al. | |
| 2010/0064258 A1 * | 3/2010 | Gorczowski | G06F 3/0482 715/841 |
| 2010/0082731 A1 | 4/2010 | Haughay et al. | |
| 2010/0199228 A1 | 8/2010 | Latta et al. | |
| 2010/0306702 A1 * | 12/2010 | Warner | G06F 3/0482 715/834 |
| 2010/0313166 A1 | 12/2010 | Nakayama et al. | |
| 2011/0047491 A1 * | 2/2011 | Hwang | G06F 3/0488 715/810 |
| 2011/0072351 A1 | 3/2011 | Shintani et al. | |
| 2011/0093815 A1 * | 4/2011 | Gobeil | G06F 9/451 715/825 |
| 2011/0115702 A1 | 5/2011 | Seaberg | |
| 2011/0119629 A1 | 5/2011 | Huotari et al. | |
| 2011/0187709 A1 * | 8/2011 | Lee | G06F 3/041 345/173 |
| 2011/0202879 A1 * | 8/2011 | Stovicek | G06F 3/0482 715/810 |
| 2011/0264996 A1 * | 10/2011 | Norris, III | G06F 16/9577 715/236 |
| 2011/0320984 A1 * | 12/2011 | Irani | G06F 3/0482 715/841 |
| 2012/0019460 A1 | 1/2012 | Matsubara et al. | |
| 2012/0023447 A1 | 1/2012 | Hoshino et al. | |
| 2012/0036434 A1 * | 2/2012 | Oberstein | G06F 3/0488 715/702 |
| 2012/0054685 A1 | 3/2012 | Su et al. | |
| 2012/0066647 A1 * | 3/2012 | Ullmann | G06F 3/0482 715/841 |
| 2012/0079427 A1 * | 3/2012 | Carmichael | G06F 16/44 715/825 |
| 2013/0019175 A1 * | 1/2013 | Kotler | G06F 3/0482 715/728 |
| 2013/0083219 A1 * | 4/2013 | Heo | G06F 3/04845 348/333.02 |
| 2013/0176202 A1 | 7/2013 | Gervautz | |
| 2013/0179777 A1 | 7/2013 | Cassistat et al. | |
| 2013/0198658 A1 | 8/2013 | Mokhtarzada et al. | |
| 2013/0238994 A1 | 9/2013 | Yurasits | |
| 2014/0068476 A1 | 3/2014 | Kosaki | |
| 2014/0082554 A1 | 3/2014 | Iwaniszczuk | |
| 2014/0101608 A1 * | 4/2014 | Ryskamp | G06F 40/103 715/810 |
| 2014/0115540 A1 * | 4/2014 | Ikeda | G06F 3/0486 715/810 |
| 2014/0195963 A1 | 7/2014 | Cheung et al. | |
| 2014/0309913 A1 | 10/2014 | Ricci et al. | |
| 2014/0368341 A1 | 12/2014 | Williams | |
| 2014/0372956 A1 | 12/2014 | Bisca et al. | |
| 2015/0002436 A1 | 1/2015 | Yano et al. | |
| 2015/0007114 A1 * | 1/2015 | Poulos | G06F 3/0482 715/852 |
| 2015/0067582 A1 | 3/2015 | Donnelly et al. | |
| 2015/0086997 A1 | 3/2015 | Linder et al. | |
| 2015/0153571 A1 * | 6/2015 | Ballard | H04N 23/61 345/8 |
| 2015/0227173 A1 | 8/2015 | Hwang | |
| 2015/0227307 A1 | 8/2015 | Lee et al. | |
| 2015/0248191 A1 | 9/2015 | Ording | |
| 2015/0261914 A1 * | 9/2015 | Kapushesky | G06F 16/9024 707/634 |

(56) References Cited

U.S. PATENT DOCUMENTS

| | | | |
|---|---|---|---|
| 2015/0286391 A1 | 10/2015 | Jacobs et al. | |
| 2015/0317049 A1* | 11/2015 | Miura | G06F 3/0482 |
| | | | 715/843 |
| 2015/0324568 A1 | 11/2015 | Publicover et al. | |
| 2015/0331589 A1 | 11/2015 | Kawakita | |
| 2015/0355827 A1 | 12/2015 | Westhuizen et al. | |
| 2016/0004322 A1 | 1/2016 | Takada et al. | |
| 2016/0062571 A1 | 3/2016 | Dascola et al. | |
| 2016/0065655 A1 | 3/2016 | Bentley et al. | |
| 2016/0103565 A1 | 4/2016 | Greenberg et al. | |
| 2016/0132132 A1 | 5/2016 | Li | |
| 2016/0132192 A1 | 5/2016 | Sutton et al. | |
| 2016/0208325 A1* | 7/2016 | Ng | C12Q 1/6881 |
| 2016/0209996 A1* | 7/2016 | Spiegel | G06F 9/453 |
| 2016/0210001 A1* | 7/2016 | Antipa | G06F 3/0482 |
| 2016/0284018 A1 | 9/2016 | Adeyoola et al. | |
| 2016/0321222 A1 | 11/2016 | Greenberg et al. | |
| 2016/0378281 A1* | 12/2016 | Sirpal | H04N 23/667 |
| | | | 715/779 |
| 2017/0039030 A1 | 2/2017 | Ikeda et al. | |
| 2017/0090703 A1 | 3/2017 | Iskandarov | |
| 2017/0094360 A1 | 3/2017 | Keighran et al. | |
| 2017/0098007 A1 | 4/2017 | Chan et al. | |
| 2017/0103502 A1 | 4/2017 | Gilra | |
| 2017/0115749 A1 | 4/2017 | Li | |
| 2017/0153712 A1 | 6/2017 | Kawai et al. | |
| 2017/0205878 A1 | 7/2017 | Hoste et al. | |
| 2017/0206004 A1 | 7/2017 | De Bruyn et al. | |
| 2017/0212875 A1 | 7/2017 | Foresti | |
| 2017/0220136 A1 | 8/2017 | Krueger et al. | |
| 2017/0236095 A1 | 8/2017 | Schreiber et al. | |
| 2017/0270610 A1 | 9/2017 | Kee et al. | |
| 2017/0315687 A1* | 11/2017 | Yoshida | G06F 3/04886 |
| 2017/0351422 A1 | 12/2017 | Wild et al. | |
| 2018/0074687 A1* | 3/2018 | Ho | G06F 3/04847 |
| 2018/0081453 A1 | 3/2018 | Ely | |
| 2018/0101240 A1 | 4/2018 | Carceroni et al. | |
| 2018/0157753 A1 | 6/2018 | Dougherty et al. | |
| 2018/0158239 A1 | 6/2018 | Piya et al. | |
| 2018/0316517 A1 | 11/2018 | Henzig et al. | |
| 2018/0329586 A1 | 11/2018 | Sundstrom et al. | |
| 2018/0365025 A1* | 12/2018 | Almecija | G06F 3/04847 |
| 2019/0011947 A1 | 1/2019 | Nakazawa et al. | |
| 2019/0032948 A1 | 1/2019 | Nayak et al. | |
| 2019/0171689 A1 | 6/2019 | Kachkach et al. | |
| 2019/0258373 A1 | 8/2019 | Davydov et al. | |
| 2019/0339820 A1* | 11/2019 | Wu | G06N 20/00 |

FOREIGN PATENT DOCUMENTS

| | | |
|---|---|---|
| CN | 101443779 A | 5/2009 |
| CN | 101556526 A | 10/2009 |
| CN | 102081942 A | 6/2011 |
| CN | 102214064 A | 10/2011 |
| CN | 102385479 A | 3/2012 |
| CN | 102947776 A | 2/2013 |
| CN | 103176714 A | 6/2013 |
| CN | 103250175 A | 8/2013 |
| CN | 103336562 A | 10/2013 |
| CN | 103970818 A | 8/2014 |
| CN | 106251136 A | 12/2016 |
| CN | 106275449 A | 1/2017 |
| EP | 1717666 A1 | 11/2006 |
| EP | 1926312 A2 | 5/2008 |
| EP | 1962207 A1 | 8/2008 |
| EP | 2088501 A1 | 8/2009 |
| EP | 2784643 A1 | 10/2014 |
| EP | 2924601 A1 | 9/2015 |
| EP | 3223130 A1 | 9/2017 |
| EP | 3425489 A1 | 1/2019 |
| JP | H11-191029 A | 7/1999 |
| JP | 2000003247 A | 1/2000 |
| JP | 2002-140143 A | 5/2002 |
| JP | 2002-514328 A | 5/2002 |
| JP | 2004259286 A | 9/2004 |
| JP | 2005032240 A | 2/2005 |
| JP | 2005-115927 A | 4/2005 |
| JP | 2005235204 A | 9/2005 |
| JP | 2006197566 A | 7/2006 |
| JP | 2006246521 A | 9/2006 |
| JP | 2009266238 A | 11/2009 |
| JP | 2012068252 A | 4/2012 |
| JP | 2013025567 A | 2/2013 |
| JP | 2017533487 A | 11/2017 |
| KR | 20150084945 A | 7/2015 |
| KR | 20177004795 A | 2/2016 |
| TW | 201621612 A | 6/2016 |
| WO | 96/009579 A1 | 3/1996 |
| WO | 0195054 A | 12/2001 |
| WO | 2006059450 A | 6/2006 |
| WO | 2006080321 A | 8/2006 |
| WO | 2007086197 A | 8/2007 |
| WO | 2008104003 A | 8/2008 |
| WO | 2009158549 A | 12/2009 |
| WO | 2010081379 A | 7/2010 |
| WO | 2010101039 A1 | 9/2010 |
| WO | 2011026566 A1 | 3/2011 |
| WO | 2011030484 A1 | 3/2011 |
| WO | 2012039140 A1 | 3/2012 |
| WO | 2013010156 A2 | 1/2013 |
| WO | 2013042315 A1 | 3/2013 |
| WO | 2013090944 A1 | 6/2013 |
| WO | 2014034031 A1 | 3/2014 |
| WO | 2014083864 A1 | 6/2014 |
| WO | 2014128775 A1 | 8/2014 |
| WO | 2014192048 A1 | 12/2014 |
| WO | 2014200729 A1 | 12/2014 |
| WO | 2015192085 A1 | 12/2015 |
| WO | 2016035800 A1 | 3/2016 |
| WO | 2016036546 A1 | 3/2016 |
| WO | 2017096096 A1 | 6/2017 |
| WO | 2018040010 A1 | 3/2018 |
| WO | 2018056755 A1 | 3/2018 |
| WO | 2019046597 A1 | 3/2019 |

OTHER PUBLICATIONS

Anonymous, Menus, Microsoft Documents, Jan. 26, 2007 (Year: 2007).

Bailly et al., "Visual Menu Techniques," Research Report, Laboratoire Traitement et Communication de l'Information, CNRS, Telecom Paris Tech., 2016.

Bier et al., "A Taxonomy of See-Through Tools," Proceedings of the SIGCHI Conference on Human Factors in Computing Systems, p. 358-364, 1994.

Friedlander et al., "Bullseye! When Fitts' Law Doesn't Fit," Proceedings of the SIGCHI Conference on Human Factors in Computing Systems, p. 257-264, 1998.

Karlson, Amy Kathleen, "Interface and Interaction Design For One-Handed Mobile Computing," Dissertation submitted to the Faculty of the Graduate School of the University of Maryland, College Park, 2007.

Lecolinet et al., "Representation focus+Contexte de listes Hierarchiques zoomables," Ecole Nationale Superieure des Telecommunications, CNRS LTCI, 2006.

McGuffin et al., "FaST Sliders: Integrating Marking Menus and the Adjustment of Continuous Values," Proceedings of Graphics Interface 2002: Calgary, Alberta, Canada, p. 35-42, 2002.

Communication pursuant to Article 94(3) EPC, European Application No. 19749073.3, dated Jul. 24, 2023.

* cited by examiner

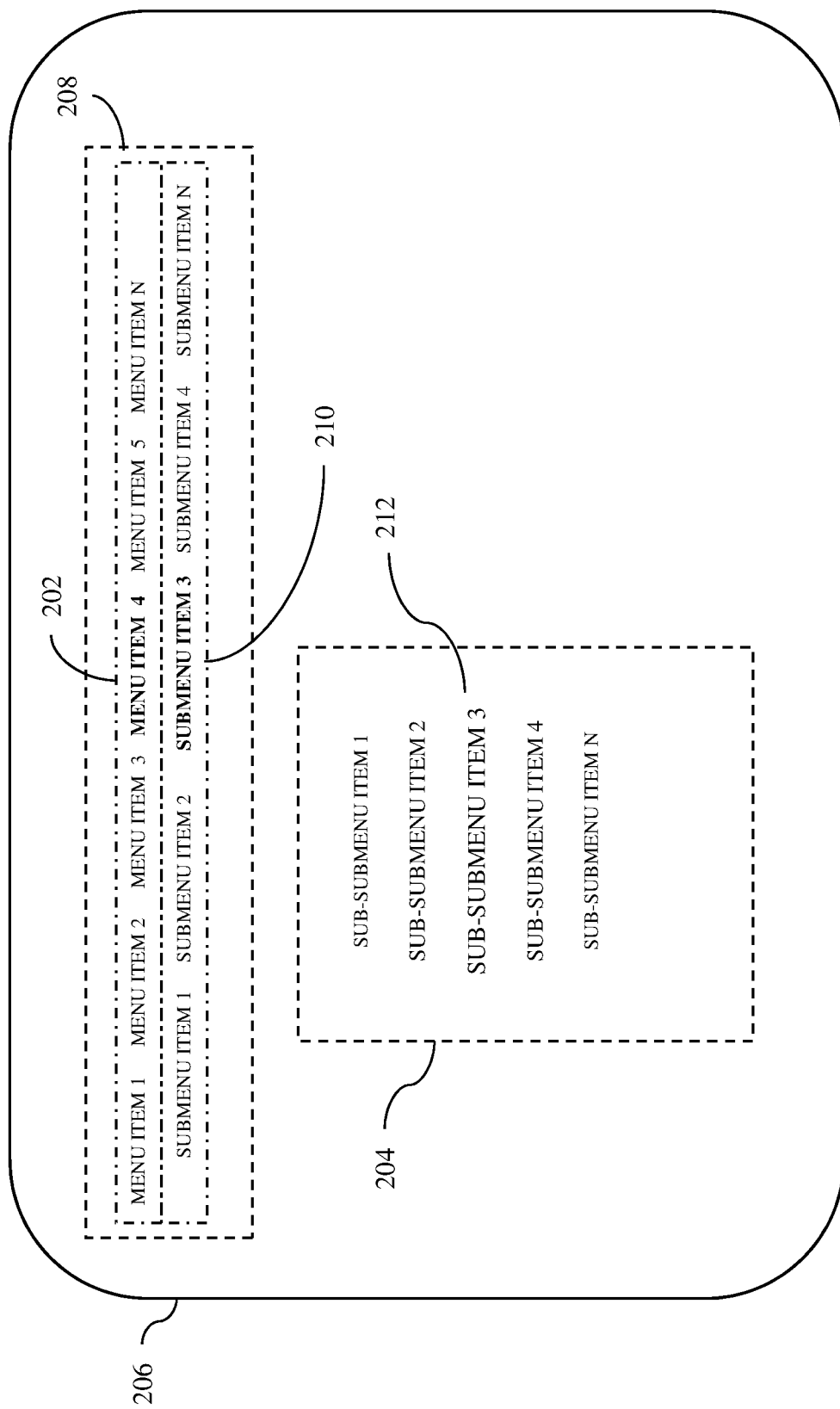

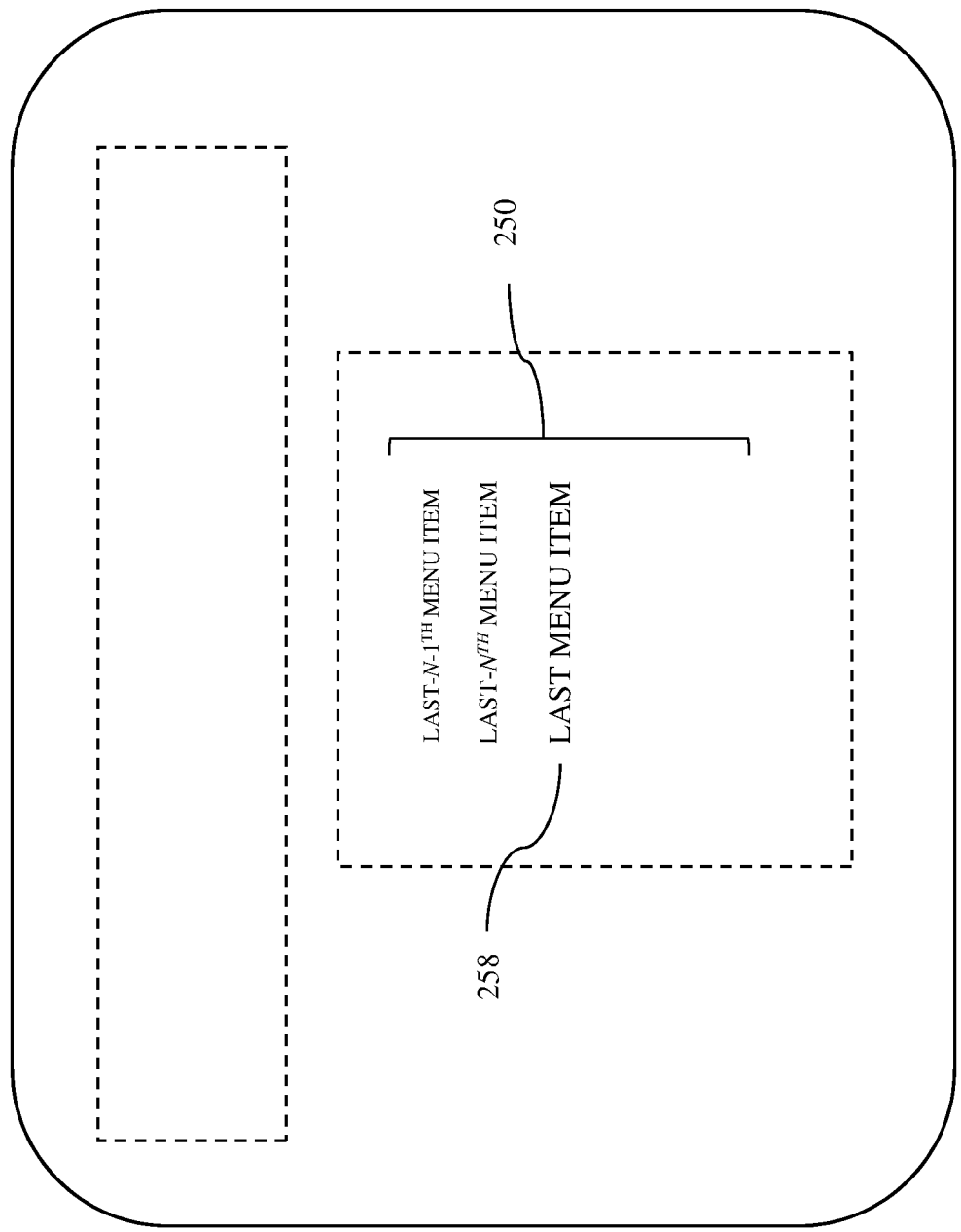

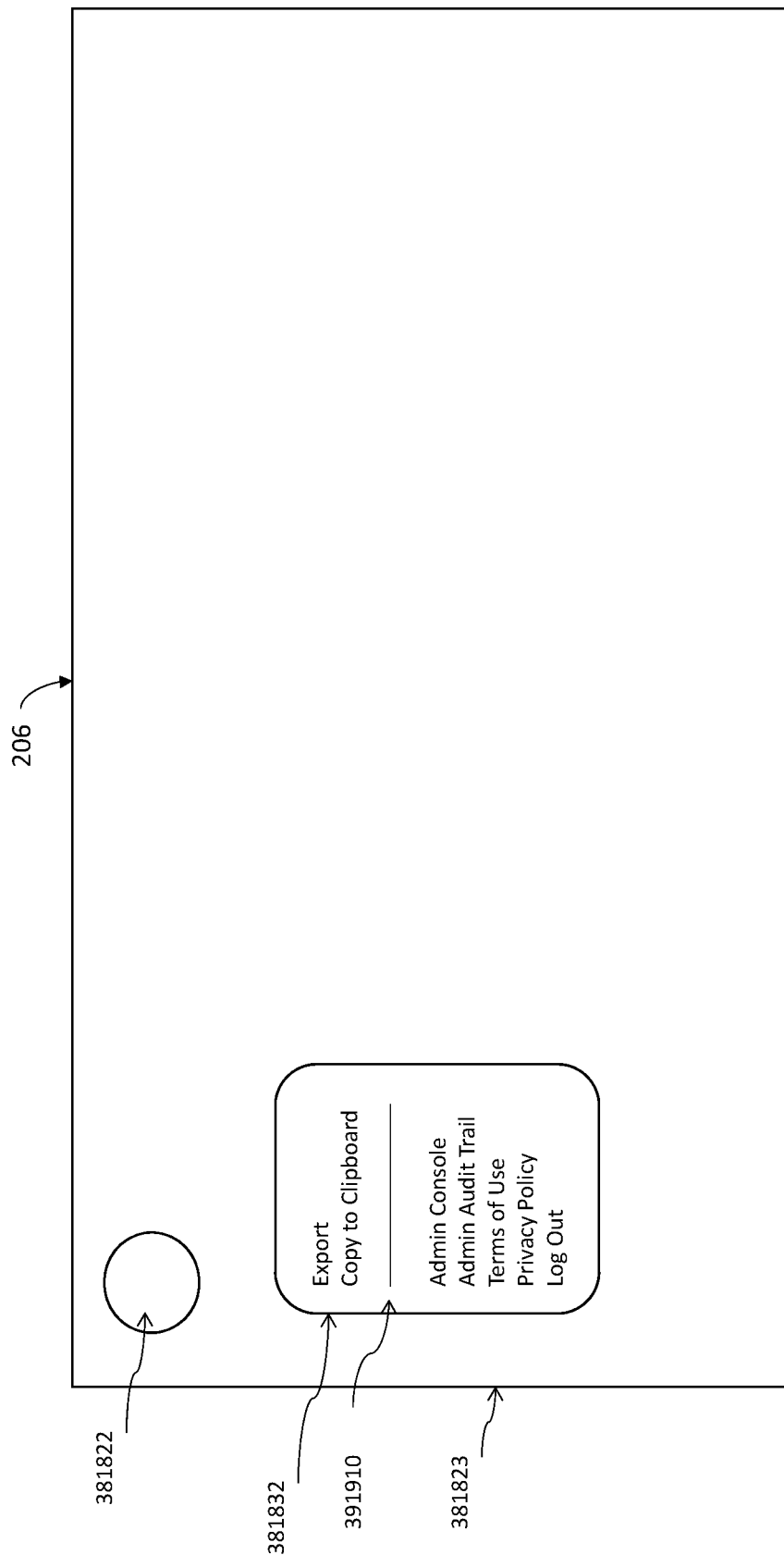

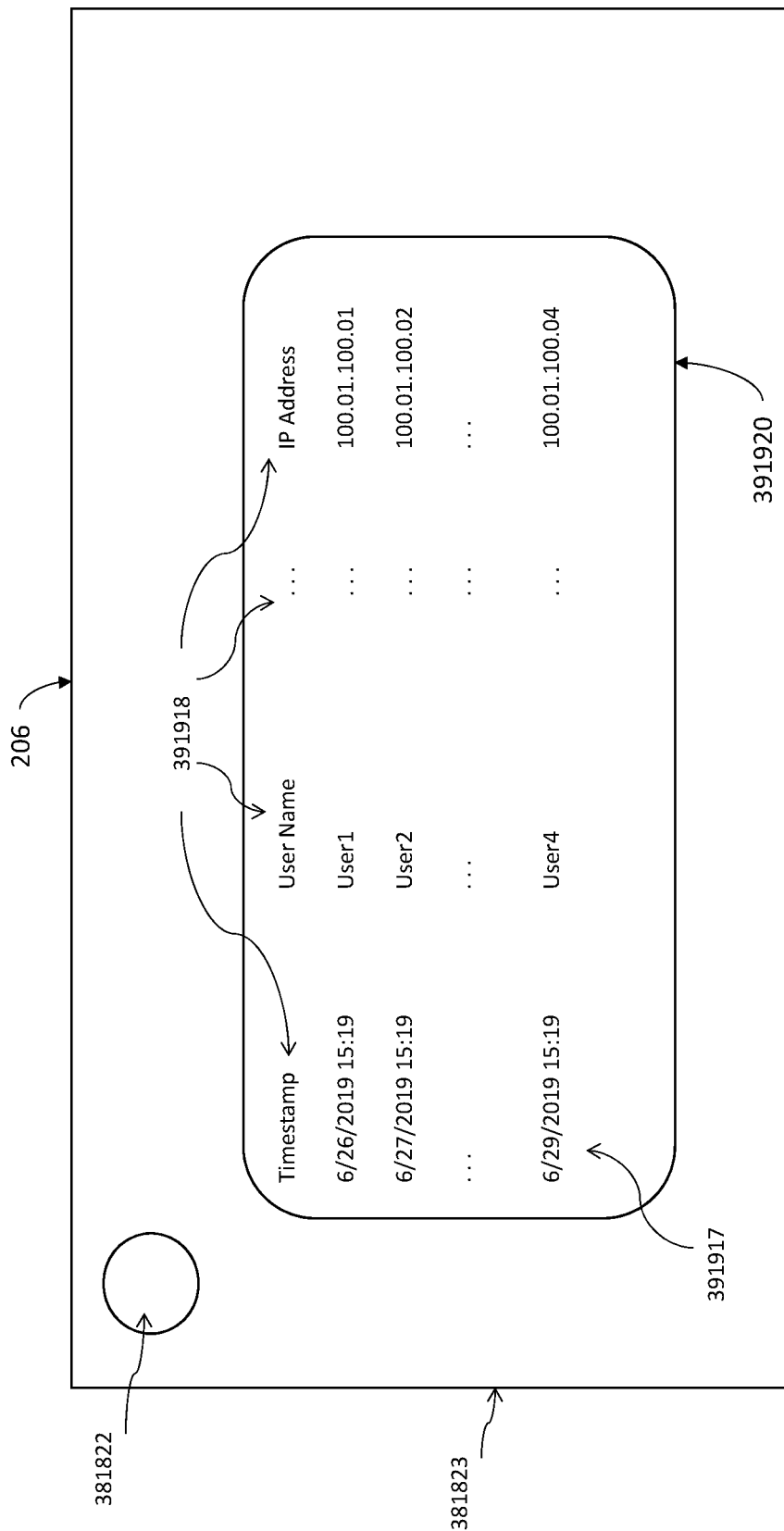

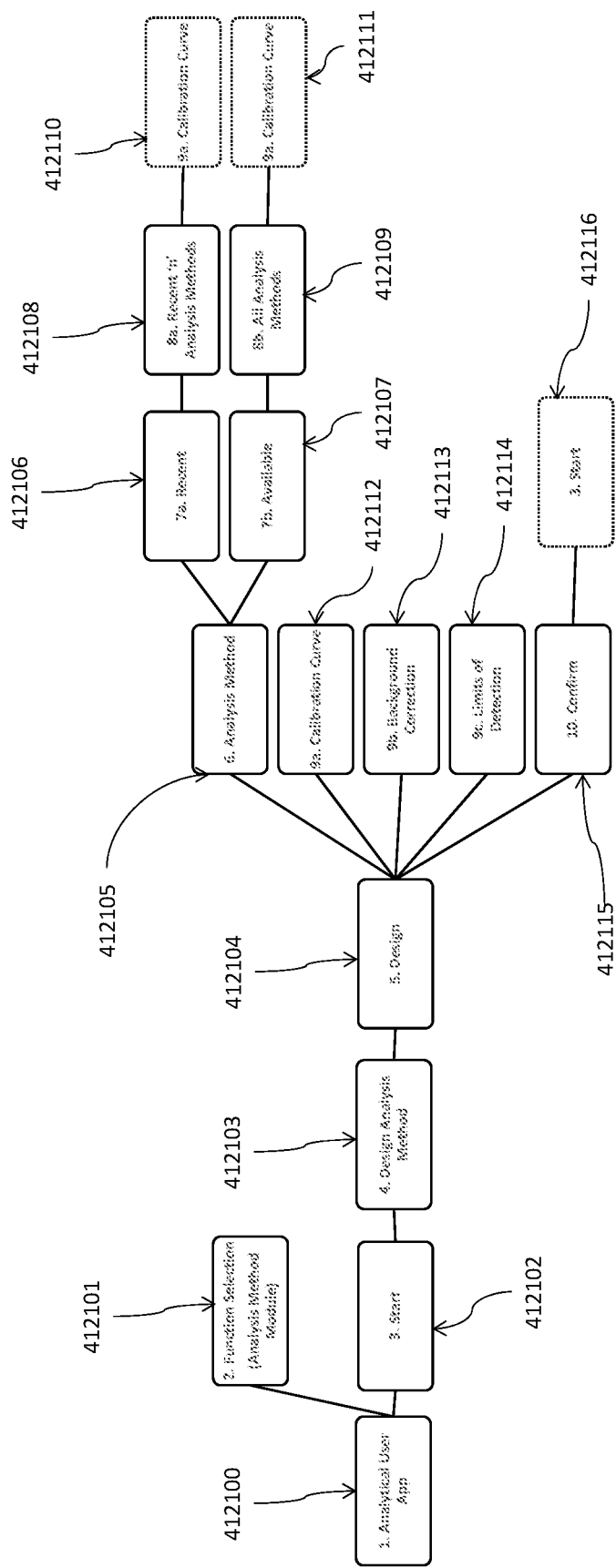
FIG. 41 – Analytical User App Analysis Method Module Flow

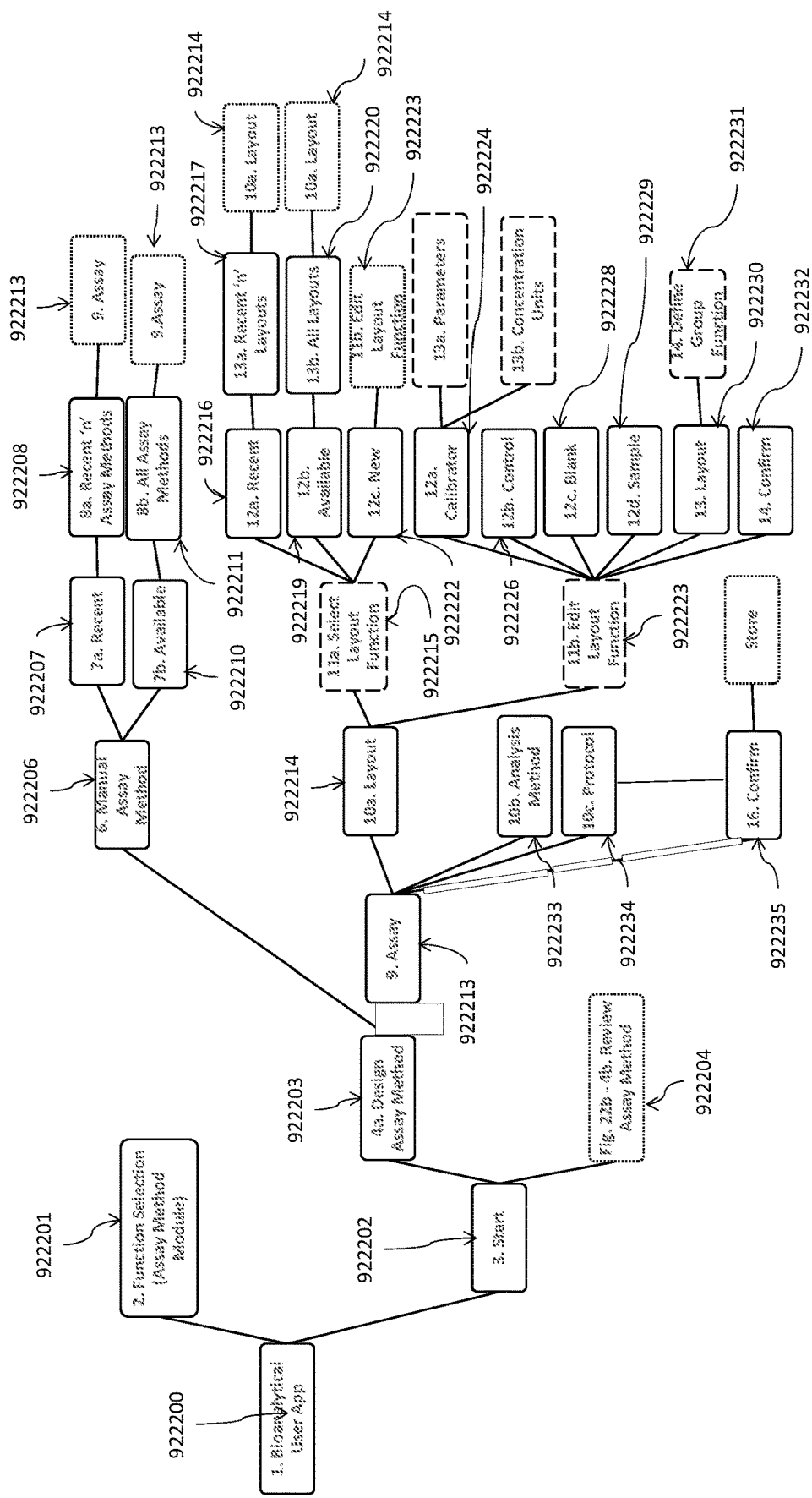
Fig. 42A – Bioanalytical User App Assay Method Module Design Flow

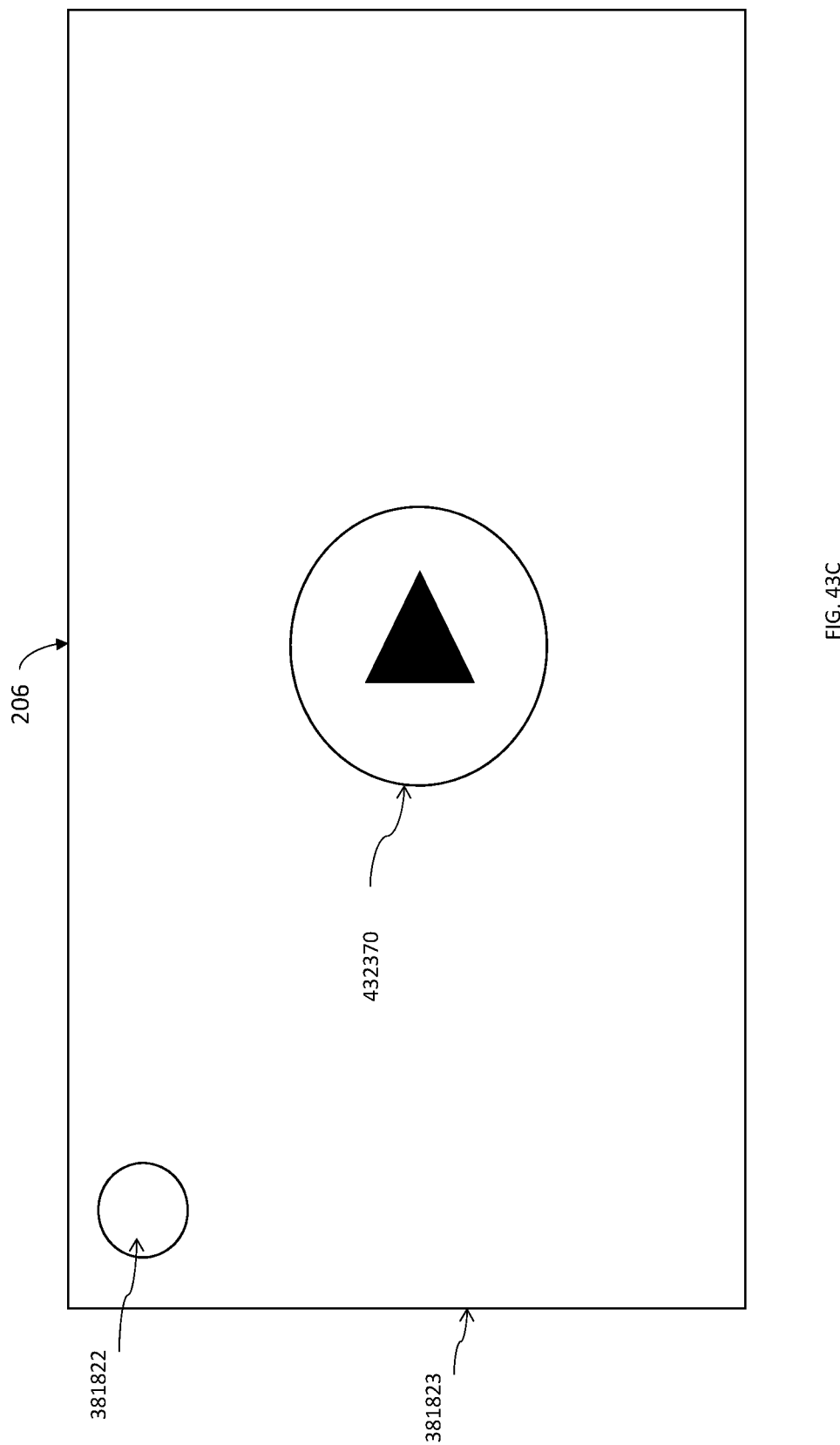

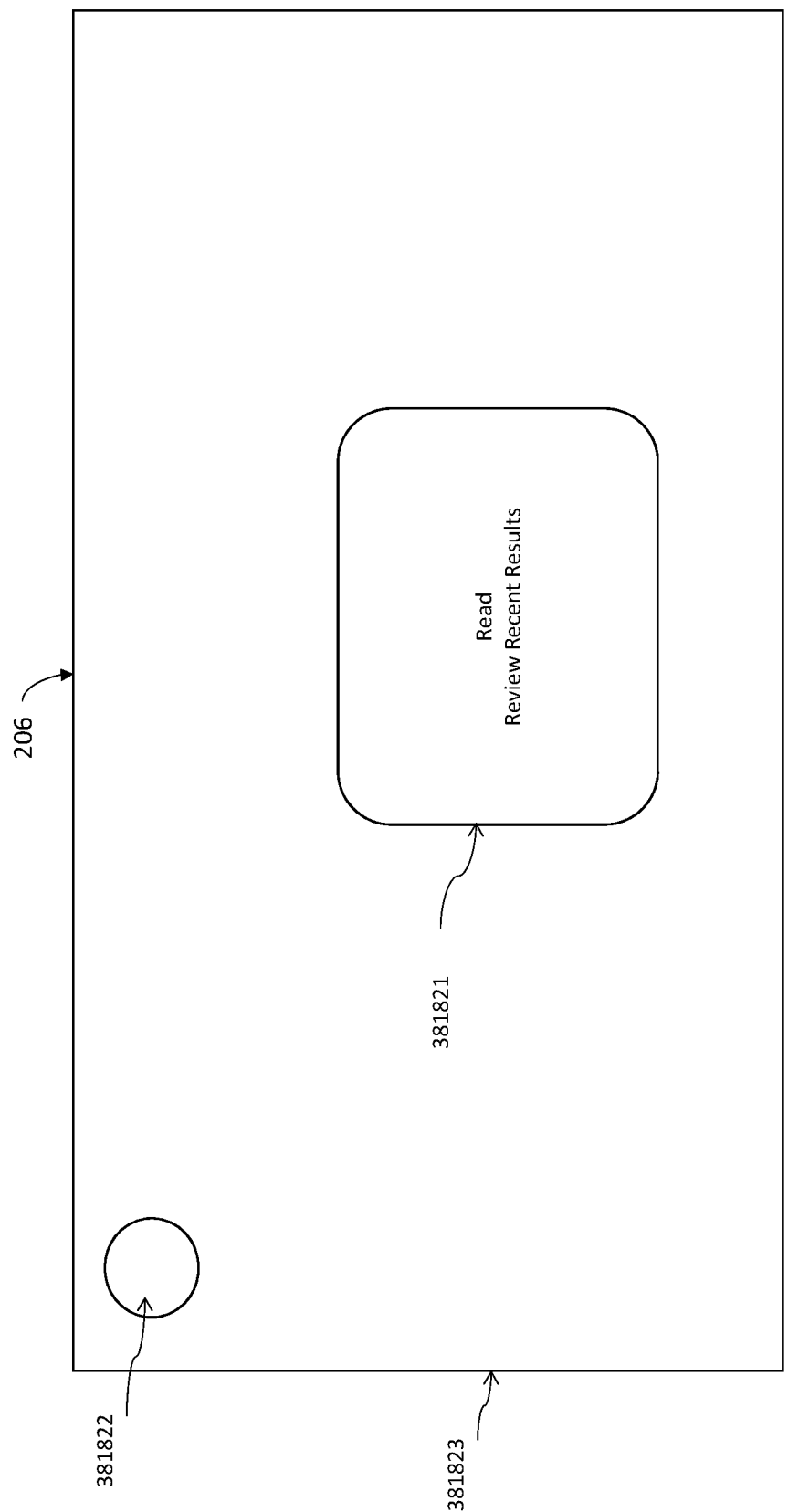

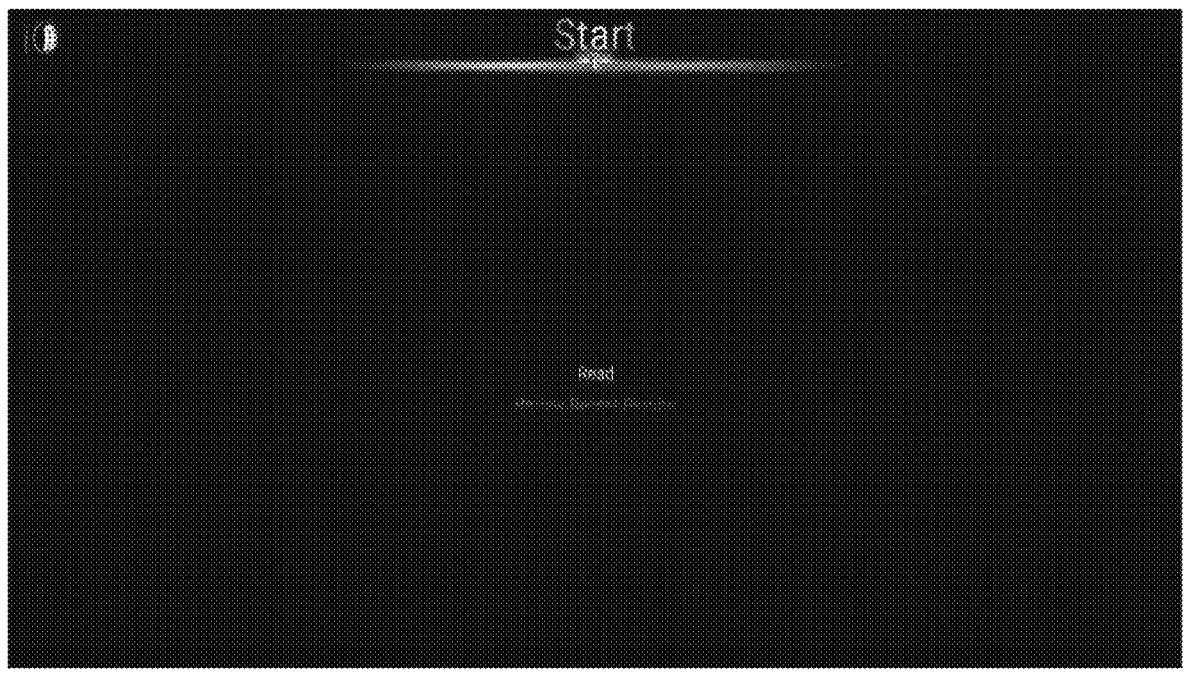
FIG. 58A
FIG. 58B
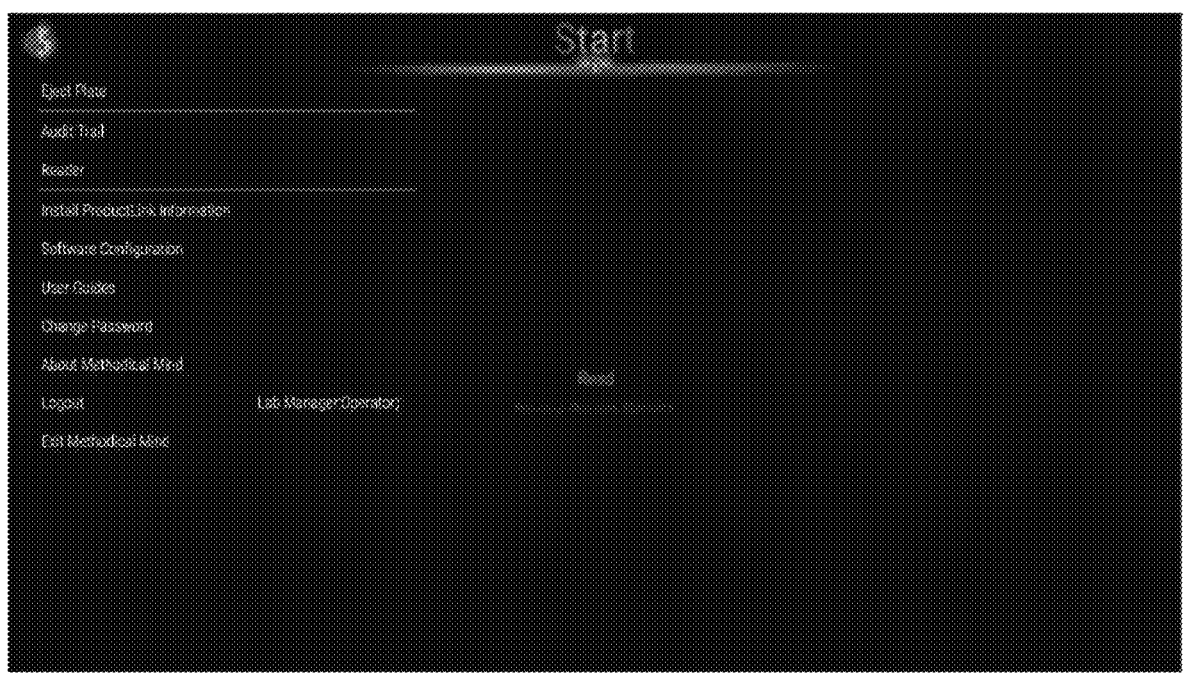

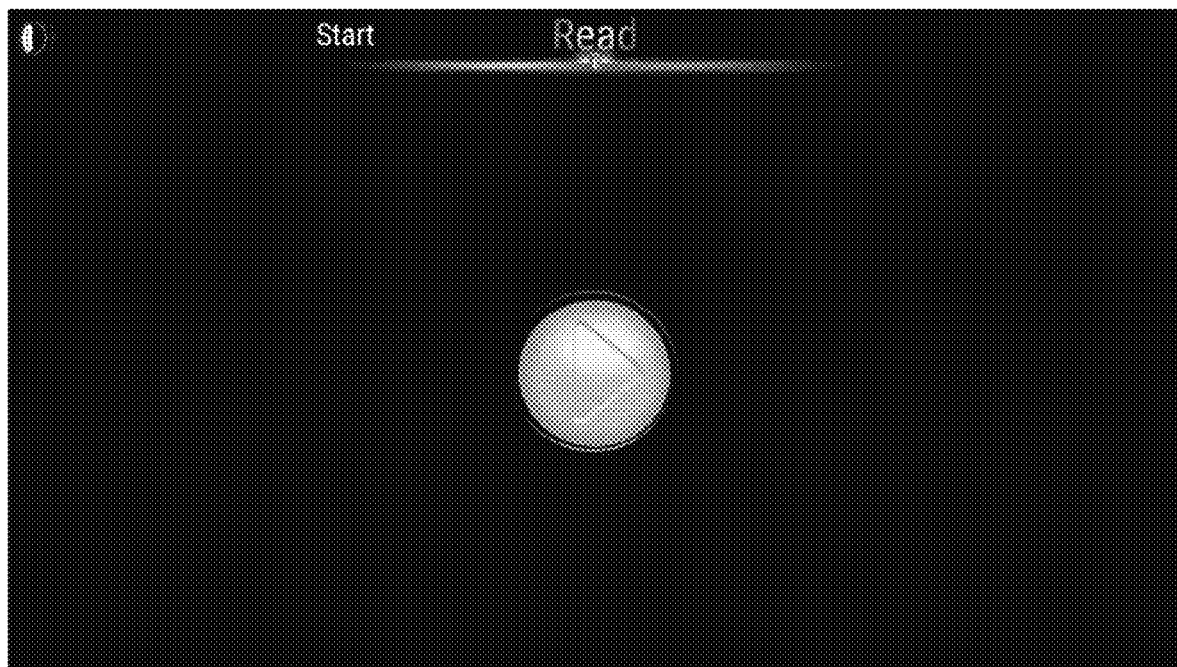
FIG. 58C
FIG. 58D
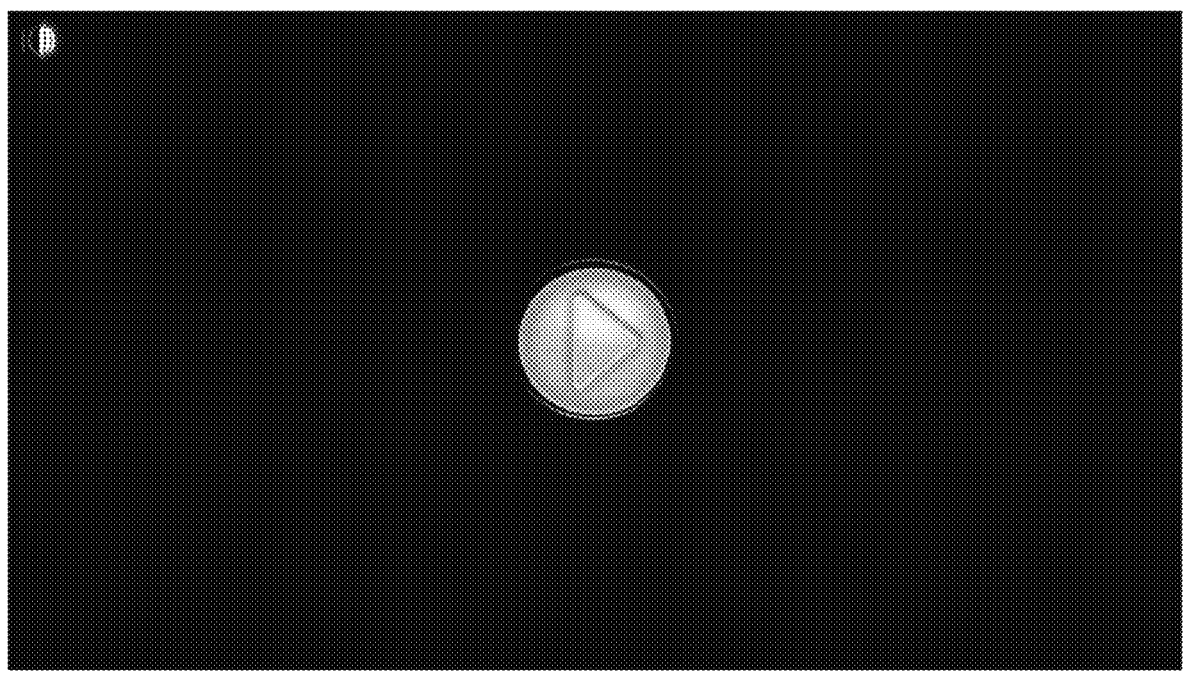

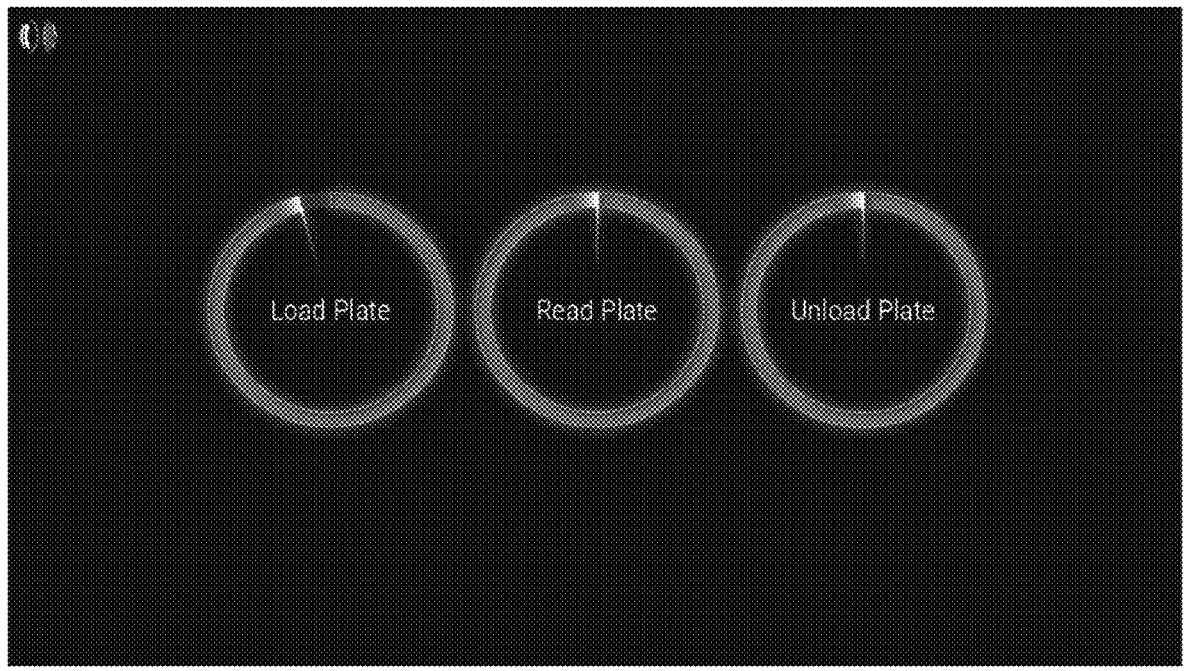
FIG. 58E
FIG. 58F
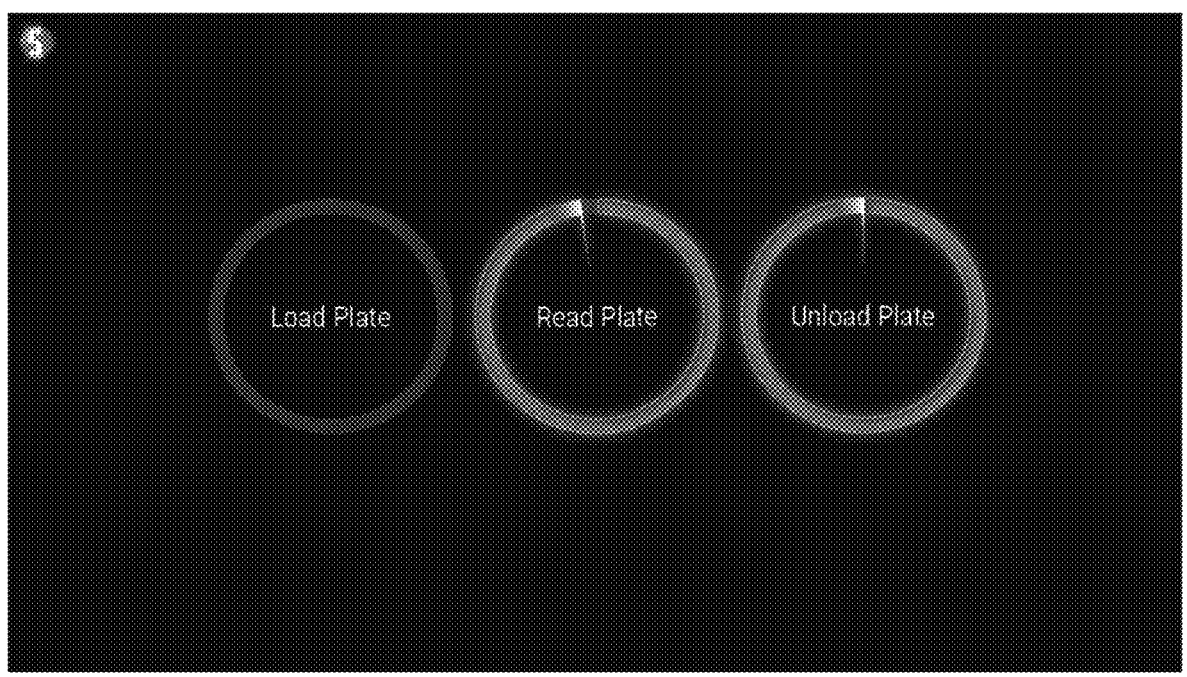

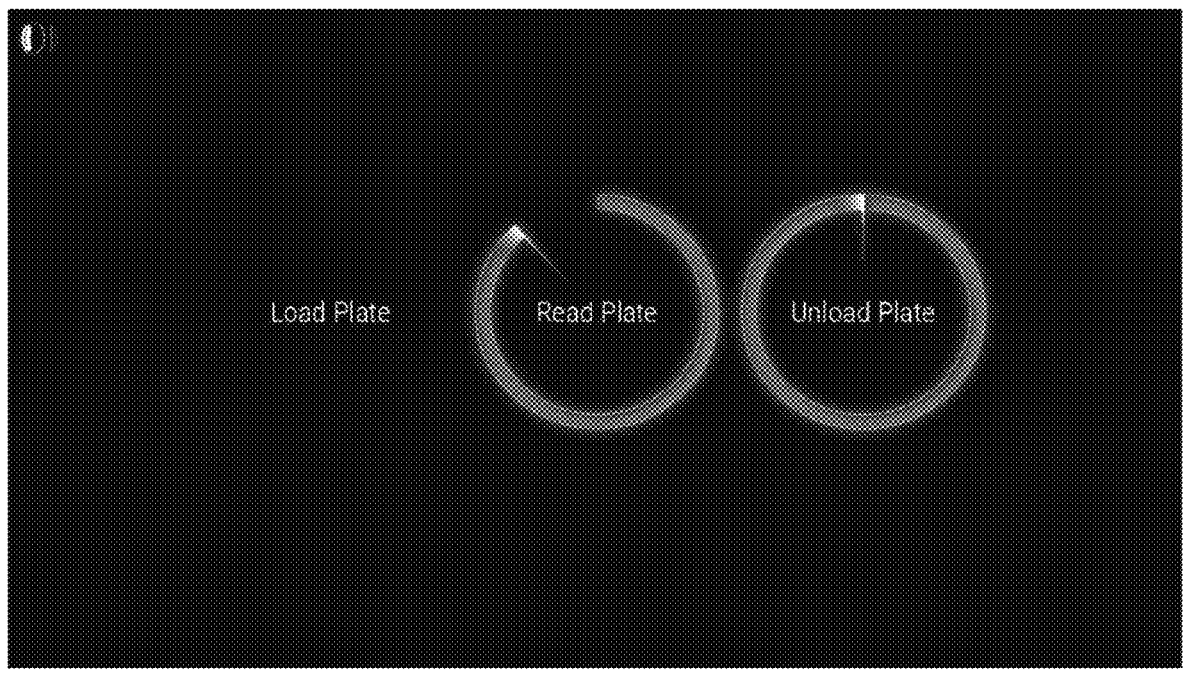
FIG. 58G
FIG. 58H
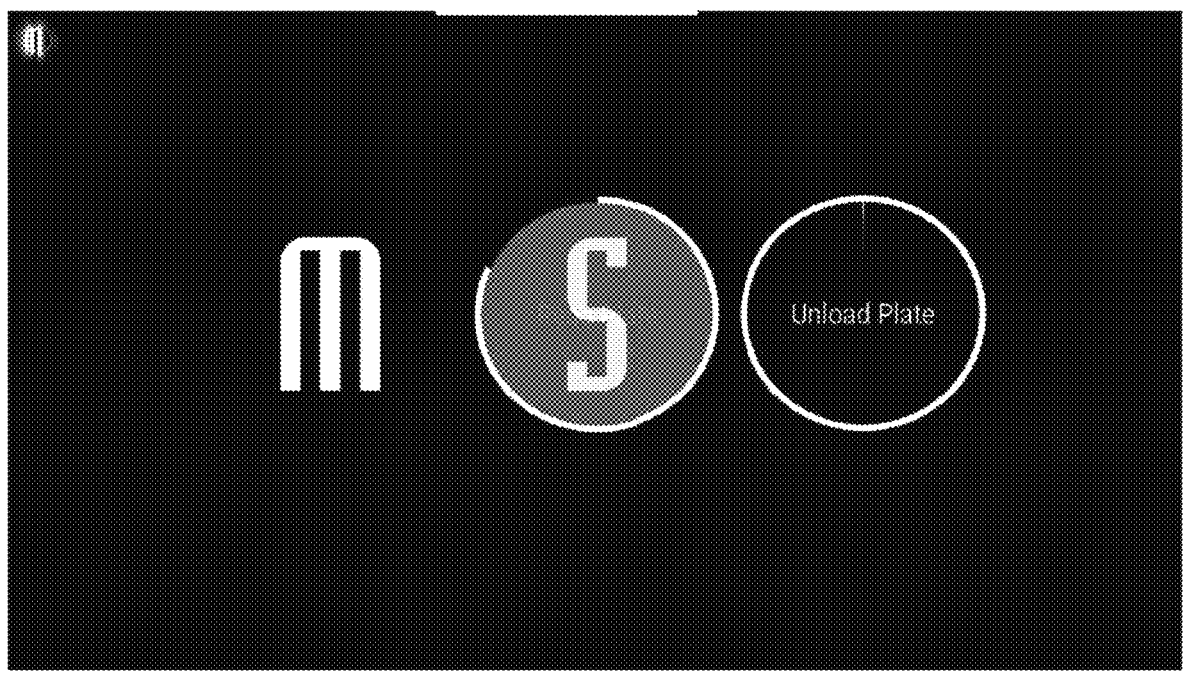

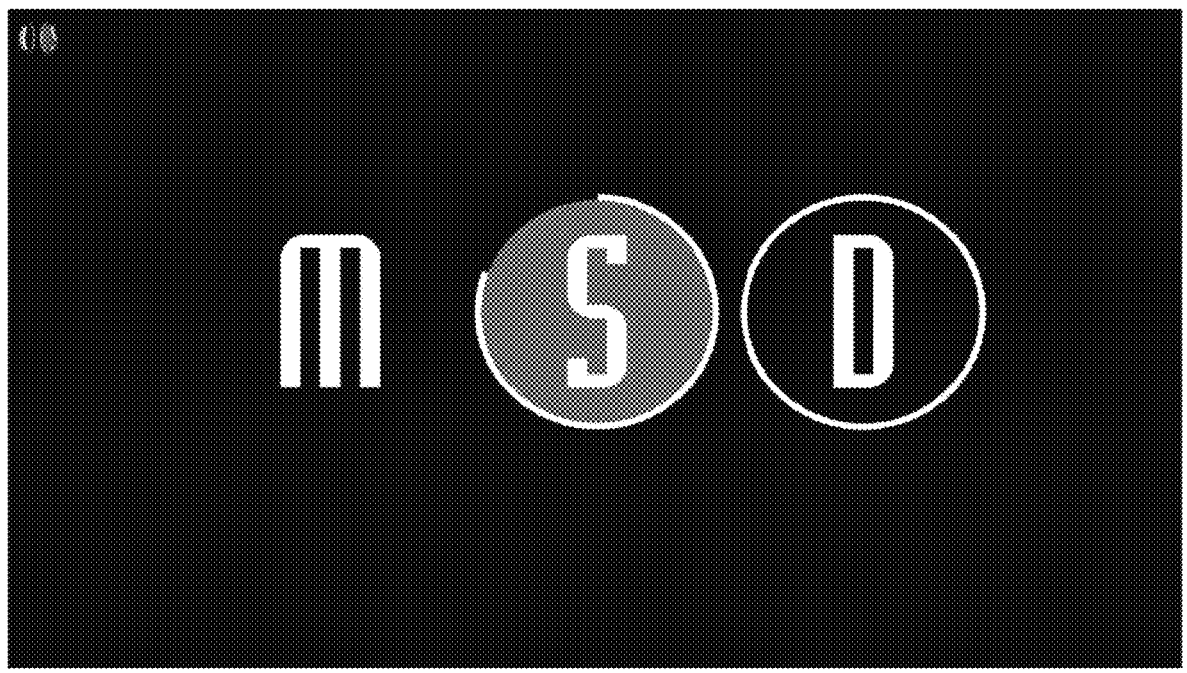
FIG. 58I
FIG. 58J
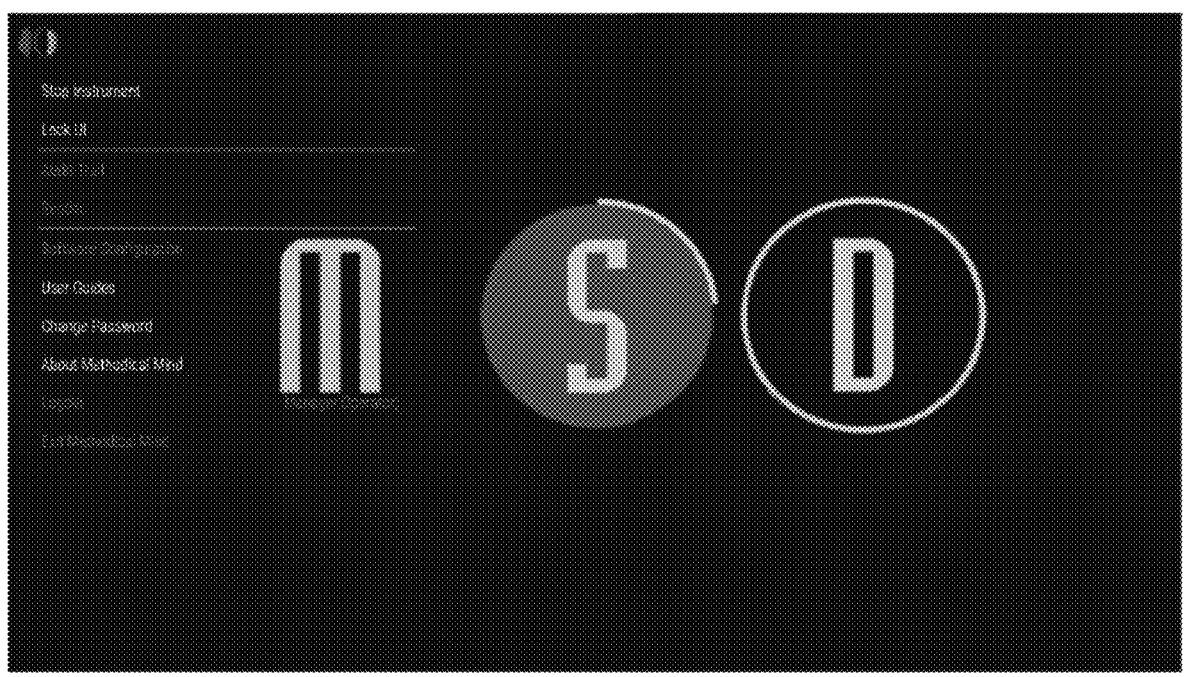

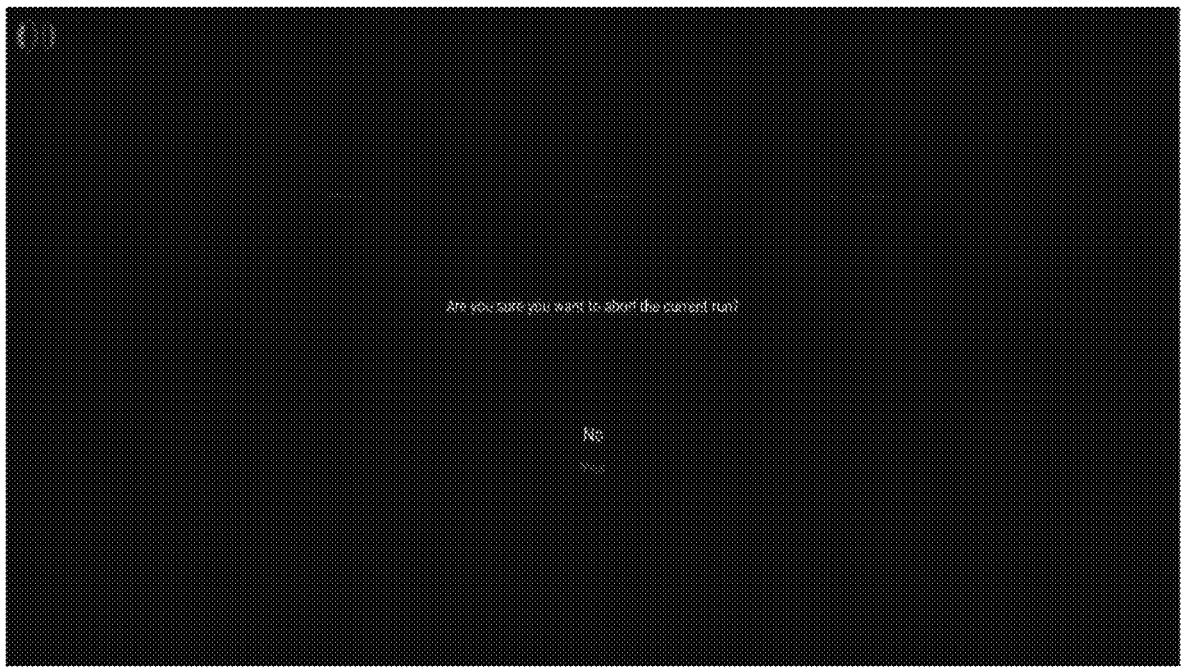
FIG. 58 K
FIG. 58L
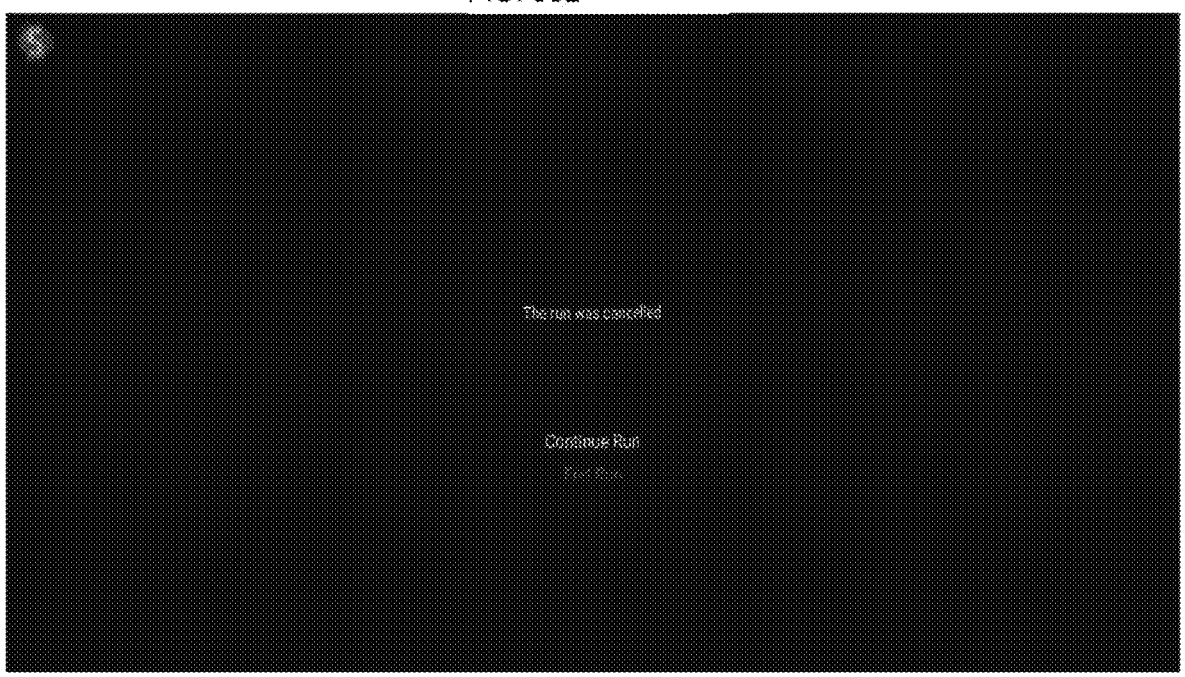

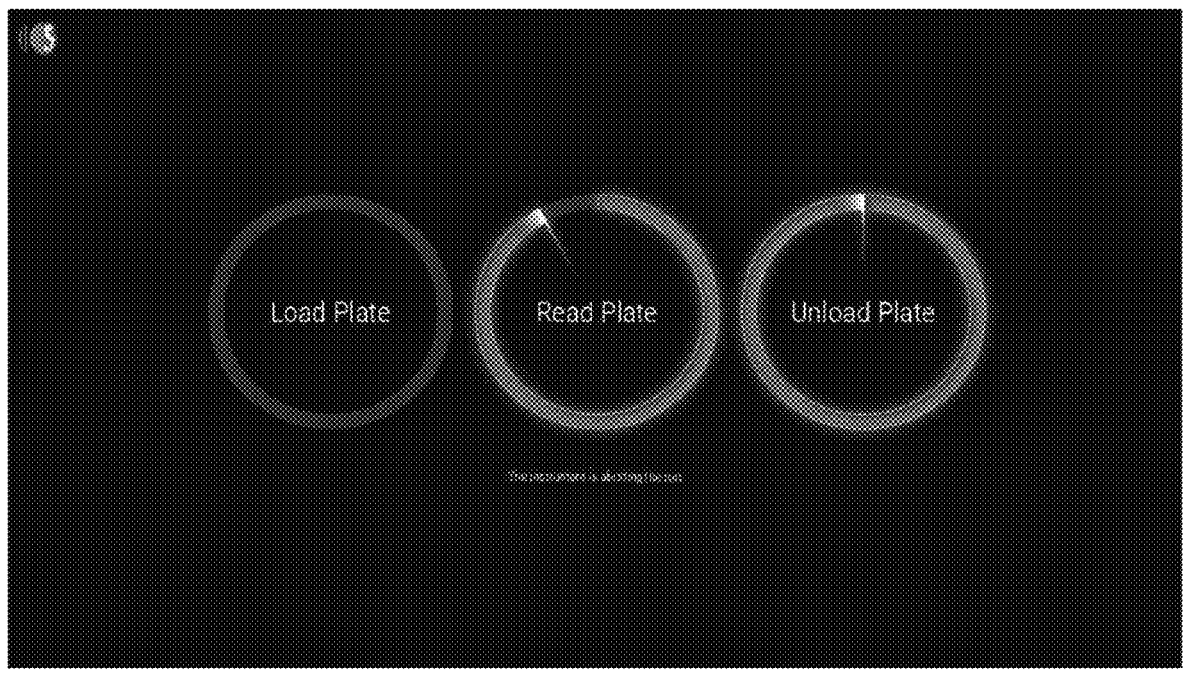
FIG. 58M
FIG. 58N
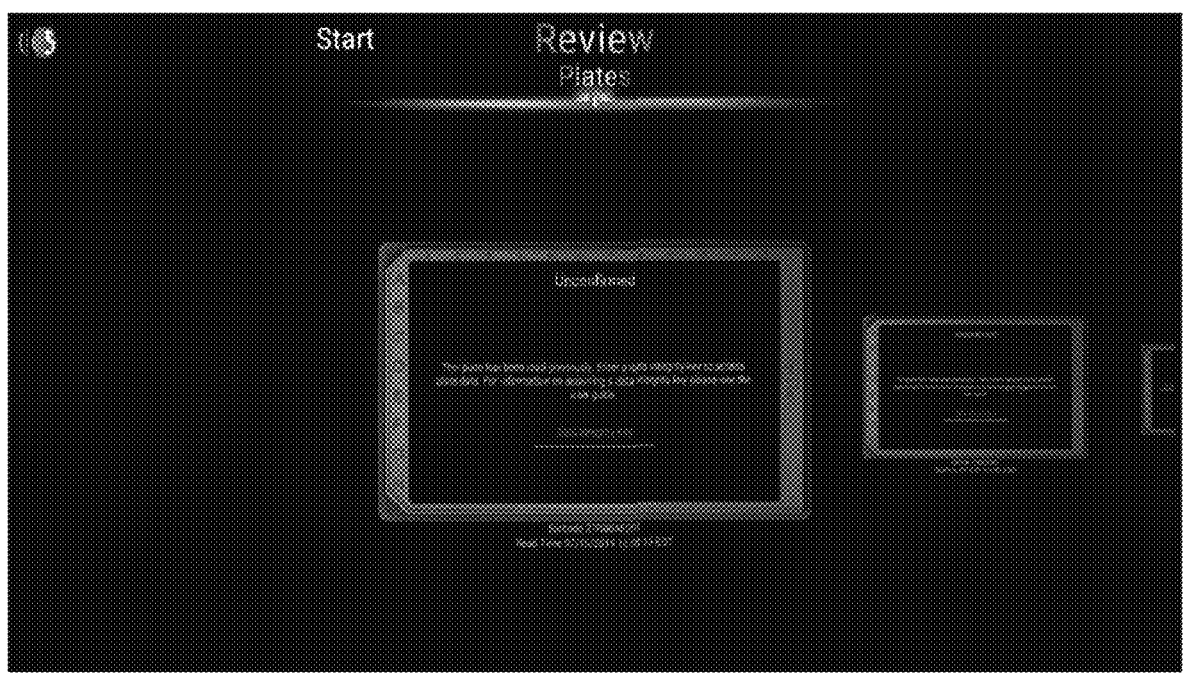

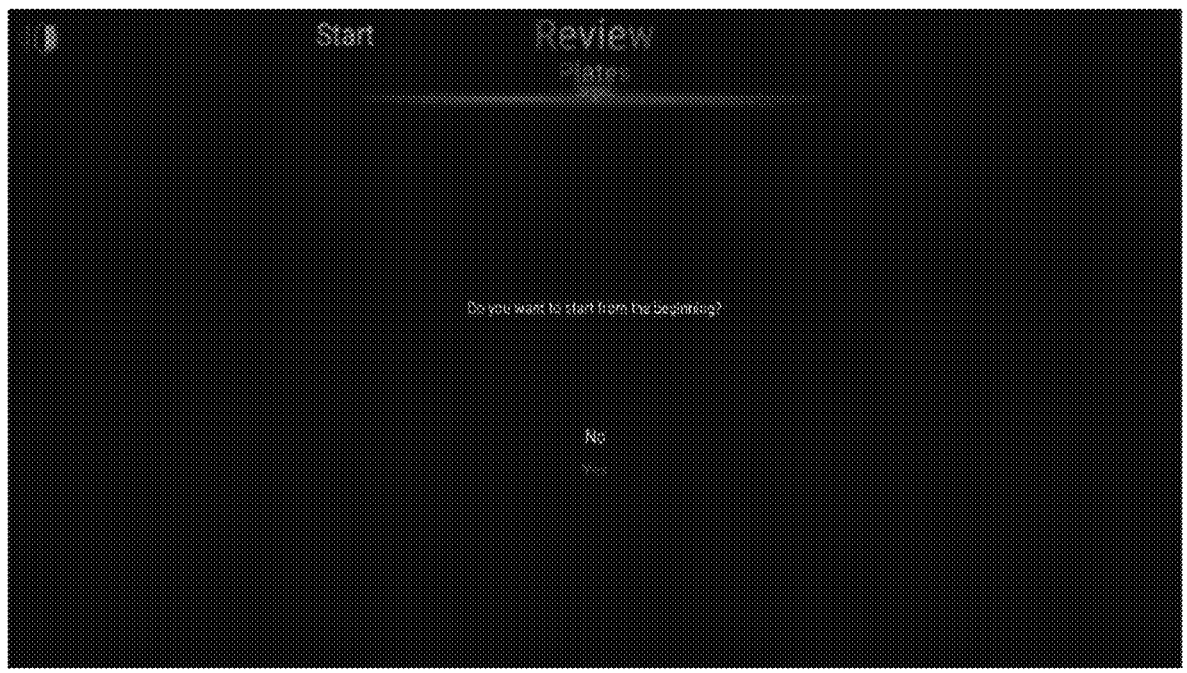
FIG. 58O
FIG. 58P
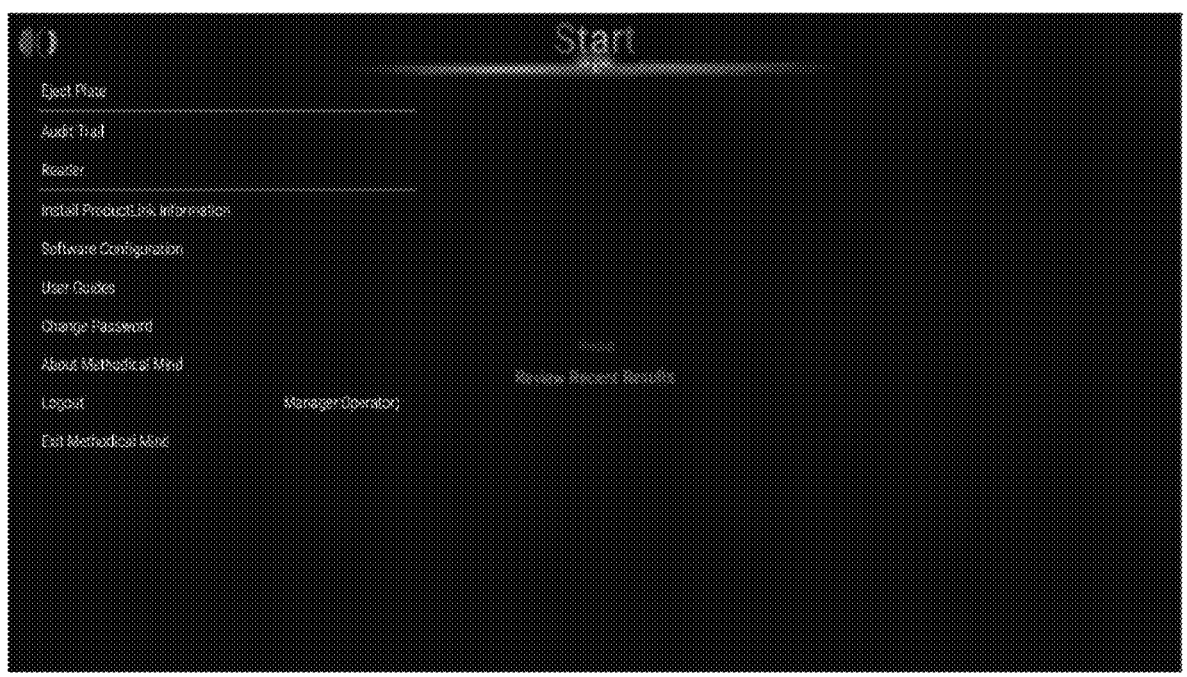

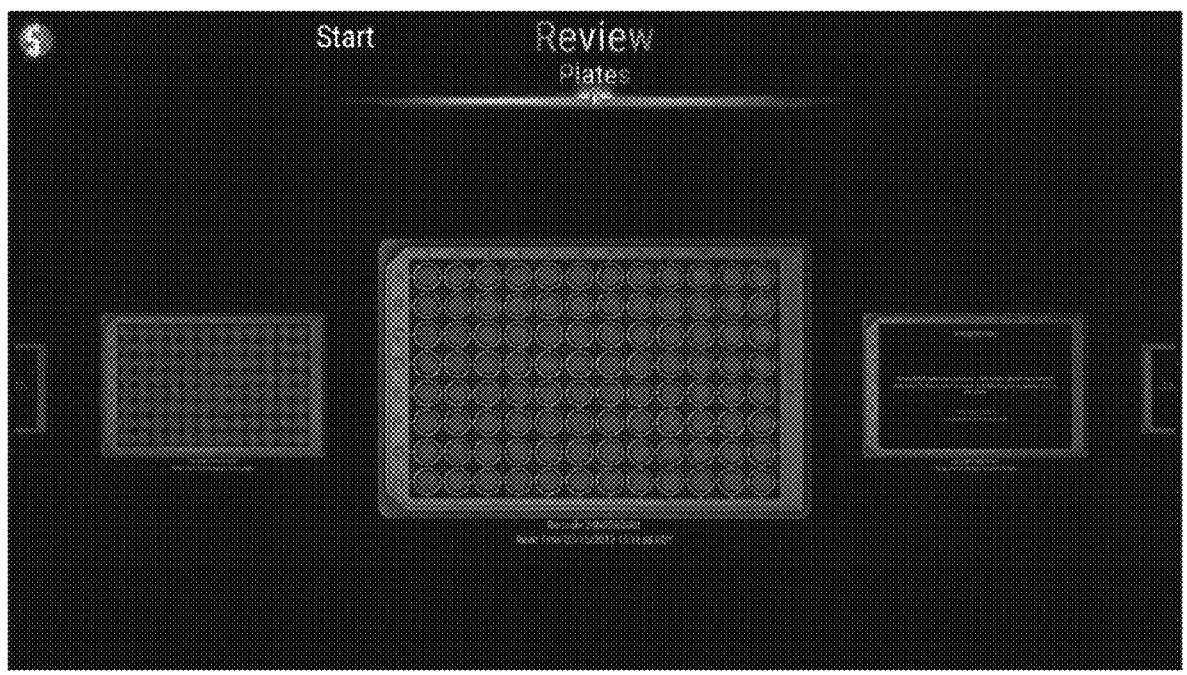
FIG. 58Q
FIG. 58R

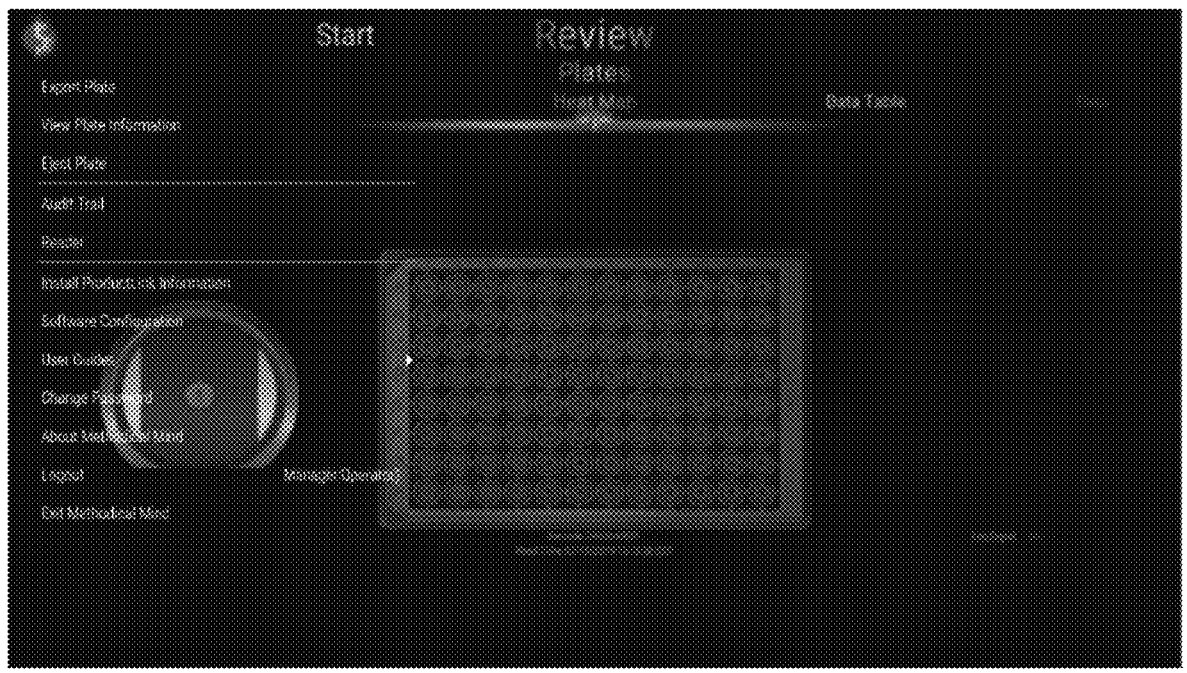
FIG. 58S
FIG. 58T
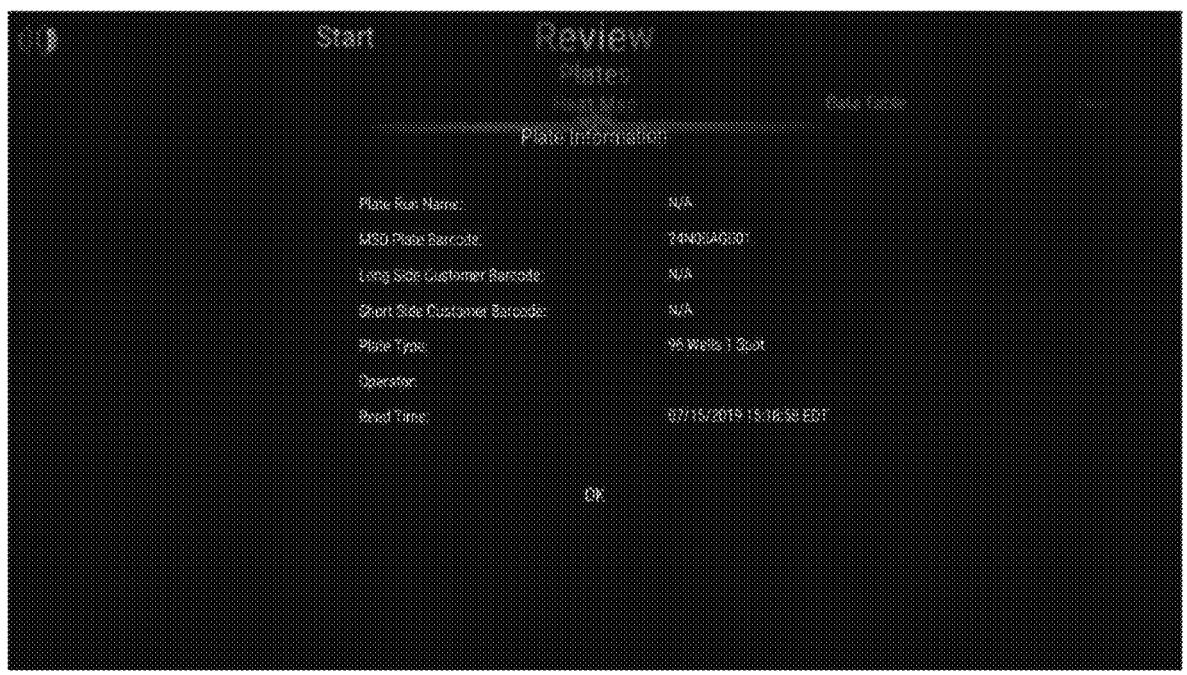

FIG. 58U
FIG. 58V
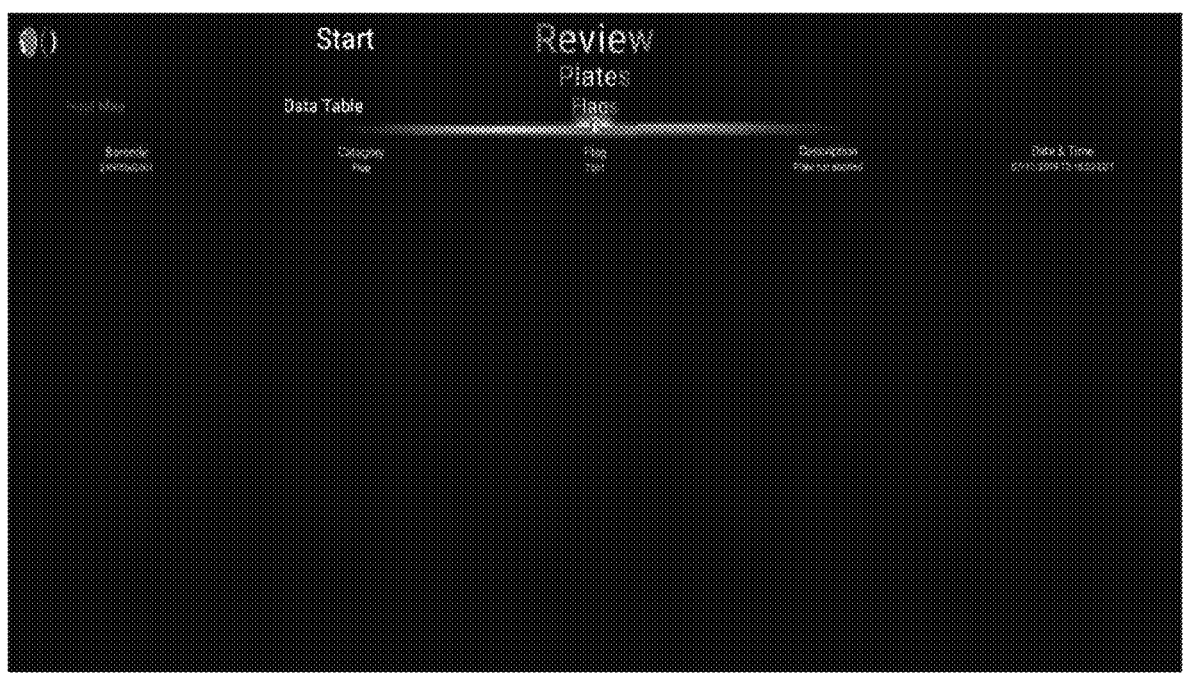

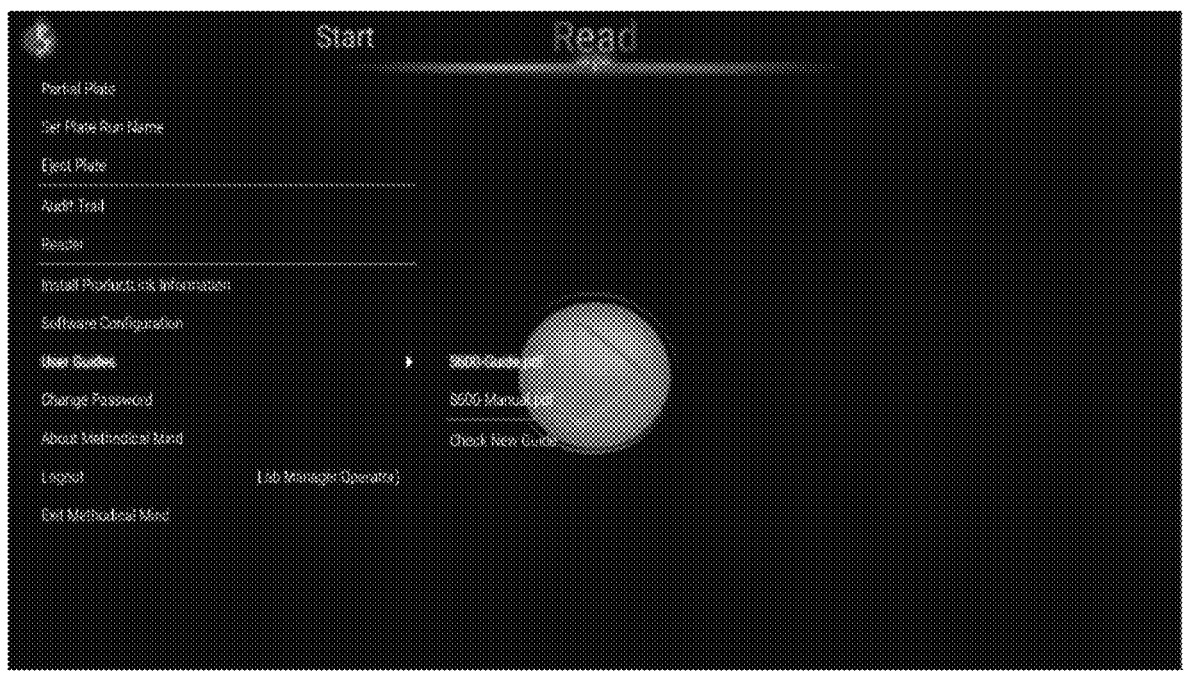
FIG. 58W
FIG. 58X
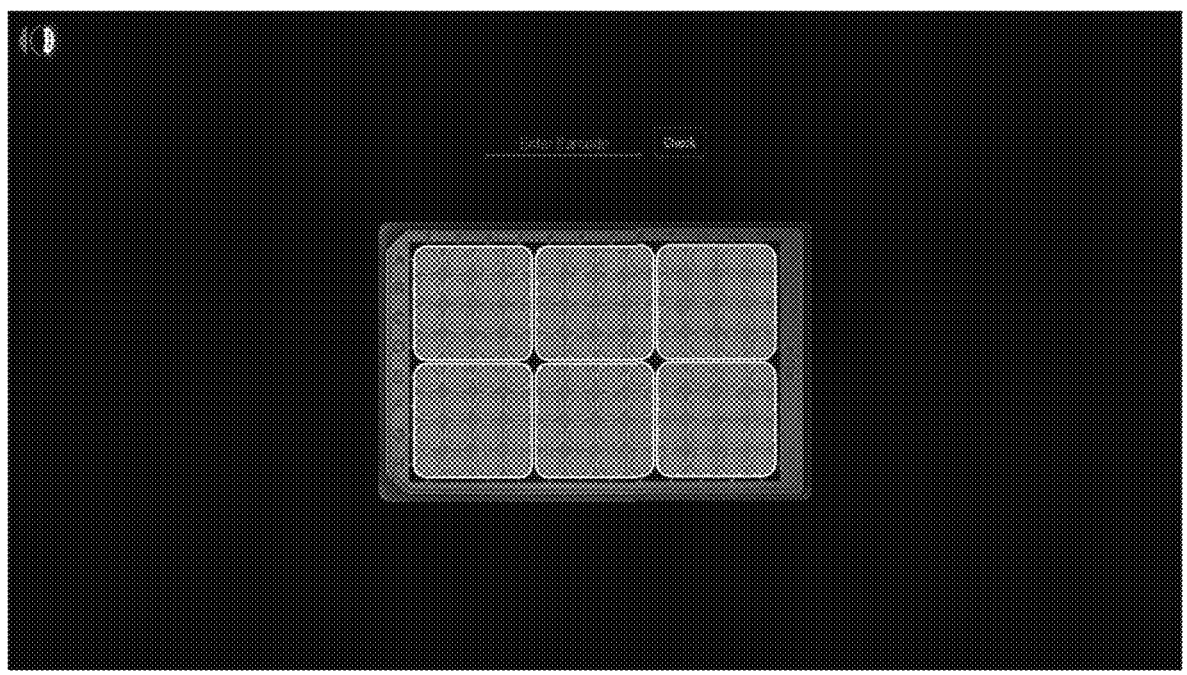

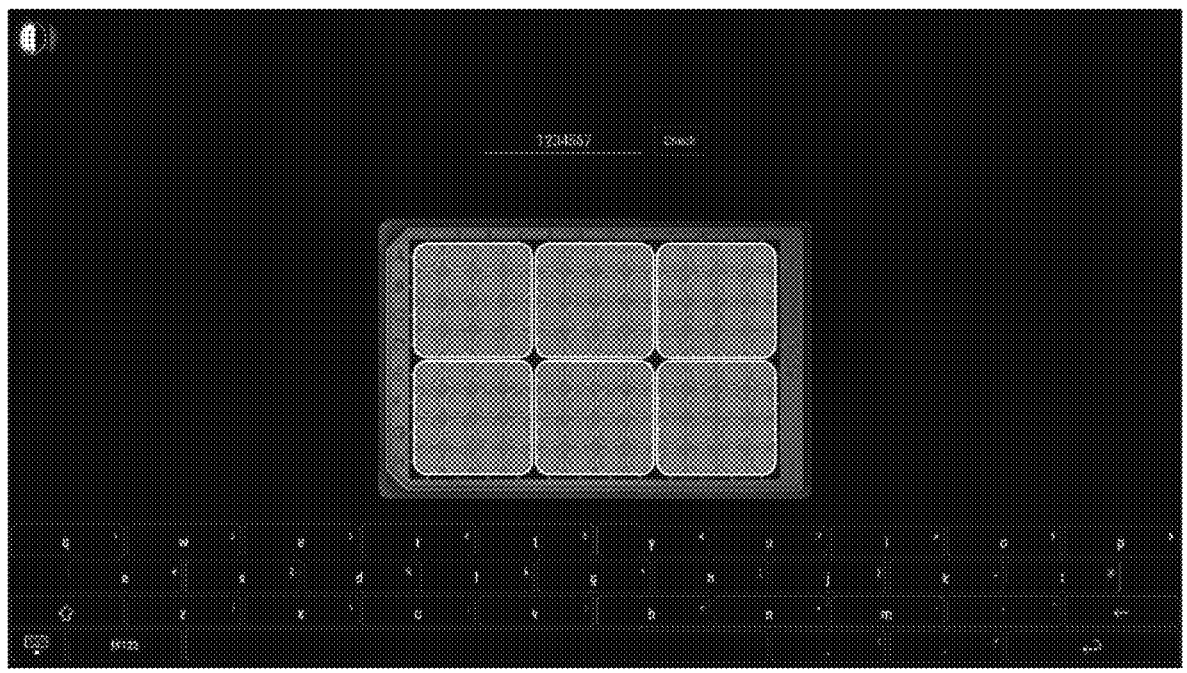
FIG. 58Y
FIG. 58Z
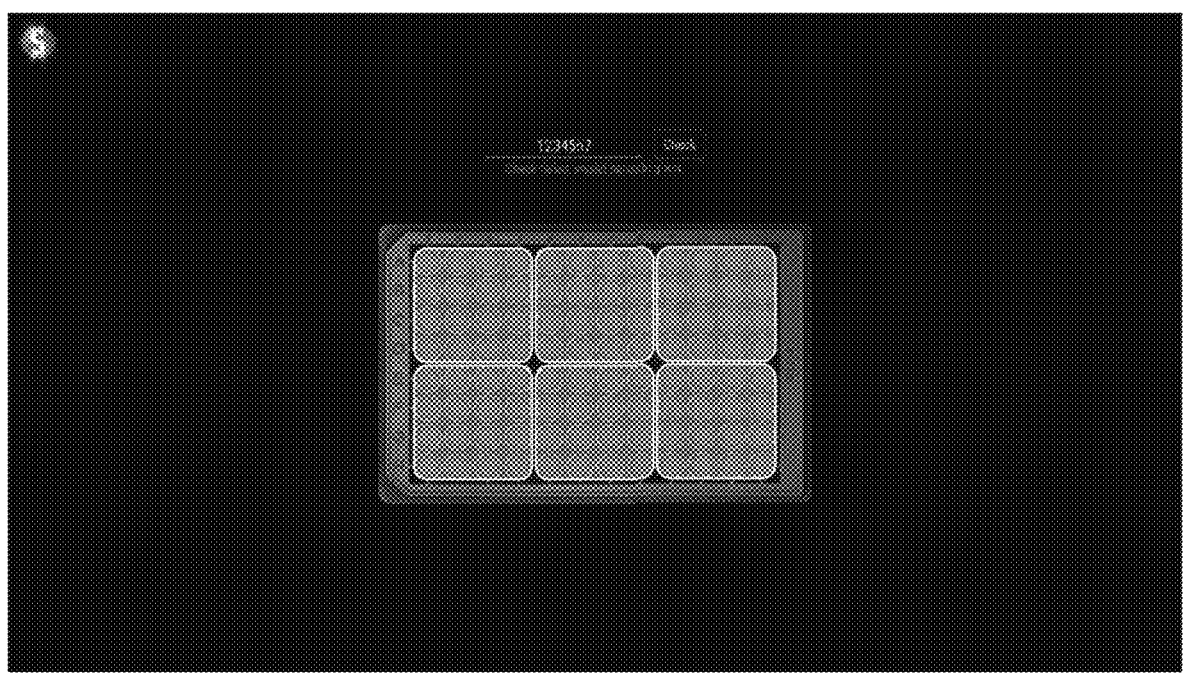

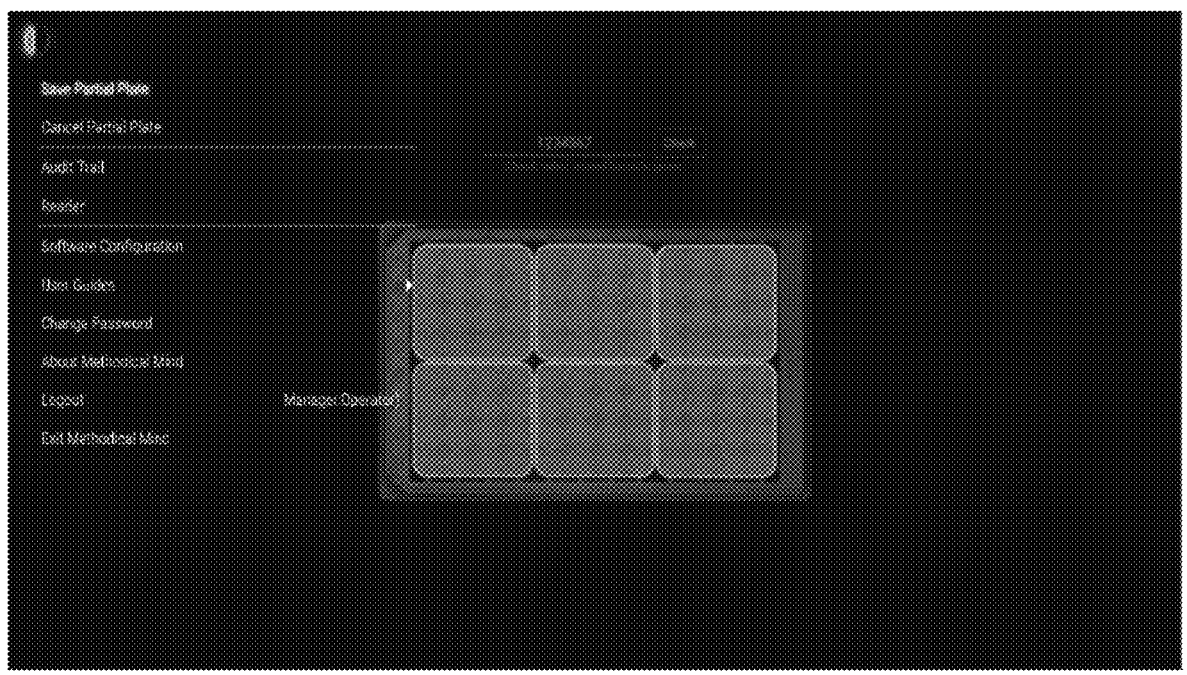
FIG. 58AA
FIG. 58BB
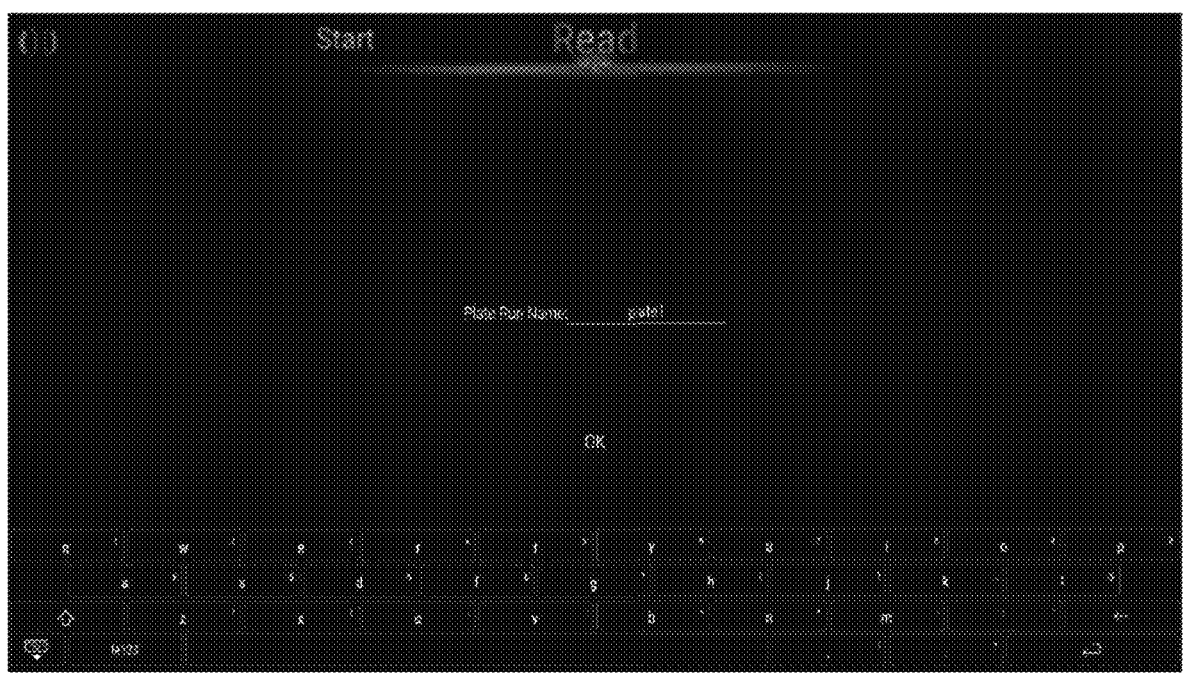

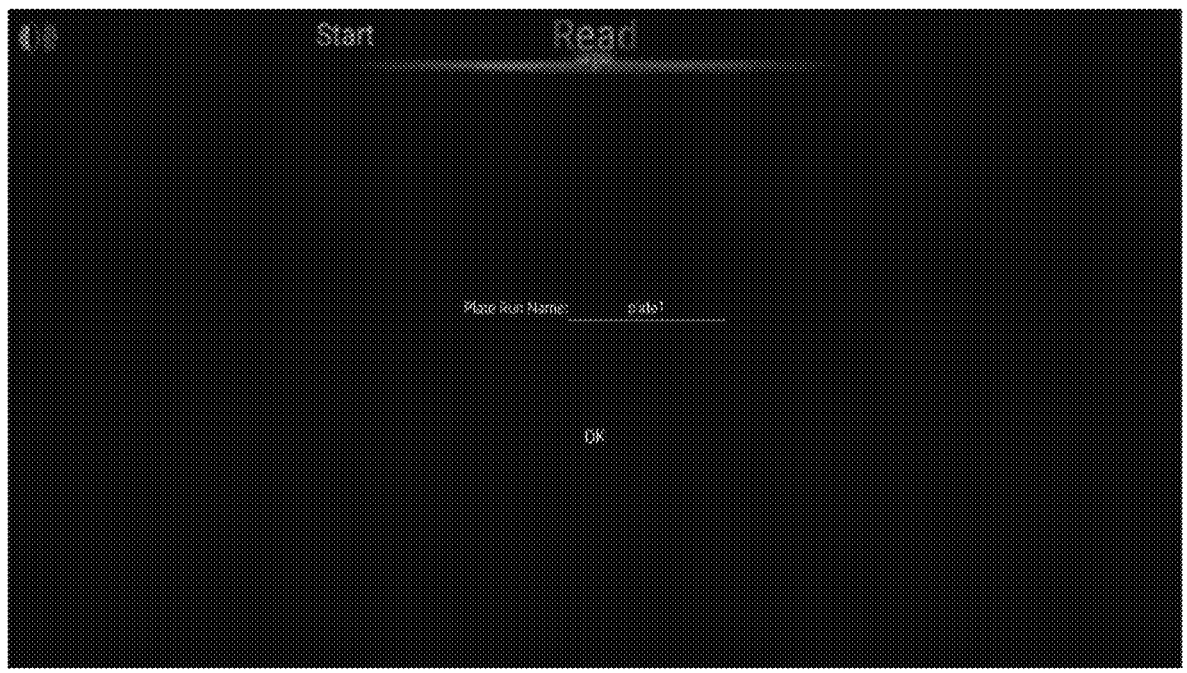
FIG. 58CC
FIG. 58DD
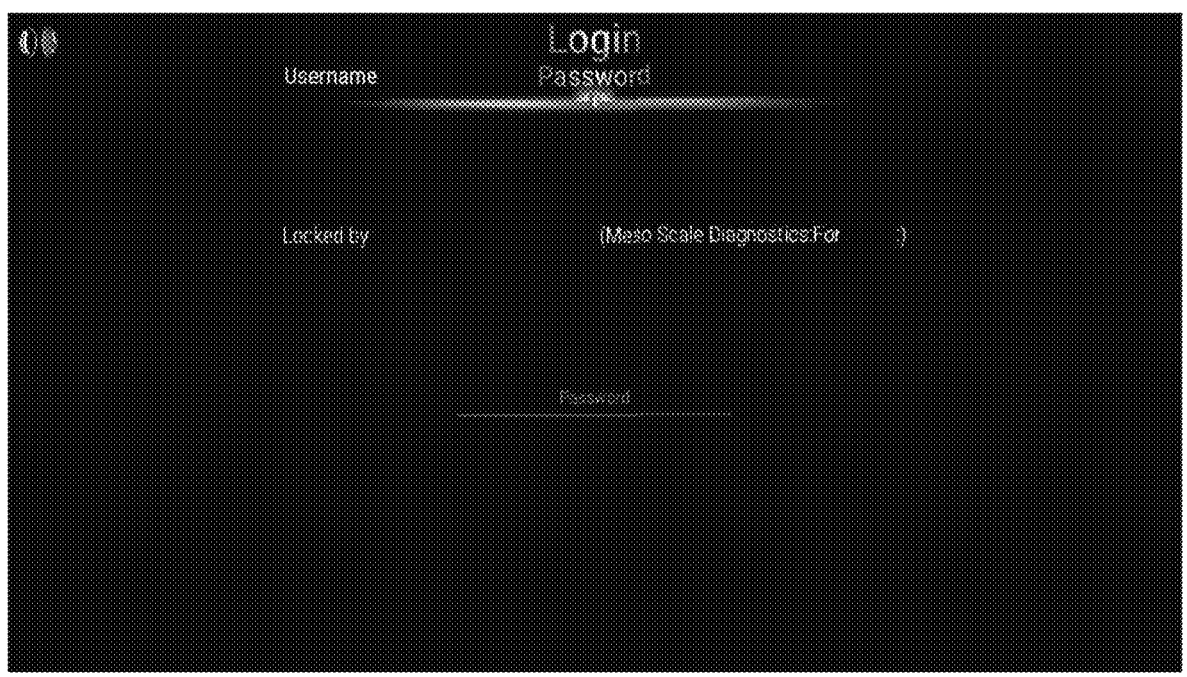

FIG. 58GG
FIG. 58HH
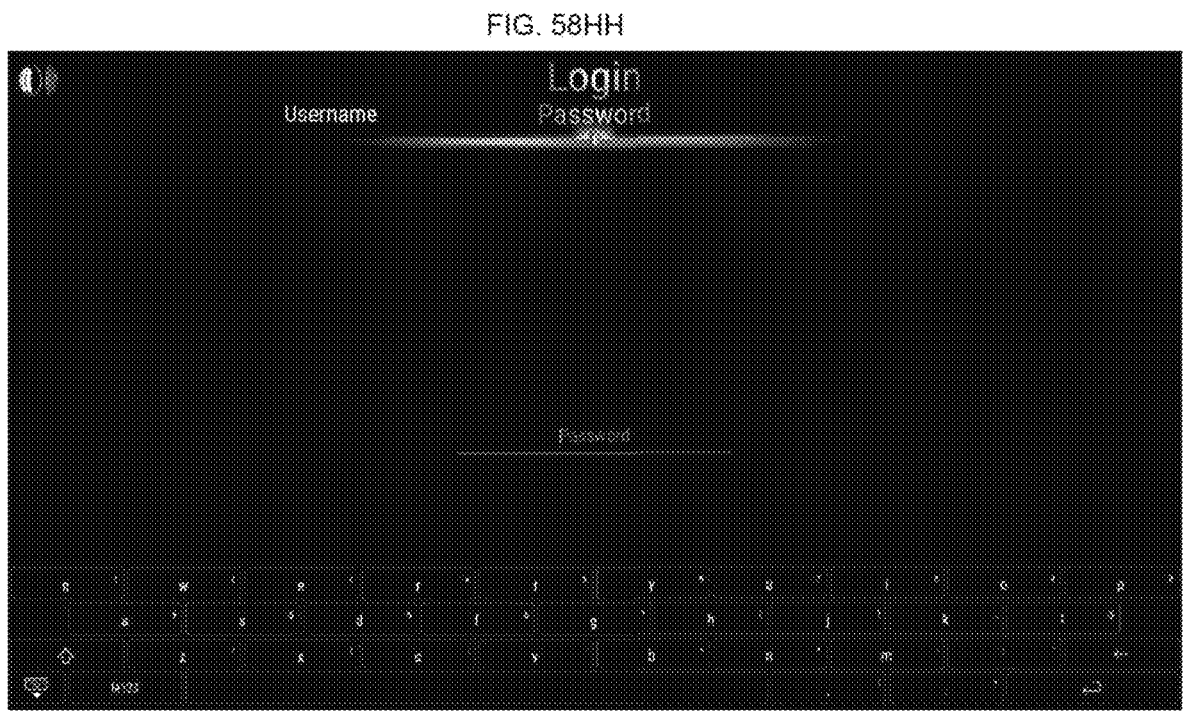

FIG. 59E
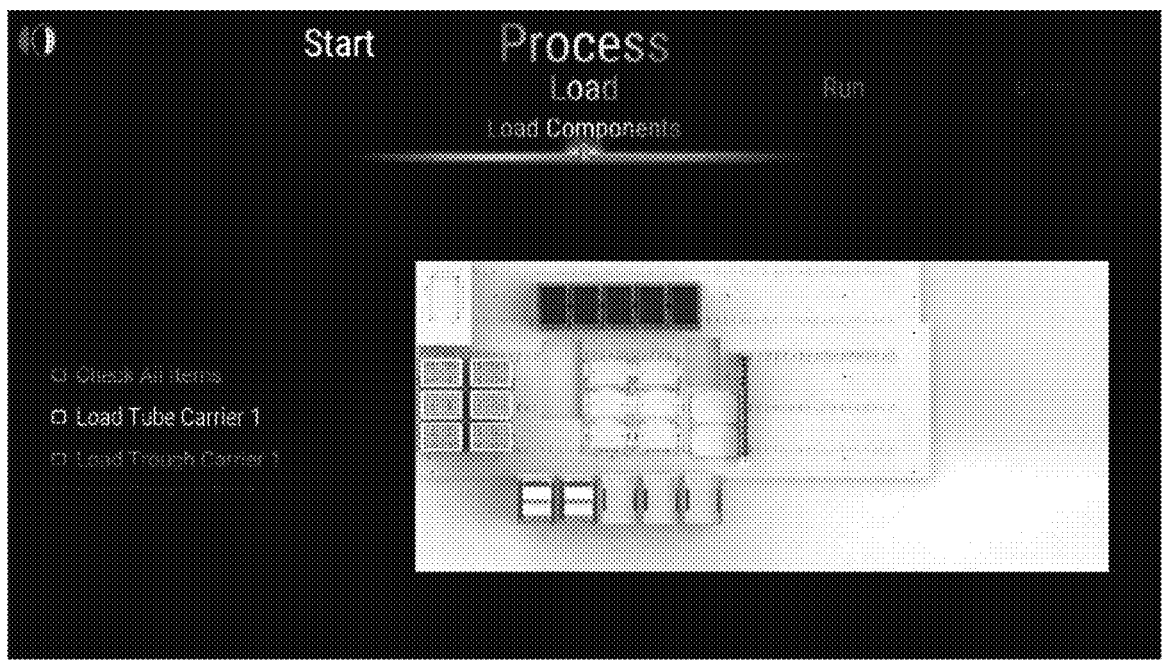
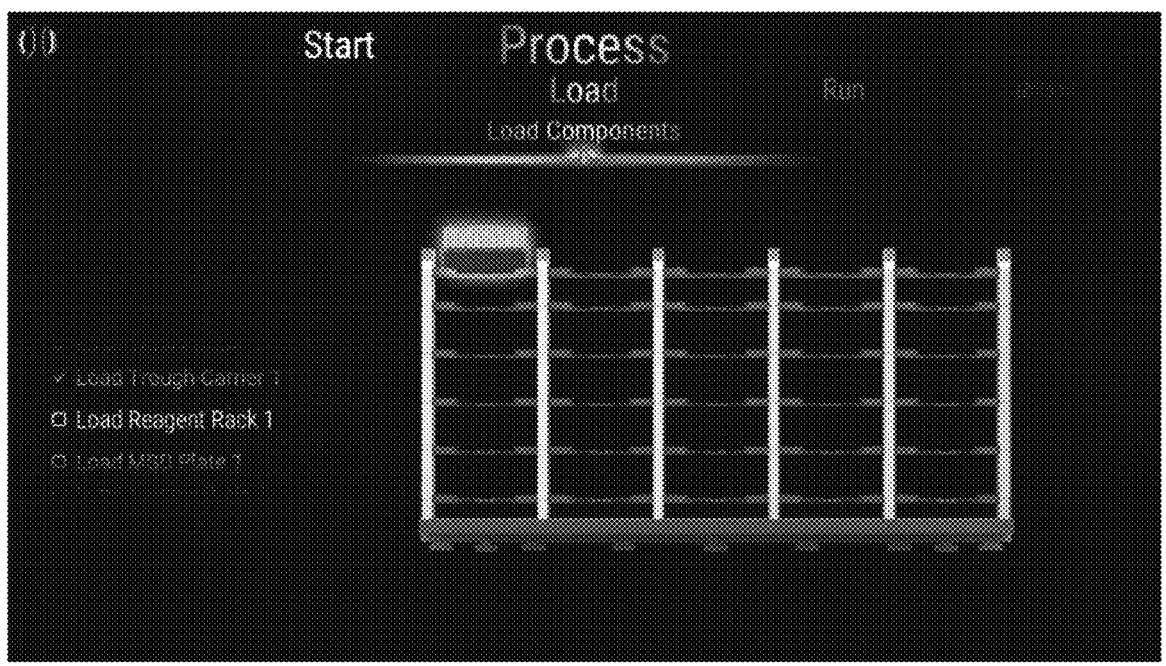
FIG. 59F

FIG. 59G
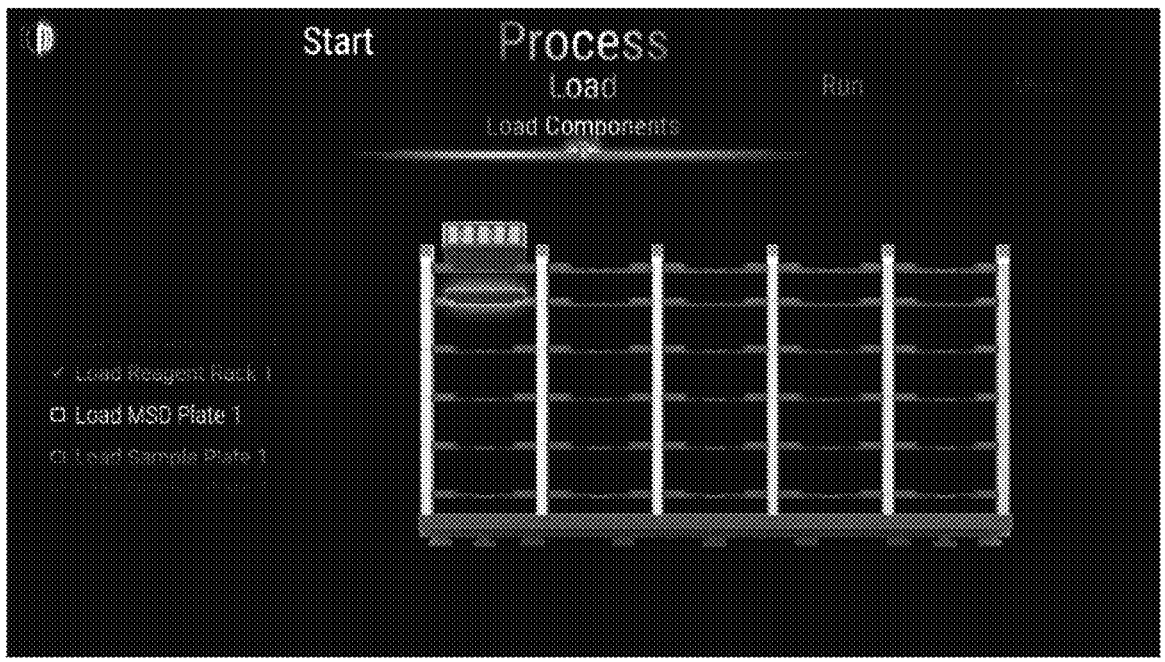
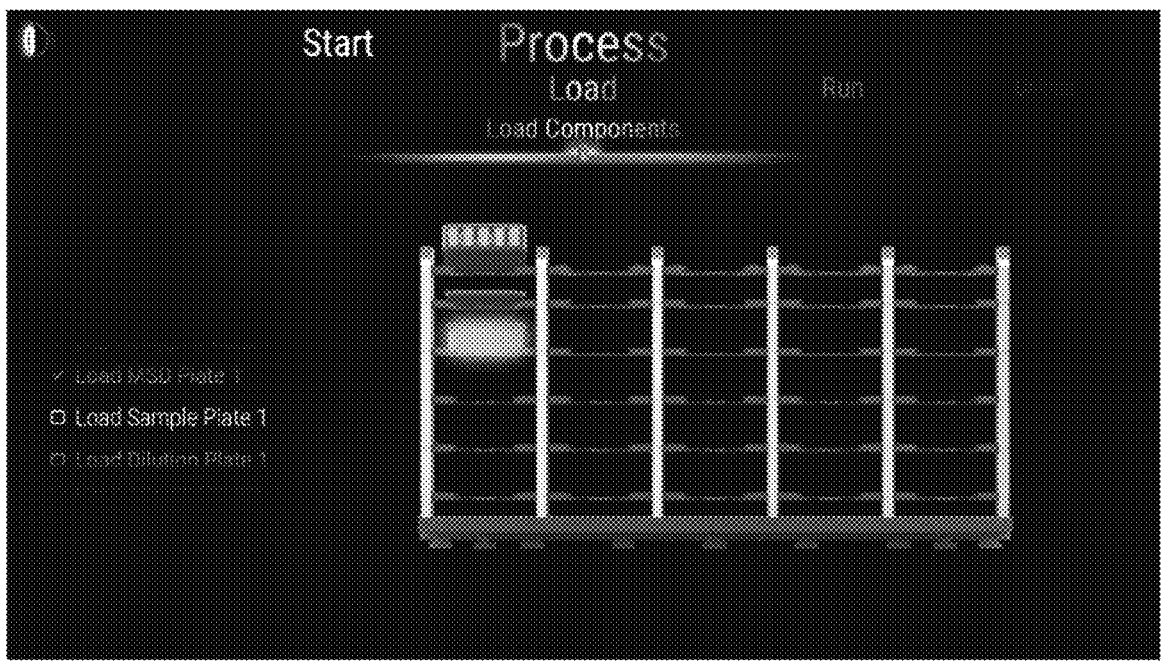
FIG. 59H

FIG. 59K
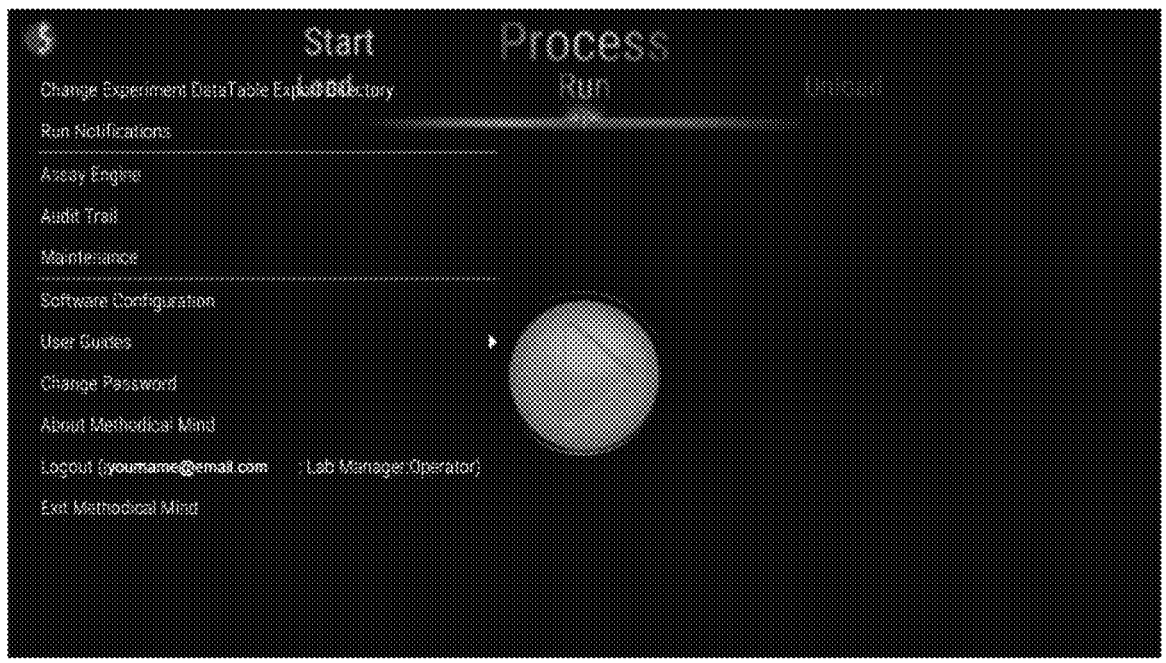
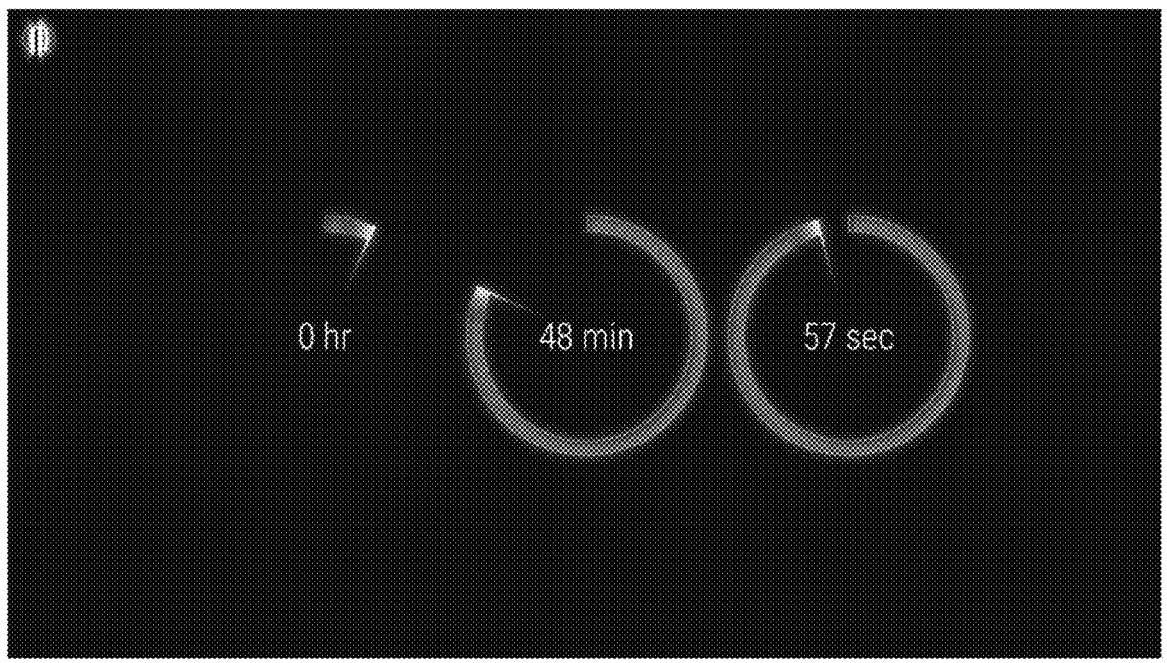
FIG. 59L

FIG. 59M
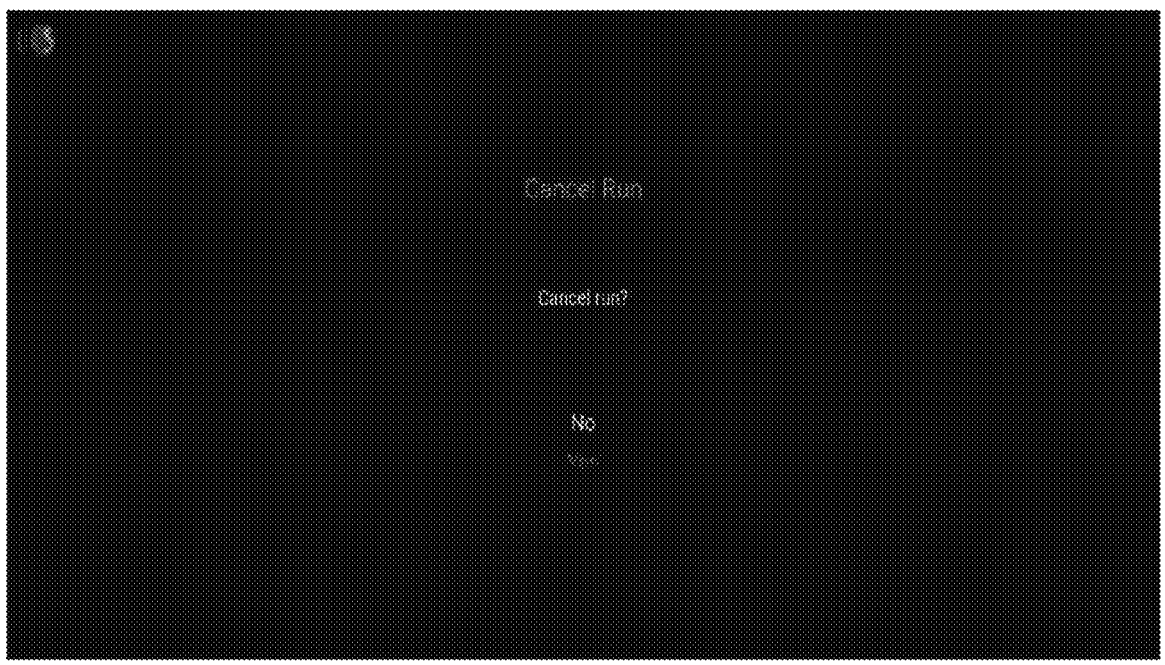
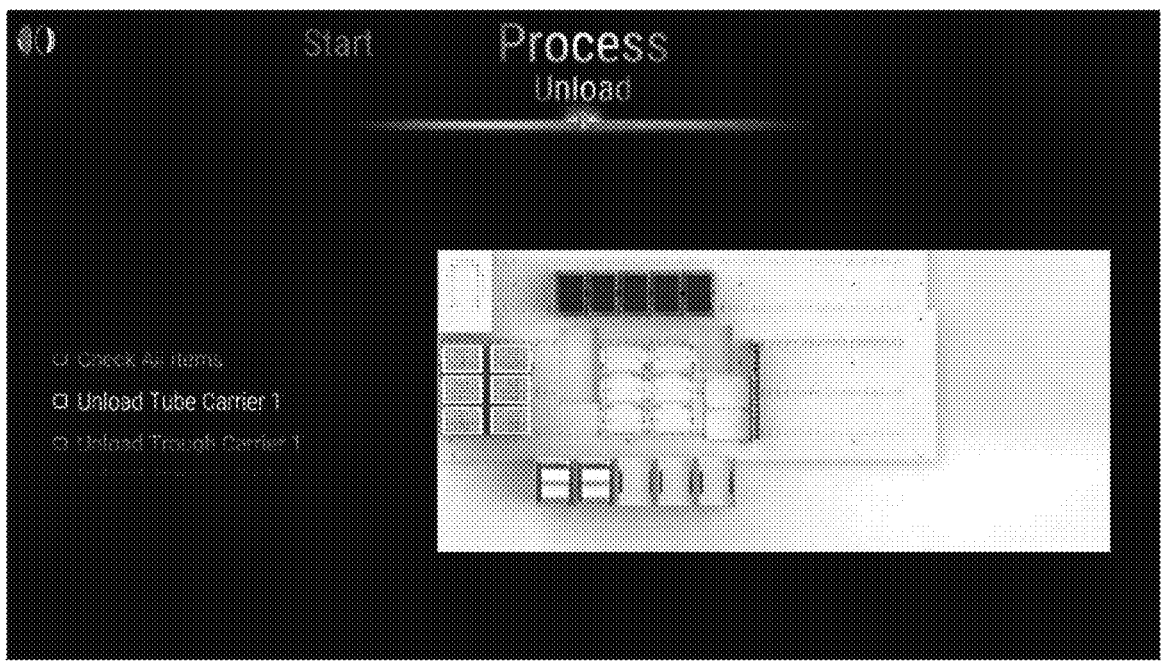
FIG. 59N

FIG. 59O
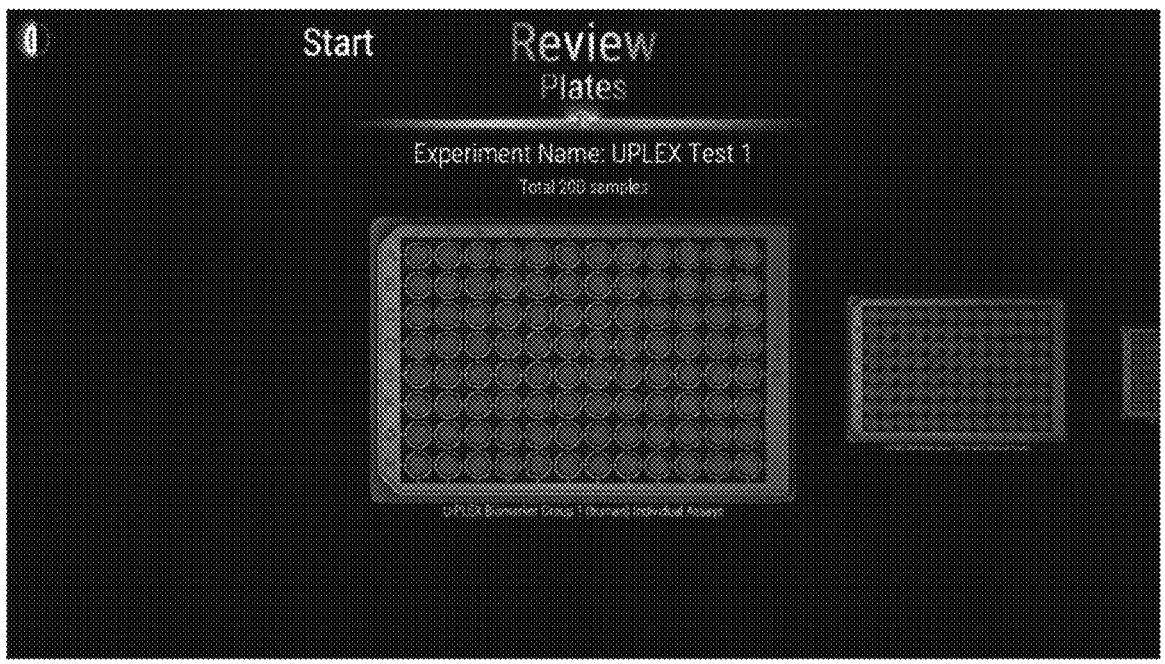
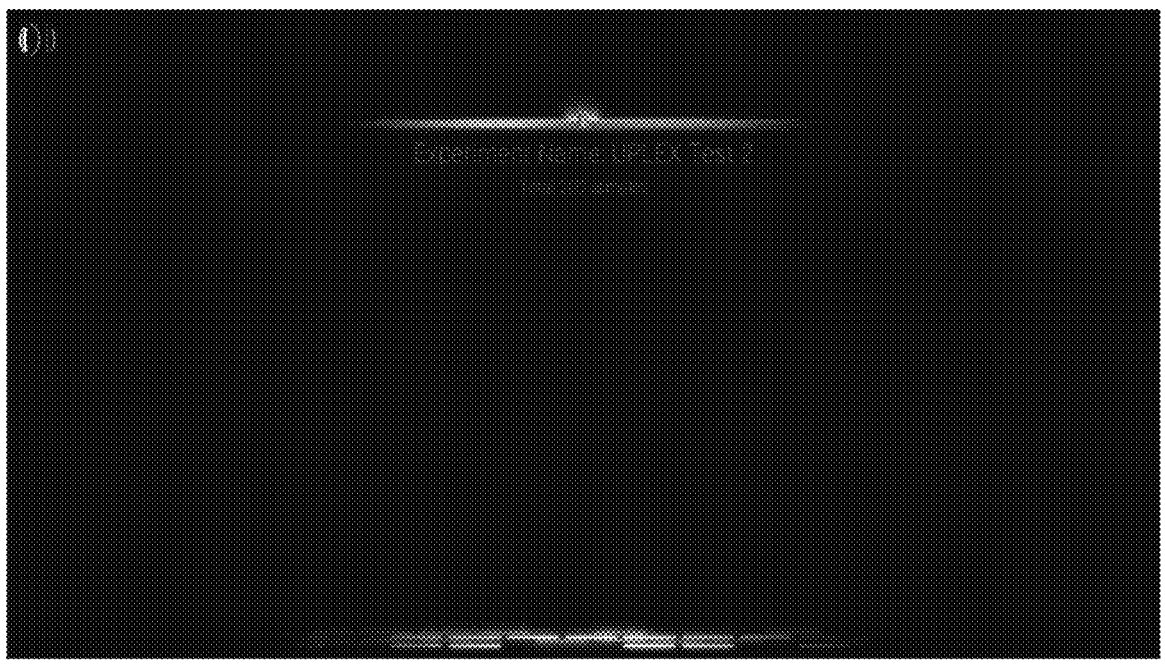
FIG. 59P

FIG. 60E
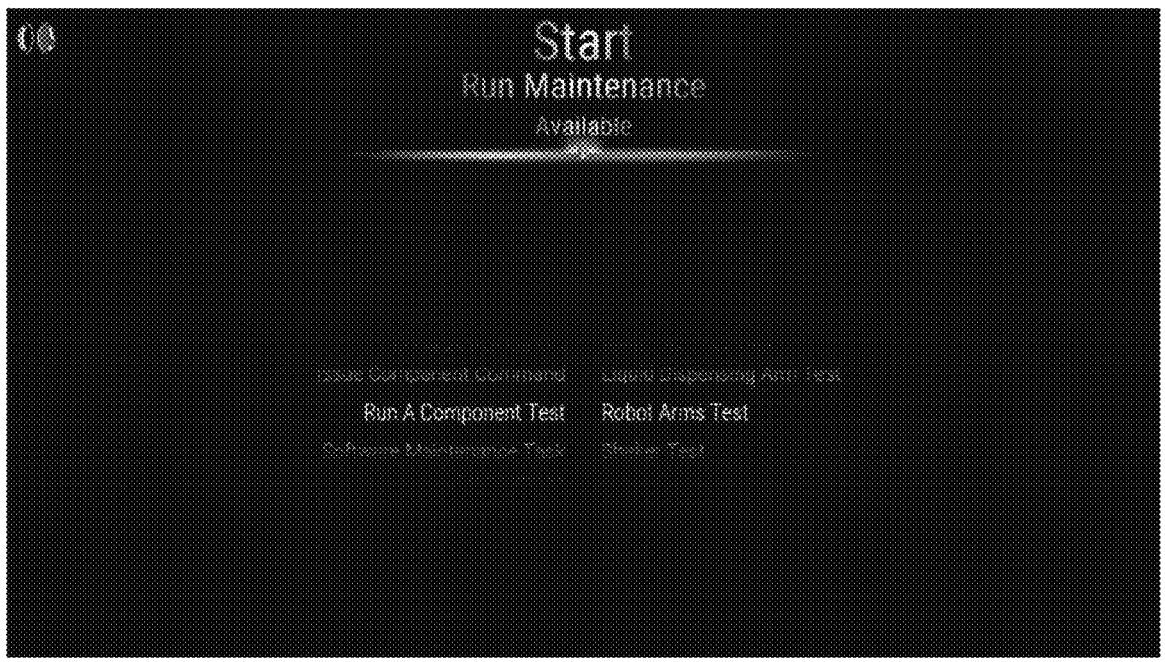
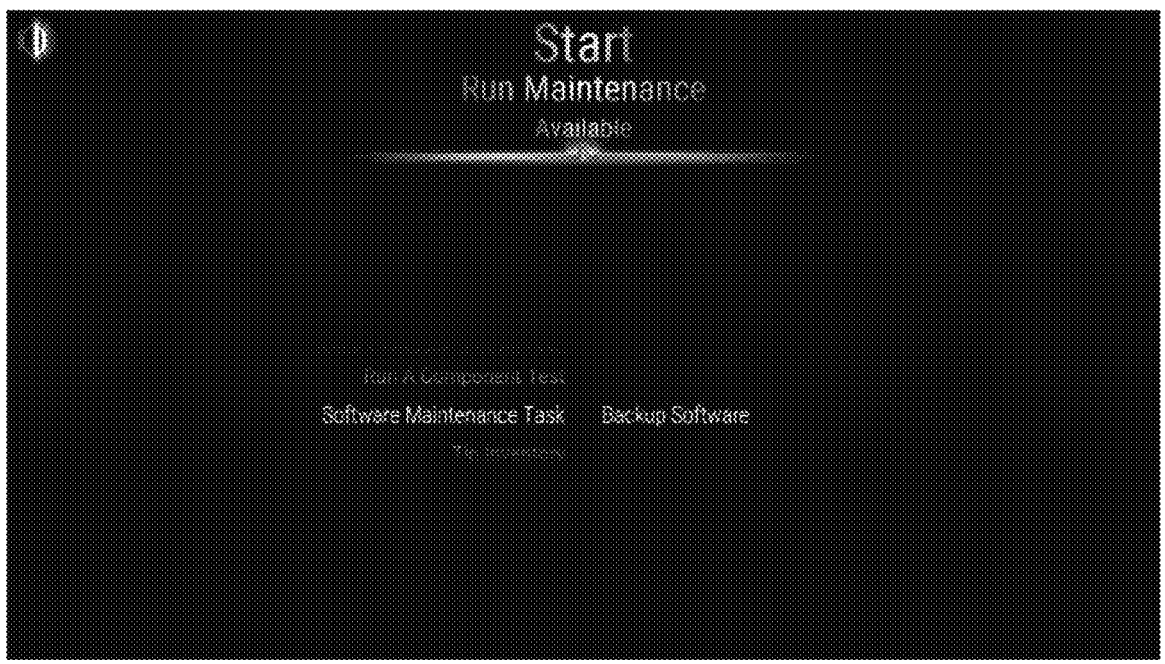
FIG. 60F

FIG. 60G
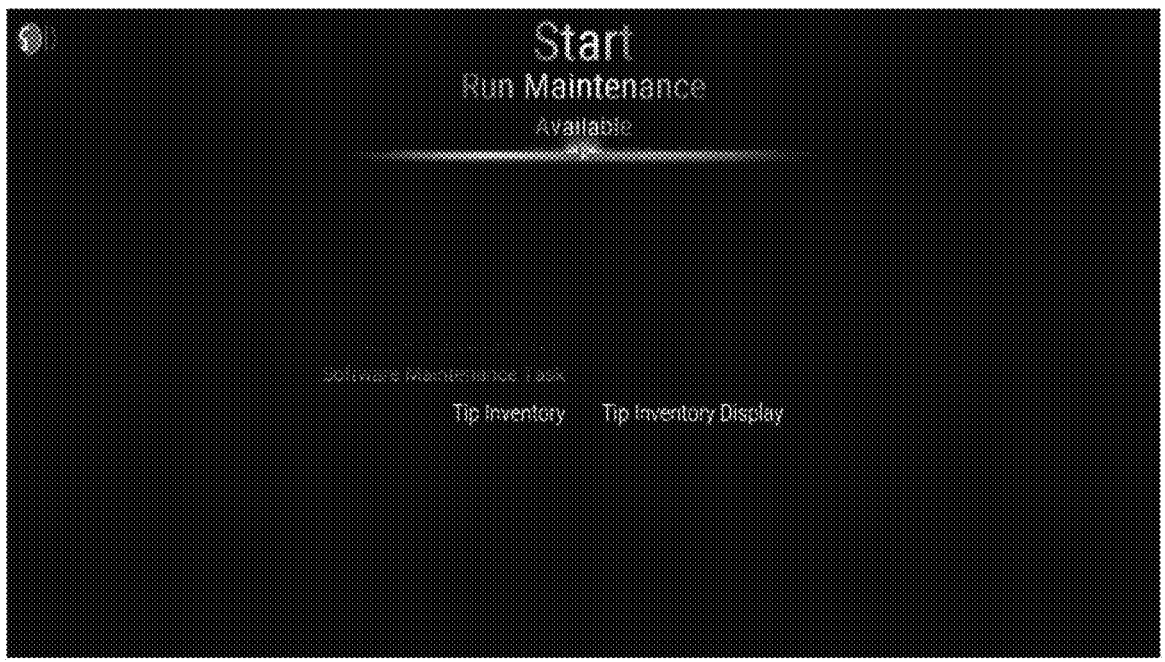
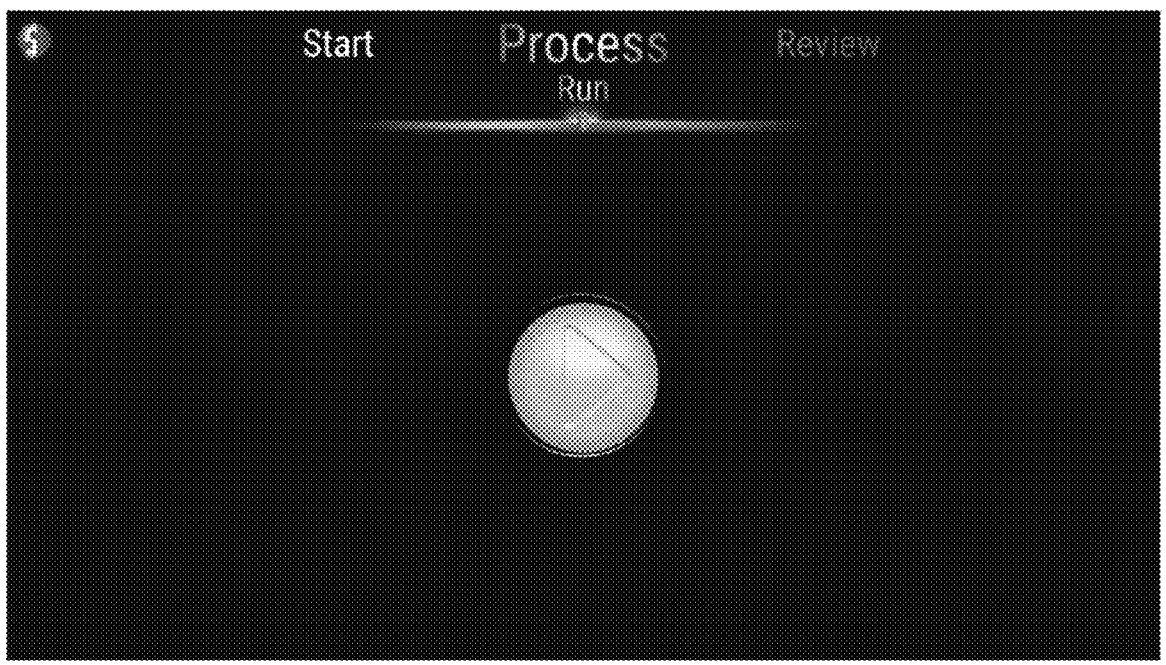
FIG. 60H

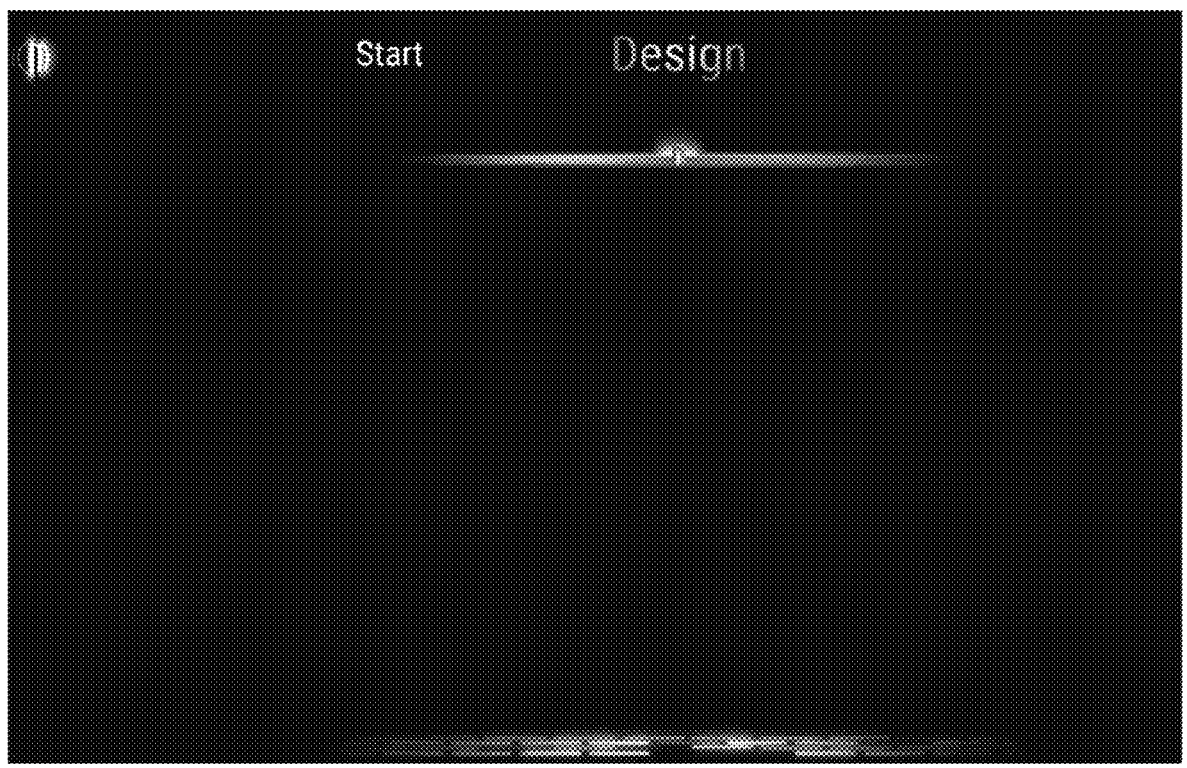
FIG. 62A
FIG. 62B
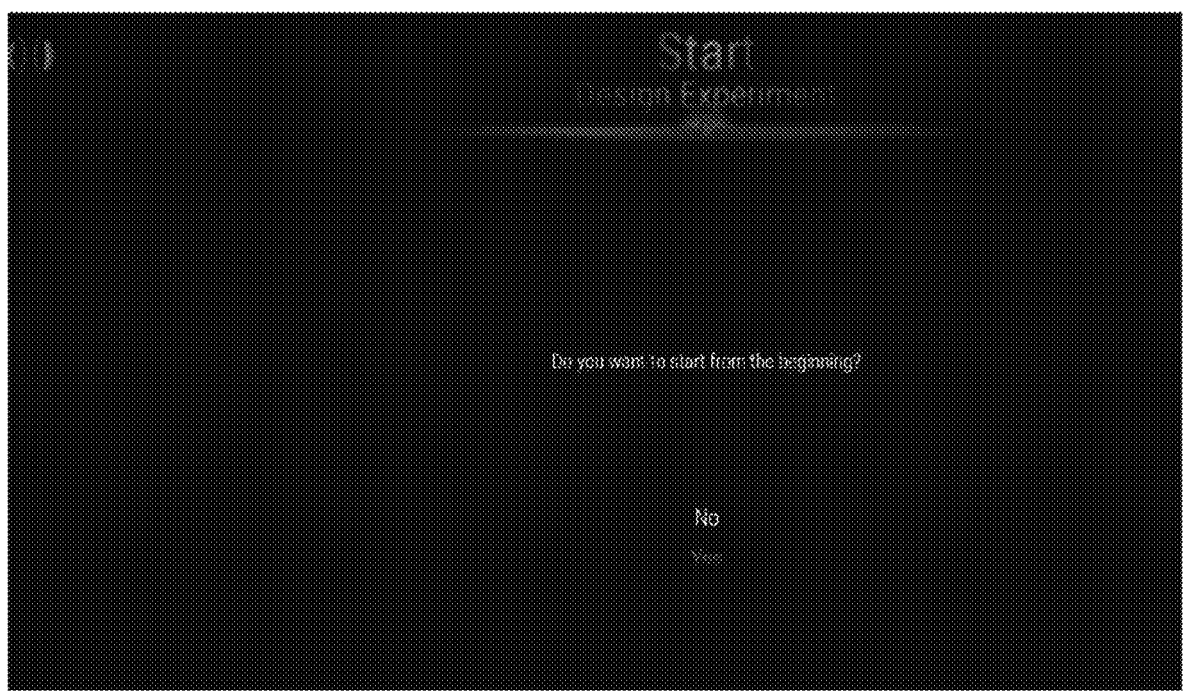

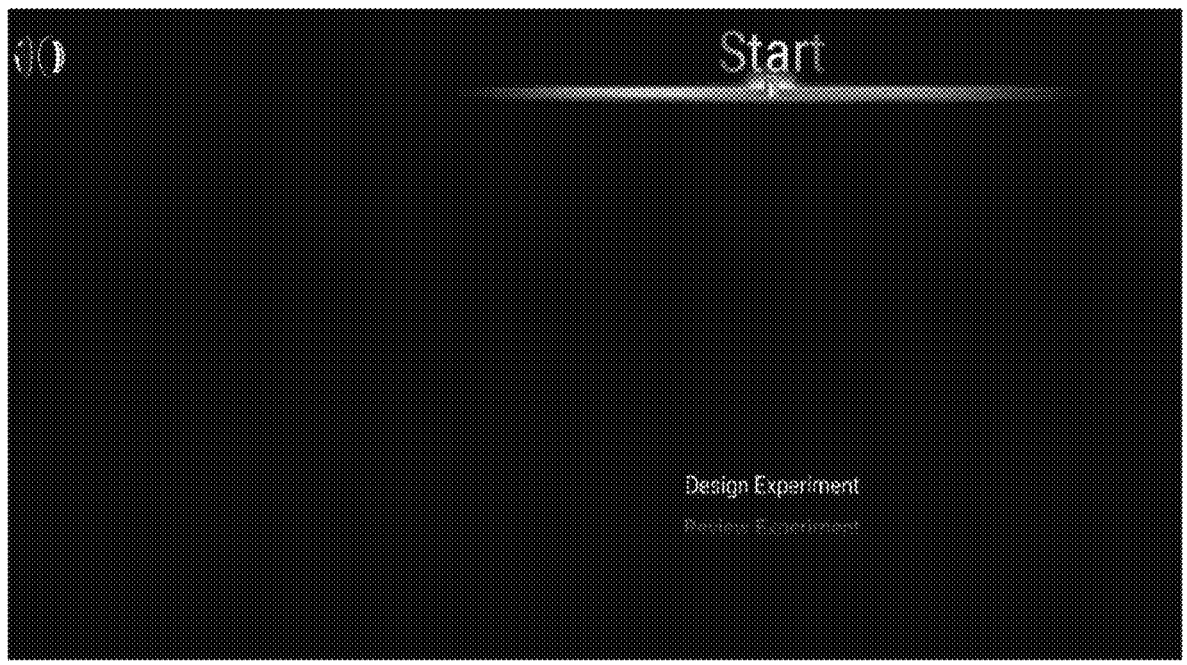
FIG. 62C
FIG. 62D
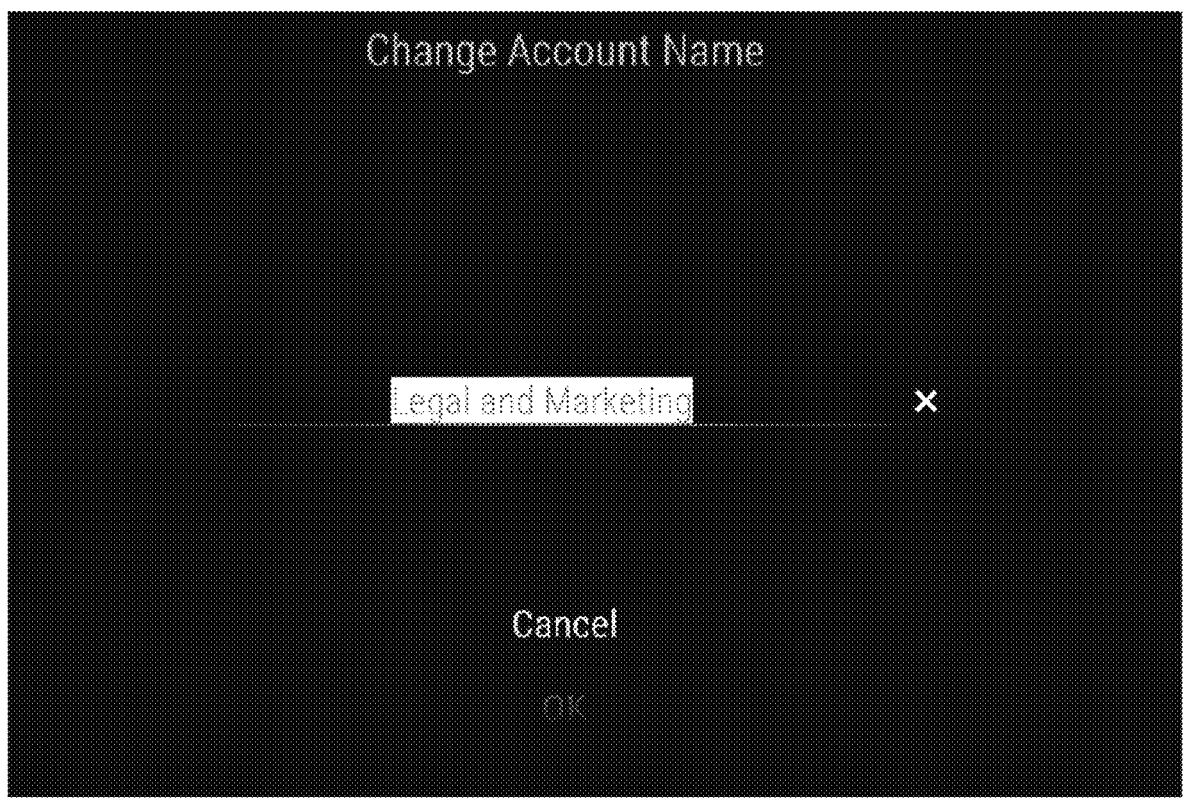

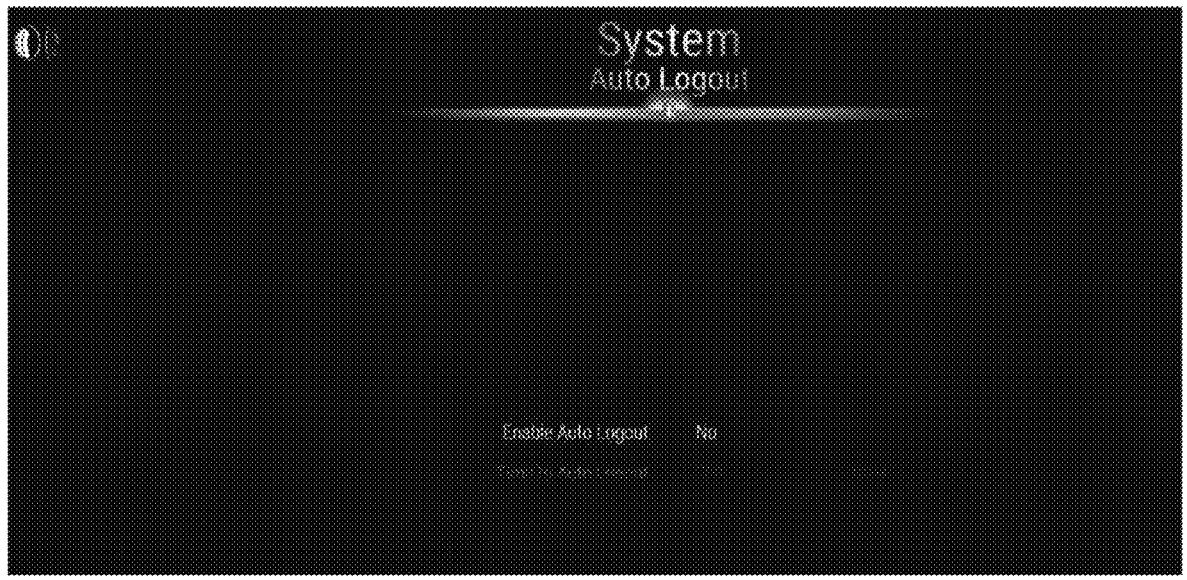
FIG. 62K
FIG. 62L
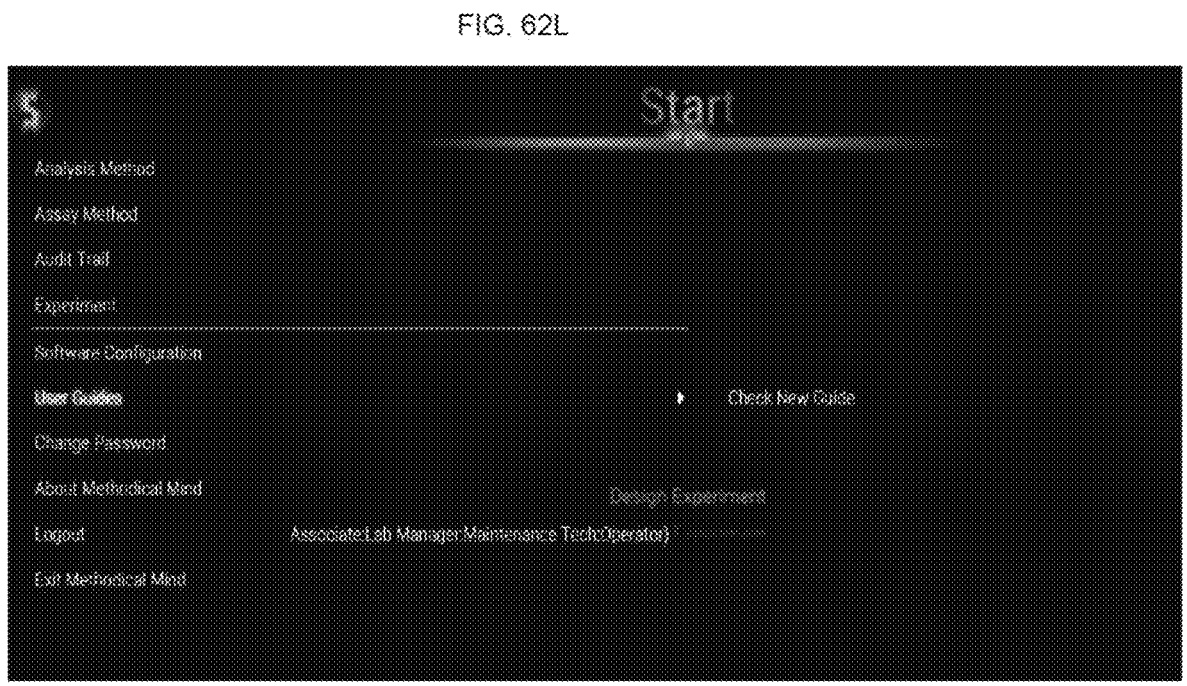

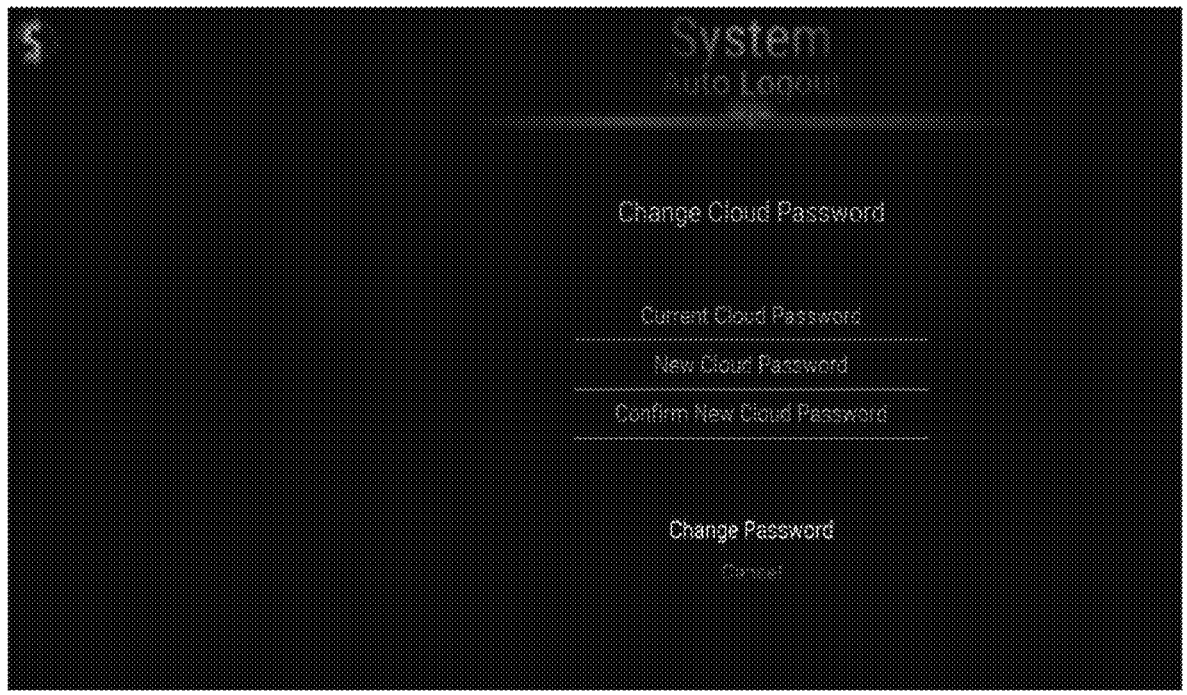
FIG. 62M
FIG. 62N
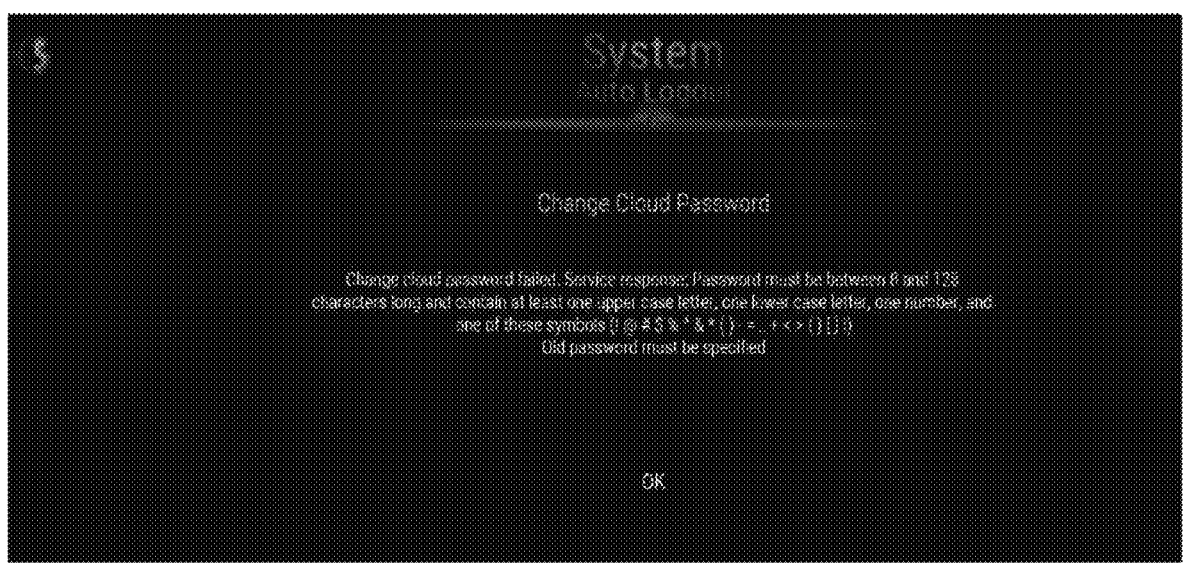

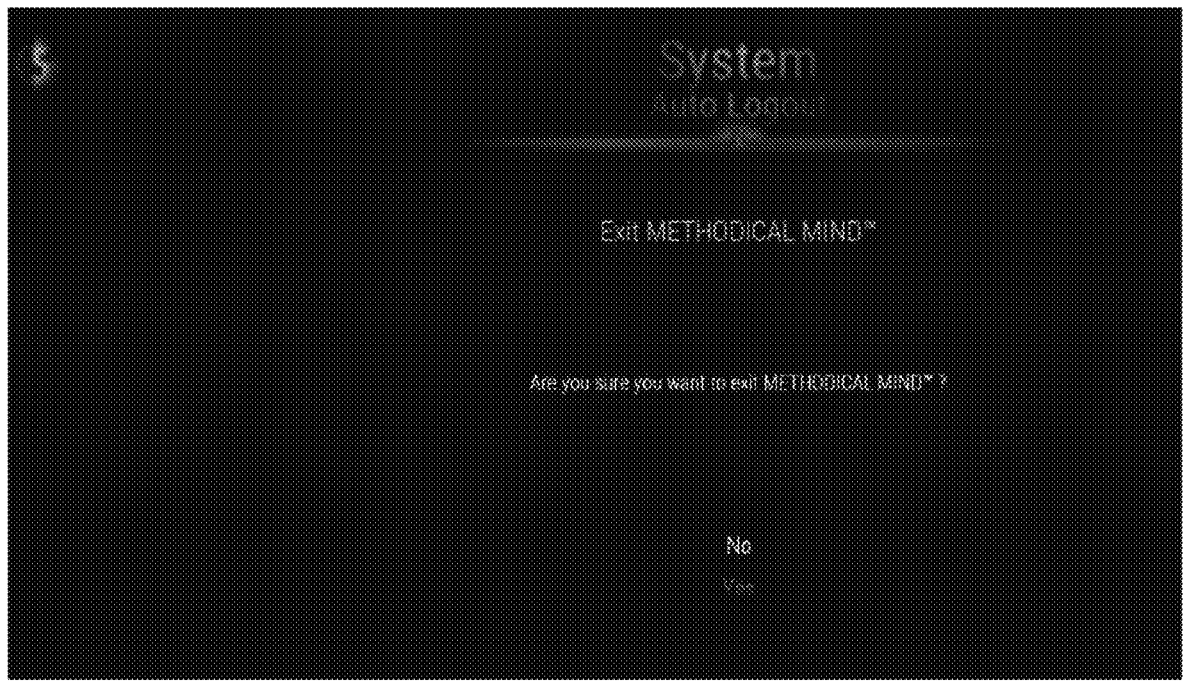
FIG. 62O
FIG. 62P

FIG. 63

GRAPHICAL USER INTERFACE SYSTEM

CROSS-REFERENCE TO RELATED APPLICATIONS

This application is a continuation of U.S. application Ser. No. 17/186,659, filed on Feb. 26, 2021, which is a continuation of U.S. application Ser. No. 16/513,526, filed on Jul. 16, 2019, now U.S. Pat. No. 10,936,163, which claims the benefit of prior U.S. Application No. 62/669,381, filed on Jul. 17, 2018, the entire contents of each of which are incorporated by reference herein.

TECHNICAL FIELD

The present application relates generally to computers and computer applications, and more particularly to a graphical user interface and a display method for displaying user interactive items on the graphical user interface.

BACKGROUND

In various applications including without limitation bioanalytical, chemical analytical, radiological analytical, other sciences (e.g., the biosciences and bioanalytical work), and industrial processes, leading into the use of instrumentation for scientific testing (e.g. biological testing, bioinstrumentation) and equipment for industrial processing, the present disclosure improves testing, analysis, and processing with the aid of integration between consistent software interfaces at various process locations and instrumentation and equipment associated with the processes.

Often, computer systems and/or applications utilize a series of menus or the like that are presented to a user for receiving input in order to perform their functions. Upon a user selecting an option or making a choice from a list of menu items, a computer system and/or application may perform its function based on the selected option, and/or present another list of menu items (for example, a list of sub menu items that depend on the selected option). The computer system and/or application continues with this process of performing its menu-driven functions, for instance, until the function is completed. In such a menu-driven system, it is often the case that an option that is previously selected, on which the current functioning of the computer system and/or application depends is not visible on the user interface. Thus, for example, the path of menu items taken is not visible at a current point in the computer system and/or application process. Moreover, not only the taken path, but also the options in the path that were not selected also may not be visible on the user interface. Thus, an improved user interface may be desirable.

Often instrumentation, for example and without limitation, bioinstrumentation, used with analytical applications is used in laboratories whereby the data generated by the instrumentation is stored as data files on a shared network drive for post-processing and import into other electronic systems—namely, a Laboratory Information Management System (LIMS). Typically, these integrations require extensive and time-consuming software development and integration to provide the generated data to end users. Typically, these data integrations are in regulated environments requiring the generated data to be stored in such a way as to ensure the generated data may not be altered by end users. Also, these integrations are provided to end-users to support post-processing of the generated data for supplemental analysis, reporting, and sharing with other end-users, often referred to as collaborators. Additionally, the use of instrumentation and the post-processing of generated data is desired to be performed under a controlled, uniform, unified, and traceable process within a collection of end-users working closely together, aiding them in creating consistent and correct supplemental analysis and reports. The use of instrumentation to generate data for supplemental analysis and reports typically requires end users to use consumables (e.g., bioconsumables, including without limitation reagents and analytes) with lot-specific information in conjunction with their sample(s) under test to create reactions to be measured to produce the generated data with the lot-specific information used in the generation of supplemental analysis and reports. To obtain these consumables requires purchase of the consumables from provider(s) who must not only ship the physical consumables to the end user, but also provide lot-specific information for those shipped consumables so that the end user may use the consumables on the instrumentation and perform the desired post-processing. Beyond normal use of instrumentation and associated consumables, there is usually a significant support function to ensure the instrumentation and/or associated consumables are performing optimally for a customer at all times. The level of workflow integration required to optimally perform the collective and collaborative work associated with using instrumentation by end users is extremely high, as well as complicated, requiring a user interface that is simple and easy to use, guiding a user through all of the complexities of their analytical workflow. Thus, an improved analytical computing system and user interface associated with and including instrumentation and associated consumables may be desired.

Additional fields beyond that of instrumentation face difficulties similar to those described above. For example, in various manufacturing settings, the integration of workflows, tracking of parts, tracking of consumables, tracking of work-in-process, documentation of processes and part production, and all of the issues described above with respect to instrumentation are difficulties. Other examples exist and the solutions disclosed herein are not limited to the problems discussed above.

BRIEF SUMMARY

A method and system of interactively navigating a user through a path of menu choices on a user interface to lead the user through a computer application may be provided. Such method being performed automatically by at least one hardware processor. The method, in an embodiment, may include displaying a current menu of choices on a first portion of a user interface display.

The method may also include allowing a user to select a menu item from the current menu of choices displayed on the first portion of the user interface display and to drill down through levels of menu choices based on selecting a menu item from a prior level of menu choices. The method may further include displaying on a second portion of the user interface display, past selected and past unselected menu items of the drilled-down levels, wherein the past unselected menu items are displayed as selectable options. The method may also include allowing the user to jump to a different path of menu choices by allowing the user to select a past unselected menu item from a previously navigated menu level displayed on the second portion of the user interface display. In an embodiment, the first portion and the second portion are viewable concurrently on the user interface display.

In another embodiment, a method of interactively navigating a user through a path of menu choices on a user interface in leading the user through a computer application may include displaying a current menu of choices on a first portion of a user interface display. The method may also include allowing a user to select a menu item from the current menu of choices displayed on the first portion of the user interface display and to drill down through levels of menu choices based on selecting a menu item from a prior level of menu choices. The method may further include displaying on a second portion of the user interface display, past selected and past unselected menu items of the drilled-down levels, wherein the past unselected menu items are displayed as selectable options. In an embodiment, the first portion and the second portion are viewable concurrently on the user interface display. In an embodiment, the graphical user interface maximizes black space by making a background of the user interface display black to thereby save storage and improve speed of presentation.

Yet in another embodiment, a method of interactively navigating a user through a path of menu choices on a user interface in leading the user through a computer application may include displaying a current menu of choices on a first portion of a user interface display. The method may also include allowing a user to select a menu item from the current menu of choices displayed on the first portion of the user interface display and to drill down through levels of menu choices based on selecting a menu item from a prior level of menu choices.

The method may further include displaying on a second portion of the user interface display, past selected and past unselected menu items of the drilled-down levels, wherein the past unselected menu items are displayed as selectable options. In an embodiment, the first portion and the second portion are viewable concurrently on the user interface display. In an embodiment, at least the first portion includes a search function box, a sub-first area and a sub-second area, wherein the first portion is scrollable as a whole and shows the current menu of choices. In an embodiment, responsive to the detecting of an entry of a search term in the search function box, the first portion is bifurcated into the sub-first area and sub-second area that are scrollable individually.

In yet another embodiment, a method of interactively navigating a user through a path of menu choices on a user interface in leading the user through a computer application may include displaying a current menu of choices on a first portion of a user interface display. The method may also include allowing a user to select a menu item from the current menu of choices displayed on the first portion of the user interface display and to drill down through levels of menu choices based on selecting a menu item from a prior level of menu choices. The method may also include displaying on a second portion of the user interface display, past selected and past unselected menu items of the drilled-down levels, wherein the past unselected menu items are displayed as selectable options.

In an embodiment, the first portion and the second portion are viewable concurrently on the user interface display. In an embodiment, the current menu of choices is displayed as a graphical rotating wheel that rotates the choices. In an embodiment, the graphical rotating wheel is rotatable from a first menu item in the current menu of choices to a last menu item in the current menu of choices, and the graphical rotating wheel is further rotatable from the last menu item to the first menu item, and the first menu item and the last menu item do not connect in the graphical rotating wheel's rotation.

Still in another embodiment, a user interface system may be provided, which may include at least one hardware processor and a memory device operatively coupled to the hardware processor. The hardware processor may be operable to retrieve from the memory device a current menu of choices and to display the current menu of choices on a first portion of a user interface display. The hardware processor may be further operable to allow a user to select a menu item from the current menu of choices displayed on the first portion of the user interface display and to drill down through levels of menu choices based on selecting a menu item from a prior level of menu choices. The hardware processor may be further operable to display on a second portion of the user interface display, past selected and past unselected menu items of the drilled-down levels, wherein the past unselected menu items are displayed as selectable options. The hardware processor may be further operable to allow the user to jump to a different path of menu choices by allowing the user to select a past unselected menu item from a previously navigated menu level displayed on the second portion of the user interface display. In an embodiment, the first portion and the second portion are viewable concurrently on the user interface display.

In another embodiment, a method executed by at least one processor for navigating a path of hierarchical menu levels adapted for output to a graphical user interface (GUI) is provided. The method includes providing, by at least one processor, a first command for a first menu of user-selectable choices to be displayed on a first portion of a user interface (UI) display; and providing, by the at least one processor, a second command for a second menu of user-selectable choices to be displayed on the first portion of the UI display in response to a user's selection. The second menu is adapted to be displayed on a second portion of the UI display and includes one or more of a past-selected menu item and a past-unselected menu item of the hierarchical menu levels and is adapted to be concurrently viewed with the first portion.

In another embodiment, a non-transitory computer readable medium having computer instructions stored thereon that, when executed by a processor, cause the processor to carry out a method for navigating a path of hierarchical menu levels adapted for output to a graphical user interface (GUI) is provided. The method includes providing a first command for a first menu of user-selectable choices to be displayed on a first portion of a user interface (UI) display; and providing a second command for a second menu of user-selectable choices to be displayed on the first portion of the UI display in response to a user's selection. The second menu is adapted to be displayed on a second portion of the UI display and includes one or more of a past-selected menu item and a past-unselected menu item of the hierarchical menu levels and is adapted to be concurrently viewed with the first portion.

In another embodiment, a system for navigating a path of hierarchical menu levels adapted for output to a graphical user interface (GUI) is provided. The system includes at least one processor; a user input device; and a computer readable storage medium configured to store a computer application, wherein the at least one processor is configured to execute instructions of the computer application. The at least one processor may execute the instructions for: providing a first command for a first menu of user-selectable choices to be displayed on a first portion of a user interface (UI) display; and providing a second command for a second menu of user-selectable choices to be displayed on the first portion of the UI display in response to a user's selection.

The second menu is adapted to be displayed on a second portion of the UI display and includes one or more of a past-selected menu item and a past-unselected menu item of the hierarchical menu levels and is adapted to be concurrently viewed with the first portion.

A computer readable storage medium storing a program of instructions executable by a machine to perform one or more methods described herein also may be provided.

Further features as well as the structure and operation of various embodiments are described in detail below with reference to the accompanying drawings.

BRIEF DESCRIPTION OF THE DRAWINGS

FIGS. 39B-39E illustrate aspects of an admin audit trail module user interface consistent with embodiments hereof.

FIG. 41 illustrates the flow for an analysis method module in an analytical user app in an embodiment.

FIG. 42A illustrates the design flow for an assay method module in an analytical user app in an embodiment.

FIGS. 43C-43H illustrate aspects of a reader module user interface consistent with embodiments hereof.

FIGS. 58A-58HH are example non-limiting embodiments of a reader module.

FIGS. 60A-60I are example non-limiting embodiments of a maintenance module.

FIG. 63 is an example non-limiting embodiment of an audit trail module.

DETAILED DESCRIPTION

Figure 1:
FIG. 1 is a method of displaying interactive items on a user interface display for computer-user interaction in one embodiment.

Embodiments described herein provide technical solutions to various technical problems via improvements to existing technologies and the creation of wholly new technologies. Among the technical problems addressed by embodiments discussed herein include inefficiencies of conventional user interfaces and difficulties in integrating disparate portions of a process workflow.

Improvements to user interfaces discussed herein provide practical applications of technical solutions to problems in conventional user interfaces related to user inefficiency, accuracy, repeatability, and computing inefficiency. The technical solutions provided herein improve each of these aspects through the use of inventive user interface methods and techniques. In particular, technical solutions provided by user interfaces disclosed herein provide users with more efficient means of navigating through menu systems for complex processes.

User interfaces for electronic devices, implemented for human-computer interactions or communications, often include a series of menus or like choice options, which a user selects (e.g., choose a series of options in a hierarchical manner) in order to have a computer or like device perform a desired function. In some embodiments, depending on types of applications, the amount of information or the number of menu choices presented to the user can become overwhelming. A wide range of available menu options can cause the user to try different choices or navigate to various menu selection hierarchies, before finding a correct or desired series of choices. In some instance, out of 100% of user interface choice and functionality options available to the user, only about 10% are used. However, presented with all of the 100% of the options, the user may have difficulty in deciding where to navigate to in order to find that 10% which is relevant to the user. Also, because a selected menu choice affects the next choice to be made down a path of menu choices, a user switching between choices will mean that the user also navigates to a number of different paths leading from that choice. Such trial and error, in scrolling and paging through many different options, which may occur during user interface navigation, is time consuming, costly and inefficient.

Systems, methods and techniques in the present disclosure may provide a user interface that guides a user through choice options to be selected via a user interface display or another presentation device, with less time to find a correct selection. In this way, fewer attempts are made at incorrect selections, and shorter amounts of time in user navigation is taken to complete a desired computing function or goal. In aspects, a user interface in the present disclosure may present the user with a selective limited number of options out of all available options in a specific manner, and guide the user through those options, streamlining operations and providing the user to be able to focus on reaching a desired computing functionality more efficiently. In another aspect, a user interface in the present disclosure can more directly connect the user to an application.

The embodiments and technical solutions provide practical applications of specific visual principles to aid users in navigating the menus and systems described herein. Such visual principles include the minimization of visible content and maximization of background or void space so as to reduce visual clutter and emphasize the area of interest. By providing a dark or otherwise uniform background and increasing contrast between the content and background, the user's attention can be drawn to the appropriate areas.

The embodiments and technical solutions provide practical applications of specific design principles to aid users in navigating the menus and systems described herein. Design principles embodied herein include, for example, minimizing a number of menus and/or selections a user must navigate at any one time.

Further design principles include presenting a user with a single new choice at any given time while providing optionality for revisiting previously made choices with ease. This principle may be implemented via a two portion display system. An active portion may be configured to display a current user choice, while an historical portion is configured to display information related to previous choices. Together, the active portion and the historical portion may provide a "direct workflow mode." The active portion presenting the current user choice may have a hard limit on the number of menu items displayed, e.g., seven, five, three (or any other number), while other potential items from the same menu are displayed elsewhere. Previously selected choices (and menus from which those selections were made) may be displayed to a user in a nested fashion or a stacked fashion. A nested fashion series of previously navigated menus may be presented in the manner of Russian nesting dolls (matryoshka), with each previously selected menu item being expanded upon in a displayed submenu. The nested or stacked previously selected menu items may also provide a breadcrumb trail illustrating to a user the pathway taken to arrive at the current menu.

Embodiments herein maintain a consistent look throughout the use of an interface, regardless of a task or process to be completed, for example by maintaining consistent screen locations for menus so a user does not have to search different locations for menu. In other words, relevant menus are moved to active portions of the screen to bring them to the user's attention as they are needed. In embodiments, the active portion of the screen remains centered top to bottom and left to right. In further embodiments, the size and shape of the menuing interface is altered according to a device or screen on which it is viewed. Menus may be spread horizontally on wider screens and/or spread vertically on taller/narrower screens.

Embodiments discussed herein improve user productivity by providing efficiency and accuracy improvements through enhancement of several aspects of the user experience. User interfaces described herein focus the user on the most-likely use cases while minimizing distractions caused by lesser utilized options. Such a focus permits the user interface to minimize visual distractions and keep the user focused on the most relevant menu choices. User interfaces described herein seek to lead the user through the user interface from one step to the next while eliminating sticking points where a user may wonder what to do next. In embodiments herein, the navigational path of the user through the interface system remains transparent to the user to facilitate selecting alternative options or backing out of a current menu. Throughout the process of using the user interface, a user may have the option of viewing, in a non-distracting way, alternative pathways through the process. Accordingly, a core function of the user interface software as provided herein is to reduce the total amount of information presented to the user at any one time while increasing the total amount of relevant information presented to the user at any one time. Additional information and options, for low use cases, remain available in a non-distracting presentation style. Such decisions, regarding what information to present through the user interface at any given time may be guided in advance through predetermined menu workflows and/or may be influenced and updated through analysis of prior user actions and choices.

Computer functionality may also be improved via embodiments provided herein. For instance, by focusing on a limited number of options, resource usage of devices (e.g., user devices and/or server devices) which may be involved in running the user interface can be reduced. For instance, memory usage, processor resources usage such as a central processing unit (CPU) usage, hard drive or like persistent storage usage, bandwidth needed for communications between devices (e.g., device to device, device to server, server to server), may be reduced. An ability to directly navigate to or reach correct selections or a path of selections, for example, without many trial and error navigations, can also increase communications efficiency between devices and servers, for instance, decrease internet communications and cost associated with such communications.

Further embodiments discussed herein relate to the integration of various process workflow aspects. As discussed herein, "process workflow" may relate to instrumentation (including bioinstrumentation) testing workflows, manufacturing workflows, analysis workflows, and/or any workflow that may involve one or more pieces of equipment controlled, at least partially, by one or more computing systems. In additional embodiments, process workflows consistent with embodiments discussed herein may include the use of one or more consumables.

Computing systems consistent with the user interfaces and process workflow management systems discussed herein may include various architectures, including but not limited to single computing device systems, desktop computing systems, laptop computing systems, tablet computing systems, mobile device computing systems, thin client computing systems, cloud based computing systems, server computing systems, multiple device computing systems, device/printer systems, device/server computing systems, systems including multiple devices and server(s), or any other suitable computing system.

The process interface systems described herein serve to increase user accuracy, efficiency, and satisfaction by providing a user interface that is faster to use, reduces time to find correct menu items, reduces selection of incorrect menu items, decreases overall workflow time. As compared to traditional systems that may provide immediate access to 100% of options, of which only 10% are frequently used, systems described herein may provide immediate access to only those functions that are frequently used (e.g., in 50, 55, 60, 65, 70, 75, 80, 85, 90, 95, 95+%, 70-95+%, 80-95+% of use cases.) In turn, the solutions provided herein serve to increase computing efficiency, decrease memory usage, decrease utilization of CPU, hard drive, power, and communications resources.

User interface systems discussed herein may be provided in the form of graphical user interfaces (GUIs), text-based user interface systems, virtual, augmented, or mixed reality (VAMR) interface systems, projection based systems, gesture controlled systems, and/or any other type of visual user interfaces. Collectively, user interface systems, consistent with embodiments hereof may be referred to as "methodical user interfaces" (MUIs). MUIs may include graphical user interfaces (GUIs), text-based user interface systems, virtual, augmented, or mixed reality (VAMR) interface systems, projection based systems, gesture controlled systems, and/or any other type of visual user interfaces. Although some of the principles discussed herein are discussed specifically with respect to, for example, a GUI, no limitation is intended, and the principles discussed herein may equally be applied to other interface systems.

MUIs described herein refer to "displays," "interfaces," and "user interfaces." As used herein, unless stated otherwise, the terms "display," "interface," and "user interface," refer to the text, images, visual components, interactive elements, and any other visual aspects that are shown or displayed on a screen, projection, or other visual display hardware. It is thus understood that "displays" and "interfaces," as used herein, may be provided via any type of visual display hardware, screen(s) and/or projector. For convenience, menus, interfaces, and other visual items are referred to herein as being viewed on a MUI or displayed by a MUI. It is understood that such references indicate that the MUI is visually presented via hardware devices as discussed herein.

As described in greater detail below, user interface systems described herein may use various visual components for presenting menu items. For example, visual components may include vertical "wheels" or horizontal wheels that rotate through various menu items. The use of a "wheel" as a visual component, as described herein, refers to the way in which prominent (emphasized) and receded (deemphasized) options are presented to the user. Wheel-type visual components can be understood as a virtual wheel with the rim facing the user and with multiple menu items disposed on the rim of the virtual wheel. Wheel-type visual components may or may not include any visual indicators of the presence of a wheel. Wheel-type visual components may present a prominent option to the user in a way that draws attention (i.e., on the portion of the wheel "closest" to the user) while other, receded options, are presented in a way that does not draw attention. Prominent menu items may be highlighted in a different color, presented in a different font, presented in a larger font, or otherwise visually marked to draw attention. As the virtual wheel is rotated, the currently prominent menu item rotates away from the user (either clockwise or counterclockwise) and a currently receded menu item becomes the new prominent option. In embodiments, the receded menu items closest to the prominent menu item may be displayed to draw more attention than receded menu items further from the prominent menu item. For example, menu items may decrease in size or brightness based on their distance from the currently prominent menu item. As the "wheel" is "rotated," receded menu items may fade from view. In this fashion, the virtual wheel provides the user with the sense and feel that the menu items are all disposed on an actual wheel. Visual components may further include horizontal or vertical sliders that slide through various menu items. Similarly, to wheels as discussed above, sliders may be used to provide a prominent menu item and receded, or less prominent menu items. In embodiments, sliders may differ from wheels in that receded menu items do not appear to fade from view as the options in the slider are slid through. Further embodiments of wheels and sliders are discussed further herein with respect to specific embodiments.

As discussed herein, menu items may variously be "selected," "highlighted," and/or "clicked." As used herein, "highlighting" a menu item means that the "highlighted" option is prominently displayed to the user, for example, as a prominent menu item in the center of a wheel. "Highlighting" may include changing the color, size, font, etc., of a menu item to visually emphasize the menu item to the user. "Dehighlighting" a user option may include changing the color, size, font, etc., of a menu item to visually deemphasize the menu item to the user. A menu item may be highlighted or dehighlighted in response to user action (e.g., via clicking a mouse, touching a touch screen, spinning a wheel, etc.) and/or may be highlighted or dehighlighted based on an action of the interface (e.g., by presenting a highlighted default option).

As used herein, "selecting" a menu item means that a menu item has been chosen by the user and that the user interface has proceeded with one or more menu steps in accordance with the selection. "Selecting" a menu item causes the computer system to execute computer instructions to advance the menu beyond simply "highlighting" the menu item. For example, "selecting" a menu item may cause a new menu to be displayed based on the selection. Selected menu items may be highlighted after selection but highlighting of a menu item does not necessarily include selecting the menu item.

In some embodiments, a menu item may be selected or highlighted via clicking on the menu item. As used herein, "clicking" refers to the user action of clicking, tapping, or otherwise using an interface device (e.g., mouse, touchscreen, etc.) to indicate or choose a menu item. "Clicking" a menu item, as used herein, differs from "selecting" a menu item. Clicking refers to the user action of indicating a menu item, while selecting refers to the computer functionality associated with the selection of the menu item.

In some embodiments of a system in accordance herewith, a menu item may be selected through clicking. Clicking on a menu item may cause the system to advance to the next series of menu items. In other aspects of the disclosed system, clicking a menu item serves to highlight the menu item, but does not select it to advance the system to the next menu item.

Menu items may be described herein as "selectable." A "selectable" menu item refers to a menu item that a user can interact with, either through selecting it or highlighting it. Selectable menu items may be displayed in a fashion that indicates that they are selectable, through changes in coloring, highlighting, fonts, etc. Menu items may be described herein as "unselectable." "Unselectable" menu items refer to menu items that a user cannot currently interact with through selection or highlighting. Unselectable menu items may be displayed in a fashion that indicates that they are unselectable, through changes in coloring, highlighting, fonts, etc.

Menu items may also be described as "past selected" and "past unselected." A "past selected" menu item refers to a menu item that was selected to arrive at the current menu interface display. It is not required that a "past selected" menu item have been actively selected by a user. If the system, by programmed default, brings a user to a menu level below a top level, a menu item or choice in the current pathway may be indicated as "past-selected," even if a user has not actively selected it during the current session. A "past unselected" menu item refers to a menu item that was not selected to arrive at the current menu interface display. For example, where a user has selected a first menu item and has not selected a second menu item, the system may proceed to display a subsequent menu or submenu responsive to the selection of the first menu item in an active portion of the MUI. In a historical portion of the MUI, the system may display the first menu item as a past selected menu item and the second menu item as a past unselected menu item. The past unselected menu item may be displayed as selectable.

For example, a user may scroll a slider or spin a wheel through various menu items. A user may settle the wheel or slider such that a specific menu item has been highlighted. In embodiments, the specific menu item may require further user interaction (e.g., a single or double click) to be "selected," which causes the MUI to present a new set of menu items or submenu items responsive to the selection. In such an embodiment, a user would spin a wheel or scroll a slider to move a desired menu item to be the highlighted prominent menu item. Then, the user would click, double click, or otherwise indicate approval of the highlighted menu item as a selection to cause the presentation of the next menu or submenu. In embodiments, the specific menu item may be "selected" at the same time that it is highlighted. In such an embodiment, spinning the wheel or scrolling the slider to move the desired menu item to the highlighted prominent menu position would cause the associated submenu to be presented as soon as the desired menu item is highlighted.

Selection or highlighting a menu item, as discussed herein, may be caused by directly choosing (i.e., clicking, touching, etc.) on the menu item, wherever it may be on a wheel, slider, and/or list of items, regardless of whether it is a prominent or receded menu item. Selection or highlighting a menu item may also occur responsive to user manipulation of various visual components to cause the menu item to move to a position where it is to be highlighted or selected. For example, a user may spin a wheel or move a slider until a particular menu item is prominent and highlighted. Manipulation of visual components and/or direct choosing may be implemented through the use of any suitable user input device, including touchscreens, mice, keyboards, arrow keys, gaze detection system, motion detection systems, gesture detection systems, etc.

Features of embodiments of the interface may be referred to as a "first portion" and a "second portion." These terms refer to specific portions of the displayed user interface at various times and are not required to be fixed to specific places on the screen. As used herein, a "first portion" may also be referred to as an "active portion." The "first portion" or "active portion" represents the portion of the MUI displaying the most current or newest set of menu items. "First portion" and "active portion" may be used interchangeably herein. The "second portion" may also be referred to as an "historical portion." The "second portion" or "historical portion" represents the portion of the interface displaying previously viewed menus and previously selected and unselected menu items. "Second portion" and "historic" portion may be used interchangeably herein.

FIG. 1 illustrates a method of interactively navigating a user through a path of menu choices on a user interface in one embodiment. The method may be performed automatically by at least one hardware processor. The method facilitates moving a user through a system by asking questions, showing past choice or choices the user has made along with other option(s) that were not chosen while drilling down through additional choice(s) based on the initial choice. As used herein, "asking questions" refers to presenting a user with one or more menu choices to select from. The method allows the user to continue down a path or jump to a different path, going back in time to a choice made in one or more earlier step(s) or going back to the latest point at which the user has made a choice. The user interface in one embodiment presents and allows the user to see the past or prior choice(s) that have been made and not made, for example at every step of the path, regardless of where the user is on the path, all on the same screen. The user interface for example, presents an outline of the user's menu choice path that also includes menu item(s) not chosen. The user interface methodology allows for more efficient navigation, leading the user along a path, allowing the user to see the path the user is going through, and allowing the user to deviate from a path that has been set for the user to a different path. The user interface methodology allows the user to be able to see backward and forward breadcrumb(s), and where the user is going and where the user could go.

As discussed herein, menus are presented as a series of hierarchical menu trees. Each level of the menu tree includes multiple menus leading to other menus. Accordingly, a first level of the menu tree includes a plurality of first menus, a second level of the menu tree includes a plurality of second menus, a third level of the menu tree includes a plurality of third menus, etc. This structure continues to an execution menu level. In some discussions herein, a first menu is referred to simply as a menu, while subsequent menu layers in the tree are referred to as submenus, sub-submenus and so on. At time, multiple layers of menus below a current menu may be collectively referred to as submenus. Thus, the submenus of a first menu may include a plurality of second menus, a plurality of third menus, a plurality of fourth menus, a plurality of execution menus, and so on. An example of a hierarchical menu tree structure is illustrated in FIG. 2K. As used herein, with reference to the hierarchical menu tree, each level is referred to as a "menu" even where it does not present a literal menu to the user. For example, a "menu" may present only an "execute" button to implement a process designed throughout other portions of the menu. Another "menu" may present a tutorial, for example.

Each of the numbered menus includes multiple menu items or choices, with each item or choice pointing to a new menu at a lower level. Thus, the items in a first menu may each point to one of the plurality of second menus. In some embodiments, a menu layer may be skipped. For example, an option in a first menu may point to one of the plurality of third menus.

In embodiments, each menu may also include, for display in the MUI, additional information. Additional menu information may provide a user information about items in the menu and/or general context regarding the menu. For example, where a menu presents a user with save file options, additional information may be provided that indicates remaining disk space. In another example, where a menu presents a user with options pertaining to assays to be run, additional information may be provided on available consumables related to the displayed assays.

At the execution menu level, i.e., a last level in a series of menus, a user may select execution menu choices or items. These choices or items do not lead to further menus, but instead represent selections of parameters for the process the menu tree is intended to facilitate. Selection of execution menu choices or items causes the system to perform a function related to the selected menu choices or items. For example, when using an assay design menu tree, execution menu choices may include options such as file name, assay parameters, reagent choices, etc.

In embodiments, execution menus may facilitate the interface between the MUI software and the physical world. Execution menus may provide, for example, execute commands that are output by the methodical user interface control system 1102 to connected systems or instruments to implement processes that were designed through use of the MUI. In examples, such execute commands may cause manufacturing systems to begin manufacturing parts, may cause assay instruments to begin conducting assays, may cause design systems to transmit design specifications, etc.

In embodiments, execution menus may provide user walkthroughs or tutorials. For example, after designing a workflow or process, an execution menu may provide a walkthrough or tutorial coinciding with the workflow, offering text based, audio based, video based, and image based tutorial steps to walk the user through each step of the designed workflow or process.

In embodiments, execution menus may provide walkthroughs and/or tutorials in conjunction with execution commands issued to physical world instruments and machines. For example, in a modular laboratory system, such a combination may provide instructions to a user to load a machine (e.g., with assay plates and reagents) and then provide execution commands to the machine to run the process. As new steps in the process require physical intervention by the user (moving assay plates, etc.), the MUI, at the execution level, may provide the user with additional instructions (text based, video based, image based, audio based, etc.) to advance the process. In embodiments, user instructions and notifications to implement a user intervention portion of a process may be provided via various communication means, including, for example, text (SMS, MMS), e-mail, phone call, instant message, slack message, and any other type of messaging protocol. Such various communication means may be useful, for example, when portions of the machine processing take some time to complete and a user may not wish to remain at the process location during processing. Accordingly, where a user has initiated a process that takes several hours, they may receive a text message indicating that their intervention is required to advance the process.

These types of "cobot" interactions, wherein the MUI integrates the physical world actions of both human operators and automated machines may be applied to various processes or workflows, including laboratory workflows, manufacturing workflows, food production workflows (e.g., beer production, bread production, etc.), shipping and logistic workflows (e.g., box filling and picking, packaging, etc.).

As used herein, "display" of a menu includes display, within the MUI, of one or more items in the menu. Display of a menu does not require display of all items or options in the menu. The menu items or items that make up the first menu remain the same, regardless of whether each menu item is displayed. As discussed in greater detail below, certain menu items may be excluded or limited for various reasons. As discussed herein, a specified "first menu" or "second menu" may be relocated to various portions of the screen. When relocated, the first menu may continue to display the same set of first menu items and/or may display a different set of first menu items.

As discussed herein, menus may also be referred to based on their temporal status. A "current menu" refers to a menu that is currently active in the active portion of the MUI from which a user is prompted to select an option. A "past menu" refers to a menu from which a user has previously selected options. Past menus may be displayed in the historical portion of the MUI. A "subsequent menu" refers to a next menu that becomes active after the current menu becomes a past menu. For example, a first menu may be displayed as a current menu. After a selection has been made from the first menu, the first menu may then be relocated to become a past menu. A subsequent menu, a second menu indicated by the selection made from the first menu, may then be displayed as a current menu. Current menus may be displayed in the first or active portion of a user interface while past menus may be displayed in the second or historical portion of a user interface.

In the historical portion, the menu items of each past menu may be displayed in the MUI in a linear fashion. All of the menu items from that menu level are displayed in a single line (horizontal or vertical). Each set of past menu items may be displayed in such a linear fashion while the menus as a whole may be displayed in a stacked or nested fashion. This feature is shown, e.g., in FIG. 2C which shows MENU ITEMS displayed in a linear fashion and SUBMENU ITEMS displayed in a linear fashion. The relationship between the MENU ITEMS and the SUBMENU ITEMS is a stacked or nested relation. Accordingly, among a single menu level, the menu items are adapted to be displayed in a linear fashion while the previously navigated and subsequent menu levels are adapted to be displayed in a nested fashion.

A menu of choices may be displayed in a graphical wheel that rotates the choices in a direction, for example, horizontal or vertical (for example, left and right, up and down) or another direction. In another aspect, a menu of choices may be displayed as a graphical slider that slides the choices in a direction, for example, horizontal or vertical (for example, left and right, up and down) or another direction. For instance, an initial menu level (first level) may be displayed in the horizontal and slide left and right and the next menu level (second level) may be displayed in the vertical and rotate up and down. Yet in another aspect, menus of choices may be displayed as a series of concentric circles, each menu level displayed as a circle with menu choices (also referred to as options or menu items). For instance, an initial menu level (first level) may be displayed in the center circle, the next menu level (second level) may be displayed in the next circle (second circle) that surrounds the center circle, further next menu level (third level) may be displayed in yet another circle that surrounds the second circle, and so forth. Still yet, menus of choices may be displayed or visualized as a graphical decision tree with nodes and edges. Each level of the graphical decision tree may represent a menu level with choices.

In one embodiment, the wheel and/or the slider need not rotate fully, for example, do not make a full revolution or circle around. For instance, the wheel and/or the slider rotates or slides from a beginning menu item to an ending menu item, and back from the ending menu item to the beginning menu item. In this way, for example, the beginning and end of the menu are always apparent because the two do not merge or come together. This technique decreases processing time because the wheel and/or the slider is able to convey (and a user is able to immediately understand) the full menu of choices with clear indication as to where or which is the first menu item and where or which is the last menu item in the choices presented by the wheel and/or the slider.

In further embodiments, the wheel and/or sliders may rotate fully to permit a user to easily access the beginning of a menu after reviewing the entire menu. In such embodiments, a visual indicator may be provided to indicate that the menu has been rotated through a full rotation and back to the beginning.

In various embodiments, the terms "software protocol" and "computer instructions" are used to describe software instructions or computer code configured to carry out various tasks and operations. As used herein, the term "manager" refers broadly to a collection of software instructions or code configured to cause one or more processors to perform one or more functional tasks. For convenience, the various managers, computer instructions, and software protocols will be described as performing various operations or tasks, when, in fact, the managers, computer instructions, and software protocols program hardware processors to perform the operations and tasks. Although described in various places as "software" it is understood that "managers," "software protocols," and "computer instructions," as used herein, may equally be implemented as firmware, software, hardware, or any combination thereof for instructing a computer or other electronic device for performing and/or carrying out a series of steps and/or instructions. Furthermore, embodiments herein are described in terms of method steps, functional steps, and other types of occurrences, such as the display of menus, the selection of options, etc. Although not explicitly stated in every instance, it will be understood that these actions occur according to computer instructions or software protocols executed by one or more computer processors.

Functionality of the managers and software protocols discussed herein may be provided by the issuance of one or more commands. As discussed herein, "commands" issued by managers and software protocols refer to the signals and instructions provided to various aspects of the computing system to cause various actions to occur. Commands may be issued from one manager to another manager and/or may be issued to other components of the system. For example, a manager may provide a command to cause display of certain visual components within a menuing interface. Such a command may be directed towards a physical display screen and may include the required signals and instructions to generate the visual components. As used herein, when a manager is described as performing an action or carrying out certain functionality, it is to be understood that the manager has issued a command to cause such action or functionality to occur.

In various embodiments, the term "module" is used herein to refer to a specific suite of software protocols and computer instructions to generate, maintain, and operate the multiple components of a MUI as described herein. The one or more processors described herein may be configured to execute multiple software protocols so as to provide a methodical user interface module. As used herein, "methodical user interface module" refers to any of a subset of modules providing specific user interfaces. For example, an admin console module, audit trail module, and reader module are provided as specific methodical user interface modules to carry out tasks related to system administration, auditing, and plate reading, respectively. Each MUI module may be understood to include at least a hierarchical menu tree including multiple layered menus. Each module may further include preferred default visual components, preferred default exclusion and limitation lists, and other features specific to the module. Other modules are discussed in greater detail below and throughout the present disclosure.

Throughout the present disclosure, multiple aspects of various MUI modules are discussed. The discussed aspects of any specific MUI module are non-exclusive and non-limiting and may equally be applied to any other MUI module. Accordingly, any MUI feature discussed herein, either broadly or with respect to a specific module, may also be applied broadly to the MUI in general and/or to any other specific MUI module discussed herein.

Figure 56:
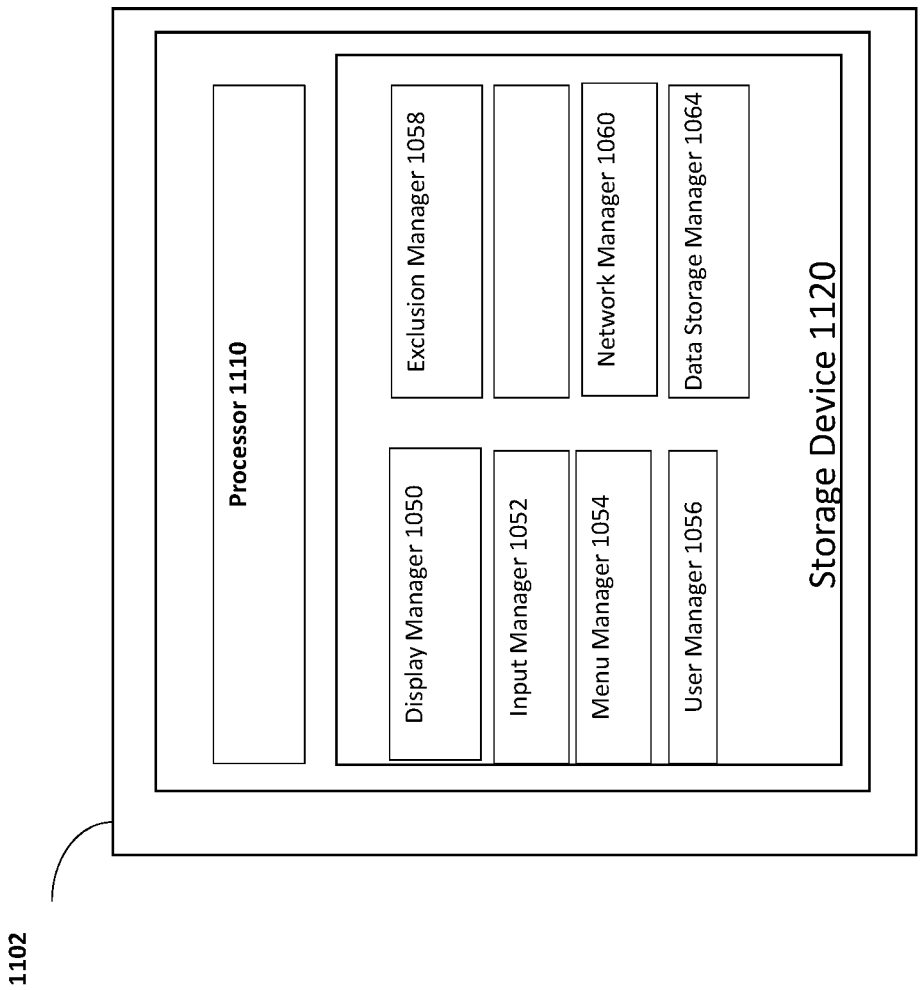
FIG. 56 illustrates a system for implementing a methodical user interface according to an embodiment.

Referring now to FIG. 56, a methodical user interface control system 1102 consistent with embodiments hereof is illustrated. The methodical user interface control system 1102 includes one or more processors 1110 (also interchangeably referred to herein as processors 1110, processor(s) 1110, or processor 1110 for convenience), one or more storage device(s) 1120, and/or other components. The CPU 2 (see FIG. 19) and the hardware processor 1804 (see FIG. 18) may be examples of a processor 1110 configured as described herein. In other embodiments, the functionality of the processor may be performed by hardware (e.g., through the use of an application specific integrated circuit ("ASIC"), a programmable gate array ("PGA"), a field programmable gate array ("FPGA"), etc.), or any combination of hardware and software. The storage device 1120 includes any type of non-transitory computer readable storage medium (or media) and/or non-transitory computer readable storage device. Such computer readable storage media or devices may store computer readable program instructions for causing a processor to carry out one or more methodologies described here. The memory 4 (see FIG. 19) and the memory device 1802 (see FIG. 18) may be examples of a storage device 1120. Examples of the computer readable storage medium or device may include, but is not limited to an electronic storage device, a magnetic storage device, an optical storage device, an electromagnetic storage device, a semiconductor storage device, or any suitable combination thereof, for example, such as a computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, but not limited to only those examples. In embodiments, the storage device 1120 may include multiple storage devices 1120. Multiple storage devices 1120 consistent with embodiments hereof may be collocated and/or non-collocated. For example, one physical system my contain a first memory storage device 1120 and a second physical system may contain a second memory storage device 1120.

In embodiments, the processor 1110 and the storage device 1120 may be implemented via a cloud computing platform or other form of distributed computing. In such implementations, the processor and the storage device may each include a plurality of processors and storage devices for carrying out the tasks and functions described herein.

The processor 1110 is programmed by one or more computer program instructions and/or software protocols, referred to as "managers" stored on the storage device 1120. For example, the processor 1110 is programmed by a display manager 1050, an input manager 1052, a menu manager 1054, a user manager 1056, an exclusion manager 1058, a network manager 1060, and a data storage manager 1064. It will be understood that the functionality of the various managers as discussed herein is representative and not limiting. Furthermore, the functionality of the various managers may be combined into one or more modules, applications, programs, services, tasks, scripts, libraries, applications, or executable code, as may be required.

The managers as discussed herein may be implemented to manage a MUI in various embodiments to complete various tasks that require process workflows. Although various software implementations of the MUI are described herein with respect to one or more specific embodiments, the methods and functionalities provided by the aforementioned managers may be implemented to provide MUIs for any process workflow. The aforementioned managers may be functionally implemented through software libraries The various components of the methodical user interface control system 1102 work in concert to provide a user with a methodical user interface display via any type of display hardware, including screens, projections, touchscreens, headsets, etc. In embodiments, the methodical user interface control system 1102 implements one or more software protocols for interactively navigating a user through path(s) of menu items, options, or choices in a MUI. The software managers described above may include sets of computer instructions, software libraries, dynamic link libraries, application program interfaces, function libraries and other compilations of executable code. The methodical user interface control system 1102 may further include appropriate graphics libraries containing the graphics required to implement and instantiate the various visual components described herein. The managers may be customized for use in a specific implementation through the use of various data structures representative of module information, including tables, linked lists, databases, b-trees, binary trees, heaps, stacks, queues, hash tables, red-black trees, binomial heaps, Fibonacci heaps, and any other suitable data structure. Accordingly, managers of the MUI may be provided as customizable code libraries configured to interface, interact, and otherwise integrate with additional computer instructions and data structures for the purpose of providing a MUI module capable of performing specific tasks.

The display manager 1050 is a software protocol in operation on the methodical user interface control system 1102. The display manager 1050 is configured to manage the methodical user interface display, including all visual components thereof. Display manager 1050 may be configured to issue commands to cause the display of various menu items as required.

The input manager 1052 is a software protocol in operation on the methodical user interface control system 1102. The input manager 1052 is configured to manage all inputs received by the methodical user interface control system 1102, including, but not limited to, user inputs and inputs from other systems. The input manager 1052 may be configured to issue commands to other managers of the methodical user interface control system 1102 according to inputs received. User actions, such as clicking and other screen interactions cause the input manager 1052 to receive a signal indicative of the user interaction. Receipt of such a signal causes the appropriate manager of the methodical user interface control system 1102 to provide a command in response to thereby cause one or more actions, including MUI navigation, menu display, etc., as discussed herein. For ease of explanation, such interactions and user inputs may be referred to as causing a specific response, when in fact the specific response is caused by the methodical user interface control system 1102 responsive to the interaction or user input.

The menu manager 1054 is a software protocol in operation on the methodical user interface control system 1102. The menu manager 1054 is configured to manage the hierarchical menu trees and all menu items associated with the menu trees. The menu manager 1054 is configured to select appropriate menu items for display, to determine a next menu to display, and otherwise manage all aspects of navigation through a menu tree. The menu manager 1054 may be configured to issue commands to other managers of the methodical user interface control system 1102 according to menu navigational requirements.

The user manager 1056 is a software protocol in operation on the methodical user interface control system 1102. The user manager 1056 is configured to manage user access to the methodical user interface control system 1102. The user manager 1506, for example, manages user authorization, including the maintenance of user authorization records, the validation of user credentials, and other required user authentication tasks.

The exclusion manager 1058 is a software protocol in operation on the methodical user interface control system 1102. The exclusion manager 1058 is configured to manage menu item exclusions and limitations. As discussed herein, menu items may be excluded or limited based on various factors. The exclusion manager 1058 may be configured to issue commands to implement such exclusions and limitations.

The network manager 1060 is a software protocol in operation on the methodical user interface control system 1102. The network manager 1060 is configured to establish, maintain, and manage all network communications between the methodical user interface control system 1102 and various other system components discussed herein. The established communications pathway may utilize any appropriate network transfer protocol and provide for one way or two-way data transfer. The network manager 1060 may establish as many network communications as required to communicate with all system components as necessary.

The data storage manager 1064 is a software protocol in operation on the methodical user interface control system 1102. The data storage manager 1064 is configured to store, retrieve, archive, manipulate, and manage all data structures and data storage devices that the methodical user interface control system 1102 may interface with. The data storage manager 1064 is configured to issue commands to any of the various data storage devices discussed herein to manage the storage and retrieval of data.

The above descriptions of the display manager 1050, input manager 1052, menu manager 1054, user manager 1056, exclusion manager 1058, network manager 1060, and data storage manager 1064 provide an overview of the capabilities and tasks of these managers. The managers are not limited by the above description, and, in various embodiments as discussed below, may have additional, different, and/or more capabilities. The described structure of the methodical user interface control system 1102 is by way of example only, and it is to be understood that the various functionalities and capabilities of the computer instruction programmed processors described herein may be carried out, implemented, or effected by a software system of alternative structure.

The methodical user interface control system 1102 may present menu choices among one or more hierarchical menu levels, wherein each menu level can include one or more menu items or choices. Hierarchical menu levels, as described herein, refer to the multiple levels in a menuing system. A selection in a first, highest, menu level causes navigation to a lower hierarchical level, i.e., second menu, a submenu, or sub-level. Selection within the second menu or submenu causes navigation to a still lower hierarchical level, i.e., a third menu or sub-submenu or sub-sub-level. Hierarchical menu structures may include any suitable number of levels. In some embodiments, selection at one level may cause navigation to a level one, two, three or more levels below the current level.

Each menu may present options in an active portion of the interface. The menu choices may be selectable, representing options for the user to select. Selection of a menu choice or option may trigger the display or presentation of a subsequent, following, or submenu, which may include several menu choices or submenu choices of its own. As the user selects menu options, that lead to new menus, the menu items of the old menu may be moved from the active portion to a historical portion of the interface, allowing the user to easily move to new menu choices while retaining knowledge of previous menu choices. These features are described in greater detail below with respect to FIGS. 2A-2O, FIG. 3, and FIG. 57.

Figure 57:
FIG. 57 illustrates a process for navigating a hierarchical menu tree via a user interface.
Figure 59A:
FIGS. 59A-59T are example non-limiting embodiments of an experiment module.
Figure 59B:
Figure 59C:
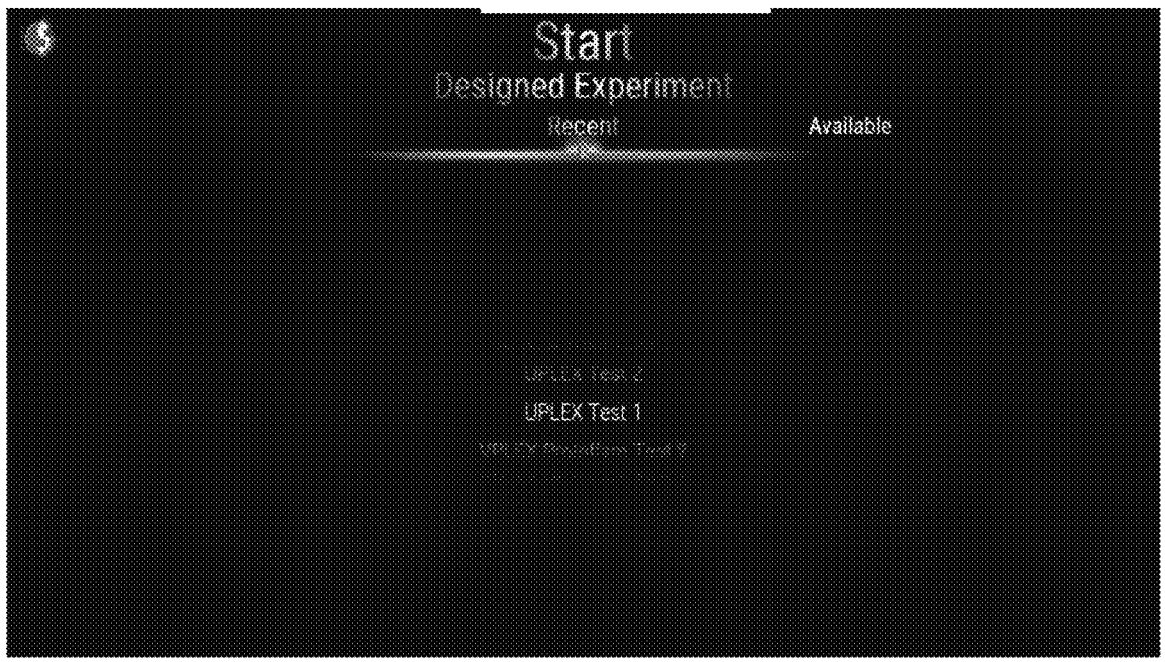
Figure 59D:
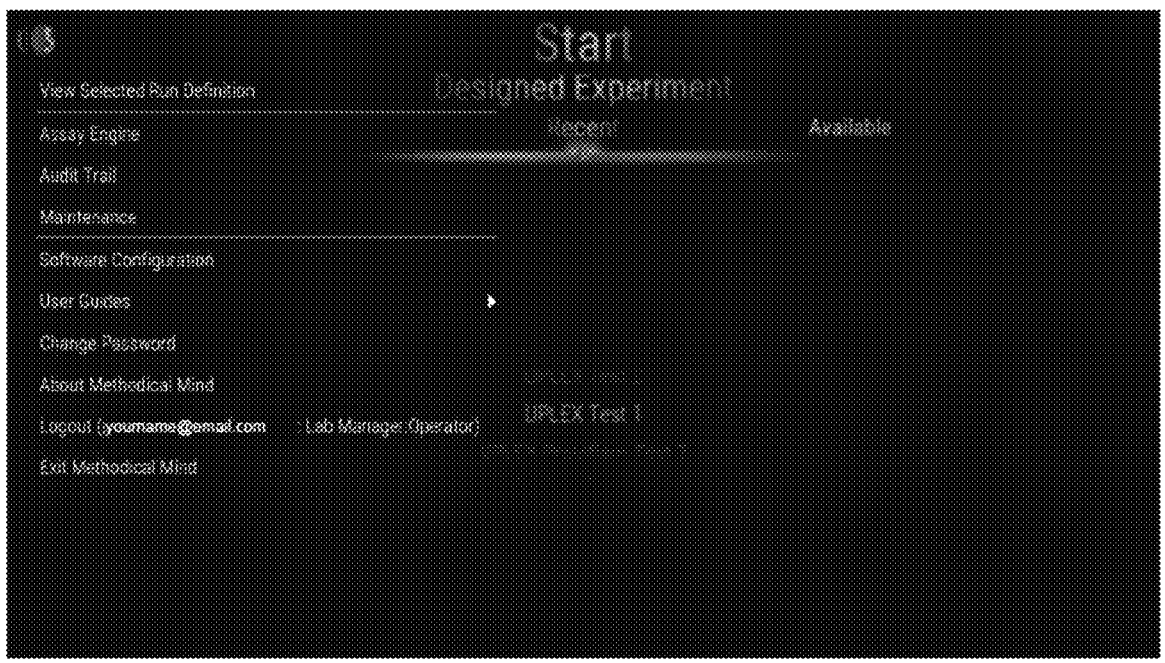
Figure 59I:
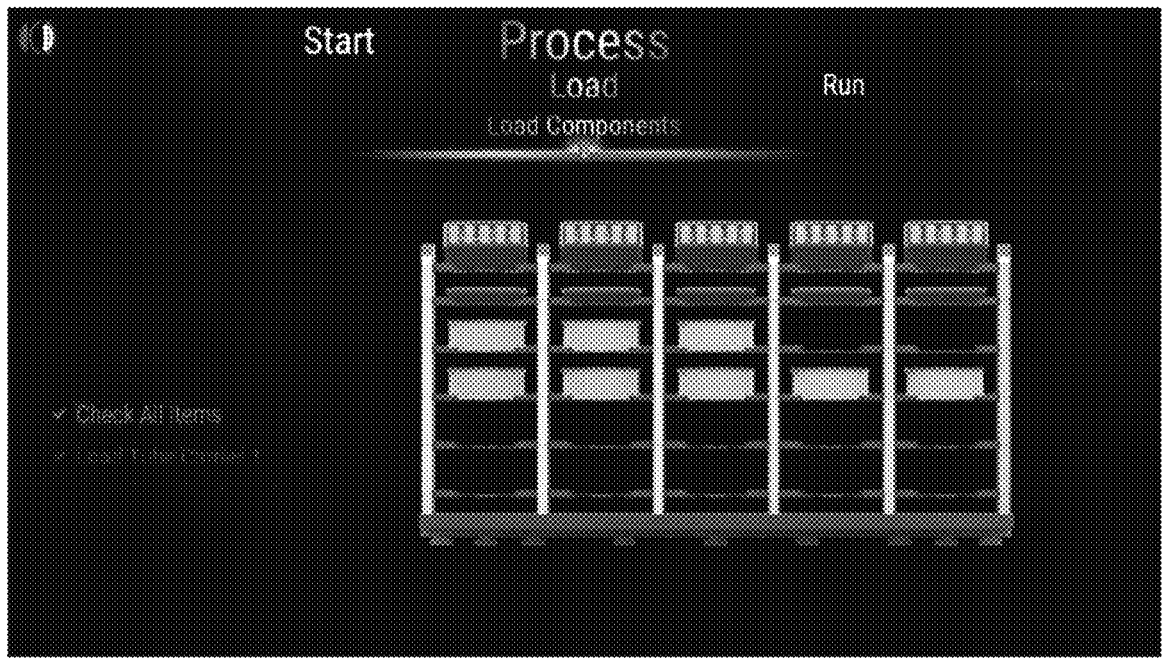
Figure 59J:
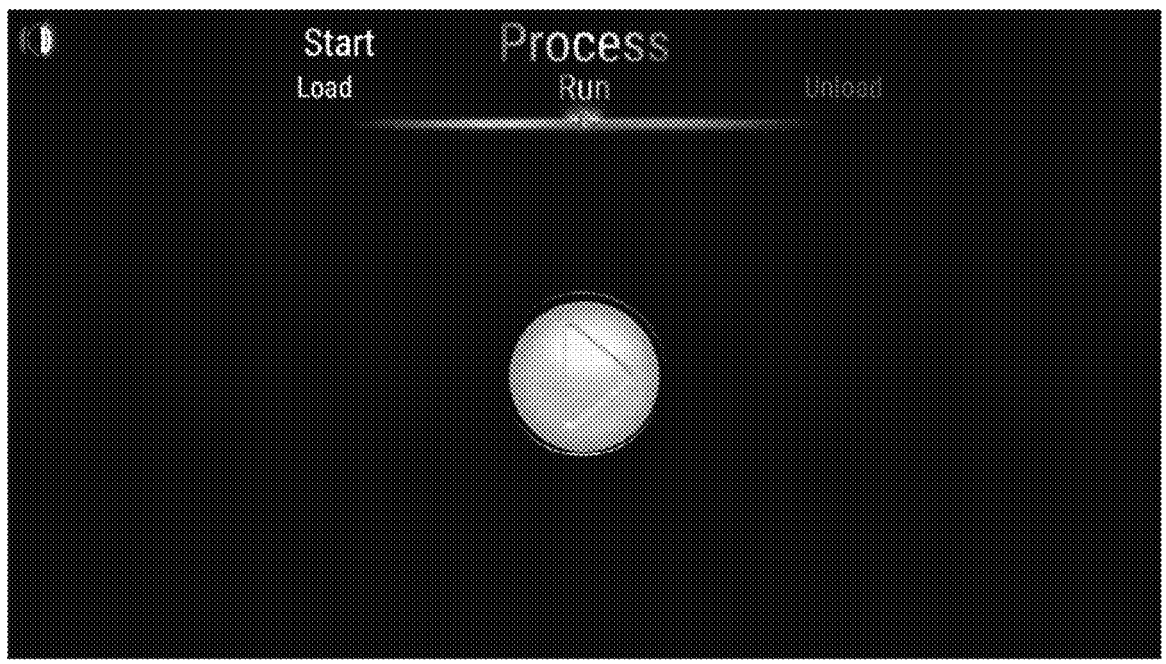
Figure 59Q:
Figure 59R:
Figure 59S:
Figure 59T:
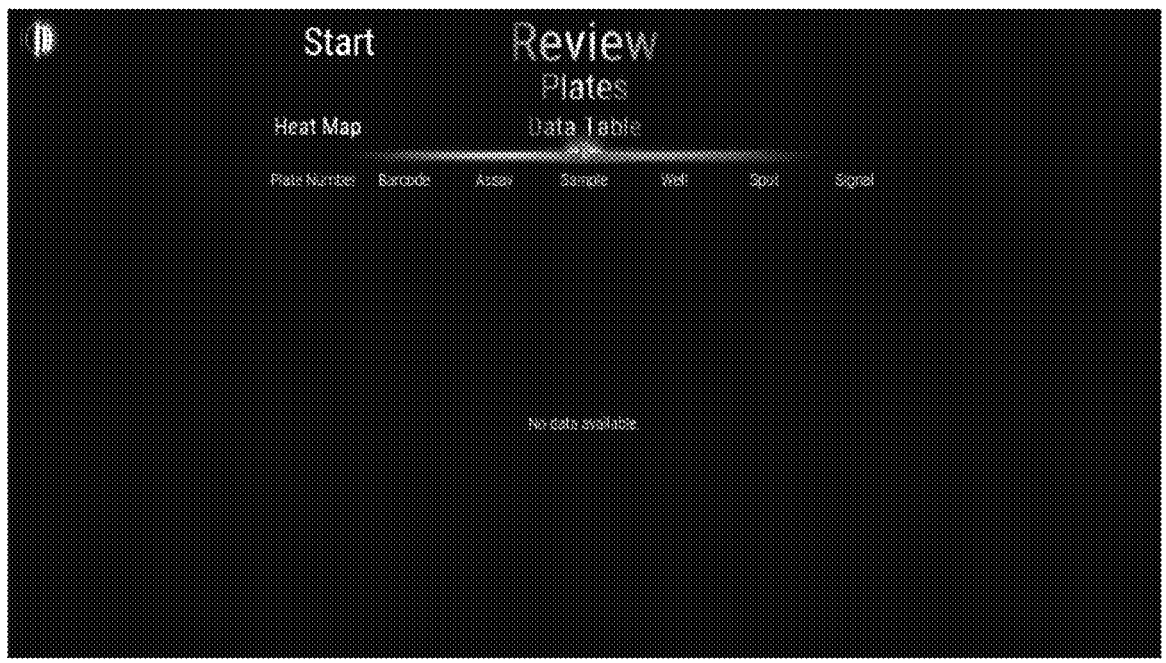
Figure 60A:
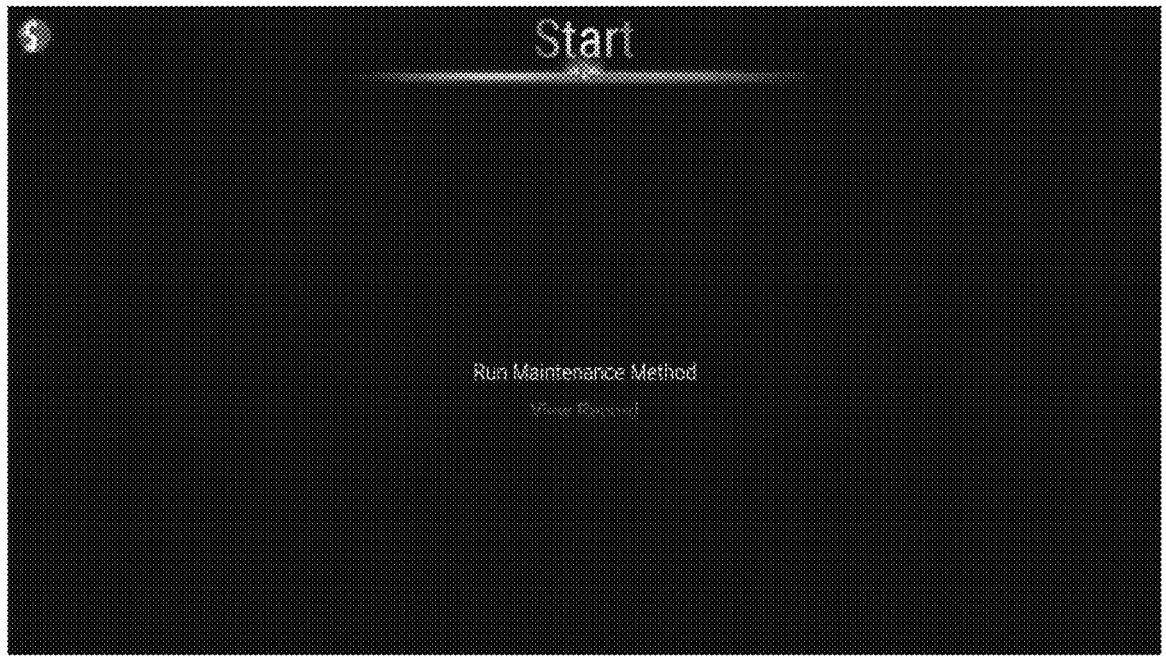
Figure 60B:
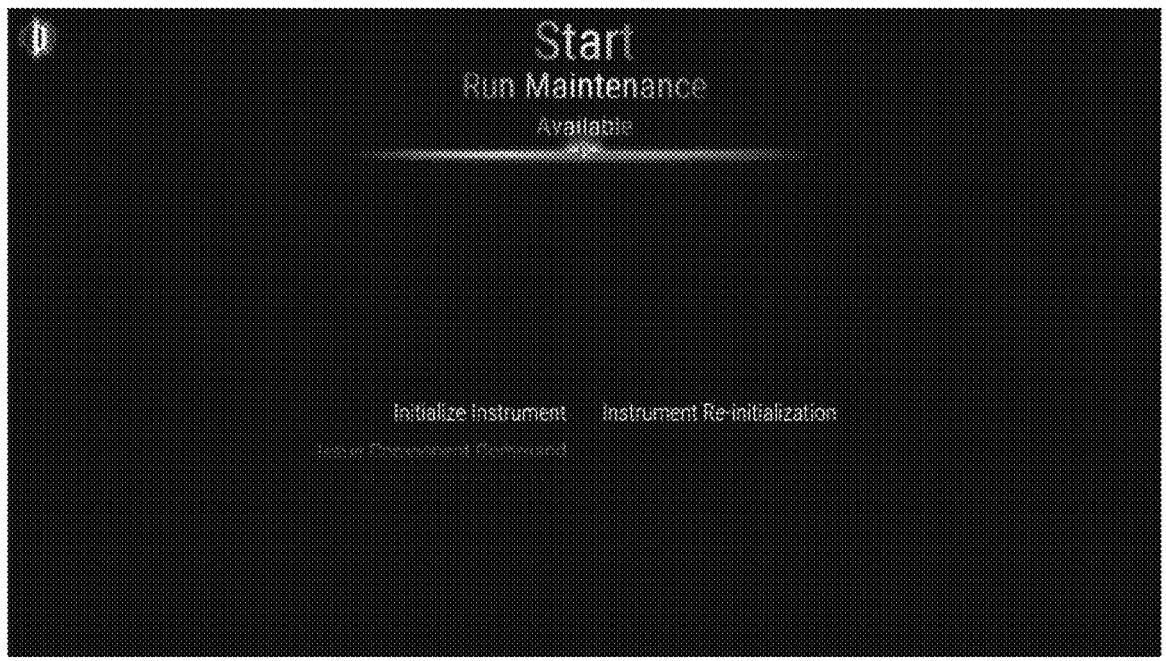
Figure 60C:
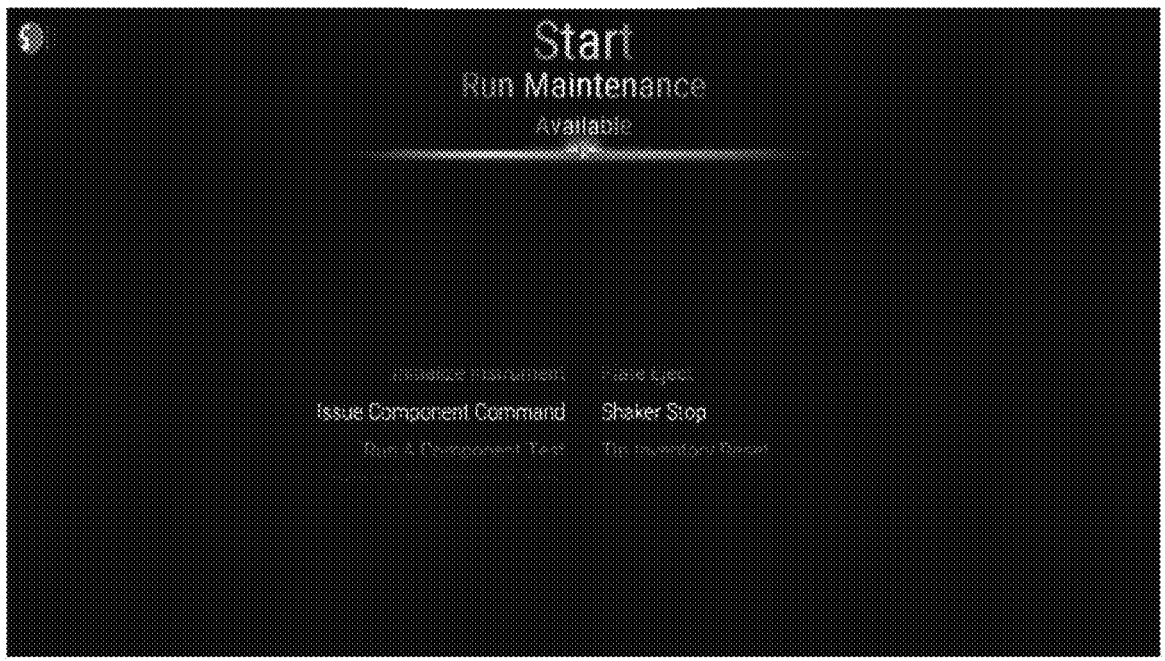
Figure 60D:
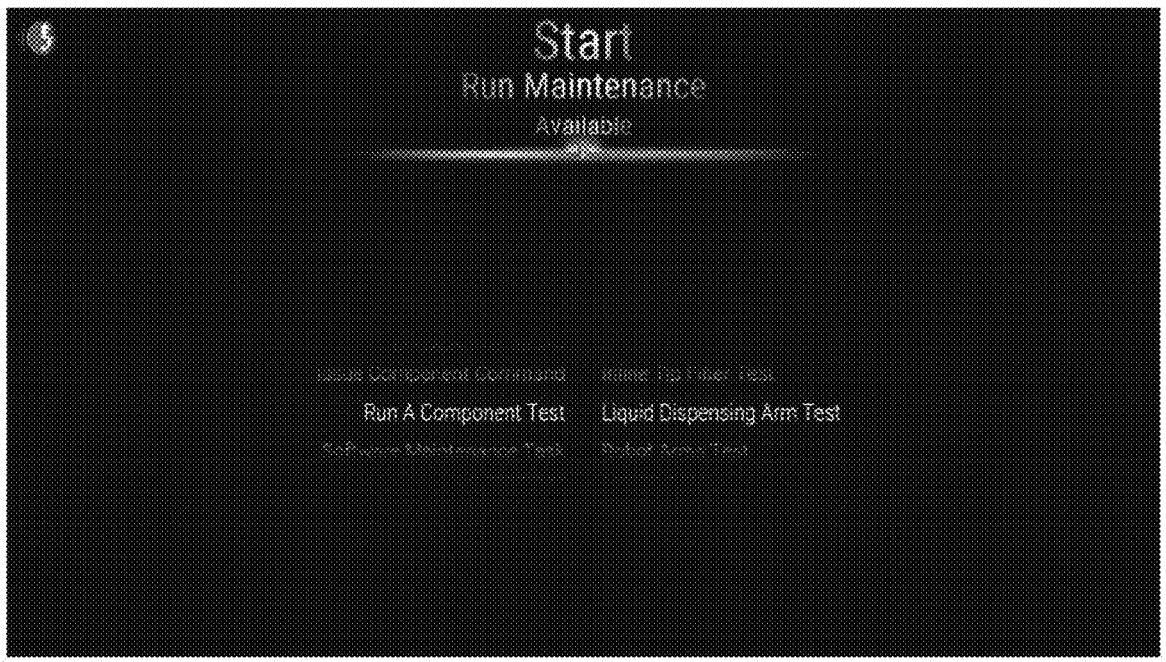
Figure 60I:
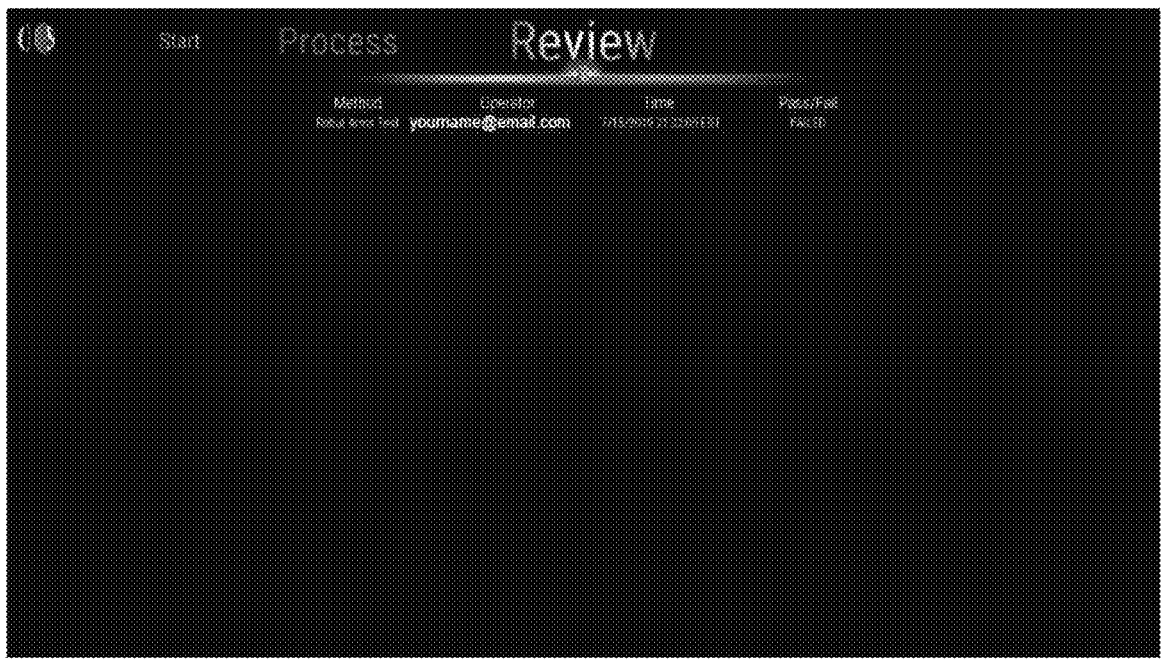
Figure 61A:
FIGS. 61A-61Q are example non-limiting embodiments of an admin console module.
Figure 61B:
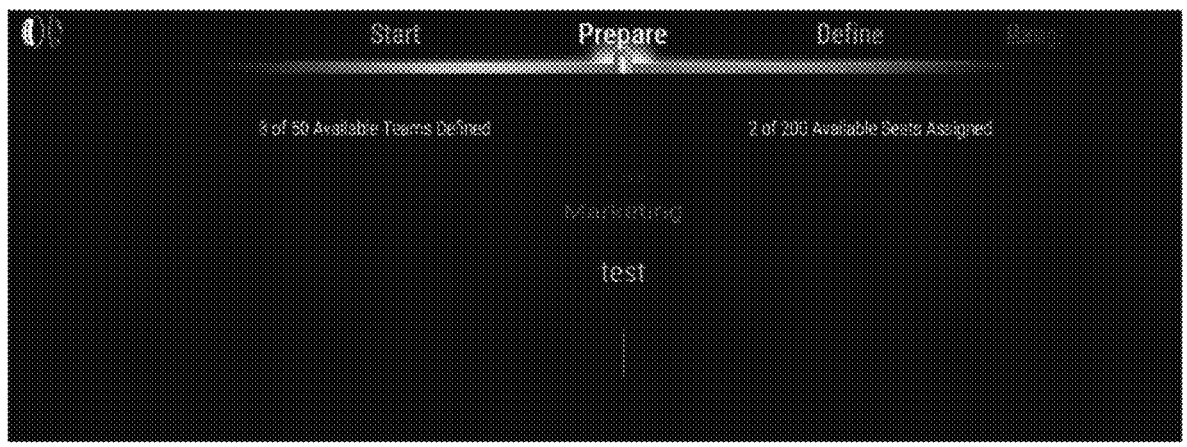
Figure 61C:
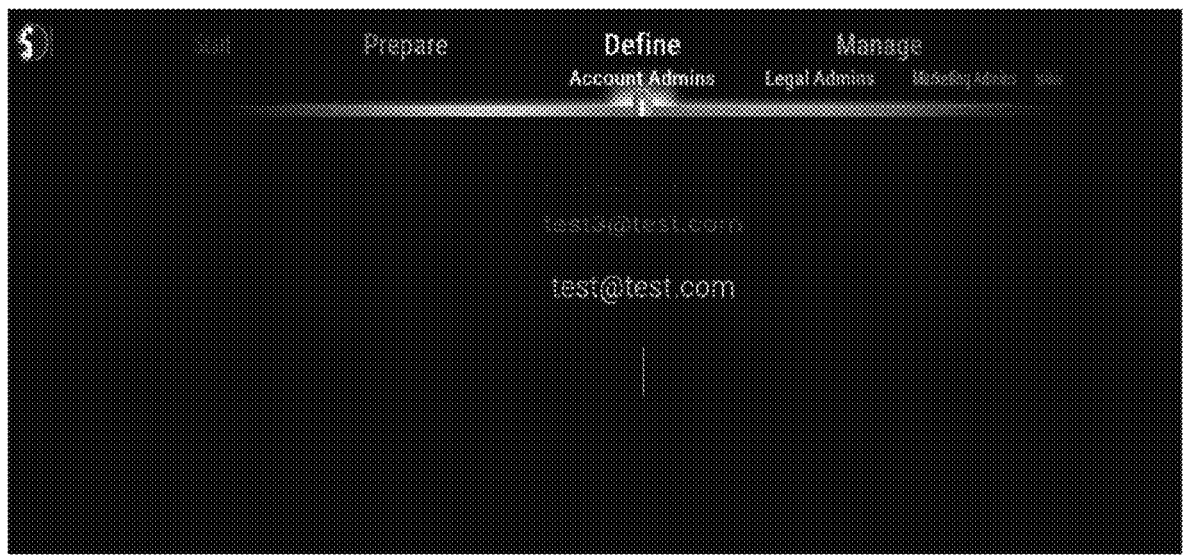
Figure 61D:
Figure 61E:
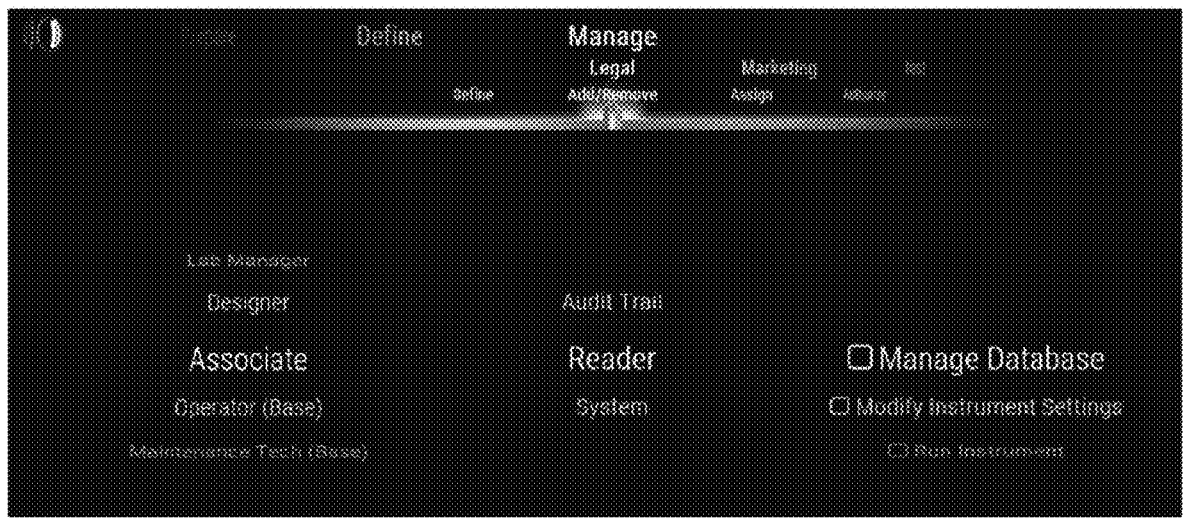
Figure 61F:
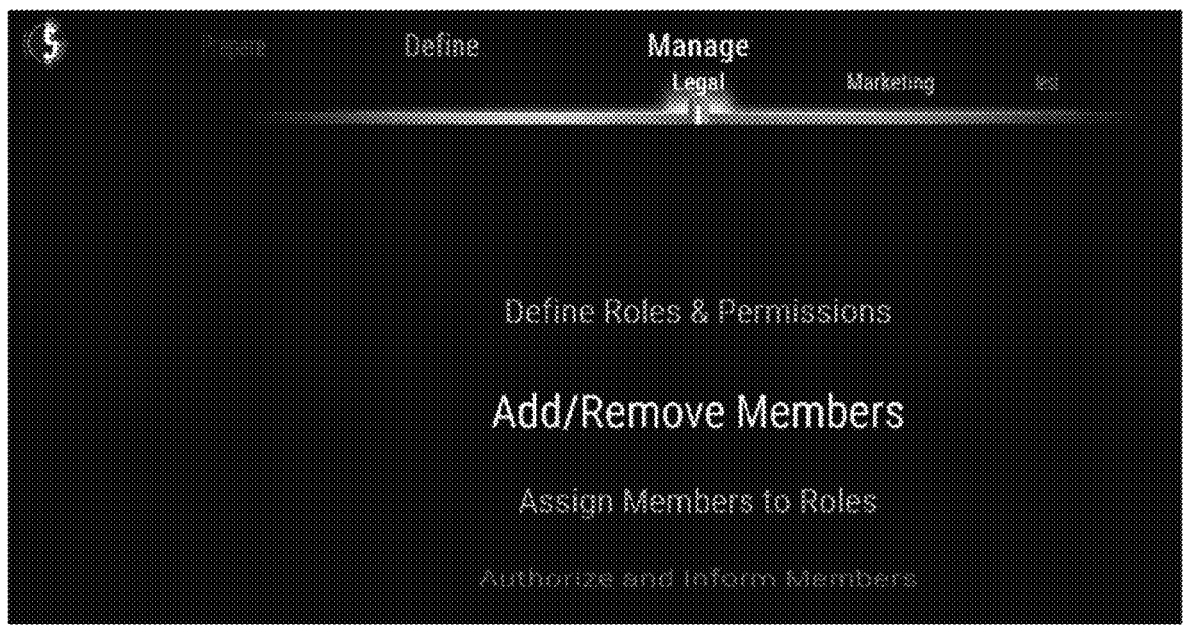
Figure 61G:
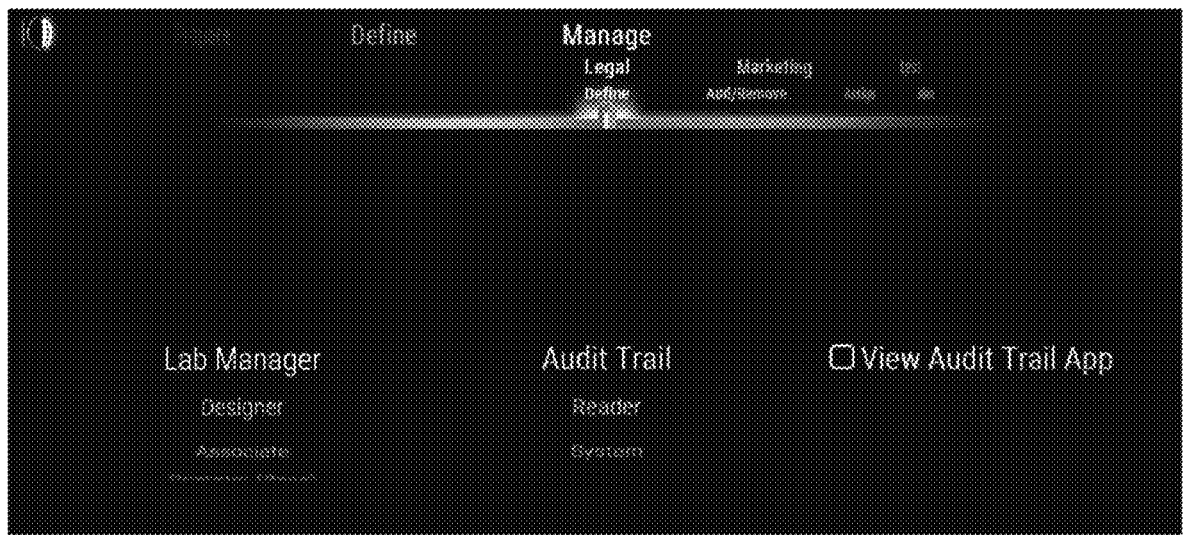
Figure 61H:
Figure 61I:
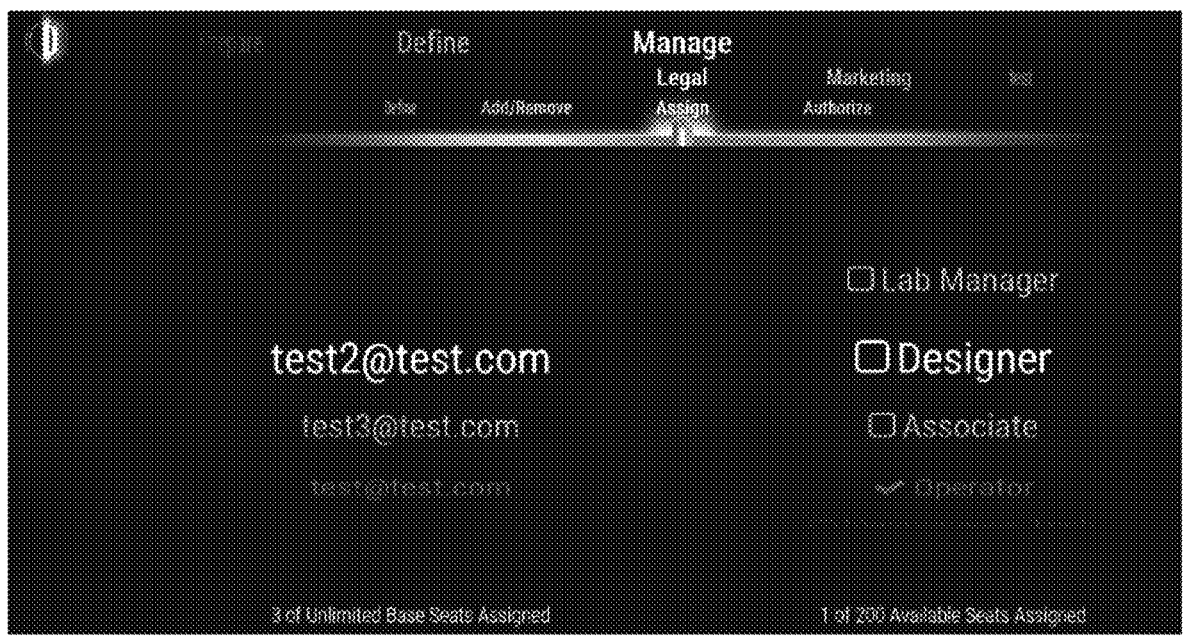
Figure 61J:
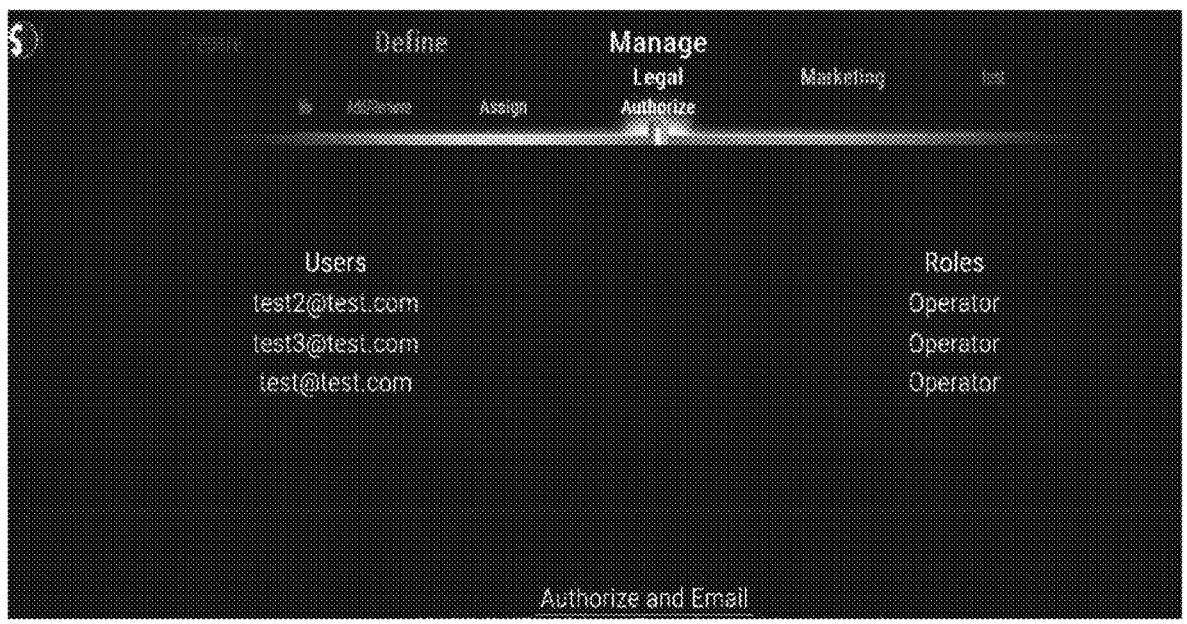
Figure 61K:
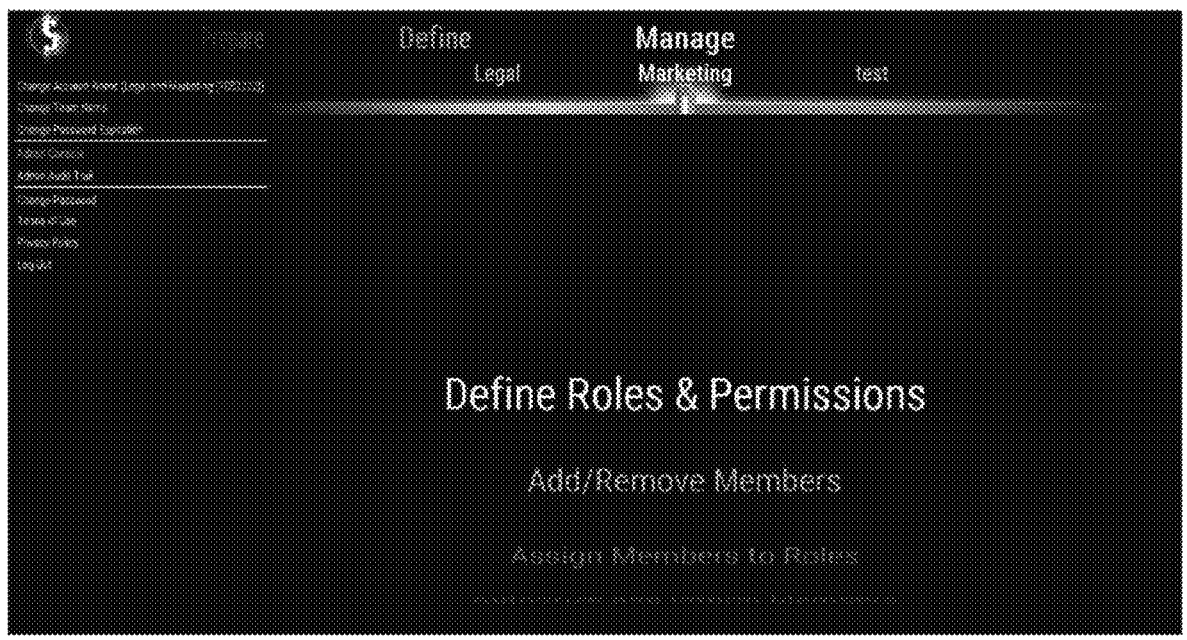
Figure 61L:
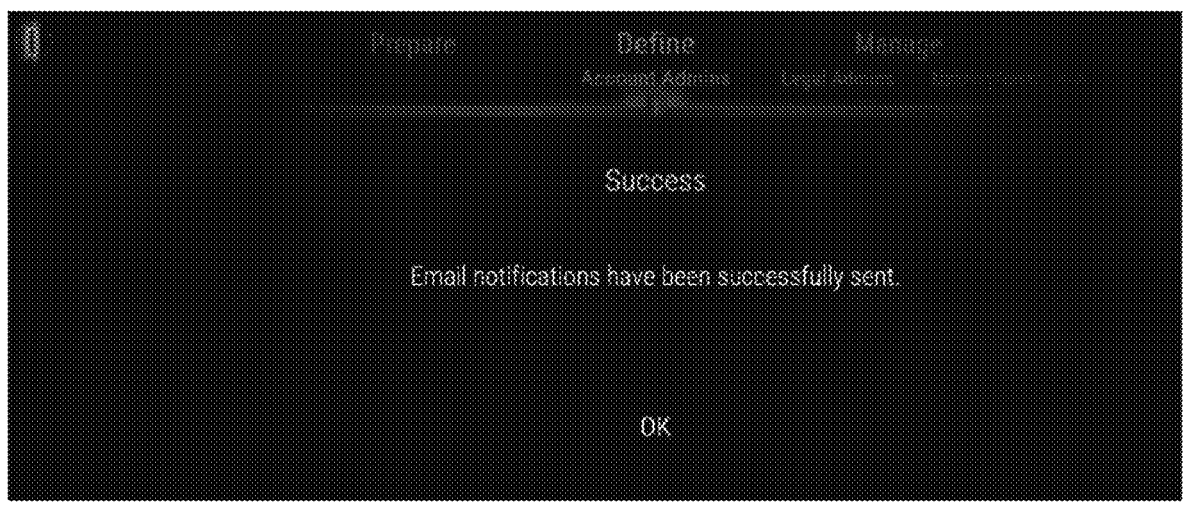
Figure 61M:
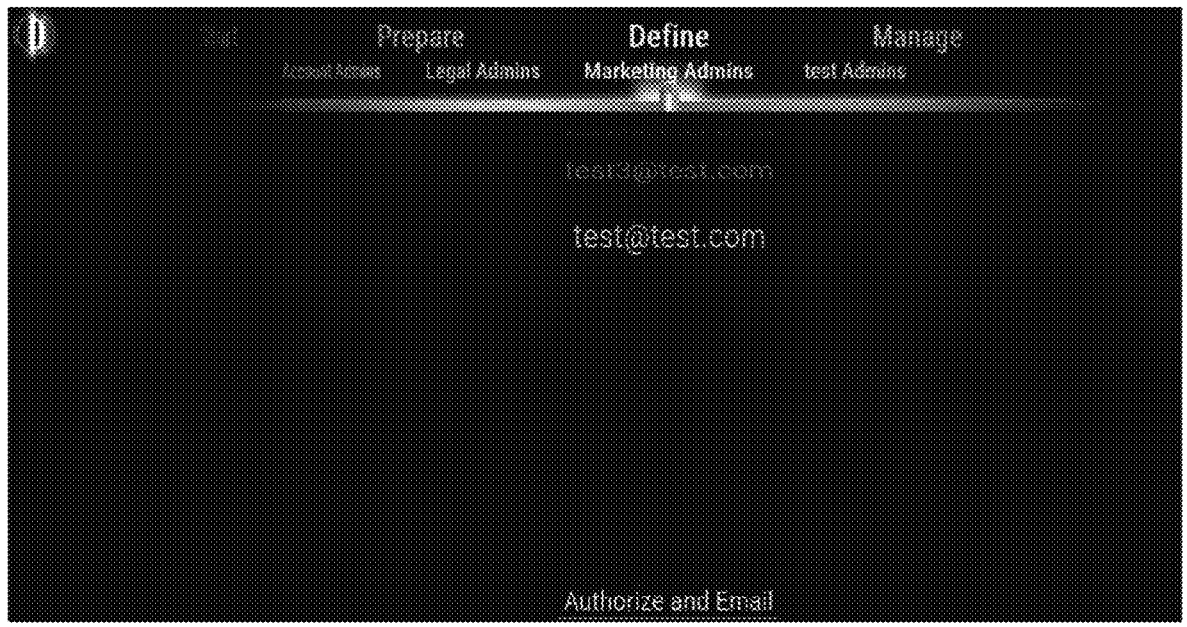
Figure 61N:
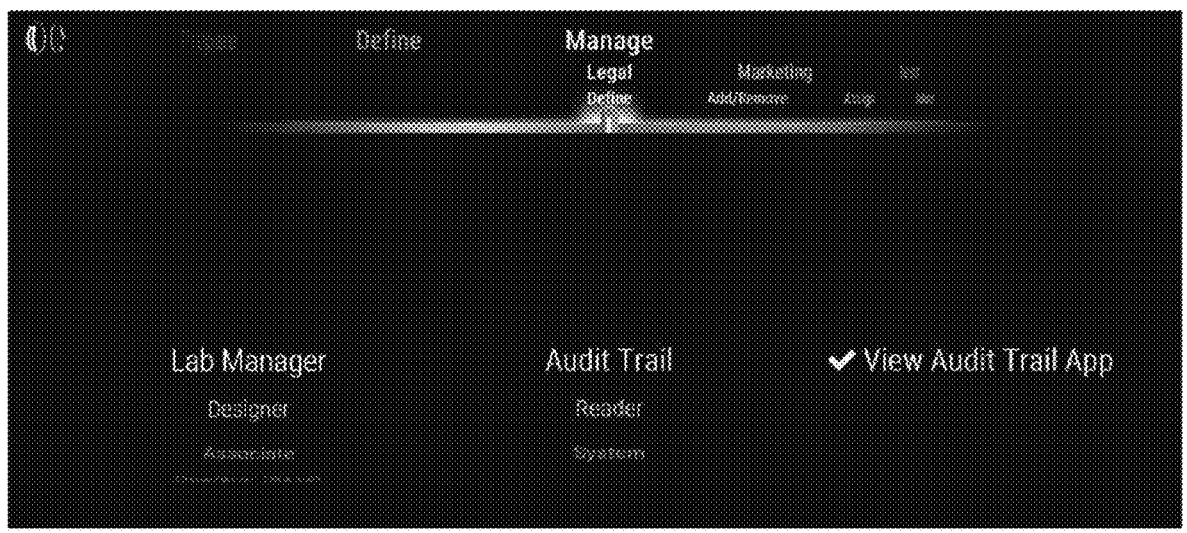
Figure 61O:
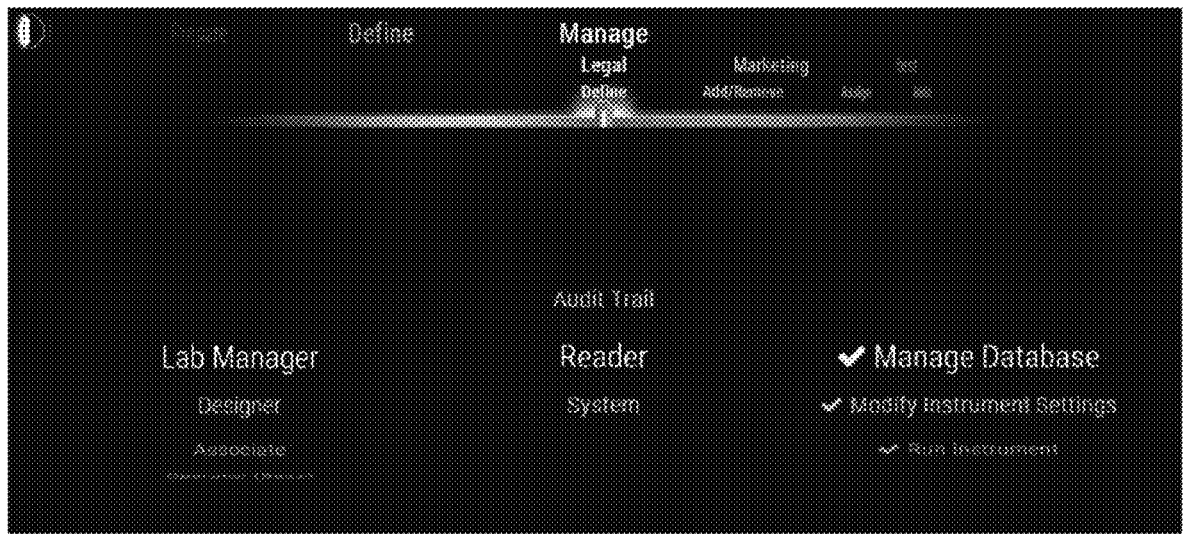
Figure 61P:
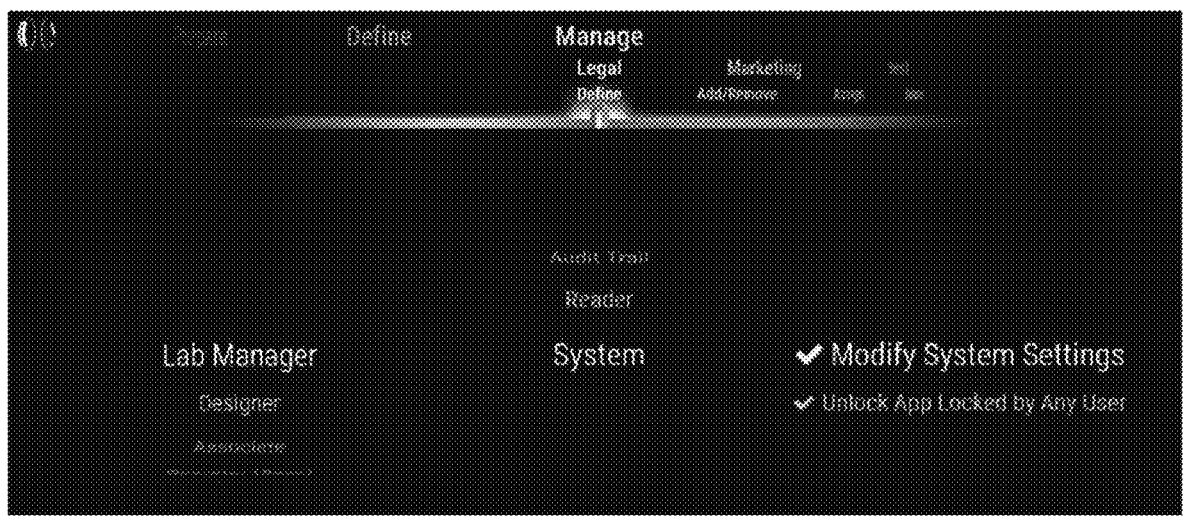
Figure 61Q:
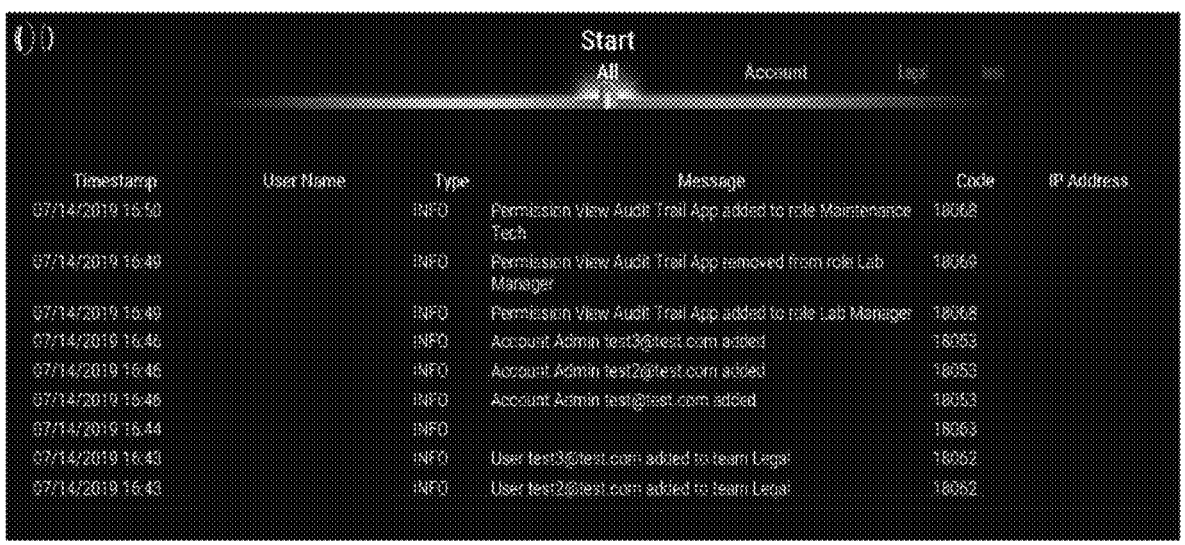
Figure 62E:
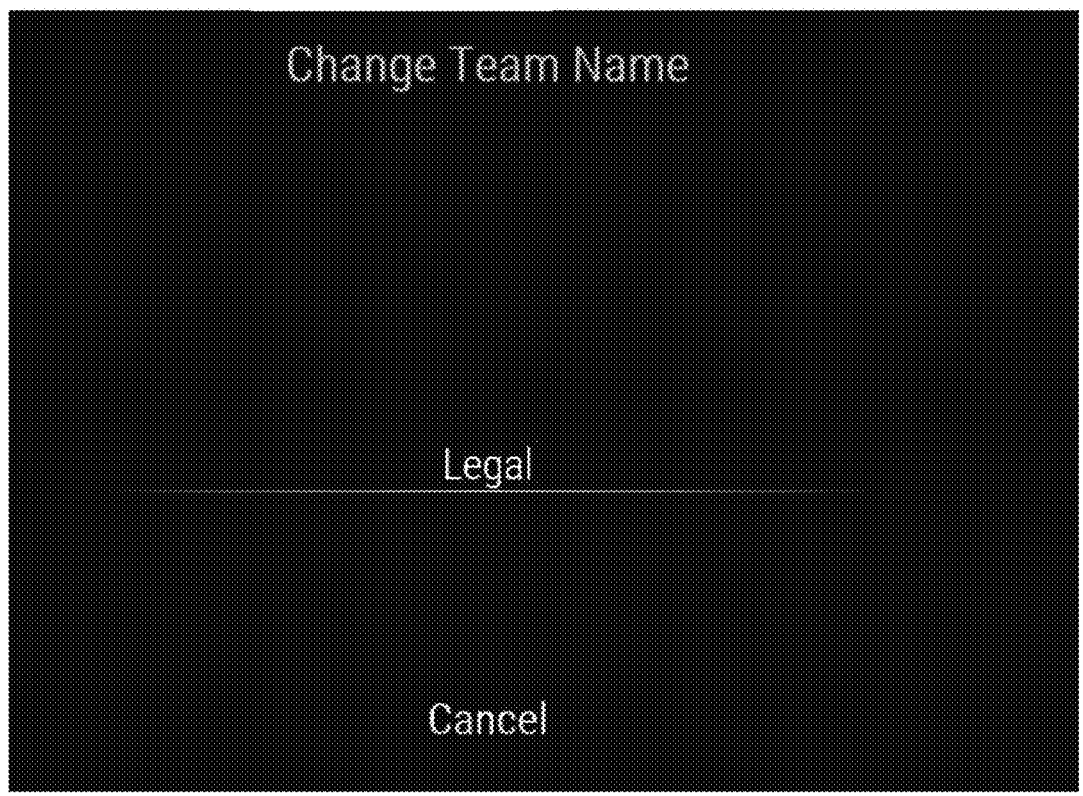
FIGS. 62A-62P are example non-limiting embodiments of generic screenshots applicable to multiple modules herein.
Figure 62F:
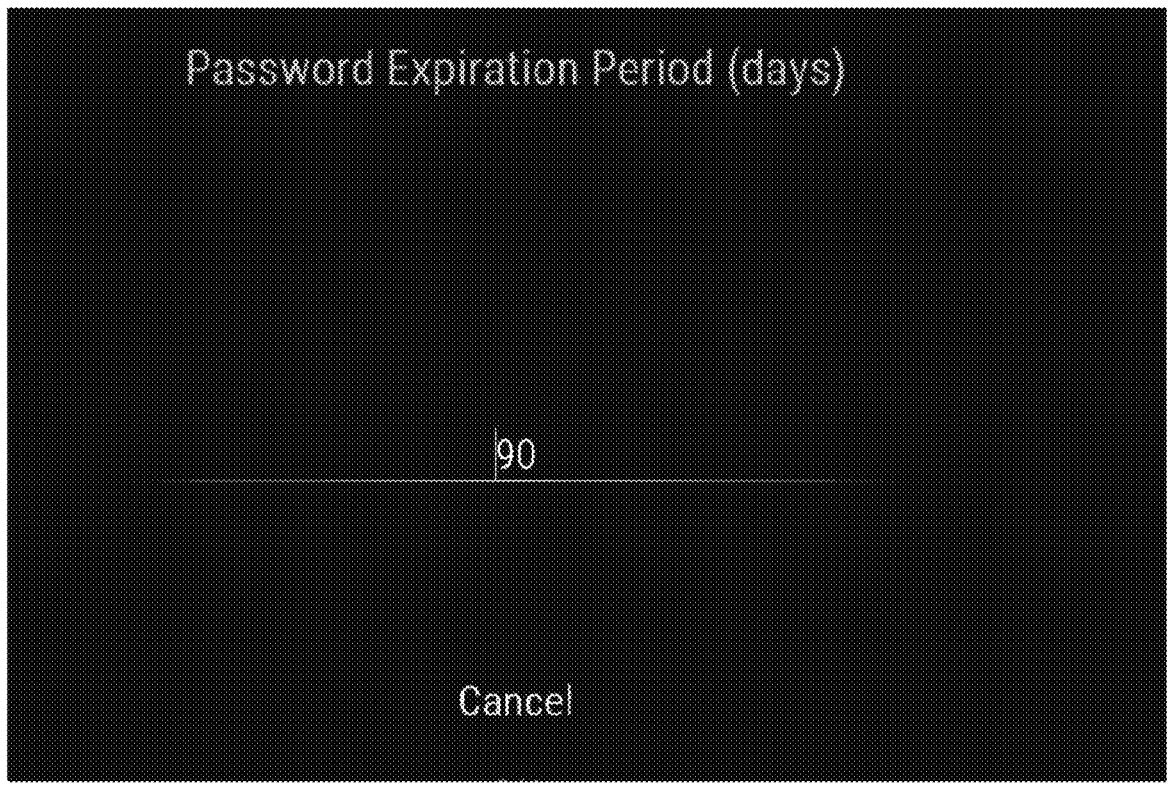
Figure 62G:
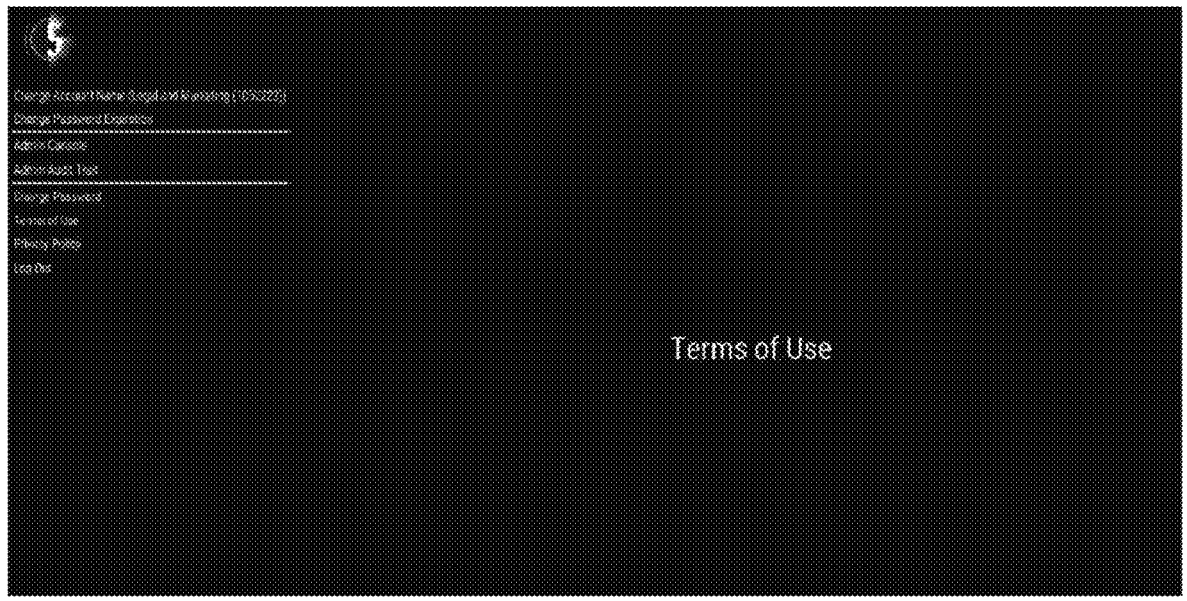
Figure 62H:
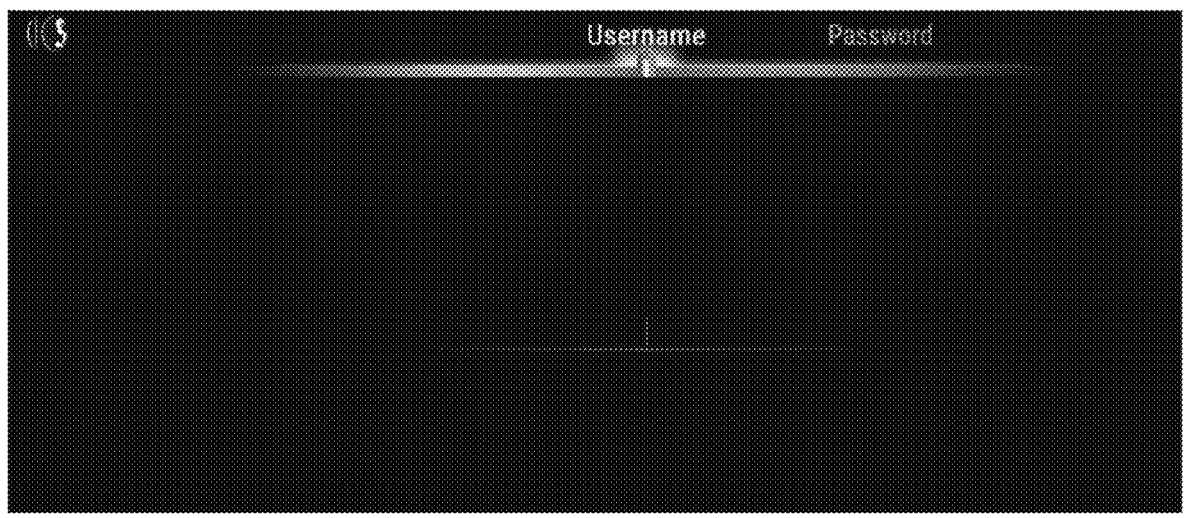
Figure 62I:
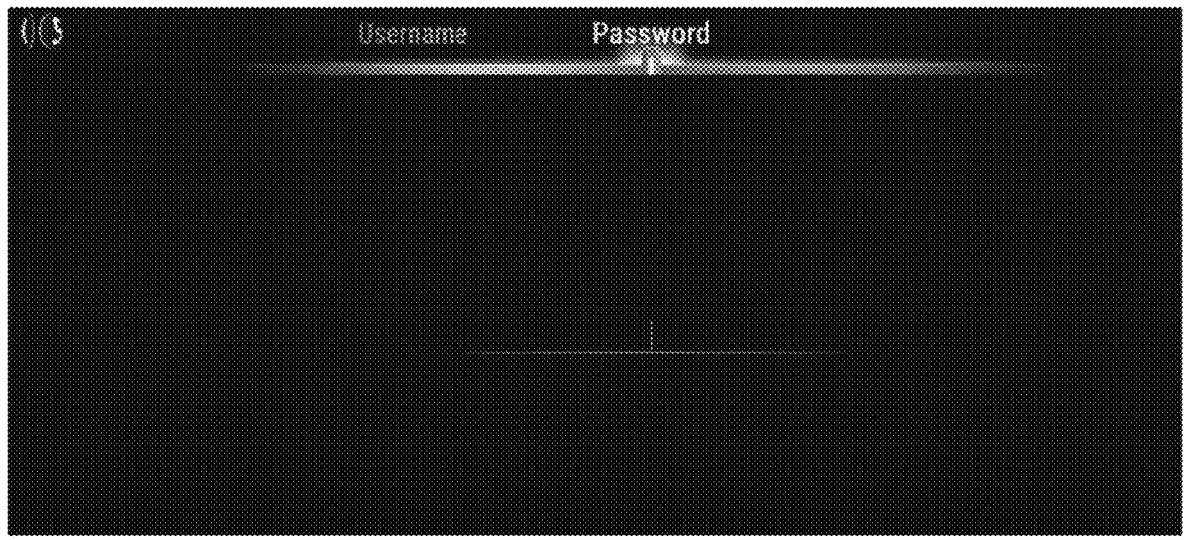
Figure 62J:
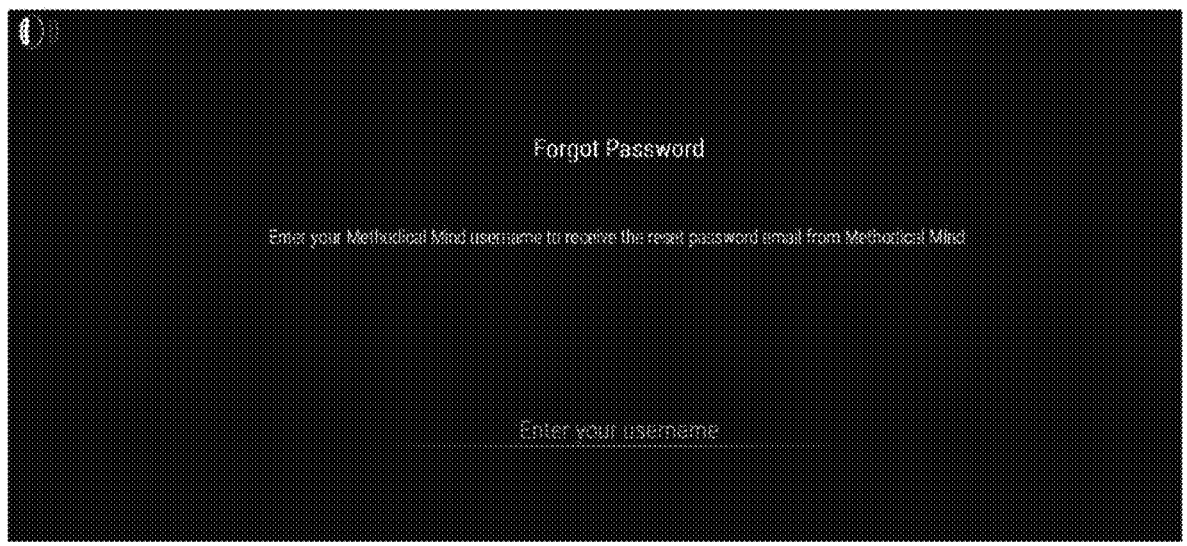

FIG. 57 is a flow chart showing a process 5200 of navigating a path of hierarchical menu levels adapted for output to a user interface, such as a GUI, MUI, and or any other type of UI discussed herein. The process 5200 is performed on a computer system having one or more physical processors programmed with computer program instructions that, when executed by the one or more physical processors, cause the computer system to perform the method. The one or more physical processors are referred to below as simply the processor. In embodiments, the process 5200 is carried out via the methodical user interface control system 1102 as described herein. The methodical user interface control system 1102 represents an example of a hardware and software combination configured to carry out the process 5200, but implementations of the process 5200 are not limited to the hardware and software combination of the methodical user interface control system 1102. The process 5200 may also be carried out and/or implemented by any other suitable computer system as discussed herein. Description of the process 5200 is not limiting, and the various operations may be altered or revised in accordance with embodiments described herein.

In an operation 5202, the process 5200 includes providing a first display command. The display manager 1050 provides the first display command for the display of a first menu having one or more user-selectable items to be displayed on a first portion of a UI display. The first menu may be displayed in the first portion according to any of the visual components disclosed herein, for example, a wheel-type visual component. The selectable items of the first menu may be determined, for example, by the menu manager 1054 as discussed herein.

In an operation 5204, the process 5200 includes receiving a selection. The input manager 1052 receives a selection of a menu item from the first menu according to an input provided to the system. The input may be a user selection and/or may be an automated selection as discussed herein. A user selection may be received, for example, from a user clicking on a highlighted or emphasized menu item. Upon selection, the menu item may be a past-selected menu item.

In an operation 5206, the process 5200 includes providing a relocation command. The menu manager 1054 provides a relocation command for the first menu to be relocated from the first portion of the UI display to the second portion of the UI display. The relocation command may be provided responsive to the selection received. Upon relocation, the menu items of the first menu include the one or more past-selected menu item(s) and past-unselected menu item(s) that were not selected to cause the relocation. Display of the first menu in the second portion may be provided according to any of the visual components disclosed herein, for example, a slider-type visual component. The relocation command of the menu manager 1054 may be sufficient to cause an update to the UI display. In another embodiments, the relocation command may be combined with and/or include a display command provided by the display manager 1050.

In an operation 5208, the process 5200 includes providing a second display command. The second display command is provided by the display manager 1050 responsive to the selection of the menu. The second display command causes a second menu of one or more user-selectable items to be displayed on the first portion of the UI display, i.e., after the first menu has been relocated. The second menu may be displayed according to any of the visual components disclosed herein, for example, a wheel-type visual component. In embodiments, the second display command may incorporate information received from the menu manager 1054 related to hierarchical menu tree navigation. After relocation of the first menu and display of the second menu, the first menu, containing one or more past-selected and past-unselected menu items of the hierarchical menu tree, may be viewed in the second portion concurrently to the second menu being viewed in the first portion.

The process 5200 may further include additional or different operational steps as described throughout the present disclosure.

Referring to FIG. 1, at an operation 102, a current menu of choices (e.g., a list of menu items) may be displayed on a first portion of the user interface display. At an operation 104, the user interface allows the user to select a menu item from the current menu of choices displayed on the first portion of the user interface display and to drill down through level(s) of menu choices based on selecting a menu item from a prior level of menu choices. At an operation 106, past selected and past unselected menu item(s) of the drilled-down levels are displayed on a second portion of the user interface display. The past unselected menu items are displayed as selectable options. The past selected menu item (or choice) may be also displayed as a selectable option. At an operation 108, the user interface allows the user to jump to a different path of menu choices by allowing the user to select a past unselected menu item from a previously navigated menu level displayed on the second portion of the user interface display. The user interface displays both the first portion and the second portion so that they are both viewable on the same screen of the user interface, for example, viewable concurrently.

In one embodiment, the first portion and the second portion are shifted to substantially center the first portion displaying the current menu of choices on the user interface display while fitting both the first portion and the second portion on the user interface display. Thus, for example, the first portion and the second portion need not remain in a fixed location of the user interface display during the navigating or drilling down (or up) through different levels of menu choices.

In one embodiment, the user interface responsive to detecting a selection of a menu item from the current menu of choices, relocates the current menu of choices to the second portion of the user interface display, and displays on the first portion of the user interface display a next level of menu choices based on the selection of the menu item. The relocated current menu of choices is shown on the second portion of the user interface display and becomes the past selected and past unselected menu items of a past menu level. The next level of menu choices is shown on the first portion as the current menu of choices.

As described above, a menu of choices may be displayed as a rotatable graphical wheel showing menu items (choices or options) in which the menu items on the wheel can be shown as the wheel is rotated. A like graphical slider in which the menu items on the slider can be shown as the slider is slid. The action of rotating or sliding may be performed responsive to a motion of a finger on a touch screen or an input from a pointing device or another input device. In another aspect, the action of rotating or sliding may be performed automatically by the user interface (or a hardware executing the user interface) in a timed manner. In one embodiment, the rotating or sliding direction may switch to different orientation as the menu of choices is relocated from the first portion to the second portion.

The current menu of choices may be displayed in first visual orientation on the first portion of the user interface display and the drilled-down levels of menu choices that include the past selected and past unselected menu items may be displayed on the second portion of the user interface display in second visual orientation.

In one embodiment, the current menu of choices is displayed as a graphical rotating wheel or a slider that rotates or slides the choices in a direction of the first visual orientation. In one embodiment, a drilled-down level in the drilled-down levels of menu choices is displayed as a graphical rotating wheel or a slider that rotates or slides choices of the drilled-down level in a direction of the second visual orientation.

In one embodiment, the second visual orientation is substantially orthogonal to the first visual orientation. In one embodiment, the first visual orientation is a vertical orientation and the second visual orientation is a horizontal orientation. In another embodiment, the first visual orientation is a horizontal orientation and the second visual orientation is a vertical orientation.

In one embodiment, the drilled-down levels of menu choices relocated to the second portion are displayed as a stack of menu levels.

In another embodiment, the first portion and the second portion may be displayed as a series of concentric circles. For instance, the first portion may be displayed as the center circle of the series of concentric circles, and the past menu levels as the circles outside or surrounding the center circle. Each circle representing a menu level may include menu items (choices or options) that are rotatable, for instance, in order for the user to be able to view all options present on that menu level. Upon selecting a menu item from the current menu of choices, that current menu of choices is relocated to an outer circle and the center circle displays the next menu of choices based on the menu item that is selected. For instance, a circle (e.g., dial) may include window(s) that show the active option and turning the circle (e.g., dial) shows other options in the window(s). While the dial options seem finite, the dial options may be infinite. For example, the dial keeps spinning until the last option (or beginning option, if turning backward) is shown.

In another aspect, the window may be opened up to show the selected option as lit up, with one (or more) option to the left and another (or more) option to the right.

In yet another embodiment, the first portion and the second portion may be displayed as a graphical decision tree.

In one embodiment, the past selected menu items in the drilled-down levels displayed on the second portion of the user interface display are displayed highlighted relative to the past unselected menu items of the drilled-down levels displayed on the second portion of the user interface display.

In an embodiment, upon encountering the last level in a chosen path of menu levels, and for example, upon performing a function related to the chosen item in the last menu level, the user interface may return the current menu view to another item in an upper level, for example, the first menu list. For instance, the current menu of choices may again be the first initial menu level and may be displayed in the first portion. In an embodiment, the first and second portions are not independent, but linked to each other to make navigation more efficient, leading the user along a path, allowing the user to see the path the user is going through, and allowing deviation from the path that has been set for the user to a different path, for example, being able to see backwards and forwards breadcrumbs to be able to see where the user has been and where the user may go in a path of menu choices. The user interface in one embodiment is able to guide the user, through efficient path choices such that the user need not wander about the user interface trying to find the next appropriate path or action. Such efficient path guidance allows for saving computer resources, for instance, in central processing unit (CPU) cycles and memory usage spent in swapping in and out of processor threads and memory elements in a computer running the user interface.

Figure 18:
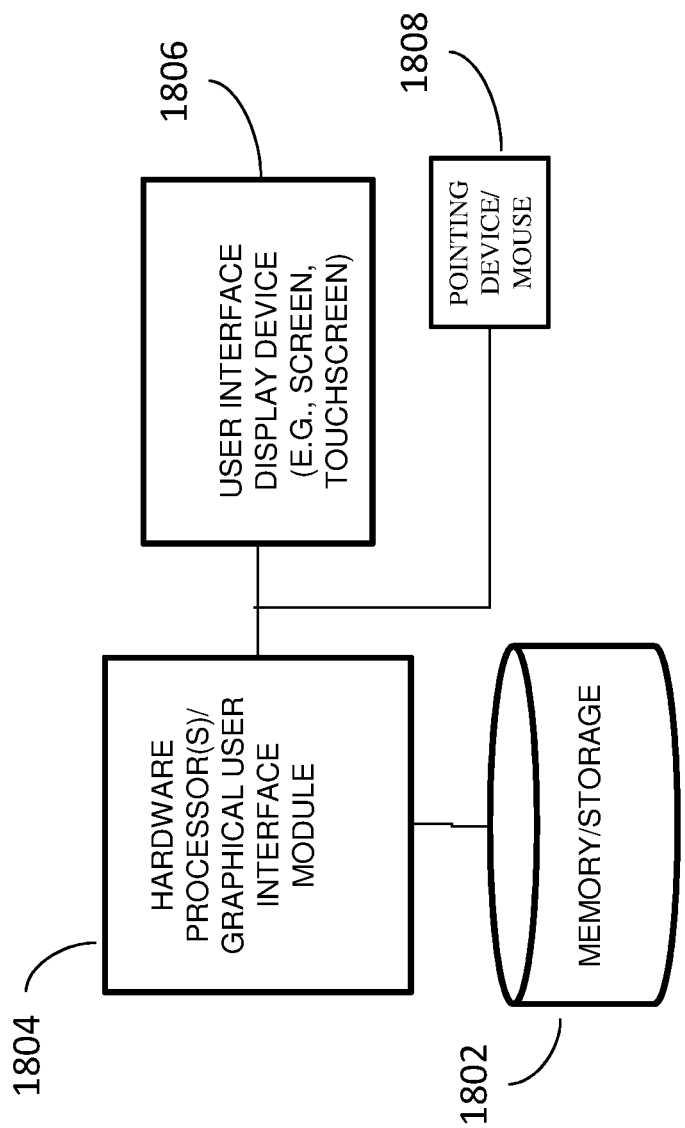
FIG. 18 illustrates components of a graphical user interface (GUI) system in one embodiment.
Figure 19:
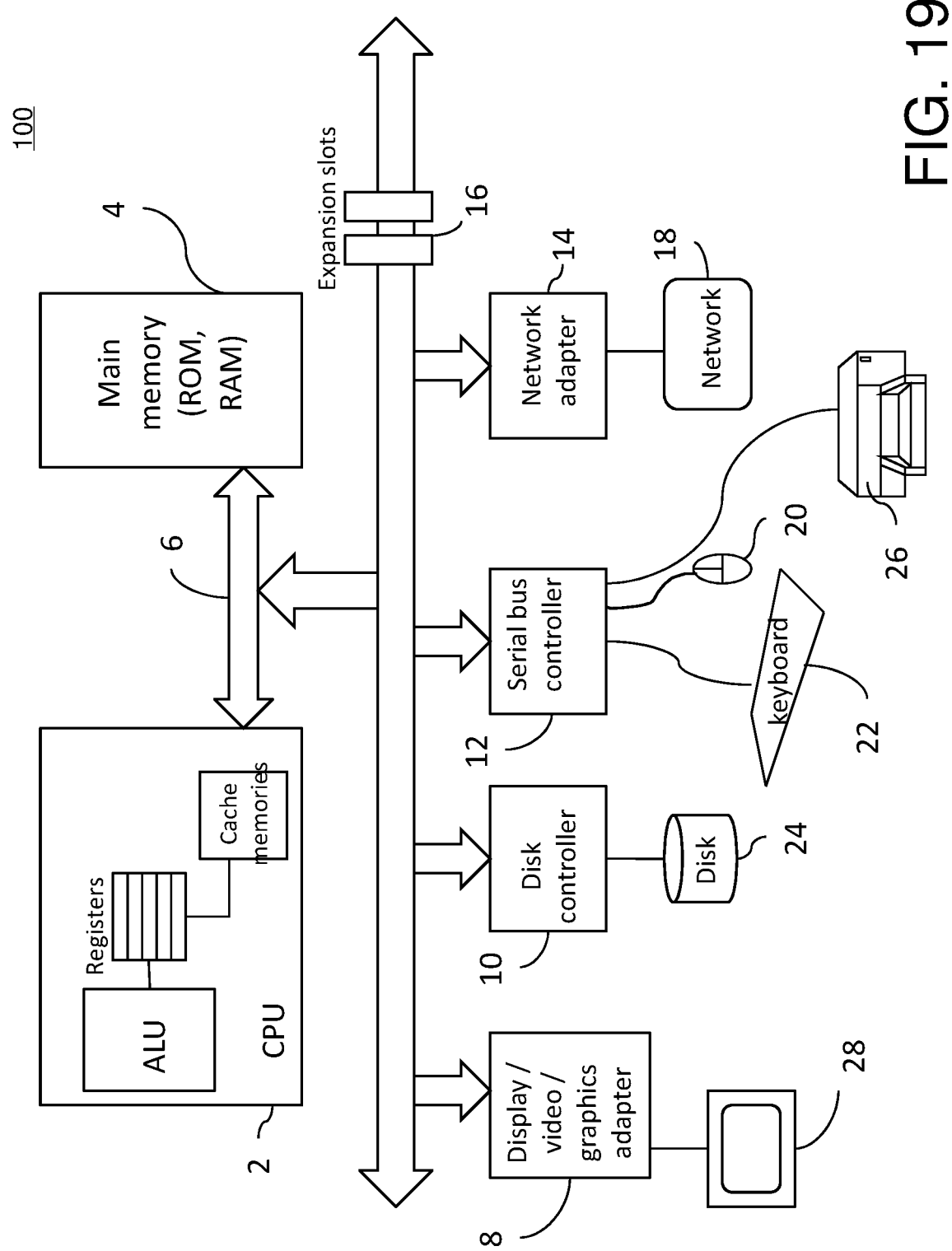
FIG. 19 illustrates a schematic of an example computer or processing system that may implement the graphical user interface system in one embodiment.

Referring now to FIGS. 18-19, additional example systems for carrying out the methods described with respect to FIG. 1 are provided. As discussed above, aspects of the systems presented in FIGS. 18 and 19 may be embodiments and/or implementations of the methodical user interface control system 1102 shown in FIG. 56.

FIG. 18 illustrates components of a graphical user interface (GUI) system in one embodiment. One or more hardware processors 1804 may execute a graphical user interface module and perform the graphical user interface functions described above, displaying the graphical elements as described above on a user interface display device 1806 coupled to the one or more hardware processors 1804. A memory device 1802 may store a list of menus and a list of menu items or choices available for each of the list of menus, which the graphical user interface module may access to display on the display device 1806. The display device 1806 may include a screen device and/or a touchscreen device. One or more pointing devices 1808 may be coupled to the one or more hardware processors 1804 for allowing input via the display device 1806.

The memory device 1802 may be any type of computer readable storage media as described herein.

Although FIG. 18 specifically refers to a GUI system, this is by way of example only. It is understood that methods and techniques described herein may also be carried out via other MUIs, including text based, virtual reality based, augmented reality based, mixed reality based, and others.

For instance, a hardware processor 1804 coupled to the memory device 1802 and the display device 1806 may display a current menu of choices on a first portion of a user interface display, allow a user to select a menu item from the current menu of choices displayed on the first portion of the user interface display and to drill down through levels of menu choices based on selecting a menu item from a prior level of menu choices. The hardware processor 1804 may also display on a second portion of the user interface display, past selected and past unselected menu items of the drilled-down levels, wherein the past unselected menu items are displayed as selectable options. The hardware processor 1804 may also allow the user to jump to a different path of menu choices by allowing the user to select a past unselected menu item from a previously navigated menu level displayed on the second portion of the user interface display.

Figure 3:
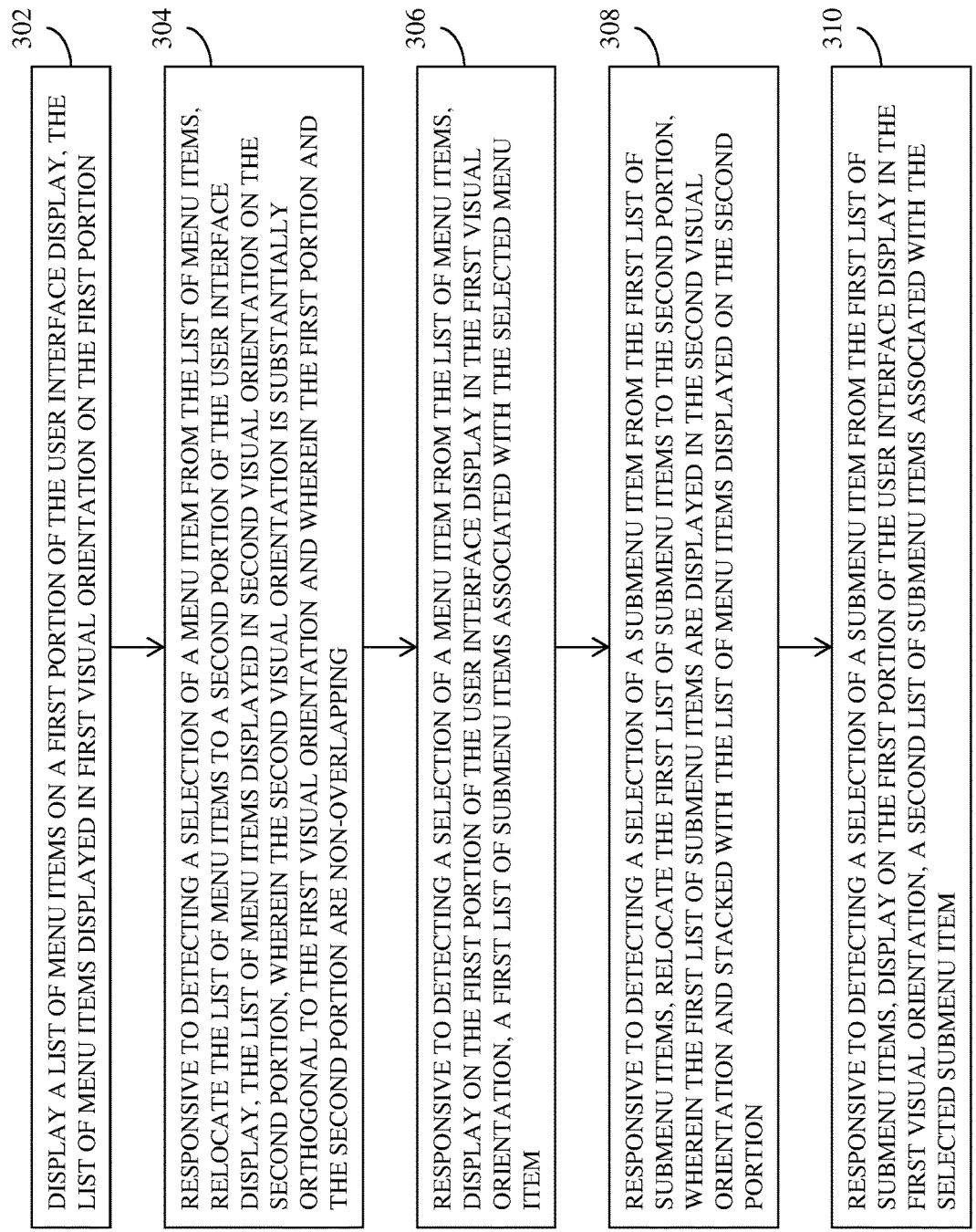
FIG. 3 is a flow diagram illustrating a method of interactively displaying interactive items on a user interface display for computer-user interaction in another aspect.

The hardware processor 1804, for instance, may perform the method described with respect to FIGS. 1 and 3.

The GUI techniques described above may be implemented using computer languages such as JAVA, and JavaScript, but not limited to those languages. In an embodiment, the functionalities and modules of the system and methods of the present disclosure may be implemented or carried out in distributed manner on different processing systems or on any single platform, for instance, accessing data stored locally or in distributed manner on a computer network. Similarly, software protocols and managers of the present disclosure may be implemented or carried out in distributed manner on different processing systems or on any single platform, for instance, accessing data stored locally or in distributed manner on a computer network.

The GUI techniques may be carried out on any type of computing device, e.g., a desktop computer, laptop computer, mobile device (e.g., android or Apple IOS), tablet, and use any type of interface, e.g., mouse, touchscreen, etc. The GUI technique may also be carried out on an instrument, e.g., an assay instrument for performing biological assays such as immunological or nucleic acid assays. In some embodiments, the instrument performs electrochemiluminescence assays. In some embodiments, the instrument is an automated assays system, for example, comprising, (a) a single robotic controlled 8-channel pipettor, (b) a single robotic controlled assay plate gripper arm, (c) a single 96-channel channel assay plate washer, (d) a single plate reader, (e) one or more plate shakers with a total capacity of at least 5 plate shaking locations, and (f) a processor adapted to execute an assay process for analyzing a plurality of samples in 96-well plates.

Various embodiments may be program, software, or computer instructions embodied or stored in a computer or machine usable, readable or executable medium, which causes the computer or machine to perform the steps of the method when executed on the computer, processor, and/or machine. For instance, a program storage device readable by a machine, tangibly embodying a program of instructions executable by the machine to perform various functionalities and methods described in the present disclosure may be provided.

The system and method of the present disclosure may be implemented and run on a general-purpose computer or special-purpose computer system (or device). The computer system may be any type of known or will be known systems and may include a hardware processor, memory device, a storage device, input/output devices, internal buses, and/or a communications interface for communicating with other computer systems in conjunction with communication hardware and software, etc. The GUI techniques of the present disclosure may also be implemented on a mobile device or the like. Implementing the various computer instructions, software protocols, and modules as described herein on a general purpose computer may serve to transform a general purpose computer into a special-purpose computer system configured to carry out the specific methods, tasks, operations, and actions described herein.

FIG. 19 illustrates an example computer system 100 that may implement the system and/or method of the present disclosure. One or more central processing units (e.g., CPUs) 2 may include one or more arithmetic/logic unit (ALU), fast cache memory and registers and/or register file. Registers are small storage devices; register file may be a set of multiple registers. Caches are fast storage memory devices, for example, comprising static random access (SRAM) chips. Caches serve as temporary staging area to hold data that the CPU 2 uses. Shown is a simplified hardware configuration. CPU 2 may include other combination circuits and storage devices.

One or more central processing units (CPUs) 2 execute instructions stored in memory 4, for example, transferred to registers in the CPU 2. Buses 6, for example, are electrical wires that carry bits of data between the components. Memory 4 may include an array of dynamic random access memory (DRAM) chips, and store program and data that CPU 2 uses in execution. The system components may also include input/output (I/O) controllers and adapters connected to the CPU 2 and memory 4 via a bus, e.g., I/O bus and connect to I/O devices. For example, display/graphic adapter connects 8 a monitor 28 or another display device/terminal; disk controller 10 connects hard disks 24, for example, for permanent storage; serial controller 12 such as universal serial bus (USB) controller may connect input devices such as keyboard 22 and mouse 20, output devices such as printers 26; network adapter 14 connects the system to another network, for example, to other machines. The system may also include expansion slots to accommodate other devices to connect to the system. For example, a hard disk 24 may store the program of instructions and data that implement the above described methods and systems, which may be loaded into the memory 4, then into the CPU's storage (e.g., caches and registers) for execution by the CPU (e.g., ALU and/or other combination circuit or logic). In another aspect, all or some of the program of instructions and data implementing the above described methods and systems may be accessed, and or executed over the network 18 at another computer system or device. FIG. 19 is only one example of a computer system. The computer system that may implement the methodologies or system of the present disclosure is not limited to the configuration shown in FIG. 19. Rather, another computer system may implement the methodologies of the present disclosure, for example, including but not limited to special processors such as field programmable gate array (FPGA) and accelerators.

In one embodiment, the present invention may be embodied as a computer program product that may include a computer readable storage medium (or media) and/or a computer readable storage device. Such computer readable storage medium or device may store computer readable program instructions for causing a processor to carry out one or more methodologies described here. In one embodiment, the computer readable storage medium or device includes a tangible device that can retain and store instructions for use by an instruction execution device. Examples of the computer readable storage medium or device may include, but is not limited to, an electronic storage device, a magnetic storage device, an optical storage device, an electromagnetic storage device, a semiconductor storage device, or any suitable combination thereof, for example, such as a computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, but not limited to only those examples. The computer readable medium can comprise both computer readable storage media (as described above) or computer readable transmission media, which can include, for example, coaxial cables, copper wire, and fiber optics. Computer readable transmission media may also take the form of acoustic or light waves, such as those generated during radio frequency, infrared, wireless, or other media including electric, magnetic, or electromagnetic waves.

The terms "computer system" as may be used in the present application may include a variety of combinations of fixed and/or portable computer hardware, software, peripherals, mobile, and storage devices. The computer system may include a plurality of individual components that are networked or otherwise linked to perform collaboratively or may include one or more stand-alone components. The hardware and software components of the computer system of the present application may include and may be included within fixed and portable devices such as desktop, laptop, and/or server. A module may be a component of a device, software, program, or system that implements some "functionality", which can be embodied as software, hardware, firmware, electronic circuitry, or etc.

The storage device 1120, of which memory 4 and memory device 1802 represent examples, may be implemented as one or more computer readable storage media as described herein and may be employed to store various data and information with respect to the computer system 100.

In an embodiment, the storage device 1120 may store registration information such as a user identifier and a user account number. Registration information may be stored via data storage commands issued by the data storage manager 1064. In an embodiment, the registration information is stored in the storage device 1120. The registration information may be stored as one or more data structures. These data structures can include linked lists, b-trees, binary trees, heaps, stacks, queues, hash tables, red-black trees, binomial heaps, Fibonacci heaps, etc. In one example, the registration information may be stored in a registration table. The registration information includes at least a user identifier associated with the user and an account number. Since multiple users may be assigned to the same account number, the system may track this using a shared account flag, such as a semaphore, bit, or the like. When multiple users are assigned to the same account number the shared account flag may be set to a first specific value. Otherwise, the shared account flag may be set to a different specific value. Using a shared account flag is one way of tracking a shared account and this disclosure is not limited to this example. Other methods may be used. The shared account flag may be a column of the registration table. For each user identifier having the same account number, the shared account flag is set to the specific value and associated with the user identifier.

In other aspects, multiple account numbers may be linked together. In embodiments, the user manager 1056 may issue commands for managing user account numbers. In an embodiment in accordance therewith, the multiple account numbers may represent a team such as a research, project, corporate, university, or experiment team. The system may track the multiple account numbers and team using a multiple account flag. When different account numbers are linked, the multiple account flag may be set to a first specific value otherwise, the multiple account flag may be set to a different specific value. Using a multiple account flag is one way of tracking the linking of the different account numbers and this disclosure is not limited to this example. Other methods may be used. In one embodiment, the multiple account flag may be a column of the registration table. For each linked account number, the multiple account flag is set to the specific value and associated with the account numbers.

In other embodiments, the storage device 1120 may also store login historical data. The login historical data may be received via the input manager 1052, organized via the user manager 1056, and stored via the data storage manager 1064. The login historical data may include the user identifier/account number and time/date information for each time a user (or different users) logs into the system. The login historical data may be maintained in the storage device 1120 for a predetermined or indeterminate period of time. The predetermined period of time may be based on a specific application being executed or to be executed.

In other embodiments, the storage device 1120 may also store user selection history. The user selection history may be received via input manager 1052, organized via user manager 1056, and stored via data storage manager 1064. The user selection history may include a selected menu item, the user identifier/user account associated with the selection and time/date of selection. The user selection history may also be stored in the storage device 1120 for a predetermined or indeterminate period of time. The predetermined period of time may be selected according to the MUI module from which the user selection was initially made. The predetermined period of time for stored user selection history and the login historical data may be the same.

In other embodiments, the storage device 1120 may include exclusion information. The exclusion information may include menu items and/or choices that are to be excluded from display in hierarchical menu levels on the MUI for one or more users, devices or interfaces. The exclusion information may be managed by commands issued via the exclusion manager 1058 and stored by commands issued via the data storage manager 1064.

The commands that are issued or provided by the menu manager 1054 of the methodical user interface control system 1102 allow for a user to move bi-directionally between hierarchical menu levels (backward and forward), backward being to a higher hierarchical menu level and forward being to a lower hierarchical menu level including being able to view past or prior menu items that have been selected or not selected. For example, various menu levels and/or choices from one or more levels of a given path of hierarchal menus, can be viewed concurrently on the MUI.

In an embodiment, a display command may be provided by the display manager 1050 for a specific set of hierarchical menu level(s) to be displayed on a specific portion of the MUI. The display command is configured to cause display of one or more menus in one or more portions of the MUI. The specific hierarchical menu level may include one or more menu items (or choices). The display command may include the one or more menu items, a specific display order, a display orientation, display size (and format) and manner in which the choices are displayed, such as scrolling method, although other manners in which to arrange and/or display the choices are contemplated as well. In an embodiment, the scrolling method may define the display orientation and thus, the display command does not necessarily include a separate display orientation and scrolling method.

In an embodiment, each menu item in a specific hierarchical menu level may be displayed in the same size. In other embodiments, one or more specific menu items may be displayed larger or smaller than other menu items.

The display command may specify the scrolling method. For example, the display command may specify that the menu items are to be displayed in a graphical wheel that rotates the items in a direction, for example, horizontal or vertical (e.g., left and right or up and down) or another direction. In another embodiment, the display command may specify that the menu items are to be displayed as a graphical slider that slides the items in a direction, for example, horizontal or vertical (e.g., left and right, up and down) or another direction.

Different display commands may specify different scrolling methods or orientations, or different commands can employ the same or similar scrolling methods or orientations. In an embodiment, the orientations in the different commands (such as the first command and the second command) may specify that the orientations are substantially orthogonal to each other. In other embodiments, orientations can be horizontal, substantially horizontal, vertical, substantially vertical, concentric, and substantially concentric vis-à-vis one another. As used herein, substantially may be + or −5°. In other aspects, substantially may be + or −10°. In other aspect, substantially may be + or −15°. In other aspects, substantially may be determined by percentage, such as 80% or 90%.

Figure 2A:
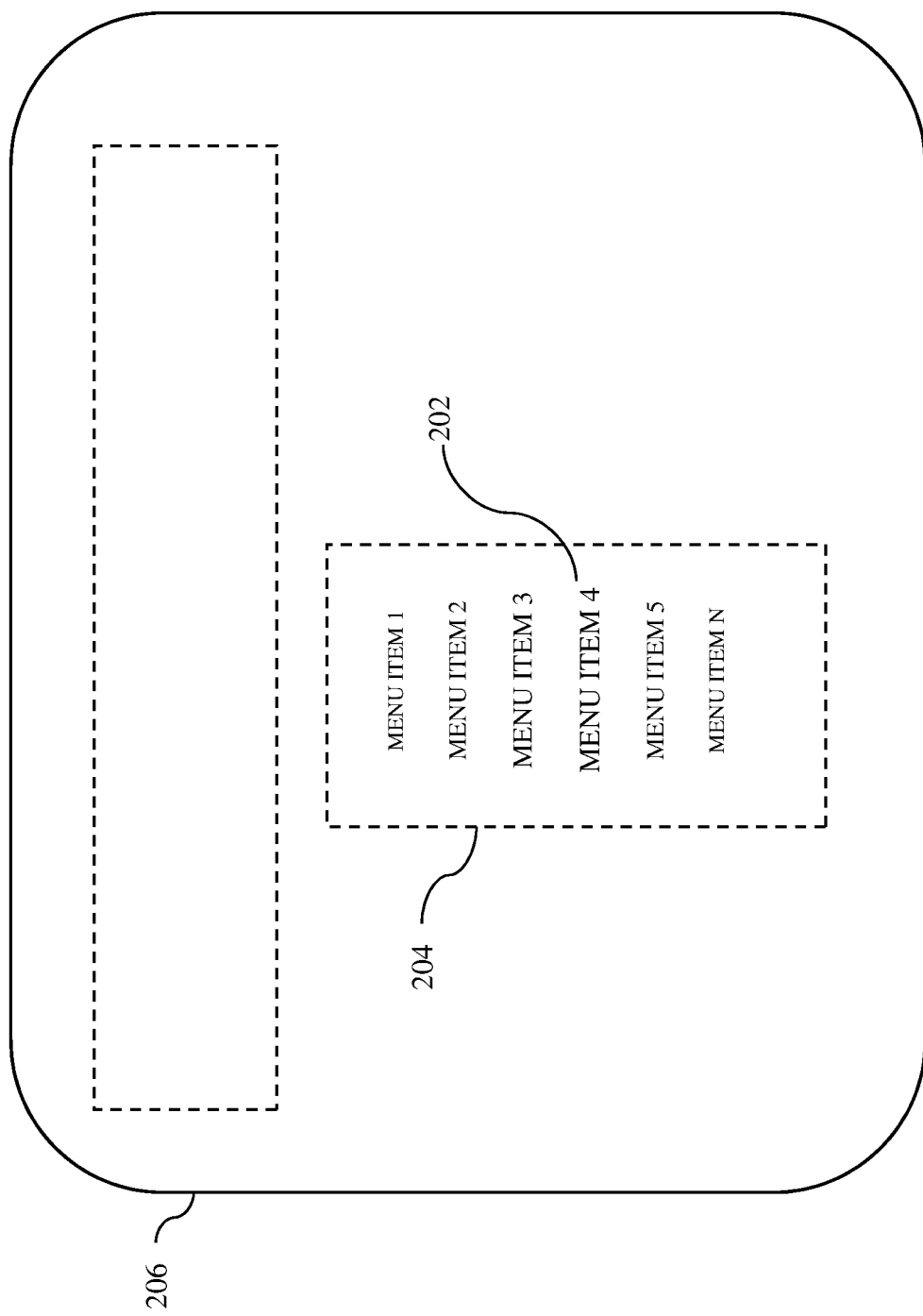
FIGS. 2A-2O illustrate sample graphical user interface displays in one embodiment.

FIGS. 2A-2O show examples of user interface displays in different embodiments, details of which are further described below.

FIG. 3 is a flow diagram illustrating a method of interactively displaying interactive items on a user interface display for computer-user interaction in another aspect, for example, details of the method wherein a vertical and horizontal switching of menu levels may take place. The method may be performed automatically by at least one hardware processor. At operation 302, a list of menu items may be displayed on a first portion of the user interface display. The list of menu items is displayed in a first visual orientation on the first portion. For instance, the first visual orientation may be a vertical orientation. The list of menu items may include one or more menu items from a first menu and may be displayed in response to a first display command provided by the display manager 1050.

FIG. 2A shows an example of a user interface display in one embodiment. As shown, the menu items 202 are displayed in one orientation, for example, vertically, in a first portion 204 of the display 206. The menu items are interactive, for example, in that the items are selectable, and a selection (e.g., a user selecting a menu item by clicking on a user interface menu item) causes a computer to execute programmed functions.

As illustrated in FIG. 2A, the menu items 202 of a first menu are provided in a first portion 204 of the interface in a wheel oriented vertically, i.e., a first orientation. The MUI includes a display 206. The first portion 204 may display the menu items 202 in response to a first display command for a first menu of user-selectable choices to be displayed on the first portion 204 of the MUI. As discussed above, the first display command may be provided by the display manager 1050.

The first display command includes the menu items for the first menu (which, in one embodiment, are stored in the storage device 1120, the scrolling method/orientation and size (and format). For example, the orientation for the menu items for the first menu (to be displayed in the first portion) may be vertical. The first display command may also include a location of display, e.g., location of the first portion. The first portion may be in a central location on the MUI. Each menu item may be selectable by the user.

In an embodiment, the first portion may include a decision-making zone. The decision-making zone may be located at a central location within the first portion. The decision-making zone may be a location in the first or active portion wherein a prominent or highlighted menu item is displayed for immediate selection. For example, in FIG. 2A, MENU ITEM 4 is shown in a decision-making zone and is shown in a larger size font than the remaining menu items so as to be a prominent or highlighted menu item displayed for immediate selection. The first display command for causing provision of the first menu may specify that menu items displayed within the decision-making zone be emphasized or highlighted, such as being displayed in a larger size font than other menu items not in the decision-making zone. In other aspects, the menu item(s) displayed within the decision-making zone may be bolded, italicized, or highlighted using a different color than the background, or underlined.

In other embodiments, the first display command may specify that menu items displayed outside the decision-making zone be deemphasized, such as making the menu items smaller, faded with respect to the other menu items in the decision-making zone.

The first display command is executed by the hardware processor and causes the first menu to be displayed on the first portion of the MUI. The MUI allows the user to select one or more menu items from the displayed menu items on the first portion 204 and to drill down through hierarchical menu level(s) of menu items based on selecting a menu item from a prior and/or subsequent hierarchical menu level(s) of menu items. When a menu item(s) is selected from the first menu displayed on the first portion 204 of the MUI, the input manager 1052 receives and interprets the selection.

As shown in FIG. 2A, all first menu items 202 displayed in the first portion 204 are selectable. MENU ITEM 4 is shown as a prominent menu item and is highlighted as being immediately selectable. As used herein, "immediately selectable" means that a single action, such as clicking by a user, causes the selection of the menu item. MENU ITEM 4 is selectable and highlighted as a prominent menu while the other MENU ITEMS (1, 2, 3, 5, and N) are unhighlighted as receded menu items. The receded menu items are non-immediately selectable, meaning that they require more than one user action for selection. Clicking on the highlighted immediately selectable menu item by the user causes it to be selected. The other menu items may be highlighted for immediate selection through rotation of the wheel or clicking on them. Receipt of a signal, by the input manager 1052, indicative of clicking on the immediately selectable menu item causes the input manager 1052 executing on the processor 1110 to detect the selection of the prominent immediately selectable menu item. Responsive to the selection, the input manager 1052 issues a command to the menu manager 1054 indicative of the selection. The menu manager 1054 then determines the new menu arrangement to be displayed according to the selection and provides a relocation command to the display manager 1050 to cause a change in the MUI.

Referring back to FIG. 3, at operation 304, responsive to detecting a selection of a menu item from the list of menu items, the list of menu items is relocated to a second portion of the user interface display. The list of menu items is displayed in a second visual orientation on the second portion, the second visual orientation being substantially orthogonal (e.g., perpendicular) to the first visual orientation. For instance, the second visual orientation may be a horizontal orientation.

Figure 2B:
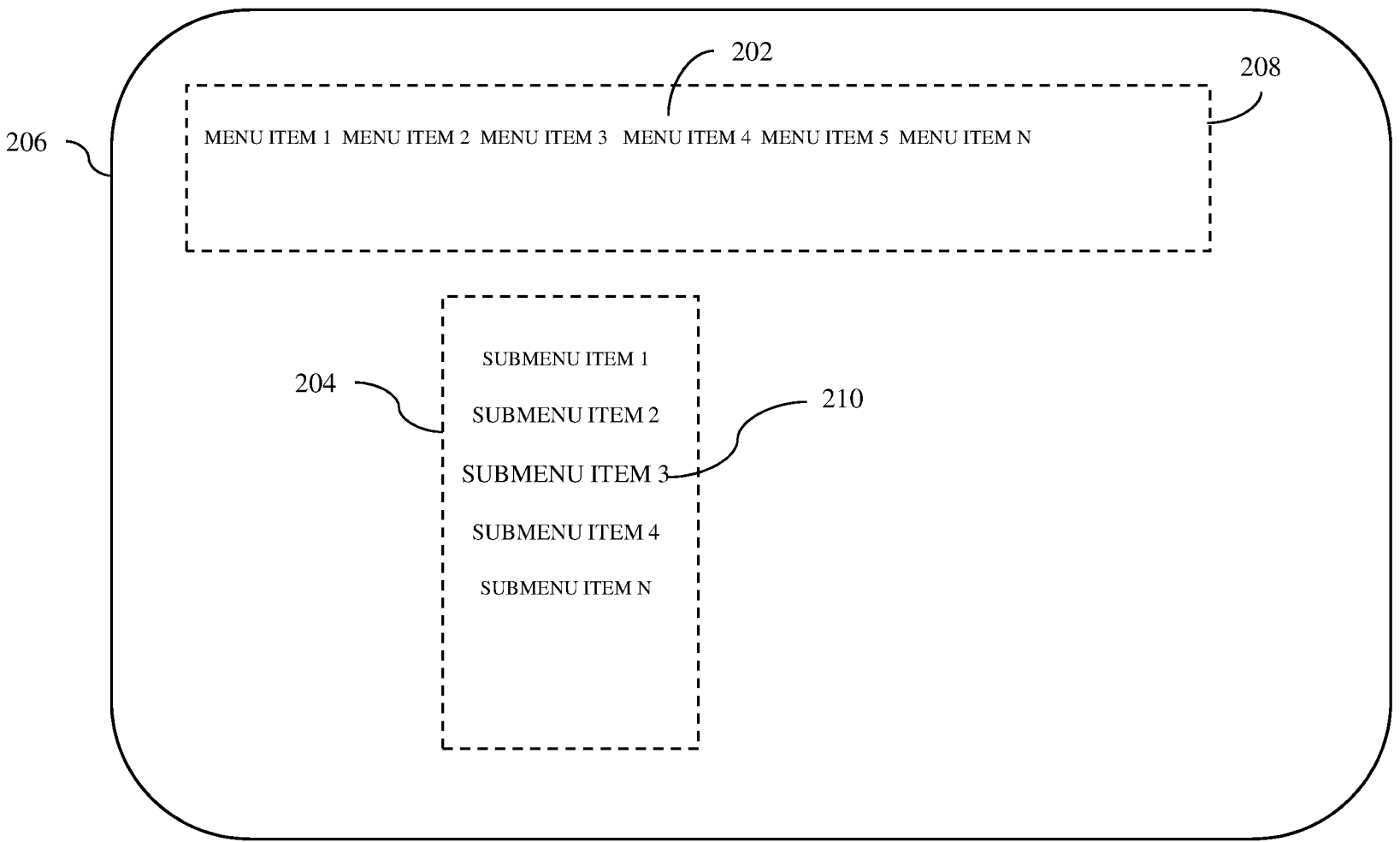
FIG. 2P illustrates an example of a methodical user interface including an advanced context menu in accordance with an embodiment hereof.

A relocation command causes the first menu of menu choices 202 to be relocated from the first portion 204 to the second portion 208 of the MUI display 206. FIG. 2B illustrates the results of the relocation command. The relocation command may include the menu choices of the first menu to be displayed in the second portion 208, the size and orientation of display, the necessary visual components for display, an indication as to which menu item was selected to cause relocation, and any other information discussed herein with respect to the display command. The relocated first menu, displayed now in the historical or second portion 208 as a past menu, may include one or more or all of the menu items 202 and choices previously made available to the user. The menu item 202 selected by the user to cause the relocation becomes a past-selected menu item while the unselected menu items from menu items 202 become past-unselected menu items. The past-unselected menu items are representative of previously navigated hierarchical menu levels. After relocation of the menu items 202 of the first menu, the display manager 1050 causes the MUI to display, in the active or first portion 204, submenu items 210 of the second menu responsive to the first menu selection as a new current or subsequent level of menu choices for the user to interact with. As illustrated in FIG. 2B, the subsequent or second level of menu choices includes second submenu items 210 displayed in the active or first portion 204 of the MUI display 206.

In a method in accordance with an embodiment, upon receiving a signal from the input manager 1052 indicating that a menu item 202 has been selected from the first portion 204, the relocation command is issued. For example, the menu manager 1054 provides the relocation command to the display manager 1050. The relocation command instructs the display manager 1050 to move the first menu from the first portion 204 of the MUI display 206 to the second portion 208 of the MUI display 206 in a second menu. The second portion 208 is at a different location on the MUI display 206 than the first portion 204. Since a menu item was selected from the first menu of menu items 202, the relocated first menu of menu items 202, as displayed in the second portion 208, will now have both a past-selected menu item(s) and past-unselected menu item(s) (e.g., one or more menu items that the user could have selected, but did not). The relocation command may include the first menu items, scroll method and/or orientation, display size (and format) and the location of the second portion.

In an embodiment, the second portion 208 is located farther from a central location of the MUI display 206 than the first portion 204.

In an embodiment, the orientation of displaying the menu items 202 in the first menu in the second portion 208 is different from the orientation of the display of the submenu items 210 in the second menu in the first portion 204. For example, orientation of the menu items 202 in the second portion 208 may be substantially orthogonal to the orientation of the submenu items 210 in the first portion 204. The relocation command may specify that the orientation of the menu items 202 is horizontal (whereas the first display command specified that the orientation of the menu items 202 was vertical). In other embodiments, the orientation may be reversed, where menu items 210 in the first portion 204 are horizontal and the menu items 202 in the second portion 208 are vertical. In embodiments, the first portion 204 is located in a central lower portion of the MUI display 206 and the second portion 208 is located in an upper portion of the MUI display 206.

The relocation command may also specify different sizes for menu items. For example, the selected menu item(s) from the first menu (which triggered the relocation) may be specified to be displayed in an emphasized manner, such as being displayed in a larger font size than unselected menu items. In other aspects, the selected menu item(s) may be bolded, italicized, or highlighted using a different color than the background, or underlined. In another aspect, the relocation command may also specify a relative position of the menu items 202 within the second portion 208. For example, a selected menu item(s) may be positioned in a central location within the second portion relative to other menu items (non-selected menu items).

In other aspects, non-selected menu items from the hierarchical menu level may be displayed in a deemphasized manner. For example, the relocation command may specify the non-selected menu items to be a smaller font size or faded relative to the selected menu items. In other aspects, the relocation command may specify the non-selected menu items to be displayed further from the central portion of the second portion than a selected menu item(s) for the same hierarchical menu level.

The first portion and the second portion may be displayed on the user interface display such that they are non-overlapping. The menu items relocated to the second portion are selectable from that position or location, and the selected menu item may be graphically highlighted, for instance, to provide a visual indication of which item from the list has been selected. The selected menu item may also be centered with other menu items to the left and/or right of the selected menu item. The submenu items that are displayed where the relocated menu items were displayed (before the relocation) are also selectable items. FIG. 2B shows an example of the user interface display in one embodiment with a relocated list of menu items. As shown, the menu items 202 are relocated to a second portion 208 of the display 206, for instance, above the first portion 204, and displayed horizontally. As described in more detail below, the second portion of the display may include many levels of menu items, for example, levels of past decisions and also the options in those levels that were not chosen. Thus, the number of levels of past decisions may be, e.g., 1, 2, 3, 4, 5, 6, 7, 8, 9, 10, 11, 12, 13, 14, 15, 16, 17, 18, 19, 20, or more, e.g., 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, and nested ranges therein, e.g., 2-20, 2-19, 2-18, 3-20, 3-19, 3-18, etc. The second portion, for instance, visualizes a representation of a path of past decisions taken and other decisions (other paths) not taken. In an embodiment, the past decisions taken (menu item chosen) may be aligned, e.g., vertically, e.g., in the center.

The second portion 208 may be caused to display the first menu items 202 in response to a relocation command for a first menu of user-selectable choices to be displayed on the second portion 208 of the MUI display 206. As discussed above, the relocation command may be provided by the menu manager 1054 to the display manager 1050. The first menu of user-selectable choices may include both past-selected and past-unselected menu items. The first menu can include one or more of the first menu items 202 that are selectable by the user. The menu items 202 may be immediately selectable or non-immediately selectable.

The second portion 208 may also include one or more decision-making zones. The relocation command may also specify that menu items displayed within the decision-making zone be emphasized or highlighted. In other aspects, the menu item(s) displayed within the decision-making zone may be bolded, italicized, or highlighted using a different color than the background, or underlined. In other embodiments, the relocation command may specify the same. In other embodiments, the relocation command may specify that menu items displayed outside the decision-making zone be deemphasized or dehighlighted.

The first portion 204 and the second portion 208 are displayed on the MUI display 206 so that they are both viewable, for example, viewable concurrently. The MUI display 206 may be presented via one or more physical display screens. The second portion 208 may contain one or more menus, each menu including both past-selected and past-unselected menu items from previously navigated hierarchical menus. In the representation shown in FIG. 2C, the second portion 208 (historical portion) includes menu items 202 and submenu items 210, each of which were included in the first portion 204 in a previous MUI representation. The menu items 202 and sub-menu items 210 which were past-selected, i.e., those menu items that led to the sub-submenu items 212 being displayed in the first portion, may be highlighted or emphasized to indicate that they were previously selected. As shown in FIG. 2C, MENU ITEM 4 and SUBMENU ITEM 3 are highlighted to indicate that they were previously selected.

The past-unselected menu and submenu items are displayed as selectable options. The past-selected menu item (or choice) also may be displayed as a selectable option, where both are displayed on the second portion 208 (e.g., a historical portion, which can include one or more menu items previously made available to a user). The historical portion contrasts with an active portion, which can include current, user-selectable choices (e.g., located on the first portion of the display) for the current hierarchal menu level. The historical portion can allow users to make selections as well, e.g., by making a selection among previously selected hierarchal levels and/or menus. In this manner, the historical second portion 208 may represent a "trail of breadcrumbs" showing to a user the ordered path of selections made to arrive at the current menu as displayed in the active first portion 204. Further details on selections made in the second portion 208 are provided below.

In some embodiments, the first portion 204 may be adapted to take up a larger portion of the display area of the MUI than the second portion 208. The second portion 208 may be displayed across a smaller area than the first portion 204. The first portion 204 and second portion 208 may be adapted for display in a manner that provides contrast against a background on which they are displayed. For example, the first portion 204 and second portion 208 may be displayed in bright pixels against a dark background or dark pixels against a bright background.

In other embodiments, a command (such as, for example, a relocation command) may be provided by the menu manager 1054 to move or relocate a menu from a portion of the MUI display 206 to another portion of the MUI display 206. In one embodiment, the moving or relocating of a menu and/or menu item(s) can include providing a command to move a menu from one portion of the display to another. In another embodiment, the moving or relocating of a menu can include issuing multiple commands, for example, one command to remove the menu from the first portion 204 of the display and another command to display the menu (either in the same format and/or orientation or in a different format and/or orientation) on a second portion 208 of the display. This relocation can occur, for example, in response to a user's selection from a menu (e.g., a first menu).

Referring back to FIG. 3, at operation 306, on the first portion of the user interface display, where the list of menu items was previously displayed before being relocated to the second portion, a first list of submenu items associated with the selected menu item is displayed in the first visual orientation. Shown in FIG. 2B, a first list of submenu items 210 is displayed in the first portion 204, for instance, vertically.

Referring back to FIG. 3, at operation 308, responsive to detecting a selection of a submenu item from the first list of submenu items, the first list of submenu items is relocated to the second portion, wherein the first list of submenu items is displayed in the second visual orientation and stacked with the list of menu items displayed on the second portion. At operation 310, on the first portion of the user interface display, a second list of submenu items associated with the selected submenu item is displayed in the first visual orientation, for example, vertically. FIG. 2C shows an example of the user interface display in one embodiment with a second list of submenu items. As shown, the first list of submenu items 210 is relocated to the second portion 208, stacked for instance below the relocated list of menu items 202, for example, stacked horizontally. The second list of submenu items 212, i.e., sub-submenu items associated with the selected submenu item, is displayed in the first portion 204. Depending on the depth of the menus or submenus navigated, the horizontal menu structure in the second portion 208 may accumulate a number of menu levels that exceed the number that can be displayed together on the display portion at the second portion 208 (e.g., the number of levels stacked exceed the screen portion allocated for the horizontal menu structure of the second portion 208). In one embodiment, the horizontal menu structure of the second portion 208 may show n number of menu levels, e.g., the last 3 submenus, allowing for scroll capability. For example, scrolling up allows the user to see the other menu items. The number n may be any number, not limited to 3, e.g., 2, 3, 4, 5, etc. In another embodiment, the top m (e.g., 2) menus may be displayed along with the bottom 1 sub-menu to provide top-level context to the last decision. The number m may be any number, not limited to 3, e.g., 2, 3, 4, 5, etc. Scroll capability allows for displaying other menu items, e.g., user can scroll to see other menu items. The user may also expand the entire multi-level of menus and submenus.

As shown in FIG. 2C, a subsequent level of menu choices, e.g., sub-submenu items 212, may be at least one hierarchical menu level (from a third menu) or more than one hierarchical menu level below (from a fourth, fifth, sixth, etc., menu) the first menu of menu items 202. In the example of FIG. 2C, sub-submenu items 212 represent a third menu that is two hierarchical levels below the first menu of menu items 202.

The process of relocating, for example, menu items from one portion to another portion of the user interface display as menu items are selected may continue up or down the levels of the menu items. For instance, the processing at operations 308 and 310 in FIG. 3 may repeat for additional levels of submenus. In another aspect, selecting menu items from the relocated list of menu items may function as a "back" button, without a user having to explicitly click on a back button to return to the previous list of menu items. Yet in another aspect, if a number of relocated lists of menu/submenu items that are stacked reach a predefined number or threshold, for example, such that stacked list in that the area of the second portion becomes too large and encroaches into the area of the first portion, the stacks themselves may be displayed as a rotating wheel or slider, for instance, in the first visual orientation. Thus, for example, menu items in each of the stacked list may be displayed in the second visual orientation (items are slidable in that direction, e.g., horizontally), while each list in the stacked lists is slidable in the direction of the first visual orientation (e.g., vertically). In this way, a vertical bread crumb may be provided on the horizontal sliders and contextualized by the other options to the left and/or right of center (a selected item). Any layer may be adjusted in real time while not having to go back. Such displaying of the vertical and horizontal sliders allows for proceeding through a tree of options and picking desired leaf options. In another aspect, the number of menu and/or submenu items can be collapsible and expandable. For instance, the bottom or last 'n' levels (e.g., 3 levels) which are the most recent may be displayed with the rest of the levels collapsed. Those collapsed levels are made expandable, for example, by user input. As another example, the top 'm' levels (e.g., 2 levels) and the bottom level (e.g., '1' level) may be displayed, representing the top-level context with the most recent option or decision the user is working on (i.e., bottom level).

While FIGS. 2A-2C show the first visual orientation as vertical and the second visual orientation as horizontal, the orientations may be switched. For instance, the first visual orientation may be horizontal and the second visual orientation may be vertical. In another aspect, the first visual orientation and the second visual orientation may be of any other positional display orientations.

As described above, the menu items and associated submenu items may be displayed as a slider graphical element, a rotating wheel graphical element, or another graphical user interface element. For example, concentric wheel elements, as described below with respect to FIGS. 2H-2J may be employed.

In embodiments, an ordering or arrangement of menu items within their menu levels may be determined according to attributes of the menu items. The manner in which the menu items are displayed may be based on attributes selected from whether a menu item is a previously selected or previously unselected item, whether a menu item is selectable or unselectable, whether a menu item includes one or more characters typed by a user, whether a menu item is part of an advanced context menu (described in greater detail below), and/or whether a menu item has a position in a list more central relative to other items in the list.

In embodiments, the way menu items are adapted to be displayed, i.e., the ordering, arrangement, coloring, and presentation of menu items, may be determined according to several different factors. For example, the menu manager 1054 and display manager 1050, in conjunction, may be configured to emphasize menu items that are selected or are past selected, are currently available to the user (i.e., selectable), and/or are positioned in a decision making zone of a first portion 204 or a second portion 208. The menu manager 1054 and display manager 1050 may further be configured to deemphasize menu items that are not selected or are past-unselected, that are currently unavailable to the user, and/or that are positioned away from the decision making zone. In some embodiments, immediately selectable menu items may be emphasized while non-immediately selectable items may be deemphasized. In some embodiments, emphasizing or deemphasizing a menu item may include highlighting or dehighlighting the menu item, as discussed herein. Highlighting or emphasizing may include, for example, bolding, increasing in font size, changing fonts, underlining, changing brightness or contrast, or adjusting position on the display relative to other items. Dehighlighting or deemphasizing may include decreasing in font size, changing fonts, fading, changing brightness or contrast, or adjusting position on the display relative to other items.

The MUI allows the user to jump to a different path of menu items (e.g., by selecting one or more additional menu items at the same, higher, or lower hierarchical level of a menu) by allowing the user to select a past-unselected menu item from a previously navigated menu level displayed on the second portion 208 of the MUI display 206 and a newly displayed menu item(s) on the first menu displayed a current menu being displayed on the first portion. As discussed above and with respect to FIG. 2C, previously navigated menu items (including submenu items, sub-submenu items, etc.) may be relocated to the second portion 208 after a menu item is selected.

The previously selected menu items in the second portion 208 may be highlighted or emphasized to visually indicate the menuing path that has been taken to arrive at the menu or submenu currently displayed in the first portion 204. Previously unselected menu items from the second portion may be selected to permit the user to jump to that branch of a menu. In the example of FIG. 2C, a user has previously selected MENU ITEM 4 and SUBMENU ITEM 3. Selection of a new and previously unselected submenu item 210 from the second portion 208 would cause the menu manager 1054 to issue commands for a new list of sub-submenu items 212 associated with the newly selected submenu item 210 to be displayed as the current menu being displayed in the first portion 204. Selection of a new and previously unselected menu item from the menu items 202 would cause the menu manager 1054 to issue commands to cause the display of a new list of submenu items associated with the newly selected menu item 202 as the current menu being displayed in the first portion 204. In this way, a user may actively jump between various portions of a menuing tree without having to navigate back through the previous decisions.

When a previously unselected menu item (or submenu item, or sub-submenu item, etc.) is selected, a save command may be issued to store a state of the current menu in the first portion before the subsequent menu in the first portion is displayed. In embodiments, as disclosed in greater detail below, navigating through the menu items to a final branch in the menuing tree at the level of an executable menu allows a user to make one or more parameter selections. Should a user navigate away from an execution level menu, the parameters that were currently selected at the time the user navigated away may be stored via a save command issued by the menu manager 1054 to the data storage manager 1064. Accordingly, if a user should later wish to return to the execution level menu, the last selected parameters will be displayer.

Previously unselected menu items may be selectable within the past menu of previously navigated menu items. In embodiments, previously unselected menu items may be immediately selectable, requiring only a click for selection, or may be non-immediately selectable, requiring another step to highlight the menu item prior to selection. In embodiments, the previously selected menu items may be unselectable, as the user has already selected them. In further embodiments, only the previously selected menu item from the lowest hierarchical level in the past menu (i.e., the menu immediately previous to the current first menu) is unselectable, while the previously selected menu items from higher hierarchical levels remain selectable. In the example provided by FIG. 2C, SUBMENU ITEM 3 may be unselectable while MENU ITEM 4 may be selectable.

In embodiments, the various menus are displayed on a background. In an embodiment, the menus are superimposed over the background. The background may consist of one or more colors. In an embodiment, at least a preset percentage of the background pixels may be monochromatic. For example, at least a preset percentage of the background pixels may be black. For instance, 75% of the background may be monochromic (e.g., black, white, gray, etc.). The specific percentage has been described by way of example and other percentages may be used.

In embodiments, display commands and relocation commands may specify the background, including the preset percentage and color, e.g., black, white, gray, etc. In certain embodiments, the background may also include areas of the menus other than text (e.g., menu items). In an embodiment, the text of the menus is displayed in a color to contrast or emphasis the text with the background. For example, when a black background is used, white or yellow may be used for the color of the text, although other colors may be used as well. In other embodiments, the backgrounds and/or text may be comprised of more than one color.

In some embodiments, an initial or first menu, i.e., the starting current menu, may be a default menu that is displayed upon a login of a registered user. In an embodiment, a default menu may be customized for a specific user identifier. In other aspects, the default menu may be specific to a MUI module. For example, the default menu may include as menu items a list of assays, tests, runs, clinical trials, etc. In embodiments in accordance herewith, the default menu is determined according to one or more of the following: a MUI module being run, a location of a device running the MUI module, a user identifier, and an application of the menu. For example, a device located at a user's desktop may run a MUI module that defaults to a default menu suitable for selecting options for experimental design or experimental analysis. In another example, a device located at a clinical instrument may run a MUI module to provide a default menu suitable for selecting options to run an experiment and collect data. In embodiments, the default menu may be a first menu, second menu, third menu, and/or any other menu from a level in a hierarchical menu tree.

In an embodiment, any menu provided in any portion of the MUI display may include search functions. The search function enables a user to enter keywords or other inputs associated with menu items (options). A user input is received via the input manager 1052 and transferred to the menu manager 1054 for searching purposes. The searching allows for the functions (menu items) to be filtered using the entered keywords or other inputs, which shortens a time needed to find a desired menu item. An interface for the search function may be positioned in a central location of respective portions of the MUI display 206, or in the alternative, other portions of the MUI display 206. In further embodiments, no visual interface is provided for the search function. In such an embodiment, a user may access the search function merely by typing.

In an embodiment, any menu item(s) that match or partially match the keyword(s) may be displayed to emphasize the menu item(s). For example, the menu item(s) may be displayed in a larger size than other menu items that do not match or partially match. In other embodiments, the menu item(s) may be bolded, italicized, or highlighted using a different color than the background, or underlined. In other embodiments, menu item(s) not matching or partially matching the keyword(s) may be deemphasized, such as the menu item(s) being smaller or fading the text with respect to the text of menu item(s) that match or partial match. In embodiments hereof, sliders or wheels may be automatically advanced and/or rotated to display menu items matching search terms.

In an embodiment, a first menu selection may operate as a filter on a second menu. In a hierarchical tree, each of several items in a first menu may lead to the same second menu. However, the first menu selection that is made determines the menu items shown when the second menu is displayed. In a simple example, the first menu may include menu items pertaining to team roles while a second menu may include a menu pertaining to team responsibilities. The selection of a specific team role at the first menu may filter the second menu to only show team responsibilities that correspond to the selected role. In some embodiments, such filtering is performed by making specific items of the second menu unselectable.

In an embodiment, any selection made in any menu operates as a filter on the menu items displayed in any other menu. For example, in an embodiment, a series of items in the first menu may be a series of category filters that each lead to a second menu. Each second menu leads to a series of submenus and, eventually, one or more execution menus, permitting the user to select parameters for the selected category filter. After selecting category filters in one or more of the category filter submenus, a user may then select another first menu item that provides a list of second menu items filtered according to the category filters that have previously been selected.

In an embodiment, one or more menus or menu levels may be presented as exceptions to the hierarchical menu tree standard discussed herein. For example, a menu level may include a visual display and/or a video display rather than a text based visual component. Exceptions may be implemented, for example, in situations where information may better be conveyed through alternate means. For example, as discussed above, an execution level menu may include a walkthrough, which may be best presented via a video or series of images. In another example, an execution level menu may be presented for data analysis, and may provide any combination of graphs, charts, tables, etc. to assist in data analysis.

In an embodiment, an advanced context menu may be provided via one or more commands issued by the menu manager 1054. FIG. 2P illustrates an example of a methodical user interface including an advanced context menu 270. The advanced context menu 270 contrasts with the first portion and the second portion, which together provide a "direct workflow mode." The advanced context menu 270 may be accessed via an advanced context menu selector 290, which may, in embodiments, be present on some or all screens of a methodical user interface. The advanced context menu 270 provides additional advanced menu items 271 beyond the items appearing in the current menu in the active first portion 204 or one or more past menus appearing in the historical second portion 208. The advanced context menu 270 may be accessed by clicking or hovering over the advanced context menu selector 290 or otherwise indicating a desire to access the advanced context menu 270. The advanced context menu 270 includes a selection of advanced menu items 271.

The selection of advanced menu items 271 may include items displayed in the current menu in the first (active) portion 204 and items displayed in the previous menus in the second (historical) portion 208. In accordance with an embodiment hereof, advanced menu item(s) 271 of the advanced context menu 270 may be emphasized. For example, the advanced menu item(s) 271 may be displayed in a larger font size. In other embodiments, the menu item(s) may be bolded, italicized, or highlighted using a different color than the background, or underlined.

Other items included in the selection of items in the advanced context menu 270 may be items related to but not currently included in one of the displayed menus. That is, the selection of items in the advanced context menu 270 is driven by the current context of the UI display. For example, five menu items of a first menu may be displayed as the current menu in the active portion. Three additional menu items related to the five menu items of the first menu may be displayed in the advanced context menu 270. The three additional menu items may be items of the first menu that were excluded or limited (as discussed further below) from the current menu display for various reasons.

The advanced context menu 270 offers the user a greater array of accessible menu items without causing clutter in the active portion or the historical portion. In embodiments, some of the advanced menu items 271 in the advanced context menu 270 may be items that are infrequently selected, for example, in less than 50, 45, 40, 35, 30, 25, 20, 15, 10, or 5% of use cases. Advanced menu items 271 of the advanced context menu 270 may be selected according to patterns of user interaction with the MUI, as explained in greater detail below.

In embodiments, the advanced context menu 270 may include three portions. A first top portion 272 of the advanced context menu 270 may include advanced menu items 271 related to the currently active menu, as described above. A second, middle portion 273 of the advanced context menu 270 may include advanced menu items 271 pertaining to MUI modules available on the same workstation at which the advanced context menu 270 is selected. These options may permit a user to swap modules based on a desired task. A third, bottom portion 274 of the advanced context 270 menu may include global functions, such as login/logout functionality, user manuals and help, EULA information, and privacy policy information. The above described ordering is not limiting, and any of the described advanced menu items 271 may be presented in a different order.

In embodiments, when the advanced context menu 270 is selected, the MUI causes other graphics, text, etc. to become faded and/or blurred. The advanced context menu 270 is displayed on a transparent background so that the advanced context menu 270 and the rest of the background are the same (e.g., black). Accordingly, the MUI provides a dialog box adapted to be displayed on the foreground of the UI display to prompt a user for additional information or notify the user of an error, wherein the background of the dialog box is further adapted to match the background of the first and second portions of the UI display, further wherein one or more of text, graphics, photos, and videos displayed in the background of the first and second portions of the UI display are adapted to displayed out of focus when the dialog box is being displayed on the foreground of the UI display.

In an embodiment, certain menu items included in a hierarchical menu tree, i.e., a first menu, second menu, third menu, etc., may be excluded or restricted from being displayed when that menu is being displayed. Exclusions and restrictions may be managed by the exclusion manager 1058 in conjunction with the menu manager 1054. Displaying any menu from a menu tree includes displaying one or more menu items from that menu but does not necessarily require display of all items from that menu. Menu items of a hierarchical menu level(s) may be excluded or restricted from being displayed based on an exclusion table. Exclusion tables may correspond to a user identifier, email address, username, team, and/or account number. In other embodiments, one or more entire menus from a menu tree may also be excluded based on an exclusion table. In certain embodiments, exclusion or restriction information may be stored in the storage device 1120. The exclusion or restriction information may be stored as a data structure. Any data structure described herein may be employed.

Exclusion or restriction information may be used to exclude menu items from the view of a particular user, group of users, type of user, etc. For example, administrative menu items or menu levels may be excluded from view of a user or operator that is an engineer or technician. In another example, design menu items or menu levels may be excluded from view of a user or operator that is a lab assistant or lab technician.

User identifiers, account numbers and the menu item(s) and/or menus for exclusion may be input by an administrator. For example, an admin console module, discussed in greater detail below, may be used to manage and generate exclusion tables. The managing may be done when a user registers with the system. In other embodiments, the exclusion information may be added after registration and periodically updated.

In embodiments, each time a user logs into the system, the hardware processor maintains a record of the login (and also a log out) via the data storage manager 1064. In an embodiment, this record, i.e., login historical data, may be in a form of any data structures described herein. In an embodiment, this login historical data may include the user identifier and/or account number, a login time/date and a log out time/date. In an embodiment, upon receipt of the login information, the data storage manager 1064 adds the user identifier and/or account number and the login time/date to the login historical data.

In certain embodiments, before issuing a command for displaying any menu, the menu manager 1054 may check the exclusion table (for example, stored in the storage device 1120) to determine if any menu items in the initial display menu (e.g., default menu) are listed to be excluded from display for the user (or account number). In an embodiment, the menu manager 1054 may match the user identifier and/or account number of the user currently logged in with user identifiers and/or account numbers listed in the exclusion table. If there is a match, then the menu items listed in the exclusion table are to be excluded from being displayed in the initial display menu. This exclusion may be carried out, through the issuance of a separate exclusion command and/or instruction, or in the alternative, the exclusion can occur by modifying any display commands that cause the available menu item(s) to be displayed. The menu manager 1054 may remove the menu items included in the list from the menu items in the initial display menu (e.g., default menu) and issue the first command without the removed menu items.

In certain embodiments, each time the input manager 1052 receives a selection of a menu item in the current menu, prior to issuing a relocation command, the menu manager 1054 may determine whether any menu item on a hierarchical menu level lower than the hierarchical menu level currently being displayed on by the MUI display 206, as the current menu, is listed to be excluded (or whether a lower hierarchical menu is to be excluded). The determination may use the login historical data and the exclusion table. The login historical data may be used to confirm that the same user (user identifier or account number) is still logged in and match the same with user identifiers and account numbers in the exclusion table. In other embodiments, the menu manager 1054 may use a user identifier and account number received from the user manager 1056 instead of the login historical data for the determination. In other embodiments, a similar determination is made prior to issuing any relocation or display command.

In yet other embodiments, different exclusion tables may be used depending on whether the menu items are to be displayed on the MUI display 206 in the first portion 204 or the second portion 208. In accordance with this embodiment, the exclusion table may have additional columns of information, one column for each portion (menu). A column for the first portion lists menu items to be excluded when displayed on the first portion 204 of the MUI display 206, a column for the second portion 208 lists menu items to be excluded when displayed on the second portion of the MUI display 206, and columns for additional portions list additional menu items to be excluded when displayed on any additional portions of the MUI display 206.

As described above, an account number may be associated with multiple users (user identifiers). Thus, when an account number is used as the basis of exclusion, all of the users associated with the account number may have the menu items excluded from being displayed on the MUI display 206.

In another embodiment, since certain account numbers may be linked, when the account number is used, any account number linked with the account number may also have menu items excluded.

In other embodiments, instead of excluding menu items, the menu items may be moved to a position of the respective menus to deemphasize the menu items with respect to other menu items. In accordance with this embodiment, the exclusion table may be used by the menu manager 1054 to reorder or change positions of the menu items on a hierarchical menu level. A subsequent command (first command, second command and/or third command) may reflect the changed position for the menu items.

In other embodiments, menu items (or hierarchical menu levels) may be excluded based on a particular device or a location of a device. The device on which exclusion is based may be based on any of the one or more devices executing the various software instructions of the methodical user interface control system 1102.

The exclusion or restriction information may be stored, for example, in storage device 1120 as a data structure. Each device may have an identifier such as a Media Access Control (MAC) address or other unique identifier. The identifier of the device is not limited to a (MAC address and other identifiers may be used, such as Internet Protocol (IP) address, machine name, etc. In an embodiment, one column in the table may include the identifier, e.g., MAC address. A second column in the table may include the menu item(s) or hierarchical menu levels that are to be excluded from display, respectively, associated with the identifier, e.g., MAC address.

In other embodiments, instead of a table (or tables), a list of menu items and/or hierarchical menu levels are stored in association with the identifier, e.g., MAC address.

The device identifiers, such as the MAC address, and the menu item(s) and/or hierarchical menu levels for exclusion may be input by an administrator and/or one or more users with appropriate permissions. This exclusion information may be input when a first MUI module is installed into a device. In other embodiments, the exclusion information may be added after installation and periodically updated.

In certain embodiments, upon receiving the login historical data or in response to receiving a notification, before issuing any command for displaying any menu (and menu items), the hardware processor executing the input manager 1052 may check the exclusion information in the storage device 1120 to determine if any menu items for the initial display menu or associated with the selection are to be excluded for the device(s).

In an embodiment, the menu manager 1054 may compare the device identifier with the device identifier(s) listed in the exclusion information. When there is a match, certain menu items are to be excluded from display on the MUI display 206. For example, when the initial display menu (e.g., default menu) or a hierarchical menu level lower than the hierarchical menu level currently being displayed on the MUI display 206 as the current menu, which is associated with a selection, includes one or more menu items listed to be excluded, the menu manager 1054 may remove the excluded menu item(s) from the menu prior to issuing a display command and then issue the display command with the menu items removed. In this example, the removed menu item will not be displayed on MUI display 206.

In other embodiments, certain menu items (or hierarchical menu levels) may be excluded based on what hierarchical menu level is currently being displayed as the current menu (in the first portion) or the previous menus (in the second portion). In an embodiment, one column in the exclusion table may include a menu identifier of a hierarchical menu level. A second column in the table may include the menu item(s) or hierarchical menu levels that are to be excluded from display, respectively, associated with the menu identifier.

The menu identifier represents the hierarchical menu level that is displayable on either the first menu or second menu. The excluded menu items are menu items that are unavailable to be selected from a displayed hierarchical menu level. These menu items may be application specific. In certain embodiments, when a hierarchical menu is displayed, as the current menu in the first portion 204 or the previous menu in the second portion 208, and a selection is made, prior to issuing a command, the menu manager 1054 checks the exclusion information to determine whether any menu items associated with hierarchical menu level which is selected to be display should be excluded. Based on the determination, the menu manager 1054 may remove the excluded menu items from the menu prior to issuing a responsive command and then issue the responsive command with the menu items removed. This exclusion may be carried out, through the issuance of a separate exclusion command and/or instruction, or in the alternative, the exclusion can occur by modifying the first, second, and/or third display commands that provide the available menu item(s) to be displayed.

In other embodiments, instead of a display or relocation command being issued with the menu items removed, an exclusion command may be issued by the exclusion manager 1058 in combination with the display or relocation command. In this embodiment, the display command would have all of the menu items associated with the menus and the exclusion command would cause the display manager 1050 to delete the executed menu items included in the exclusion command prior to causing the display.

In other embodiments, a number of menu items to be displayed may be limited by the menu manager 1054 based on a frequency of usage. For example, in an embodiment, the number of menu items may be limited based on a frequency of selection. In certain embodiments, the frequency can be determined over a predetermined period of time. The frequency of selection can be preset or customizable, and can include, for example, between 50%-80% frequency, although other frequencies of selection are contemplated as well. By limiting display of menu items to include only menu items that are used at greater than a specific threshold frequency, the amount of clutter in the menuing system is reduced and the menuing experience is streamlined.

In accordance with this embodiment, the input manager 1052 tracks selection of all menu items and stores the same in the storage device 1120. In an embodiment, the list of previously selected menu items is stored in a data structure.

For example, the data structure may be a menu item selection table or any other data structures (e.g., those specifically described herein).

In certain embodiments, a user's or users' selections may be tracked over a preset period of time. The period of time may be one day, one week, one month, or other preset or customizable periods of time. The specific period of time may be based on an application, such as a clinical trial or type of research, type of test, type of organization (e.g., university, corporate), etc. The tracking may be repeated for each preset period of time.

Each time a notification is received by the hardware processor executing the input manager 1052, within the preset period of time, the input manager 1052 may record, the user identifier, username, email address, and/or account number, the selected menu item and the time and date of the selection. The time and date may be obtained from a timestamp included in the notification. In an embodiment, the user identifier and account number may be obtained from the login history table. In other embodiments, the user identifier and account number may be included in the notification.

At the end of a specific period of time, the input manager 1052 determines a frequency of selection for each menu item. In an embodiment, the input manager 1052 may determine for a user identifier, the frequency of selection. The frequency of selection is based on the number of times that the menu item was selected verses a total number of selections (within the specified period) by the user identifier.

In other embodiments, the determination may be based on account number in addition to user identifier. For example, the input manager 1052 may determine a frequency of selection of a menu item by at least two user identifiers having the same account number. In this example, users form teams, where a single account number is associated and/or linked with two or more user identifiers. In another example, a team can include two or more account numbers associated and/or linked together. In still a further example, teams can be formed whereby N unique users are associated and/or linked with M unique account numbers, where N is greater than M. Identifying user identifiers having the same account number may be achieved using the shared account flag in the registration table in combination with the menu item selection table to determine that the at least two user identifiers made a selection within the period of time.

For a menu item, a number of selections of the menu item is aggregated for the at least two user identifiers (as determined from the menu item selection table). Similarly, the total number of selections is aggregated for the at least two user identifiers (also as determined from the menu item selection table). The frequency is then based on the aggregated selections of the menu item and the aggregated total selections.

In other embodiments, the frequency determination may be based on selections where the user identifier is associated with an account number that is linked to other account numbers (e.g., a team of users). In accordance with this embodiment, the input manager 1052 may identify the linked account numbers using the multiple account flag which is set to a specific value when the account number is linked. Once identified, the input manager 1052 may determine the frequency of selection by using selections from a user identifier which is associated with one of the linked account numbers. In this embodiment, selections from other user identifiers or the same user identifier that is not associated with one of the linked account numbers (in the case where the same user identifier is associated with different account numbers) may be ignored (not used in the determination). Similar to above, the input manager 1052 may determine the number of selections of a menu item and the total number of selections to determine the frequency. In other embodiments, the methodical user interface control system 1102 may use selections from any user identifier(s) which is/are associated with one of the linked account numbers for the determination (and may aggregate the selections).

In other embodiments, the frequency determination may be based on selections of at least two user identifiers where the user identifiers are associated with one or more account numbers that are linked to other accounts. In accordance with this embodiment, the hardware processor executing the input manager 1052 may identify the linked account numbers using the multiple account flag which is set to a specific value when the account number is linked. Once the linked account numbers are identified, the hardware processor executing the input manager 1052 may further identify at least two user identifiers (associated with the linked account numbers) that made selections within the period of time, using the menu item selection table.

For the identified at least two user identifiers that made a selection, for a menu item, a number of selections of the menu item is aggregated for the at least two user identifiers (as determined from the menu item selection table). Similarly, the total number of selections is aggregated for the at least two user identifiers (also as determined from the menu item selection table). The frequency is then based on the aggregated selections of the menu item and the aggregated total selections.

In other embodiments, the frequency determination may be based on all selections regardless of the user identifier and/or account numbers. In accordance with this embodiment, the input manager 1052, for each menu item, may determine the number of selections of the respective menu item verses the total number of selections (of any menu item) within the period of time to determine the frequency.

The frequency described above can be used in conjunction with a limiting command issued by the menu manager 1054. The functionality of the limiting command is similar to the functionality of the exclusion command, as discussed above. The limiting command serves to limit certain menu items to be displayed based on a criterion or two or more criteria. For example, the limiting command can be based on: (a) the frequency with which a user has previously selected the item while he/she was logged into his/her account. In one example, this determination can occur based on a given period of time. In another example, it can be based on the number of times a given user logged into his/her account. Another criterion includes: (b) the frequency with which at least two users have previously selected the item while they were logged into an account. In certain embodiments, this can include an amount of time for a given user or based on the total time the users were logged into their accounts. Alternatively, it can be based on the total number of logins of a given user or the total number of logins in the aggregate. Still further, the criterion can include: (c) the frequency with which a user has previously selected the item while he/she was logged into an account associated with multiple accounts; or (d) the frequency with which at least two users have previously selected the item while they were logged into one or more accounts associated with multiple accounts. For both of these examples, as described with regard to examples (a) and (b), above, the frequency can be based on one or more combinations of the period of time one or more users remained logged into their accounts or the number of account logins. Still further, the criteria can include: (e) the frequency with which any users have previously selected the item while logged into any account; and/or (f) the frequency with which any users have previously selected the item while logged into any account associated with multiple accounts. In these two examples, the previously selected item can be tracked with the use of a data structure, such as table (or any other data structure described herein), which can be periodically cleared after a given period of time elapses or a certain number of total logins by one or more users occurs. In certain embodiments, the criteria described in (c), (d), and (f), above, can be applied to team accounts, in particular, where users of those accounts are team members with one or more team that are associated with multiple accounts.

When the determined frequency is greater than or equal to a threshold percentage, menu items may be limited for an immediate subsequent period of time. The threshold may be based on the application. In an embodiment, the threshold percentage may be 50% or more. In other embodiments, the threshold percentage may be 60% or more. In yet other embodiments, the threshold percentage may be 70% or more. In further embodiments, the threshold percentage may be 80% or more. In other embodiments, the threshold may be a percentage range. For example, the threshold percentage may be in a range of between 75% and 85%. The specific percentages have been described herein by way of example, and the threshold percentage is not limited to the same. Any threshold percentage or range may be used.

In other embodiments, a ratio of selection may be used in place of a frequency of selection. The ratio is defined as the number of selections of the menu item divided by a number of selections of other menu items. For example, ratios of 9:1, 7:1, 5:1, 3:1, or any other suitable ratio may be used.

In other embodiments, a number of times the menu item is selected may be used in place of a frequency of selection. For example, a specific selection threshold may be used instead of a percentage. The specific selection threshold may be 5, 10, 15, etc.

Once it is determined that the menu items may be limited, the hardware processor may determine which menu items may be displayed on the MUI display 206 in the immediate subsequent period of time, and which menu item(s) are to be limited. In accordance with embodiments, any menu item determined to have a frequency above the threshold percentage may be displayed (e.g., not limited).

In further embodiments, a display limitation may be based on menu items having a selection frequency below a certain threshold, e.g., below 50%, 40%, 30%, 20%, 10%, etc.

In several embodiments, limiting commands can be issued based on various criteria. For example, one or more menu item(s) could be excluded based on menu item(s) being designated as unavailable to a particular user. This can occur, for example, if a particular user has not selected one or more menu item(s) over a certain period of time. Similarly, one or more menu item(s) could be limited based on a menu item(s) being designed as unavailable to an aggregation of two or more users. In this example, the frequency of two or more users selecting or not selecting one or more menu item(s) over a period of time can affect whether a limiting command issues for those menu item(s). Other embodiments contemplate issuing limiting commands in a similar fashion for the previous two examples, but for individual team and/or aggregation of teams (i.e., based on the frequency of selection of menu item(s) by users that are associated with teams). Still further, other embodiments can limit menu items based on a particular machine or aggregation of machines that are executing the computer application that one or more users have logged into.

In an embodiment, the menu manager 1054 may issue a limiting command to the hardware processor executing the display manager 1050. In accordance with this embodiment, the limiting command may include the menu items determined to have a frequency above the threshold percentage. The limiting command may be issued in conjunction with the one or more display commands. Upon receipt of the display command and the limiting command, the display manager 1050 may delete or remove menu items included in the display command that are not also included in the limiting command prior to causing the menu items to be displayed on the MUI display 206.

In other embodiments, the limiting command may include menu items other than the menu items determined to have a frequency above the threshold percentage. Upon receipt of the display command and the limiting command, the display manager 1050 may delete or remove menu items included in the display command that are also included in the limiting command prior to causing the menu items to be displayed on the MUI display 206.

In other embodiments, instead of a separate limiting command, the display command may be modified by the menu manager 1054 to remove menu items other than the menu items determined to have the frequency above the threshold percentage.

Through use of the limiting command, menu items (user-selectable options or choices) may be limited to fewer than a number of menu items on the first menu and the second menu. For example, the first menu may include nine menu items, but the use of a limiting command restricts the total number of menu items to be displayed to be less than nine. For example, a total number of menu items (user-selectable options) may be fewer than or equal to seven (or fewer than the seven), fewer than or equal to five, fewer than or equal to three, or fewer than or equal to any other number. The number of menus (limited number) described herein is just an example, and the number may be any number selected to provide a limited display to avoid or prevent the user from being overwhelmed with choices. In embodiments, menu items that are excluded from display due to a limiting command are provided in the advanced context menu 270. In embodiments, menu items excluded from display based on a limiting number may be selected according to frequency of selection.

In some embodiments, if after determining the number of menu items that has a selection frequency greater than the threshold percentage and the number of menu items is greater than the limiting number, e.g., seven, the menu manager 1054 may increase the threshold percentage to lower the number of menu items that has a selection frequency greater than the threshold percentage. Thus, the menu manager 1054 may be configured to select and display a specific number of menu items having the highest selection frequencies.

In an embodiment, the limiting function may operate as follows, as applied to any type of MUI module. The threshold percentage may be used to determine which menu items will be displayed (e.g., not limited). For example, a threshold percentage of 90% or 80% may be used, meaning that only menu items with a selection frequency higher than 90% or 80% are displayed. In an example, the selection frequency may be applied based on user login sessions, meaning that only menu items used 90% or 80% of the time that a user logs in are displayed. The limiting function may be applied to one or more menu levels, i.e., to a first menu level, a second menu level, etc. In some embodiments, the threshold may vary based on the menu level (e.g., lower levels may have lower frequency requirements for display—as there are often a greater number of options at lower levels, they may be selected less often.) Those menu items that do not meet the threshold (e.g., used 10% or less, or used 20% or less) are displayed in the advanced context menu, which changes according to the current menu being displayed. In this manner, the user's choices are limited to those that are most frequently used throughout the MUI, permitting significantly faster navigation by the user.

The 90%/10% and/or 80%/20% values are exemplary only and other values may be selected according to the MUI module being implemented. In an example, the limiting function may also be based on a default protocol as compared to a user customized protocol. For example, a vendor may market an assay kit including a standard protocol that further permits customer modifications. The standard protocol options may be included in the available menu items displayed in the active portion as the user moves through the menuing system, while the available customer modifications may be displayed in the advanced context menu. This division of menu items may be adjusted based on actual user operation after that particular assay kit has been used several times by a user.

Similarly, by using the limiting command, menu items (user-selectable options) may be limited to fewer than a number of menu items on the first menu, the second menu and the third menu.

In certain embodiments, when the period of time expires, the menu item selection table may delete the selection history for a new determination. In this example, the menu item(s) that were previously excluded will again be made available.

In embodiments, the MUI may provide team integration via communications between multiple MUI modules. An integrated system managed by systems consistent with embodiments hereof may be managed by multiple MUI modules configured for completing different tasks by different operators. For example, using the example of a laboratory information management system (LIMS), an admin console module, an experimental design module, an inventory control module, an experimental analysis module, and an experimental procedure module may be provided. The admin console module may provide the features and functionality to manage the various users, operators, instruments, and teams. The experimental design module may permit one or more members of a team to design experiments that other members of the team will conduct. The inventory control module may permit other team members to review inventory and order more consumables, taking into account experimental history and future scheduled experiments. the experimental procedure module may permit team members responsible for running the experiments to access the already designed experiments and implement them, through interaction between the MUI, the operator, and external systems. Finally, the experimental analysis module may permit other team members to access results of experiments after they have been conducted. Based on user and team set-up prepared via the admin console, each user may log-in to the system and be provided with access to the requisite modules for completing the tasks that they are responsible for. In embodiments, the requisite modules may be installed on computing devices in appropriate locations for completing tasks (i.e., an experimental procedure module may be installed on a device connected to a laboratory instrument while an admin console module may be installed on a desktop device). Accordingly, the systems provided herein permit the integration of workflows between multiple team members through the use of a single and consistent interface.

In embodiments, the display manager 1050 may be configured to provide one or more icons or animations to designate a "working" status of the methodical user interface control system 1102. When the methodical user interface control system 1102 is processing, a working status indication is provided to alert a user that processing is occurring to prevent impatience. In an embodiment, a working status indication may be provided via a light fountain display presented in a portion of the screen not occupied by active or historical portions. For example, a bottom portion of the screen, centered beneath the active portion, may be used for a light fountain display. The light fountain may provide a series of cascading bars shown in colors consistent with the remainder of the MUI. In an embodiment, the cascading bard may be presented in white and various shades of blue. In an embodiment, the bars are presented in four rows of elongated bars. Each row may contain, for example, a plurality of bars between two and twenty of varying lengths. When the system is processing, the bars may flash on and off in different shades of white and blue and in different lengths, giving the impression of a waterfall or light fountain.

Embodiment described herein further include methods of designing user interface system. For example, such methods may include the design of MUIs consistent with embodiments hereof. Methods of designing user interface systems may include generating hierarchical menu trees as described herein. Hierarchical menu trees may include a series of menus, each including menu items that lead to a subsequent series of menus. Methods of designing user interface systems may further include selecting execution menus to terminate branches of the hierarchical menu tree, wherein the execution menus are configured to execute one or more commands within the software, to provide one or more sets of instructions to a user, and/or to output one or more commands to a connected device, system, instrument, or machine. Methods of designing user interface systems may further include configuring each of the menus in the hierarchical menu tree with one or more display modes, including at least an active display mode for display in an active portion of a user interface and an historical display mode for display in an historical portion of user interface. Further aspects of methods of user interface design may further include design methods for any of the menu functionalities described herein.

In further embodiments, MUIs consistent with the disclosure may provide integrated help options during hierarchical menu navigation. A user may request help with a given menu by pressing a particular key combination and/or by accessing a help option displayed by the advanced context menu. Integrated help options may include one or more dialog boxed designed to provide explanations to a user regarding the options presented. As discussed above, the MUI provides a large amount of blank or background space. Thus, help options may be presented as pop-ups or dialog boxes pointing to the portions of the MUI for which a user seeks help without compromising the original MUI display. In embodiments, enabling the help functionality may cause a dialog box to appear as a user hovers over or otherwise indicates any item in the MUI.

In further embodiments, the MUI historical portion may be further adapted to display menu items of menus subsequent to the current menu. For example, as a user navigates a current menu, they may, for example, scroll a vertical wheel, causing different menu items to be highlighted or emphasized. A submenu related to the highlighted menu item may be displayed in the historical portion to provide a visual representation of a subsequent menu to the current menu including future items that can be subsequently selected.

In embodiments, as discussed above, the first active portion and the second historical portion are each adapted to for consistent display in a same portion of the MUI. Although the positioning of each of these portions is not limited to a specific place on the MUI, in certain embodiments, the location, once selected, is maintained. Accordingly, the active portion of the MUI display is adapted to be consistently displayed within a first same area of the UI display to optimize a user's focus while interacting with the UI display and the historical portion of the MUI display is adapted to be consistently displayed within a second same area of the UI display to optimize a user's focus while interacting with the UI display.

The prior description provides example menu configurations for providing a UI display of multiple menus in a hierarchical menu tree. FIGS. 2D-2M provide additional examples of menu display configurations. The following menu display configurations may be used, without limitation, in any combination with each other and with the menu configurations previously disclosed. For example, selection of a particular menu item anywhere in the hierarchical menu tree may cause the processor to execute commands to cause the UI display to shift to any of the menu configurations described herein. In particular, specific menu display configurations may be associated with specific menu selections.

Figure 2D:
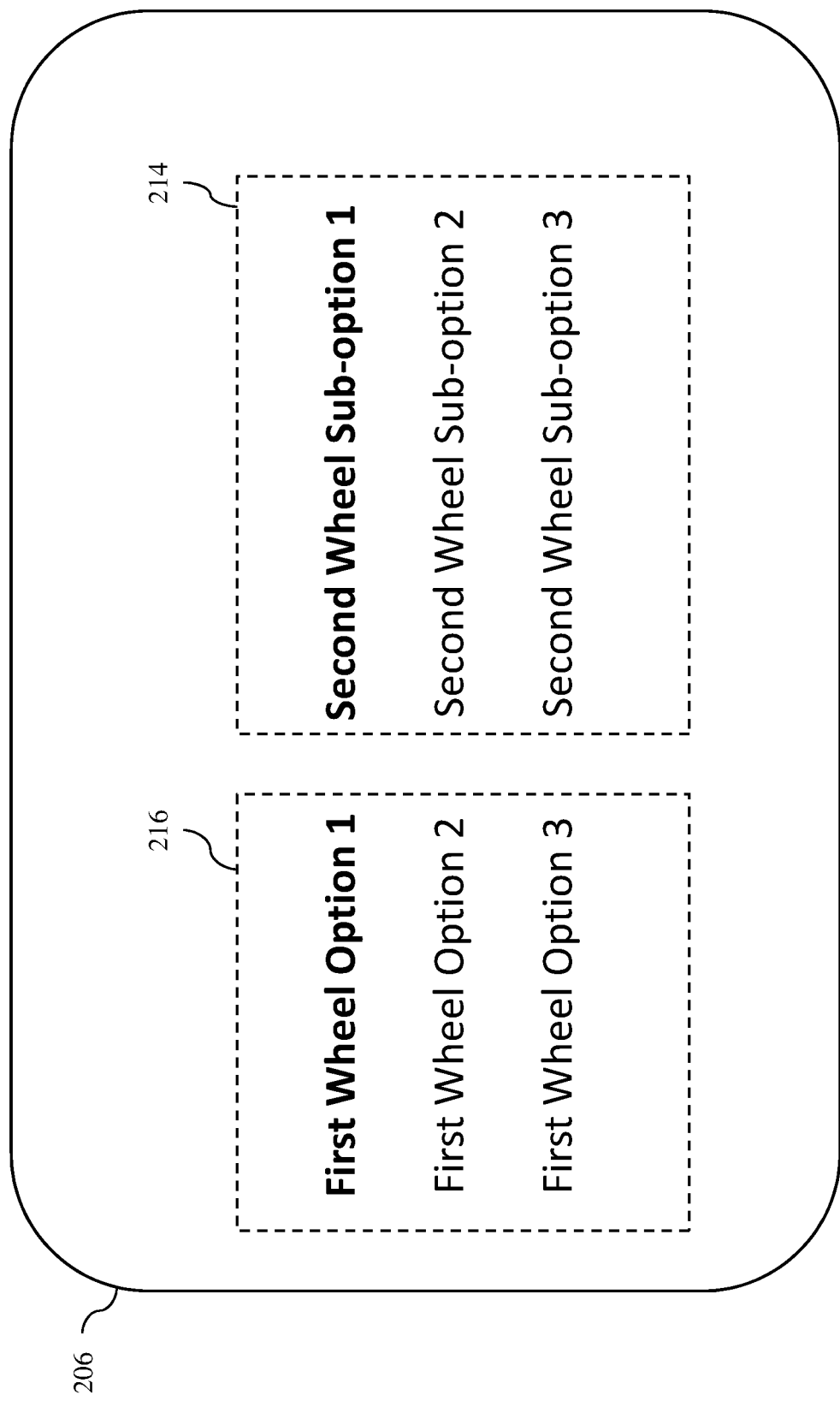

FIG. 2D shows another example of a menu display configuration in one embodiment. FIG. 2D illustrates a two wheel configuration in which the first wheel option has sub-options in a second wheel. For instance, selecting an option in a first wheel of options displays in the second wheel, the sub-options associated with the selected option. In an embodiment, a first portion 214 of the display may initially display the first wheel, and responsive to a selection of an option from the first wheel, the first wheel with its options may be relocated to a second portion 216 adjacent to the first portion. The first portion may then display the second wheel with sub-options to the first option, for example, in a parallel fashion (first wheel displayed in parallel to the second wheel in the same visual orientation).

In further embodiments of this embodiment, both the first wheel and the second wheel may be displayed in the first portion 214 of the MUI display 206. The first wheel may be displayed in a first sub-portion of the first portion 214 and the second wheel may be displayed in a second sub-portion of the first portion 214. As used herein, sub-portions may be divided portions of a larger portion. Sub-portions may also be used interchangeably with sub-sections. In embodiments, selection of a menu item in the first wheel may be caused simply by clicking on any menu item in the first wheel or by rotating any menu item in the first wheel to a prominent, emphasized position. Selection of an item from a first menu on the first wheel may cause the second menu displayed on the second wheel to be revised accordingly. In still further embodiments of this embodiment, the first portion 214 may be split into more than two sub-portions, with each sub-portion including a wheel displaying a corresponding menu. Thus, three wheels may display a first menu, a second menu, and a third menu, representing different levels of a hierarchical menu tree. In another example, three wheels may display a second, third, and fourth menu. Other examples may include any number of wheels.

In further embodiments, multiple wheels may be displayed in multiple sub-portions of the first portion 204 to permit the user to select from multiple menus at a same hierarchical menu level. For example, selection of a specific menu item at one menu level may lead to the display of multiple submenus at the same level. Thus, selection of an item at a second menu level may lead to display of multiple third menus, each containing a plurality of third menu items. In embodiments, the multiple submenus displayed may be execution menus, permitting a user to make multiple execution menu selections concurrently. In embodiments, where multiple submenus are displayed, the multiple submenus may be related or otherwise associated with one another.

Figure 2E:
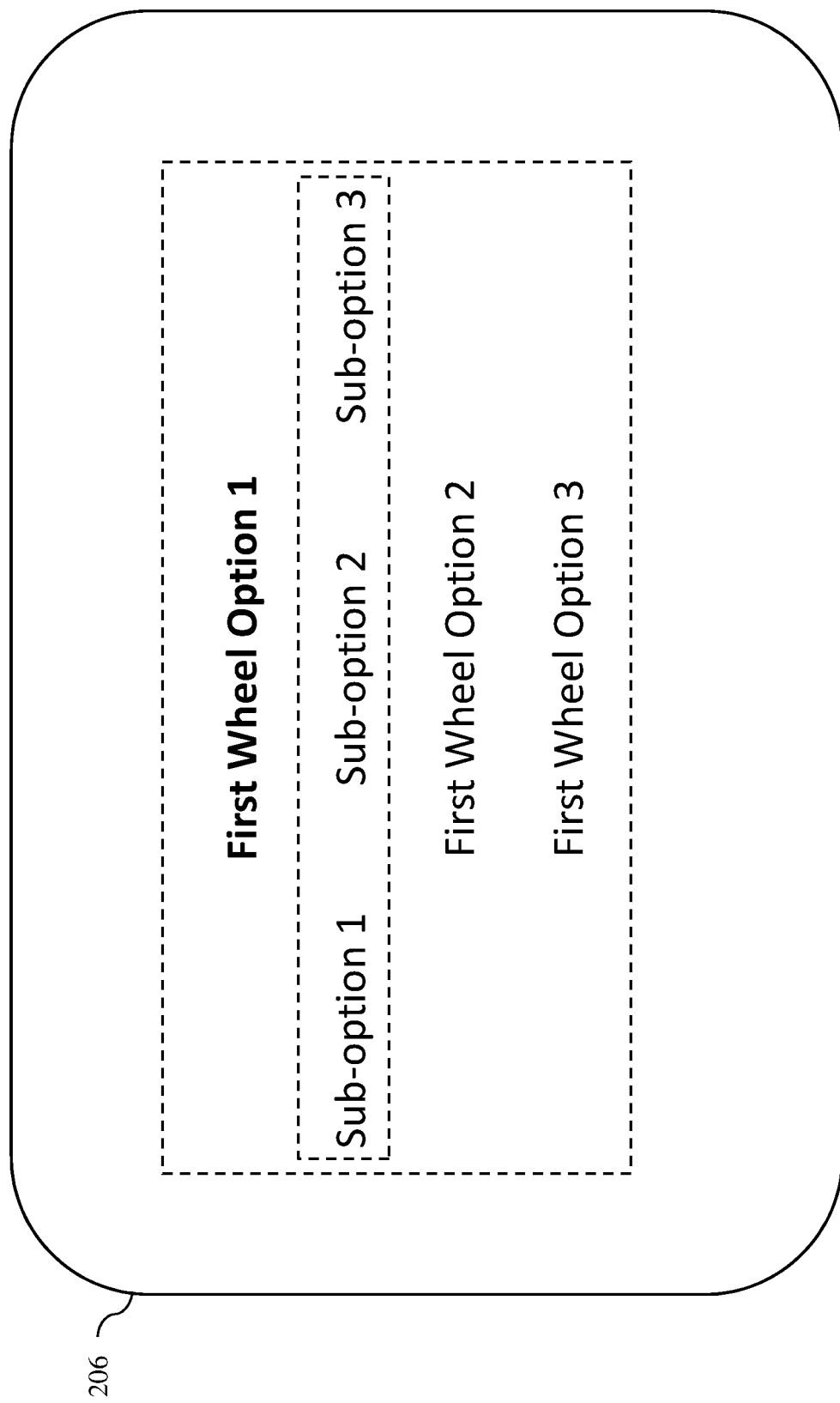

FIG. 2E shows yet another example of a menu display configuration in one embodiment. In this display configuration, two wheels are compressed into one wheel. Wheel option has sub-options which are expressed within the one wheel associated with the active wheel option. In this configuration, the first portion and the second portion of the display overlap but still all menu items are visible (or can be made visible by expanding in case of collapsed items, sliding or rotating a wheel of items). For instance, the second wheel of options may be displayed within the first wheel. The first wheel of options may be rotatable in one direction (e.g., vertically up and down) while the second wheel of options may be rotatable in another direction (e.g., horizontally sides ways, left and right). Selected path is also made visible in the second portion. For instance, selecting 'Sub-option 2' shown in the display moves that selected option below the 'First Wheel Option 1'.

Figure 2F:
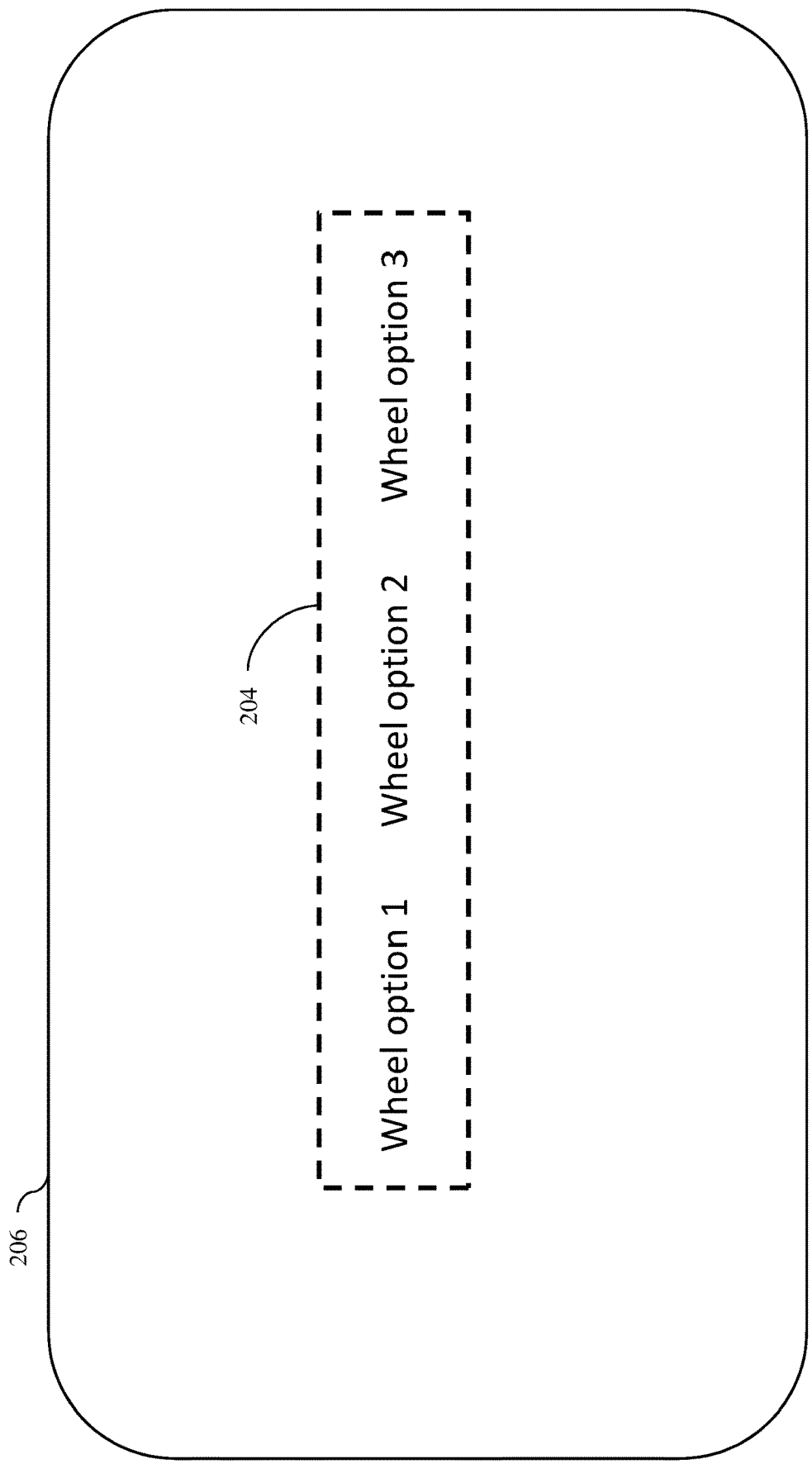
Figure 2G:
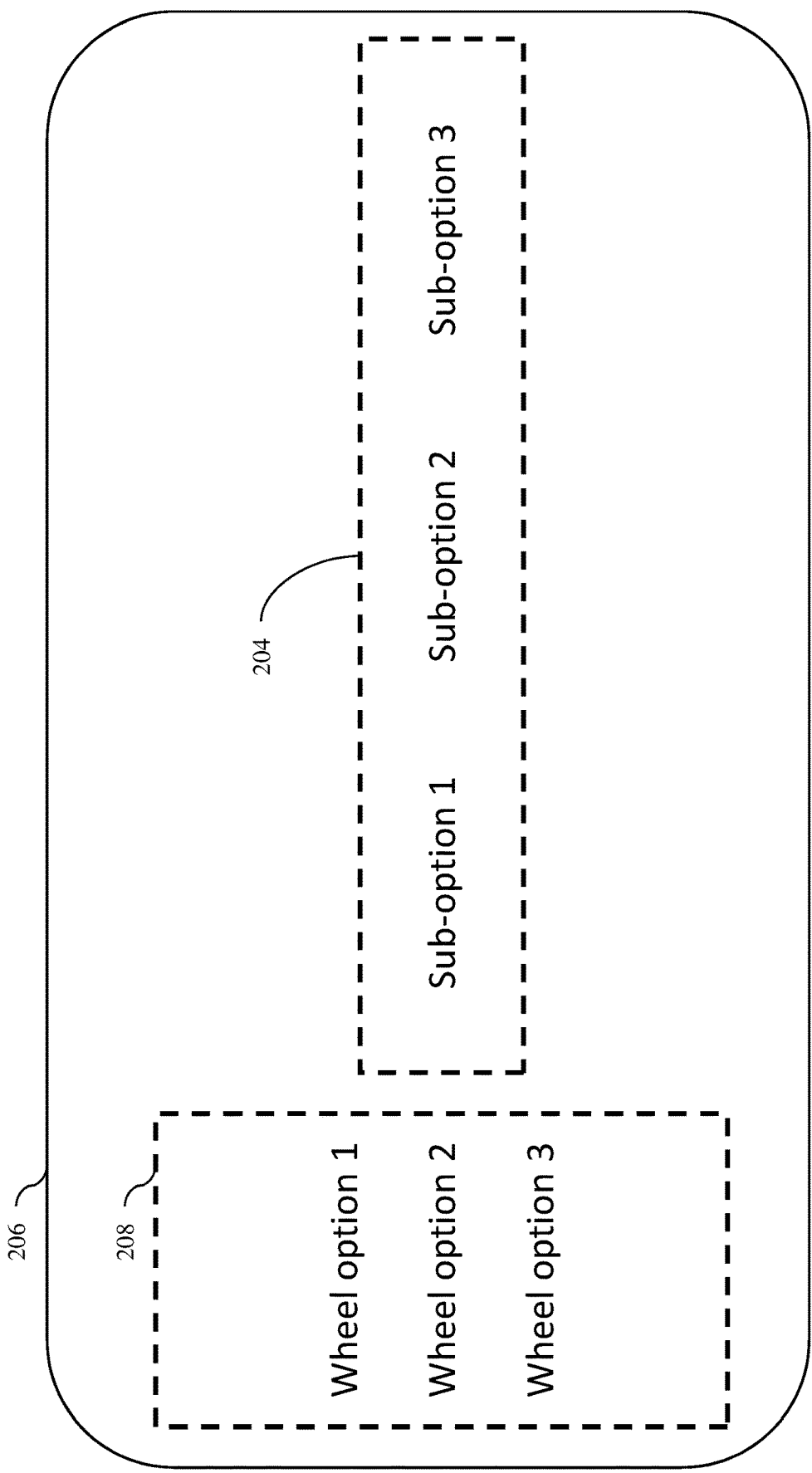

FIGS. 2F-2G show still yet another example of a menu display configuration in one embodiment. The figures show switching of wheel options from horizontal to vertical. FIG. 2F shows a menu of options displayed in a graphical wheel, for example, whose displayed options are rotatable in horizontal direction (left and right). The wheel is displayed in a first portion of a graphical user interface display. Upon selecting an option (a menu item in the list of options), the graphical wheel is switched to a vertically rotatable wheel. For instance, the wheel is moved or relocated to a second portion of the graphical user interface display, and the first portion of the graphical user interface display now displays a list of sub-options related to the option selected in the previous menu of options.

In one embodiment, the second portion of the display may display up to a threshold number of menu levels, for example, after which a different visualization configuration may be employed for displaying the past menu levels, to keep the second portion from growing too large.

For instance, referring to FIG. 2C, if there are more than a threshold number of menu levels (as an example, FIG. 2C shows 2 levels (202, 210)), a visualization mechanism may be employed that is able to visualize all past menu levels without having to grow the second portion of the display (e.g., FIG. 2C at 208). Consider for example, a threshold number to be 3. In that example, the second portion of the display may show 3 menu levels. When an additional choice for the next level is made (e.g., 4-th menu level), the second portion may show the most recent past 3 selections (the bottom 3 levels), with the items in the second portion made scrollable up and down. So, in this example, the first menu level choice is visible by scrolling on the second portion. As another example, the second portion may always show the top 2 levels, i.e., the first 2 decisions, and the last decision. In this way, the user is shown an overall context of a workflow, for instance, top-down. Tapping or scrolling the second portion allows the user to expand out the menu items, for example, like an accordion.

In another aspect, a search function may be provided associated with a wheel. Search keywords allow for filtering the wheel options available to the user. The search function helps in handling a long wheel of options or multi-wheel of options, which may take a long time to navigate.

Figure 2J:
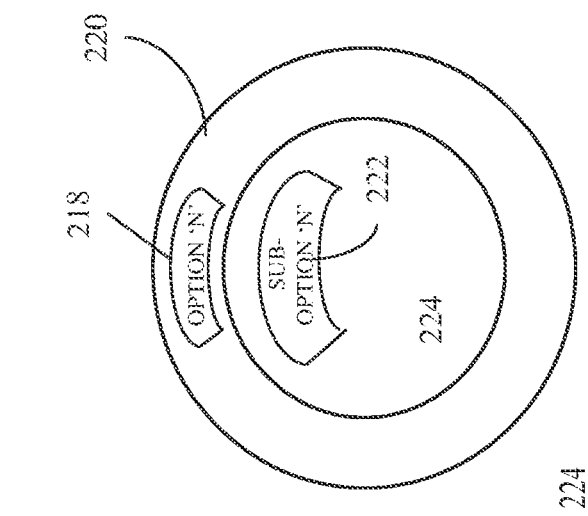
Figure 2I:
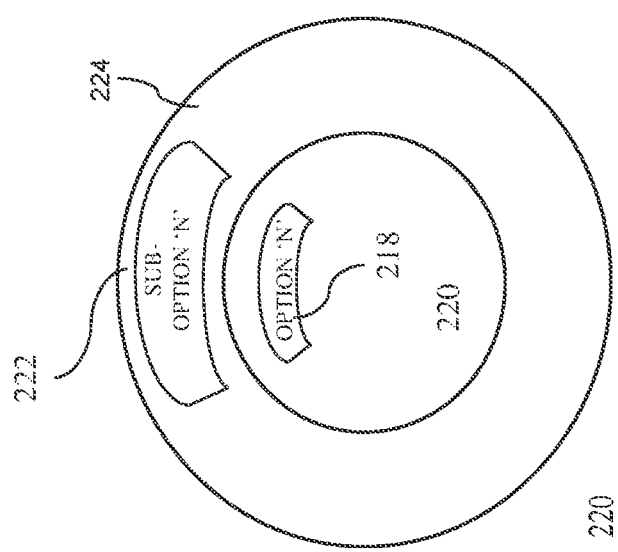
Figure 2H:
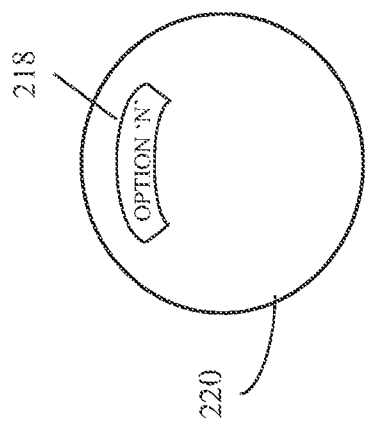
Figure 2K:
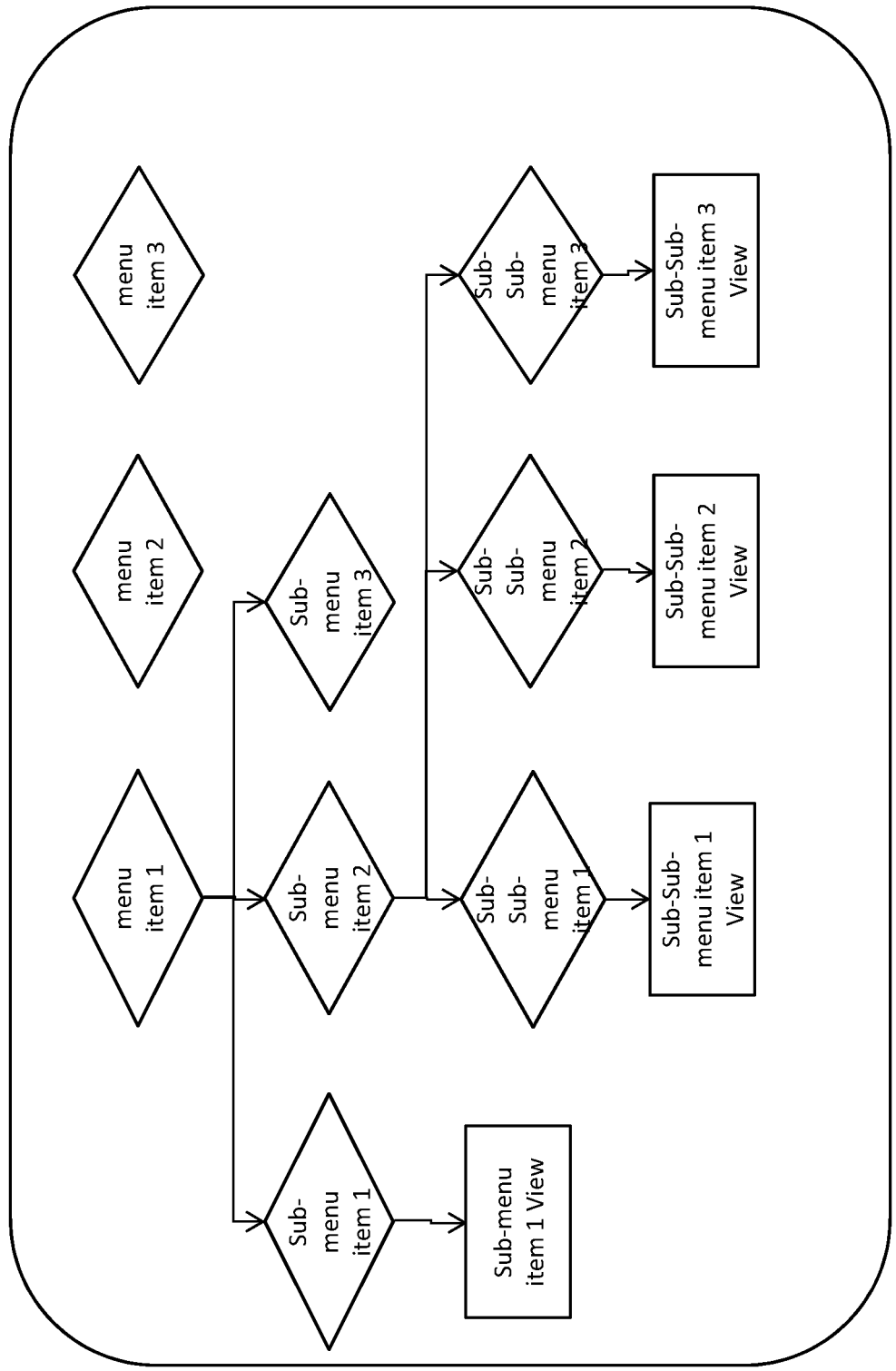

FIGS. 2H-2J show an example of the first portion and the second portion displayed as a series of concentric circles in one embodiment. Referring to FIG. 2H, a dial 220 may be rotated clockwise or counterclockwise to view in an option window 218, a menu item or item to select. Tapping on the area of the dial (e.g., circle) 220 selects the option. Selecting an option, for example, viewed via an option window 218, transitions the user interface to a configuration shown in FIG. 2I. For instance, in FIG. 2I, concentric dials expand inside out, showing another concentric circle to represent another level (e.g., sub-level) of menu items or paths. Sub-options may be viewed via an option window 222 on that circle 224 (also referred to as a dial) by rotating that dial 224 clockwise or counterclockwise. Selection of an option in that level (shown as sub-option 'n') 222 may be made by tapping on the area of that circle 224 (that is non-overlapping with the inner circle or dial 220). In another embodiment, selecting an option from the dial or circular menu user interface (for example, as shown in FIG. 2H) may transition the user interface state to the configuration shown in FIG. 2J. For instance, the next level of option selection billows out from the selected option, expanding the dial to show another inner dial 224 with an option window 222. In an embodiment, the number of options that can be viewed on an option window (e.g., 218 and 222) need not be limited, such that an unlimited number of options may be shown and selected as applicable for an application.

In an embodiment, an option window (e.g., 218) may be enlarged to show a selected option (e.g., as highlighted) and one or more unselected options, for example, an unselected option that appears before the selected option and another unselected option that appears after the selected option.

In another aspect, an option window (e.g., 219) may show more than one item or option at a time, for instance, 3 menu items or options. In this example, tapping on a menu item in the option window selects the option. After a selection is made, the selected option may be displayed in a highlighted format or another differentiating format, for instance, to distinguish the selected option from unselected options appearing in the option window.

In another embodiment, the relocation command may specify that the second portion is concentric with the first portion and that the relocated menu be displayed adjacent to the first portion (and concentric) where the first portion and the second portion are to be displayed on the MUI display 206 as a series of concentric circles. For example, the first portion may be displayed as the center circle of the series of concentric circles, and a relocated menu level(s) of the hierarchy being displayed as the circles outside or surrounding the center circle.

FIG. 2K shows a tree type of menu levels in an embodiment.

The hierarchical menu tree shown in FIG. 2K includes a first menu of menu items, a second menu of submenu items, a third menu of sub-submenu items, and four execution menus. One execution menu is associated with submenu item 1 and three more are associated with sub-submenu items 1-3. Selection of menu item 1 from the first menu leads to display of the second menu of submenu. Selection of submenu item 1 leads to an execution menu for submenu item 1 in which process parameters may be selected. Selection of submenu item 2 leads to a third menu of sub-submenu items. Selection of any one of sub-submenu items 1-3 leads to execution menus for these respective third menu items.

Figure 2L:
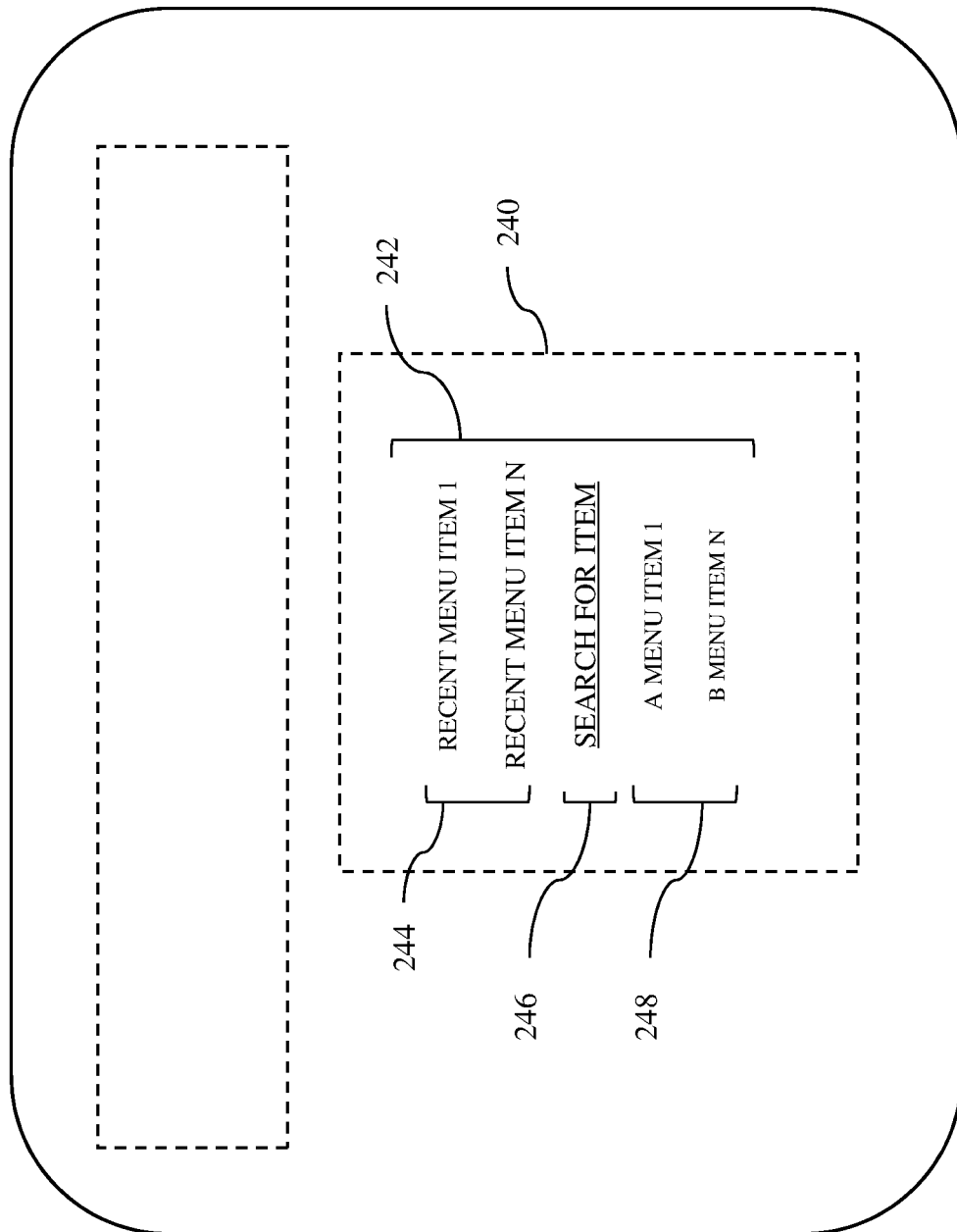

FIG. 2L shows another example of a menu display configuration in one embodiment. A graphical element 242 such as a wheel or a slider (or another graphical element) is displayed in a portion 240 of a display screen. The graphical element 242, e.g., a wheel, is ordered with the most "n" recent items first (reverse chronological) 244 with a search function such a search box or area 246 next followed by a list, for example, an alphanumerically sorted list, of the all of the menu items 248. In another embodiment, the menu items shown at 248 appear as indexed, for instance, as a search term is entered in the search box 246. The entire wheel 242 is made scrollable. For instance, a user can scroll through the entire wheel 242 or enter a search string in the search box 246. Entering a search term in the search area 246 displays menu items that match the search term as a search character is entered. For instance, on each character entered, one or more menu items closest to matching the search character(s) are indexed at 248. The wheel 240 is bifurcated into two independent wheels, one that displays recently chosen menu items 244 and another that displays indexed list or all menu items 248. The two wheels 244 and 248 are scrollable or movable independently from one another. So, for example, the entire wheel 242 is made to move or scroll as one wheel. Responsive to receiving or detecting an entry of a search term or character in the search area 246, the wheel is bifurcated into two separate wheels 244 and 248, which can be independently scrolled. One of the two separate wheels, e.g., 248, shows a filtered list of menu items based on the search.

Figure 2M:
Figure 2N:
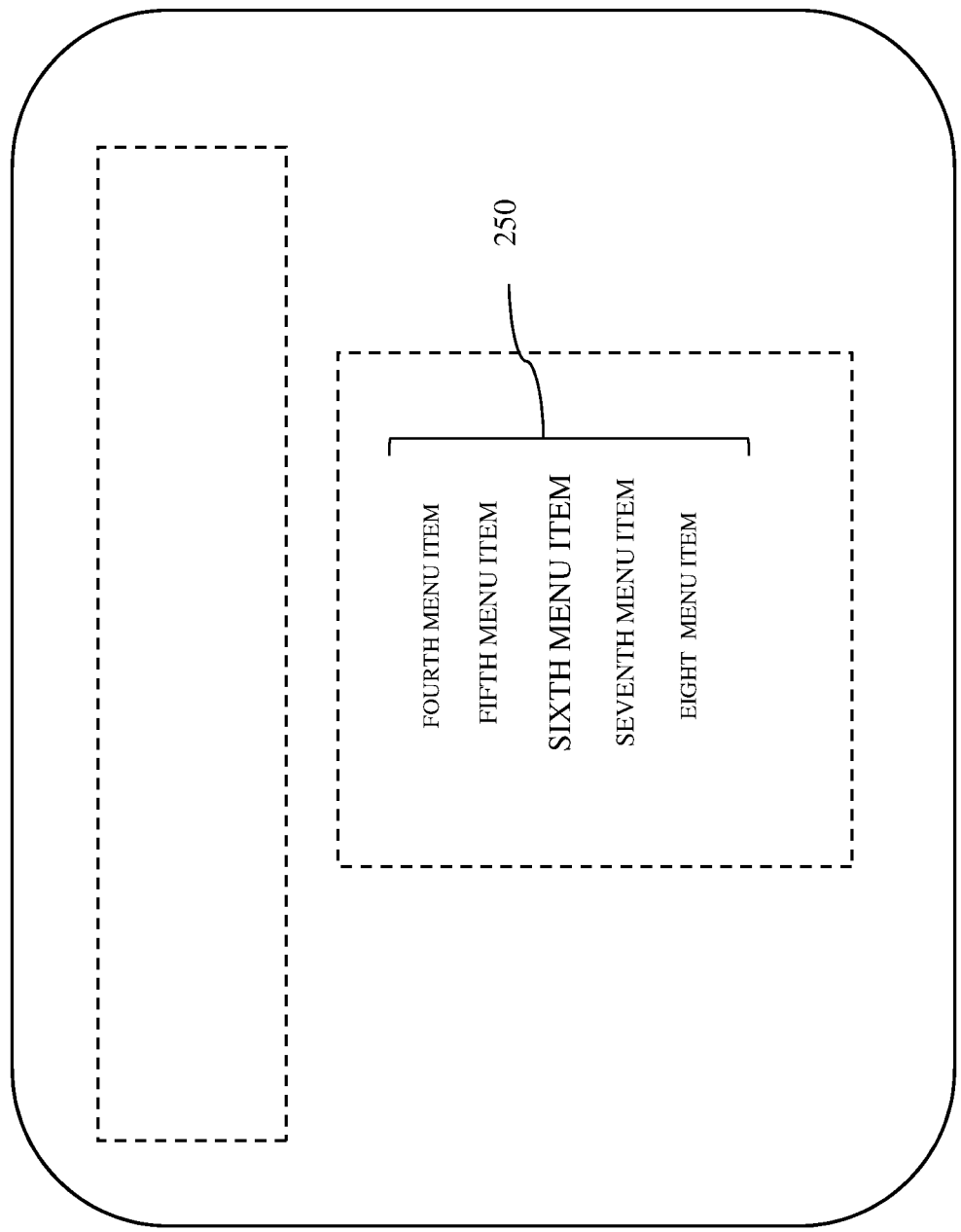
Figure 2P:
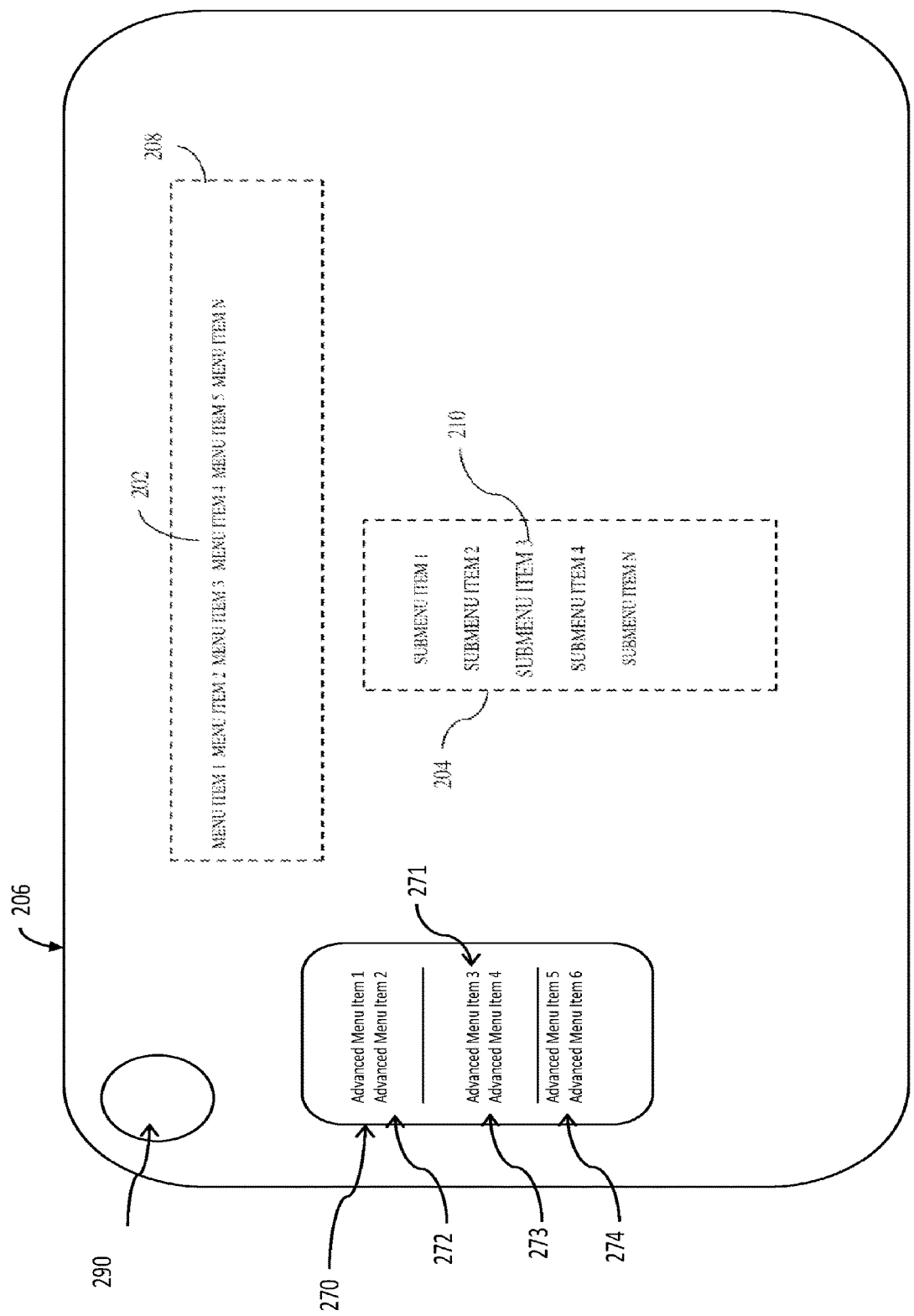

FIGS. 2M-2O show examples of scrollable wheels that scroll or slide from a first menu item to a last menu item and back from the last menu item to the first menu item. In this embodiment, a graphical element (e.g., a wheel or slider) that shows the menu items do not revolve or rotate around fully but stops at the last menu item or the first menu item (if rotating from the last menu item). In this way, for example, the beginning and end of the menu are always apparent because the two do not merge or connect. This technique reduces computer processing cycle time because the wheel and/or the slider is able to convey (and user is able to immediately understand) the full menu of choices with clear indication as to where or which is the first menu item and where or which is the last menu item in the choices presented by the wheel and/or the slider such that the wheel or the slider need not repeatedly scroll in an attempt to determine which menu item is the first and which is the last, or to determine whether all menu items have been visited.

In embodiments, the wheel and/or the slider need not rotate fully; for example, do not make a full revolution or complete circle. For instance, the wheel and/or the slider rotates or slides from a beginning menu item to an ending menu item, and reverses to rotate or slide back from the ending menu item to the beginning menu item. In this way, for example, the beginning and end of the menu are always apparent because the two are spaced apart as to not merge or come together. This technique decreases processing time because the wheel and/or the slider is able to convey (and user is able to immediately understand) the full menu of choices with clear indication as to where or which is the first menu item and where or which is the last menu item in the choices presented by the wheel and/or the slider. Further, as the wheel and/or slider rotates, selectable choices can be displayed in a more prominent fashion, such as using larger text, bolder font, etc. Choices that were previously selectable when the wheel and/or slider was rotated/slid to a different position or will be selectable as the wheel and/or slider continues to rotate/slide, can be displayed in a less prominent fashion, such as by shrinking or fading the text. In one embodiment, the more prominently displayed choices can be displayed to appear as if they are closer to the user vis-à-vis the less prominent choices.

Referring to FIG. 2M, the first menu item 252 is shown in the center of the wheel (or slider) 250. A menu item shown at the center may be shown in highlighted format (e.g., bigger characters, different color font, etc.). Blank space appears before the first menu item (e.g., above the center of the wheel where the first menu item is displayed). The next menu items (e.g., 254, 256) appear adjacent to (e.g., below) the first menu item. Scrolling the wheel (e.g., in vertical direction) shows additional menu items, e.g., as shown at FIG. 2N. For instance, shown in FIG. 2N, next menu items are shown as the wheel 250 is scrolled up. FIG. 2O shows the last menu item at the center of the wheel, with the previous menu items appearing adjacent to (e.g., above) the last menu item. The wheel or the slider 250 in this embodiment does not rotate around to show the first menu item after the last menu item 258. Instead the wheel stops rotating at the last menu item 258. Below the last menu item 258 shows blank space. Similarly, navigating back (e.g., scrolling the wheel in the opposite direction) shows the previous menu items up to the first menu item.

While the example graphical wheel shown in FIGS. 2M-2O illustrates a vertical wheel, a horizontal wheel would function in similar manner. For instance, a first menu item may appear at a center of a horizontal wheel with the next menu items appearing horizontally adjacent to the first menu item (e.g., right of the center). Scrolling the wheel to the left in this example would display additional menu items. When the last menu item is reached by scrolling, that last menu item appears at the center with blank space beyond the last menu item (e.g., to the right of the last menu item). In another aspect, the orientation of the rotation may be reversed: e.g., with vertical wheel, scrolling down (instead of up) to navigate from the first to the last menu item; with horizontal wheel, scrolling right to navigate from the first to the last menu item. The number of menu items (options) shown on a wheel at one time is configurable, for example, based on screen size and/or area of the screen allocated for the wheel, etc., and is not limited to 6 items shown in FIG. 2N.

A non-limiting application of such a user interface is in selecting a channel to watch on television (TV). Broader categories may be displayed on top horizontal area with finer categorizations stacked below, and leaf item may be displayed vertically, for example, on a vertical wheel. For example, referring to FIG. 2E, the 'Wheel Option 1' may represent a genre and the 'Sub-options 1' may represent shows and/or movies organized in a grid.

In an embodiment, the methodical user interface control system 1102 provides an interface to a user for the running of a process. A process may include conducting an experiment, performing one or more manufacturing operations, or any other procedure.

The following describes in detail various instructions for conducting experiments consistent with embodiment hereof. Instructions for conducting an experiment may be for manipulating, designing, performing, reviewing, measuring, analyzing, storing, and conducting any other task related to the experiment. The experiment may be but is not limited to one or more assays. The methodical user interface control system 1102 may be incorporated into and/or associated with an assay system and provide commands to generate a MUI display 206 for the system. The MUI display 206, in response to the commands is able to display or provide a visual representation of a path of a workflow and/or menu items for the assay. The assays may include one or more electrochemiluminescence (ECL) assays.

The methods of the present embodiments may be used in conjunction with a variety of assay devices and/or formats. The assay devices may include, e.g., assay modules, such as assay plates, cartridges, multi-well assay plates, reaction vessels, test tubes, cuvettes, flow cells, assay chips, lateral flow devices, etc., having assay reagents (which may include targeting agents or other binding reagents) added as the assay progresses or pre-loaded in the wells, chambers, or assay regions of the assay module. These devices may employ a variety of assay formats for specific binding assays, e.g., immunoassay or immunochromatographic assays. Illustrative assay devices and formats are described herein below. In certain embodiments, the methods of the present embodiments may employ assay reagents that are stored in a dry state and the assay devices/kits may further comprise or be supplied with desiccant materials for maintaining the assay reagents in a dry state. The assay devices preloaded with the assay reagents can greatly improve the speed and reduce the complexity of assay measurements while maintaining excellent stability during storage. The dried assay reagents may be any assay reagent that can be dried and then reconstituted prior to use in an assay. These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports.

A wide variety of solid phases are suitable for use in the methods of the present embodiments including conventional solid phases from the art of binding assays. Solid phases may be made from a variety of different materials including polymers (e.g., polystyrene and polypropylene), ceramics, glass, composite materials (e.g., carbon-polymer composites such as carbon-based inks). Suitable solid phases include the surfaces of macroscopic objects such as an interior surface of an assay container (e.g., test tubes, cuvettes, flow cells, cartridges, wells in a multi-well plate, etc.), slides, assay chips (such as those used in gene or protein chip measurements), pins or probes, beads, filtration media, lateral flow media (for example, filtration membranes used in lateral flow test strips), etc.

Suitable solid phases also include particles (including but not limited to colloids or beads) commonly used in other types of particle-based assays e.g., magnetic, polypropylene, and latex particles, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Microparticles may be inanimate or alternatively, may include animate biological entities such as cells, viruses, bacterium and the like.

The particles used in the present method may be comprised of any material suitable for attachment to one or more binding partners and/or labels, and that may be collected via, e.g., centrifugation, gravity, filtration or magnetic collection. A wide variety of different types of particles that may be attached to binding reagents are sold commercially for use in binding assays. These include non-magnetic particles as well as particles comprising magnetizable materials which allow the particles to be collected with a magnetic field. In one embodiment, the particles are comprised of a conductive and/or semi conductive material, e.g., colloidal gold particles.

The microparticles may have a wide variety of sizes and shapes. By way of example and not limitation, microparticles may be between 5 nanometers and 100 micrometers. Preferably microparticles have sizes between 20 nm and 10 micrometers. The particles may be spherical, oblong, rod-like, etc., or they may be irregular in shape.

The particles used in the present method may be coded to allow for the identification of specific particles or subpopulations of particles in a mixture of particles. The use of such coded particles has been used to enable multiplexing of assays employing particles as solid phase supports for binding assays. In one approach, particles are manufactured to include one or more fluorescent dyes and specific populations of particles are identified based on the intensity and/or relative intensity of fluorescence emissions at one or more wave lengths. This approach has been used in the Luminex xMAP systems (see, e.g., U.S. Pat. No. 6,939,720) and the Becton Dickinson Cytometric Bead Array systems. Alternatively, particles may be coded through differences in other physical properties such as size, shape, imbedded optical patterns and the like.

The methods of the embodiments can be used with a variety of methods for measuring the amount of an analyte and, in particular, measuring the amount of an analyte bound to a solid phase. Techniques that may be used include, but are not limited to, techniques known in the art such as cell culture-based assays, binding assays (including agglutination tests, immunoassays, nucleic acid hybridization assays, etc.), enzymatic assays, colorimetric assays, etc. Other suitable techniques will be readily apparent to one of average skill in the art. Some measurement techniques allow for measurements to be made by visual inspection, others may require or benefit from the use of an instrument to conduct the measurement.

Methods for measuring the amount of an analyte include label free techniques, which include but are not limited to i) techniques that measure changes in mass or refractive index at a surface after binding of an analyte to a surface (e.g., surface acoustic wave techniques, surface plasmon resonance sensors, ellipsometric techniques, etc.), ii) mass spectrometric techniques (including techniques like MALDI, SELDI, etc. that can measure analytes on a surface), iii) chromatographic or electrophoretic techniques, and iv) fluorescence techniques (which may be based on the inherent fluorescence of an analyte), etc.

Methods for measuring the amount of an analyte also include techniques that measure analytes through the detection of labels which may be attached directly or indirectly (e.g., through the use of labeled binding partners of an analyte) to an analyte. Suitable labels include labels that can be directly visualized (e.g., particles that may be seen visually and labels that generate a measurable signal such as light scattering, optical absorbance, fluorescence, chemiluminescence, electrochemiluminescence, radioactivity, magnetic fields, etc.). Labels that may be used also include enzymes or other chemically reactive species that have a chemical activity that leads to a measurable signal such as light scattering, absorbance, fluorescence, etc. The use of enzymes as labels has been well established in in Enzyme-Linked ImmunoSorbent Assays, also called ELISAs, Enzyme ImmunoAssays or EIAs. In the ELISA format, an unknown amount of antigen is affixed to a surface and then a specific antibody is washed over the surface so that it can bind to the antigen. This antibody is linked to an enzyme, and in the final step a substance is added that the enzyme converts to a product that provides a change in a detectable signal. The formation of product may be detectable, e.g., due a difference, relative to the substrate, in a measurable property such as absorbance, fluorescence, chemiluminescence, light scattering, etc. Certain (but not all) measurement methods that may be used with solid phase binding methods according to the embodiments may benefit from or require a wash step to remove unbound components (e.g., labels) from the solid phase Accordingly, the methods of the embodiments may comprise such a wash step.

Methods disclosed herein may be performed manually, using automated technology, or both. Automated technology may be partially automated, e.g., one or more modular instruments, or a fully integrated, automated instrument.

Example automated systems are discussed and described in commonly owned International Patent Appl. Pub. Nos. WO 2018/017156 and WO 2017/015636 and International Patent Appl. Pub. No. WO 2016/164477, each of which is incorporated by reference herein in its entirety.

Automated systems (modules and fully integrated) on which the methods herein may be carried out may comprise the following automated subsystems: computer subsystem(s) that may comprise hardware (e.g., personal computer, laptop, hardware processor, disc, keyboard, display, printer), software (e.g., processes such as drivers, driver controllers, and data analyzers), and database(s); liquid handling subsystem(s), e.g., sample handling and reagent handling, e.g., robotic pipetting head, syringe, stirring apparatus, ultrasonic mixing apparatus, magnetic mixing apparatus; sample, reagent, and consumable storing and handling subsystem(s), e.g., robotic manipulator, tube or lid or foil piercing apparatus, lid removing apparatus, conveying apparatus such as linear and circular conveyors and robotic manipulators, tube racks, plate carriers, trough carriers, pipet tip carriers, plate shakers; centrifuges, assay reaction subsystem(s), e.g., fluid-based and consumable-based (such as tube and multi well plate); container and consumable washing subsystem(s), e.g., plate washing apparatus; magnetic separator or magnetic particle concentrator subsystem(s), e.g., flow cell, tube, and plate types; cell and particle detection, classification and separation subsystem(s), e.g., flow cytometers and Coulter counters; detection subsystem(s) such as colorimetric, nephelometric, fluorescence, and ECL detectors; temperature control subsystem(s), e.g., air handling, air cooling, air warming, fans, blowers, water baths; waste subsystem(s), e.g., liquid and solid waste containers; global unique identifier (GUI) detecting subsystem(s) e.g., 1D and 2D bar-code scanners such as flat bed and wand types; sample identifier detection subsystem(s), e.g., 1D and 2D bar-code scanners such as flat bed and wand types. Analytical subsystem(s), e.g., chromatography systems such as high-performance liquid chromatography (HPLC), fast-protein liquid chromatography (FPLC), and mass spectrometer can also be modules or fully integrated. Automated systems consistent with embodiments hereof may be controlled and/or managed by the methodical user interface control system 1102.

Systems or modules that perform sample identification and preparation may be combined with (or be adjoined to or adjacent to or robotically linked or coupled to) systems or modules that perform assays and that perform detection or that perform both. Multiple modular systems of the same kind may be combined to increase throughput. Modular system(s) may be combined with module(s) that carry out other types of analysis such as chemical, biochemical, and nucleic acid analysis.

The automated system may allow batch, continuous, random-access, and point-of-care workflows and single, medium, and high sample throughput.

The system may include, for example, one or more of the following devices: plate sealer (e.g., Zymark), plate washer (e.g., BioTek, TECAN), reagent dispenser and/or automated pipetting station and/or liquid handling station (e.g., TECAN, Zymark, Lab systems, Beckman, Hamilton), incubator (e.g., Zymark), plate shaker (e.g., Q. Instruments, Inheco, Thermo Fisher Scientific), compound library or sample storage and/or compound and/or sample retrieval module. One or more of these devices is coupled to the apparatus via a robotic assembly such that the entire assay process can be performed automatically. According to an alternate embodiment, containers (e.g., plates) are manually moved between the apparatus and various devices (e.g., stacks of plates).

The automated system may be configured to perform one or more of the following functions: (a) moving consumables such as plates into, within, and out of the detection subsystem, (b) moving consumables between other subsystems, (c) storing the consumables, (d) sample and reagent handling (e.g., adapted to mix reagents and/or introduce reagents into consumables), (e) consumable shaking (e.g., for mixing reagents and/or for increasing reaction rates), (f) consumable washing (e.g., washing plates and/or performing assay wash steps (e.g., well aspirating)), and (g) measuring ECL in a flow cell or a consumable such as a tube or a plate. The automated system may be configured to handle individual tubes placed in racks, multiwell plates such as 96 or 384 well plates.

Methods for integrating components and modules in automated systems as described herein are well-known in the art, see, e.g., Sargeant et al., Platform Perfection, Medical Product Outsourcing, May 17, 2010.

In embodiments, the automated system is fully automated, is modular, is computerized, performs in vitro quantitative and qualitative tests on a wide range of analytes and performs photometric assays, ion-selective electrode measurements, and/or electrochemiluminescence (ECL) assays. In embodiments, the system includes the following hardware units: a control unit, a core unit and at least one analytical module.

In embodiments, the control unit uses a graphical user interface to control all instrument functions, and is comprised of a readout device, such as a monitor, an input device(s), such as keyboard and mouse, and a personal computer using, e.g., a Windows operating system. In embodiments, the core unit is comprised of several components that manage conveyance of samples to each assigned analytical module. The actual composition of the core unit depends on the configuration of the analytical modules, which can be configured by one of skill in the art using methods known in the art. In embodiments, the core unit includes at least the sampling unit and one rack rotor as main components. Conveyor line(s) and a second rack rotor are possible extensions. Several other core unit components can include the sample rack loader/unloader, a port, a barcode reader (for racks and samples), a water supply and a system interface port. In embodiments, the analytical module conducts ECL assays and includes a reagent area, a measurement area, a consumables area and a pre-clean area.

The methods of the invention may be applied to single-plex or multiplex formats where multiple assay measurements are performed on a single sample. Multiplex measurements that can be used with the invention include, but are not limited to, multiplex measurements i) that involve the use of multiple sensors; ii) that use discrete assay domains on a surface (e.g., an array) that are distinguishable based on location on the surface; iii) that involve the use of reagents coated on particles that are distinguishable based on a particle property such as size, shape, color, etc.; iv) that produce assay signals that are distinguishable based on optical properties (e.g., absorbance or emission spectrum) and/or v) that are based on temporal properties of assay signal (e.g., time, frequency or phase of a signal).

The invention includes methods for detecting and counting individual detection complexes. In embodiments, the surface comprises a plurality of binding domains, and each analyte forms a complex in a different binding domain of the plurality of binding domains. In embodiments, the surface is a particle. In embodiments, the surface is a bead. In embodiments, the surface is a plate. In embodiments, the surface is a well in a multi-well array. In embodiments, the surface comprises an electrode. In embodiments, the electrode is a carbon ink electrode. In embodiments, each binding domain for each analyte of the one or more additional analytes is on a separate surface, and the surfaces are beads in a bead array. In embodiments, each binding domain for each analyte of the one or more additional analytes is on a single surface, and the binding domains form the elements of a capture reagent array on the surface. In embodiments, the surface comprises an electrode and the detection step of the method comprises applying a potential to the electrode and measuring electrochemiluminescence. In embodiments, applying a potential to the electrode generates an electrochemiluminescence signal.

In a specific embodiment, the surface comprises a plurality of capture reagents for one or more analytes that are present in a sample, and the plurality of capture reagents are distributed across a plurality of resolvable binding regions positioned on the surface. Under the conditions used to carry out and analyze a measurement, a "resolvable binding region" is the minimal surface area associated with an individual binding event that can be resolved and differentiated from another area in which an additional individual binding event is occurring. Therefore, the method consists of binding one or more analytes to one or more capture reagents on the surface, determining the presence or absence of the analytes, in a plurality of resolvable binding regions on the surface, and identifying the number of resolvable binding regions that contain an analyte of interest and/or the number of domains that do not contain analyte.

The resolvable binding regions can be optically interrogated, in whole or in part, i.e., each individual resolvable binding region can be individually optically interrogated and/or the entire surface comprising a plurality of resolvable binding regions can be imaged and one or more pixels or groupings of pixels within that image can be mapped to an individual resolvable binding region. A resolvable binding region may also be a microparticle within a plurality of microparticles. The resolvable binding regions exhibiting changes in their optical signature can be identified by a conventional optical detection system. Depending on the detected species (e.g., type of fluorescence entity, etc.) and the operative wavelengths, optical filters designed for a particular wavelength can be employed for optical interrogation of the resolvable binding regions. In embodiments where optical interrogation is used, the system can comprise more than one light source and/or a plurality of filters to adjust the wavelength and/or intensity of the light source. In some embodiments, the optical signal from a plurality of resolvable binding regions is captured using a CCD camera. Other non-limiting examples of camera imaging systems that can be used to capture images include charge injection devices (CIDs), complementary metal oxide semiconductors (CMOSs) devices, scientific CMOS (sCMOS) devices, and time delay integration (TDI) devices, as will be known to those of ordinary skill in the art. In some embodiments, a scanning mirror system coupled with a photodiode or photomultiplier tube (PMT) can be used for imaging.

In embodiments, the binding of each analyte to its corresponding capture reagent is performed in parallel by contacting the one or more surfaces with a single liquid volume comprising a plurality of analytes. In embodiments, the plurality of analytes includes the analyte and one or more additional analytes. In embodiments, each step of the method is carried out for each analyte in parallel. In embodiments, the method is a simultaneous multiplexed assay. Multiplexed measurement of analytes on a surface are described herein; see also, e.g., U.S. Pat. Nos. 10,201,812; 7,842,246 and 6,977,722, incorporated by reference herein in their entireties.

In a specific embodiment, the methods of the invention can be used in a multiplexed format by binding a plurality of different analytes to a plurality of capture reagents for those analytes, the capture analytes being immobilized on coded bead, such that the coding identifies the capture reagent (and analyte target) for a specific bead. The method may further comprise counting the number of beads that have a bound analyte (using the detection approaches described herein).

Alternatively or additionally, the capture reagents can be bound, directly or indirectly, to different discrete binding domains on one or more solid phases, e.g., as in a binding array wherein the binding domains are individual array elements, or in a set of beads wherein the binding domains are the individual beads, such that discrete assay signals are generated on and measured from each binding domain. If capture reagents for different analytes are immobilized in different binding domains, the different analytes bound to those domains can be measured independently. In one example of such an embodiment, the binding domains are prepared by immobilizing, on one or more surfaces, discrete domains of capture reagents that bind analytes of interest. Optionally, the surface(s) may define, in part, one or more boundaries of a container (e.g., a flow cell, well, cuvette, etc.) which holds the sample or through which the sample is passed. In a preferred embodiment, individual binding domains are formed on electrodes for use in electrochemical or electrochemiluminescence assays. Multiplexed measurement of analytes on a surface comprising a plurality of binding domains using electrochemiluminescence has been used in the Meso Scale Diagnostics, LLC, MULTI-ARRAY® and SECTOR® Imager line of products (see, e.g., U.S. Pat. Nos. 10,201,812; 7,842,246 and 6,977,722, incorporated herein by reference in their entireties).

Still further, the capture reagents can be bound, directly or indirectly, to an electrode surface, which optionally includes different discrete binding domains, as described above. The electrode surface can be a component of a multi-well plate and/or a flow cell. Electrodes can comprise a conductive material, e.g., a metal such as gold, silver, platinum, nickel, steel, iridium, copper, aluminum, a conductive allow, or the like. They may also include oxide coated metals, e.g., aluminum oxide coated aluminum. The electrode can include working and counter electrodes which can be made of the same or different materials, e.g., a metal counter electrode and carbon working electrode. In one specific embodiment, electrodes comprise carbon-based materials such as carbon, carbon black, graphitic carbon, carbon nanotubes, carbon fibrils, graphite, graphene, carbon fibers and mixtures thereof. In one embodiment, the electrodes comprise elemental carbon, e.g., graphitic, carbon black, carbon nanotubes, etc. Advantageously, they may include conducting carbon-polymer composites, conducting particles dispersed in a matrix (e.g. carbon inks, carbon pastes, metal inks, graphene inks), and/or conducting polymers. One specific embodiment of the invention is an assay module, preferably a multi-well plate, having electrodes (e.g., working and/or counter electrodes) that comprise carbon, e.g., carbon layers, and/or screen-printed layers of carbon inks.

In embodiments, each binding domain comprises a targeting reagent complement capable of binding to a targeting reagent complement and each anchoring reagent and capture reagent comprise a supplemental linking reagent capable of binding to a linking reagent, and the method further comprises immobilizing a capture reagent and anchoring agent in each binding domain by: (1) binding the capture and anchoring reagent through the supplemental linking reagent to a targeting reagent complement connected to the linking reagent; and (2) binding the product of step (1) to the binding domain comprising the targeting reagent complement, wherein (i) each binding domain comprises a different targeting reagent complement, and (ii) each targeting reagent complement selectively binds to one of the targeting reagents.

Accordingly, in embodiments, the surface comprises the targeting reagent complement; the targeting reagent is connected to the linking reagent; and each of the capture reagent and anchoring reagent comprises the supplemental linking reagent. Thus, in embodiments, the targeting reagent complement on the surface binds to the targeting reagent, which is connected to the linking reagent, which binds to the supplemental linking reagent on the capture reagent and the anchoring reagent.

In embodiments, the linking reagent has more than one binding site for supplemental linking reagents, and the immobilization of the capture reagent and anchoring reagent further comprises: binding the capture and anchoring reagent through the supplemental linking reagent to a targeting reagent connected to the linking reagent; and binding the product of to the binding domain comprising the targeting reagent complement, wherein, (i) each binding domain comprises a different targeting reagent complement, and (ii) each targeting reagent complement selectively binds to one of the targeting reagents. For example, in the case where the targeting agent is an oligonucleotide, the linking reagent is streptavidin and the supplemental linking agent is biotin, a biotin-labeled oligonucleotide can be bound to a first of the four biotin binding sites of a streptavidin to form the targeting reagent connected to a linking reagent. A biotin-labeled capture reagent (i.e., a capture reagent linked to the supplemental linking agent) can then bind to a remaining biotin binding site on the streptavidin to connect the targeting agent to the capture reagent.

Exemplary targeting reagents and targeting reagent complements are described herein. In embodiments, the targeting reagent and targeting reagent complement are two members of a binding partner pair selected from avidin-biotin, streptavidin-biotin, antibody-hapten, antibody-antigen, antibody-epitope tag, nucleic acid-complementary nucleic acid, aptamer-aptamer target, and receptor-ligand. In embodiments, the targeting reagent is biotin and the targeting reagent complement is streptavidin. In embodiments, the linking reagent and supplemental linking reagent pair is a different binding partner pair than the targeting reagent and targeting reagent complement pair. In embodiments, the linking reagent is avidin or streptavidin, and the supplemental linking reagent is biotin. In embodiments, the targeting reagent and targeting reagent complement are complementary oligonucleotides.

In embodiments, the methods of the invention are applied to singleplex or multiplex formats where multiple assay measurements are performed on a single sample. Multiplex measurements that can be used with the invention include, but are not limited to, multiplex measurements i) that involve the use of multiple sensors; ii) that use discrete assay domains on a surface (e.g., an array) that are distinguishable based on location on the surface; iii) that involve the use of reagents coated on particles that are distinguishable based on a particle property such as size, shape, color, etc.; iv) that produce assay signals that are distinguishable based on optical properties (e.g., absorbance or emission spectrum) or v) that are based on temporal properties of assay signal (e.g., time, frequency or phase of a signal). Exemplary assay formats include V-PLEX (www.mesoscale.com/en/products and services/assay kits/v-plex) and U-PLEX (www.mesoscale.com/en/products and services/assay kits/u-plex gateway, and U.S. Pat. Nos. 10,201,812 and 10,189,023, each of which is incorporated herein by reference in its entirety). Additional ultrasensitive assay formats include those disclosed in U.S. Provisional Appl. No. 62/812,928, filed Mar. 1, 2019, and U.S. Provisional Appl. No. 62/866,512, filed Jun. 25, 2019, each of which is incorporated herein by reference in its entirety.

Exemplary plate readers include the MESO SECTOR S 600 (www.mesoscale.com/en/products and services/instrumentation/sector_s_600) and the MESO QUICKPLEX SQ 120 (www.mesoscale.com/en/products and services/instrumentation/quickplex_sq_120), both available from Meso Scale Diagnostics, LLC., and the plate readers described in U.S. Pat. No. 6,977,722 and U.S. Provisional Patent Appl. No. 62/874,828, Titled: "Assay Apparatuses, Methods and Reagents" by Krivoy et al., filed Jul. 16, 2019, each of which is incorporated by reference herein in its entirety.

The user interface methodology described above may also be incorporated into a user interface of an assay system. The assay system that is described below allows a user to perform assays via the user interface. The following describes an example of a user interface incorporated into the assay system for assay method. The term "system software" or "system" referred to below in describing the functions of the assay system and its user interface refer to software that implements the assay system. The user interface is able to display or visualize a path of a workflow and/or menu items.

The following terminologies are used in describing the assay system and its user interface workflow.

Advanced Context Menu—A menu of options dependent on the particular context (such as current screen, sub-step, and the state of the screen) for advanced users.

Assay Method—The method by which an assay is performed, including but not limited to: 1. Instrument protocol that should be executed and the parameters for execution of that protocol; 2. Test plate layouts; 3. Calibrator titration scheme such as dilution factors; 4. Control layout; and 5. Sample replicate schemes.

Audit Log—A continuous record of events both automated and user-initiated that happened in the system that may impact the results generated. This record is used to trace issues and to ensure proper operations in controlled environments. The Audit Log is persistent and immutable. It includes a subset of the information in the Instrument Log.

Compatible Protocols—Protocols are compatible if they have the same basic outline and steps, although dilution ratios, times of incubation, washing, and others, may vary between them. Protocols are considered compatible if they can run on an automated platform together during the same run.

Completed Run—A run that has been aborted, completed with flag(s), or completed successfully.

CV—Coefficient of Variation.

Database Clean—Resets the entire database, restoring it to the state it was in at system installation.

ECL—Electrochemiluminescence. A proprietary format for detecting molecules of biological interest.

Existing Run—A run that has been planned, aborted, completed with flag(s), or completed successfully.

Global Product Data (GPD)—Data that is for a specific item identified with a GPI. While the same data can be used for multiple items, the GPI allows for matching of data to one specific item. The GPD may comprise information used to identify at least one element including (i) an assay consumable, (ii) one or more test sites within the consumable, (iii) a reagent and/or sample that has been or will be used in the consumable, or (iv) combinations thereof. Further, the GPD can be used to distinguish a first test site within the consumable from a different test site within the consumable. The GPD can comprise lot identification information, lot specific analysis parameters, manufacturing process information, raw materials information, expiration date, calibration data, threshold information, the location of individual assay reagents and/or samples within one or more test sites of the assay consumable, Material Safety Data Sheet (MSDS) information, or combinations thereof, The GPD can also comprise one or more analytical tools that can be applied by the system to analyze data generated during and/or after the conduct of an assay, assay system maintenance information, system-consumable promotional information, system and/or consumable technical support information, or combinations thereof. In addition, GPD includes consumable identification and/or configuration information, and one or more steps of an assay protocol that can be applied by the system in the conduct of an assay using the consumable.

Test sites may also be referred to as spots. Spot layouts may refer to arrays of test sites, for example, within a single well of a test plate or assay plate.

Global Product Identifier (GPI)—A system/instrument/consumable vendor-specified, unique identifier for an individual specific product such as an assay consumable. The identifier can be any number of configurations. In the case of consumables such as assay plates, the identifier may be an associated manufacturing barcode.

Instrument Log—A detailed log file that records all actions carried out by the system and any failures or error states that have occurred during a run. The Instrument Log is a rolling circular log with stored information, limited by the amount of memory space allocated to this log file; for instance, older entries are overwritten over time.

Instrument Software—Software that controls the instrument hardware

LED—Light-emitting diode. A light source.

Normal State—Instrument is considered to be in a normal state if the software is functioning without any error or warning. Instrument is returned to normal state once error state is recovered and/or warning message is acknowledged.

Run—A run includes 0 or more named samples and 1 or more assay methods and tests the samples according to the information described in the assay methods.

Run Owner—User who created the run.

Sample—A generic term encompassing materials to be analyzed including Calibrators, Controls, Blanks, and Unknowns.

Sample ID—The unique identifier for each sample.

Sample Layout—The sample locations and sample IDs on a plate.

Sample Type—The functional type of a sample such as Calibrator, Control, Blank, or Unknown.

Spot Layout—The analyte locations and names in a well on a plate.

Step—One of a sequence of separate, consecutive stages in the progression towards a goal. Steps constitute broad stages that may consist of multiple sub-steps.

Sub-step—One of a sequence of separate, consecutive stages in the progression towards completion of a step. Sub-steps constitute focused activities within a step.

Unexpected Barcode—A barcode that is different than the one expected. A consumable may also be considered to have an "unexpected barcode" if no barcode is read.

User Interface (UI)—The software interface that the user of the instrument interacts with to control and monitor the system.

UI Warning Event—Any attention messages that require a user response. The user should fix the error and/or acknowledge the message before proceeding. For example, a UI Warning Event may be that the instrument is in a "Not Ready" state.

System Events Log—A persisted log of events that occurred in the software that are not instrument related.

Figure 4:
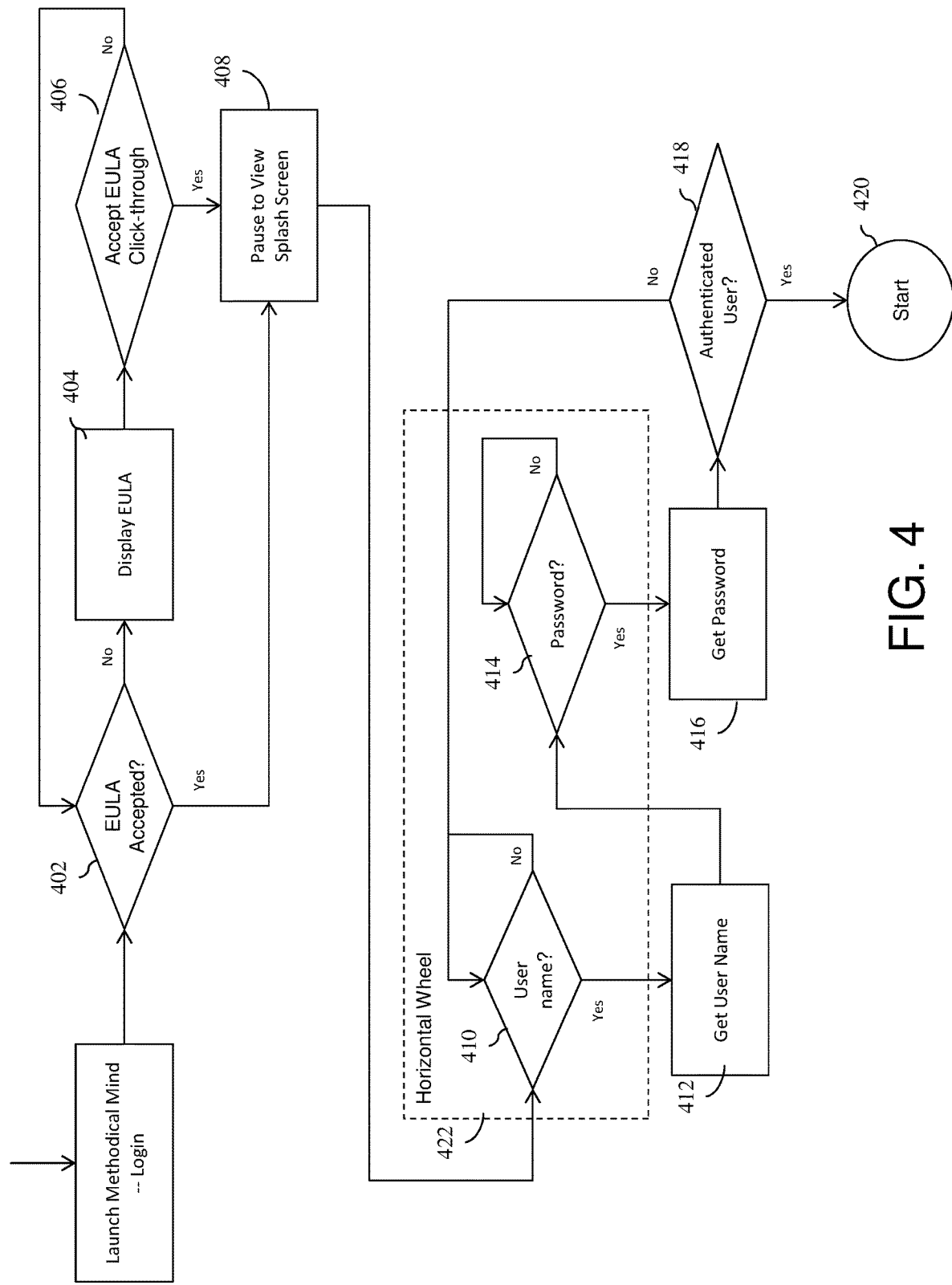
FIG. 4 is a flow diagram illustrating a user login interface for an assay system in one embodiment.

FIG. 4 is a flow diagram illustrating a first user login user interface for an assay system in one embodiment. 402, system software for assay method may check that the End User License Agreement (EULA) associated with the assay system has been accepted every time it starts. When the user first starts the system software, the EULA is presented. A record of the username and date and time is created when the user accepts the agreement. If the user has not previously accepted the agreement, at 404, EULA is displayed and allows the user to accept the agreement. At 406, if the user does not accept the agreement, the software closes. At 408, a splash screen is displayed that contains: System software branding, Copyright, Legal notice, Software Version. The initial login screen requests the username at 410. In one embodiment, the system software may present the past usernames used to login on the system to minimize error due to typing the username. The user is allowed to also enter a new username that has not previously been used to login. After selecting (or receiving) the username at 412 the software prompts the user to enter the password for the username at 414. In one embodiment, the system software may also use biometric ways such as facial recognition, voice, and/or fingerprint, to login or to verify login. In another embodiment, the system software may use a badge keycard that contains information that can be scanned or read via near field communication. At 416, the system software receives entered password. Once the username and password have been entered, the system software authenticates the user at 418. If the user is authenticated successfully, the user interface proceeds to a start screen at 420. Otherwise, the system software via the user interface prompts the user to retry. The system software in one embodiment next requires all users to login to access the software. In one embodiment, authentication may be performed through the Microsoft Windows® authentication facility and may be configured to authenticate through Active Directory. In this first user interface display, the username and password prompt may be displayed in one orientation, for example, horizontally on a horizontal wheel graphical element 422.

Figure 5:
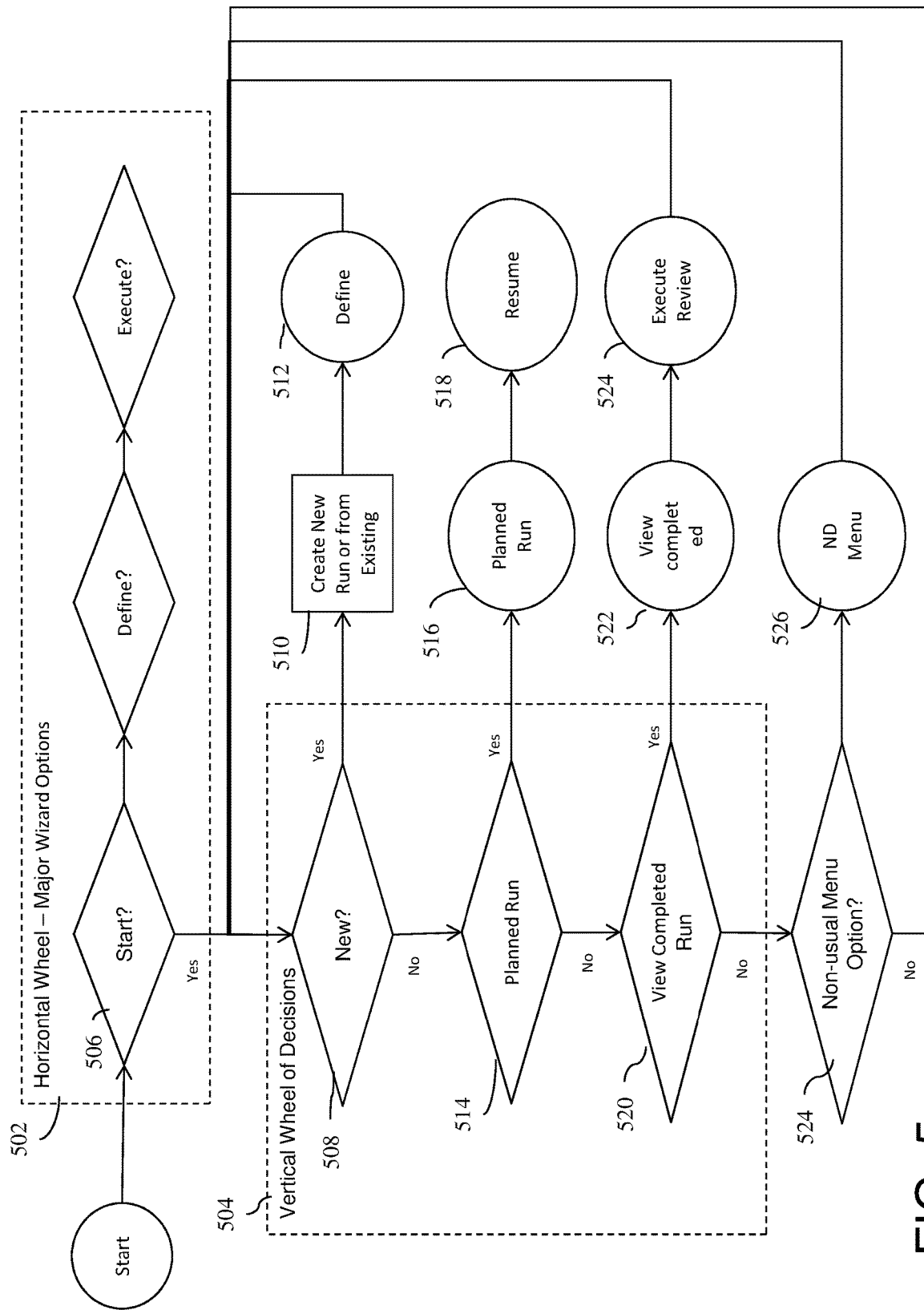
FIG. 5 is a flow diagram illustrating a method of displaying a start user interface screen display in one embodiment.

FIG. 5 is a flow diagram illustrating a method of displaying a start user interface screen display in one embodiment. This display screen includes lists of menu items in two different visual orientations, for example, horizontal and vertical. Thus, for example, a more general category of menu items is displayed on a horizontal wheel 502 and the submenu items are displayed on a vertical wheel 504. For instance, the START option 506, which has been selected from the login user (FIG. 4) is presented on the horizontal wheel 502. The second level of options stemming from the START option 406 is presented on the vertical wheel 504. In this example assay method, the start screen is the initial software screen displayed to the user. The workflows that a user can perform are listed as options (sub options) on a vertical wheel they can selected from. In this assay method example, less common and advanced workflows may be grouped under an advanced menu. In this example assay method, the options for the workflows for the system include: Create a new run 508, when the user selects the create new run workflow 510 the user can create a run from scratch or base it on a previously defined run 512; Continue a run that was previously planned or started 514, when the user selects to continue a previously planned or started run 516, the software automatically resumes 518 from the last step the user completed in the run; View the results of a completed run 520, when the user selects to view a completed run 522, the software brings the user to the review screen 524. After the user selects any of the options from the vertical wheel 504, the options on the vertical wheel are added to a new horizontal wheel above the screen. This horizontal wheel allows the user to change their selection. For example, after selecting "Create New" the options for Planned and Completed runs are moved to the horizontal wheel allowing the user to change their mind.

Figure 6:
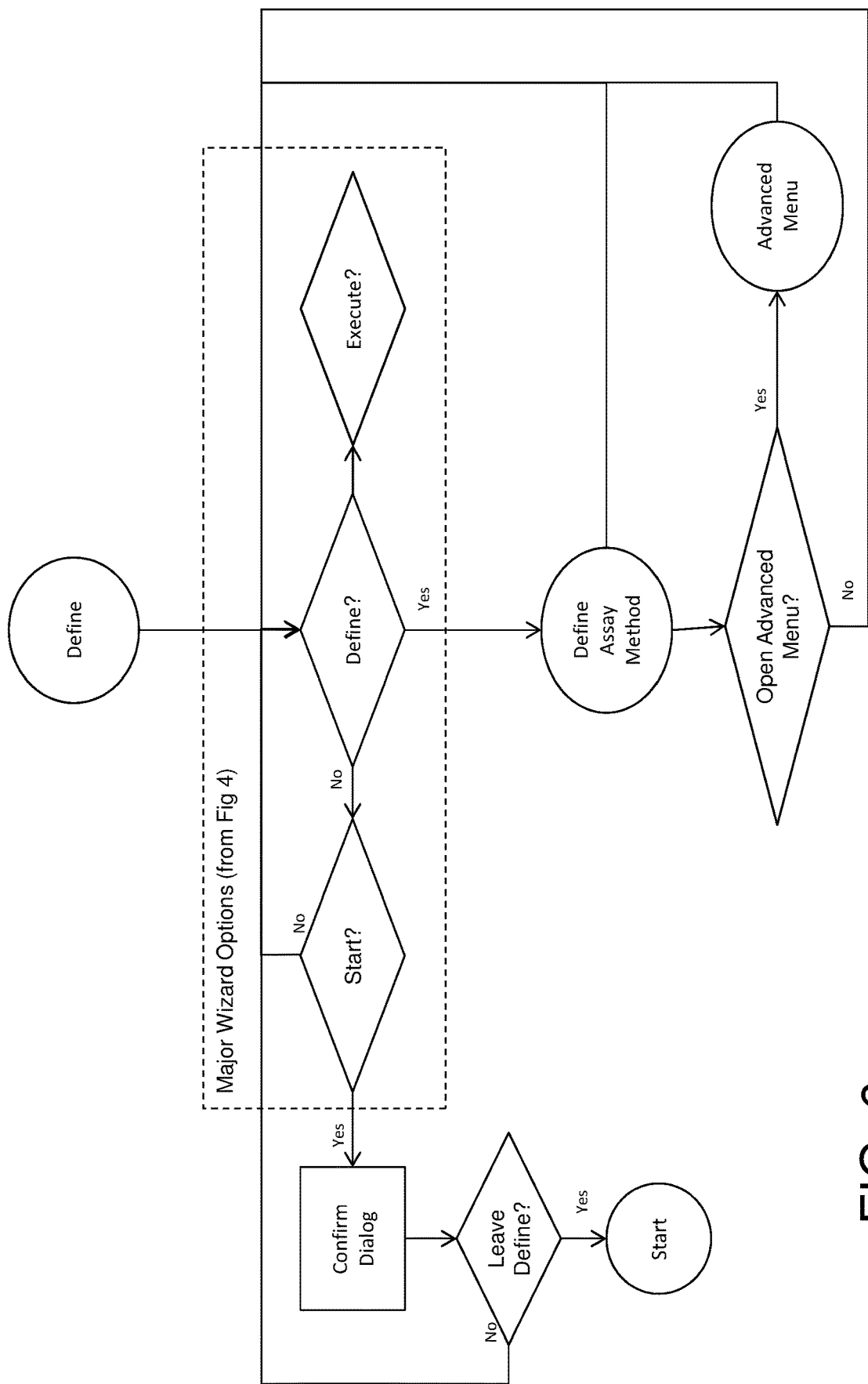
FIG. 6 is a diagram illustrating a workflow of a define assay method screen in one embodiment.

FIG. 6 is a diagram illustrating a workflow of a define assay method screen in one embodiment. In this example, the software requires an Assay Method in order to process the samples being considered. The processing shown in this screen may be performed responsive to the DEFINE option (FIG. 5, 512) being executed. The assay method defines: The assays on the plate; The plate layout; Number of calibrators, controls, and max number of samples; Control, Calibrator, and sample dilutions; Number of replicates for controls, calibrators, and samples; The instrument protocol (incubation time, perform blocker, and/or others). A default Assay Method is provided for every kit, the system software allows the user to create a custom Assay Method based on a default. In one embodiment, the Assay Method is distributed in the Global Product Data (GPD) file. The GPD contains, for example: Product barcode; Assays; Placement of assays in the well; Lot identification for Kit, Plate, Antibodies, Calibrators, Controls; Measured concentration of: Calibrators, Controls; Instrument instructions on how to process the product; and Recommended plate layout.

Figure 7:
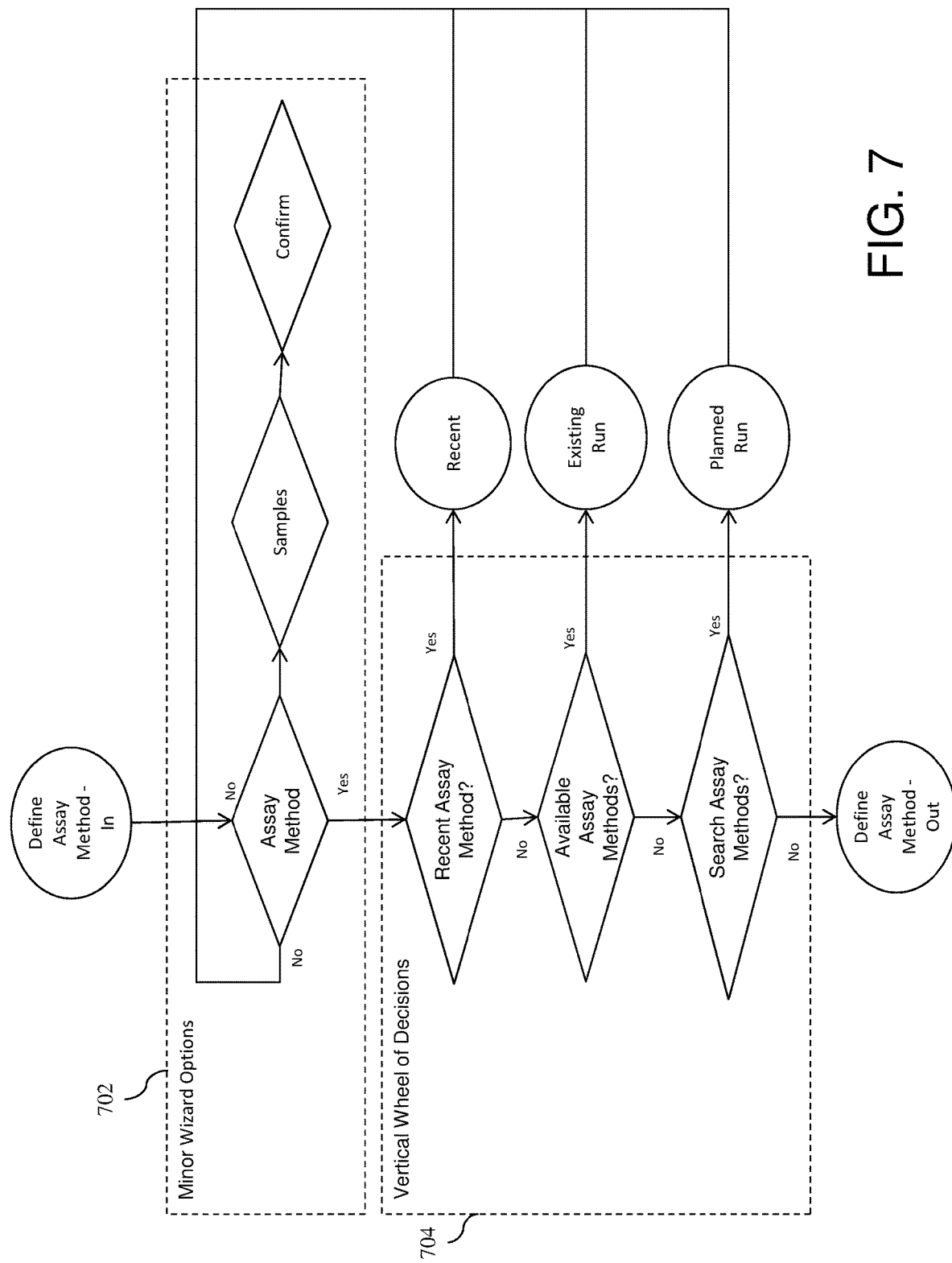
FIG. 7 is a diagram illustrating a user interface workflow for selecting an assay method in one embodiment.

FIG. 7 is a diagram illustrating a user interface workflow for selecting assay method in one embodiment. This user interface workflow may follow a selection or execution of defining assay method, for instance, selected or executed as an option in the workflow shown in FIG. 6. Options under Define Assay Method may include Assay Method selection option, Samples option and Confirm option, which are shown in horizontal orientation, for example, on a horizontal wheel graphical element 702. The selected Assay Method option may be highlighted and/or centered on that horizontal wheel over other unselected options. The sub-level options below the Assay Method option may be displayed in vertical orientation, for example, on a vertical wheel graphical element 704. In this example, there may be 3 ways the user can select an Assay Method: a) Selecting from recent Assay Methods used on the system sorted by reverse chronological order; and b) Selecting from all available Assay Methods installed on the system. In this screen the UI uses multiple wheels, and each wheel filters the results of the following wheel until the final wheel contains just the results: c) Searching for an Assay Method installed on the system, which can be done using free text search.

When the user selects one of the sub-level options, the sub-level options move into the horizontal wheel to allow the user to change their Assay Method selection model. After the user makes the initial selection of the assay method, the user is allowed to select whether the user only wants to run a single assay method or multiple assay methods: Single assay method, wherein all Mesoscale Diagnostics test plates in the run use the same assay method; Multiple assay method, wherein there are at least one Mesoscale Diagnostics test plate per assay method in the run.

Figure 8:
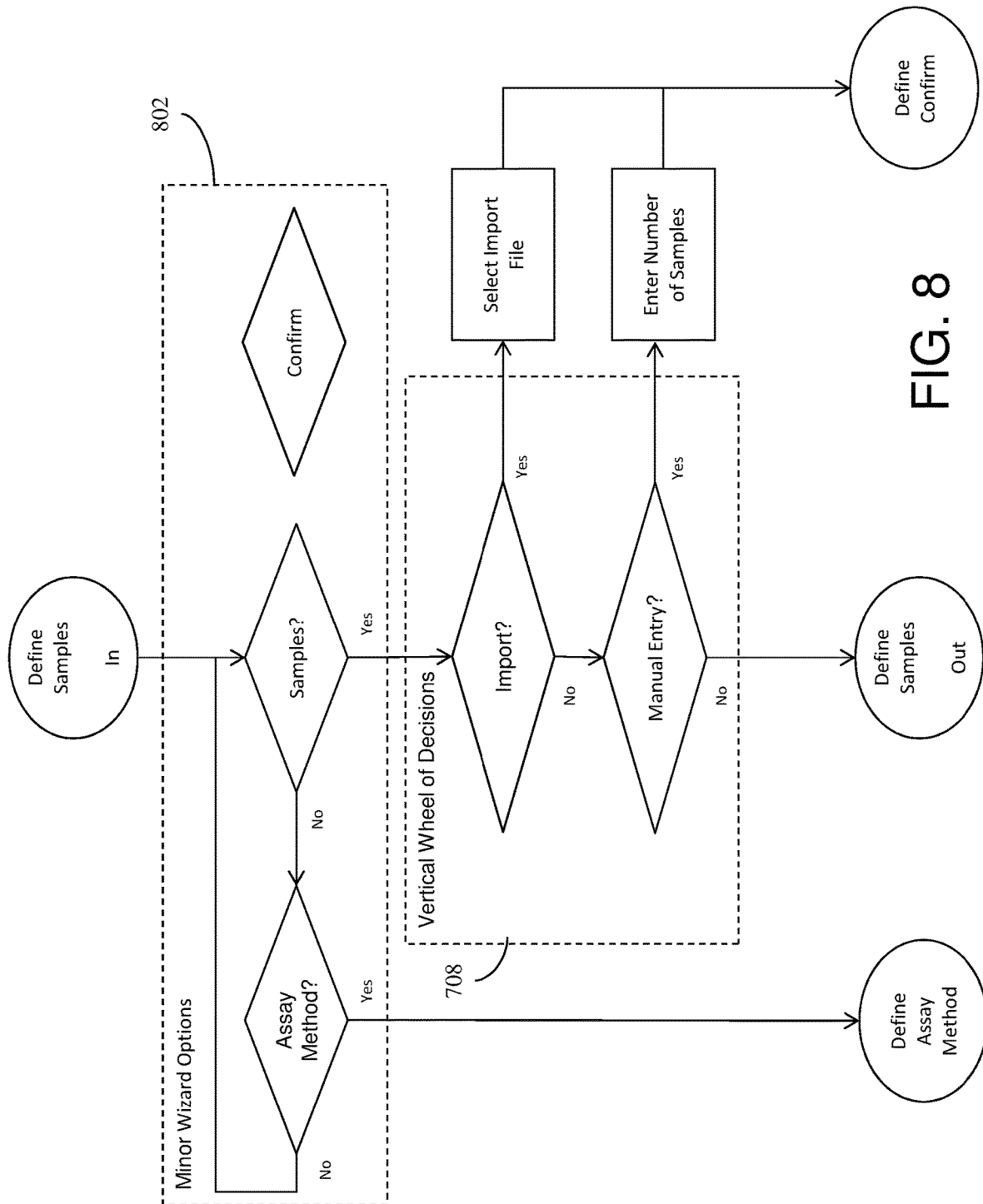
FIG. 8 is a flow diagram illustrating a workflow of a user interface displayed for defining samples in one embodiment.

FIG. 8 is a flow diagram illustrating a workflow of a user interface displayed for defining samples in one embodiment. Based on selecting "Define Samples" option, that option is shown in horizontal orientation, for example, on a horizontal wheel graphical element 802, which may be stacked under the Define option, its parent menu item. The sub-level of options associated with the "Define Samples" options are displayed vertically, for example, on a vertical wheel graphical element 804.

In the Define samples screen the user interface allows the user to select to import samples or manually define the samples. These options move to the horizontal wheel after the user selects an option. When the user selects to import samples from a file, the software via the user interface presents the sample files the user can use in a vertical wheel. The system can alternatively import from a Laboratory Information System or a Laboratory Information Management System.

The system can also import from a sample management system. When the user selects to manually define samples, the user may define the number of samples to run. The software automatically assigns samples IDs.

Figure 9:
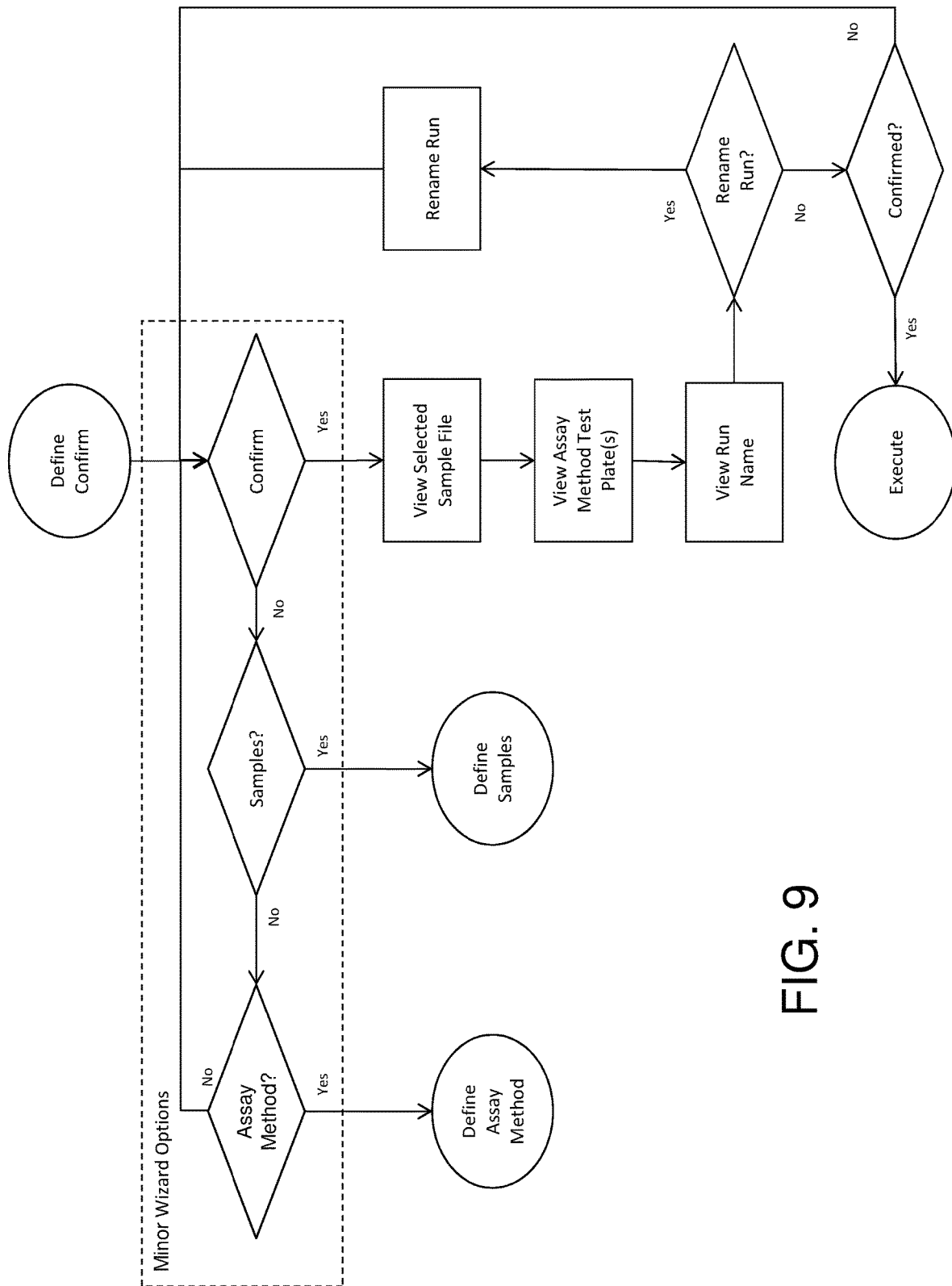
FIG. 9 is a flow diagram illustrating a workflow of a user interface displayed for confirming a run definition in one embodiment.

FIG. 9 is a flow diagram illustrating a workflow of a user interface displayed for confirming a run definition in one embodiment. Based on selecting "Confirm Run Definition" option, a submenu item of "Define" option, the "Confirm Run Definition" option is displayed on a horizontal wheel graphical element, for example, stacked below its parent menu item, "Define" option. After the user has defined the run in the previous steps, the system provides a summary of the run for the user to review and confirm. The following information is displayed to the user: The number of samples in the run. The user may also select the number of samples to view the sample identifiers (IDs), the number of Mesoscale Diagnostics plates in the run, the layout of the plates, and the name of the run. The system gives a default name to the run and allows the user to change it. Once the user has confirmed the run, the system prompts the user requesting whether the user wants to continue to execute the run or return to the Start Goal.

Figure 10:
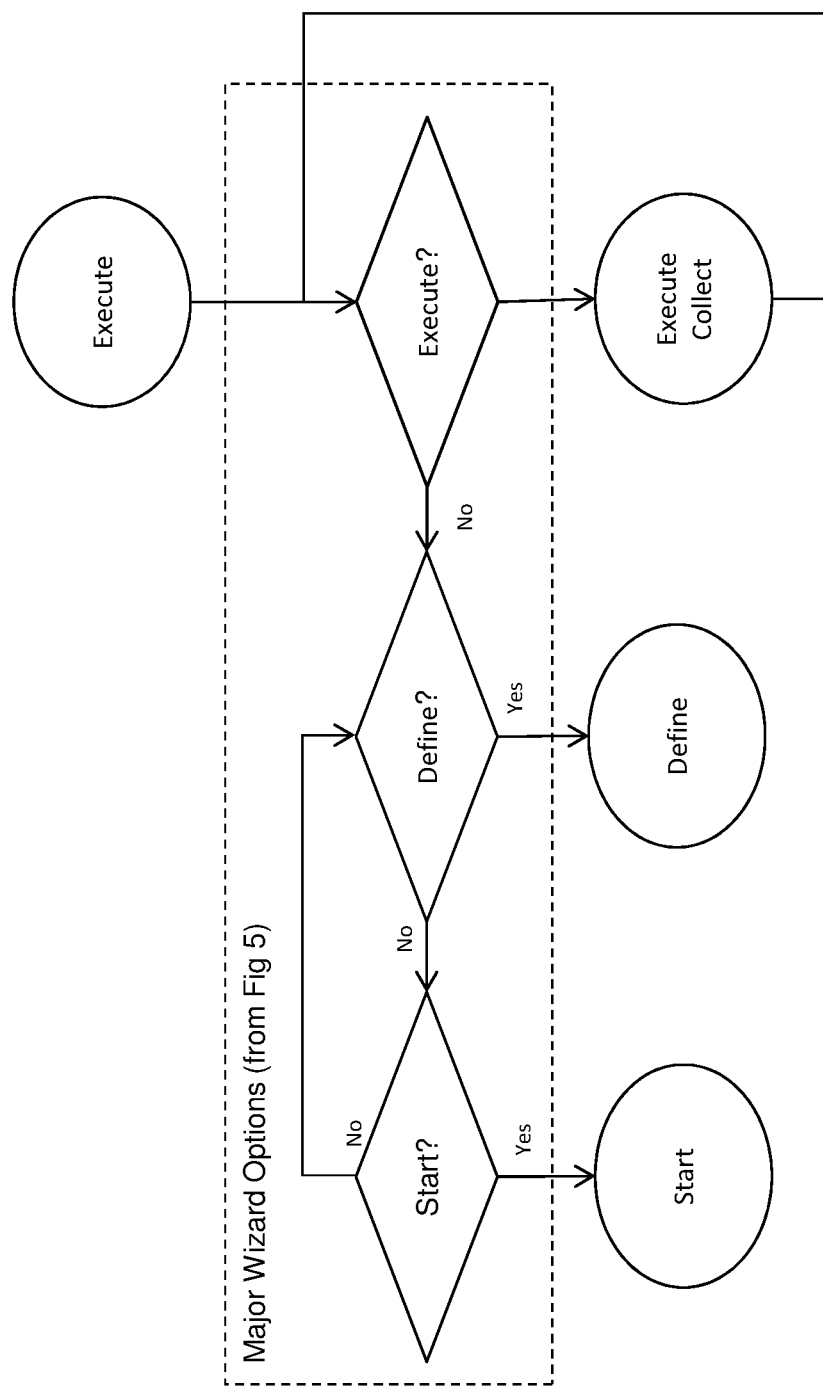
FIG. 10 is a flow diagram illustrating a workflow of a user interface displayed for notifying the user of the accomplished tasks in one embodiment.

FIG. 10 is a flow diagram illustrating a workflow of a user interface displayed for notifying the user of the accomplished tasks in one embodiment. The system may walk the user through accomplishing tasks via the user interface in a wizard (an automated help feature). The major logical steps may be broken down into Goals. In this example, the system has three major goals in the wizard: Start, wherein the user begins and selects what the user wants to do in the system; Define, wherein after the user picks what the user wants to do, the wizard walks the user via the user interface through defining any information needed; and Execute, wherein the system walks the user through execution of the task the user has selected.

Figure 11:
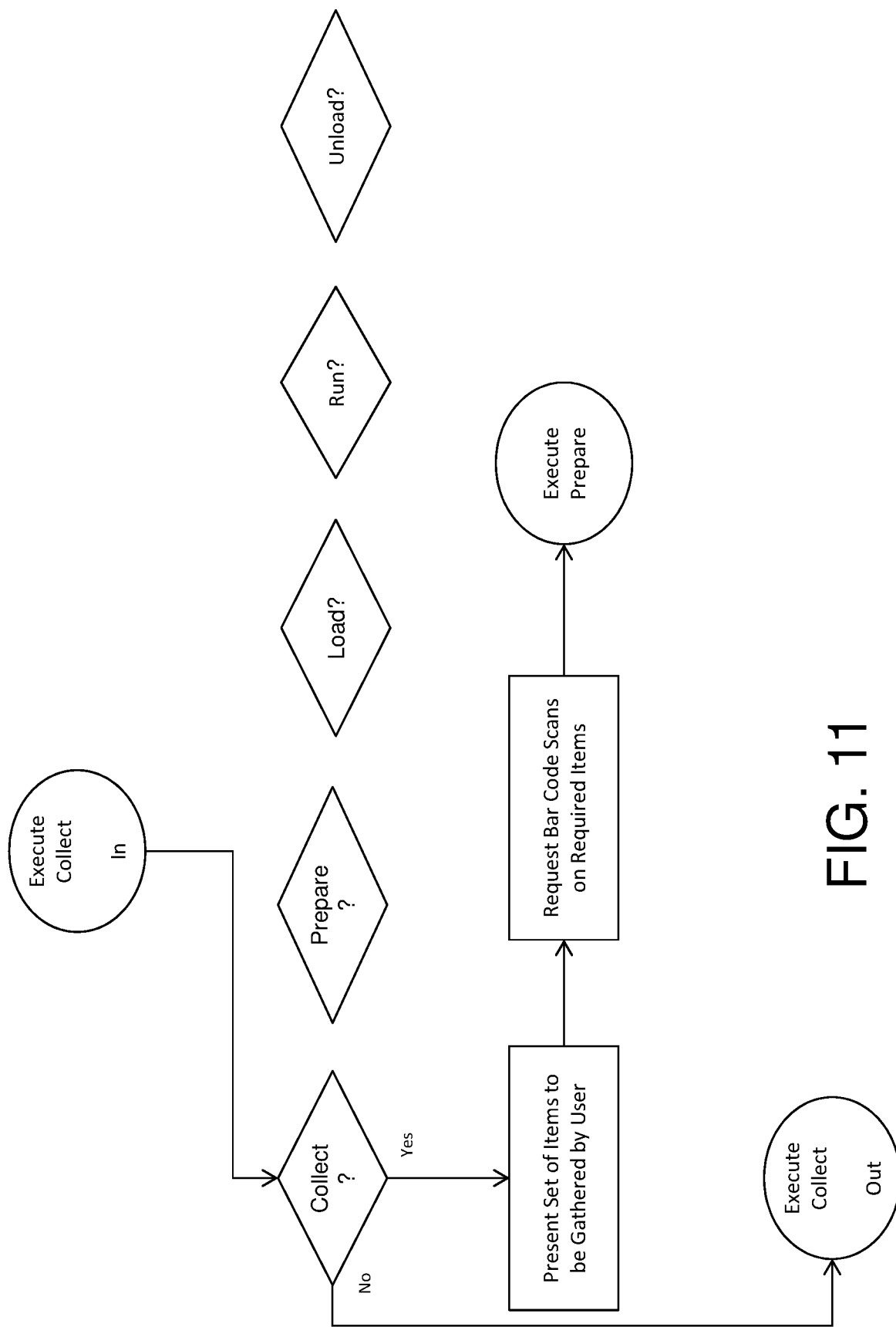
FIG. 11 is a flow diagram illustrating a workflow of a user interface displayed for an execute/collect option in one embodiment.

FIG. 11 is a flow diagram illustrating a workflow of a user interface displayed for execute/collect option in one embodiment. In this collect screen the system creates a list of items that the user needs to collects in order to perform the run. Each item has to be marked as collected before proceeding. The system also allows the user to print this list or use a tablet computer for collection. For each item to be collected the item may optionally be scanned so the system can check it is the correct item, expiration date, lot information. For instance, the system may request bar code scans on items. This is done using the barcode (GPI) to retrieve the GPD.

Figure 12:
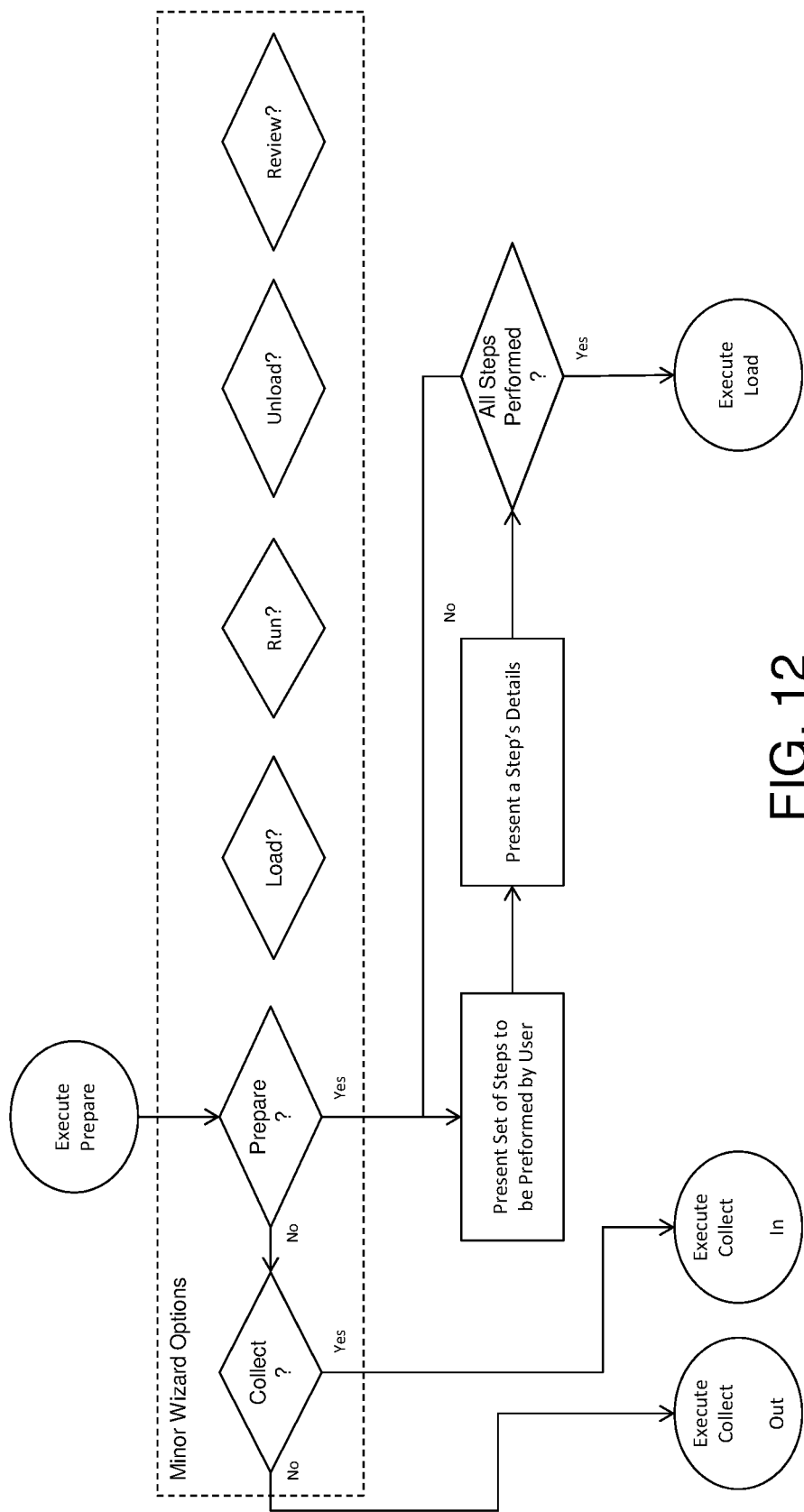
FIG. 12 is a flow diagram illustrating a workflow of a user interface displayed for an execute/prepare option in one embodiment.

FIG. 12 is a flow diagram illustrating a workflow of a user interface displayed for execute/prepare option in one embodiment. In this prepare screen, the system presents a list of steps needed to prepare items that were collected in a wheel. For each step in the wheel the system presents the detailed instructions for that prepare step when it is selected. The detailed prepare step may include: Text that describes the actions to be taken; Images that visually indicate the actions; Video that demonstrates the actions; and Web content, as in Web pages, that provide further details or context about the actions. The user is prompted to indicate that all the prepare steps have been completed before proceeding to the next step. The user may also print the prepare steps or complete them using the tablet.

Figure 13:
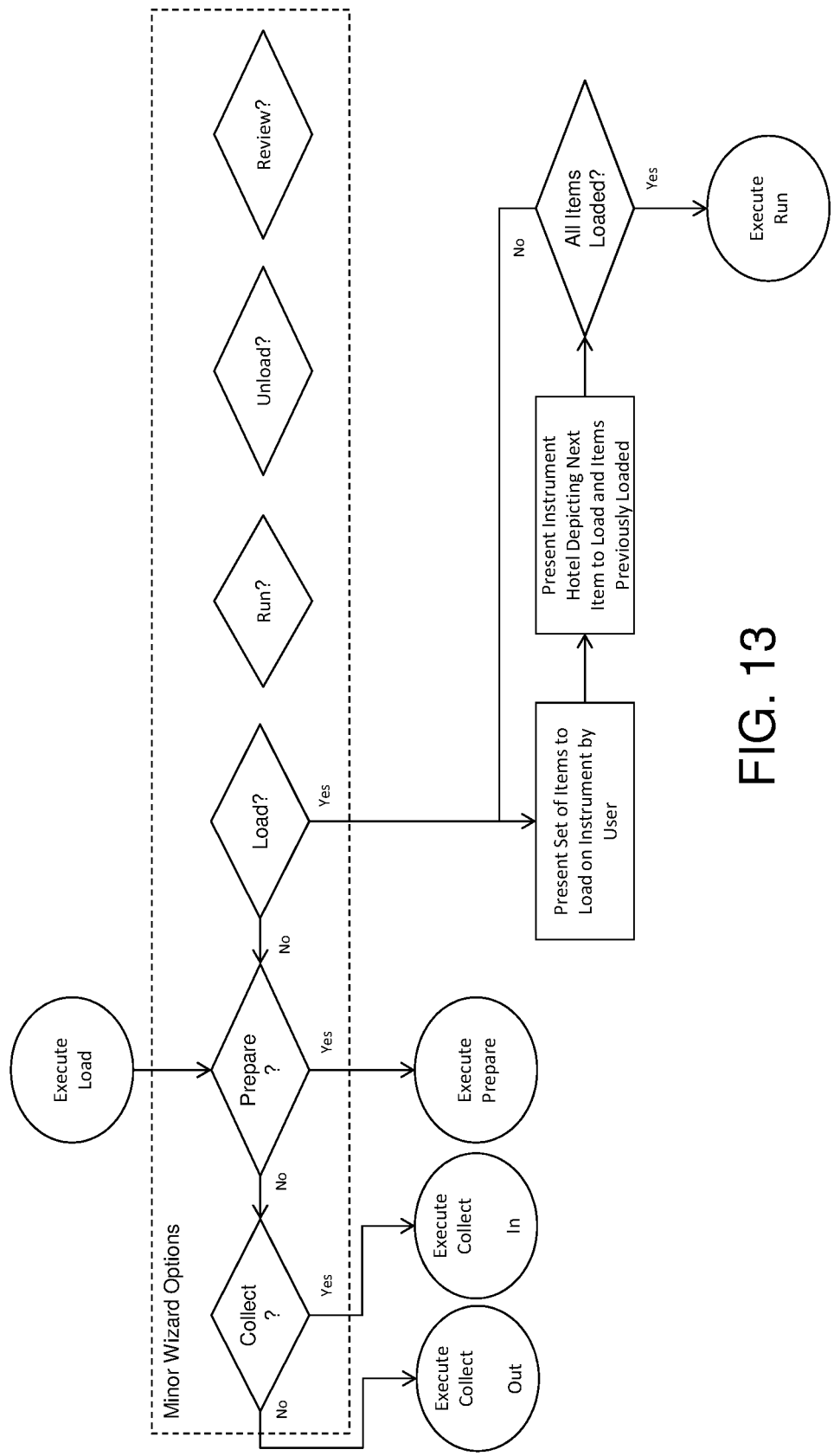
FIG. 13 is a flow diagram illustrating a workflow of a user interface displayed for an execute/load option in one embodiment.

FIG. 13 is a flow diagram illustrating a workflow of a user interface displayed for execute/load option in one embodiment. In this load screen the system displays a list of the items to load onto the instrument in a wheel format. For each item the system displays graphically where the item should be loaded. The system provides a graphical indication of whether the item was loaded or is empty. The system checks whether all the items have been loaded before proceeding to the next screen.

Figure 14:
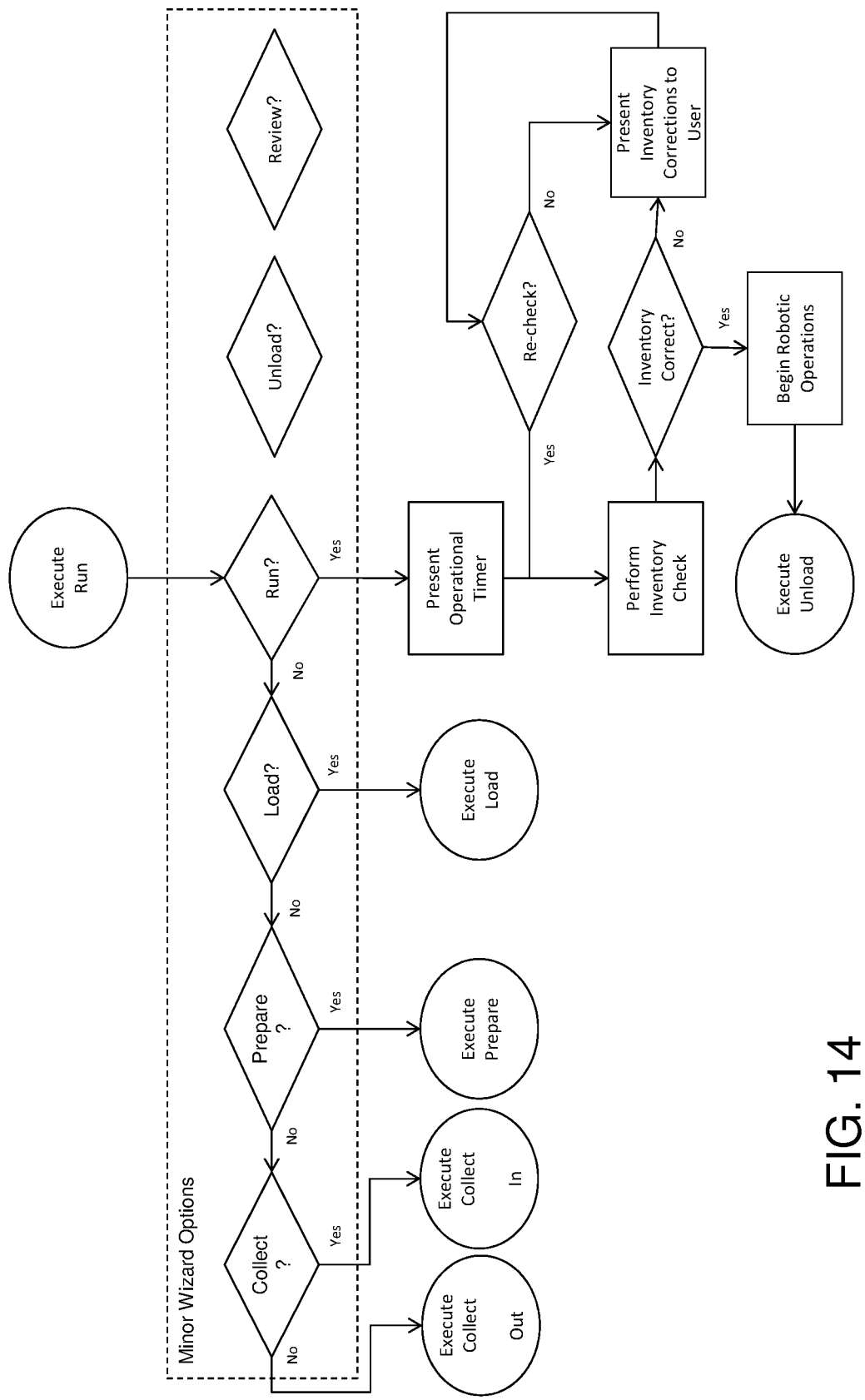
FIG. 14 is a flow diagram illustrating a workflow of a user interface displayed for an execute/run option in one embodiment.

FIG. 14 is a flow diagram illustrating a workflow of a user interface displayed for execute/run option in one embodiment. This run screen allows the user to indicate to the system to start the run, for example, via a run button UI control. This screen also allows the user to register other users for system update messages. The updates may be distributed through for example, electronic mail (email), text such as short message service (SMS), social network applications and/or blogs, and/or others. Once the user initiates the run, the system transitions to present a timer of the estimated time to completion. In one embodiment, there are 3 modes to the timer; 1) Estimated time in an analog watch format; 2) Estimated time in a digital watch format; and 3) A live camera feed of the instrument. The user may also request the run to stop through the advanced context menu.

Figure 15:
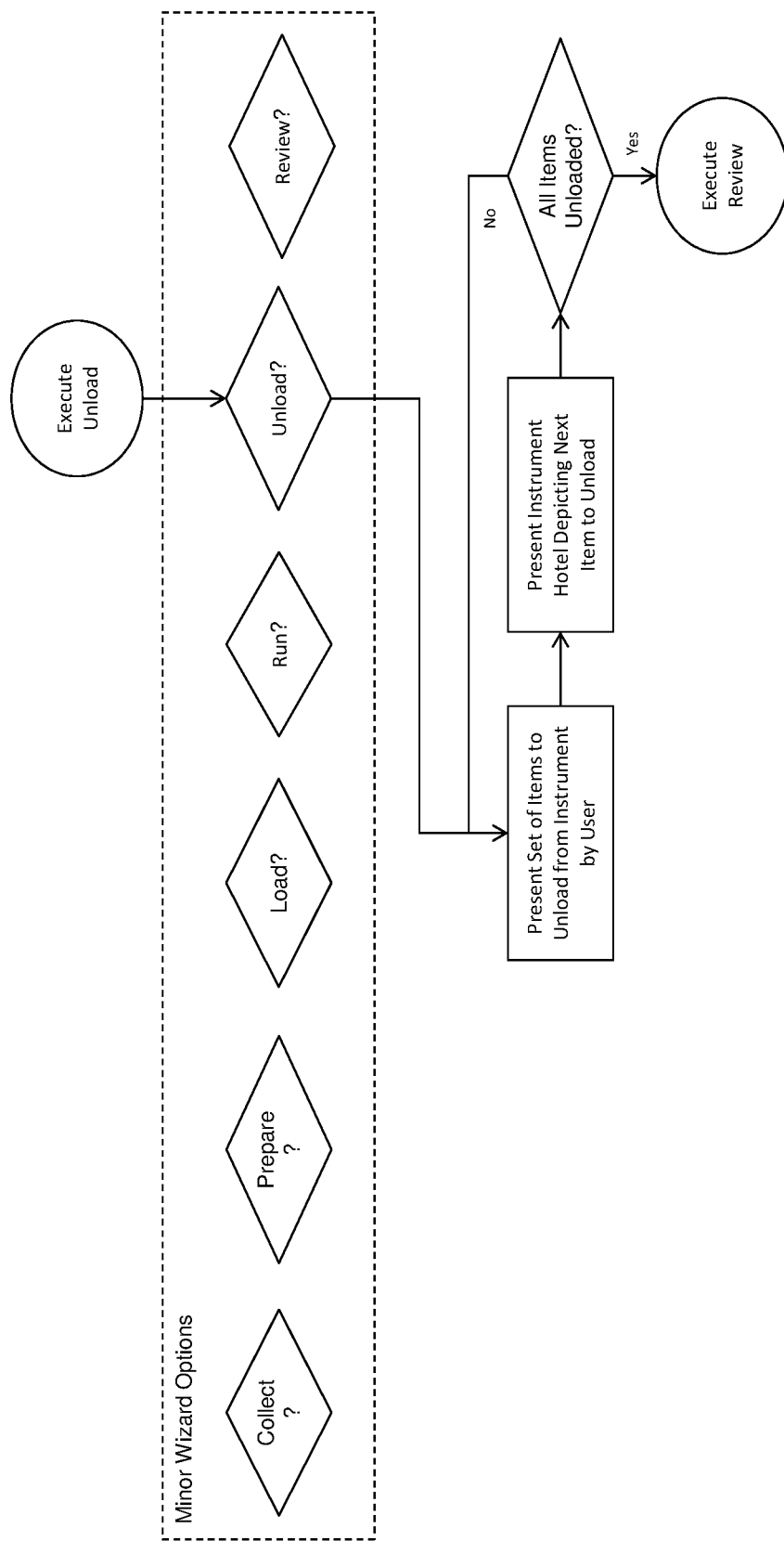
FIG. 15 is a flow diagram illustrating a workflow of a user interface displayed for an execute/unload option in one embodiment.

FIG. 15 is a flow diagram illustrating a workflow of a user interface displayed for execute/unload option in one embodiment. After a run completes, the system transitions to this unload screen. At the unload screen a list of steps is presented to unload the system in a wheel. For each item the system displays graphically where the item should be unloaded. The system provides a graphical indication of whether the item is loaded or is unloaded. The user needs to unload all the items before proceeding to the next screen.

Figure 16:
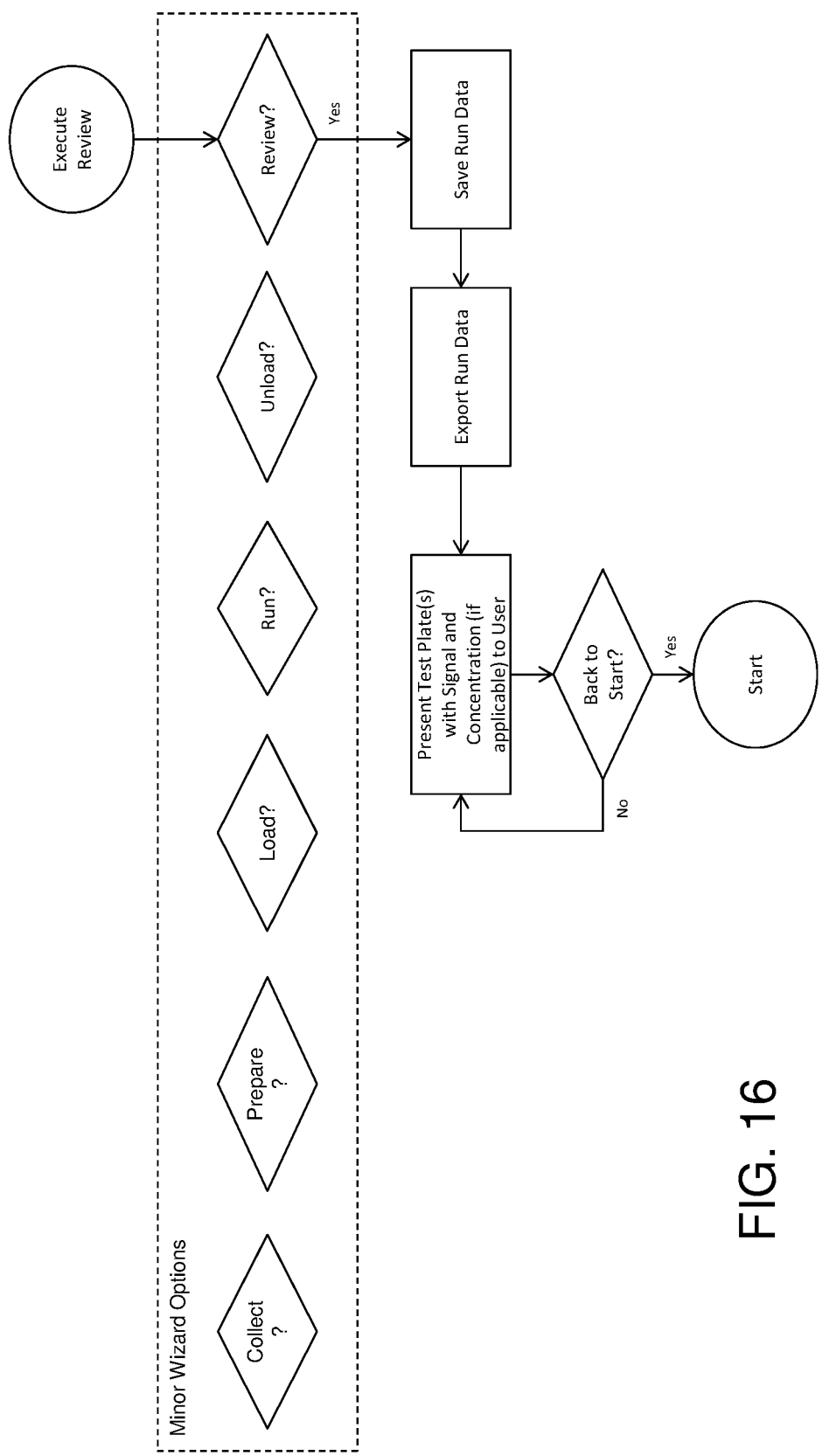
FIG. 16 is a flow diagram illustrating a workflow of a user interface displayed for an execute/review option in one embodiment.

FIG. 16 is a flow diagram illustrating a workflow of a user interface displayed for execute/review option in one embodiment. At the review screen, the system presents the results of the run. The results are also automatically exported in: File format; Transmitted to LIMS/LIS system; and Email. The results are presented and can be viewed: a) Graphically as a plate representation. ECL or Calculated Concentration is displayed using a luminosity scale, where a dark/black color indicates a low result and a bright color indicates a high result. A scale is presented to annotate the color luminosity to number; b) The results are also available as a table. This table can be exported through File format; Transmitted to LIMS/LIS system; and/or Email. The system records any unusual operations or results in a table, for instance, if the temperature during the run was not in the specified range. After the user is done reviewing the run data, the user may go to the Start goal to begin another run or view results.

Figure 17:
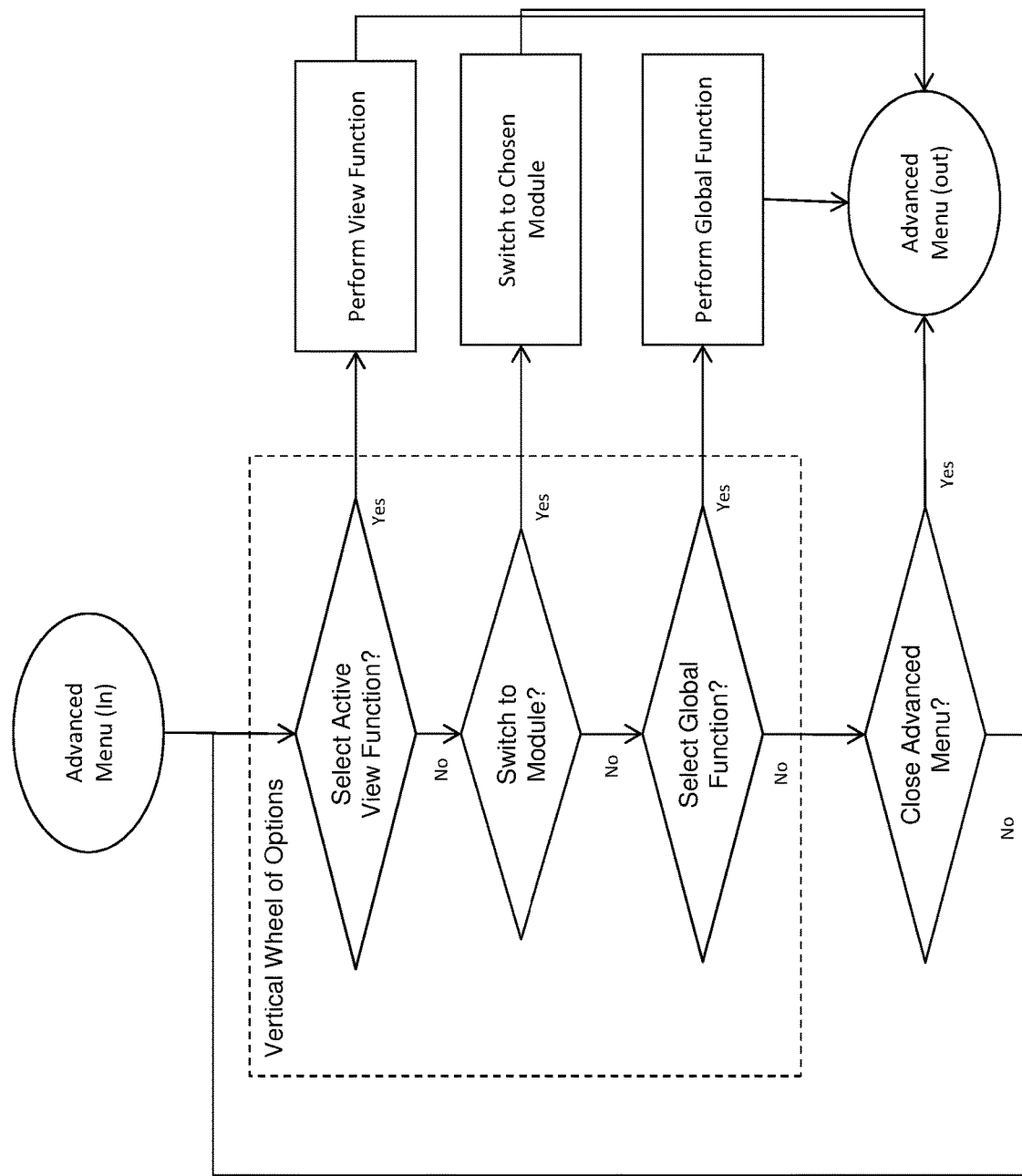
FIG. 17 is a flow diagram illustrating a workflow of a user interface displayed for an execute/review option in one embodiment.

FIG. 17 is a flow diagram illustrating a workflow of a user interface displayed for execute/review option in one embodiment. In one embodiment, the system categorizes tasks the user may do into major workflows and advanced workflows. Major workflows are those the user will routinely perform and are optimized for ease of execution. The major workflows are represented in the wizard Goals and steps. Advanced workflows are present in the advance context menu and represent workflows that are not routinely done or restricted to configuration manager. The user opens the advanced context menu by clicking on the Mesoscale Diagnostics Globe. The advanced context menu items are contained in a vertical wheel with 3 main groups: Functions related to the current screen—context sensitive items, which change depending on the active screen; Modules that can be switched to; and Functions that are applicable across all modules, for instance login and logout of the software. In this screen, the selected option, advanced menu is displayed horizontally on a horizontal graphical wheel, while the sub-options of the advanced menu are shown vertically on a vertical graphical wheel.

Figure 20:
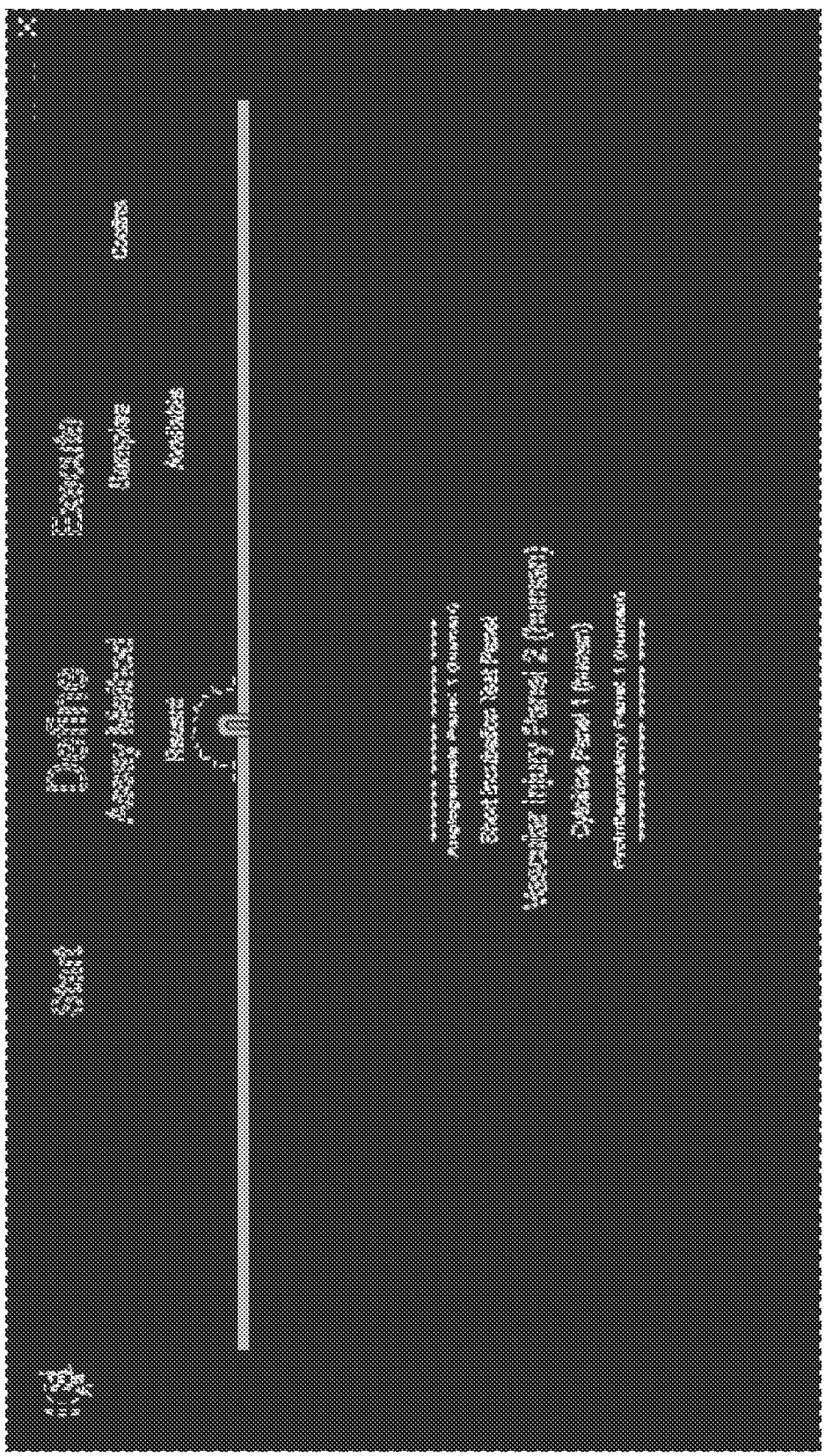
FIG. 20 is an example screen shot of a screen displaying a graphical wheel/slider, which maximizes screen black space, in one embodiment.

In one embodiment, the graphical user interface in one embodiment maximizes black space by making the background black, thereby minimizing coloring of pixels in the user interface display (e.g., display screen), save storage and improve speed of presentation. FIG. 20 is an example screen shot of a screen displaying graphical wheel/slider, which maximizes screen black space, in one embodiment.

Figure 63:
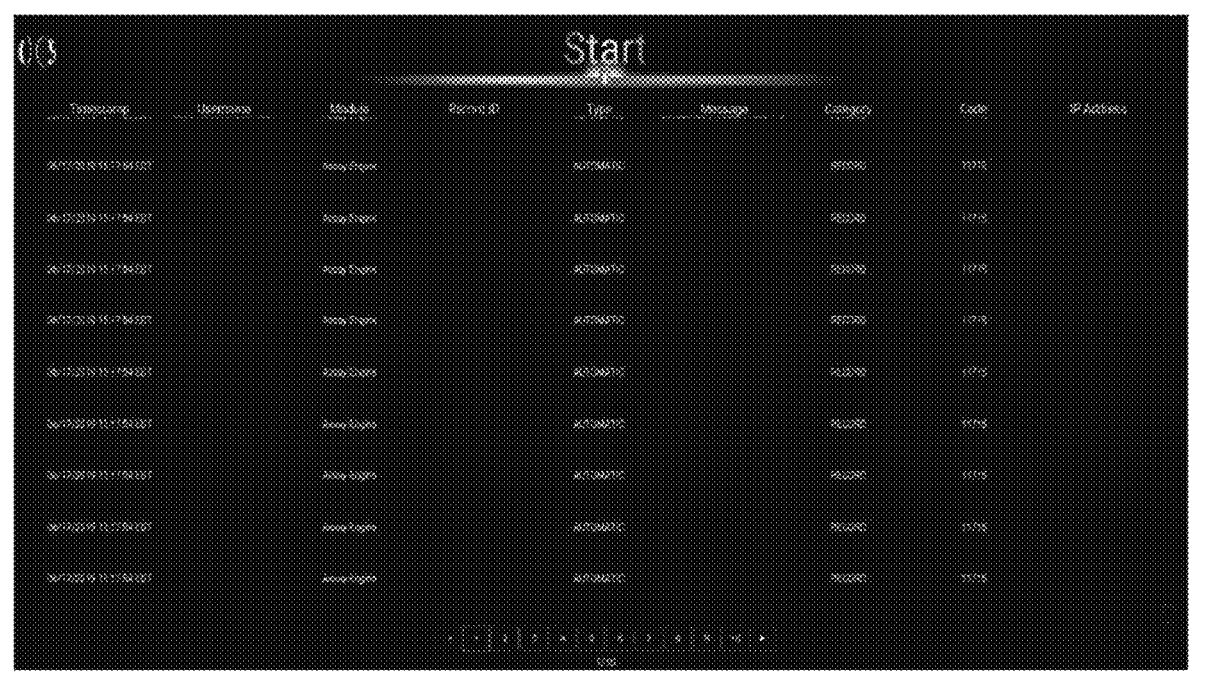
Figure 64A:
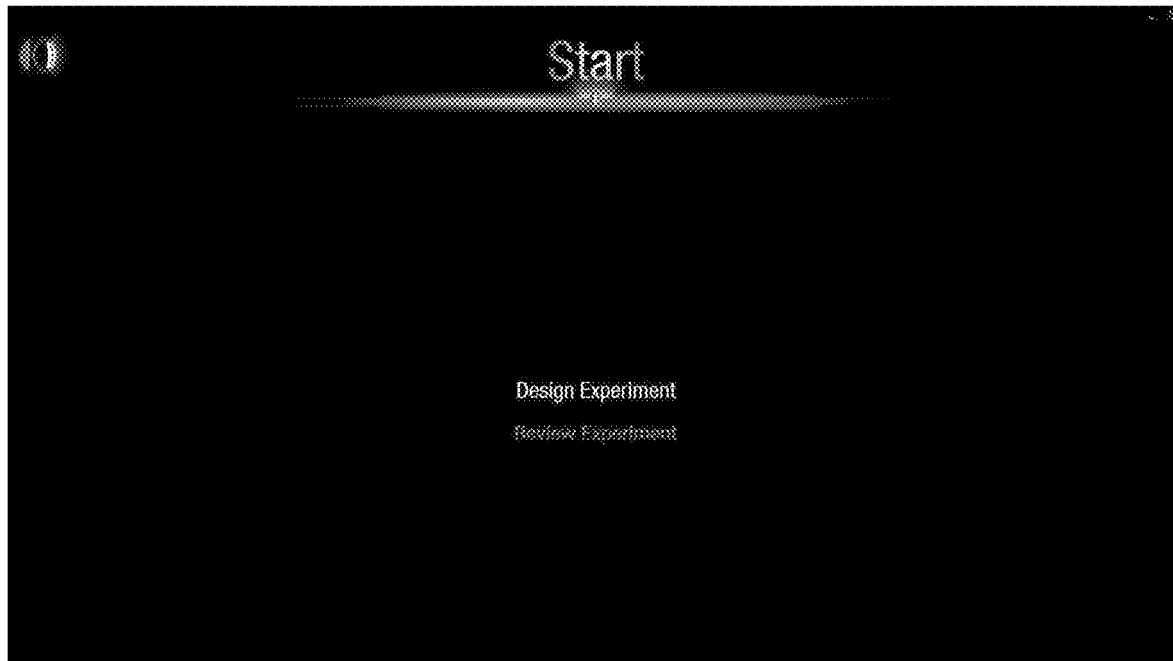
FIGS. 64A-64RR are example non-limiting embodiments of an assay method module.
Figure 64B:
Figure 64C:
Figure 64D:
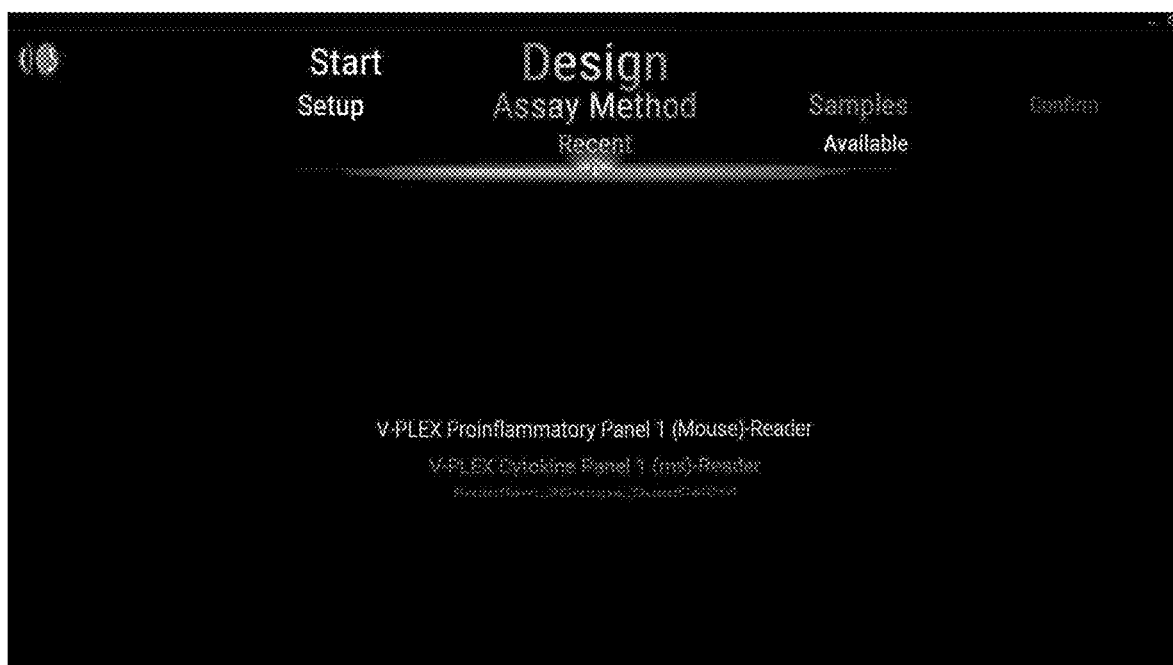
Figure 64E:
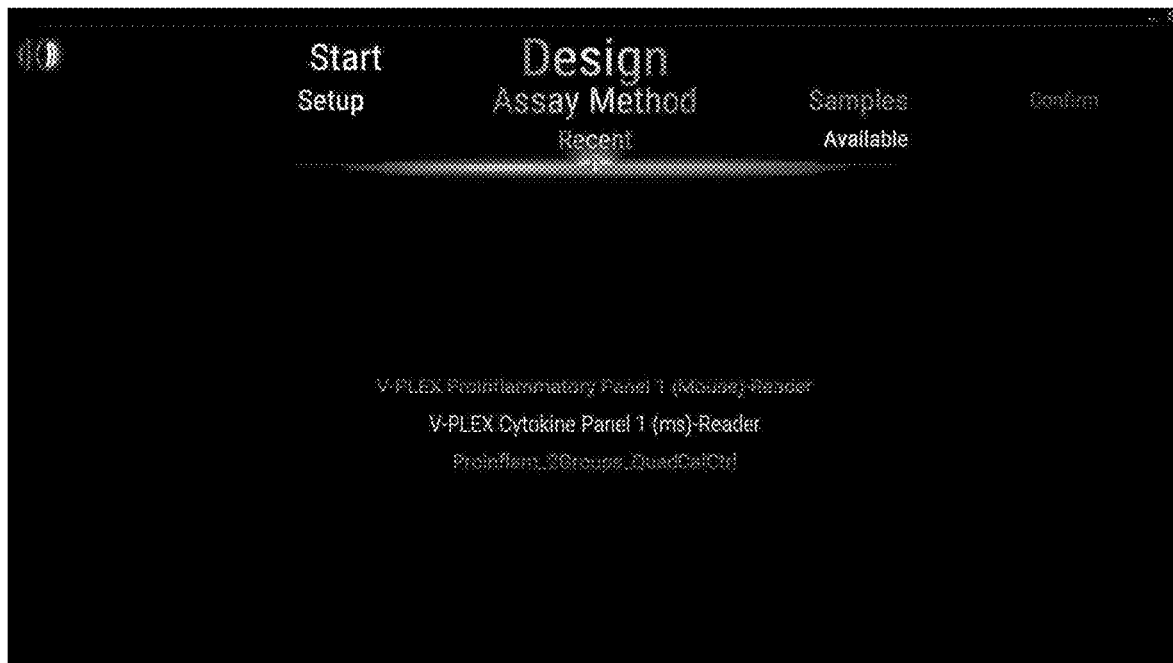
Figure 64F:
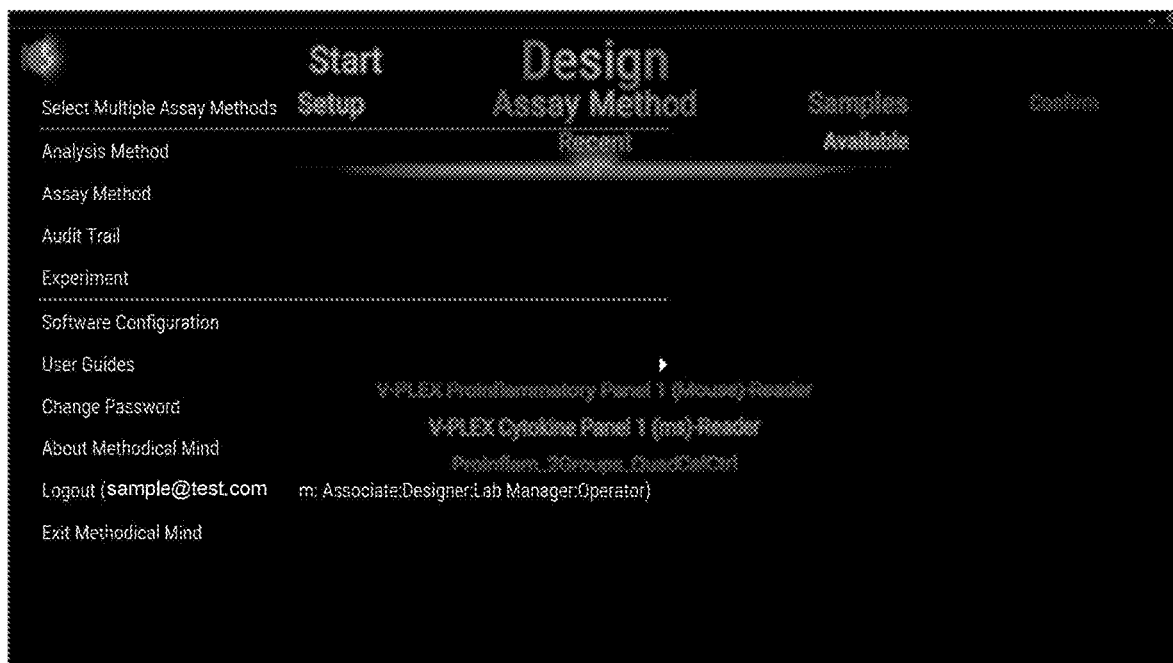
Figure 64G:
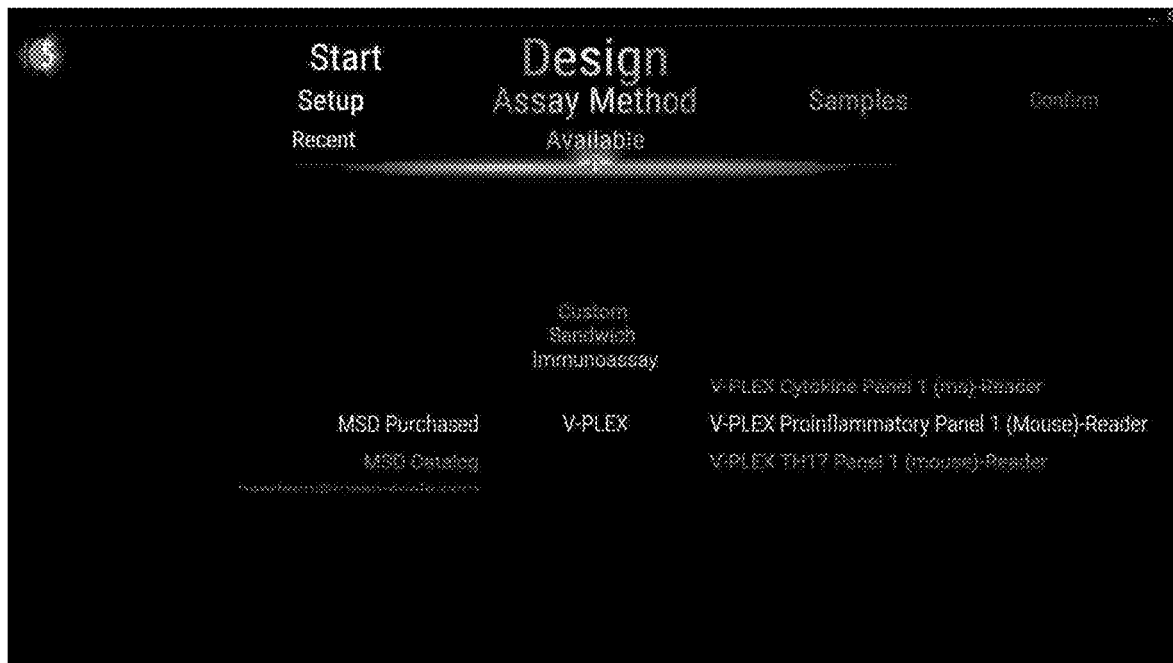
Figure 64H:
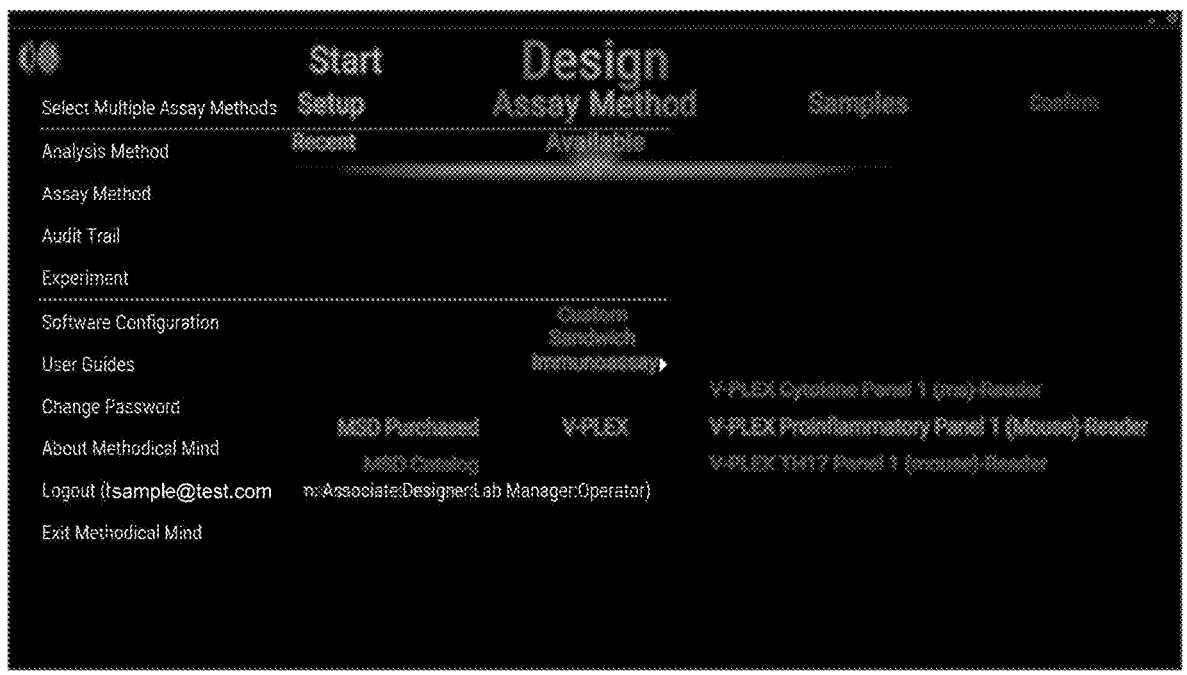
Figure 64I:
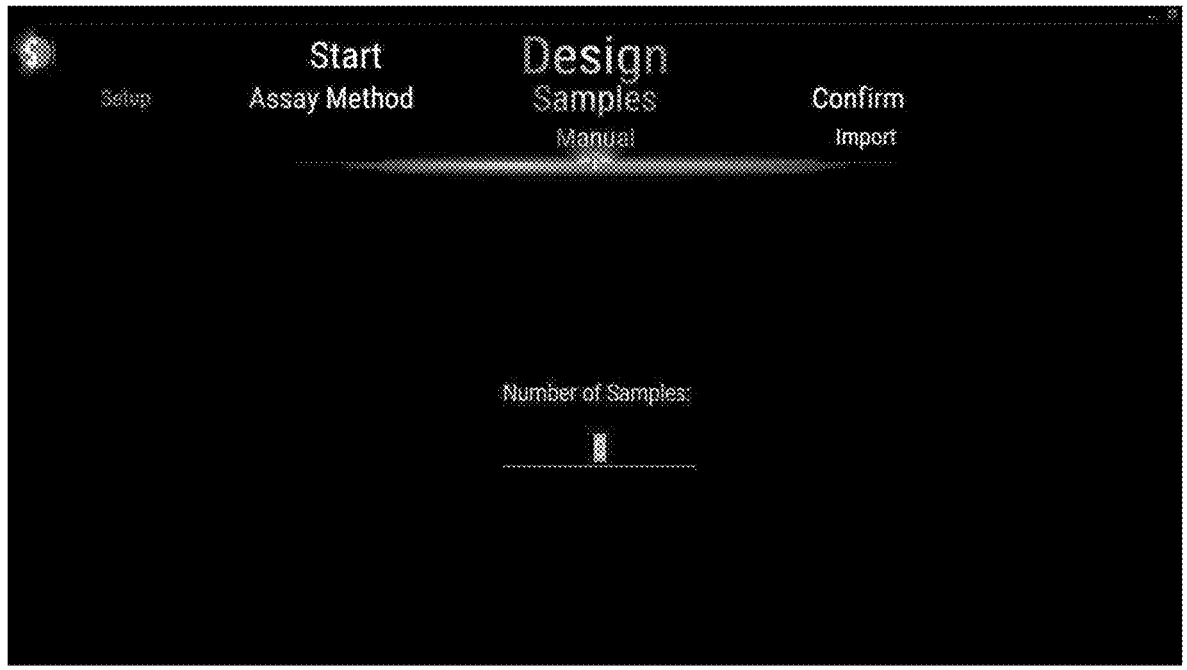
Figure 64J:
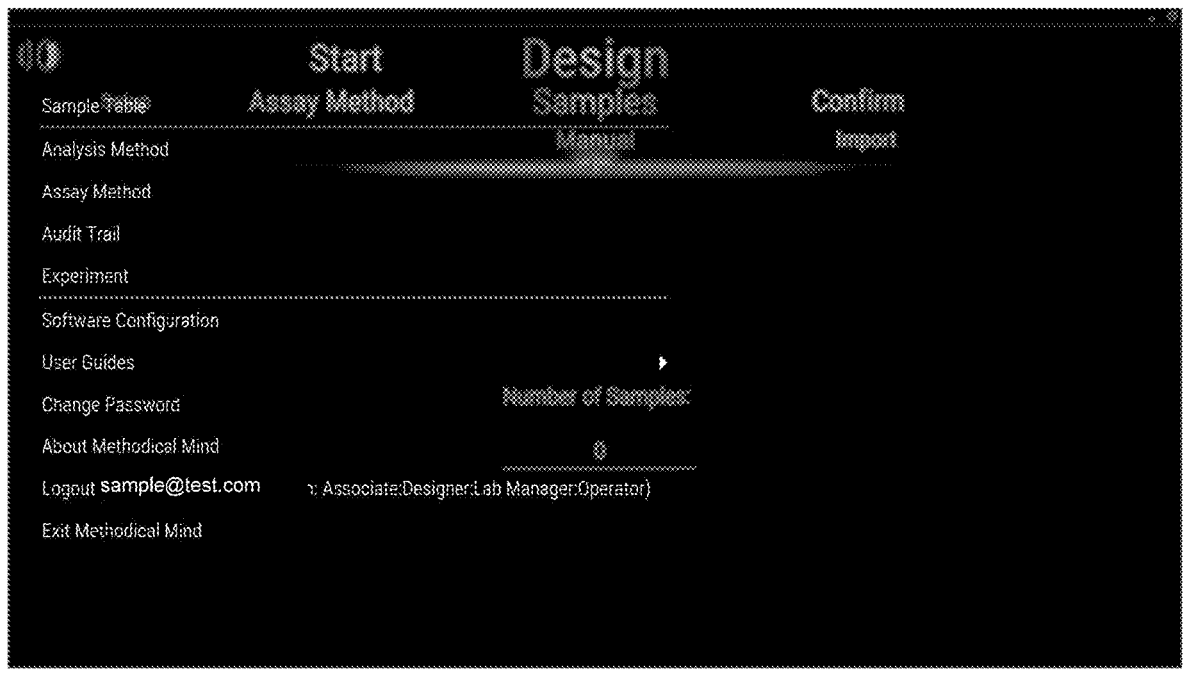
Figure 64K:
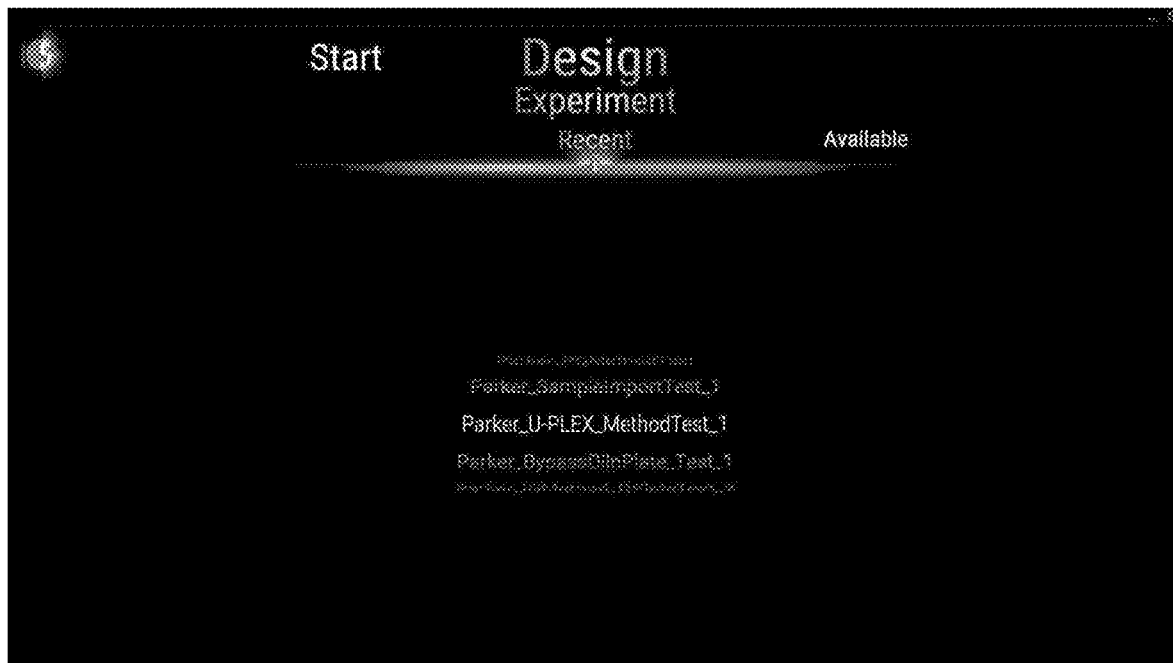
Figure 64L:
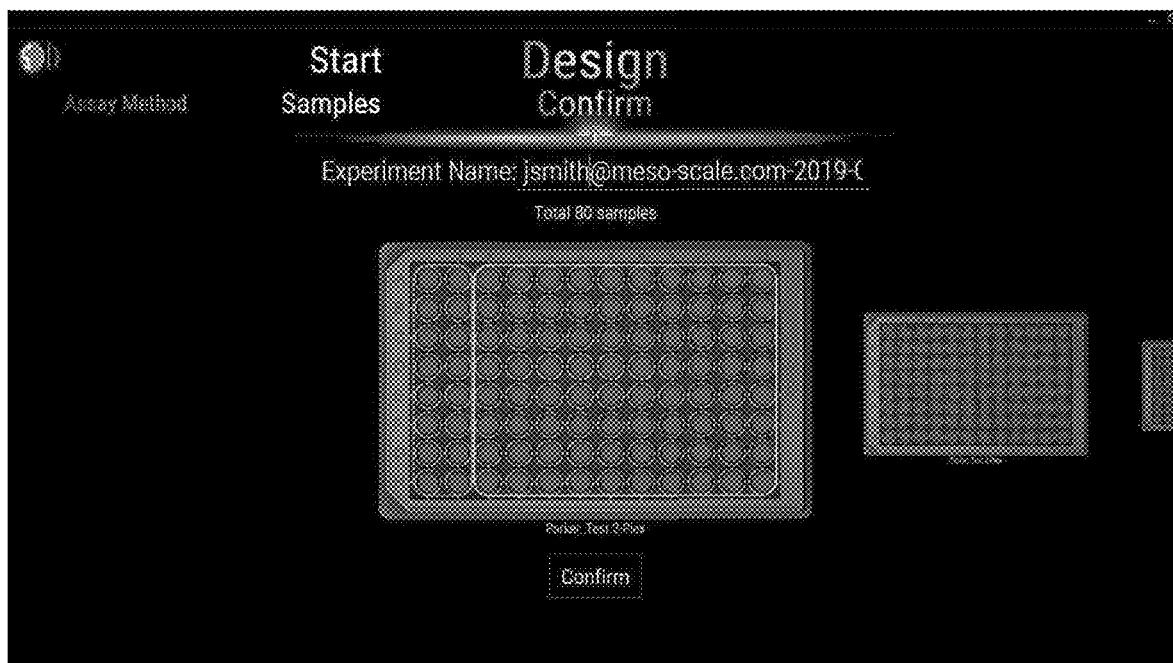
Figure 64M:
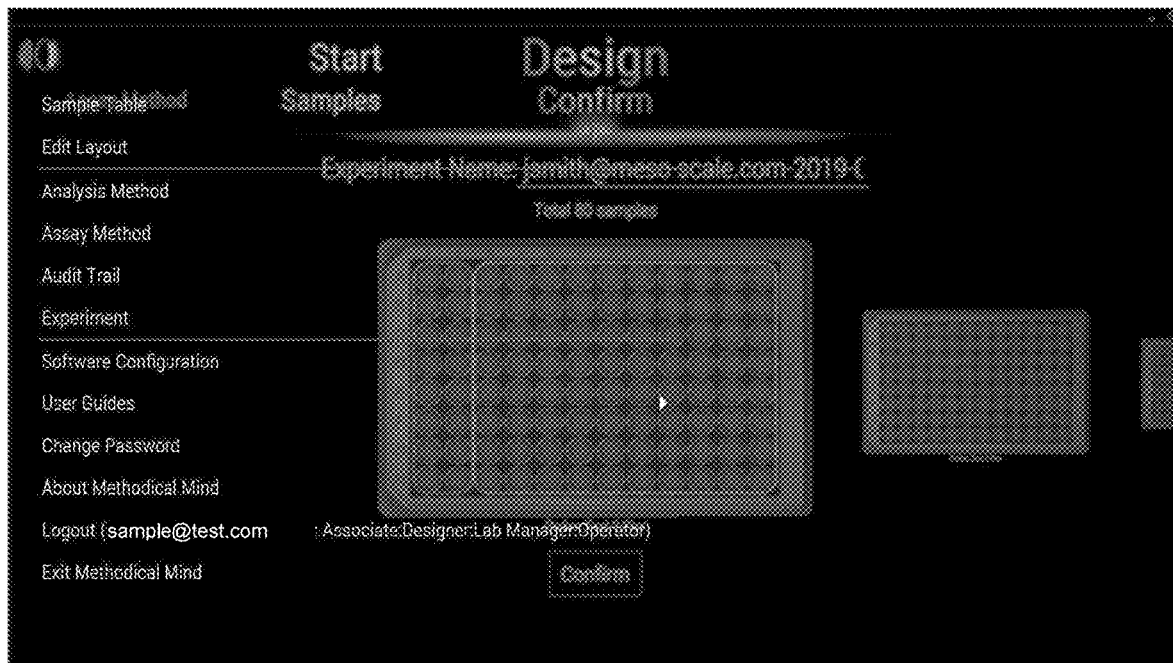
Figure 64N:
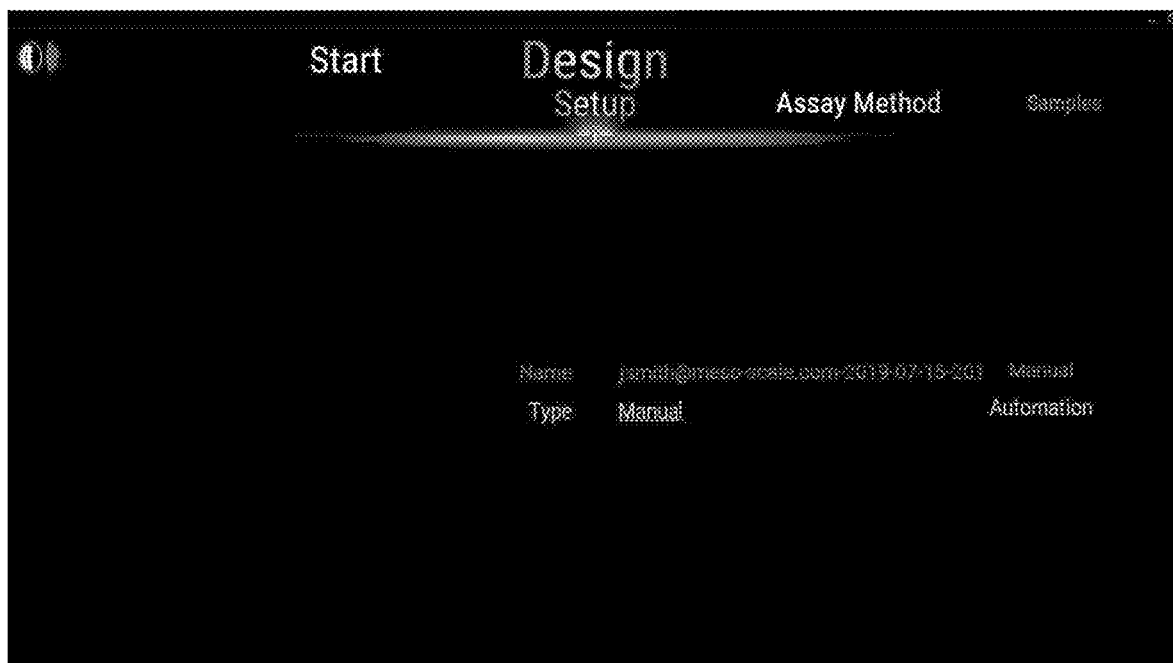
Figure 64O:
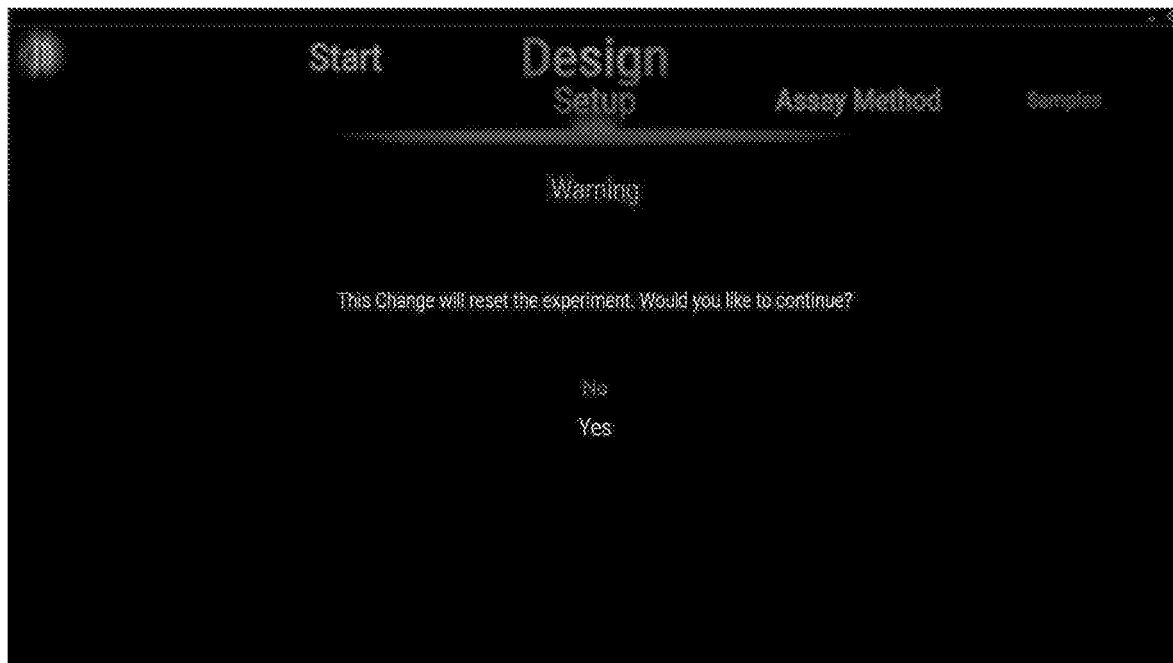
Figure 64P:
Figure 64Q:
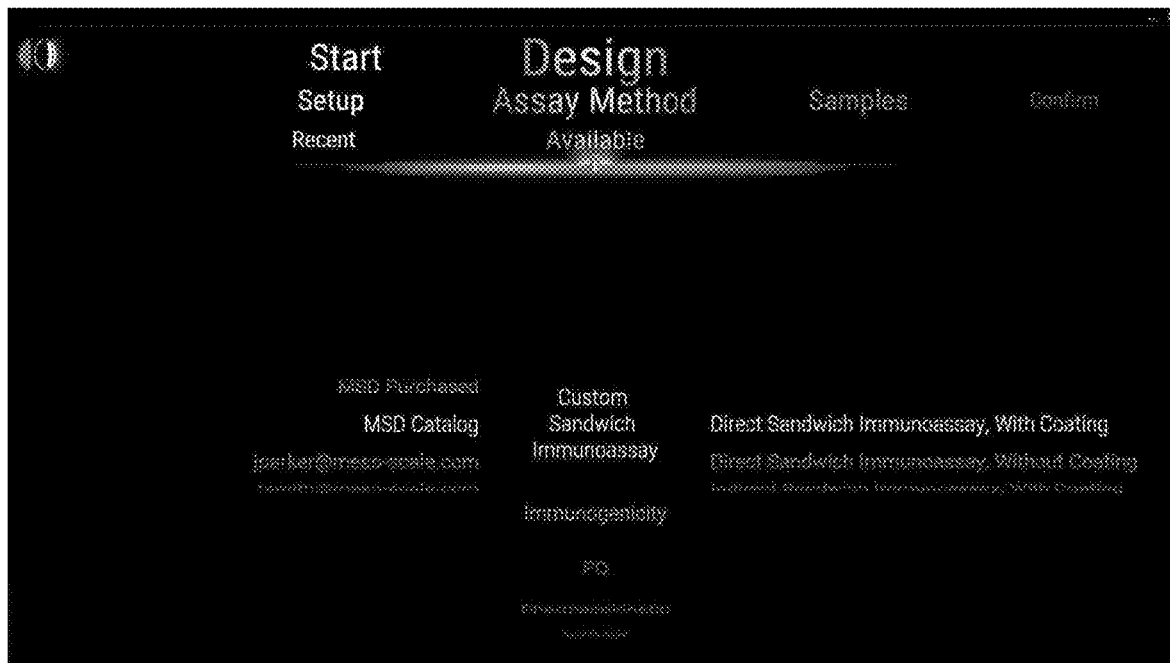
Figure 64R:
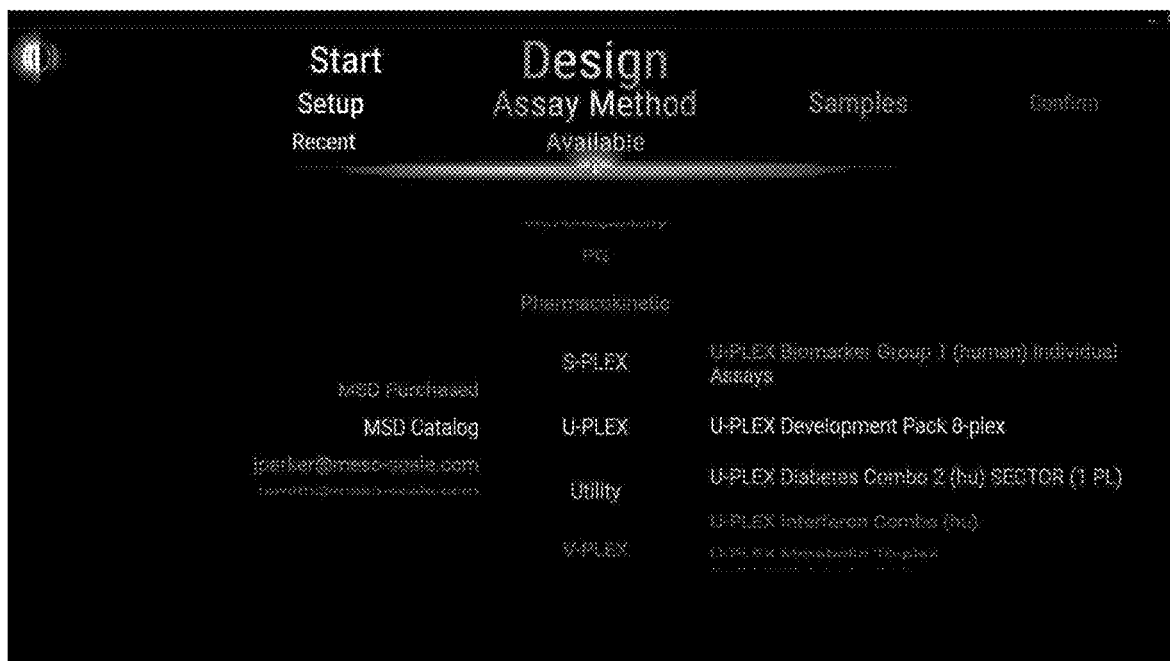
Figure 64S:
Figure 64T:
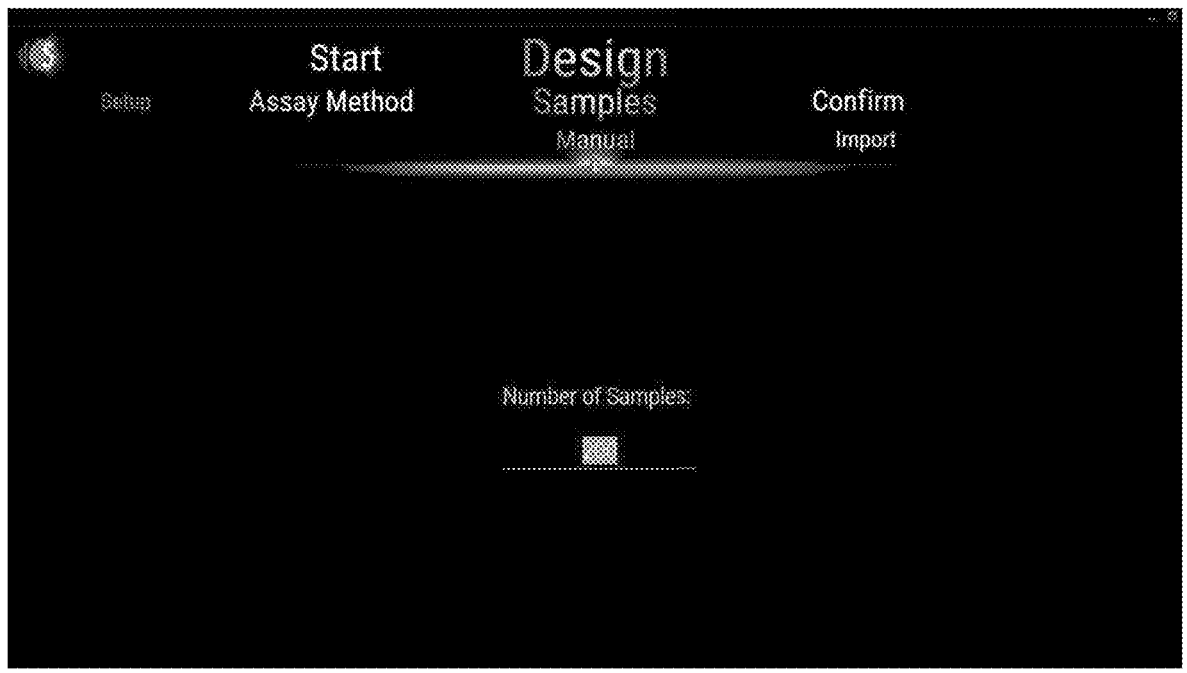
Figure 64U:
Figure 64V:
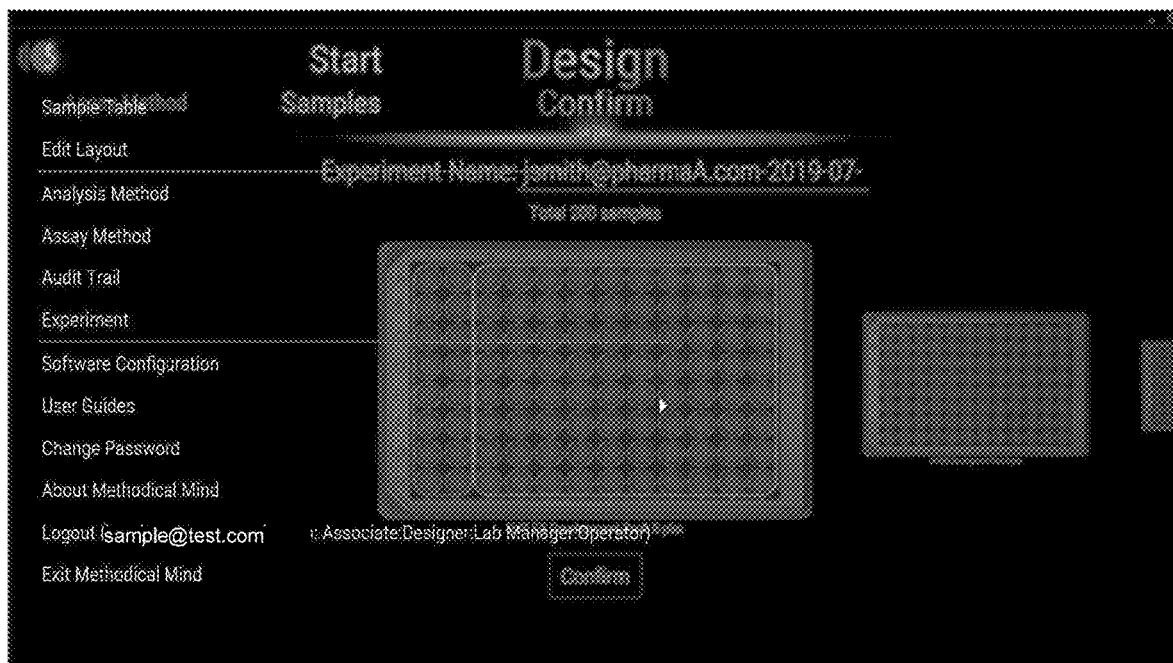
Figure 64W:
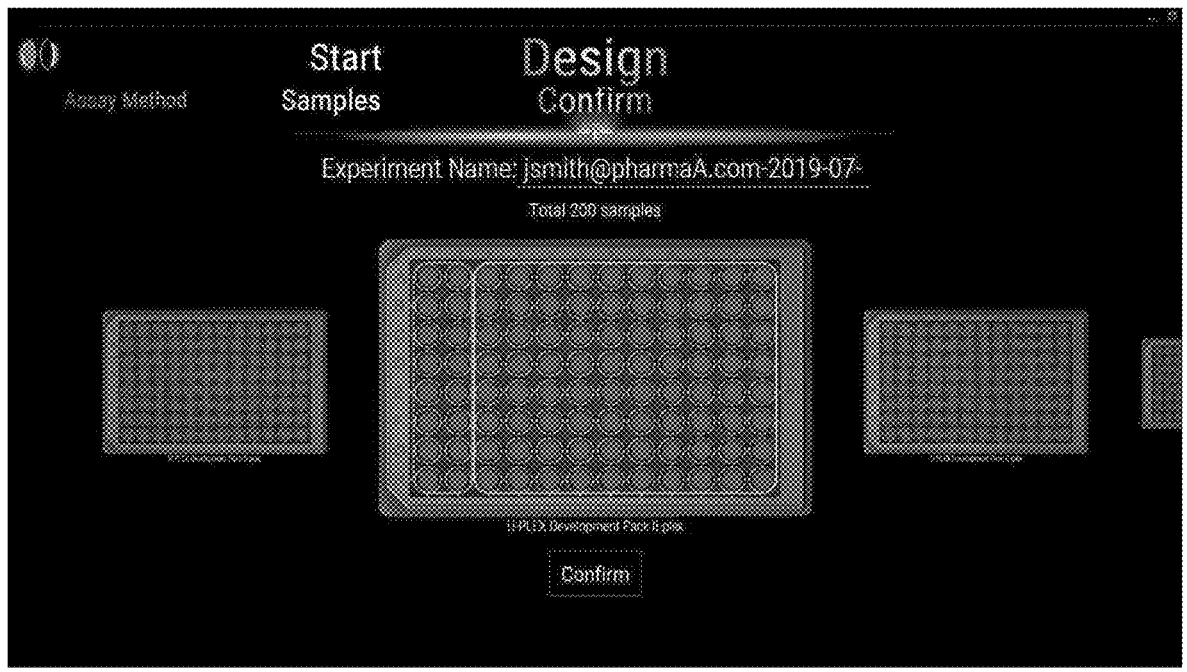
Figure 64X:
Figure 64Y:
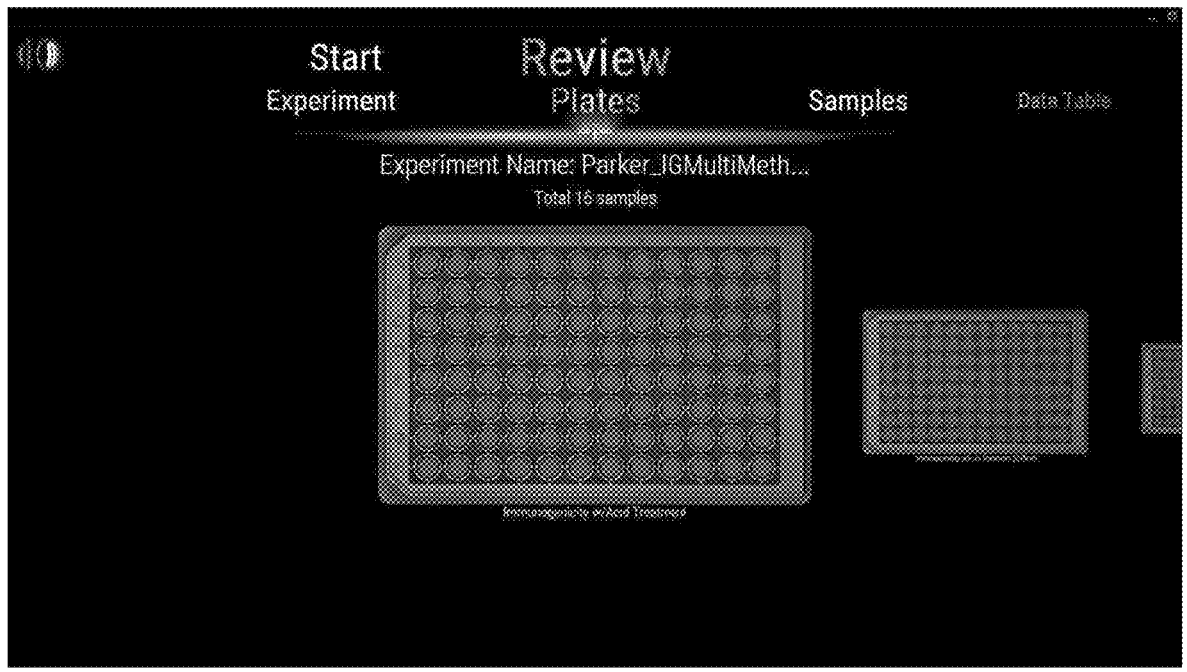
Figure 64Z:
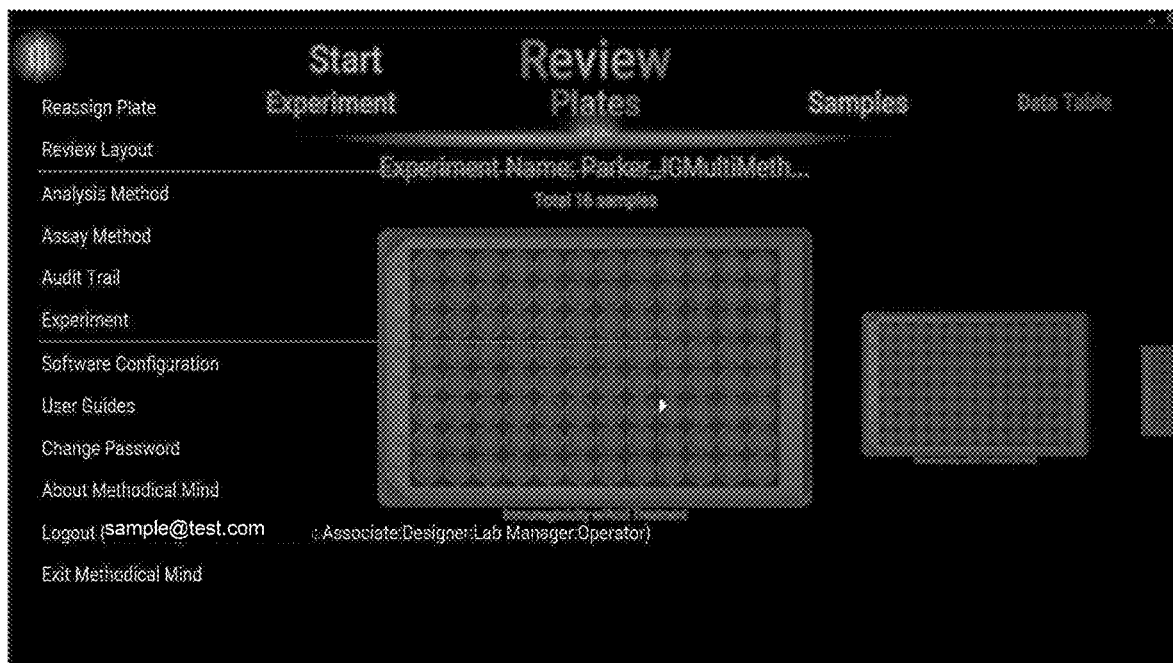
Figure 64A:
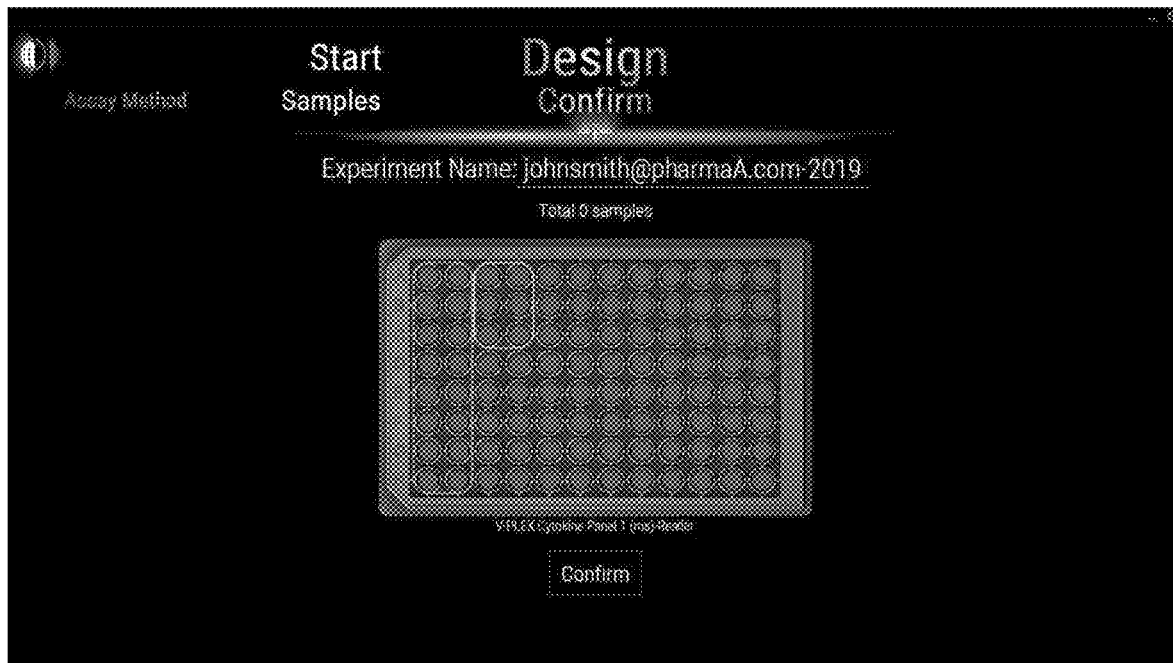
Figure 64B:
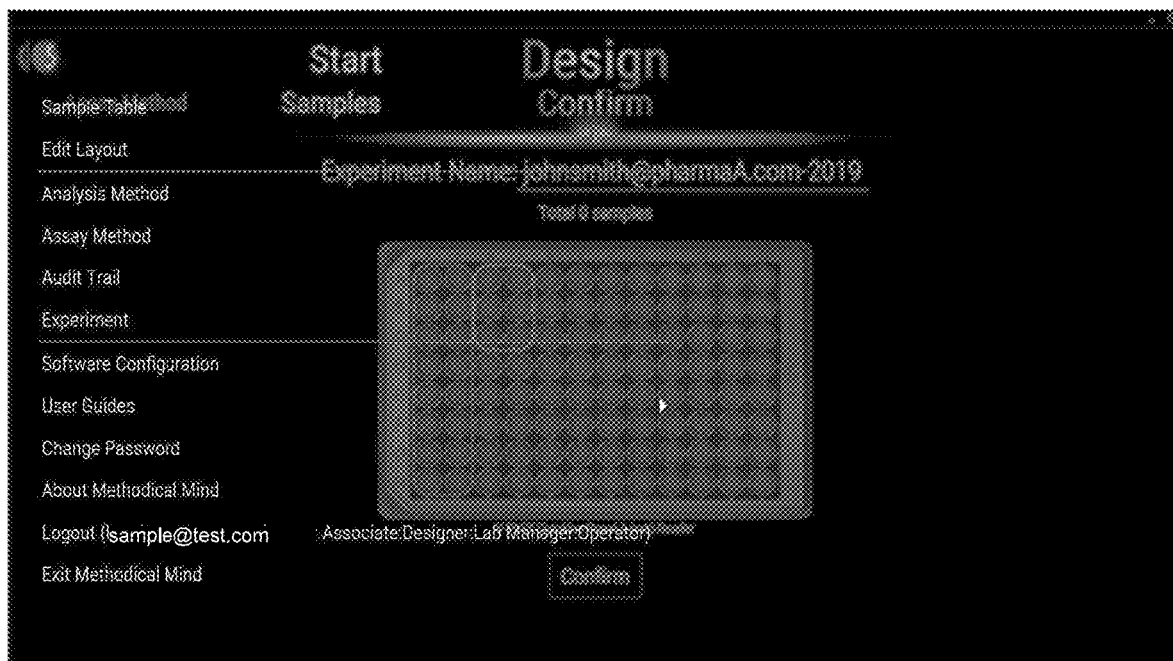
Figure 64C:
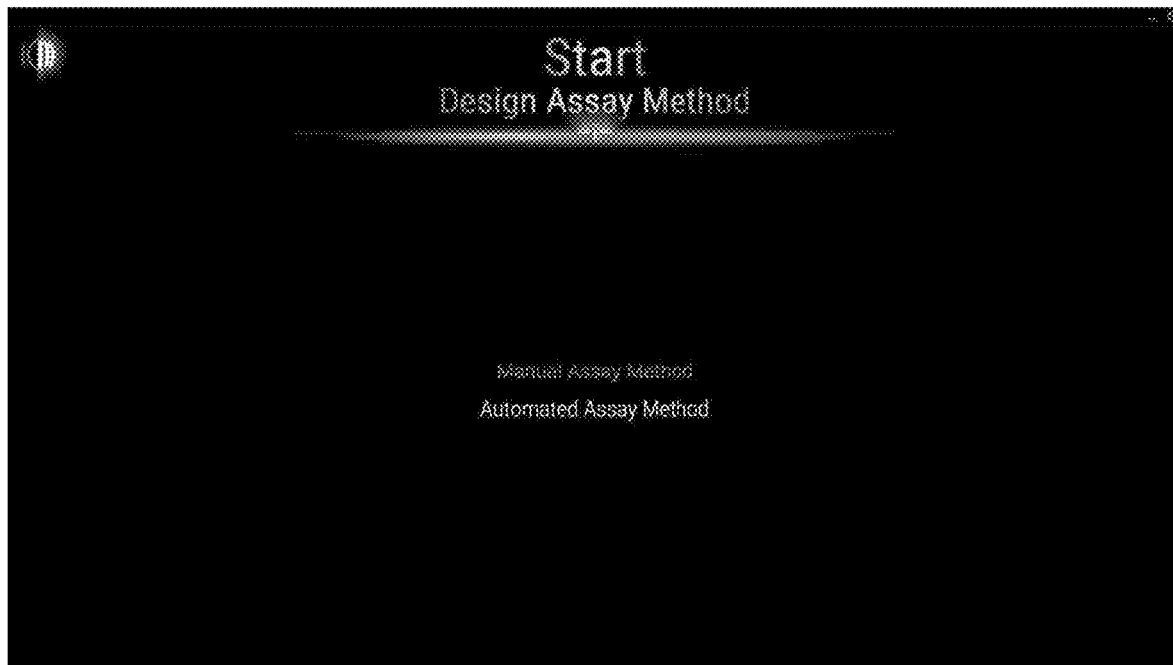
Figure 64D:
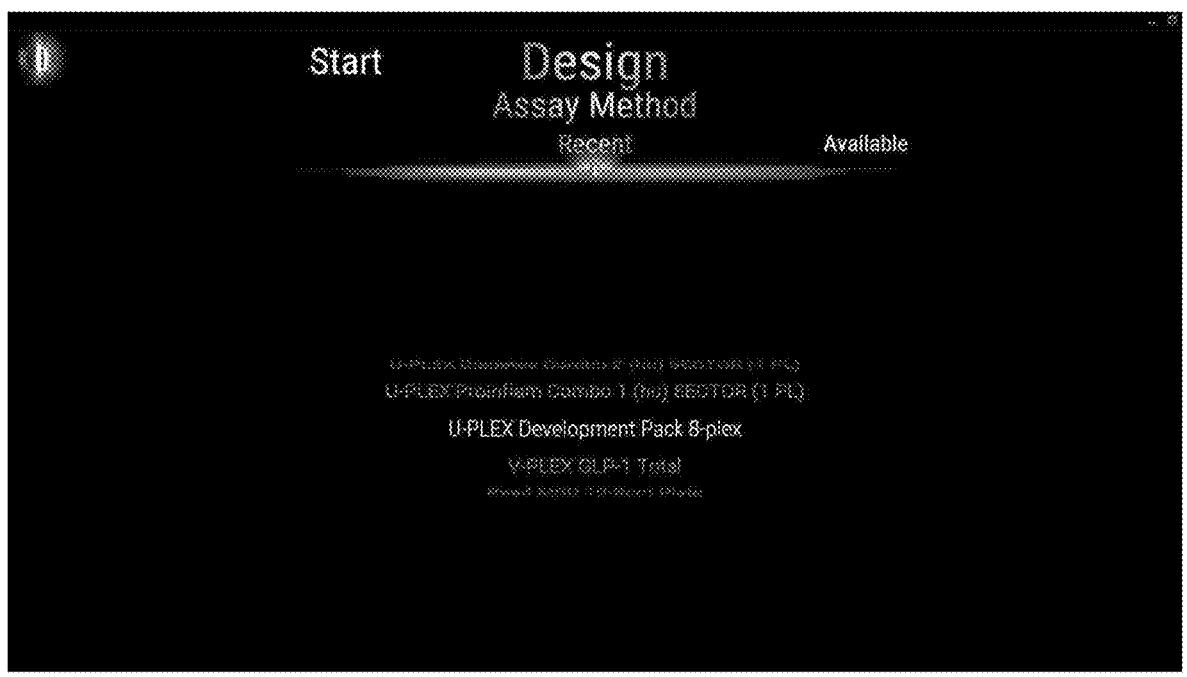
Figure 64E:
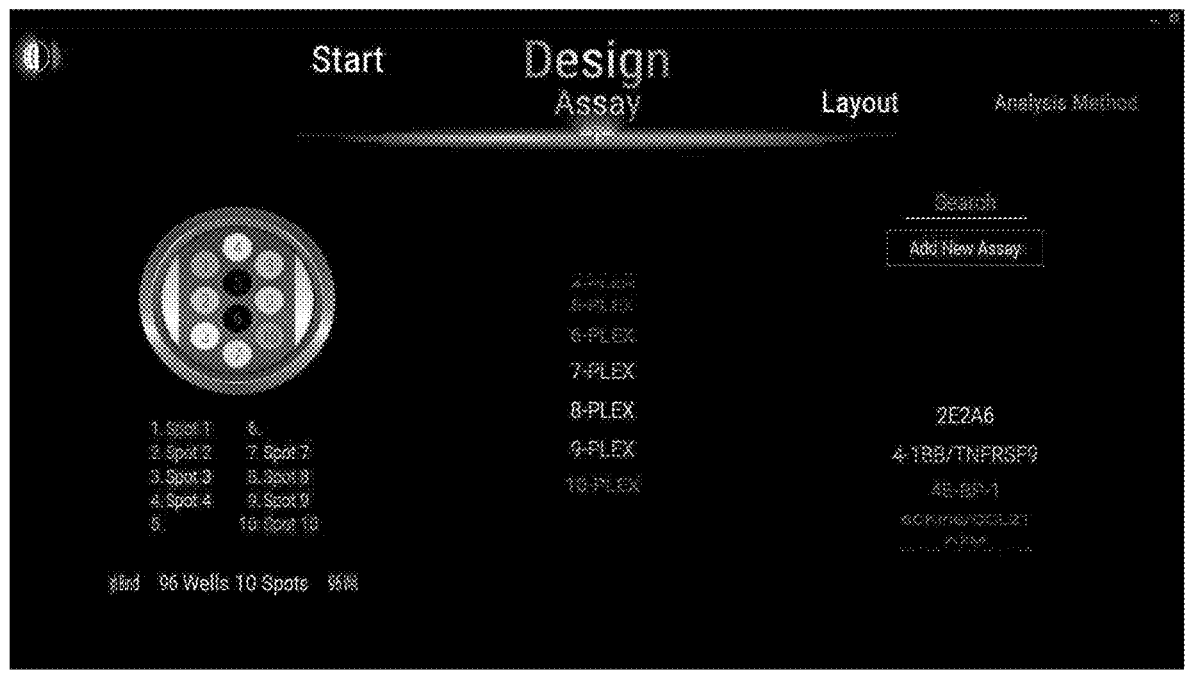
Figure 64F:
Figure 64G:
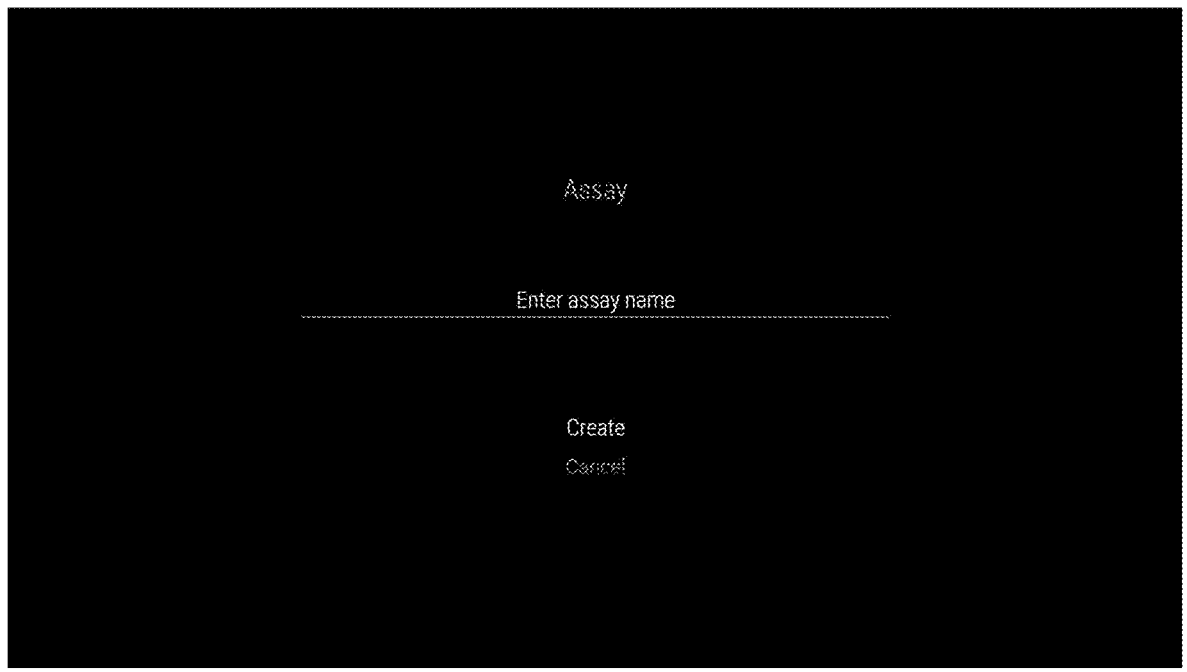
Figure 64H:
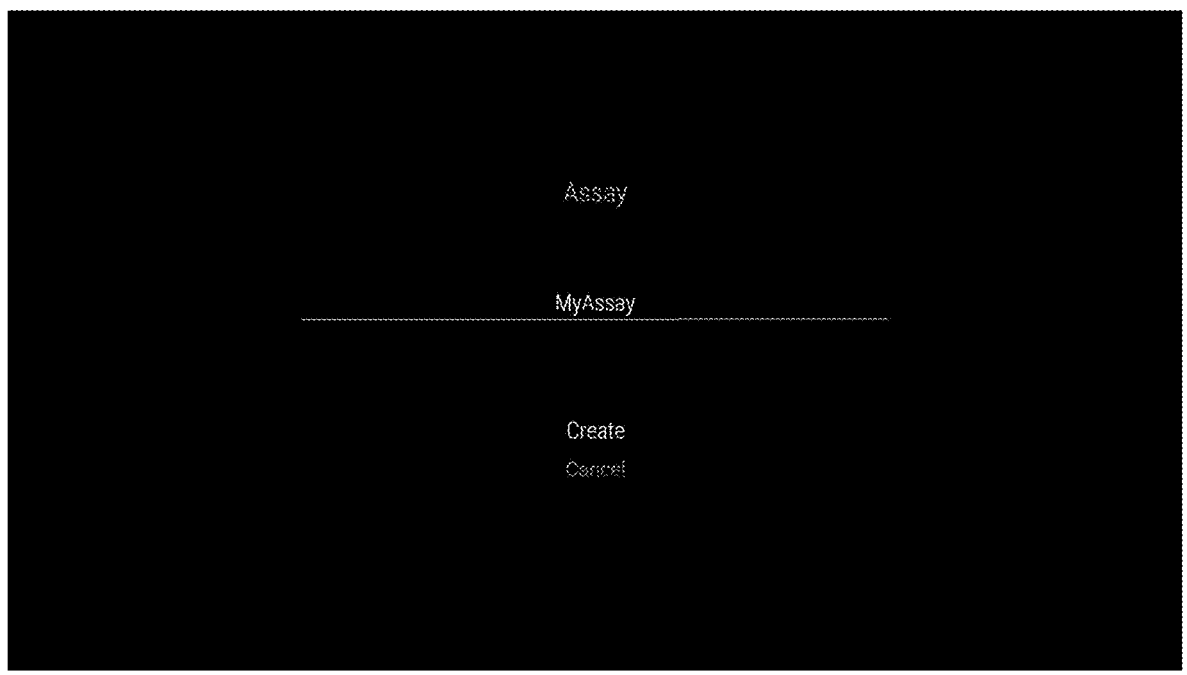
Figure 64I:
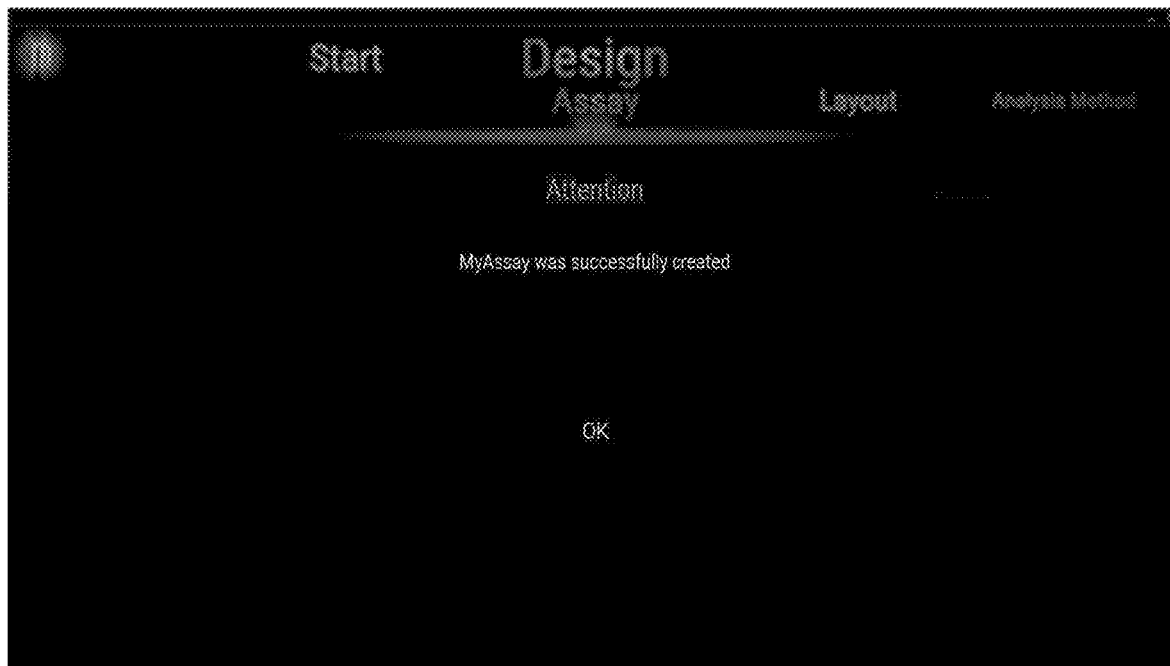
Figure 64J:
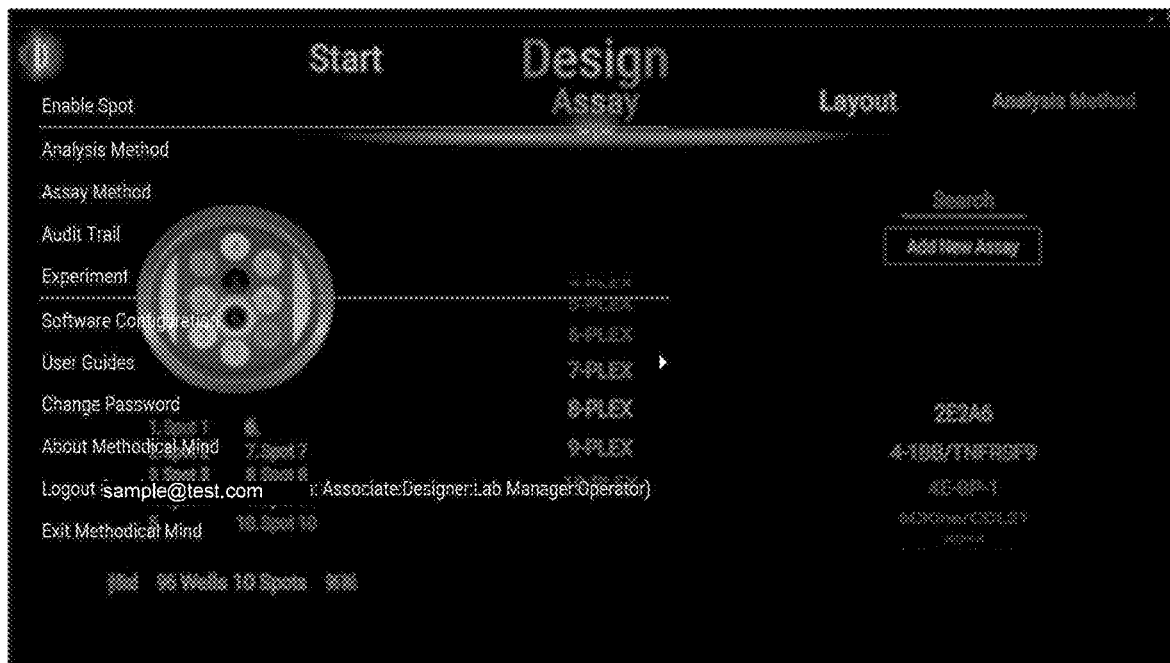
Figure 64K:
Figure 64L:
Figure 64M:
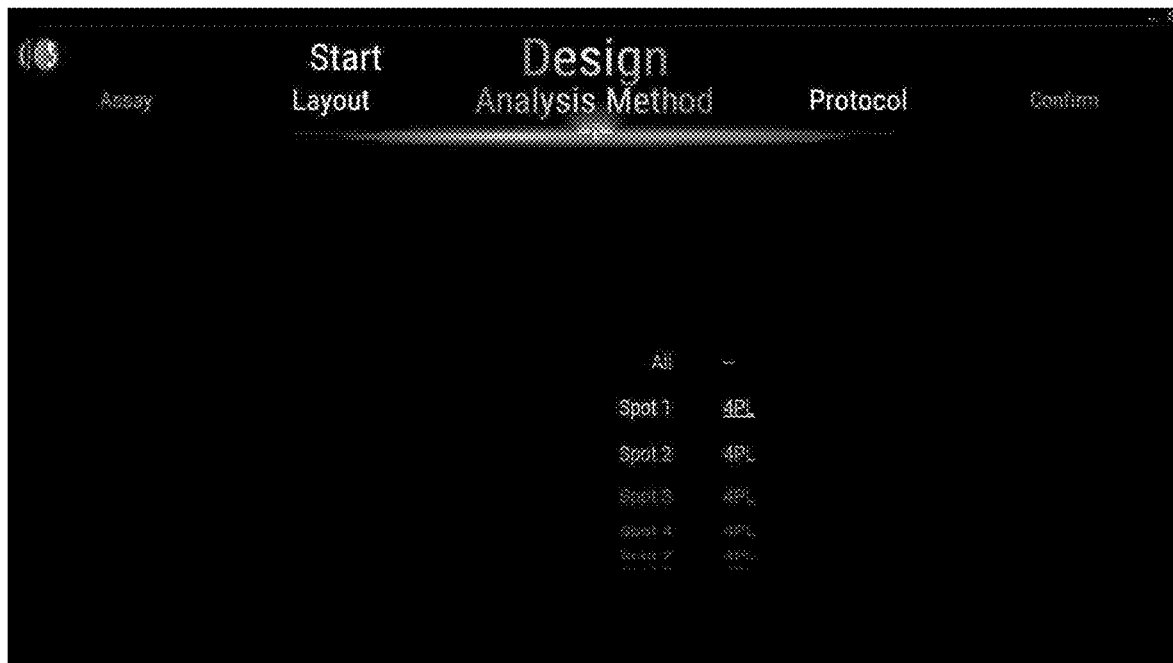
Figure 64N:
Figure 64O:
Figure 64P:
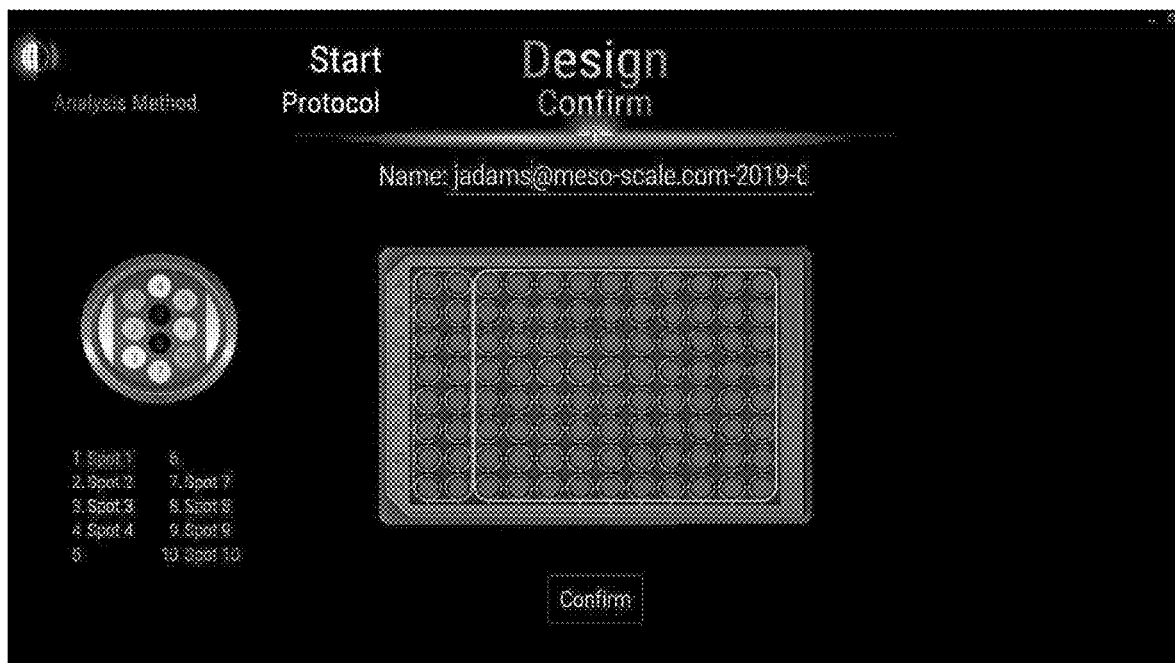
Figure 64Q:
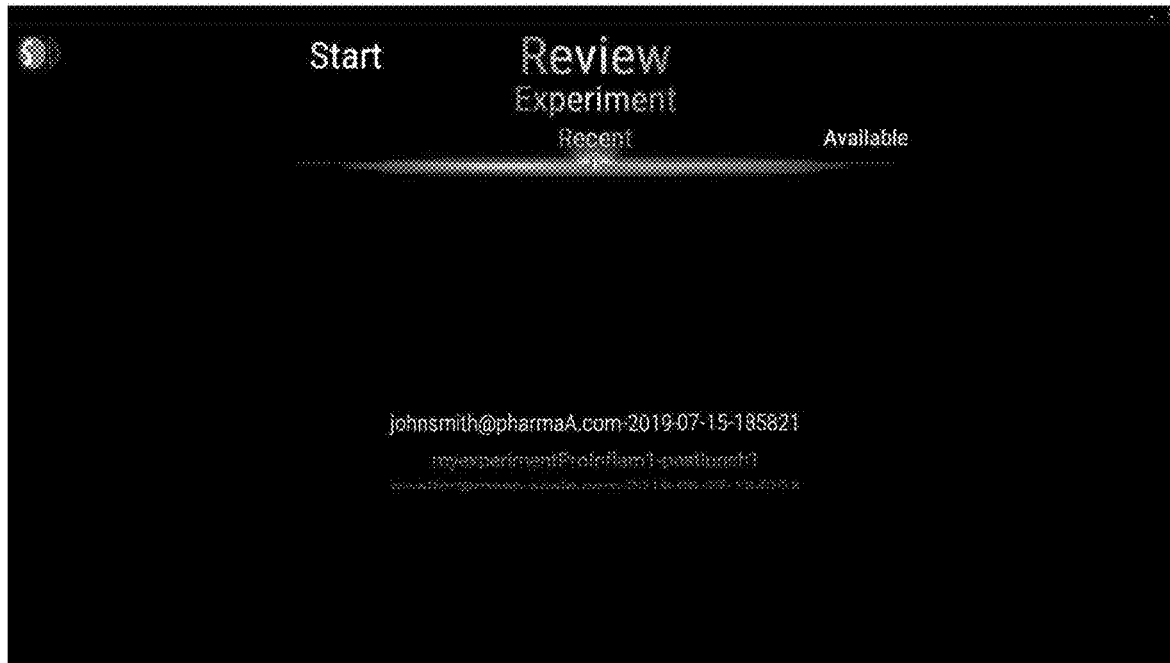
Figure 64R:
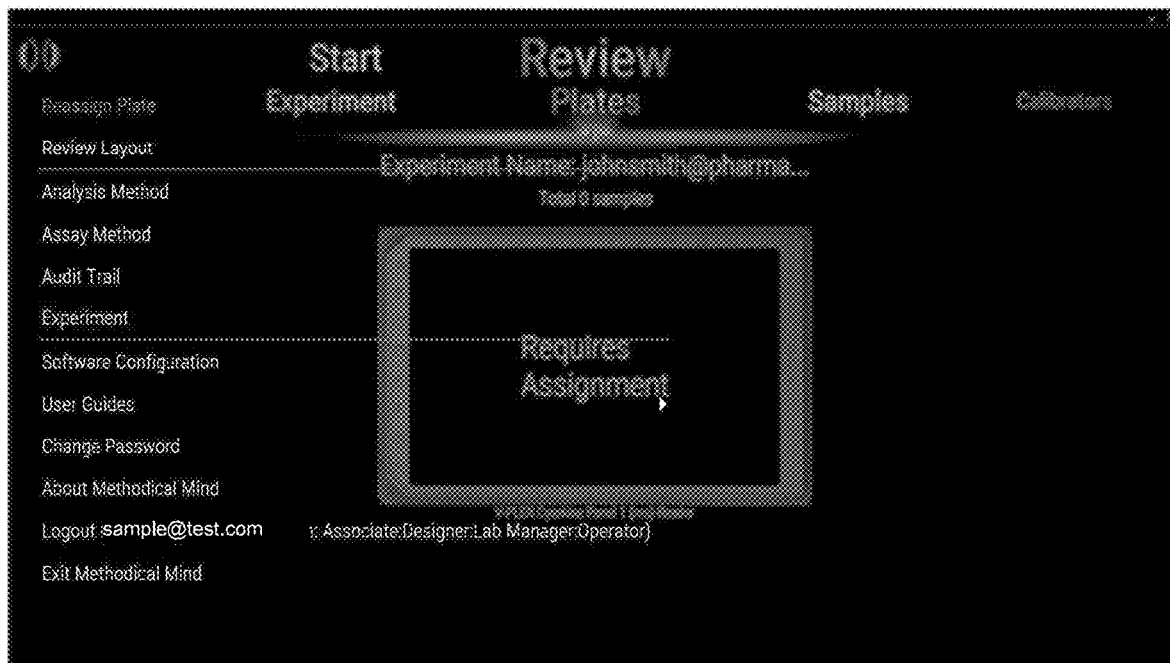

Further screen shot examples consistent with embodiments hereof are shown in FIGS. 58-64RR. FIGS. 58A-58HH are example non-limiting embodiments of the reader module. FIGS. 59A-59T are example non-limiting embodiments of an experiment module. FIGS. 60A-60I are example non-limiting embodiments of a maintenance module. FIGS. 61A-61Q are example non-limiting embodiments of an admin console module. FIGS. 62A-P are example non-limiting embodiments of generic screenshot applicable to multiple modules herein. FIG. 63 is an example non-limiting embodiment of an audit trail module. FIGS. 64A-64RR are example non-limiting embodiments of screenshots applicable to an assay method module.

Further screen shot examples consistent with embodiments hereof are included in U.S. Design patent application No. 29/675,777, Titled "Display Screen with Graphical User Interface," and filed on Jan. 4, 2019, which is incorporated by reference herein in its entirety.

As described above, the user interface in the present disclosure, whether used in an assay system or another system, is capable of presenting the complete trail on a single screen of a user interface display, for example, on a graphical wheel, and allowing the user to select any item on any level to go back from the current path of selected items, for example, instead of having to enter or type a series of back buttons on a keyboard or another input device. The user interface allows for past decisions to be visible, for example, primary decision and last n recent decisions (the history of decision may be visible via scrolling through the graphical wheel or another graphical element such as a graphical slider).

In one embodiment, the graphical user interface minimizes the number of menu choices the user needs to make in order to navigate through the assay system. For instance, the order in which the menu choices are presented may minimize the number of user options.

In one embodiment, by minimizing options or choices to present to the user and receive input from those choices, computer processing time may be improved. The user interface leads the user through the next step in the application, while providing minimal number of choices the user needs to make.

The following discussion provides additional embodiments and implementations of the system as presented herein. The user interface systems discussed above may be broadly applicable to a variety of applications, including manufacturing environments, testing environments, instrumentation environments, experimental environments, and others. In a series of embodiments, the user interface systems discussed above may be employed to provide a user interface into a comprehensive bioinstrumentation system encompassing software, hardware, testing equipment, and all additional required features. The following discusses such a comprehensive bioinstrumentation system. In particular, the following discusses an embodiment of the systems described herein as a cloud-based platform. The embodiments discussed below, e.g., with respect to FIGS. 21-50 may also be implemented via alternative networked hardware and software platforms.

The description herein is made with reference to the figures for purposes of convenience only; it is not restrictive as to the scope of embodiments hereof. The ensuing description is adaptable to a variety of analytical applications, including without limitation, bioanalytical applications, chemical analytical applications, radiological analytical applications, and the like.

The components shown may include computer-implemented components, for instance, implemented and/or run on one or more hardware processors, or coupled with one or more hardware processors. One or more hardware processors, for example, may include components such as programmable logic devices, microcontrollers, memory devices, and/or other hardware components, which may be configured to perform respective tasks described in the present disclosure. Processors and cloud-based processing systems as disclosed in FIGS. 21-50 may be examples of processor 1110. Coupled memory devices may be configured to selectively store instructions executable by one or more hardware processors. Memory devices and cloud-based storage systems as disclosed in FIGS. 21-50 may be examples of storage device 1120. Examples of a processor may include, but are not limited to, a central processing unit (CPU), a graphics processing unit (GPU), a field programmable gate array (FPGA), an application specific integrated circuit (ASIC), a cloud based processing unit, another suitable processing component or device, or one or more combinations thereof.

Figure 21:
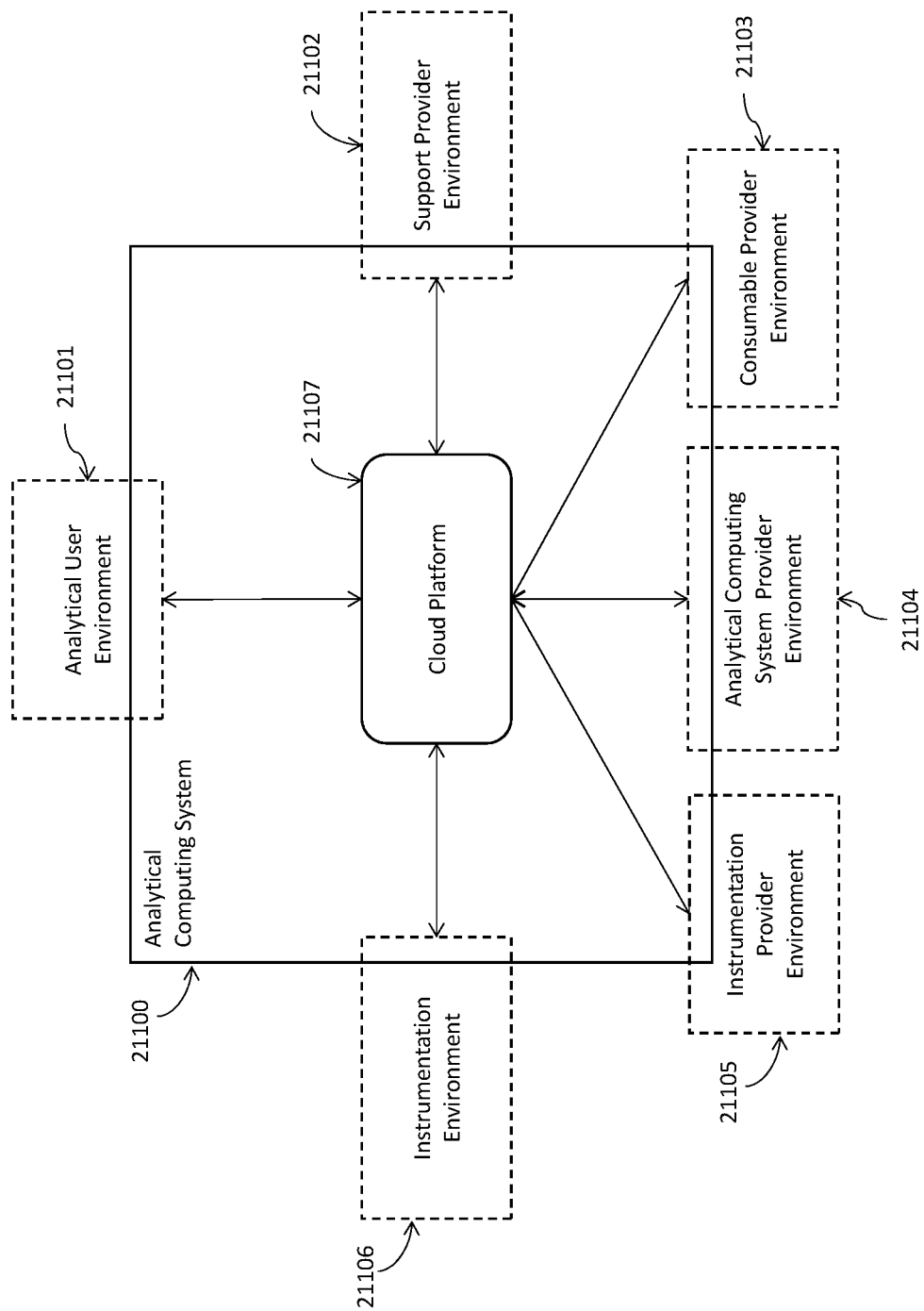
FIG. 21 illustrates a cloud-based analytical computing system in an embodiment.

FIG. 21 is an embodiment of a cloud-based system providing seamless integration of other systems, computers, and instruments, e.g. bioinstruments, supporting and optimizing users doing analytical work, e.g., bioanalytical work. 21100 is the system boundary around the other systems, computers, and instruments either wholly or partly makes up the analytical computing system 21100, wherein, the operating system on each computer and/or instrument, in whole or part, includes the analytical computing system 21100 can include, e.g., Windows™, UNIX, Linux, MacOS™, iOS™, Android™, and/or any other commercial, open-source, and/or special-purpose operating system. At 21101 is an analytical user environment including one or more servers, desktop computers, laptop computers, tablet, and/or mobile devices of which one or more of same can be used in system 21100. One or more analytical user environments 21101 can use the analytical system 21100. At 21102 is a support provider environment including one or more servers, desktop computers, laptop computers, tablet, and/or mobile devices of which one or more of same can be used in system 21100 supporting instruments, consumables, and/or software used by analytical users in analytical user environment 21101. There can be one or more support provider environments at 21102 using the analytical computing system 21100. At 21103 is a consumable provider environment including one or more servers, desktop computers, laptop computers, tablet, and/or mobile devices of which one or more of same can be used in analytical computing system 21100 for providing consumables to be used by users in analytical user environment 2001, optionally in conjunction with instrumentation including instrumentation environment 21106. There can be one or more consumable provider environments at 103 using the analytical computing system 21100.

At 21105 is an analytical instrumentation provider environment for a provider of instrumentation that can be used in instrumentation environment 21106 and that includes one or more servers, desktop computers, laptop computers, tablet, and/or mobile devices of which one or more of same can be used in analytical computing system 21100 for providing, e.g., selling or otherwise transferring instruments to be used by users in analytical user environment 21101. There can be one or more instrumentation provider environments at 21105 using the analytical computing system 21100. At 21104 is an analytical computing system provider environment for the provider of analytical computing system 21100, which includes one or more servers, desktop computers, laptop computers, tablet, and/or mobile devices of which one or more same can be used in system 211000 to manage the business interaction with analytical computing system 21100 to be used by analytical users in analytical user environment 2001. Each of the "providers" associated with the environments at 21102, 21103, 21104, and 21105 can include one or more entities, including without limitation, a multiplicity of independent businesses, a single independent business, a combination of different independent businesses, or one or more businesses within any one of the "providers" herein. At 21106 is an instrumentation environment including one or more instruments, each with at least one computer that in one practice can be at least partially used by analytical computing system 21100 to run tests on samples for users in an analytical user environment 21101. At 21107 is a cloud platform leveraged to connect, e.g., bi-directionally connect, through computers, networking, and software some or all of the computers in analytical computing system 21100 having in one practice, a common computing, software services, and data architecture such that data can be collected and shared by any computer having associated software of the analytical computing system 21100, wherever a particular computer with associated software in analytical computing system 21100 is located throughout the world, in a secure manner, wherein cloud platform 21107, in the preferred embodiment, is hosted by a public-cloud provider providing a shared computing environment, for example, Amazon™ Web Services, Google™ Cloud, Microsoft™ Azure, or others. In other embodiments, the cloud platform 21107 can be hosted by the analytical computing system provider at 21104; or it can be self-hosted by an analytical user environment being a user of the analytical computing system 21100; or it can be hosted by a private-cloud provider providing a dedicated computing environment, for example, Oracle™ Cloud, IBM™ Cloud, Rackspace, or others; or it can be hosted on some combination of public-cloud, private-cloud, self-hosted, and hosted by the analytical computing system provider 21104. All communication with cloud platform 21107 can be done through the preferred embodiment over a secure communication protocol, such as without limitation https, to encrypt all communication between sender and receiver; but an unsecure communication protocol, such as without limitation Hypertext Transfer Protocol Secure (HTTPS), can be used as well using optionally in either the secured or unsecured case connected technologies, such as Ethernet for local area network (LAN), metropolitan area network (MAN), and/or wide area network (WAN) configurations, and/or unconnected technologies, such as WIFI, Bluetooth, and/or other like technologies for a distributed LAN. Additionally, analytical computing system 21100 can be wholly deployed on one computer such that all operations of analytical computing system 21100 occur on that computer with the only external communication occurring between computers and associated software running outside of analytical computing system 21100.

Figure 22:
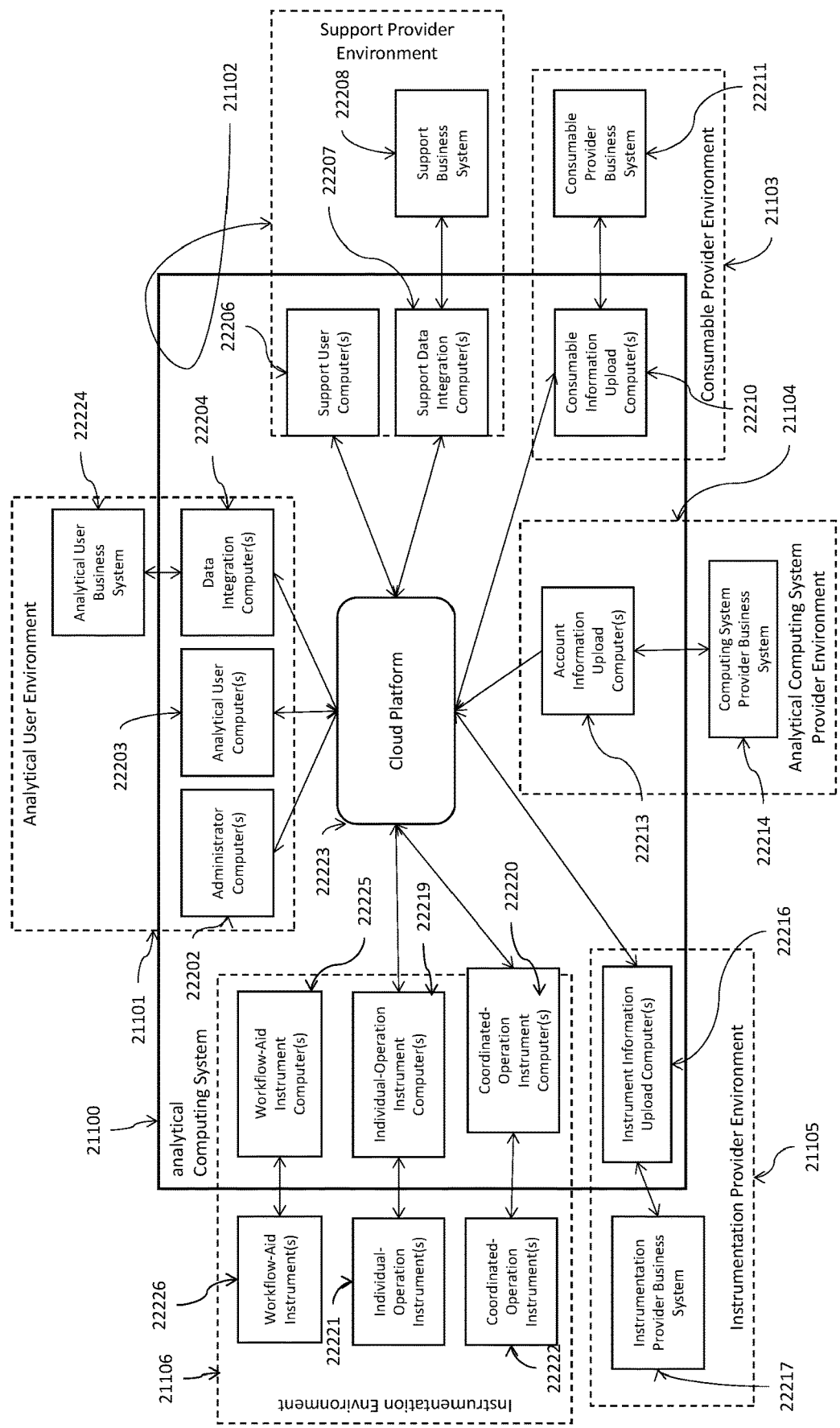
FIG. 22 illustrates a system architecture for a cloud-based analytical computing system in an embodiment.

FIG. 22. is an embodiment of a cloud-based system as shown in FIG. 21 that provides seamless integration of other systems, computers, and instruments supporting and optimizing users doing analytical work. 21100 depicts the boundary of the analytical computing system that encompasses other systems, computers, and instruments that include either wholly or partly the system bounded by 21100. At 21101 is an analytical user environment including one or more servers, desktop computers, laptop computers, tablets, and/or mobile devices of which one or more of same can be used in analytical computing system 21100. Administrator computer(s) 22202 includes one or more computers with software used by system administrators to manage the use of system 21100 by users in analytical user environment 21101 through services and data storage/retrieval provided by the cloud platform 22223. Analytical user computers 22203 includes one or more computers with software used to perform analytical tasks by users in an analytical user environment at 21101 through services and data storage/retrieval provided by the cloud platform 22223. Data integration computers 22204 includes one or more computers with software used to integrate, e.g., bi-directionally integrate, other business systems 22224 in analytical user environment 21101 with the analytical computing system 21100 providing services for the analytical user business systems 22224 through services and data storage/retrieval provided by cloud platform 22223. Analytical user business system 22224 can be hosted internally, externally, and/or some combination of internally and externally to analytical user environment 21101 and can include one or more computer systems optionally with software, examples being laboratory information systems (LIMS), data analysis applications, data visualization applications, data reporting applications, business productivity applications, relational and/or non-relational databases, file servers, and/or any other systems providing access to the data of the analytical computing system 21100 to users directly using the analytical computing system 21100, to users not directly using the analytical computing system 21100, and/or to one or more other computer systems included with the business system 22224 not directly interfacing with the analytical computing system 21100.

Support provider environment 21102 is a support provider for users of analytical computing system 21100, users of consumables from a consumable provider, and/or instrumentation in instrumentation environment 21106 including one or more servers, desktop computers, laptop computers, tablets, and/or mobile devices of which one or more of same can be used in the analytical computing system 21100 supporting instruments, consumables, and/or software used by analytical users in the analytical user environment 21101.

Support user computer 22206 includes one or more computers with software provided to users associated with a support provider environment 21102 that, among other things, can monitor, manage, and/or report on activity on the analytical computing system 21100 through services and data storage/retrieval provided by the cloud platform 22223; and support data integration computer 22207 includes one or more computers with software and/or firmware used to integrate other support business systems 22208 in support provider environment 21102 with analytical computing system 21100 providing services for support business systems 22208 through services and data storage/retrieval provided by the cloud platform 22223. Support business systems 22208 can be hosted internally, externally, and/or by some combination of internally and externally to support provider environment 21102 and can include one or more computer systems optionally with software, examples being customer relationship management, enterprise data systems, data analysis applications, data visualization applications, data reporting applications, business productivity applications, relational and/or non-relational databases, file servers, and/or any other systems providing access to the data of analytical computing system 21100 to users directly using the support user computer(s) 22206, to users not directly using the support user computer(s) 22206, and/or one or more other computer systems included with support business system 22208 not directly interfacing with the analytical computing system 21100.

Consumable provider environment 21103 is a consumable provider environment including one or more servers, desktop computers, laptop computers, tablets, and/or mobile devices of which one or more of same can be used in analytical computing system 21100 for a provider of consumables to users in analytical user environment 21101, which can be optionally used in conjunction with instrumentation in instrumentation environment 21106 for providing consumables to users in analytical user environment 21101 to optionally be used with instruments in instrumentation environment 21106. Consumable information upload computer 22210 includes one or more computers with software used to deliver consumable information regarding provided consumables from consumable provider business systems 22211 to analytical computing system 21100 through services and data storage provided by cloud platform 22223. Consumable information, as used herein, may include, but is not limited to, global product data (GPD). Consumable provider business system 22211 can be hosted internally, externally, and/or by some combination of internally and externally to consumable provider environment 21103 and can include one or more computer systems optionally with software, examples being customer relationship management, enterprise data systems, data reporting applications, business productivity applications, relational and/or non-relational databases, file servers, and/or any other systems supporting business operations for the consumable provider to support delivery of consumable information to the analytical computing system 21100 or which is not used at all in the delivery of consumable information to the analytical computing system 21100.

Analytical computing system provider environment 21104 is the analytical computing system provider environment for the provider of analytical computing system 21100 including of one or more servers, desktop computers, laptop computers, tablets, and/or mobile devices of which one or more of same can be used in the analytical computing system 21100 for providing analytical computing system 21100 to users in analytical user environment 21101 and instrumentation in instrumentation environment 21106, as well as for various providers at 21102, 21103, and 21105, wherein, account information upload computer(s) 22213 includes one or more computers with software used to prepare and control the use of analytical computing system 21100 by users in analytical user environment 21101 and instrumentation in instrumentation environment 21106 through services and data storage provided by cloud platform 22223. Computing system provider business system 22214 can be hosted internally, externally, and/or some combination of internally and externally to analytical computing system provider environment 21104 and can include one or more computer systems optionally with software, examples being customer relationship management, enterprise data systems, data reporting applications, business productivity applications, relational and/or non-relational databases, file servers, and/or any other systems supporting business operations for the analytical computing system provider to support preparing and controlling the use of analytical computing system 21100, or not used at all in preparing and controlling the use of the analytical computing system 21100.

Instrumentation provider environment 21105 includes one or more servers, desktop computers, laptop computers, tablets, and/or mobile devices of which one or more of same can be used in analytical computing system 21100 for a provider of instrumentation to users in analytical user environment 21101 and which can optionally be used as instrumentation in instrumentation environment 21106 for processing samples under test and optionally with one or more consumables provided by consumables provider environment 21103. The instrument information upload computer(s) 22216 includes one or more computers with software used to deliver instrument information regarding provided instrumentation from an instrumentation provider business system 22217 to analytical computing system 21100 through services and data storage provided by the cloud platform 22223. Instrumentation provider business system 22217 can be hosted internally, externally, and/or by some combination of internally and externally to instrumentation provider environment 21105 and can include one or more computer systems optionally with software, examples being customer relationship management, enterprise data systems, data reporting applications, business productivity applications, relational and/or non-relational databases, file servers, and/or any other systems supporting business operations for the instrumentation provider to support delivery of instrument information to the analytical computing system 21100, or not used at all in the delivery of instrument information to the analytical computing system 21100.

Instrumentation environment 21106 including one or more instruments with each instrument being either an individual-operation instrument 22221, a coordinated-operation instrument 22222, or a workflow-aid instrument(s) 22226 provided by instrumentation provider environment 21105 which can be leveraged by users in analytical user environment 21101 to process samples optionally in conjunction with consumables provided by consumable provider environment 21103 to generate data for analysis by users in analytical user environment 21101, wherein, an individual-operation instrument 22221 can have an individual-operation instrument computer 22219 providing integration between the individual-operation instrument 22221 and the analytical computing system 21100 through services and data storage provided by the cloud platform 22223, as well as optionally providing operational control over the individual-operation instrument 22221; a coordinated-operation instrument 22222 can also have a coordinated-operation instrument computer 22220 that provides integration between the coordinated-operation instrument 22222 and the analytical computing system 21100 through services and data storage provided by the cloud platform 22223, as well as optionally providing operational control over the coordinated-operation instrument 22222; and workflow-aid instrument 22226 can have a workflow-aid instrument computer 22225 that provides integration between the workflow-aid instrument 22226 and the analytical computing system 21100 through services and data storage provided by the cloud platform 22223, as well as optionally providing operational control over workflow-aid instrument 224. Examples of an individual-operation instrument 22221 include without limitation a plate reader, plate washer, plate incubator, plate shaker, plate incubator-shaker, pipetting system, or any other type of instrument used in analytical sample testing. Coordinated-operation instrument 22222 can combine some or all of the functions provided by one or more of the individual-operation instruments 22221 into an integrated platform automating execution of the individual operations of individual-operation instruments 22221, thereby relieving a user from executing the various individual operations of individual-operation instruments 22221. Workflow-aid instrument 22226 can provide support to a user leveraging either individual-operation instrument(s) 22221 and/or coordinated-operation instruments 22222 to test assays on samples in the instrumentation environment 21106 where the support includes, but is not limited to, collecting various consumables stored at various temperatures potentially in different physical locations, preparing consumables to be used in the processing of one or more assays, and/or leading a user through the overall assay steps using one or more of the individual-operation instruments 22221. In the alternative, the consumable provider environment analytical user app 21103 can assist with other tests in addition to or in place of the assay tests and/or plate-based tests described herein.

Instrumentation in instrumentation environment 21106 can include zero or more individual-operation instruments 22221 each with their corresponding individual-operation instrument computer 22219, zero or more coordinated-operation instruments 22222 each with their corresponding coordinated-operation instrument computers 22220, and/or zero or more workflow-aid instruments 22224 each with their corresponding workflow-aid instrument computers 22225. A preferred embodiment for instrumentation environment 21106 includes providing a separate computer integrating zero or more individual-operation instruments 22221, zero or more coordinated-operation instruments 22222, zero or more workflow-aid instruments 22224, zero or more individual-operation instrument computers 22219, zero or more coordinated-operation instrument computers 22220, and zero or more workflow-aid instrument computers 22225 to analytical computing system 21100 through services and data storage provided by cloud platform 22223.

Figure 23:
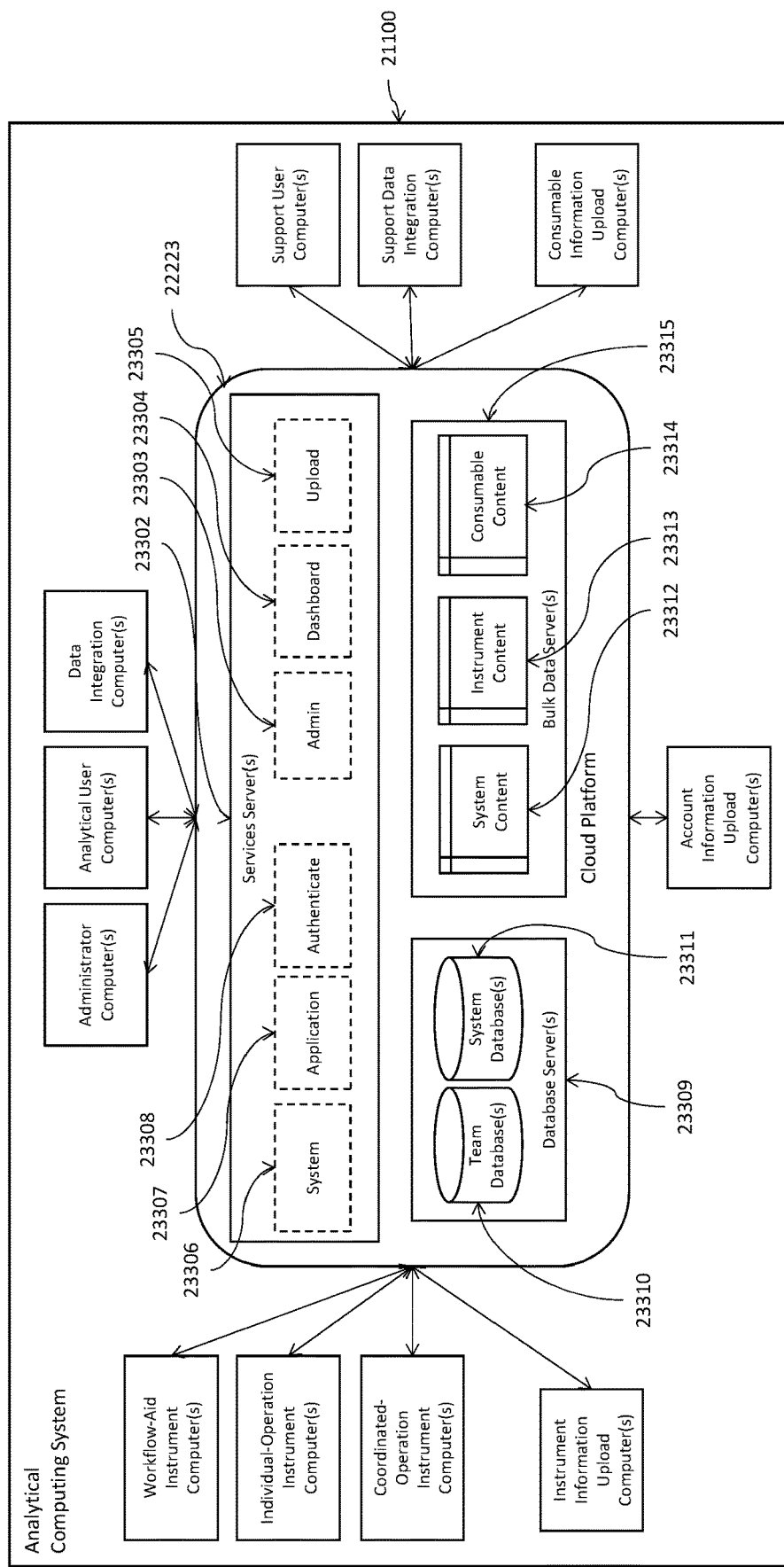
FIG. 23 illustrates a system architecture for a cloud platform in a cloud-based analytical computing system in an embodiment.

In FIG. 23 is an embodiment of system architecture for cloud platform 22223 as part of the analytical computing system 21100 providing common computing, software services, and data architecture such that data are collected and shared by any computer anywhere in the world having associated software of the analytical computing system 21100 (FIG. 21), wherein, one or more services servers 23302 provide a scalable, robust, and high-performing computing and associated software platform to support services specific to the analytical computing system 21100 for retrieving, storing, transferring, and/or transforming data associated with the use of the analytical computing system 21100; one or more database servers 23309 (e.g., including one or more team databases 23310 and one or more system databases 23311) providing a scalable, robust, and high-performing computing and associated software platform for one or more structured databases used for storing and/or retrieving data produced by and/or for users of the analytical computing system 21100, as well as, for storing and/or retrieving data produced and/or used by the analytical computing system 21100 for its preparation for use as well as through its use, wherein, the database technology can be relational in nature as e.g. SQL Server, Oracle, MySQL, Postgres, Aurora, and/or other like relational database technologies; and/or can be non-relational in nature as e.g. Dynamo DB, Mongo DB, and/or other like non-relational database technologies; with one or more bulk data servers 23315, which may include system content 23312, instrument content 23313 and consumable content 23314, providing a scalable, robust, and high-performing computing and associated software platform for storing and retrieving file-based data provided for use of the analytical computing system 21100 and/or produced through the use of the analytical computing system 21100. The services server(s) 23302 has associated with it, in one embodiment, a logical collection of services, namely: admin 23303 including a logical collection of services to support administration of the use of analytical computing system 21100; dashboard 23304 including a logical collection of services to support monitoring and control of the use of analytical computing system 21100; upload 23305 including a logical collection of services supporting upload of consumable and instrument information to analytical computing system 21100; system 23306 including a logical collection of services supporting various non-user-specific functions associated with overall use of analytical computing system 21100; application 23307 including a logical collection of services supporting typical scientific use of analytical computing system 21100 by analytical users; and authenticate 23308 including a logical collection of services supporting secure log-in to analytical computing system 21100 as well as log-out from analytical computing system 21100. In one practice, services server(s) 23302 is an easily scaled computing infrastructure from one or more servers as represented by services server(s) 23302 wherein, in a preferred embodiment, each server has deployed all logical collection of services 23303, 23304, 23305, 23306, 23307, and 23308 to enable a load balancer to equally distribute requests for services across the one or more servers represented by services server(s) 23302 to optimize user interaction. This load balancing technique can be effectuated, e.g., if the logical collection of services 23303, 23304, 23305, 23306, 23307, and 23308 are designed using a RESTful (representational state transfer) design pattern, i.e., each provided service is stateless, i.e., does not store or hold data, and therefore any request made on the service can be fulfilled by any available server on which the service deployed in services server(s) 23302 based on demand at the time of request. To support optimal deployment and operation of the logical collection of services 23303, 23304, 23305, 23306, 23307, and 23308 on one computer or on many computers, the preferred embodiment is for these services to be built on a distributed-object platform such as, e.g., Java Platform Enterprise Edition to be able to support cross-platform computing architectures, .NET Framework for Windows-only computing architectures, or other like distributed-object platform, or leveraging some combination of one or more of these distributed-object platforms. Database Server 23310 can include one or more databases, for example, Team Database 23310 and System Database 23311. Team Database 23310 is adapted to store information, data, and/or metadata as it relates to Teams (e.g., Team name, members, permissions, etc.). System Database 23111 can include files, data, and/or other information as it relates system functionalities. Further, Bulk Data Server 23315 can include various content, e.g., System Content 23312, e.g., data or content relating to the system's functionality, etc., Instrument content 23313, e.g., type of instrument, parameters, etc., and Consumable Content 23314, e.g., type of consumable, quantities, etc.

Figure 24:
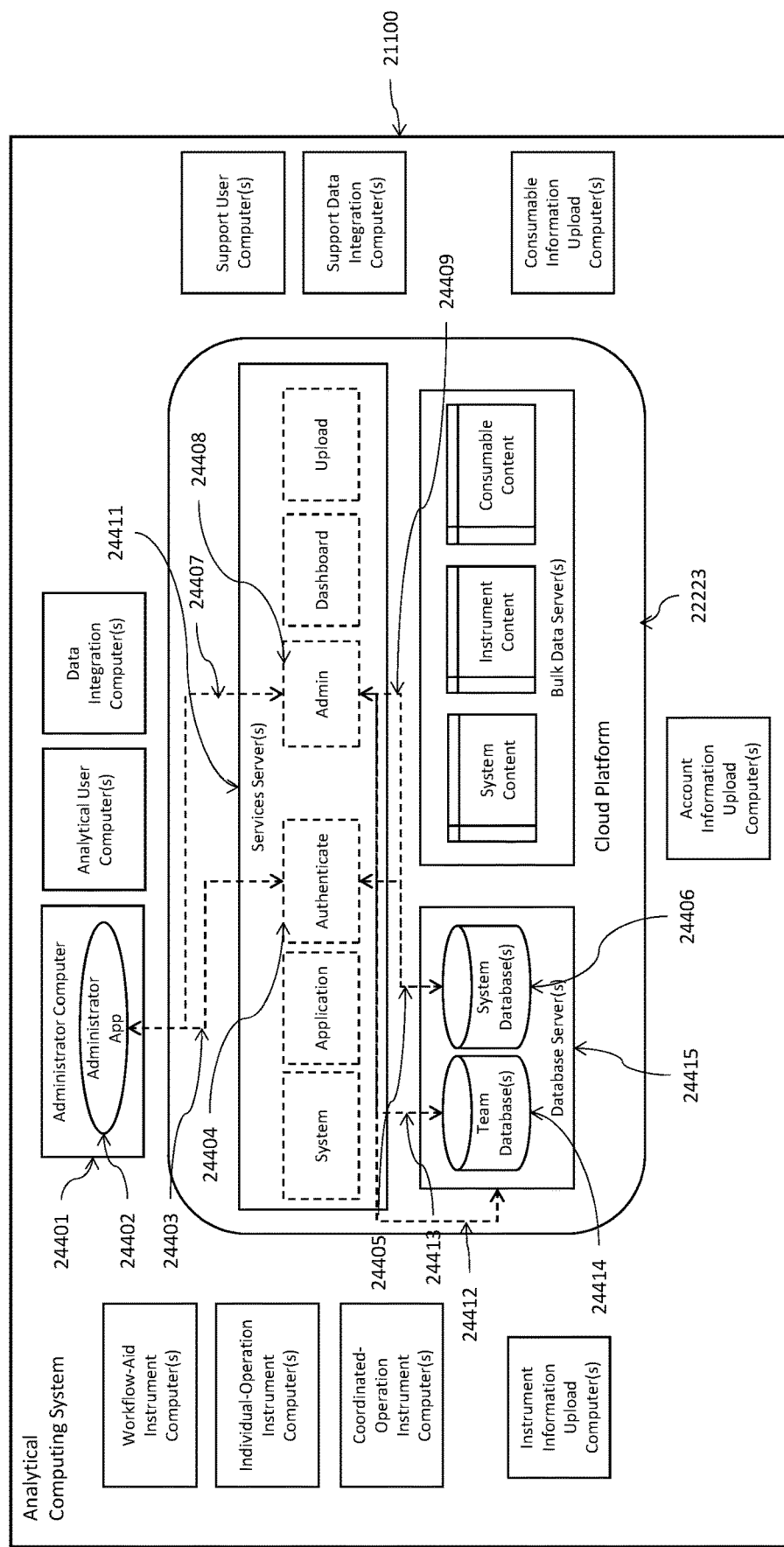
FIG. 24 illustrates interactions between administrator computers and a cloud platform in an embodiment.

In FIG. 24 is an embodiment of an administrator using an Administrator Computer 24401 to run administrator app software 24402 to perform administrative functions provided by the analytical computing system 21100 through services provided through the cloud platform 22223. The administrator app software, as discussed herein, may employ a MUI as described above to facilitate user access to the functionality provided. As such, embodiments of the methodical user interface control system 1102 may be provided by a combination of the administrator computer 24401 and the cloud platform 22223. By way of example, one or more services servers 24411 can provide various functionalities such as authentication, one or more other administrative functionalities, capability for uploading data, e.g., to one or more database servers, one or more system functionalities, one or more applications, e.g., app functions, and/or graphical visualization support via a dashboard. The administrator app 24402 can be executed on the administrator computer 24401 through either a distinct application installed on the administrator computer 24401, or accessed via an internet browser installed on the administrator computer 24401 pointing to a Uniform Resource Locator (URL) with a web site part of the services provided by cloud platform 22223 logically organized with admin 24408 in this embodiment but not limited to that organization. In one embodiment, the first interaction between an administrator and the cloud platform occurs through use of administrator app 24402 requesting login services, e.g., via a user manager 1056 of methodical user interface control system 1102, through service link 24403 to authenticate, 24404, with appropriate credentials that, e.g., include a unique username and password and/or metric identification and can also include an optional or required additional authentication input, commonly referred to as two-factor authentication, previously configured for use by an administrator. In this embodiment, the login service retrieves a user's encrypted credentials, through a service link 24405, from system database 24406 to verify that the administrator can access and administer analytical computing system 21100 with the login updating data stored in system database 24406 through the service link 24407 to track usage of analytical computing system 21100. An administrator can also reset their own password via administrator app 24402 through service link 24403 to authenticate 24404 if they forgot or do not know their password, with the password reset updating data stored in system database 24406 through service link 24407 to track usage of analytical computing system 21100. Administrators can also configure their additional authentication input via administrator app 24402 through service link 24403 to authenticate 24404 so as to retrieve and change the configuration of their additional authentication input through service link 24405 to system database 24406 with the configuration change updating data stored in system database 24406 through the service link 24407 to track usage of analytical computing system 21100. After an administrator is authenticated on login, they can use services provided by admin 24403 through use of administrator app 24402 through service link 24407 to perform administrative functions of the analytical computing system 21100, wherein, these services, as required, use the service link 24407 to create, read, update and/or delete data stored in system database 24406, e.g., via data storage manager 1064, with the use of these services also creating and updating data stored in system database 24406 through the service link 24407 to track usage of analytical computing system 21100. Additionally, an administrator in performing administrative functions for analytical computing system 21100, as provided by administrator app 24402, can create one or more new groups of users whose use of the analytical computing system 21100 is through a shared team database 24414 through a service link 24413 as well as create a new database server 24415 through a service link 24412 to which the new team database 24414 can be added so as to optimize performance of database server(s) 24415. Ultimately, an administrator can logout from use of analytical computing system 21100 via administrator app 24402 through service link 24403 to terminate their current use of analytical computing system 21100 with the logout service of authenticate 24404 updating the administrator's login information through a service link 24409 to the system database 24406 with the logout updating data stored in system database 24406 through service link 24407 to track usage of analytical computing system 21100. Analytical Computing System 21100 can include one or more Services Servers 24411. These servers are adapted to host various applications and/or modules including, system modules, application modules, authentication modules, administrative modules, dashboard modules, and upload modules. In one embodiment, the authentication and administration modules allow users to communicate, e.g., through one or more service link, with System Database 24406 and/or the Team Database 24414 through the Administrator App 24402.

Figure 25:
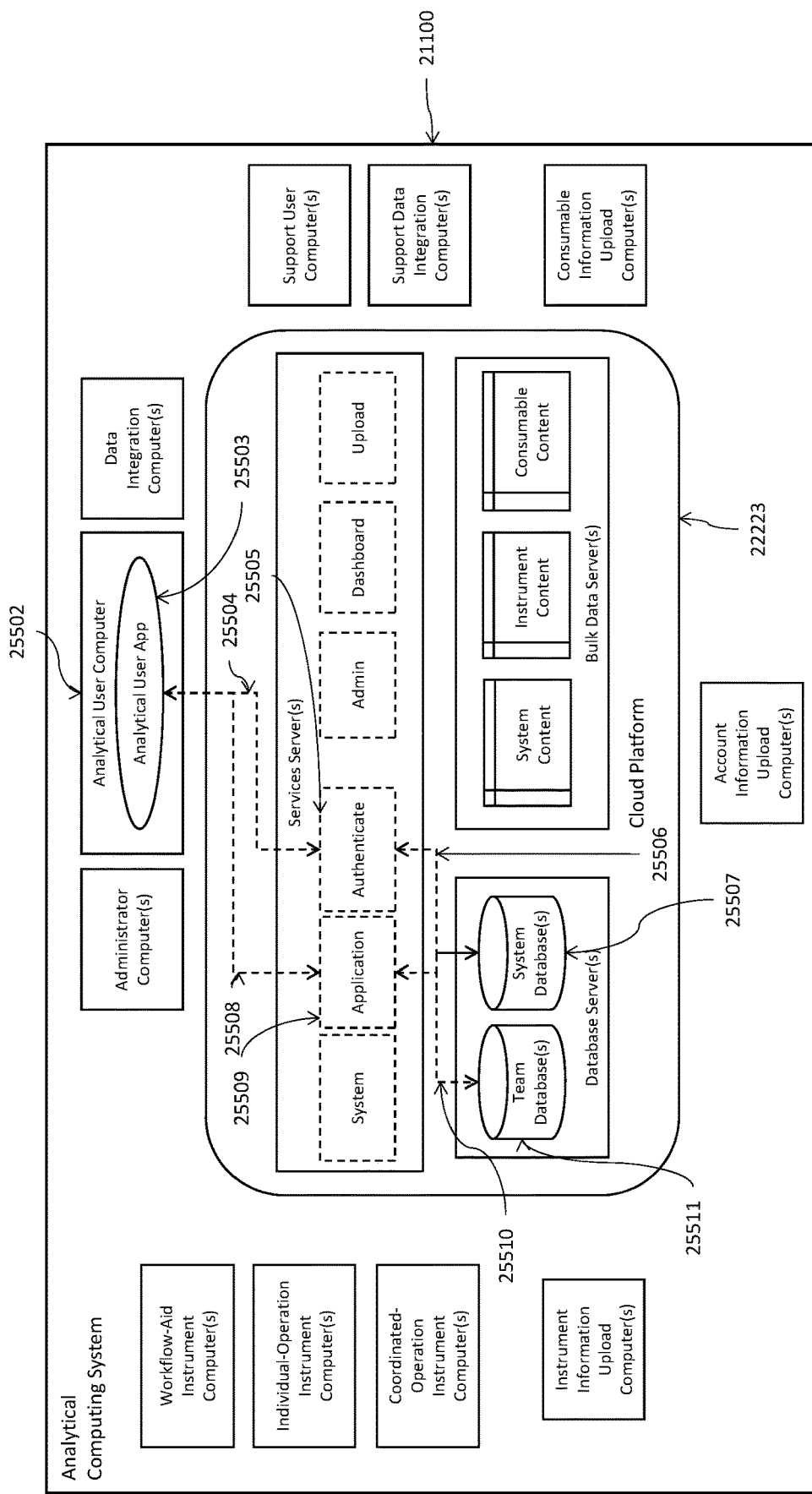
FIG. 25 illustrates interactions between analytical user computers and a cloud platform in an embodiment.

FIG. 25 is an embodiment of an analytical user using an analytical user computer 25502 to run an analytical user app software 25503 to perform analytical functions provided by an analytical computing system 21100 through services provided through a cloud platform at 22223. The analytical user app software 25503, as discussed herein, may employ a MUI as described above to facilitate user access to the functionality provided. As such, embodiments of the methodical user interface control system 1102 may be provided by a combination of the analytical user computer 25502 and the cloud platform 22223. The analytical user app 25503 can be executed on analytical user computer 25502 through either a distinct application installed on the analytical user computer 25502 or accessed via an internet browser installed on the analytical user computer 25502 pointing to a URL with a web site part of the services provided by cloud platform 22223 logically organized with an application 25509 in this embodiment but not limited to that organization. In one practice, the first interaction for an analytical user with cloud platform 22223 is through use of an analytical user app 25503 requesting login services through a service link 25504 to authenticate, 25505, with appropriate credentials that can include a unique username and password and/or another information such as biometric identification and can also include an optional or required additional authentication input, commonly referred to as two-factor authentication, previously configured for use by an administrator, wherein, the login service can retrieve a user's encrypted credentials through a service link 25506 from a system database 25507 to verify that the analytical user may access and use analytical computing system 21100 with the login updating data stored in system database 25507 through the service link 25506 to track usage of analytical computing system 21100. An analytical user can also reset their password via analytical user app 25503 through service link 25504 to authenticate, 25505, if they forgot or do not know their password with the password reset updating data stored in system database 25507 through service link 25506 to track usage of analytical computing system 21100. An analytical user can also configure their additional authentication input via analytical user app 25503 through service link 25504 to authenticate, 25505, so as to retrieve and change the configuration of their additional authentication input through service link 25506 to system database 25507 with the configuration change updating data stored in system database 25507 through the service link 25506 to track usage of analytical computing system 21100. After an analytical user is authenticated on login, they can use services provided by an application 25509 through use of the analytical user app 25503 through a service link 25508 to perform analytical functions provided by application 25509, wherein, these services, as required, use the service link 25510 to create, read, update, and/or delete data stored in team database 25511 with the use of these services also creating and updating data stored in system database 25507 through the service link 25510 to track usage of analytical computing system 21100. Ultimately, an analytical user can logout from use of the analytical computing system 21100 via analytical user app 25503 through service link 25504 to terminate their current use of analytical computing system 21100 with the logout service of authenticate 25505 updating the analytical user login information through service link 25506 to the system database 25507 with the logout updating data stored in system database 25507 through the service link 25506 to track usage of analytical computing system 21100.

Figure 26:
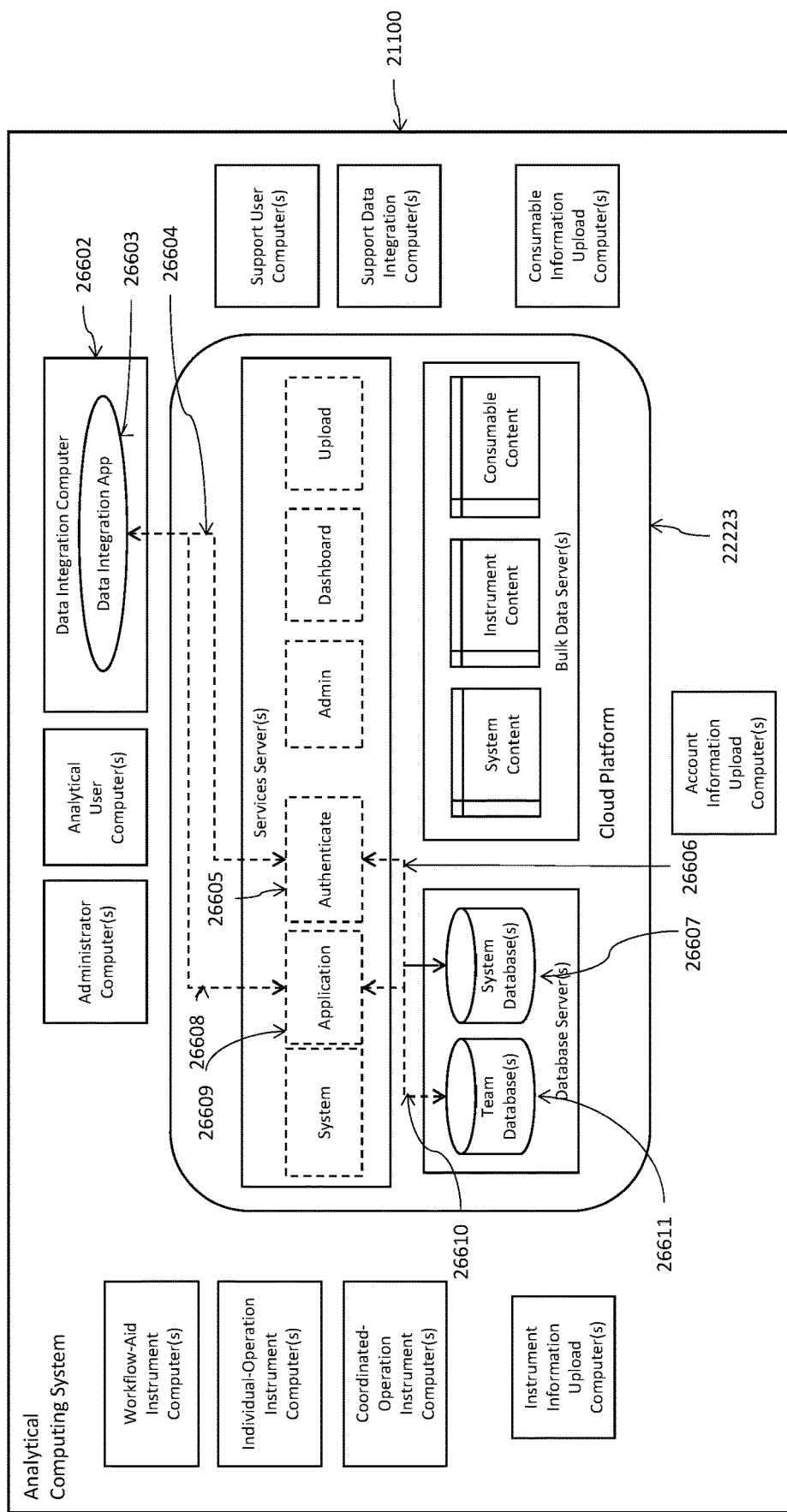
FIG. 26 illustrates interactions between data integration computers and a cloud platform in an embodiment.

In FIG. 26 is an embodiment of a data integration computer 26602 running data integration app software 26603 to perform data integration functions provided by an analytical computing system 21100 through services provided through a cloud platform at 22223 between the analytical computing system 21100 and, optionally, computing system(s) not part of analytical computing system 21100. The data integration app software 26603, as discussed herein, may employ a MUI as described above to facilitate user access to the functionality provided. As such, embodiments of the methodical user interface control system 1102 may be provided by a combination of the data integration computer 26602 and the cloud platform 22223. The data integration app 26603 can be provided as part of analytical computing system 21100 and/or can be provided by an analytical user or someone working with an analytical user. In one practice, the first interaction for data integration app 26603 with cloud platform 22223 is requesting login services through a service link 26604 to authenticate 26605 with appropriate credentials configured by an administrator that preferably include a unique username and password and can also include an optional or required additional authentication input, commonly referred to as two-factor authentication, previously configured for use by an administrator, wherein, the login service can retrieve the encrypted credentials for data integration app 26603 through service link 26606 from a system database 26607 to verify that the data integration app 26603 can access and use analytical computing system 21100 with the login updating data stored in system database 26607 through the service link 26606 to track usage of the analytical computing system 21100. After a data integration app 26603 is authenticated on login, it can use services provided by application 26609 through use of data integration app 26603 through a service link 26608 to perform analytical functions provided by the application 26609, wherein, these services, as required, use a service link 26610 to create, read, update, and/or delete data stored in a team database 26611 with the use of these services also creating and updating data stored in system database 26607 through the service link 26610 to track usage of the analytical computing system 21100. Ultimately, a data integration app can logout from use of the analytical computing system 21100 via data integration app 26603 through service link 26604 to terminate the current use of analytical computing system 21100 with the logout service of authenticate 26605 updating the data integration app login information through the service link 26606 to system database 26607 with the logout updating data stored system database 26607 through the service link 26606 to track usage of the analytical computing system 21100.

Figure 27:
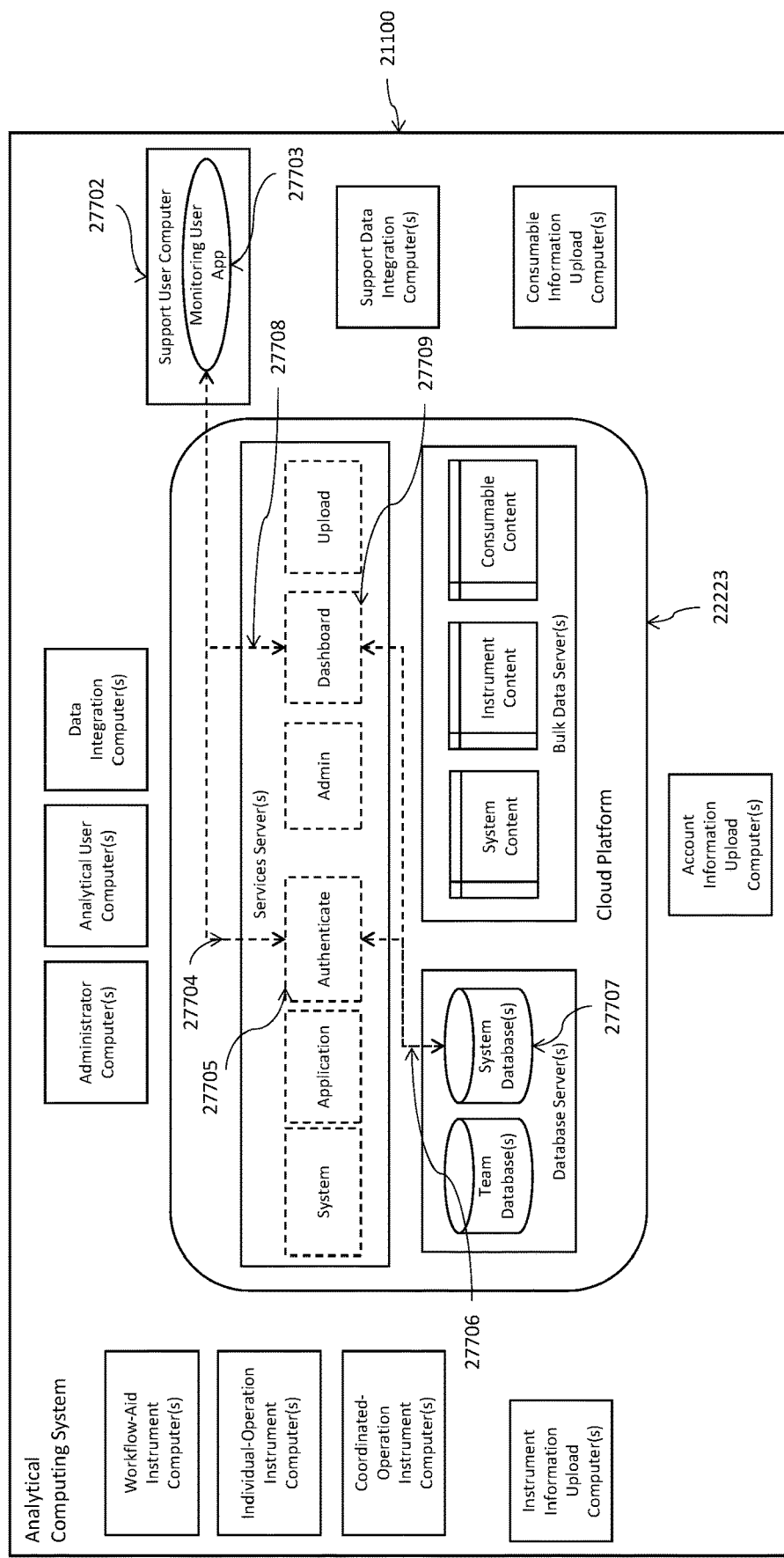
FIG. 27 illustrates interactions between support user computers and a cloud platform in an embodiment.

In FIG. 27 is an embodiment of a user monitoring the use of an analytical computing system 21100 using a support user computer 27702 to run the monitoring user app software 27703 to perform monitoring functions provided by the analytical computing system 21100 through services provided through a cloud platform 22223. The monitoring user app software 27703, as discussed herein, may employ a MUI as described above to facilitate user access to the functionality provided. As such, embodiments of the methodical user interface control system 1102 may be provided by a combination of the support user computer 27702 and the cloud platform 22223. The monitoring user app 27703 can be executed on the support user computer 27702 through either a distinct application installed on the support user computer 27702 or accessed via an internet browser installed on the support user computer 27702 pointing to a URL with a web site part of the services provided by cloud platform 22223 logically organized with a dashboard 27709 in this embodiment, but not limited to that organization. In one practice, the first interaction for a support user computer with the cloud platform is through use of the monitoring user app 27703 requesting login services through a service link 27704 to authenticate 27705 with appropriate credentials that preferably include a unique username and password and/or metric identification and could also include an optional or required additional authentication input, commonly referred to as two-factor authentication, previously configured for use by an administrator, wherein, the login service can retrieve a user's encrypted credentials through a service link 27706 from a system database 27707 to verify that the monitoring user can access and monitor the analytical computing system 21100 with the login updating data stored in system database 27707 through the service link 27706 to track usage of analytical computing system 21100. A monitoring user can also reset their password via the monitoring user app 27703 through service link 27704 to authenticate 27705 if they forgot or do not know their password with the password reset updating data stored in system database 27707 through the service link 27706 to track usage of analytical computing system 21100. A monitoring user can also configure their additional authentication input via the monitoring user app 27703 through service link 27704 to authenticate 27705 so as to retrieve and change the configuration of their additional authentication input through the service link 27706 to the system database 27707 with the configuration change updating data stored in system database 27707 through the service link 27706 to track usage of analytical computing system 21100. After a monitoring user is authenticated on login, they can use services provided by a dashboard 27709 through use of the monitoring user app 27703 through a service link 27708 to perform monitoring functions of the analytical computing system 21100, wherein, these services, as required, use a service link 27710 to create, read, update, and/or delete data stored in system database 27707 with the use of these services also creating and updating data stored in system database 27707 through the service link 27710 to track usage of the analytical computing system 21100. Ultimately, a monitoring user can logout from use of the analytical computing system 21100 via monitoring user app 27703 through a service link 27704 to terminate their current use of the analytical computing system 21100 with the logout service of authenticate 27705 updating the administrator's login information through the service link 27706 to the system database 27707 with the logout updating data stored in system database 27707 through the service link 27706 to track usage of the analytical computing system 21100.

Figure 28:
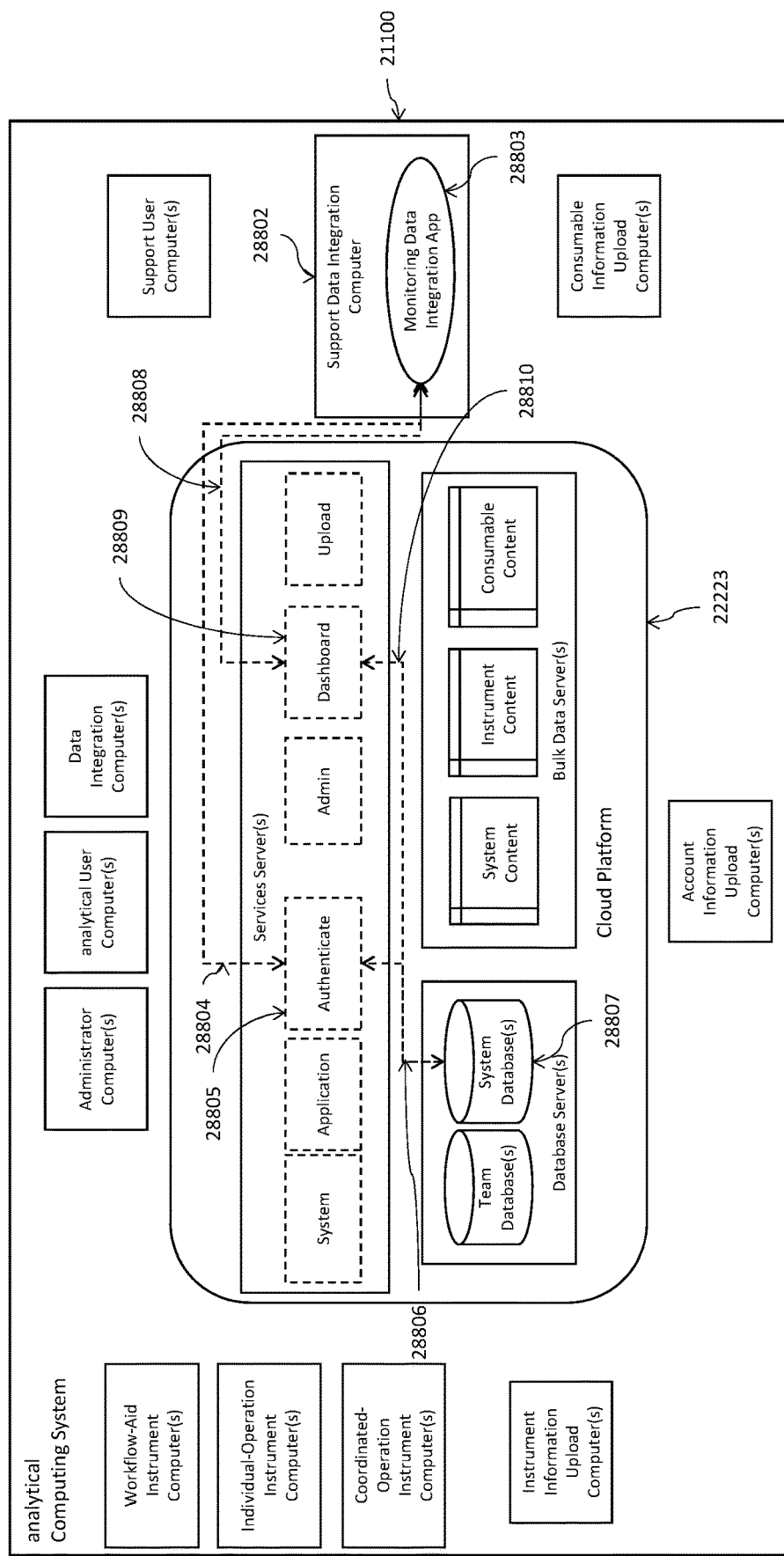
FIG. 28 illustrates interactions between support data integration computer and a cloud platform in an embodiment.

In FIG. 28 is an embodiment of a support data integration computer 28802 running monitoring data integration app software 28803 to perform monitoring data integration functions provided by the analytical computing system 21100 through services provided through a cloud platform at 22223 between analytical computing system 21100 and, optionally, computing system(s) not part of the analytical computing system 21100. The monitoring data integration app software 28803, as discussed herein, may employ a MUI as described above to facilitate user access to the functionality provided. As such, embodiments of the methodical user interface control system 1102 may be provided by a combination of the support data integration computer 28802 and the cloud platform 22223. Thus, the monitoring data integration apps software is adapted to track, review, and/or monitor one or more features of the data integration functions described herein. In one practice, the first interaction for a monitoring data integration app 28803 with the cloud platform at 22223 is requesting login services through a service link 28804 to authenticate 28805 with appropriate credentials configured by an administrator that preferably include a unique username and password and can also include an optional or required additional authentication input, commonly referred to as two-factor authentication, previously configured for use by an administrator, wherein, the login service can retrieve the encrypted credentials for a monitoring data integration app 28803 through a service link 28806 from a system database 28807 to verify that the monitoring data integration app can access and use the analytical computing system 21100 with the login updating data stored in system database 28807 through the service link 28806 to track usage of the analytical computing system 21100. After a monitoring data integration app 28803 is authenticated on login, it can use services provided by a dashboard 28809 through use of the monitoring data integration app 28803 through a service link 28808 to perform monitoring functions provided by dashboard 28809, wherein, these services, as required, use a service link 28810 to create, read, update, and/or delete data stored in system database 28807 with the use of these services also creating and updating data stored in system database 28807 through the service link 28810 to track usage of the analytical computing system 21100. Ultimately, a monitoring data integration app 28803 can logout from use of the analytical computing system 21100 via monitoring data integration app 28803 through a service link 28804 to terminate the current use of the analytical computing system 21100 with the logout service of authenticate 28805 updating the monitoring data integration app login information through the service link 28806 to the system database 28807 with the logout updating data stored in system database 28807 through the service link 28806 to track usage of the analytical computing system 21100.

Figure 29:
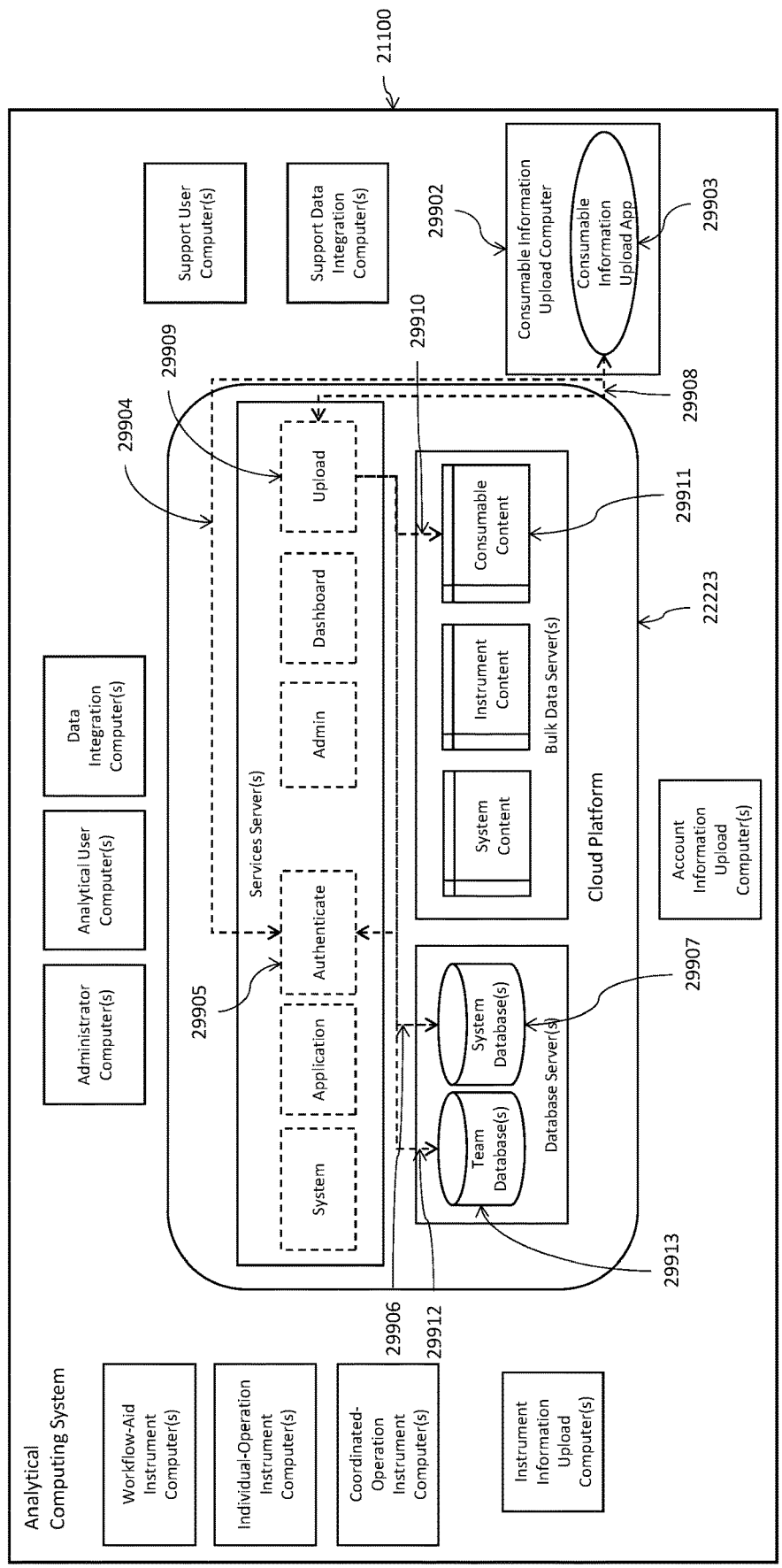
FIG. 29 illustrates interactions between a consumable information upload computer and a cloud platform in an embodiment.

In FIG. 29 is an embodiment of a consumable information upload computer 29902 running a consumable information upload app software 29903 to perform consumable information upload functions provided by analytical computing system 21100 via services provided through a cloud platform at 22223 between the analytical computing system 21100 and, optionally, computing system(s) not part of the analytical computing system 21100. The consumable information upload app software 29903, as discussed herein, may employ a MUI as described above to facilitate user access to the functionality provided. As such, embodiments of the methodical user interface control system 1102 may be provided by a combination of the consumable information upload computer 29902 and the cloud platform 22223. In one practice, the first interaction for a consumable information upload app 29903 with the cloud platform at 22223 is requesting login services through a service link 29904 to authenticate 29905 with appropriate credentials configured to preferably include a unique username and password, wherein, the login service can retrieve the encrypted credentials for a consumable information upload app 29903 through a service link 29906 from a system database 29907 to verify that the consumable information upload app can access and use the analytical computing system 21100 with the login updating data stored in system database 29907 through the service link 29906 to track usage of analytical computing system 21100. After a consumable information upload app 29903 is authenticated on login, it can use services provided by upload 29909 through use of the consumable information upload app 29903 through a service link 29908 to perform consumable information upload functions provided by upload 29909, wherein, these services, as required, use the service link 29910 to push data to be stored in consumable content 29911 associated with a particular customer account for subsequent storage to one or more team databases 29913 that are associated with a particular customer account by upload 29909 transferring the data via the service link 29912 with the use of these services also creating and updating data stored in system database 29907 through the service link 29906 to track usage of the analytical computing system 21100. Once upload is complete, a consumable information upload app 29903 can logout from use of the analytical computing system 21100 via consumable information upload app 29903 through a service link 29904 to terminate the current use of analytical computing system 21100 with the logout service of authenticate 29905 updating the consumable information upload app login information through the service link 29906 to the system database 29907 with the logout updating data stored in system database 29907 through the service link 29906 to track usage of the analytical computing system 21100.

Figure 30:
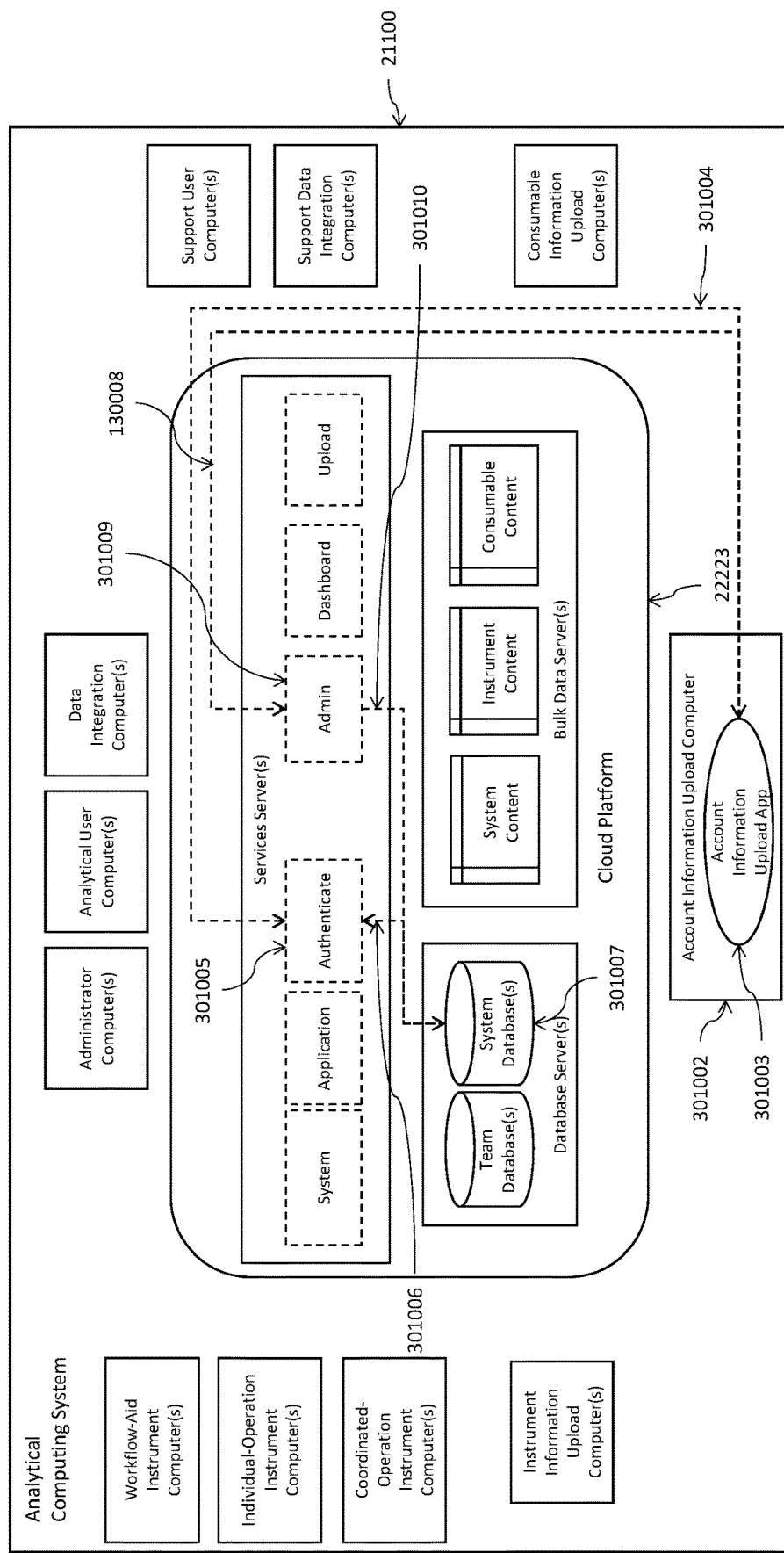
FIG. 30 illustrates interactions between an account information upload computer and a cloud platform in an embodiment.

In FIG. 30 is an embodiment of an account information upload computer 301002 running account information upload app software 301003 to perform account update functions provided by analytical computing system 21100 via services provided through a cloud platform at 22223 between the analytical computing system 21100 and, optionally, computing system(s) not part of the analytical computing system 21100. The account information upload app software 30103, as discussed herein, may employ a MUI as described above to facilitate user access to the functionality provided. As such, embodiments of the methodical user interface control system 1102 may be provided by a combination of the account information upload computer 301002 and the cloud platform 22223. The account update functions can include adding, modifying, and/or deleting information as it relates to one more given accounts including, for example, usernames, passwords, permissions, and other attributes associated with one or more individual or team accounts. In one practice, the first interaction for the account information upload app 301003 with cloud platform 22223 is requesting login services through a service link 301004 to authenticate 301005 with appropriate credentials configured that preferably include a unique username and password, wherein, the login service can retrieve the encrypted credentials for an account information upload app 301003 through a service link 301006 from a system database 301007 to verify that the account information upload app can access and use the analytical computing system 21100 with the login updating data stored in system database 301007 through the service link 301006 to track usage of the analytical computing system 21100. After an account information upload app 301003 is authenticated on login, it can use services provided by admin 301009 through use of the account information upload app 301003 through a service link 301008 to perform the account information upload functions provided by admin 301009, wherein, these services, as required, use a service link 301010 to push data to be stored in system database 301007 associated with creating or updating a customer account with the use of these services also creating and updating data stored in system database 301007 through the service link 301010 to track usage of the analytical computing system 21100. Once upload is complete, an account information upload app 301003 can logout from use of the analytical computing system 21100 via account information upload app 301003 through a service link 301004 to terminate the current use of the analytical computing system 21100 with the logout service of authenticate 301005 updating the account information upload app login information through the service link 301006 to the system database 301007 with the logout updating data stored in system database 301007 through the service link 301006 to track usage of the analytical computing system 21100.

Figure 31:
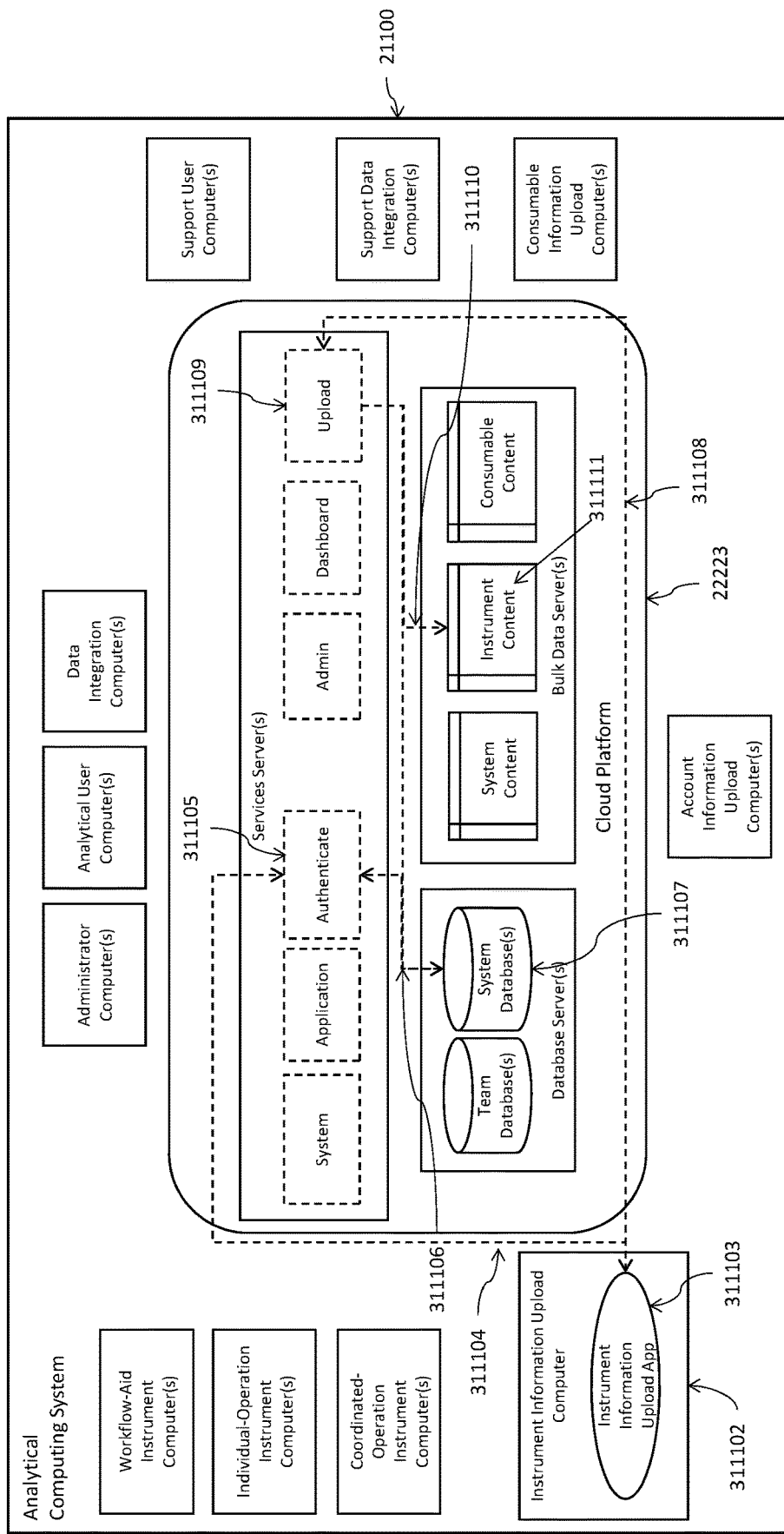
FIG. 31 illustrates interactions between an instrument information upload computer and a cloud platform in an embodiment.

In FIG. 31 is an embodiment of an instrument information upload computer 311102 running instrument information upload app software 311103 to perform instrument information upload functions provided by analytical computing system 21100 via services provided through a cloud platform at 22223 between the analytical computing system 21100, and optionally computing system(s) not part of analytical computing system 21100. The running instrument information upload app software 311103, as discussed herein, may employ a MUI as described above to facilitate user access to the functionality provided. As such, embodiments of the methodical user interface control system 1102 may be provided by a combination of the instrument information upload computer 311102 and the cloud platform 22223. The first interaction for an instrument information upload app 311103 with the cloud platform at 22223 is requesting login services through a service link 311104 to authenticate 311105 with appropriate credentials configured that preferably include a unique username and password, wherein, the login service can retrieve the encrypted credentials for an instrument information upload app 311103 through a service link 311106 from a system database 311107 to verify that an instrument information upload app can access and use the analytical computing system 21100 with the login updating data stored in system database 311107 through the service link 311106 to track usage of the analytical computing system 21100. After an instrument information upload app 311103 is authenticated on login, it can use services provided by upload 311109 through use of an instrument information upload app 311103 through a service link 311108 to perform instrument information upload functions provided by upload 311109, wherein, these services, as required, use the service link 311110 to create a new instrument on first occurrence of an instrument and push data to be stored in instrument content 311111 associated with the instrument for a particular customer account for subsequent storage to an account in the system database 311107 through the service link 311106 with the use of these services also creating and updating data stored in system database 311107 through the service link 311106 to track usage of the analytical computing system 21100. Once upload is complete, an instrument information upload app 311103 can logout from use of the analytical computing system 21100 via instrument information upload app 311103 through a service link 311104 to terminate the current use of the analytical computing system 21100 with the logout service of authenticate 311105 updating the instrument information upload app login information through the service link 31106 to the system database at 1107 with the logout updating data stored in system database 311107 through the service link 311106 to track usage of the analytical computing system 21100.

Figure 32:
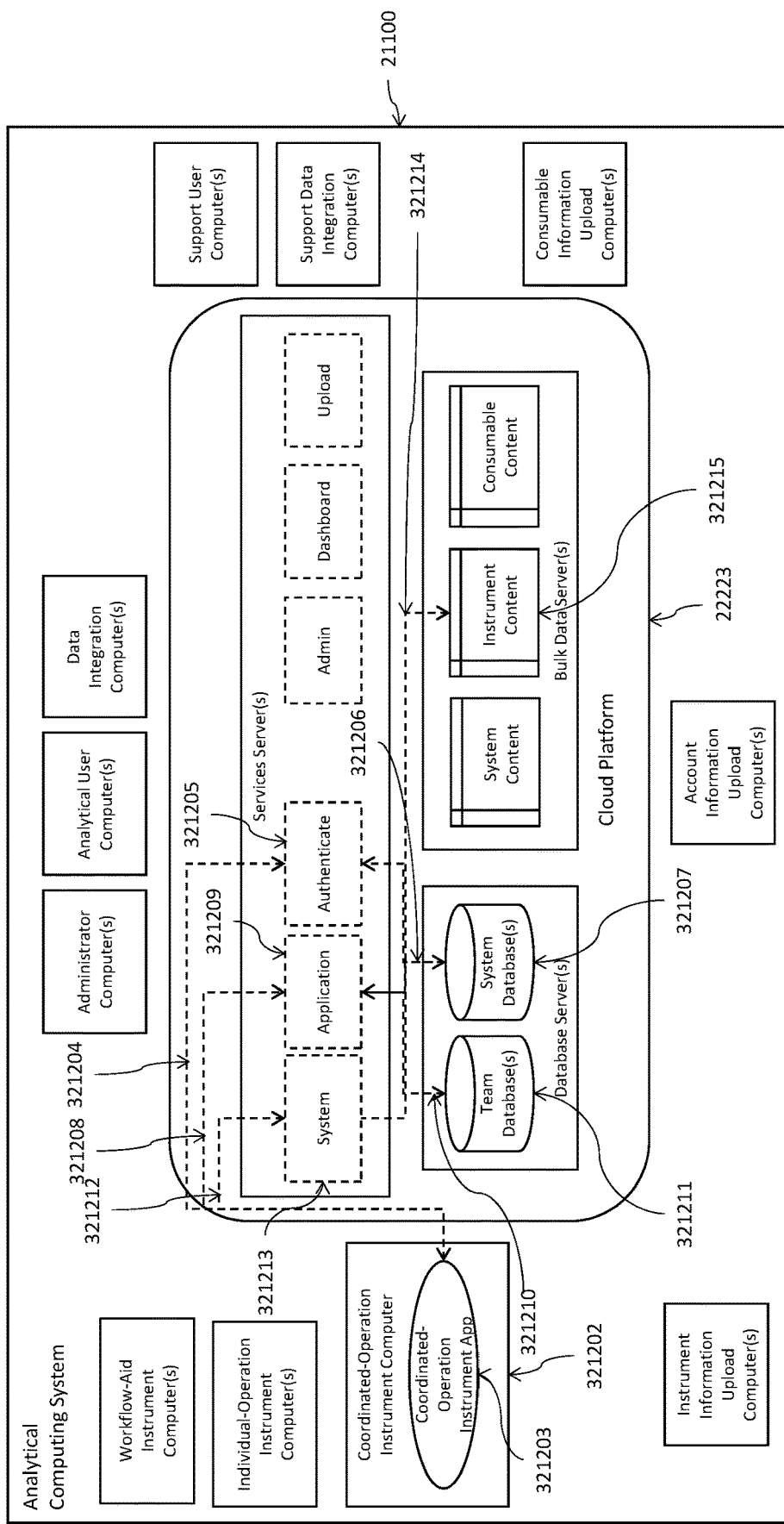
FIG. 32 illustrates interactions between a coordinated-operation instrument computer and a cloud platform in an embodiment.

In FIG. 32 is an embodiment of a coordinated-operation instrument computer 321202 running coordinated-operation instrument app software 321203 to perform coordinated-operation instrument functions provided by analytical computing system 21100 via services provided through a cloud platform at 22223 associated with instrumentation processing where a coordinated-operation instrument provides an integration of one or more individual operation instruments; an integration of custom-designed hardware; or a combination of one or more individual-operation instruments with custom-designed hardware. The coordinated-operation instrument app software 321203, as discussed herein, may employ a MUI as described above to facilitate user access to the functionality provided. As such, embodiments of the methodical user interface control system 1102 may be provided by a combination of the coordinated-operation instrument computer 321202 and the cloud platform 22223. In one practice, the first interaction for a coordinated-operation instrument app 321203 with the cloud platform at 22223 is requesting login services through a service link 321204 to authenticate 321205 with appropriate credentials configured that preferably includes a unique username and password, wherein, the login service can retrieve the encrypted credentials for a coordinated-operation instrument app 321203 through a service link 321206 from a system database 321207 to verify that a coordinated-operation instrument app 321203 can access and use the analytical computing system 21100 with the login updating data stored in system database 321207 through the service link 321206 to track usage of the analytical computing system 21100. The coordinated-operation instrument computer 321202 running coordinated-operation instrument app software 321203 can communicate with a system component 321213 of a services server via a service link 321212, which may communicate with a team database 321211 via a service link 321210; the coordinated-operation instrument computer 321202 running coordinated-operation instrument app software 321203 can communicate with an application component 321209 of a service server via a service link 321208. One or more services server components, e.g., 321213, 321209, 321205, may communicate with a bulk data server, e.g., access instrument content 321215, via a service link 321214.

Figure 33A:
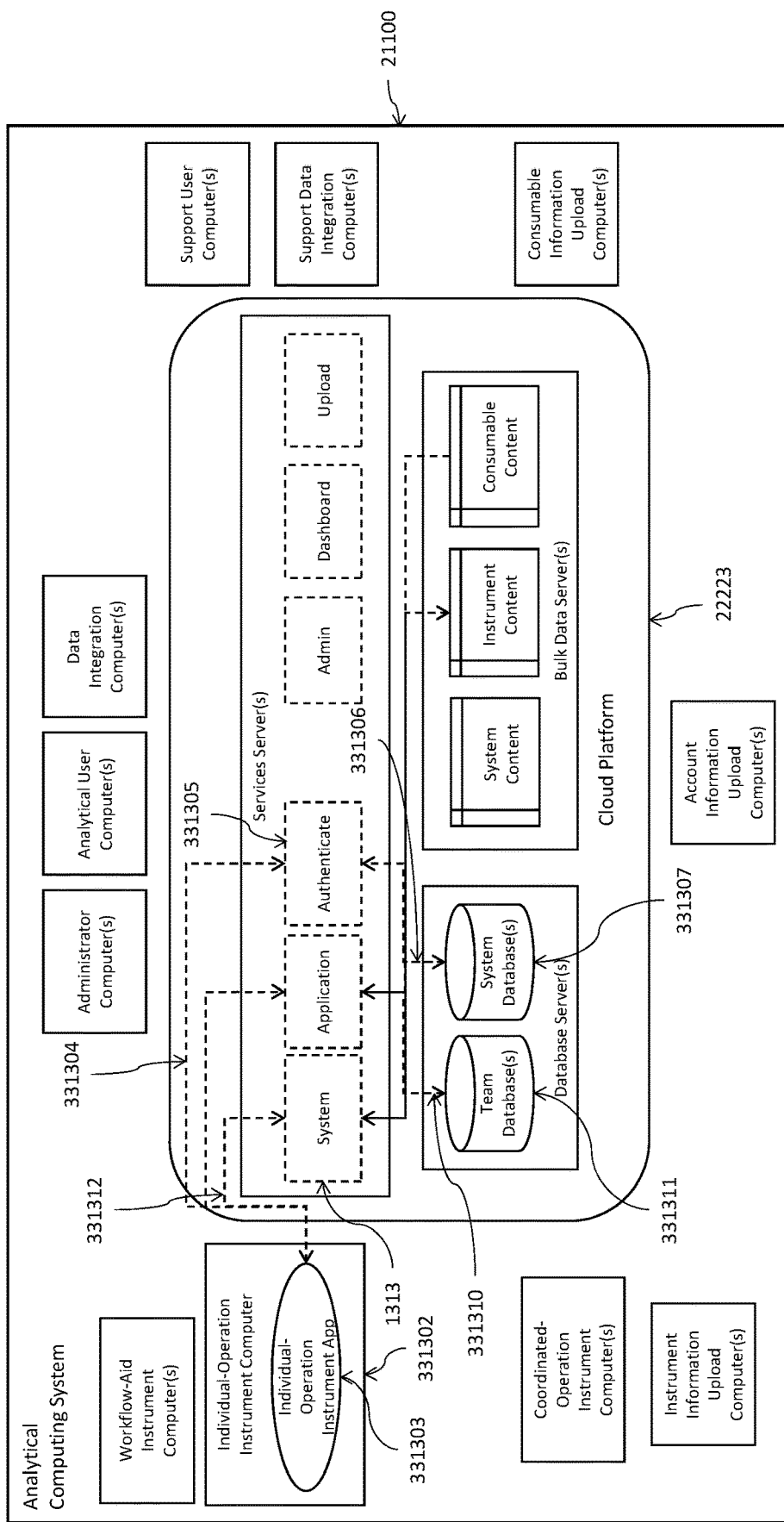
FIG. 33A illustrates interactions between an individual-operation instrument computer and a cloud platform in an embodiment.

In FIG. 33A is an embodiment of an individual-operation instrument computer 331302 running individual-operation instrument app software 331303 to perform individual-operation instrument functions provided by analytical computing system 21100 via services provided through a cloud platform at 22223 associated with instrumentation processing. The individual-operation instrument app software 331303 as discussed herein, may employ a MUI as described above to facilitate user access to the functionality provided. As such, embodiments of the methodical user interface control system 1102 may be provided by a combination of the individual-operation instrument computer 331302 and the cloud platform 22223. In one embodiment, an individual-operation instrument performs one or more logical assay steps on one or more samples in a stepwise process to collect data about the samples under test. In this embodiment, the individual-operation instrument does not perform all assay steps, which can include, without limitation, steps that relate to a plate reader, plate washer, plate incubator, plate shaker, plate incubator-shaker, pipetting system, or any other type of instrument used in support of analytical sample testing. In other embodiments, the individual-operation instrument can perform all assay steps. The first interaction for an individual-operation instrument app 331303 with the cloud platform at 22223 is requesting login services through a service link 331304 to authenticate 331305 with appropriate credentials configured that preferably includes a unique username and password, wherein, the login service can retrieve the encrypted credentials for an individual-operation instrument app 331303 through a service link 331306 from a system database 331307 to verify that an individual-operation instrument app 331303 can access and use the analytical computing system 21100 with the login updating data stored in system database 331307 through the service link 331306 to track usage of the analytical computing system 21100. In the alternative, the individual-operation instrument computer 331302 can assist in performing other functions in addition to or in place of the assay steps and/or plate-based tests described herein.

Figure 33B:
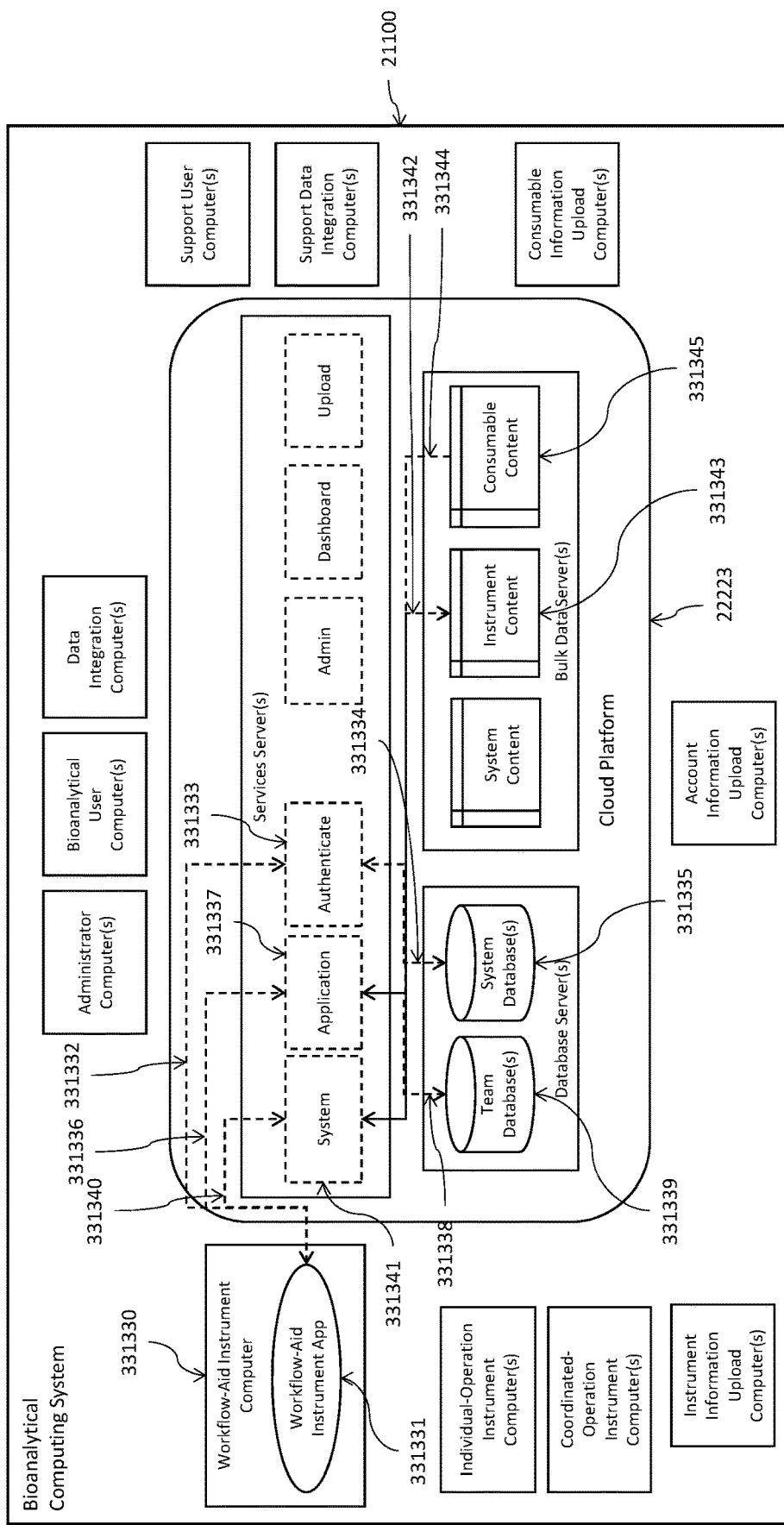
FIG. 33B illustrates interactions between a workflow-aid instrument computer and a cloud platform for the embodiment shown in FIG. 33A.

In FIG. 33B is an embodiment of an individual-operation instrument computer 331302 running workflow-aid instrument app software 331331 to perform individual-operation instrument functions provided by analytical computing system 21100 via services provided through a cloud platform at 22223 associated with instrumentation processing. The individual-operation instrument app software 331331 as discussed herein, may employ a MUI as described above to facilitate user access to the functionality provided. As such, embodiments of the methodical user interface control system 1102 may be provided by a combination of the individual-operation instrument computer 331330 and the cloud platform 22223. The workflow-aid instrument helps a user perform collection of assay components used in the processing of the assays in an associated experiment, as well as, preparing bioassay components that require preparation prior to be used in the processing of an assay, for example but not limited to, rehydrating lyophilized reagents, thawing frozen reagents, pretreating samples, and/or any other step required to prepare constituent components to be used in processing one or more assays in a chosen experiment. The first interaction for an workflow-aid instrument app 331331 with the cloud platform 22223 is requesting login services through a service link 331332 to authenticate 331333 with appropriate credentials configured with preferably unique username and password, wherein, the login service would retrieve the encrypted credentials for an workflow-aid instrument app 331331 through a service link 331334 from system database 331335 to verify a workflow-aid instrument app 331331 may access and use the analytical computing system 21100 with the login updating data stored in system database 331335 through the service link 331334 to track usage of the analytical computing system 21100. After workflow-aid instrument app 331331 is authenticated on login, it will use services provided by application 331337 through use of a workflow-aid instrument app 331331 through a service link 331336 to perform workflow-aid instrument app functions provided by application 331337 wherein, these services as required use the service link 331338 to retrieve experiments ready to be processed 331339; to store data 331339 as an experiment is processing; and/or to store data 331339 after an experiment completes processing, with the use of these services also creating and saving data stored in system database 331335 through the service link 331334 to track usage of the analytical computing system 21100. Once a user has completed use of a workflow-aid instrument app 331331, they could logout from use of the analytical computing system 331300 via workflow-aid app 331331 through a service link 331332 to terminate the current use of the analytical computing system 21100 with the logout service of authenticate 331333 updating a workflow-aid instrument app login information through the service link 331334 to the system database 331335 with the logout updating data stored in system database 331335 through the service link 331334 to track usage of the analytical computing system 21100.

Figure 34A:
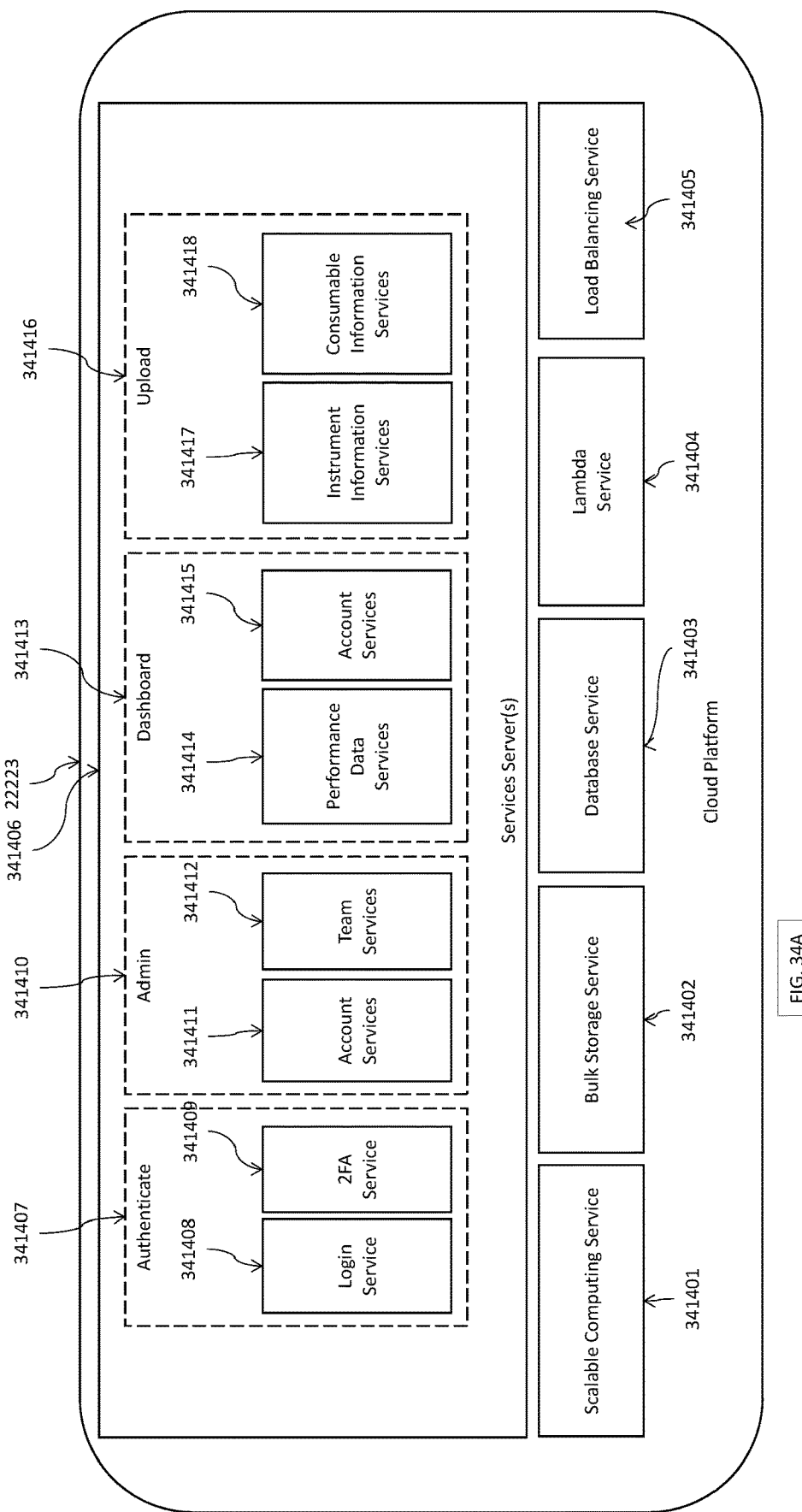
FIG. 34A illustrates a first part of a software architecture for cloud platform services in an embodiment.
Figure 34B:
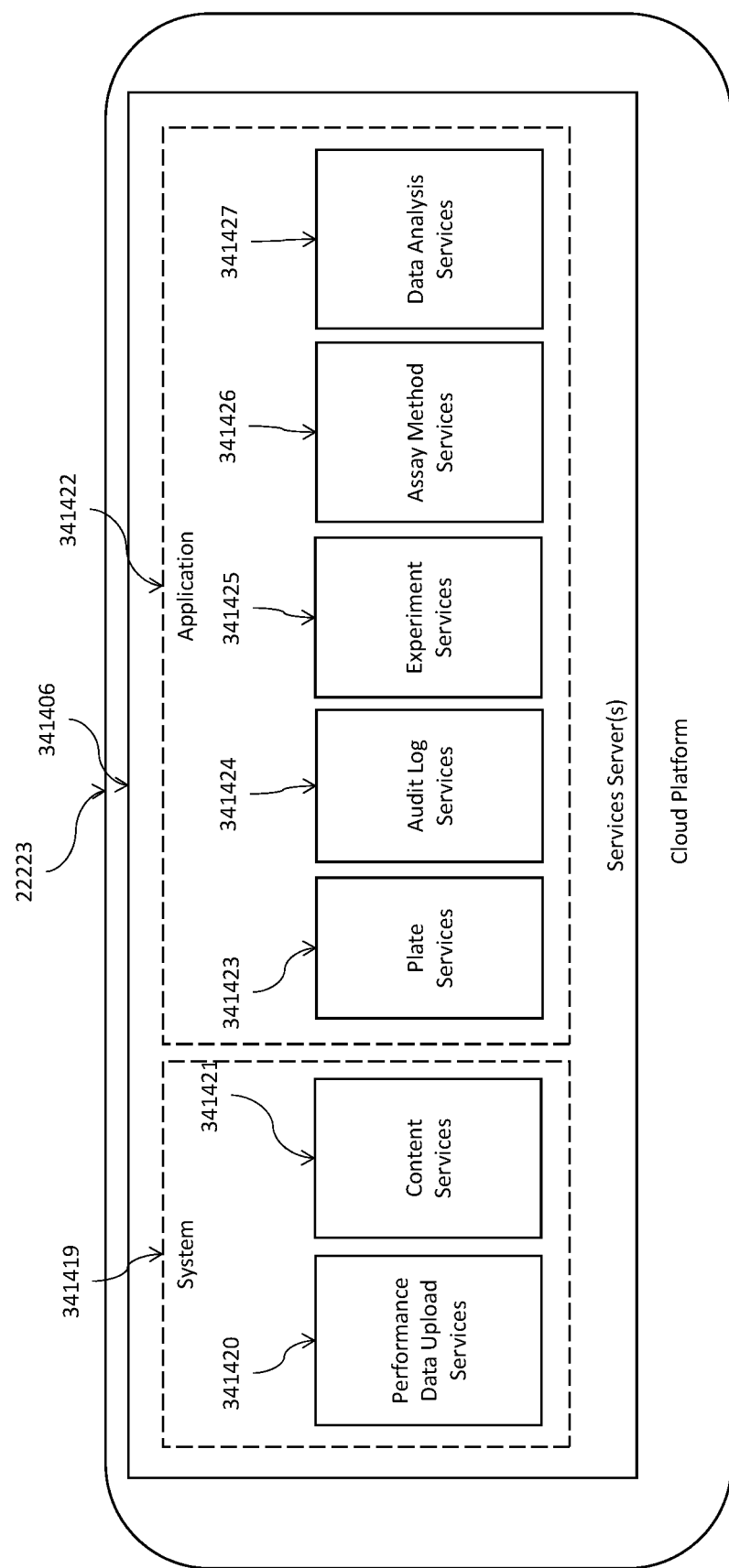
FIG. 34B illustrates a second part of the software architecture for the cloud platform services for the embodiment shown in FIG. 34A.

In FIG. 34A and FIG. 34B is a combined embodiment of software architecture for services deployed on cloud platform 22223. Scalable computing service 341401 associated with cloud platform 22223 provide a secure computing environment for scaling the server utilization of services servers 341406 as system computing requirements change, as well as supporting the building of failure-resilient applications and isolating them from common failure scenarios. Bulk storage service 341402 associated with cloud platform 22223 provides unlimited data storage space in a highly available and durable way for any kind of data to be stored, such as images, video, documents, binary data files, and/or other types of files. Database service 341403 associated with cloud platform 22223 provides a secure, distributed, scalable database system used to store structured data for applications and system, supporting and easily distributing one or more databases across one or more servers. Lambda function service 341404 associated with cloud platform 22223 provides an event-driven computing platform for running special-built utility applications in response to configured events, while automatically managing computing resources required by these special-built utility applications. Load balancing service 341405 with cloud platform 22223 provides distribution of incoming service requests from clients across multiple services servers 341406 to meet continuous performance demands, as well as performing health checks on the scalable computing service 341401 to ensure the service is operational before sending requests and providing an extra security layer by isolating the scalable computing service 341401 from direct access from the internet. Logical collection of authenticate services 341407 deployed on services servers 341406 provides login services 341408 supporting a user logging in with username and password with strong password policy and customizable password expiration period; and services 341409 supporting two-factor authentication (2FA) for a supplemental method of confirming a user's claimed identity by using another form of authentication other than a username and password, for example using a Time-based One-time Password algorithm (TOTP) optionally configured on or off for an account. Logical collection of admin services 341410 deployed on services servers 341406 provides account services 341411 supporting account preparation, team creation, team administration, software releases, and instrument service plan; and team services 341412 supporting managing team membership, defining role permissions per each module, assigning users one or more roles, and notifying users via email of key events in the system pertinent to them. Logical collection of dashboard services 341413 deployed on services servers 341406 provides performance data services 341414 supporting gathering use and performance data from all instruments and consumables in the field operating within the system for analysis and presentation as well as, supporting export of this data to external systems; and account services 341415 providing visibility into the structure and operation of various teams and their users in an account plus across all accounts and supporting export of this data to external systems, as well as providing ability to monitor and disable suspicious and/or undesired behavior. Logical collection of upload services 341416 deployed on services servers 341406 provides instrument information services 341417 supporting import of instrument information from external systems for an account and teams associated with an account; and consumable information services 341418 supporting import of consumable information from external systems for an account and teams associated with an account. Logical collection of system services 341419 deployed on services servers 341406 providing performance data upload services 341420 supporting storing instrument and consumable performance data from instruments in the field operating within the system to be stored using bulk storage service 341402; and content services 341421 supporting dissemination of user manuals and application installers for various versions of applications.

Logical collection of application services 341422 deployed on services servers 341406 providing plate services 341423 supporting storing for a user plate data, including signal, plate identifier, username who processed the plate, timestamp of execution, and plate type, in a team database associated with the requesting user; audit log services 341424 supporting capturing time-stamped events linked to a user's actions with data and services in the system to be stored in the team's database associated with a user performing the actions; experiment services 341425 supporting creating an experiment with selected assay methods and samples to process, committing an experiment for execution and storing to a requesting user's team database, retrieving plate data from instruments to store with an experiment in a requesting user's team database, retrieving a collection of recent or all experiments from a requesting user's team database, initiating calculation of results using one or more associated analysis methods and storing to a requesting user's team database, and retrieving a specific experiment with its plate data including calculated results from a requesting user's team database; assay method services 341426 supporting retrieving a collection of recent or all assay methods from a requesting user's team database, retrieving a specific assay method from a requesting user's team database with assay method configuration data including but not limited to assay method name, associated assays to be tested, layout of different sample types being optionally calibrators, optionally controls, optionally blanks, and optionally samples (i.e., unknowns), analysis method assignments to the assay method as well as optionally to one or more assays associated with the assay method, and protocol parameters configuring the performance of the assay method either manually or automatically, and committing the assay method for use storing it in the requesting user's team database; and data analysis services 341427 supporting retrieving a collection of recent or all analysis methods from a requesting user's team database, retrieving a specific analysis method from a requesting user's team database with analysis method configuration data including but not limited to analysis method name, algorithm and associated configuration, background detection configuration, and limits of detection configuration, and committing the analysis method for ultimate use storing it in the requesting user's team database. In the alternative, the logical collection of application services 341422 can assist in performing other services in addition to or in place of the assay services and/or plate based tests described herein.

Figure 35A:
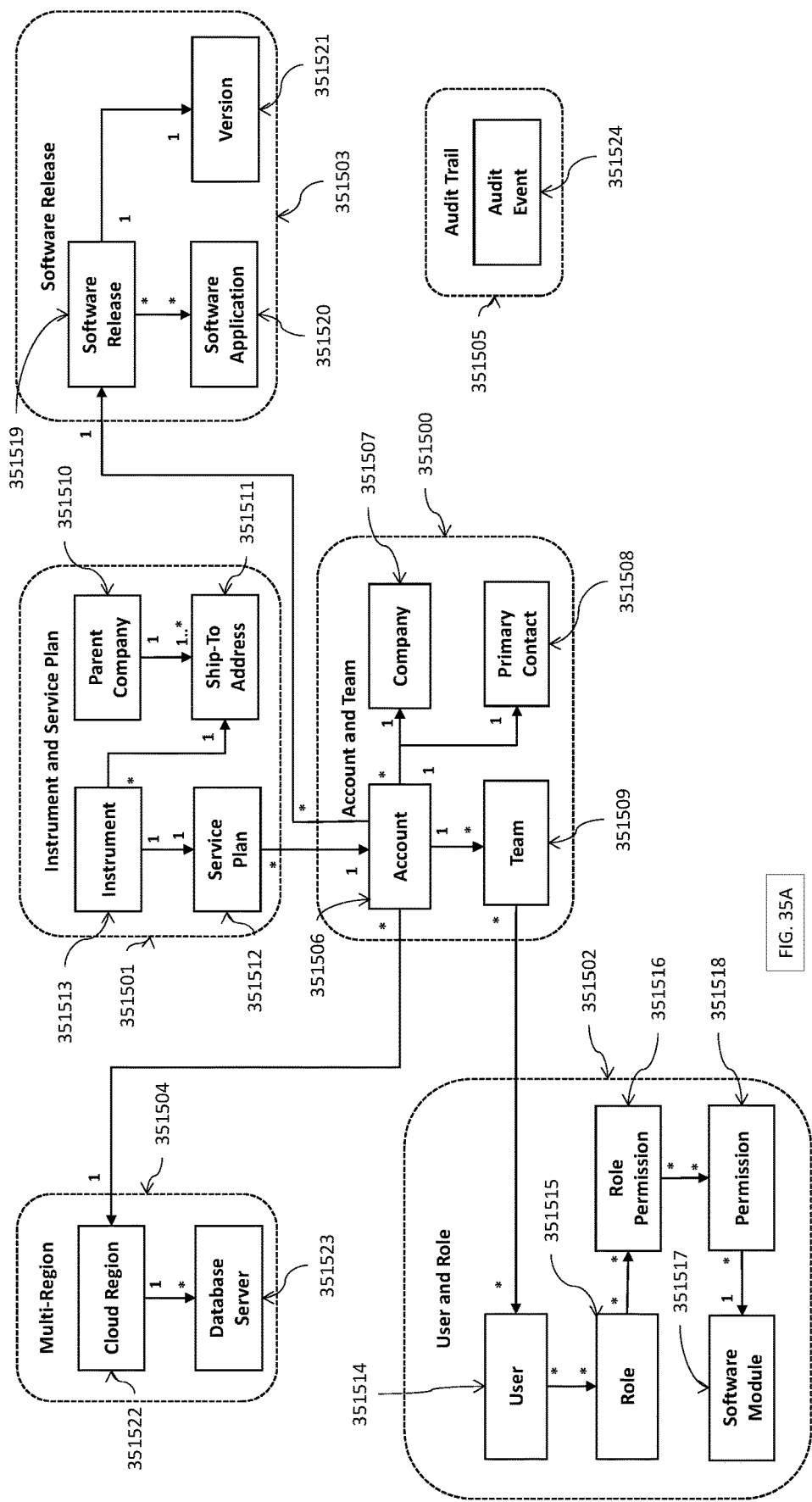
FIG. 35A illustrates a logical design for system data in an embodiment.

In FIG. 35A is an embodiment of a logical design for system data for the analytical computing system with the data entities organized in logical groups as defined by Account and Team 351500, Instrument and Service Plan 351501, User and Role 351502, Software Release 351503, Multi-Region 351504, and Audit Trail 351505, wherein, Account and Team 351500 includes one or more data entities associated with managing an account of users organized into teams on the analytical computing system; Instrument and Service Plan 351501 includes one or more data entities associated with instrumentation used in conjunction with the analytical computing system; User and Role 351502 includes one or more data entities associated with managing the users assigned to zero or more teams on the analytical computing system; Software Release 351503 includes one or more data entities associated with managing new releases of software for the analytical computing system; Multi-Region 351504 includes one or more data entities associated with managing deployment of an account on a cloud platform providing support for a geographically distributed computing environment providing localized performance improvement and/or meeting governmental restrictions such that an account could be located to a desired geographical location; and Audit Trail 351505 includes one or more data entities associated with capturing a log of actions performed by administrators of the analytical computing system. Account and Team 351500 having a data entity 351506 representing one or more accounts on the analytical computing system where each account has associated with it a data entity 351509 representing one or more teams organized within an account and a data entity 351507 representing a company establishing a specific account for which is a data entity 351508 representing a contact who is responsible for preparing use of the account for a company, such that each company 351507 can have more than one account associated with it as prepared by a specific primary contact 351508. Instrument and Plan 351501 has a data entity 351513 representing one or more instruments to be used in conjunction with an account on the analytical computing system where each instrument has associated with it a data entity 351511 representing the ship-to address associated with a data entity 351510 representing a parent company to which the associated instrument was shipped, such that a Parent Company 351510 may have associated with it one or more Ship-To Addresses 351511 that in turn can have associated with it one or more Instruments 351513 that have associated with each instrument a data entity 351512 representing a service plan either active or inactive for an instrument that itself is associated with an Account 351506 to aid an administrator in managing service plan renewals of one or more instruments potentially in use with the account on the analytical computing system. User and Role 351502 has a data entity 351514 representing a distinct user of the analytical computing system associated with one or more teams 351509 prepared for an Account 351506 where each user has for a team an association with a data entity 351515 representing a role in the use of the analytical computing system with a prescribed set of software function permissions as defined in the associated data entity 351516 derived from the permissions defined by the data entity 351518 associated with the data entity 351517 representing each software module in the analytical computing system, such that, a distinct User 351514 may participate with one or more teams 351509 where each team could be in the same or different accounts 351506 and the user assuming one or more roles 351515 for each team that enables and disables one or more functions of the software as configured for each role 351516. Software Release 351503 has a data entity 351519 representing the overarching software release of a collection of one or more applications in the analytical computing system as represented by the data entity 351520, such that each Account 351506 is using a particular software release 351519 and may upgrade to one of one or more new software releases 351519, but all users 351514 associated with an Account 351506 have up to upgrade to the new software release 351519 when an Account 351506 performs the upgrade. Multi-Region 351504 has a data entity 351522 representing the geographical region supported by the cloud platform and associated a data entity 351523 representing the database server for user for creating databases for use, such that, an Account 351506 is associated with a specific geographical region 351522 to which all of its Teams 351509 will have their associated databases 351523 created for use by each respective team so that only Users 351514 assigned to a Team 351509 may access the assigned database created 351523. Audit trail 351505 includes data entity 351524 representing an audit event. Software release 351503 can include version control 351521, which is adapted to document, maintain, and/or track previous versions of the Software release 351503. In one embodiment, version control 351521 includes information as it relates to the existing version and all previous versions of Software release 351503 along with information to changes to the software that propagated through the various versions of the software. Moreover, version control 351521 can include information as it relates to future plans for additional revisions to Software release 351503. Audit trail 351505 can further include an audit event 351524, which can be used to trigger a system audit and/or audit various user- or instrument-based operations.

Figure 35B:
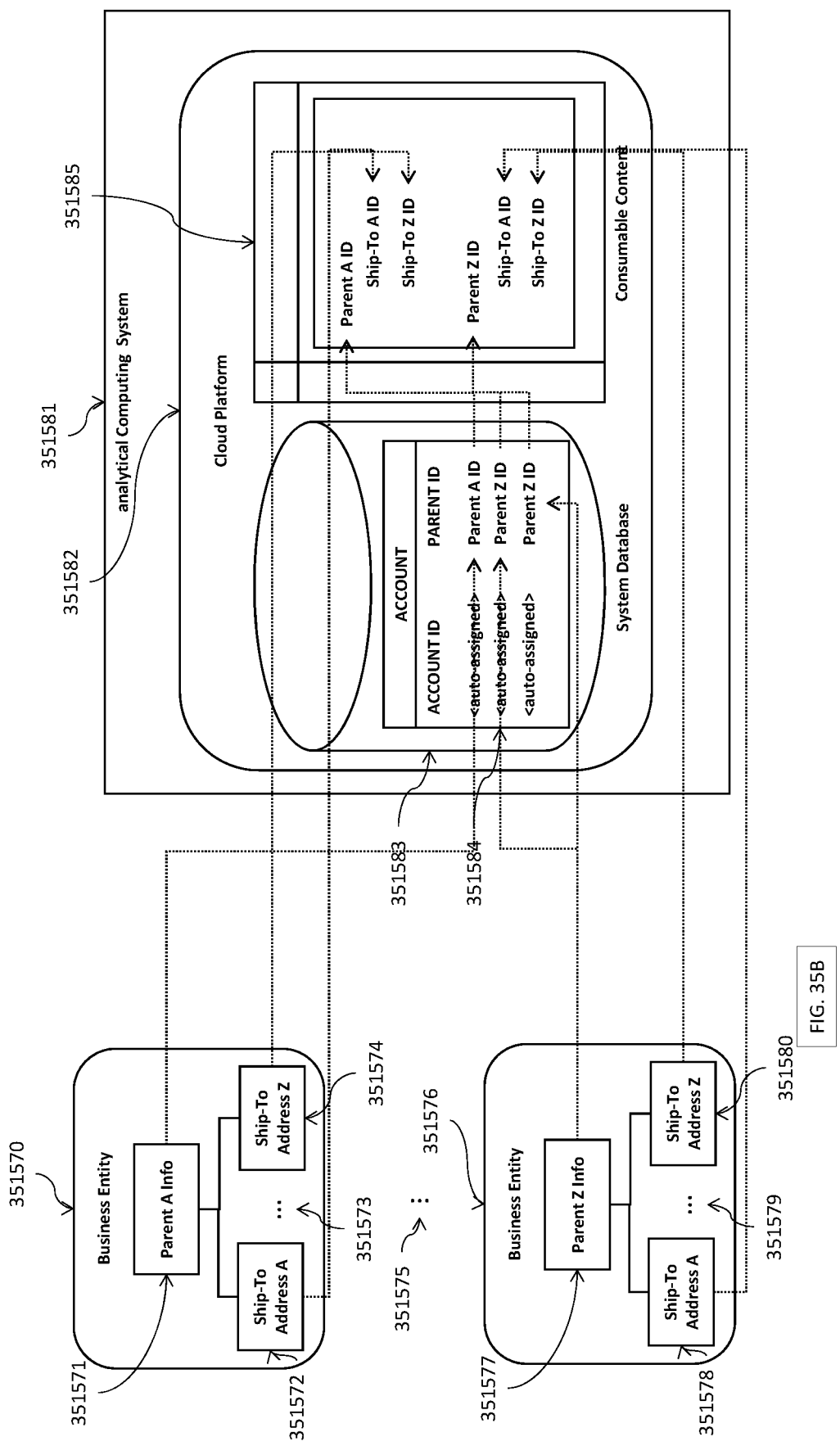
FIG. 35B illustrates a mapping of business entities to an account using an analytical computing system in an embodiment.

In FIG. 35B is an embodiment of a mapping between one or more business entities 351570 and 351576 using an analytical computing system 351581 to the analytical computing system 351581 through the cloud platform 351582 used in delivering electronic information about purchased products as the products prepared for physical shipping. Business entity 351570 can include, but is not limited to, a corporation, limited liability company, sole proprietorship, non-profit company, academic institution, government agency or affiliate, private individual or group of individuals, research institute, or any other type entity using the analytical computing system 351581, wherein the business entity 351570 is described by parent business information 351571 that can have associated with it zero or one or more ship-to addresses 351572 and 351574, wherein the ellipse 351573 illustrates the potential for zero or one or more ship-to addresses, where each ship-to is a unique address to which the business entity 351570 wants products it purchases to be delivered for ultimate use within the targeted business entity. The ship-to 351572 labelled "A" and the ship-to 351574 labelled "Z" is merely illustrative as any number of ship-to addresses associated with any business entity are contemplated. A business entity 351570 or 351576 can have zero ship-to's associated with it such that it purchases one or more products to be delivered to some other business entity; regardless, each business entity can have an account with the analytical computing system 351581. As shown by element 351575, there can be zero or more business entities as depicted 351570 and 351576 using the analytical computing system 351581, but the parent information 351571 labelled "A" and the parent information 351577 labelled "Z" illustrates up to 26 business entities 351570 and 351576 with their respective parent information 351571 and 351577, but any other number is contemplated as well. Similarly, the business entity 351576 can be described by parent business information 351577 that can have associated with it zero or one or more ship-to addresses 351578 and 351580, with an wherein the ellipse 351579 to illustrates the potential for zero or one or more ship-to addresses, where each ship-to is a unique address to which the business entity 351576 wants products it purchases to be delivered for use within the targeted business entity. The ship-to 351578 labelled "A" and the ship-to 351580 labelled "Z" represents 26 ship-to's associated with any business entity, but any other number is contemplated as well. 351581 is the analytical computing system with its associated computing platform 351582 and its system database 351583 and consumable content 351585 wherein the system database 351583 has stored with it in part a collection of data 351584 being account information of business entities using the analytical computing system 351581 having an auto-generated unique identifier from cloud platform 351581 for tracking a business entity's use of the analytical computing system 351581 along with the account's identifier being associated with the unique identifier of the business entity in this example of an embodiment being either Parent A ID for business entity 351570 or Parent Z ID for business entity 351576, while also being depicted that a business entity could have more than one account on the analytical computing system 351581 since Parent Z ID is repeated; and consumable content 351585 having stored with it a collection of purchased consumable content being the general and lot-specific content for a purchased product as shipped to a business entity, Parent A ID being the business entity 351570 and Parent Z ID being the business entity 351576, to particular ship-to addresses of the associated business entity 351570 and 351576, where the ship-to addresses are unique within a business entity 351570 and 351576, but not necessarily unique between the two business entities, which is to say, two different business entities can share a common ship-to address, such that the cloud platform 351581 may transfer consumable content to each account on the analytical computing system that can desire to use a purchased consumable available to it as determined through the PARENT ID mechanism of ACCOUNT 351584 mapped to the associated ship-to's as defined in consumable content 351585.

Figure 35C:
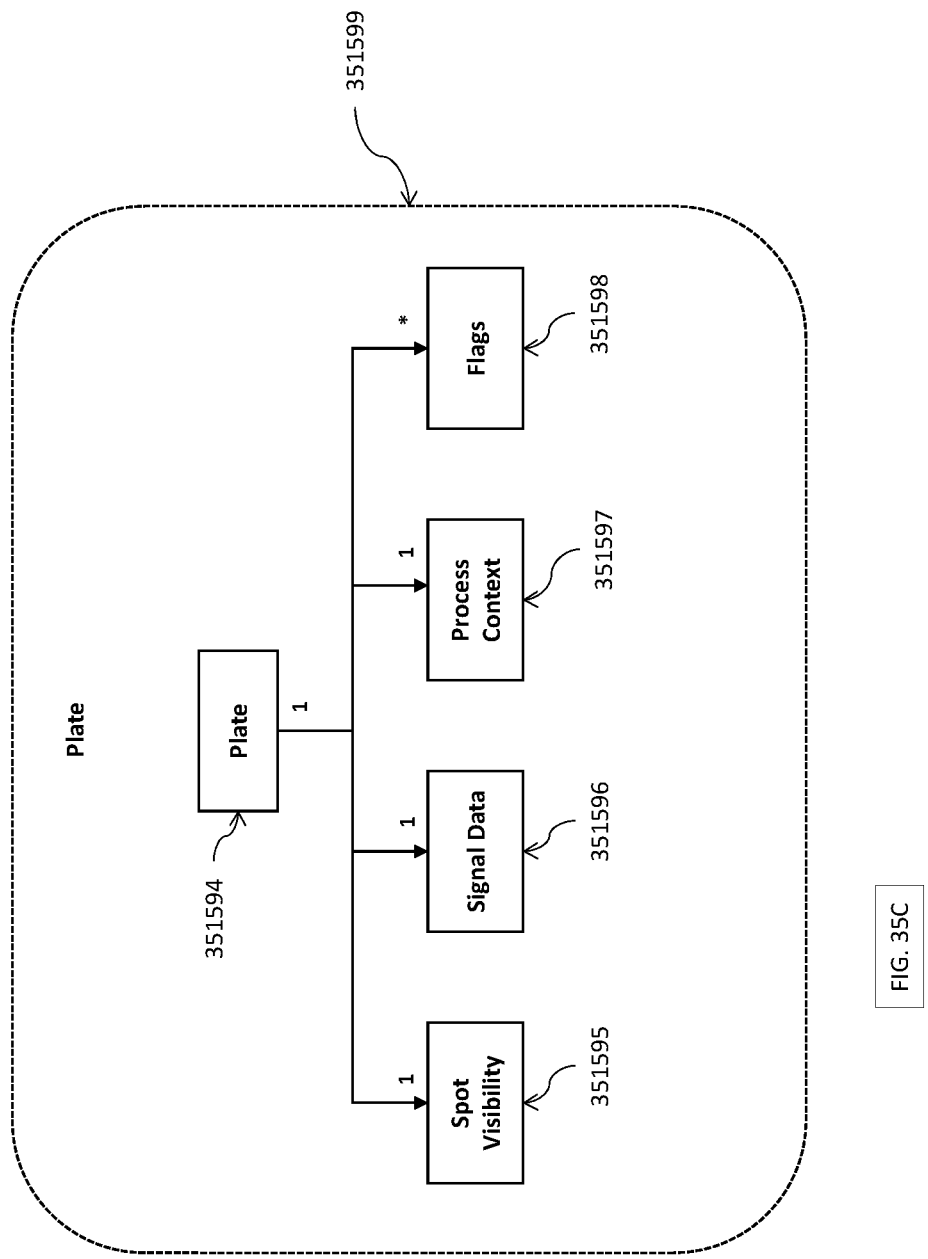
FIG. 35C illustrates a logical design of team data relating to plate data in an embodiment.

In FIG. 35C is an embodiment of a logical design for data representing plate data generated by a user for a team using instrumentation in conjunction with the analytical computing system with the data entities 351599 logically organized have a data entity 351594 representing a physical plate processed and/or analyzed by instrumentation where each plate has an association with a data entity 351595 representing a definition of how many measurements of the possible measurements this plate will provide for each tested sample; an association with a data entity 351596 representing the collected data produced from the plate; an association with a data entity 351597 representing the configuration of the instrumentation used to produce the collected data; and an association with a data entity 351598 representing any abnormal events that might have occurred on the instrumentation in the process of producing the collected data 351596 from the plate 351594. Although this embodiment describes plate-reader operations and/or applications, the methods described herein can be applied in the alternative to the logical design of other experiments and tests in the alternative.

Figure 35D:
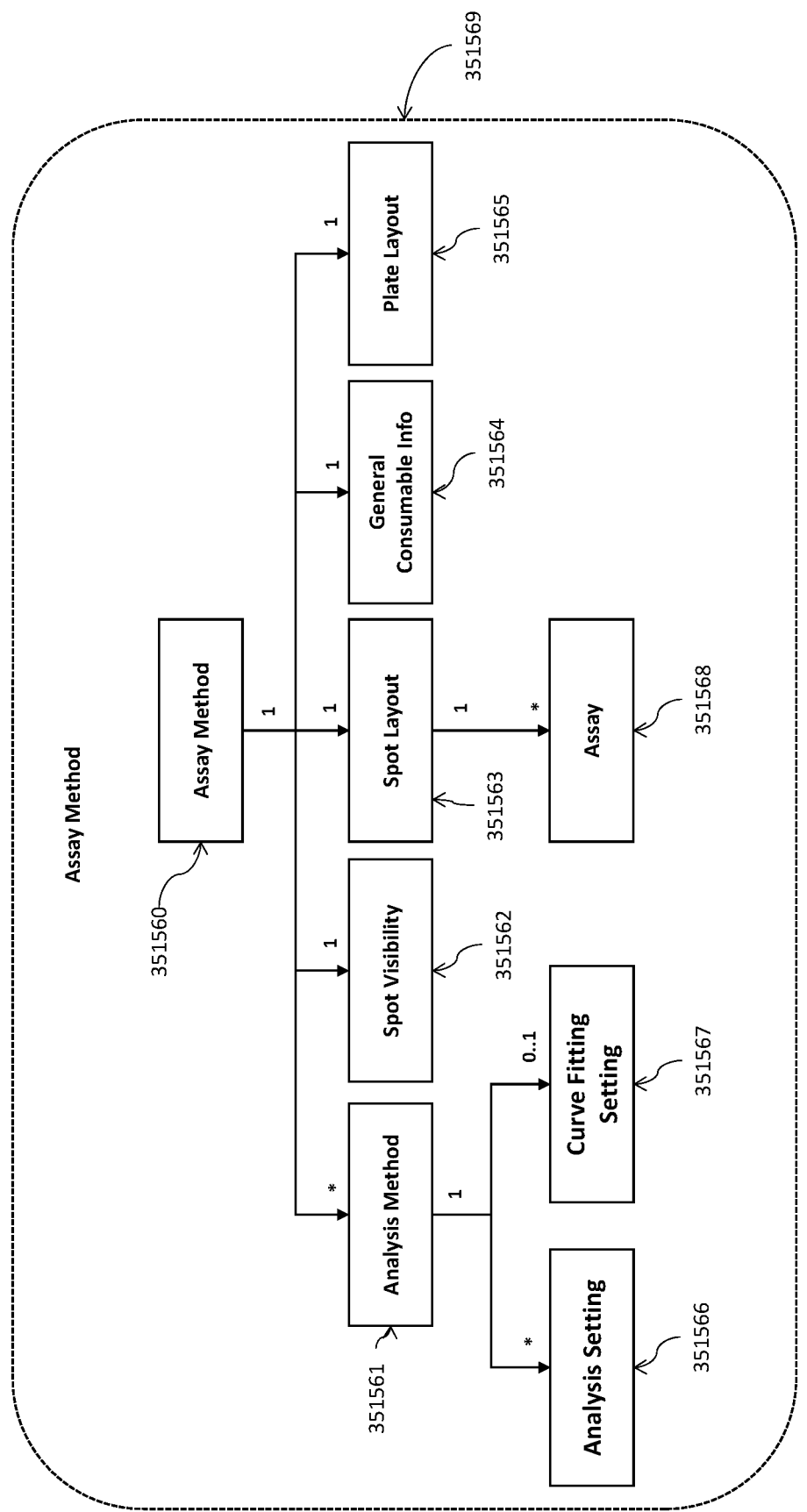
FIG. 35D illustrates a logical design of team data relating to assay method data in an embodiment.

In FIG. 35D is an embodiment of a logical design for data representing methods for performing assays in the analytical computing system with the data entities 351569 logically organized having a data entity 351560 representing a named assay method to be performed using consumables and instrumentation where each assay method has an association with a data entity 351561 representing a named method by which data collected from instrumentation is post-analyzed to provide assay context to the collected data in association with a data entity 351566 representing the configuration of settings relevant to a prescribed analysis as well as an optional association with a data entity 351567 representing the configuration of settings relevant to a prescribed analysis leveraging a curve fitting technique; an association with a data entity 351562 representing a definition of how many measurements of the possible measurements this plate will provide for each tested sample; an association with a data entity 351563 representing a definition of the available measurements each plate will provide for each tested sample in association with a data entity 351568 representing the specific assay to be measured; an association with a data entity 351564 representing general information about a consumable to be used with the assay method; and an association with a data entity 351565 representing a definition of the layout of various types of samples to be dispensed on a plate where the types of samples are calibrators, controls, blanks, and samples (also referred to as unknowns or samples under test), such that, the collection of these data entities provides the assay-specific context to help a user determine what the measured data collected from instrumentation means about the samples they are testing. Although this embodiment describes methods for performing assays and/or plate-based tests, other experiments and tests are contemplated as well.

Figure 35E:
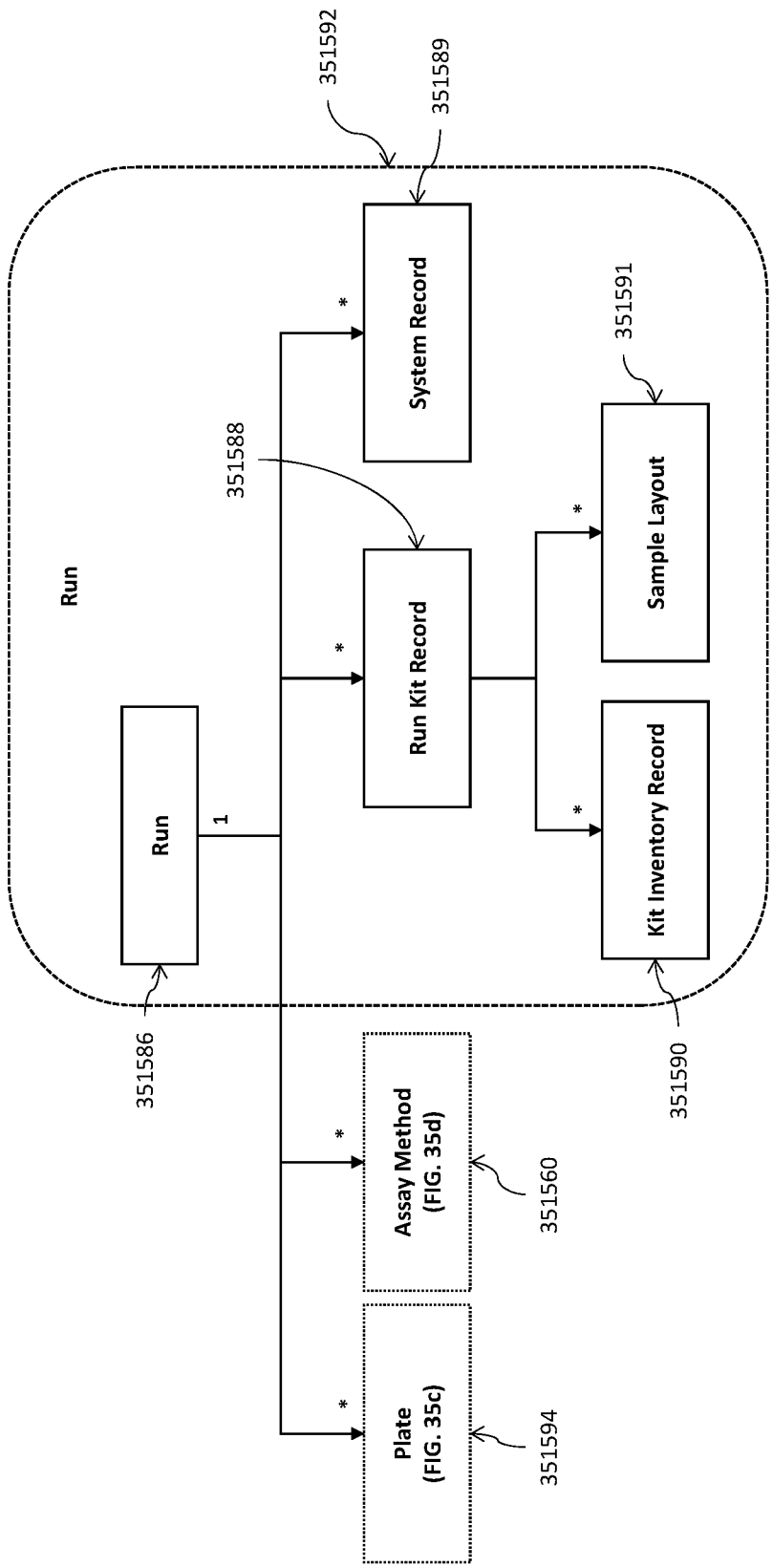
FIG. 35E illustrates a logical design of team data relating to run data in an embodiment.

In FIG. 35E is an embodiment of a logical design for data representing a collection of plates organized to be processed together or independently, either way a unit of schedulable work referred to as a run, with the data entities 351592 logically organized having a data entity 351586 representing a run to be processed using instrumentation with the run having an association with a data entity 351594 representing a physical plate processed by instrumentation; an association with a data entity 351560 representing each assay method used with each corresponding plate for the run; an association with a data entity 351588 representing a run record; and an association with a data entity 351589 representing a system record. The data entity 351588 has associations with a data entity 351590 representing a kit inventory record and with a data entity 351591 representing a sample layout. Although this embodiment describes plate-based operations and/or applications, the methods described herein can be applied in the alternative to the review of other experiments and tests in the alternative.

Figure 35F:
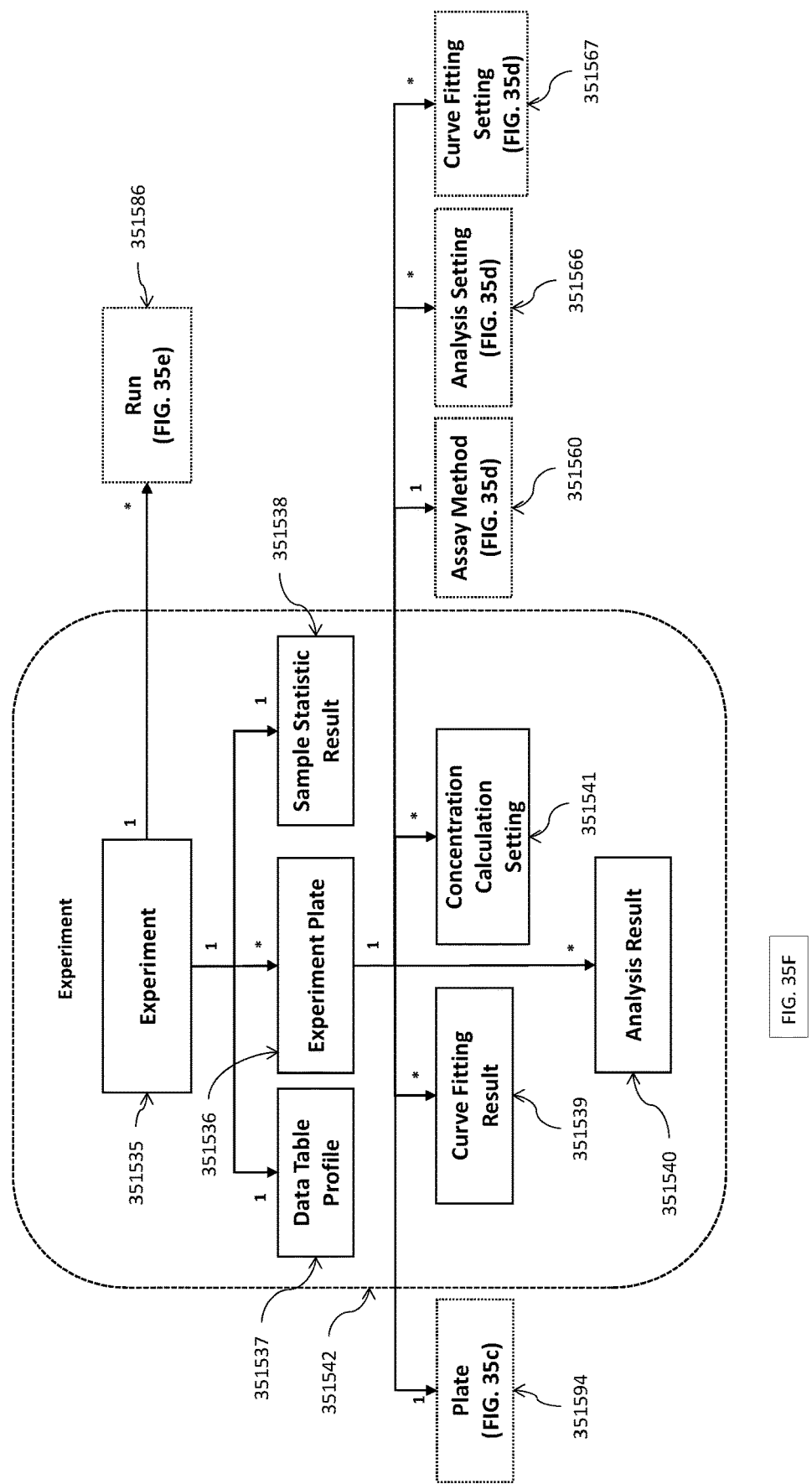
FIG. 35F illustrates a logical design of team data relating to experiment data in an embodiment.

In FIG. 35F is an embodiment of a logical design for data representing the definition of a collection of sample(s) to be measured, assay method(s) to be used to prepare the samples to be measured on plates, and analysis results determined from the measured data using analysis algorithm(s) defined in association with an assay method and/or its constituent assays, all referred to as an experiment, with data entities 351542 logically organized having 351535 a data entity representing an experiment to be processed using instrumentation with the experiment having an association with a data entity 351536 representing a plate processed in the context of an experiment where one or more of these processed plates are associated with a run 351586 and associations with data entities 351539 and 351541 used to post-analyze the measured data from a plate using assay method setup to determine results 351540; an association with a data entity 351537 representing a specification of the structure of data table to be presented for the measured data from plates; and an association with a data entity 351538 representing a collection of sample statistics determined from the measured and analyzed data. Although this embodiment describes methods for performing assays and/or plate-based experiments, other experiments and tests are contemplated as well.

Figure 36A:
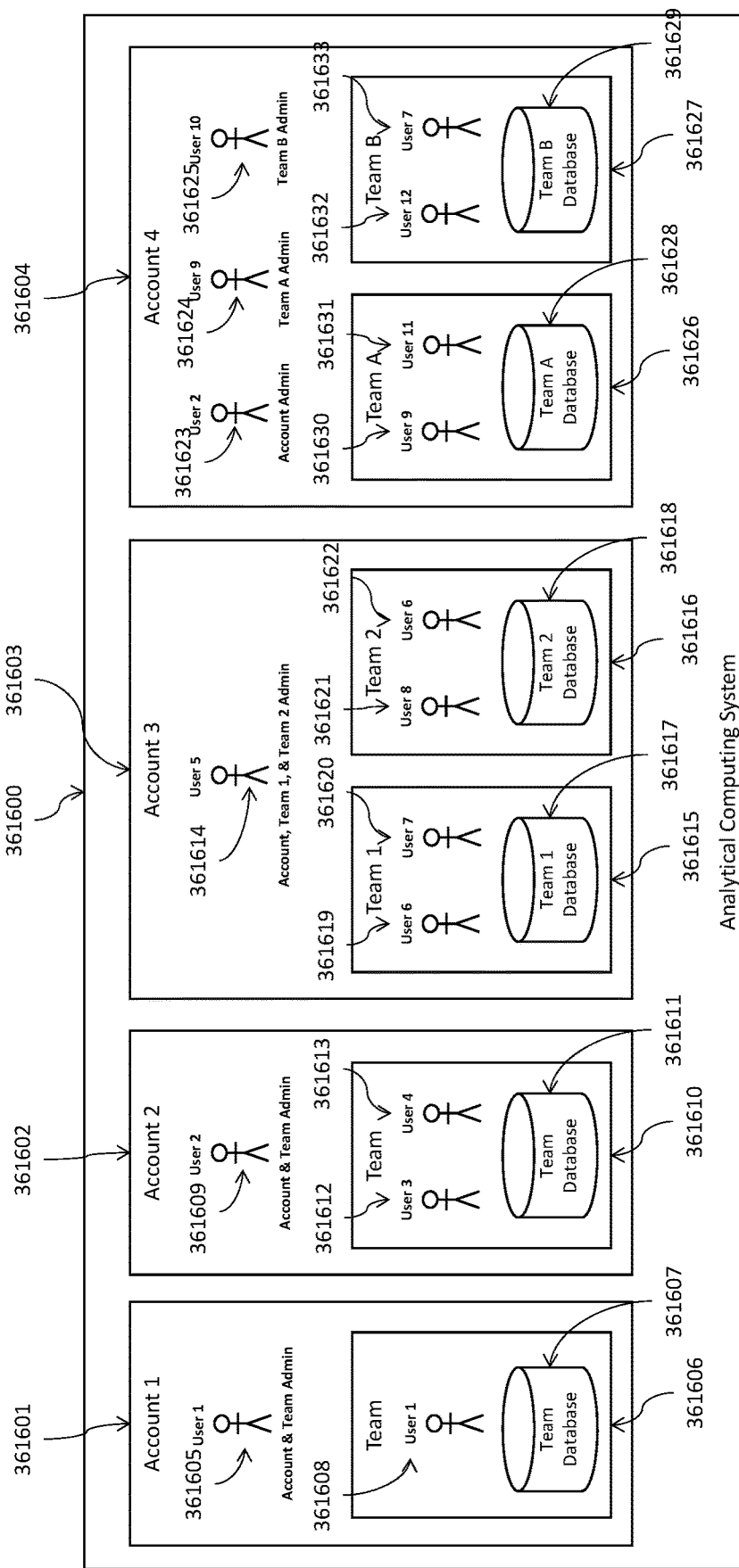
FIG. 36A illustrates an exemplary structure of accounts for users of an analytical computing system in an embodiment.

In FIG. 36A is an embodiment of an example of account structure for users of analytical computing system 361600, but this example is not intended to limit the account structure in any way since the analytical computing system 361600 can support an infinite number of accounts, an infinite number of teams in an account, and an infinite number of administrators and/or other users assigned to accounts and/or teams. In the example for this embodiment there are shown four accounts prepared on analytical computing system 361600 as represented by Account 1 361601, Account 2 361602, Account 3 361603, and Account 4 361604, these account names used to aid in the example. Each account has associated with it one or more teams where, Account 1 361601 has one team named Team with a team database 361607 dedicated to that team; Account 2 361602 has one team named Team to illustrate team names are only unique within an account, also with its dedicated team database 361611; Account 3 361603 has two teams named Team 1 361615 with its dedicated team database 361617 and Team 2 361616 with its own dedicated team database 361618; and Account 4 361604 has two teams named Team A 361626 with its dedicated team database 361628 and Team B 361627 with its own dedicated team database 361629. The users in the various accounts and teams are uniquely named as well to illustrate users can be uniquely named for easy end-user identification with User 1 361605 and 361608, User 2 361609 and 361623, User 3 361612, User 4 361613, User 5 361614, User 6 361619 and 361622, User 7 361620 and 361633, User 8 361621, User 9 361624 and 361630, User 10 361625, User 11 361631, and User 12 361632, but in the preferred embodiment the username would be a fully expressed unique email address and/or username of a user, simplified for this example. Additionally User 1 361605 illustrates a user could be an account admin, a team admin, and/or a team member; User 2 361609 illustrates a user could only be an account admin and a team admin; User 2 361623 illustrates a user could only be an account admin and also illustrates a user could be an admin of more than one account; User 5 361614 illustrates a user could be a team admin for more than one team; User 6 361619 and 361622 illustrates a user could be a team member of more than one team in an account; User 7 361620 and 361633 illustrates a user may be a team member of more than one team in more than one account; User 9 361624 illustrates a user could be a team admin and a team member (e.g., shown 361630); User 10 361625 illustrates a user could only be a team admin; User 3 361612, User 4 361613, User 6 361619, User 7 361620 and 361633, User 8 361621, User 11 361631, and User 12 361632 illustrates users could only be assigned as a team member with no administrative permissions; and not explicitly illustrated but should be obvious is there are no constraints placed by the system on how a particular user is assigned to an account and teams associated with an account, since user assigned is fully the responsibility of the person or people managing an account and team(s) associated with an account. Additionally the analytical computing system 361600 in a preferred embodiment would provide a role-based permission mechanism beyond account administrator and team administrator to help control access to various system functions of the analytical computing system 361600 for various users on a team in an account where predefined and user-changeable user roles could be but not limited in name and/or number to lab manager, designer, associate, operator, and maintenance technician; such that, an account administrator would have permissions associated with managing an account shared by users on all teams; a team administrator would have permissions associated with managing user participation on a team; a lab manager could have permissions with greatest responsibility compared to other roles for users on a team; a designer and associate could have permissions different than each other befitting each of their normal job functions; an operator could only have permissions for normal operation of instrumentation; and a maintenance technician could only have permissions for maintenance and diagnosis of instrumentation, where a user could be assigned more than one role and given permissions aggregated across the assigned roles, hence, as an example User 1 361605 would have account permissions for Account 1 361601, team administration of Team 361606 plus whatever other permissions based on the role(s) User 1 361605 assigned themselves as the team administrator.

Figure 36B:
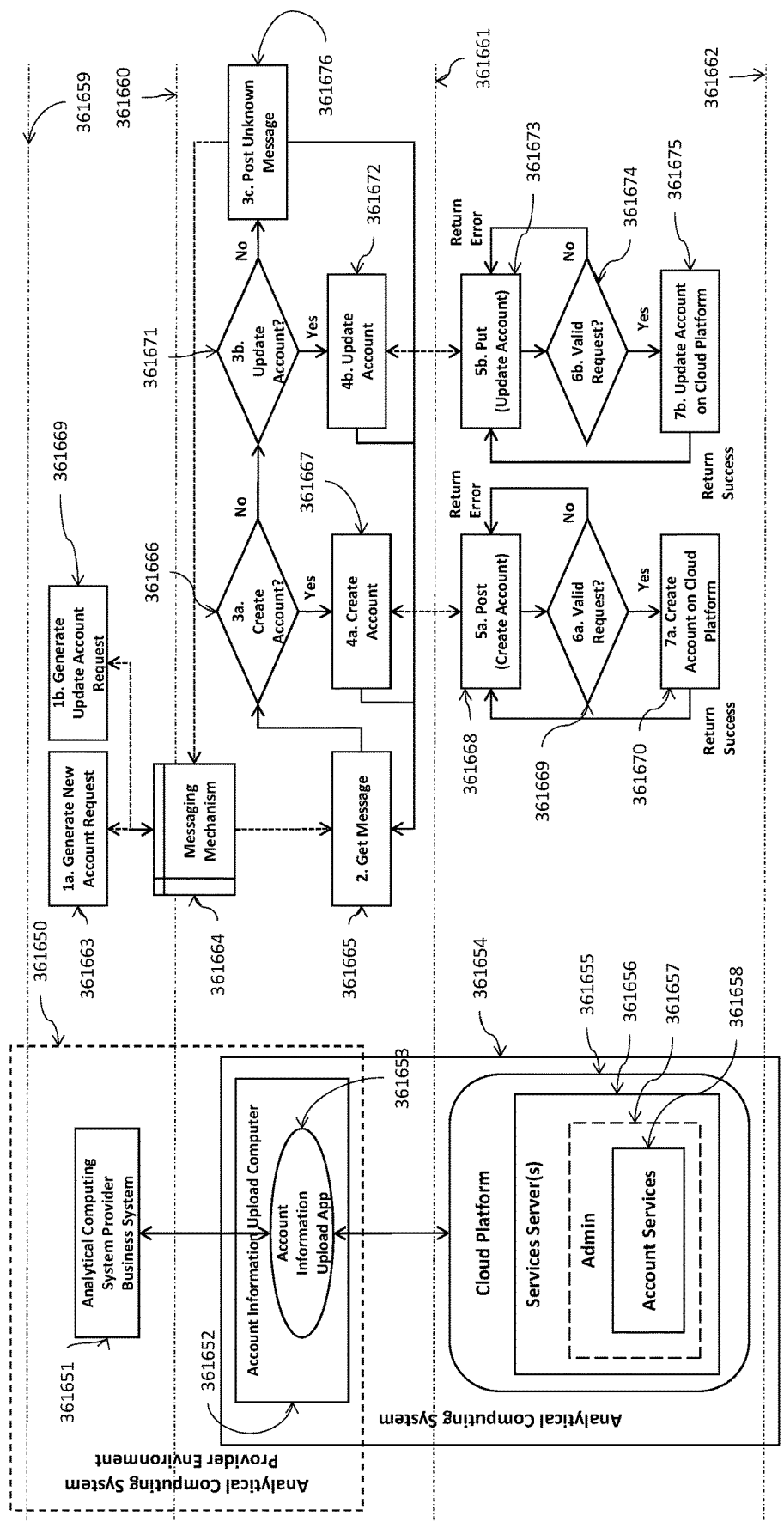
FIG. 36B illustrates the flow of the creation of an account for a user of an analytical computing system in an embodiment.

In FIG. 36B is an embodiment of the computing flow for creation and update of an account on the analytical computing system 361654. The computing flow of the account information upload app 361653 may be managed, for example, by a MUI provided via methodical user interface control system 1102 operating, at least in part, on the account information upload computer 361652 and the analytical computing system 361654. For example, an admin module may be used to manage the interface embodiments of the computing flow. The flow is represented in a "swim lane" diagram depicting independent computing systems, analytical computing system provider business system 361651, account information upload computer 361652, and cloud platform 361655, each operating concurrently to each other with processing swim lanes for analytical computing system provider business system 361651 depicted between lines 361659 and 361660, processing swim lanes for account information upload computer 361652 with its software application account information upload app 361653 depicted between lines 361660 and 361661, and processing swim lanes for cloud platform 361655 with its software account services 361658 depicted between lines 361661 and 361662. The processing of analytical computing system provider business system 361651 is depicted as out of scope for the analytical computing system 361654 with the dotted-line outline of analytical computing system provider environment 361650, but other embodiments are contemplated as well. Analytical computing system provider business system 361651 can cause generation of a request for a new account 361163 or an update to an existing account 361669. The interface mechanism for processing between analytical computing system provider business system 361651 and account information upload app 361653 occurs through a messaging mechanism 361664 that can be a file share, a message queue like Java Messaging Service, Microsoft Message Queue or some other queuing service, email, or some other mechanism for software applications to communicate with each other, wherein the processing 361663 can be to prepare a message with proper format and content per a prescribed interface definition with information about an account defined in the analytical computing system provider business system 361651 and post it to the messaging mechanism 361664 for ultimate processing by the account information upload app 361653. First flow to be described is account creation as initiated 361663 to generate new account request based on an event that occurs in the analytical computing system provider business system 361651 by posting a message via messaging mechanism 361664 with information including, but not limited to, the account number as managed by analytical computing system provider business system 361651, primary contact information including but not limited to name, business contact address and phone number, the email address of the first person the analytical computing system 361654 automatically contacts to initiate their setup and use of the analytical computing system 361654, the unique identifier for the account in the analytical computing system provider business system 361651, and any other information deemed necessary for an account. The message is received at step 361665 and checked for the type of message being received first for a request to create an account at step 361666 then for updating an account at step 361671 and if neither posting an error message at step 361676 to messaging mechanism 361664 and returning wait for the next message at step 361665. On receiving a create account request at step 361666, a create account request is constructed at step 361667 from the message content received from messaging mechanism 361664 to post at step 361668 using the cloud platform 361655, e.g., using services server 361656 which may include admin functionality or component 361657, wherein on receipt of the post it is verified at step 361669 to ensure the request has all relevant content and on failure returning an error response at step 361668 and on success create the account at step 361670 and store all of the account information in the create post in the system database on the cloud platform 361655 and making the primary contact identified in the create post the first account administrator for the new account emailing the primary contact with instructions of how to log into the analytical computing system 361654 returning success to the requester at step 361668, and returning at step 361667 the account information upload app 361653 to waiting for a message 361665. On receiving an update account request 361671, an update account request is constructed 361672 from the message content received from messaging mechanism 361664 to post at step 361673 using the cloud platform 361655, wherein on receipt of the post it is verified at step 361674 to ensure the request has all relevant content and on failure returning an error response at step 361673 and on success update the account at step 361675 and store all of the account information in the update post in the system database on the cloud platform 361655, returning success to the requester at step 361673, and returning at step 361672 the account information upload app 361653 to waiting for a message at step 361665.

Figure 36C:
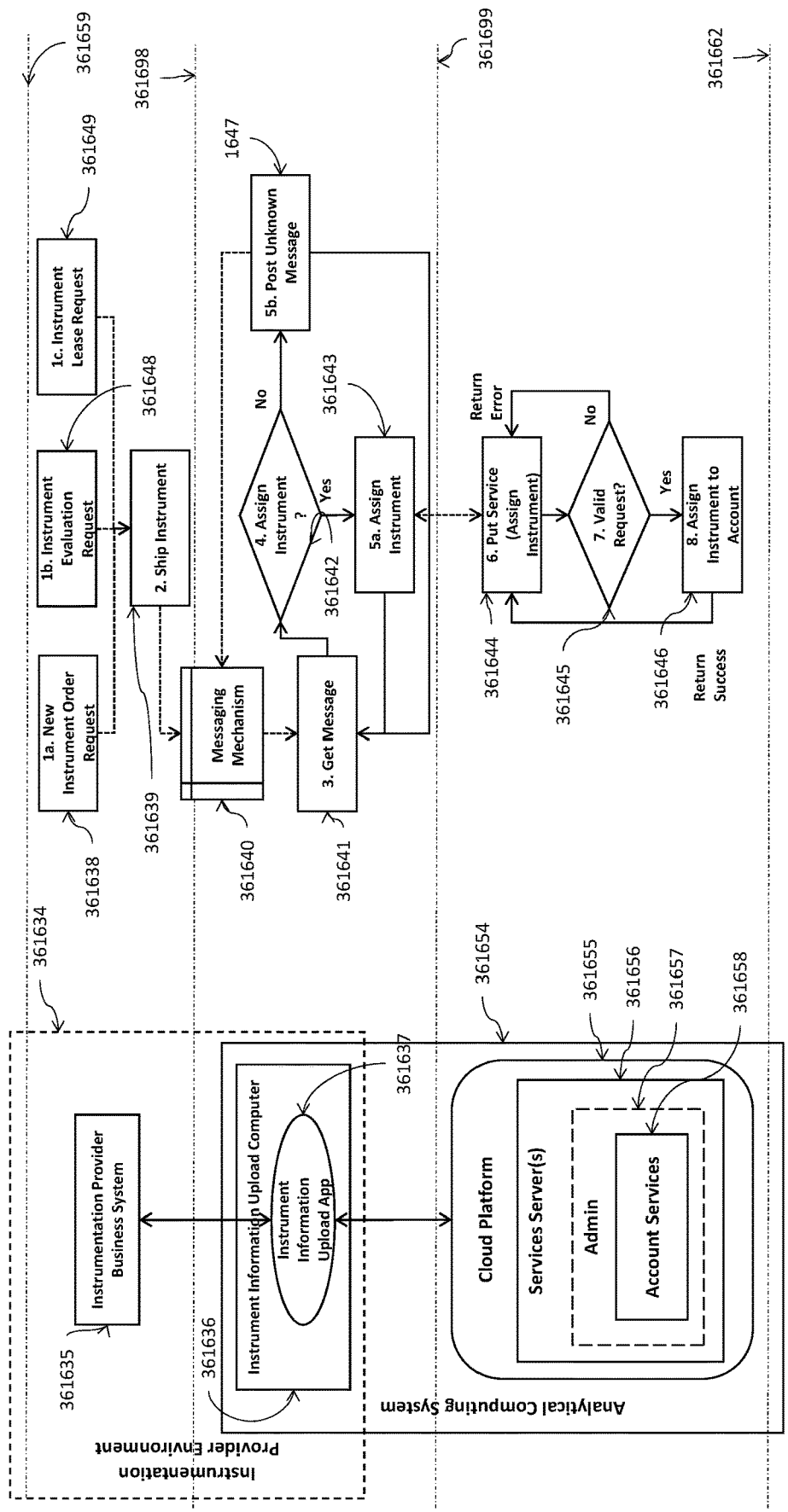
FIG. 36C illustrates the flow of an association of instruments with an account for a user of an analytical computing system in an embodiment.

In FIG. 36C is an embodiment of the computing flow for instrument association with an account on the analytical computing system 361654. The computing flow of the instrument information upload app 361637 may be managed, for example, by a MUI provided via methodical user interface control system 1102 operating, at least in part, on the instrument information upload computer 361636 and the analytical computing system 361654. For example, an admin module may be used to manage the interface features of the computing flow. The flow is represented in a "swim lane" diagram depicting independent computing systems, instrumentation provider business system 361635, instrument information upload computer 361636, and cloud platform 361655 (which may include services server 361656 providing, e.g., an admin functionality or component 361657), each operating concurrently to each other with processing swim lanes for instrumentation provider business system 361635 depicted between lines 361659 and 361698, processing swim lanes for instrument information upload computer 361636 with its software application instrument information upload app 361637 depicted between lines 361698 and 361699, and processing swim lanes for cloud platform 361655 with its software account services 361658 depicted between lines 361699 and 361662. The processing of instrumentation provider business system 361635 is depicted as out of scope for the analytical computing system 361654 with the dotted-line outline of instrumentation system provider environment 361634, but other embodiments are contemplated as well. Instrumentation provider business system 361635 results in a generation of a request for a new instrument purchase at step 361638, a request for an instrument evaluation at step 361648, or a request for an instrument lease 361649, wherein, each request results in a ship of the instrument at step 361639. The interface mechanism for processing between instrumentation provider business system 361635 and instrument information upload app 361637 occurs through a messaging mechanism 361640 that can be a file share, a message queue like Java Messaging Service, Microsoft Message Queue or some other queuing service, email, or some other mechanism for software applications to communicate with each other, wherein the processing at step 361638 and at step 361648 and at step 361649 can be to prepare a message with proper format and content per a prescribed interface definition with information about an instrument purchase at step 361638, evaluation at step 361648, or lease at step 361649 including the ship-to address defined in the instrumentation provider business system 361635 and post it to the messaging mechanism 361640 for ultimate processing by the instrument information upload app 361637. The resulting flow on purchase at step 361638, evaluation at step 361648, or lease at step 361649 is identical so the description can focus on new instrument purchase as initiated at step 361638 to generate new instrument purchase request based on an event that occurs in the instrumentation provider business system 361635 by posting a message via messaging mechanism 361640 with information including, but not limited to, the account number of the analytical computing system to which the instrument will be assigned as managed by instrumentation provider business system 361635, instrument serial number, the unique identifier of the parent company of the organization expecting the instrument(s), and the unique identifier of the ship-to location to which the instrument will be shipped as managed by the instrumentation business system 361635, the service plan details associated with duration of the plan and the available number of seats for users to use the analytical computing system 361654, and any other information deemed necessary for an account on the analytical computing system 361654. The message is received at step 361641 checking the message at step 361642 to confirm it is assigning an instrument to an account and if the message is assigning an instrument to an account then processing continues at step 361643 but if not processing continues at step 361647 to post an error message to messaging mechanism 361640 and returning to get messages at step 361641. On receipt of a correct instrument assignment request 361642, processing continues at step 361643 to construct from the message content received from messaging mechanism 361640 a request and put at step 361644 using the cloud platform 361655, wherein on receipt of the put it is verified at step 361645 to ensure the request has all relevant content and on failure returning an error response at step 361644 and on success assigning the instrument to the account at step 361646 and storing all of the instrument information in the put request in the system database for the account on the cloud platform 361655 returning success to the requester at step 361644, and returning at step 361643 the instrument information upload app 361637 to waiting for a message at step 361641.

Figure 36D:
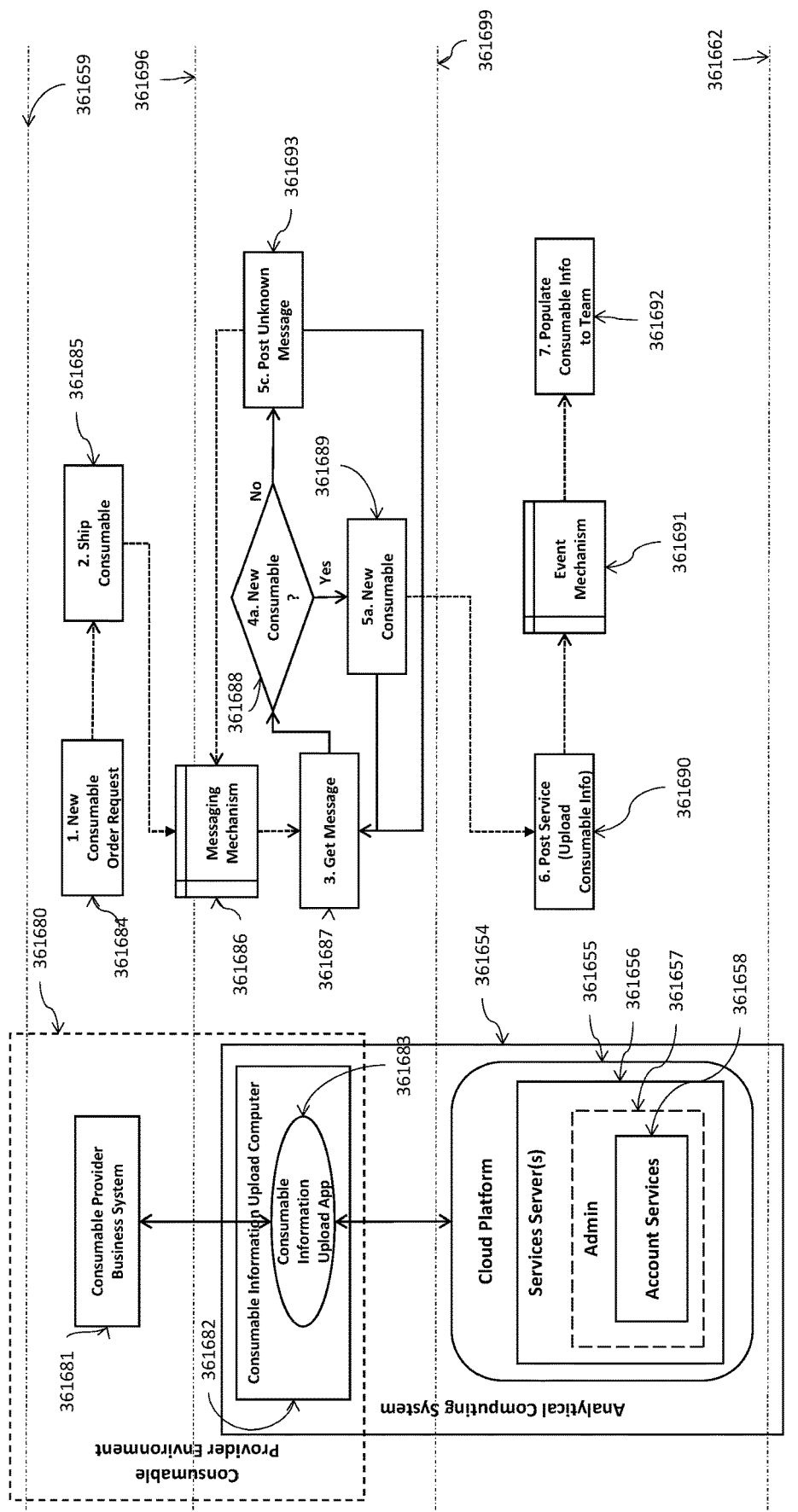
FIG. 36D illustrates the flow of associating consumables with an account for a user of an analytical computing system in an embodiment.

In FIG. 36D is an embodiment of the computing flow for consumable association with an account on the analytical computing system 361654. The computing flow of the consumable information upload app 361683 may be managed, for example, by a MUI provided via methodical user interface control system 1102 operating, at least in part, on the consumable information upload computer 361682 and the analytical computing system 361654. For example, an admin module may be used to manage the interface features of the computing flow. The flow is represented in a "swim lane" diagram depicting independent computing systems, consumable provider business system 361681, consumable information upload computer 361682, and cloud platform 361655, each operating concurrently to each other with processing swim lanes for consumable provider business system 361681 depicted between lines 361659 and 361696, processing swim lanes for consumable information upload computer 361682 with its software application consumable information upload app 361683 depicted between lines 361696 and 361699, and processing swim lanes for cloud platform 361655 (e.g., services server 361656 which may include admin functionality or component 361657) with its software account services 361658 depicted between lines 361699 and 361662. The processing of consumable provider business system 361681 is depicted as out of scope for the analytical computing system 361654 with the dotted-line outline of consumable system provider environment 361680, but other embodiments are contemplated as well. Analytical computing system 361654 results in a generation of a request for a new consumable purchase at step 361684 with each request resulting in a ship of a consumable at step 361685. The interface mechanism for processing between consumable provider business system 361681 and consumable information upload app 361683 occurs through a messaging mechanism 361686 that can be a file share, a message queue like Java Messaging Service, Microsoft Message Queue or some other queuing service, email, or some other mechanism for software applications to communicate with each other, wherein the processing at step 361685 can be to prepare a message with proper format and content per a prescribed interface definition with information about a consumable purchase as well as lot-specific content associated with the consumable(s) being purchased, including the unique identifier of the parent company expecting the consumable(s), and the unique identifier of the ship-to address defined in the consumable provider business system 361681, and post it to the messaging mechanism 361686 for ultimate processing by the consumable information upload app 361683. The resulting flow on purchase at step 361684 generates a new consumable purchase request based on an event that occurs in the consumable provider business system 361681 by posting a message via messaging mechanism 361686 with information including but not limited to the barcodes of constituent components associated with a consumable, general and lot-specific content associated with the consumable, the unique identifier of the parent company, and the unique identifier of the ship-to location to which the consumable(s) will be shipped as managed by the consumable business system 361681 and any other information deemed necessary for an account on the analytical computing system 361654. The message is received at step 361687 checking the message at step 361688 to confirm it is assigning a consumable to a site account and if the message is assigning a consumable to a site account then processing continues at step 361689 but if not processing continues at step 361693 to post an error message to messaging mechanism at step 361686 and returning to get messages at step 361687. On receipt of a correct consumable purchase request at step 361688, processing continues at step 361689 to construct from the message content received from messaging mechanism 361686 a request and post it at step 361690 using the cloud platform 361655, wherein on receipt of the post at step 361690 it is processed to store the new consumable information to consumable content on the cloud platform organizing the content on consumable content by parent account provided with the new consumable information for ultimate dissemination to instrument(s) and account(s) associated with the ship-to associated with the consumable, posting an event to trigger the ultimate dissemination to account(s) associated with the ship-to of the consumable returning success to the requester at step 361690, and returning at step 361689 the consumable information upload app 361683 to waiting for a message at step 361687. At step 361692 processing trigged by an event being delivered at step 361691 that initiates the deployment of all new consumable information to one or more accounts associated with ship-to's of the new consumables via the unique identifier of the parent company expecting the consumable(s).

Figure 37:
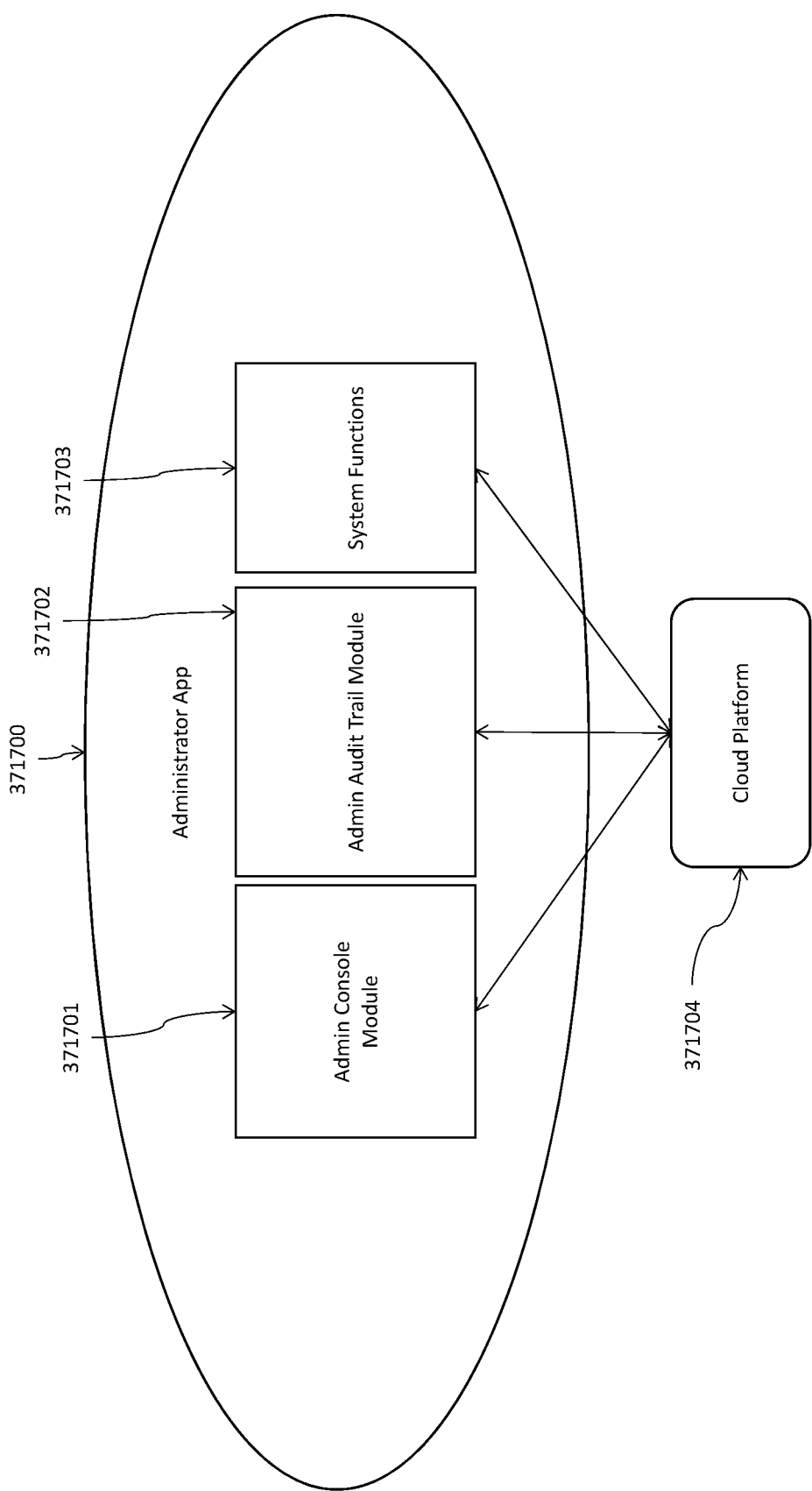
FIG. 37 illustrates the modules in an administrator software application in an embodiment.

In FIG. 37 is an embodiment of software modules in administrator app 371700 forming the primary user interface experience for administrative work typically but not limited to using data configured and generated through the use of services provided by cloud platform 371704 to create, read, update, and/or delete any and all data relevant to each module's processing, as well as any other services needed for each module's processing, wherein admin console module 371701 can be the active module by default when the administrator app 371700 starts. Admin audit trail module 371702 provides visibility into the actions various account admins and/or team admins perform in the administrator app 371700. Collection of system functions 371703 provides typical utilities in support of use of a system such as but not limited to logging off, viewing help information, viewing user guide, viewing legal notices and/or documents, changing user password, and/or other utilities. The collection of system function 371703 may be provided as a separate MUI module and/or a series of software protocols that operate alongside the other discussed MUI modules. As discussed above, the administrator app 371700 may employ a MUI supplied by a methodical user interface control system 1102 for interface purposes. The admin console module 371701, the admin audit trail module 371702, and the system functions 371703 may all employ a MUI for user interface purposes. A user will log into the administrator app 371700 through system functions 371703 using services provided by cloud platform 371704. If authentication of an administrator by a login service on cloud platform 371704 returns an administrator has more than one account, an administrator could be required to select the default account, but if an administrator does not belong to more than one account and/or team, the service on the cloud platform 371704 can auto-assign an administrator to the sole account for that administrator. On completing login, the user lands at start of the admin console module 371701 and begins using the administrator app 371700 as they need.

Figure 38A:
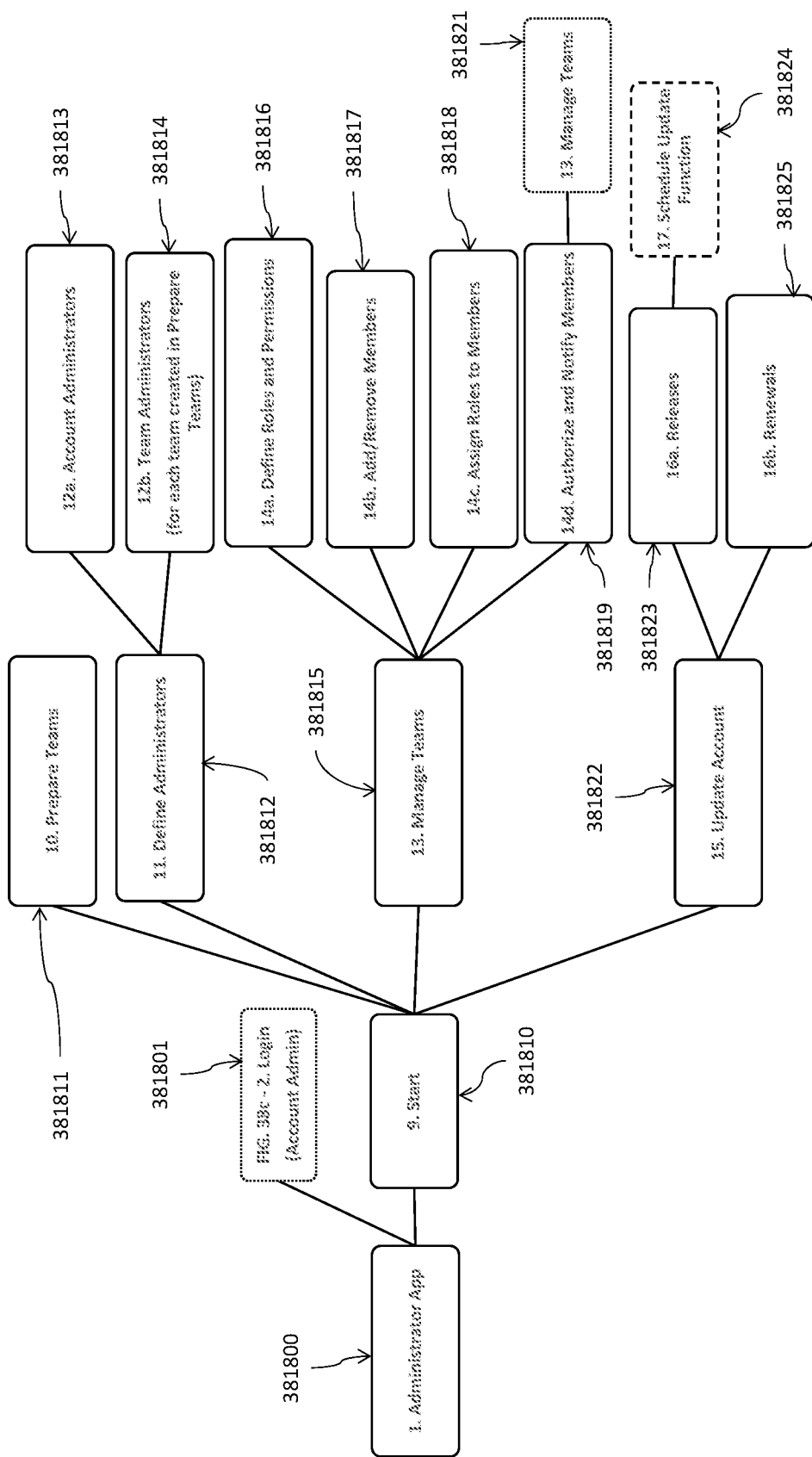
FIG. 38A illustrates the flow for an admin console module in an administrator app for an account administrator in an embodiment.

In FIG. 38A is an embodiment of a user experience flow through admin console module for an account admin whose responsibilities are to administer the overall account for an analytical computing system, as well as, administering all teams associated with an account using administrator app at 381800 running on an admin's computer with each step through a user interface numbered sequentially 1 through 'n' to represent the stepwise flow from begin (1) to end ('n') for an admin as depicted in administrator app at 381800 being labelled "1." The user experience flow of FIG. 38A may be managed by a MUI as discussed herein. FIGS. 38D-38H provide screenshots illustrating embodiments of the experience flow illustrated in FIG. 38A. At 381801 an admin is requested to login and in this case the authentication service on the cloud platform recognizes the user logging in is identified as an account administrator per user configuration allowing the user to log in and if not recognized as an account administrator denied access with an error message informing the user. At 381810 the user interface auto-transitions to presenting a first menu of options including prepare teams at 381811, define administrators at 381812, manage teams at 381815, and/or update account at 381822. On selecting prepare teams at 381811 user interface presents an execution menu including information on the number of seats available for an account, the maximum number of teams an account may have, and the current set of named teams, if any. A field to enter a new team name is provided with an execution function that will initiate the creation of new teams. The user may type in a unique team name and presses enter. The team name, if unique, is added to the set of teams ready to be created for the account on initiating execution function, with the execution function invoking service(s) on the cloud platform to create each new named team for an account in the system database and create a new team database on a database server using database service, as well as updating the new team database(s) through a lambda service invoked on the cloud platform to populate consumable information from consumable content for potential use by each new team. Subsequent to execution, the user interface transitions back to start at 381810 to display the first menu again. Additionally, at 381811 an account admin can change the name of a previously created team.

On selecting define administrators at 381812, transitions the user interface to present the set of account admins, as well as admins for each team created in prepare at 381811, a second menu of options is presented including account administrators at 318813 and team administrators at 381814. The first menu may be relocated to an historical portion of the MUI. A user can optionally navigate to an execution menu under account administrators at 381813 to add users named by unique username to the set of account admins or to remove a previously defined account admin for which on completion of the add or remove invokes a service on the cloud platform to update the account admin information in system database and notify the added account admin via email and/or other electronic communication mechanism. The user may also optionally navigate to an execution menu under team administrators at 381814 for one or more teams to add users named by unique username to the set of the associated team's admins or remove previously defined team admins for which on completion of the add or remove invokes a service on the cloud platform to update the team admin information in system database and notify the added team admin(s) via email and/or other electronic communication mechanism, where by default each account admin would be assigned as a team admin to each team to simplify team admin setup.

On selecting manage teams at 381815 from the first menu, the system relocates the first menu to a historical portion and presents a list of the one or more teams being administered as a second menu (not shown). After selecting a team from the second menu, a third menu of items including define roles and permissions 361816, add/remove members at 381817, assign roles to members at 381818, and/or authorize and notify members at 381819. On selecting define roles and permissions at 381816 a user is provided an execution menu presenting options to configure each role in the system on a module-by-module basis based on all of the modules available in the analytical computing system is presented. A user may also change one or more of the default roles names to whatever they want. On selecting add/remove members at 381817 a user is provided an execution menu presenting the collection of usernames identified as members of the team, as well as the open seats available for new members, and enabling an account administrator to enter new member usernames to add members if there are open seats and/or remove existing members using services on the cloud platform to update account team configuration on each request updating the open seats available. On selecting assign roles to members at 381818 a user is provided an execution menu presenting the collection of members with the ability to turn on or off each role available for the account member by member, using services on the cloud platform to update account team configuration on each request. On selecting authorize and notify members at 381819 a user is provided an execution menu presenting a synopsis of all members and their assigned roles with an authorize and notify option to notify new members of being added to a team if any and/or informing existing members of changes to their assigned role(s) if any. The notification may be invoked through a service request on cloud platform causing an email and/or other electronic communication mechanism to be sent to each affected user, and on completing transitioning the user interface back to manage teams at 381815, also shown at 381821.

On selecting update account at 381822 the MUI transitions the user interface to present a second menu of item to view software releases and renewals associated with the account. On selection of releases at 381823 the account administrator is presented information displaying the status of the current release as well as available new releases. On selecting to upgrade to a new software release affecting the entire account the user interface transitions to an execution menu for scheduling the software update at 381824 presenting an account admin a function to set the date and time for the update to occur. On acceptance of an admin's configuration invoking a service on the cloud to store the scheduled update in system database, the MUI transitions back to releases at 381823 and displays the scheduled date and time associated with the view of software releases, and notifies all account members via email and/or other electronic communication mechanism of the impending update and periodically notifying the account members at various configurable date/time intervals so they are fair warned of an approaching update. When the update occurs, the system locks the account from use until such time as the software and database(s) for an account have been updated per the software release. Additionally, an account admin may cancel or change the date and time of an update at any time prior to the update occurring through selecting the scheduled date and time for a software release to transition to schedule update at 381824 to either cancel or change the data. On selecting renewals at 381825 the account administrator is presented renewal status for all instrumentation associated with the account, as well as, the available number of user seats for the account.

Figure 38B:
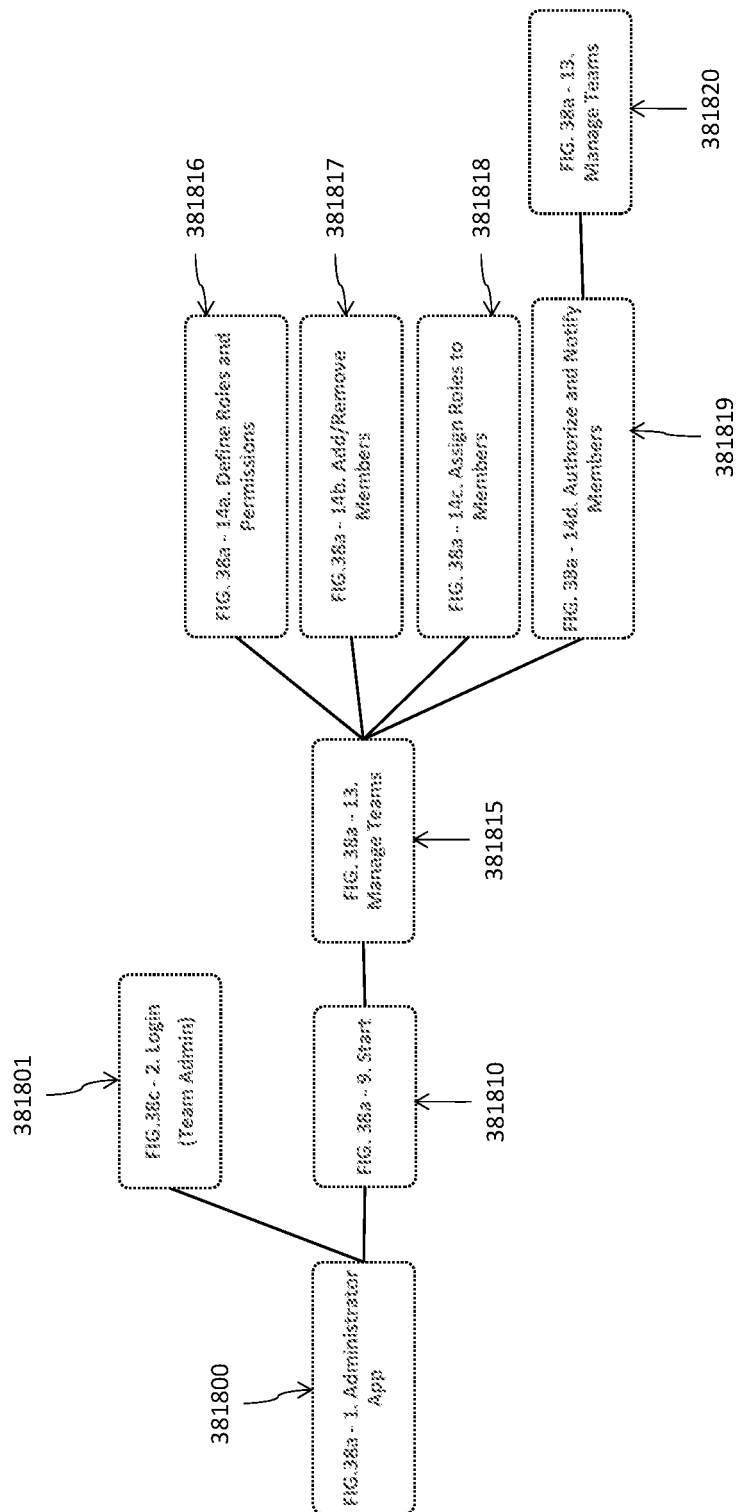
FIG. 38B illustrates the flow for an admin console module in an administrator app for a team administrator in an embodiment.

In FIG. 38B is an embodiment of a user experience flow through admin console module for a team admin whose responsibilities are to administer one or more teams associated with an account with administrator app at 381800 running on an admin's computer with each step through a user interface numbered sequentially 1 through 'n' to represent the stepwise flow from begin (1) to end ('n') for an admin as depicted in administrator app at 381800 being labelled "1." as the first step. The user experience flow of FIG. 38A may be managed by a MUI as discussed herein. Thus, as an admin works through the flow of the user interface, they may easily back track to one or more previous steps through historical portions displaying previous menus. At 381801 an admin is requested to login and in this case the authentication service on the cloud platform recognizes the user logging in is identified as a team administrator per user configuration allowing the user to log in and if not recognized as a team administrator denied access with an error message informing the user. At 381810 the user interface automatically selects manage teams at 381815 as a first menu item because the user is identified as only a team administrator that has no additional account administration permissions. The team administrator is then presented with a second menu (not shown) permitting the selection of a team. After selection of a team from the second menu, the MUI may move to the third menu, which display options for managing the team selected in the second menu, including the options for each managed team being to define roles and permissions at 381816, add/remove members at 381817, assign roles to members at 381818, and/or authorize and notify members at 381819. If only one team is managed by the administrator, the MUI may skip the second menu and jump immediately to the third menu.

On selecting define roles and permissions at 381816 the MUI transitions the user interface to an execution menu presenting options to configure each role in the system on a module-by-module basis based on all of the modules available in the analytical computing system as pre-configured in system content. On selecting add/remove members at 381817 the MUI transitions the user interface to an execution menu presenting the collection of usernames identified as members of the team, as well as, the open seats available for new members, enabling a team administrator to enter new member usernames to add members if there are open seats and/or remove existing members using services on the cloud platform to update account team configuration on each request updating the open seats available. On selecting assign roles to members at 381818 the MUI transitions the user interface to an execution menu presenting collection of members with the ability to turn on or off each role available for the account member by member, each member may have one or more roles with the corresponding permissions module-by-module, using services on the cloud platform to update account team configuration on each request. On selecting authorize and notify members at 381819 the MUI transitions the user interface to an execution menu presenting a synopsis of all members and their assigned roles with a authorize and notify option to notify new members of being added to a team if any and/or informing existing members of changes to their assigned role(s) if any.

Figure 38C:
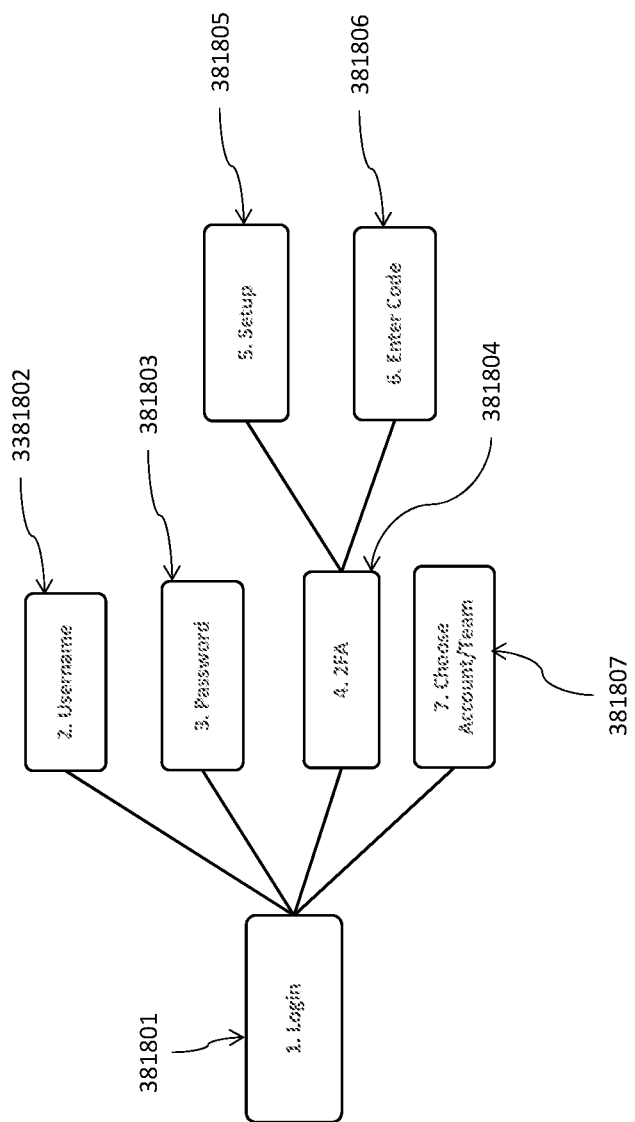
FIG. 38C illustrates the flow for a user's login process in an embodiment.

In FIG. 38C is an embodiment of a user experience flow through logging in to use any admin or user application in the analytical computing system beginning with login at 381801 with each step through the login user interface numbered sequentially 2 through 'n' to represent the stepwise flow from begin (1) to end ('n') for any user as depicted in login at 381801 being labelled "1." as the first step of login, also, as a user works through the flow of logging in they could easily back track to one or more previous steps. The user experience flow of FIG. 38C may be managed by a MUI, as discussed herein. At 381801 a user is first presented an option to enter a unique username at 381802 as either an email address, a user-provided name, or a system-provided name. On entering or selecting a username the username can be checked through a service request to the cloud platform to confirm this is a known username and on confirmation of being a known username transitioning to password at 381803 for the user to provide the secure password associated with the unique username that uniquely confirms authenticity of a user logging in, passing username and password through a service request on the cloud platform to provide authentication. On proper authentication a user is permitted to use the application they wish to use. When authentication is not possible, an error message is presented to inform the user they were not granted access. Optionally at 381804 it may be required of a user to provide two-factor authentication (2FA) credentials to further secure access to the analytical computing system because an account admin has configured this security feature on for the account they administer. If 2FA is configured on for an account, a user logging in the first time would have to perform a setup function at 381805 typically, but not limited to, a user scanning a barcode or typing a code provided in 2FA setup at 381805 into a separate 2FA application running on another computing device, mobile or otherwise, that synchronizes the user's use of an account with the separate 2FA application to provide another unique, independent credential to further confirm the user is as logged in. Completing setup at 381805 causes transition to enter code at 381806 for a user to use the separate 2FA application to produce a one-time unique code for them to enter into login for the code to be passed through a service request on the cloud platform to perform the final authentication of the user logging in, on success granted access and on failure getting an error message informing a user the access is not granted. At 381807, the user may be allowed to proceed, for example, choose account and/or team.

In further embodiments, the admin console module 371701 can be used to create, modify, and/or delete teams and/or accounts; add, remove, and modify individuals users within teams and/or accounts; and set, modify, and/or remove permissions for one or more individual users, teams, instruments, and/or accounts. Once these administrative procedures have been carried out (e.g., by one or more administrators), notifications and/or instructions can be transmitted to one or more of the users, accounts, and/or teams, for example, via electronic mail or through the cloud. In certain embodiments, users, accounts, and/or teams can receive these notifications and/or instructions through a uniquely assigned email address.

Figure 38D:
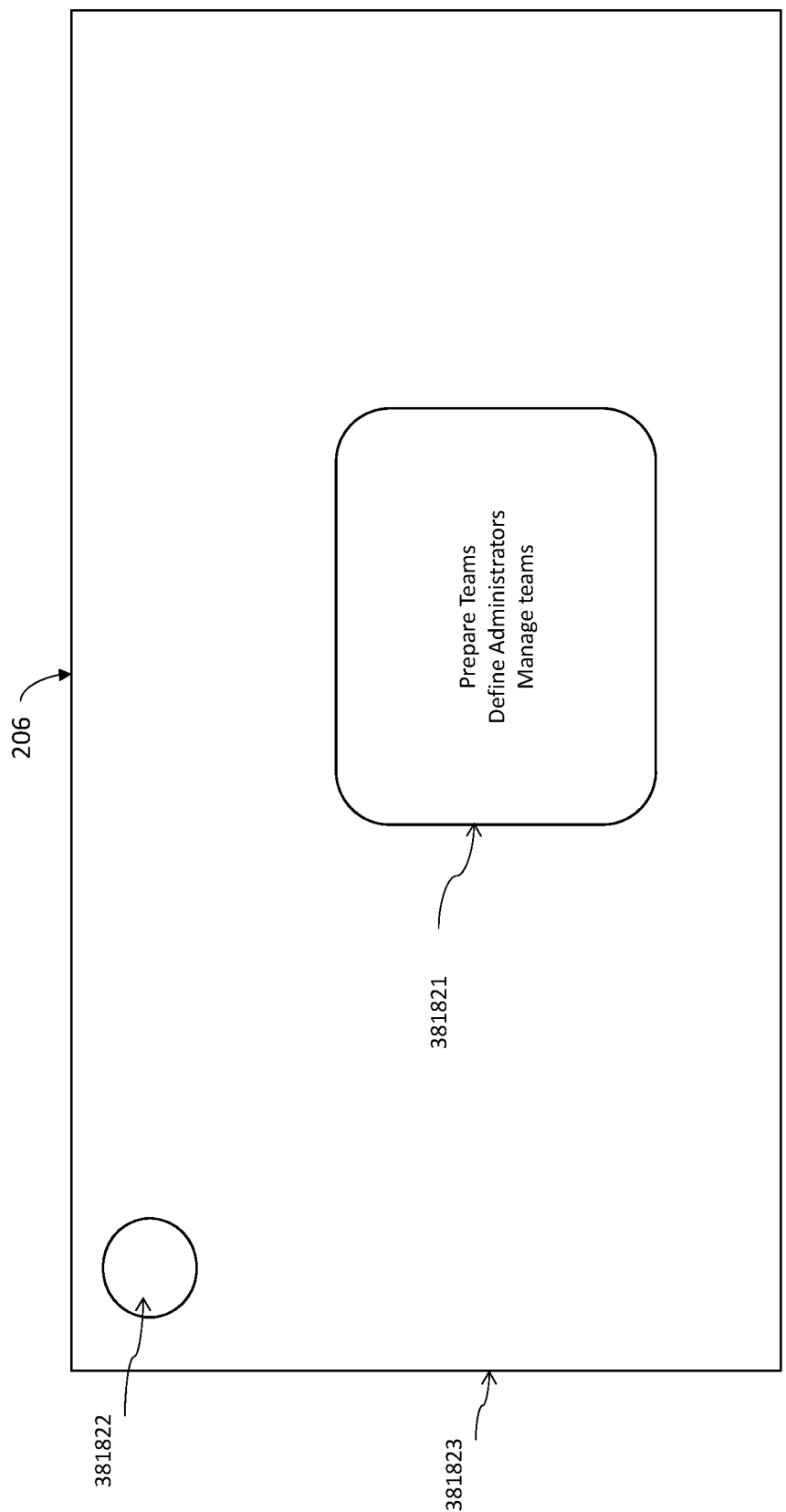
FIGS. 38D-38H provide screenshots illustrating aspects of the work-experience flow illustrated in FIG. 38A.

Referring specifically to FIG. 38D, in certain embodiments, first portion 381821 can include a first menu of user-selectable choices, including one or more of the following choices: Prepare Teams Define Administrators and Manage teams (i.e., a first set of choices). In another embodiment (not shown), first portion 381821 can include a first menu of user-selectable choices, including a Define Roles and Permissions choice; an Add/Remove Members choice; and Assign Members to Roles choice; and an Authorize and Inform Members choice, i.e., a second set of choices. Certain features and/or particular embodiments of these choices are described in additional detail in conjunction with FIGS. 38A and 38B, above.

One feature of the admin console module allows users to prepare and define teams. For example, regarding the first menu, in response to a selection of the Prepare Teams choice, the second menu of user-selectable choices includes one or more previously added teams. Previously defined teams can be viewed in this aspect and additional teams can be created and/or defined. Teams can be defined, and permissions can be assigned, based on role, experiment type, user, etc. The previously added teams may have been added by the same user, e.g., an administrator, or by other users who have access to the admin console module, e.g., with appropriate permissions.

In addition to displaying previously added teams, in response to a selection of the Prepare Teams choice, the second menu of user-selectable choices is adapted to receive one or more new teams to add among the one or more previously added team. These new members can be added, for example, by a user manually entering the information into the MUI through an input device, such as a keyboard, touchscreen, etc. Further, new teams can be added through an automated process, such as with a barcode reader, or an input file that contains a list of one or more of the new teams the user wishes to add. In one example, the team name can be preassigned.

Figure 38E:
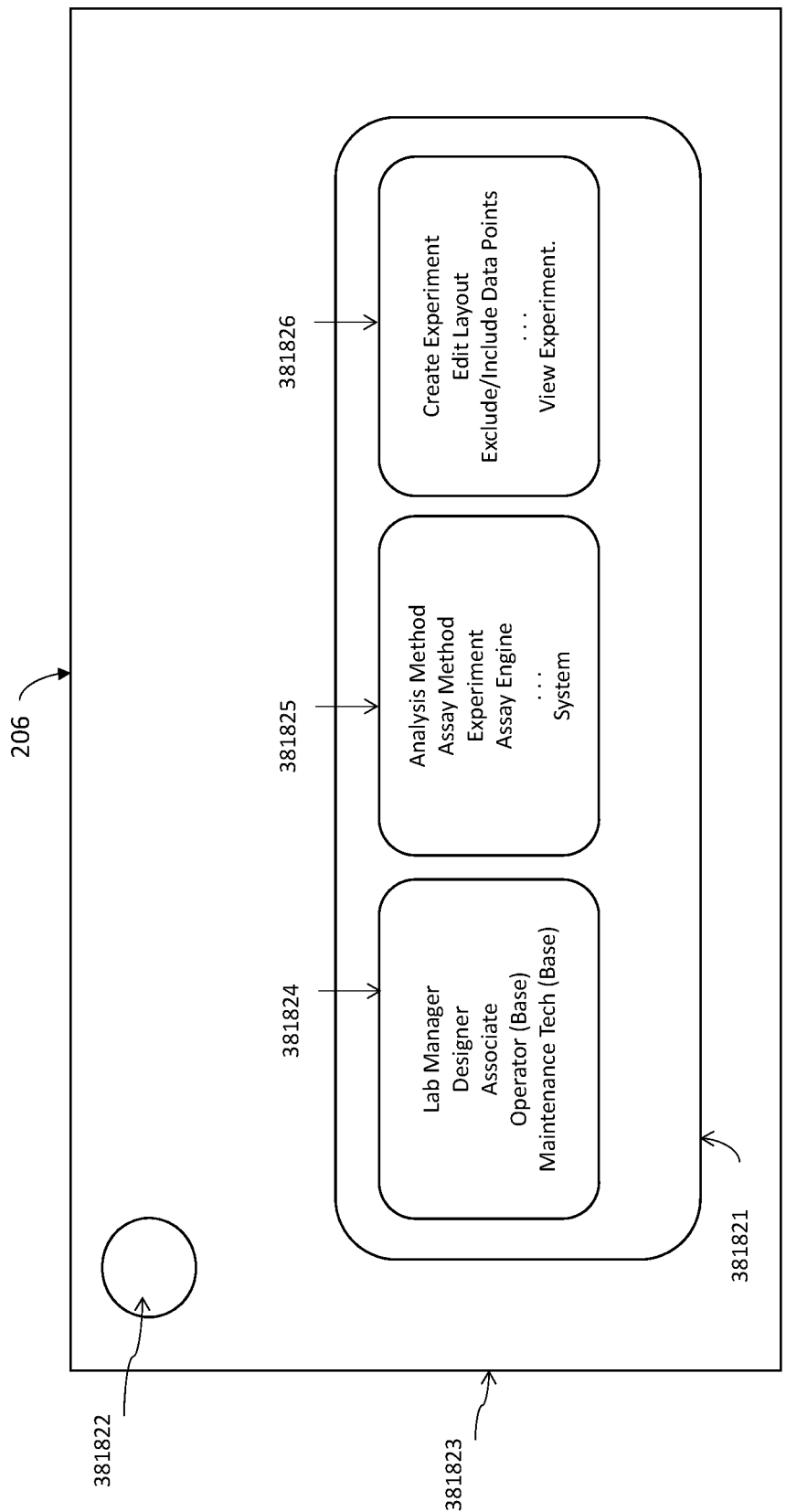

Once teams have been added, in response to the Prepare Teams choice, the user can add, modify, remove, or otherwise define certain aspects of one or more of the teams. Referring specifically to FIG. 38H, for example, in response to the Prepare Teams choice, the first portion 381821 can be adapted to display the previously entered teams in a second menu of user-selectable choices. In the embodiment provided in this figure, the user has selected Team3, as designated by the choice being represented by all capital letters, although a user's selection can be depicted in other manners, for example, any of those described herein for displaying a particular choice in a more predominate fashion as described in greater detail above. In this embodiment, the second portion 381830 is adapted to display one or more of a number of available teams defined, a number of available seats assigned, a total number of available teams, and a total number of available seats as additional information. In the embodiment shown in this figure, this may be displayed as Team Availability Information 381831. Although particular numbers of teams defined, total teams, seats assigned, and total seats are depicted in this embodiment, other examples, e.g., totals, are contemplated as well. As users add, modify, and/or remove teams and seats, the numbers provided in the Team Availability Information 381831 will vary accordingly and will be updated as such. Further, certain users, e.g., an administrator, can override and/or change the totals defined.

The example in FIG. 38H shows first menu 381829 having been moved from the first portion 381821 to the second portion 381830 as a previous menu. In this embodiment, the first menu 381829 illustrates the first set of choices, with the "Prepare" choice highlighted as past-selected. In response to a user's selection of the "Define" choice within the first menu (which, in this example, equates to the Define Administrators item from the first menu when the first menu was displayed in the first portion 381821), a second menu of user-selectable choices of usernames and/or e-mail addresses for defining administrators may be displayed in the first portion 381821. Further, the usernames and/or email addresses displayed are adapted to be deleted from the second menu of user-selectable choices in response to a user's deletion input. Moreover, in response to the Define Administrators choice, the second menu of user-selectable choices is adapted to receive new usernames and/or email address to add among the previously added usernames and/or email addresses. These aspects, e.g., the adding, deleting, user's deletion inputs, etc. for usernames and/or email addresses, are described in greater detail below, e.g., in conjunction with Add/Remove Member choice.

In an embodiment, in response to a selection of the Define Administrators choice, a menu of the one or more previously added teams, e.g., Team1, Team2, Team3, may be displayed in either the first portion 381821 or the second portion 381830. In this example, the previously added usernames and/or email addresses can be associated with a particular team among the one or more previously added teams from that menu of choices. Further, in response to the Define Administrator choice, the first portion is adapted to display an execution menu having an Authorize and Email choice. With this feature, authorizations and/or team-assignment information is adapted to be transmitted to the previously added email addresses in response to a selection of the Authorize and Email Install Instructions choice. This Authorize and Email choice is described in greater detail below in conjunction with FIG. 38G, e.g., as applied to the Authorization Summary 381828 described below. Just as the Authorization Summary 381828 relates to providing authorization, instructions, and/or notification vis-à-vis user's defined roles, the Authorization Email choice described in conjunction with the Define Administrators features relates to authorization, instructions, and/or notification of teams and administrator functions. By utilizing the Define Administrators feature, users can establish and/or create teams based on particular users, account, etc., so that groups of individuals can work collaboratively and/or cohesively as a team, In response to a selection of, for example, a particular team from the second menu and a specific action from a third menu, the first portion 381821 can be adapted to display two or more subsections of user-selectable choices, e.g., from successive hierarchical menus. Regarding the multiple subsection embodiments, as illustrated in FIG. 38E, three subsections can be displayed in the first portion 381821, including first subsection 381824, second subsection 381825, and third subsection 381826, respectively. In certain embodiments, the user-selectable choices available in these subsections will depend upon the section from the first menu, e.g., the original three choices discussed previously in connection with FIG. 38D. In other embodiments, the choices are static, so that the user can be presented with the same choices no matter which choice was previously selected. In the example shown in FIG. 38E, the choices available are successive hierarchical levels below the first menu, in which many teams may have been selected, the second menu, in which a particular team was selected, and a third menu, in which define roles/permissions was selected. Although three subsections are depicted in this example, fewer or greater numbers of subsections of user-selectable choices can be adapted to be displayed as well. Further, their display configuration is not necessarily limited to the horizontal arrangement illustrated in is figure, as other configuration, such as those provided by way of example herein, e.g., vertical, concentric, etc., are contemplated as well.

In response to the user-selectable choices available in the multiple subsections, the user-selectable choices displayed in one or more of the other subsection can change depending on the previous selection. Specifically, one feature of the admin console is to define roles of individual users and/or teams, and to assign permissions to those one or more users and or teams. Teams can be formed and permissions can be assigned based on role, experiment type, user, etc. These actions can be performed through the Define Roles and Permissions menu. For example, in response to a selection of the Define Roles and Permissions choice, the first subsection 381824 of user-selectable choices can include one or more of the following choices: Lab Manager, Designer, Associate, Operator (Base), and Maintenance Tech (Base). In this particular embodiment, if the user selects the one or more of the Lab Manager, Designer, or Associate choices, the second subsection 381825 of user-selectable choices can include one or more of the following choices: Analysis Method, Assay Method, Experiment, Assay Engine, Audit Trail, Maintenance, Reader, and System.

In contrast, if the user selects the one or more of the Operator (Base), and Maintenance Tech (Base) choices, the second subsection 381825 of user-selectable choices can include one or more of the following choices: Assay Engine, Audit Trail, Maintenance, Reader, System. User-selectable options displayed in the third, fourth, etc. subsections can further depend on the choices made from choices previously made from one or more of the of the other subsections. For example, in response to a selection of an Analysis Method choice from the second subsection 381825, the third subsection 381826 of user-selectable choices can include a Run Analysis Method choice. Similarly, in response to a selection of the Assay Method choice from the second subsection 381825, the third subsection 381826 of user-selectable choices can include a Run Assay Method choice. Still further, in other examples, the third subsection 381826 can include multiple user-selectable choices. By way of example, in response to a selection of the Experiment choice from the second subsection 381825, the third subsection 381826 can include the following choices: Create Experiment, Edit Layout, Exclude/Include Data Points, Export Data Table, Export Sample Result Table, and View Experiment. Additional exemplary, non-limiting embodiments are presented below.

In response to a selection of the Assay Engine choice from the second subsection 381825, the third subsection 381826 can include the following choices: Export Data Table; Modify Instrument Settings; Override Mesoscale Diagnostics Kit Lot Assignment; Retry Inventory Validation; Run Instrument; and Show ECL for Unverified Run. In response to a selection of the Audit Trail choice from the second subsection 381825, the third subsection 381826 can a include a View Audit Trail App choice. In response to a selection of the Maintenance choice from the second subsection 381825, the third subsection 281826 can include the following choices: Run Maintenance; Run Maintenance Method; and View Maintenance Records. In response to a selection of the Reader choice from the second subsection 381825, the third subsection 381826 can include the following choices: Manage Database; Modify Instrument Settings; and Run Instrument. In response to a selection of the System choice from the second subsection 381825, the third subsection 381826 can include the following choices: Modify System Settings; and Unlock App Locked by Any User. The foregoing examples are non-limiting, as other user-selectable choices can be made available for display as well through the multiple subsections of the first portion. In some embodiments, one or more of the subsections and/or user-selectable choices within the one or more subsections can be user-customizable, e.g., by an administrator, team leader and/or member, user with permission, etc.

Another feature of the admin console module is to add and/or remove members, such as from a team or other grouping of one or more users and/or accounts. Teams can be formed, and permissions can be assigned, based on role, experiment type, user, etc. These actions can be performed through the Add/Remove Members choice. For example, in response to a selection of the Add/Remove Members choice, a first or second portion of the MUI (FIG. 38H, 381830) displays a menu including previously added usernames and/or email addresses. These previously added usernames and/or email addresses could have been added by the same user or by other users who have access to the admin console module. In an embodiment, the usernames and/or email addresses can be modified or deleted in response to a user's deletion input, assuming the user accessing them has the appropriate permissions, either by overwriting the previously entered information or by making a selection, e.g., clicking a portion of the MUI display 206, such as an "x", to remove the username and/or email address entirely. In other embodiments, any user logged into the admin console module can modify or delete the usernames and/or email addresses regardless of permissions. The previously added usernames and/or email addresses, and the ones that have been modified can then later be associated with particular teams, accounts, instruments, etc. through the admin console module.

Figure 38F:
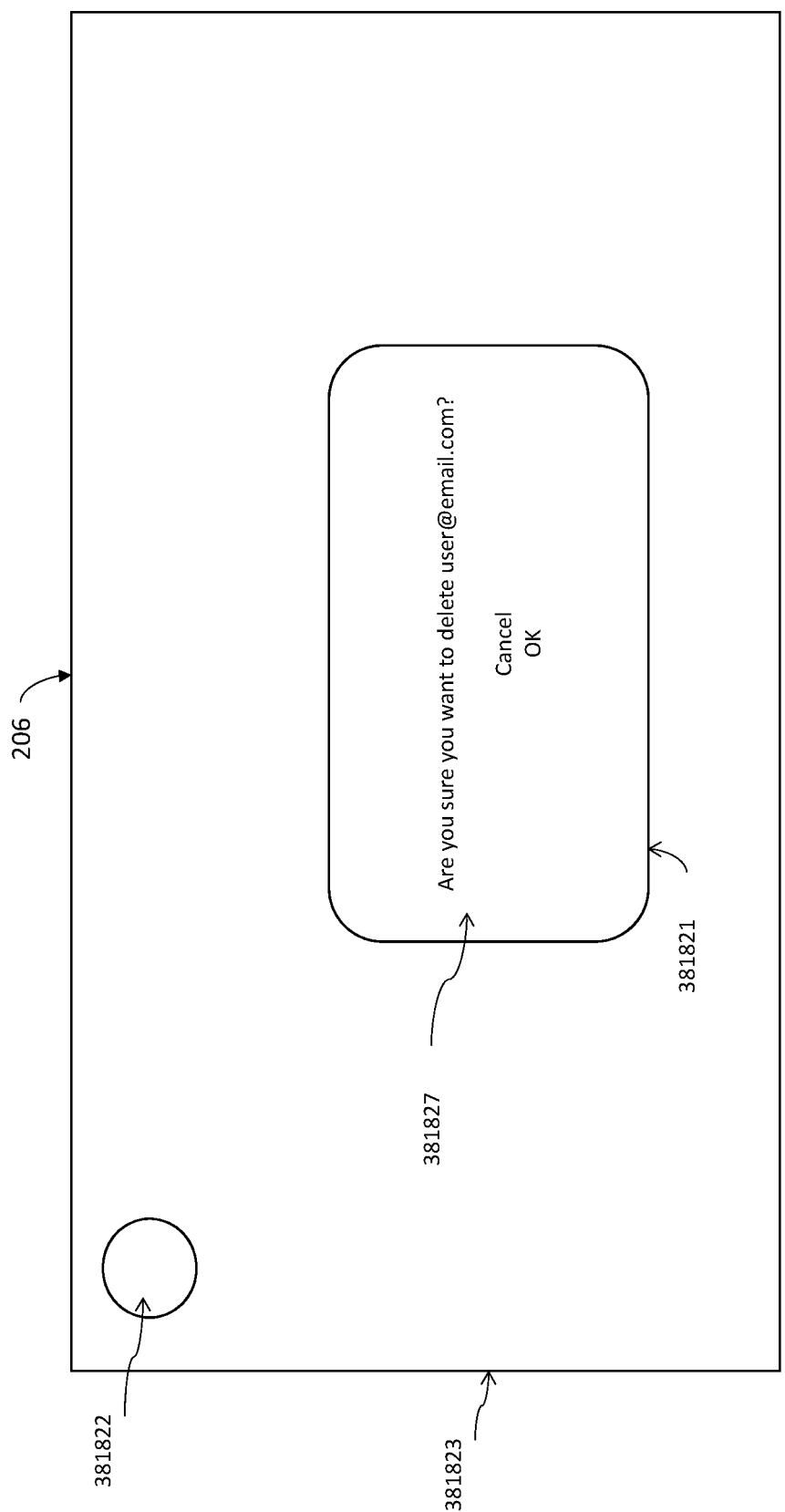
Figure 38G:
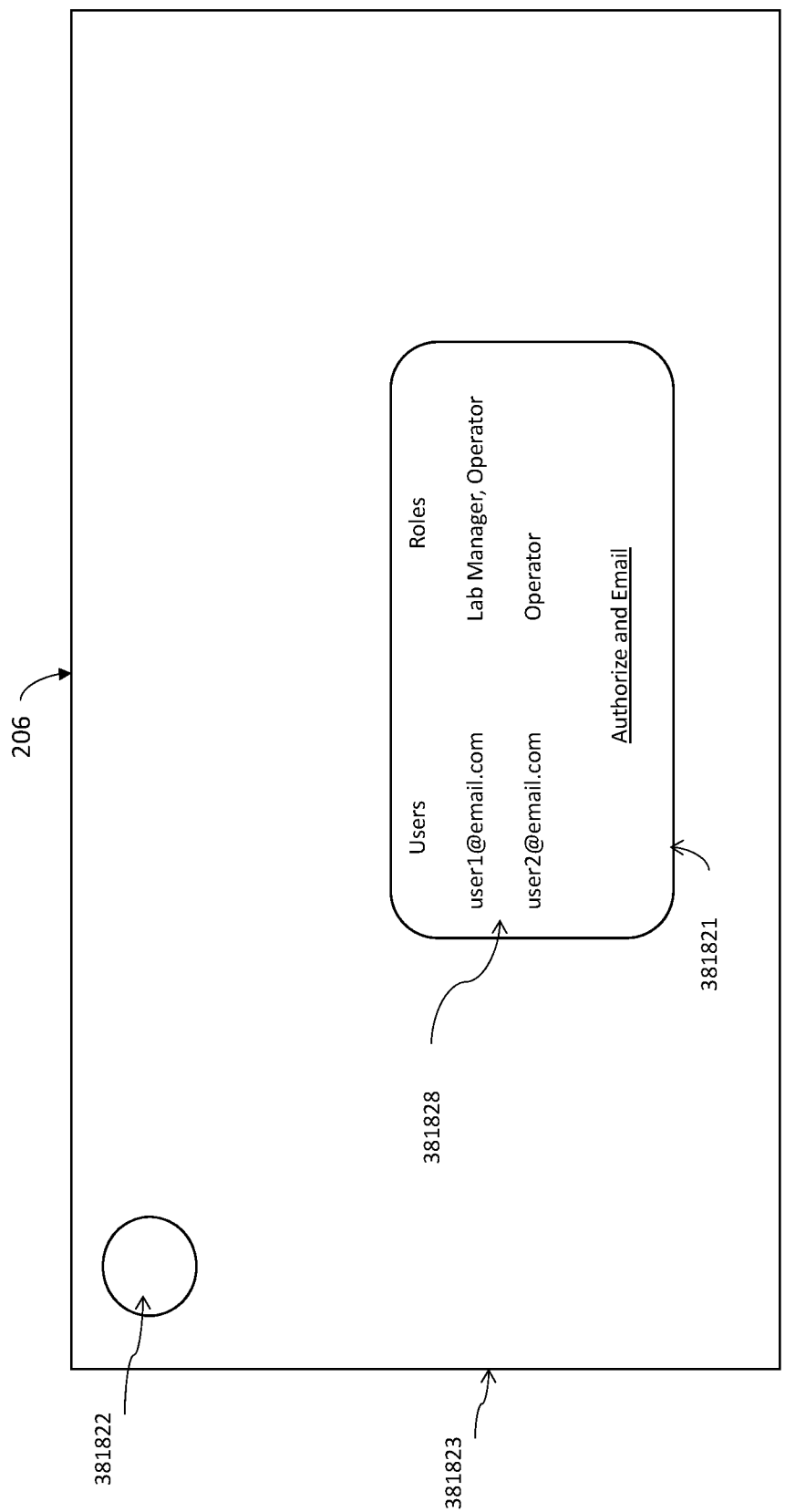
Figure 38H:
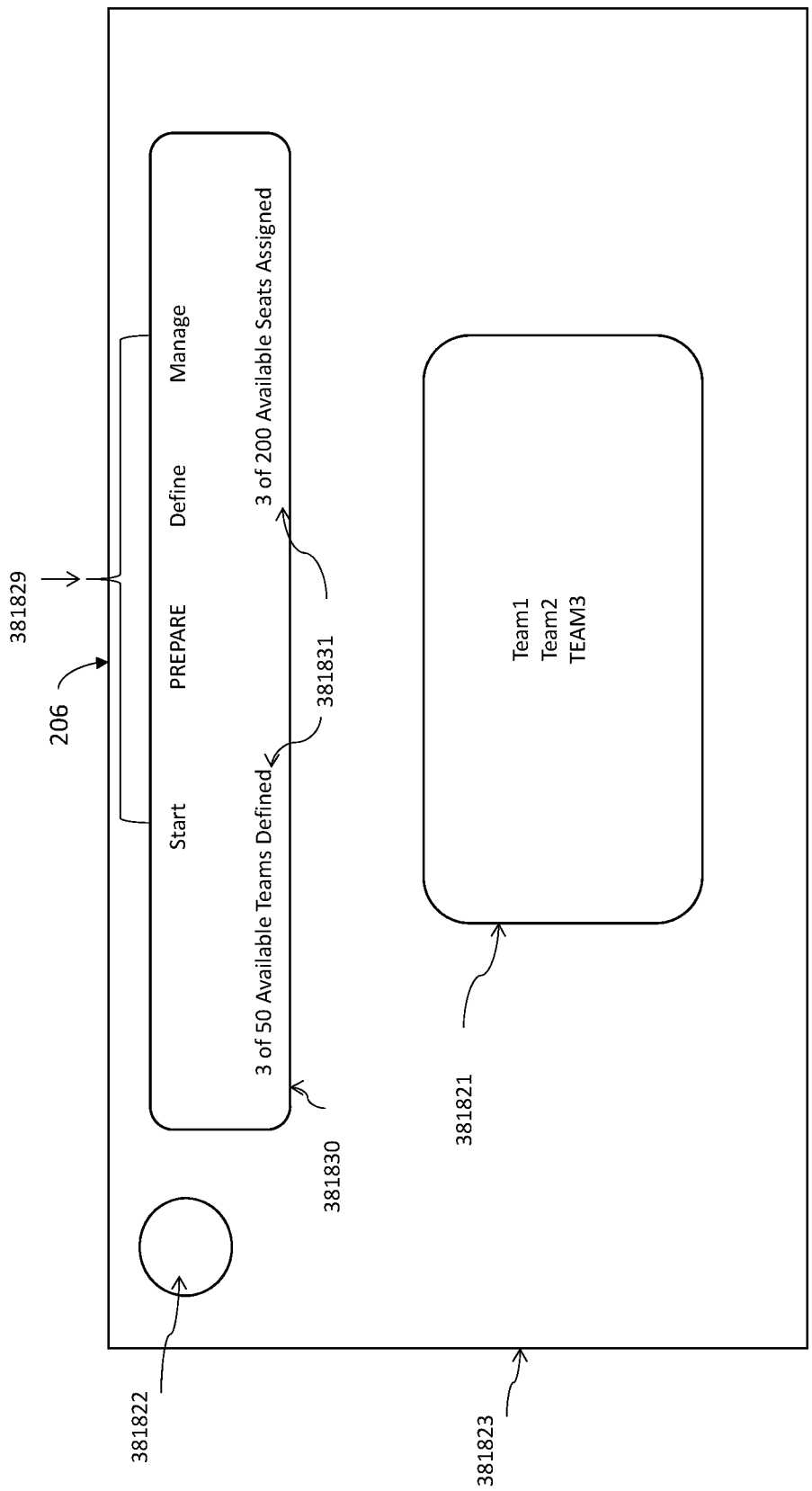
Figure 38I:
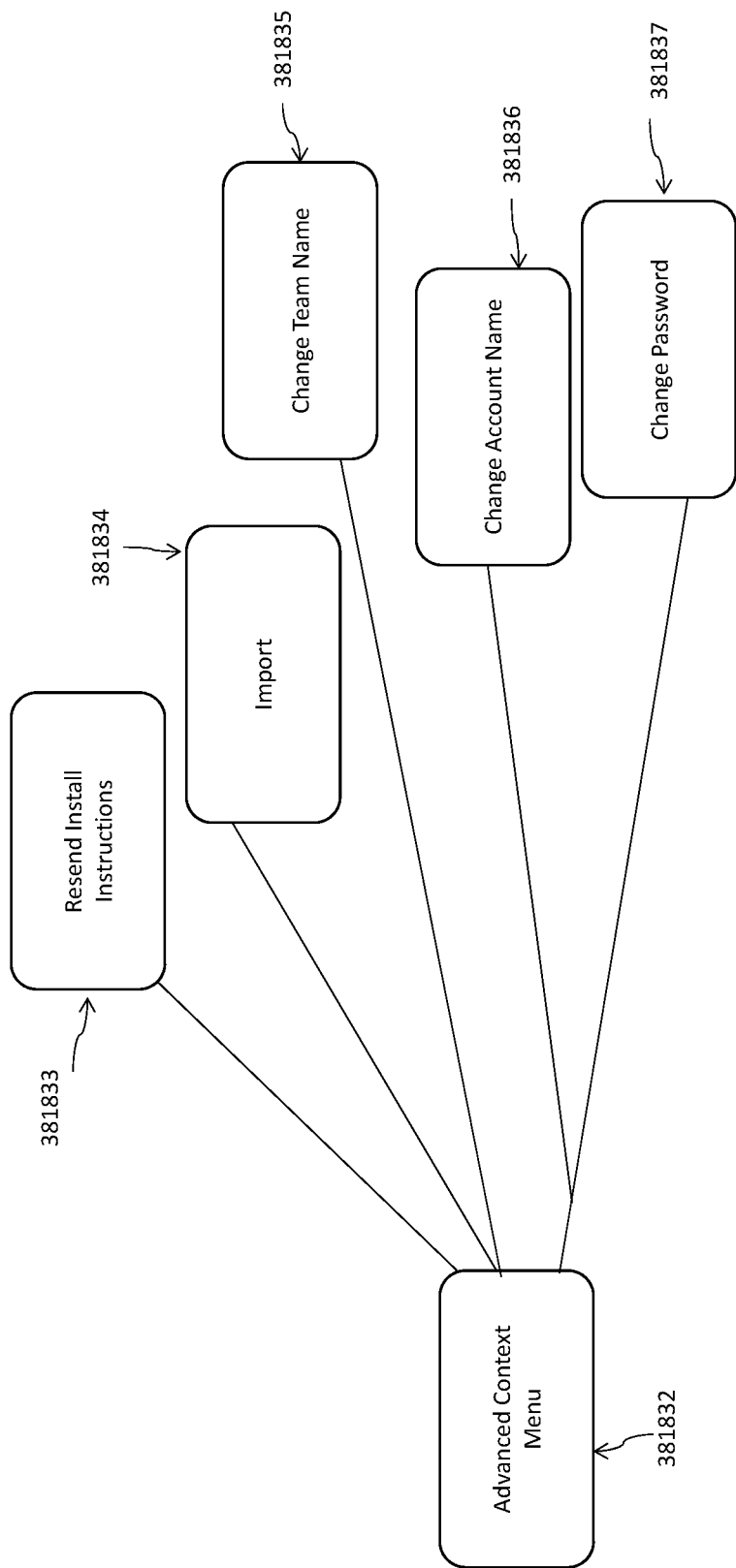
FIG. 38I presents an illustration of an advanced context menu associated with an admin console module.

Turning to the embodiment depicted in FIG. 38F, in response to user's deletion input (as described above), the first portion 381821 is adapted to display a confirmation choice 381827 before removing one or more the users and/or teams. A similar confirmation choice is described below in conjunction with the reader module (e.g., FIG. 43F) for issuing a stop instrument command. In the context of the admin console module, a similar confirmation process can be employed with regard to deleting one or more the users and/or teams. The confirmation choice (FIG. 38F, 381827) can be adapted to be displayed to provide one or more users with the ability to confirm whether they want to delete the current user from a particular team, account, roles, etc. When this Confirmation choice 381827 is displayed, the user can be presented with a choice as to whether he wishes to delete the selected user, for this example the user is represented by the user@email.com email address. In this example, the user can either select "Cancel" from the menu, thereby terminating the decision to remove this member, or select "OK," thereby removing the member. These options are merely exemplary as other choices and/or command prompts are contemplated as well.

In addition to deleting and modifying members, in response to the Add/Remove Members choice at a third menu, the first portion 381821 may be configured to display an execution menu for receiving new usernames and/or email addresses to add among the previously added usernames and/or email addresses. These new members can be added, for example, by a user manually entering the information into the MUI display 206 through an input device, such as a keyboard, touchscreen, etc. Further, new members can be added through an automated process, such as with a barcode reader, or an input file that contains a list of one or more of the new members the user wishes to add.

Another feature of the admin console module is to assign members to roles, e.g., based on title, responsibility, application performed, etc. These actions can be performed through the Assign Members to Roles choice at a third menu. For example, in response to a selection of this choice, an execution menu of user-selectable items may include previously added usernames and/or email addresses displayed in a first subsection 381824. These previously added usernames and/or email addresses can, for example, be displayed in a similar manner as to those described in conjunction with the Add/Remove Members choice, above. In response to Assign Members to Roles choice, the second subsection 381825 can include one or more of the following role-assignment choices: Lab Manager, Designer, Associate, Operator (Base), and Maintenance Tech (Base). These are merely exemplary and additional and/or hybrid roles can be included in addition to or in place of these particular roles. In one embodiment, in response to selecting the Assign Members to Roles choice, first subsection, FIG. 38E, 381824, can include the previously entered username and/or email address, and second subsection, FIG. 38E, 381825, can include the role-assignment choices, such as the five provided above. In this embodiment, a one-to-one correspondence can be displayed between the username and/or email address and its respective role assignments. In this regard, selections from the first and second subsections (FIG. 38E, 381824 and 381825, respectively) are adapted to create an association among one or more of the previously added usernames and/or email addresses with one or more of the role-assignment choices. For example, if the user selects a first username, the second subsection (FIG. 38E, 381825) can display all the roles that particular user is currently assigned. Additionally, the second subsection (FIG. 38E, 381825) can display additional roles for which that particular user is not currently assigned. This is described in greater detail below in conjunction with FIG. 38G.

Whether the user is designated to a particular role can, for example, be displayed through an indicator associated with each role to indicate whether the user is assigned (or not assigned) to that particular role. The indicator can include, for example, a checkbox, although other indicators are contemplated as well, such as text-based indicators, e.g., an "x," "1," "0," etc. In the checkbox embodiment, a box can be displayed as unchecked if that user is not currently assigned that that particular role, and the box can be checked, or otherwise marked in some fashion, if that user is currently assigned to that particular role. The marking or checking can occur, for example, by a user's input, e.g., mouse click, touchscreen, etc. In this example, the user accessing the admin console module can select and deselect one or more role assignments, by adding, removing, etc. roles to be associated with the given user, through the interaction with the MUI display 206. Notably, the marking or checking selection process described with regard to this particular aspect of the admin console module can be applied to other selections from within this module, or any other module and/or user-selectable choices described herein.

Another feature of the admin console module is to authorize user-specific roles and inform those users of the roles for which they have been assigned. These actions can be performed through the Authorize and Inform choice. As described in greater detail in conjunction with FIG. 38E, an association among one or more of the users, e.g., by way of their usernames and/or email addresses, can be created with one or more of the role-assignment choices. In one embodiment, the association of one or more these users to their one or more roles can be displayed in response to a selection of the Authorize and Inform choice. Turning to the embodiment depicted in FIG. 38G, an Authorization Summary 381828 can be displayed, for example, in the first portion of the MUI display 206) in response to the Authorize and Inform choice, such that a table is created, although other structures and/or formats are contemplated as well, that summarizes those assignments. In this embodiment, two columns are created, e.g., a User column and a Roles column, although other additional columns are contemplated as well, that provide a one-to-one correspondence of user to assigned role, although other correspondences are contemplated as well. The rows depicted in this example each represent an individual user, although teams, accounts, etc. could be included as well. Additionally, the Authorization Summary 381828 is adapted to display an Authorize and Email Install Instructions choice, located at the lower portion of the Authorization Summary 381828, although it is not limited to this embodiment. In response to a user's selection of the Authorize and Email Install Instructions choice, the role-assignment information and/or instructions are adapted to be transmitted to the previously added email addresses, or alternatively through the cloud. Thus, by selecting the transmit Authorize and Email Install Instructions choice, the user can inform one or more of the users of the role or roles for which they have been selected, and/or provide those users with information and instructions as it relates to their assigned roles.

Accordingly, an Admin Console MUI provides an operator with a wide array of access control abilities, e.g., by using teams, individual user permissions, role assignments, specific permissions, and other functionality. The Admin Console is not specific to a laboratory setting and may be applied for adjusting user permissions in further settings such as manufacturing settings, parental controls over computer and media use, and others.

In a particular embodiment, in response to a user's selection of the advanced context menu selector 381822 (FIG. 38D), the advanced context menu 381832 (FIG. 39I) can be outputted to the MUI display 206. The advanced context menu 381832 may include various commands and/or user-selectable choices. For example, with specific reference to FIG. 38I, this menu can include an Resend Install Instructions command 381833. This command, when selected, will resend installation instructions, e.g., to install the application that runs one or more of the modules as described herein, to one or more selected users, including the user who selected this command. Those instructions can be transmitted via electronic mail, e.g., to the users' email addresses, or over the cloud. The Import command 381834, when selected allow the users to import names and/or email addresses of users, account information, team information, etc. without the need to manually input that information. Further the Change Team Name command 381835 and Change Account Name command can be used to allow the user to change the team or account, respectively, for one or more users, accounts, and/or teams. Finally, the Change Password command 381837 allows the user to change the password for her account. In other embodiments, depending on permissions, this command will allow a user, such as an administrator, to change the password of one or more additional users as well.

Figure 39A:
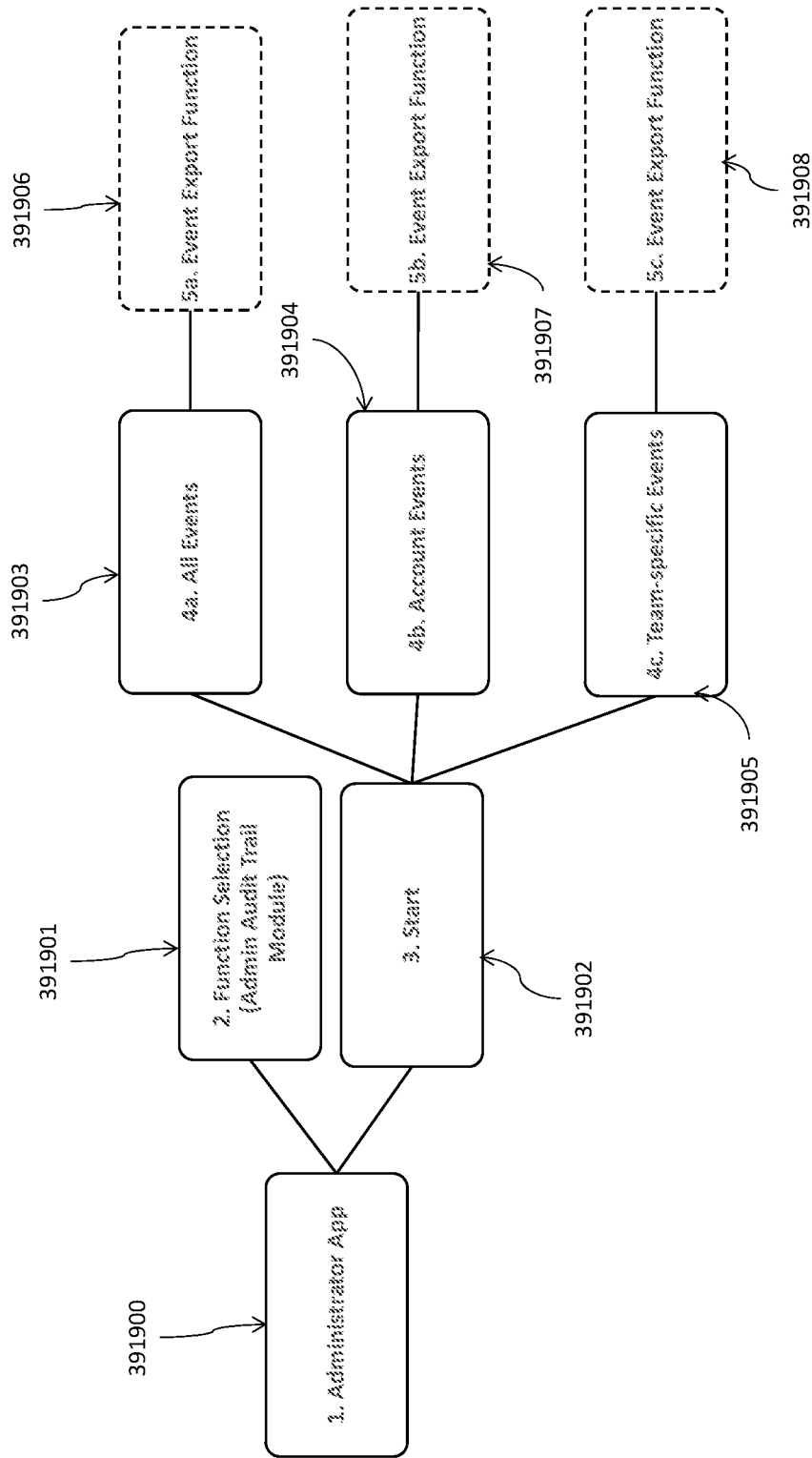
FIG. 39A illustrates the flow for an admin audit trail module in an administrator app in an embodiment.

In FIG. 39A is an embodiment of a user experience flow through an admin audit trail module beginning with administrator app at 391900 running on an admin's computer with each step through a user interface numbered sequentially 1 through 'n' to represent the stepwise flow from begin (1) to end ('n') for an admin as depicted in administrator app at 391900 being labelled "1." as the first step, also, as an admin works through the flow of a user interface they could easily back track to one or more previous steps. The user experience flow of FIG. 39A may employ a MUI for interface purposes as discussed herein. At 391901 an admin can select a module to access. In this illustration, an admin audit trail module is selected, and the MUI transitions the application to start at 391902 providing an admin a first menu including options to view all admin events at 391903, view account admin events at 391904, or view team-specific events at 391905. On selection of an option the MUI transitions to a selected second menu at 391903, 391904, or 391905. At 391903 only an account admin is presented all events captured across the entire account including, but not limited to, account and team-specific actions taken by every admin with each event including, but not limited to, username of originator, date and timestamp, the source, and information pertaining the event as returned from a service request made via the cloud platform. At 391904 only an account admin is presented all account admin events captured across the entire account including only overall account admin events for account actions taken by every admin with each event including but not limited to username of originator, date and timestamp, the source, and information pertaining the event as returned from a service request made via the cloud platform. At 391905 either an account admin or a team admin is presented all team-specific events captured for each team one team at a time for which an admin has administrative rights including team-specific administrative actions taken by every team-specific admin and account admin with each event including but not limited to username of originator, date and timestamp, the source, and information pertaining to the event as returned from a service request made via the cloud platform, wherein, an admin could easily transition to view other team-specific events without leaving the view at 391905. The menus at 391903, 391904, and 391905 each enable a user to sort the view in forward or reverse ordering by username, date and timestamp, source, or information about the event. The menus at 391903, 391904, or 391905 each allow an admin to access an execution menu permitting export of the entire collection of events provided at 391903, 391904, or 391905 to a file format easily importable to other computer applications like Excel, Word, and/or any other computer application, such as, CSV, tab-delimited text, JSON, XML, and/or any other format. At 391903, 391904, or 391905 an admin may use an execution menu to export the entire collection of events provided at 391903, 391904, or 391905 to a computer operating system mechanism used for copying and pasting content from one computer application to another computer application often referred to as a clipboard. Based on the execution menu selection, appropriate event export function (e.g., 391906, 391907, 391908) can be executed for exporting the event or events. At interfaces 5 (e.g., 5a, 5b, 5c) the information and/or data related to the events specified at interfaces 4 (e.g., 4a, 4b, 4c) can exported. For example, in 391906, all the events from interface 4a can be exported. Similarly, in 391907 and 391908, account events and team-specific events can be exported, respectively. This exportation can be provided in a user-readable format or in a file format easily importable to other computer applications such as, without limitation, Excel, Word, and/or any other computer application, such as, CSV, tab-delimited text, JSON, XML, and/or any other format.

Further examples of the audit trail feature are disclosed with respect to FIGS. 39B-39E. The audit trail module can be adapted to provide a summary of information as it relates to one or more users' and/or teams' interactions with the UI display specifically, or more generally based on actions that users have performed while logged into their accounts. For example, the audit trail module can include the usernames and/or email addresses of the users that have logged in to an account, the time of each login, the IP address of the computing device from which the users accessed their account, which instruments the users used while logged in, etc.

In one embodiment, as shown in FIG. 39B, the audit trail module can be accessed through the advanced context selector 381822 as part of the advanced context menu 381832. In this example, the advanced context menu 381832 is adapted to be displayed in response to a selection of an advanced context selector 381822 when outputted to the UI display 381823. When displayed, advanced context menu 381832 can include a plurality of commands and/or user-selectable choices arranged in a menu that may take the form of various configurations, e.g., vertically, horizontally, etc. In addition, one or more menu dividers 391910 can be employed to group and/or divide particular commands and/or choices. For example, the menu divider 391911 can be used to group commands on one portion of the advanced context menu 381832 and user-selectable choices on the other. In other embodiments, one or more of these dividers can used to group and or/divide according to other attributes or traits of the menu items. In some embodiments, the location, grouping, and/or division of the menu items can be user-customizable. Advanced context selector 381822 is described in greater detail above, thus, details are omitted here aside from examples and/or embodiments provided below as they relate to the audit trail module feature.

In a particular embodiment, in response to a user's selection of the advanced context selector 381822, the advanced context menu 381832 can be outputted to the MUI display 206, e.g., by the menu manager 1054. The advanced context menu 381832 can include various commands and/or user-selectable choices. For example, with specific reference to FIG. 39C, this menu can include an export command 391911, or a command to copy data to a clipboard (not shown). It further can include user-selectable choices including an admin console choice 391912, which, when selected, can allow a user to access the admin console module, as described in greater detail above in conjunction with that module, or an admin audit trail choice 391913, which, when selected, will allow a user to access the audit trail module described herein. Other commands and/or user-selectable choices are available to users as well in the advanced context menu 381832, for example, and with reference to FIG. 39C, Terms of Use 391914, Privacy Policy 391915, and a command to log the users out of their accounts, e.g., Log Out command 391916. Although the advanced context selector 381822 is depicted in FIG. 39B near the top left portion of MUI display 206, with the advanced context menu 381832 directly below it, other configurations are contemplated as well.

Figure 39C:
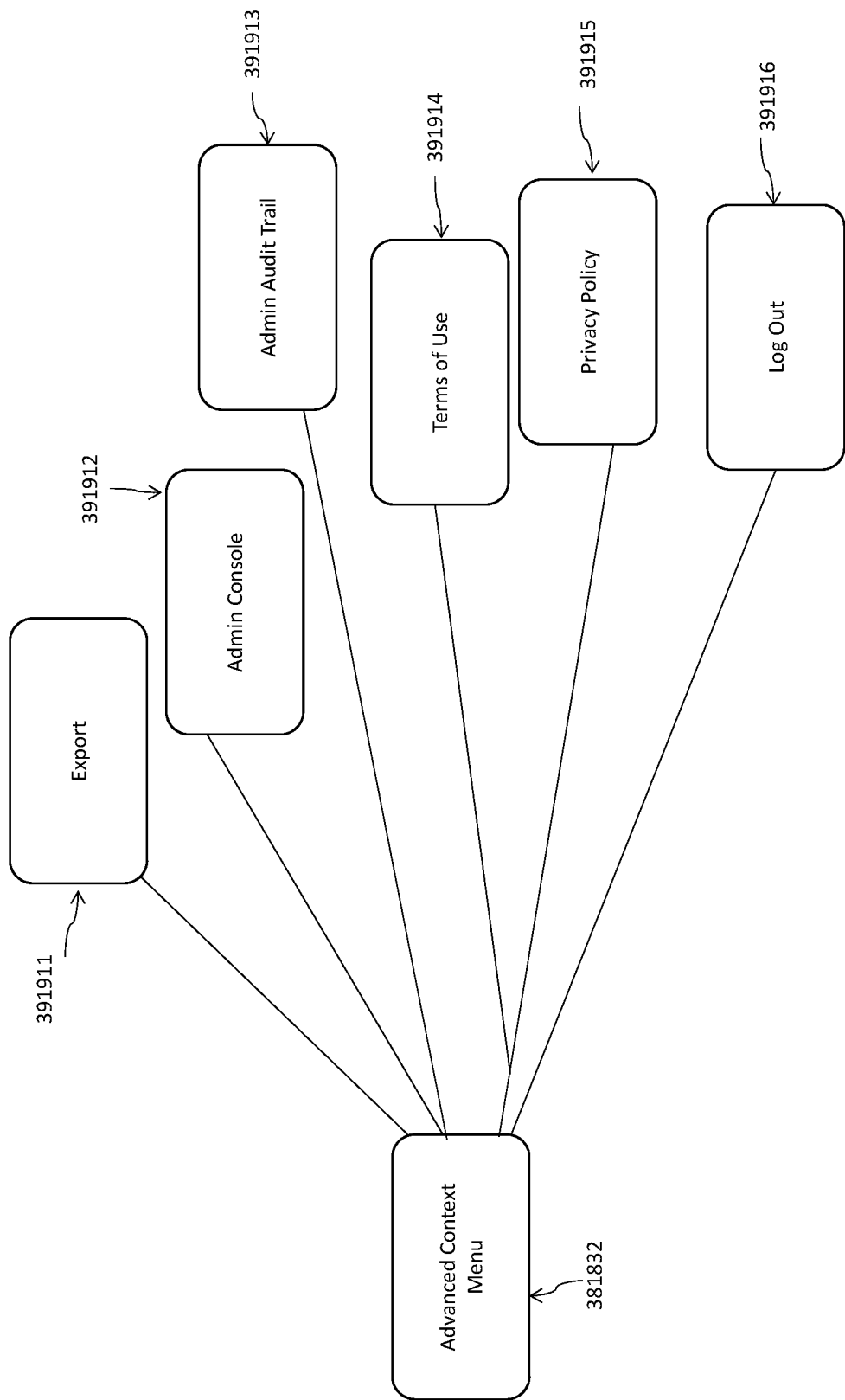
Figure 39E:
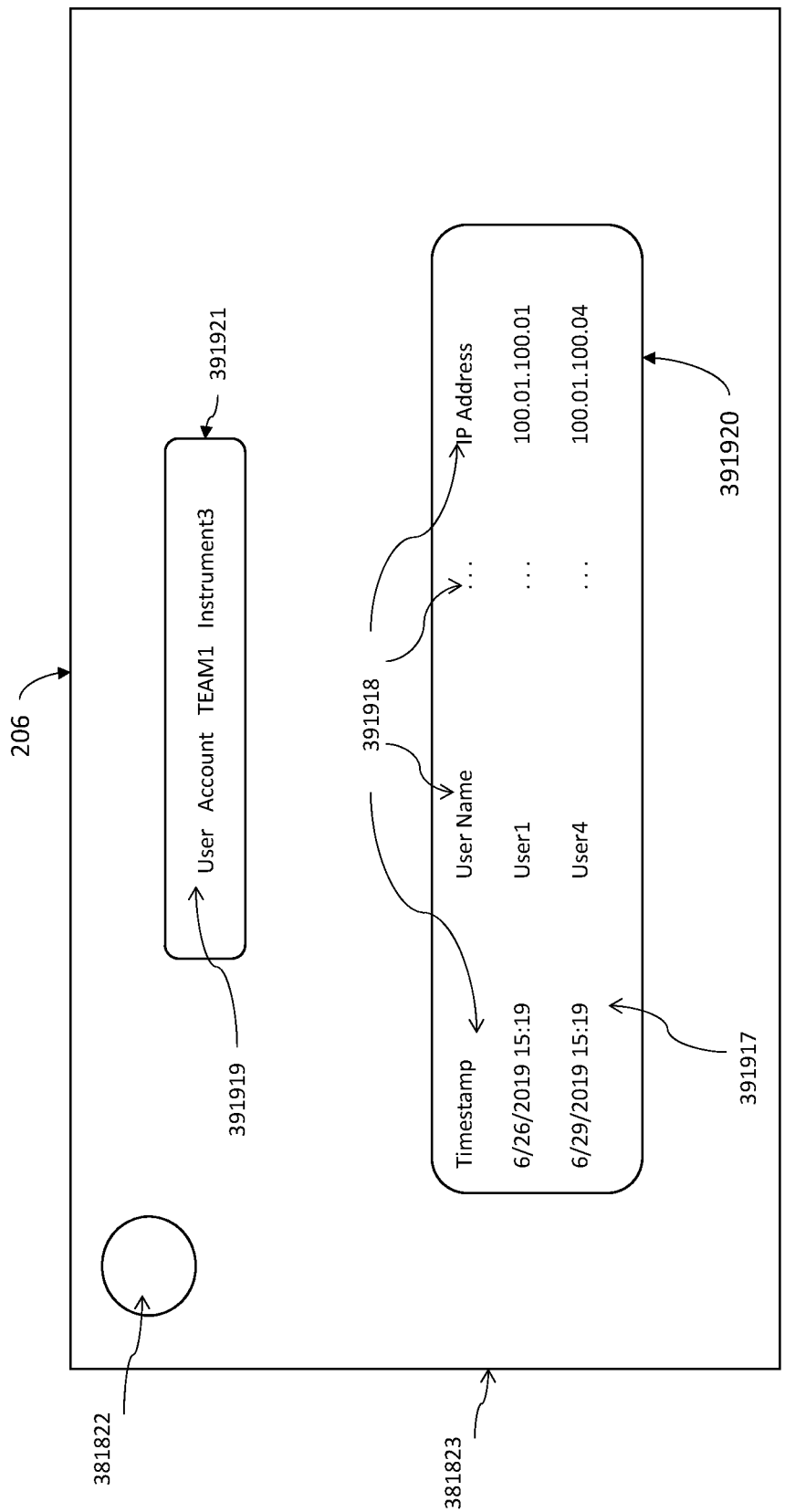

With specific reference to FIGS. 39C and 39D, in response to a selection of Admin Audit Trail choice 391913, the first portion 391920 of the MUI 206 is adapted to display audit information 391917, divided into one or more fields 391918. The audit information 391917 can be arranged as a table, or in the alternative, as a list, or any other suitable arrangement of data. The embodiment illustrated by FIG. 39D depicts the displayed audit information 391917 as including fields 391918 as the columns of a table, with each entry provided vertically in rows. Fields 391918 of audit information 391917 can include, for example, one or more of a timestamp, a username and/or email address, module, record ID, type, message, category, code, and IP address of a user.

The timestamp can include when (e.g., date and/or time) the audit was generated. In one example, this field can be presented in MM/dd/yyyy HH:mm:ss format, although other formats are contemplated as well, including those that convey more or less information than this particular format (e.g., just recording the date, but not the time). The timestamp can also record each instance a particular user logged into her account, how long she was logged into for, and when she logged out. This information can be tracked by either the username, email address, and/or any other user, team, and/or account indicator. For example, the Username field will record the username of the user that was logged in when the event was generated. The module field can include the module that generated the audit event, e.g., Reader, Experiment, etc. In this manner, this field can be populated with one or more of the modules that were utilized during that particular log-in instance. For example, if a user utilized the Assay Method and Experiment modules, this field would indicate the same. In some embodiments, multiple modules can be displayed on a single row for that particular log-in instance, and in other embodiments, audit information 391917 can be arranged across multiple rows, one for each module that particular user utilized while logged in.

The Record ID field may be included to show the ID of the record associated with the audit event. By way of example, if an experiment relates to the use of plates, the Record ID can include the plate barcode. It further can include information as it relates to the what experiments, assays, and/or functions a particular user performed while logged in, more generally. For example, it can include the file name, either default or user-customizable, associated with a particular experiment. In other examples, it can include information relating to actions performed while analyzing and assay plate, such the plate's loading, reading, ejection, etc. The Type field can include the type of audit event including, for example, Info, Action, Warning, or Error. This field can relate to other information summarized in the audit information 391917, for example, whether the user received a warning and/or an error while logged in. Or it can include additional information related to the users' actions and/or interactions with the application, equipment, and/or experiments. Further, it can convey that an analysis was performed manually or automatically, etc. The Message field can include one or more of a static, dynamic, and/or user-customizable message that relates to the audit event. A separate field is provided for the category, e.g., Category field, of the audit event, e.g., record, system, equipment, etc. In one example, the Category field provide additional characterizations of the messages provided in the Message field.

Further, the IP Address field can provide the IP address of the computing device, e.g., laptop, desktop, tablet, etc., from which the users accessed their account, which instruments the users used while logged in, etc. The Code field can be related to the IP Address in some embodiments, or unrelated in others, whereby a unique numerical value, such as an integer, for identifying the event. In some embodiments, this identifier can be predetermined. In other examples, they can be user-defined, such as by an administrator. In the latter example, the Code field can be customized to accommodate one or more users' specific needs. Additional fields such as permissions, team identifiers, etc. are contemplated as well. Thus, the audit information 391917 can be arranged in such a manner that associates one or more of these fields to provide a trail of information that summarizes the tasks, equipment, and/or instruments associated with one or more users' experiences while logged into their accounts.

In several embodiments, the amount of information displayed can vary depending on the user's preferences. For example, a user can filter the audit information 391917 such that the information limited to one or more users, accounts, and/or teams, e.g., previously added teams by utilizing the Admin Console module as described above. An example of this is depicted in the embodiment shown in FIG. 39D. An audit menu 391919 can be outputted to MUI display 206, shown here by way of example in the second portion 391921 of MUI display 206, that can be used to filter this information. In this embodiment, a user has selected to filter the audit information 391917 by team, which is illustrated by depicting the "Team1" selection in all capital letters in this particular embodiment, although a user's selection can be depicted in other manners, for example, any of those described throughout for displaying a particular choice in a more predominate fashion as described in greater detail herein. In this example, only User1 and User4 are members of this particular team (i.e., Team1), and, thus, the audit information 391917 has been filtered by the that team. In other embodiments, all audit information can be made available for display, or user can narrow the audit information to be displayed by one or more users, accounts, teams, and/or instruments. In one example, the audit menu 391919 can be outputted to MUI display 206 in response to a command to display an audit menu 391919 by selecting the Admin Audit Trail choice.

In addition to being displayed by the MUI display 206, the audit information 391917 can be copied and/or exported. For example, in response to an export command 391911 (FIG. 39C), the audit information 391917 can be outputted to an export file, such as a Microsoft Excel® or other data processing and/or spreadsheet software. Alternatively, it can be provided in a comma-separated file, e.g., CSV file. In response to the export command 391911, the requested file containing audit information 391917 can be exported to a user, either by the user selecting and/or viewing the exported file. Alternatively, it can be exported by emailing it to the user and/or transmitting it over the cloud. Further, in response to the copy to clipboard command (e.g., as depicted within the advanced context menu 381832 as shown FIG. 39B), all or a subset of the data including the audit information 391917 can be temporarily stored to a buffer, such that the user can later access and/or view it (e.g., using a cut-and-paste command). In this example, the user is not confined to the formats for which the data are presented in the exported file, providing users with the ability to customize the data format and/or utilize one or more applications of their choice to access, modify, and delete those data.

Figure 40:
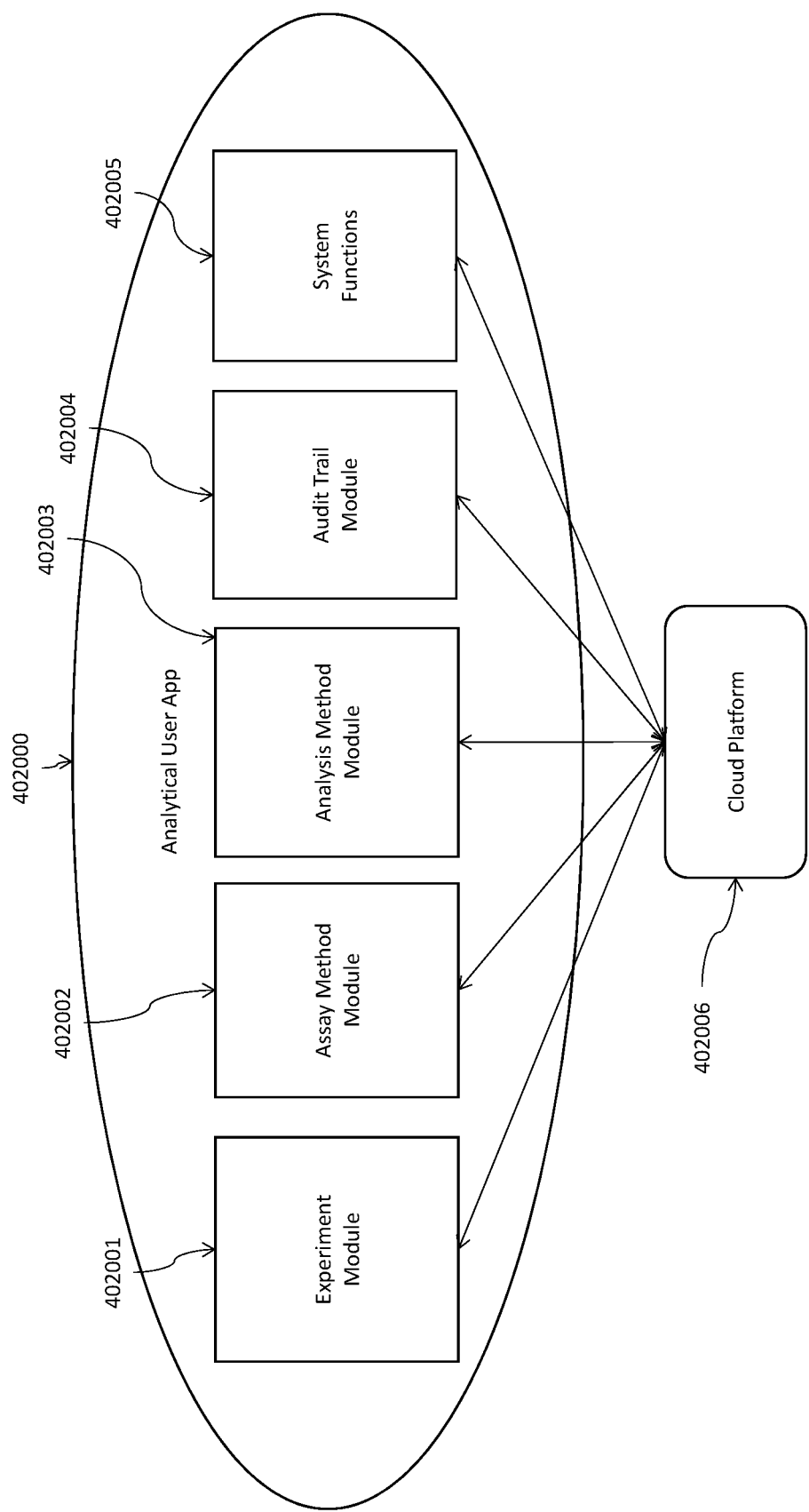
FIG. 40 illustrates the modules in an analytical user software application in an embodiment.

In FIG. 40 is an embodiment of software modules in an analytical user app 402000 forming the primary user interface experience for analytical work typically, but not limited to, using data generated through the use of instrumentation with each module using services provided by cloud platform 402006 to create, read, update, and/or delete any and all data relevant to each module's processing, as well as any other services needed for each module's processing, wherein experiment module 402001 would be the active module by default when the analytical user app 402000 starts. As discussed above, the analytical user app 402000 may employ a MUI supplied by a methodical user interface control system 1102 for interface purposes. The experiment module 402001, assay method module 402002, analysis method module 402003, audit trail module 402004, and the system functions 402005 may all employ a MUI for user interface purposes. An analysis method module 402003 provides a construct referred to as an analysis method to be used in post-read analysis of signal collected from a test plate by a plate reader, wherein an analysis method is used to configure an existing process and/or create a new process by which data collected from tested samples using instrumentation and/or consumables can be transformed through an algorithm configured by associated parameters into a quantitative or qualitative determination. Assay method module 402002 is used to configure an existing process and/or create a new process by which samples will be processed using consumables and/or instrumentation to generate data from the samples under test so they may be appropriately analyzed using a prescribed analysis method. Experiment module 402001 is used to design a test of one or more samples using one or more selected assay method(s) to collect the data from the samples through the use of instrumentation and/or consumables that may be reviewed and analyzed to ensure the experiment ran properly, as well as to learn from the data collected from the tested samples. Audit trail module 402004 is used to view all events generated through use of the analytical computing system by users from the same team who are creating, modifying, and/or deleting electronic records associated with the analytical computing system. The collection of system functions 402005 provides typical utilities in support of use of the system such as, but not limited to, logging off, viewing help information, viewing user guide, viewing legal notices and/or documents, changing software configuration, changing user password, and/or other utilities. The collection of system function 402005 may be provided as a separate MUI module and/or a series of software protocols that operate alongside the other discussed MUI modules. A user can log into the analytical user app 402000 through system functions 402005 using services provided by cloud platform 402006.

If authentication of a user by login service on cloud platform 402005 the service returns that a user has more than one account and/or team, a user will be required to select the default account and/or team, but if a user does not belong to more than one account and/or team, the service on the cloud platform 402006 would auto-assign a user to the sole account and team for that user. On completing login, the user lands at start of the experiment module 402001 and begins using the analytical user app 402000 as they need. In the alternative, the analytical user app 402000 can assist in performing other experiments in addition to or in place of the assay and/or plate-based experiments described herein.

In FIG. 41 is an embodiment of a user experience flow through an analysis method module beginning with analytical user app at 412100 running on a user's computer with each step through a user interface numbered sequentially 1 through 'n' to represent the stepwise flow from begin (1) to end ('n') for a user as depicted in analytical user app at 412100 being labelled "1." as the first step. The experience flow of FIG. 41 may be provided via a MUI as discussed herein. At some point in the flow a user could have alternate flows based on a decision they are to make as denoted by a lowercase letter after a numbered step as depicted at 412112, 412113, and 412114 where a user chooses between configuring calibration curve at 412112, background correction at 412113, and/or limits of detection at 412114, also as a user works through the flow of a user interface they could easily back track to one or more previous steps through the use of an historical portion of the MUI. At 412101 a user may select a user interface mechanism presenting one or more options including, but not limited to, module-specific functions, modules to select, and/or system functions being either a horizontal menu and/or toolbar, a vertical menu and/or toolbar, a scroll-wheel menu and/or toolbar, a drop-down menu and/or toolbar, a keyboard function, a voice-activated command, and/or any other like user interface mechanism to choose an option, in this case choosing analysis method module and transitioning the application to start at 412102. At 412103 a user is presented one option to design an analysis method and a user on choosing to do so transitions to design at 412104. At 412104 a first menu is presented, allowing the user to select between menu items analysis method 412105, calibration curve 412112, background correction 412113, limits of detection 412114, and confirm 412115. Upon selecting analysis method at 412105 a second menu is presented including options to select from recent analysis methods at 412106 or available analysis methods at 412107. A default may be recent analysis method at 412106. The MUI may auto-transition to all analysis methods at 412109 if recent analysis methods at 412106 is empty. At 412106, on selection of recent analysis methods, a user is presented a configurable amount, for example twenty five, of the most recently used analysis methods at 412108 as returned from a service request made via the cloud platform. Alternatively, selection of available at 412107 presents to a user a new execution menu of all analysis methods at 412109 as returned from a service request made via the cloud platform with the analysis methods organized by system-provided default analysis methods and user-provided analysis methods, enabling a user to browse the various analysis methods and to select the analysis method of choice. On selection of an analysis method at the execution menus 412108 or 412109 the user interface returns to the first menu at 412104, presenting the options of configuring calibration curve at 412112, background correction at 412113, and limits of detection at 412114. In embodiments, calibration curve at 412112 is the default, and the MUI is configured to walk the user through the subsequent menus 412112, 412113, and 412114 as the user executes a selection in each. On selection of calibration curve at 412112 a user is given options on the view to select an algorithm from the available set being system-provided algorithms 4PL, 5PL, Linear, Log-Log, Exponential, or any other algorithm potentially provided by the system, as well as, any user-provided algorithms.

The 4PL algorithm may be calculated as $$y = b_1 + \frac{b_2 + b_1}{1 + (x/b_3)^{b_4}}$$

where y is the response signal from a plate reader, x is the concentration, b1 is maximum response plateau or calculated top, b2 is minimum response plateau or calculated bottom, b3 is concentration at which 50% of the maximal response is observed or calculated mid-point, and b4 is the slope or shape parameter or calculated Hill Slope The 5PL algorithm may be calculated as $$y = b_1 + \left(\frac{b_2 + b_1}{1 + (x/b_3)^{b_4}}\right)^{b_5}$$

where y is the response signal from a plate reader, x is the concentration, b 1 is maximum response plateau or calculated top, b2 is minimum response plateau or calculated bottom, b3 is concentration at which 50% of the maximal response is observed or calculated mid-point, and b4 is the slope or shape parameter or calculated Hill Slope, and b5 is asymmetry factor or calculated asymmetry factor.

The Linear algorithm may be calculated as $y=mx+b$ where y is the response signal from a plate reader, x is the concentration, m is the slope or calculated Hill Slope, and b is y-axis intercept or calculated y intercept.

The Log-Log algorithm may be calculated as $\log_{10}(y)=m(\log_{10}(x))+b$ where y is the response signal from a plate reader, x is the concentration, m is the slope or calculated Hill Slope, and b is y-axis intercept or calculated y intercept.

The Exponential algorithm may be calculated as $y=ae^{bx}$ where y is the response signal from a plate reader, x is the concentration, a is plate reader response signal at minimum response or calculated y intercept, and b is a constant describing the magnitude of increase or decrease or Hill Slope; with selection of an algorithm making it the default for the analysis method being configured.

On selection of an algorithm in calibration curve at 412112, a user may then define a weighting factor for the chosen algorithm to be used in calculations to compensate for the differences in magnitude of the residuals at low and high analyte concentrations with options $1/y^2$, $1/y$, or none; then a user may choose input signal with options to use from the calibrators the raw input signal or the background-corrected signal; and finally a user defines to calculate replicates either individually or as an average of the replicates.

At 412113 a user is provided a view for selection of background detection configuration provides options for a user each for calibrators, controls, and unknowns (i.e., samples under test) where a user may choose to do no signal correction or in calculating a corrected signal the software would adjust the raw signal from a plate reader by subtracting or dividing it by the background count of the plate reader. At 412114 the selection of limits of detections provides options for a user in determining the limits of detection using the standard deviation of the high and low calibrators or as a percentage of the ECL counts above or below the high and low calibrators.

At 412115 selection of confirm by a user presents a user the option to use a system-provided name for the new analysis method or provide their own name and accept the new analysis method for inclusion in the set of user-provided analysis methods with any changes to the analysis method at 412112, at 412113, and/or at 412114 resulting in a service request made via the cloud platform creating a new analysis method as defined for a user's current team database and a user transitioning at 412116 back to start at 412102.

A user may also confirm at 412115 or, in any other step along the flow, reject their changes to the analysis method and return to start at 412102 not creating a new analysis method. Although these embodiments describe plate-based tests and/or experiments, the methods described herein can be applied in the alternative to the review of other experiments and tests in the alternative.

In FIG. 42A is an embodiment of a user experience flow through an assay method module focused on designing an assay method beginning with bioanalytical user app at 922200 running on a user's computer with each step through a user interface numbered sequentially 1 through 'n' to represent the stepwise flow from begin (1) to end ('n') for a user as depicted in bioanalytical user app at 922200 being labelled "1." as the first step. The user experience flow of FIG. 42A may be implemented via a MUI as discussed herein.

Figure 42B:
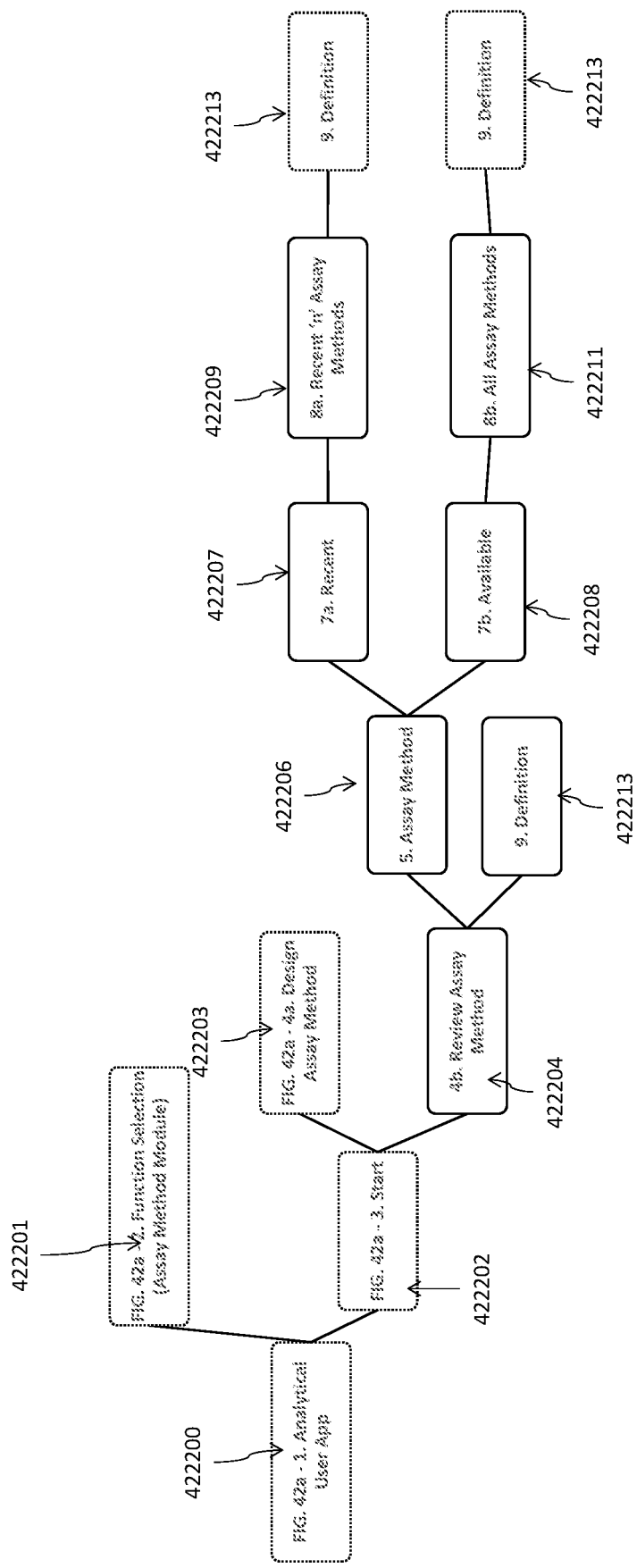
FIG. 42B illustrates the review flow for an assay method module in an analytical user app in an embodiment.

At 922201 a user may select a user interface mechanism presenting one or more options including but not limited to module-specific functions, modules to select, and/or system functions being either a horizontal menu and/or toolbar, a vertical menu and/or toolbar, a dropdown menu and/or toolbar, a keyboard function, a voice-activated command, and/or any other like user interface mechanism to choose an option, choosing assay method module. On selection of assay method at 922201 the application transitions at 922202 to the start of the assay method module presenting at 922203 and at 922204 an option to design an assay method or review an assay method. If the user opts for design assay at 922203, the flow continues as discussed below. FIG. 42B shows the process flow after 92204 is selected. On selection of design at 922203 a user may be presented a next menu including manual assay method at 922206 and automated assay method at 922205.

Should the user select manual assay an assay method at 922206, they are presented options to select from recent assay methods at 922207 or available assay methods at 922210. The default is recent assay methods at 922207 and the MUI may autotransition to all assay methods at 922211, the recent assay methods are empty as returned from a service request made via the cloud platform. At 922207 on selection of recent assay methods, a user is presented a configurable amount, for example twenty five, of the most recently used assay methods at 922208 as returned from a service request made via the cloud platform. Alternatively, selection of available assay methods at 922210 presents to a user all assay methods at 922211 as returned from a service request made via the cloud platform. The assay methods are organized by source, such as, but not limited to an overall catalog of available assay methods, purchased consumables associated with available assay methods, and by each username those who have created new assay methods, then the consumable family that organizes assay methods based on a common use model, and then assay method name, enabling a user to efficiently browse the various assay methods and to select the assay method to base their new assay method design.

On selection of a specific assay method at either 922208 or 922211 the user interface transitions to 922213 to present the user the assay configuration on the test plate associated with the assay method as returned from a service request made via the cloud platform, wherein the user may alter the test plate and assay assignment using either purchased assays or user-provided assays to various spots in a well on the associated type of test plate, including being able to disable desired assay assignments, and on completion of edits to the assay configuration a user will select layout at 922214 storing the changes via web service(s) on the cloud platform before transitioning. At 922214 a user is presented a graphical representation of a test plate and a visual representation of where on the test plate, i.e., which spots in which wells, various types of samples are allocated, which is key for properly processing an assay method on a test plate. In the layout menu at 922214, the user is presented items to select previously defined layout of samples on a plate at 922215 or an edit layout function at 922223. The previously defined layout selection at 922215 provides recently used layouts at 922216 as a carousel of plates with the sample layout and layout name being a configurable set of up to but not intended to limit to 25 layouts or all available layouts at 922219. A user, may, from the select layout menu at 922215, also select to create a new layout from scratch at 922222, which advances the user to the edit layout function at 922223.

On selecting a layout at 922217 or 922220 a user transitions back to 922214 to see the selected layout. Anytime a user transitions to layout at 922214 they may edit the layout via edit layout at 922223.

On choosing to edit layout at 922223, a user is presented a collection of options of equal importance to enable a user efficiently navigating to various options requiring attention. Thus, these options may be presented as a series of concurrently adjustable menus. At 922224 a user may configure parameters associated with calibrators used in the assay method, most notably, the number of calibrators and number of replicates which dictates how many wells on the test plate will be taken up calibrators. At 922226 a user may configure parameters associated with controls used in the assay method, most notably, the number of controls and number of replicates which dictates how many wells on the test plate will be taken up controls. At 922228 a user may configure parameters associated with blanks used in the assay method representing the expectation of very low signal purposefully, most notably, the number of blanks and number of replicates which dictates how many wells on the test plate will be taken up blanks. At 922229 a user may configure parameters associated with a samples used in the assay method representing a placeholder for samples that will be tested when this assay method is used in an experiment, most notably, the number of samples and number of replicates which dictates how many wells on the test plate will be taken up samples, by default samples take up all remaining wells on the plate after accounting for calibrators and/or controls and/or blanks but a user is enabled to set a specific number at or below the maximum number of unused wells on the test plate.

On completing configuration of the various types of samples that are expected to be on a test plate for the assay method, a user at 922230 may edit the layout of the different sample types on the test plate, manipulating where wells are located by either moving rows in total and/or columns in total and/or moving individual sample types assigned to a well. A user may then select to define one or more groups at 922231 to provide one or more name groups that subdivide a test plate into one or more sub-plates each named as a user provides at 922231.

Once groups are defined at 922224, at 922226, at 922228, and at 922229 each group may have a sub-definition associated with them per the number of defined and named groups for which a user may configure or not one or more of the prescribed sampled types, with an additional capability to assign to assign to one group the calibration curve of another group to allow sharing of calibrators across one or more groups on the plate and one more additional capability to assign blanks in one group to allow sharing of blanks across one or more groups on the plate. On completion of all of the edits under layout at 922214, a user may select a confirm option at 922232. Although this option is shown as a submenu of the edit layout function at 922232, it may also be accessible as a submenu of the layout function at 922214

At 922232 a user is presented a summary view of the layout for the assay method they have designed enabling a user to navigate to a previous steps to alter any decisions they made in the process of designing the layout and if all their decisions are in line with their expectations they would select confirm storing their layout via web service(s) to the cloud platform for future use in an experiment and on completion of the invocation of web service(s) the MUI transitions back to the assay menu at 922213, where the user may further select assay analysis methods at 922233.

At 922233 a user is presented the assignment of analysis methods to either the assay method and/or the one or more assays assigned to the assay method with the option to select a particular analysis to canvas all assays in the assay method, that on selection automatically applies the chosen analysis method to all assays in the assay method. A user may also alter the analysis method for any or all individual assays in the assay method by choosing the analysis method assigned to an assay with the user interface presenting the available system-default analysis methods as well as any user-provided analysis methods from which the user chooses the desired analysis method for the assay. A user may use this previously disclosed mechanism of analysis method selection for selecting an analysis method at the assay method level to assign the same analysis method to all assays in the assay method.

On completion of analysis method assignment at 922233 a user may select protocol configuration at 922234 with the software automatically storing the user's selections via web service(s) on the cloud platform before transitioning at 922234. At 922234 a user is presented the various parameters associated with the processing of the assay method either on a coordinated-operation instrument or manually leveraging one or more individual-operation instrument. The parameter set would be instrument specific but could include but not intended to limit to incubation time(s), wash cycle(s), read buffer incubation(s), reagent addition(s), and/or any other step in the processing of a protocol that could be parameterized and configured. In some embodiments, an assay method may have no protocol defined for it and therefore this step may be not shown to a user for an assay method with no protocol. On completion of protocol configuration at 922234 a user may select confirm at 922235, although this is shown as a submenu of the protocol menu at 922234, it may also be accessible as a submenu of the assay menu at 922213, with the software automatically storing the user's selections via web service(s) on the cloud platform before transitioning at 922235. At the confirmation menu of 922235 a user is presented a summary view of the assay method they have designed to confirm they made all the right choices, enabling a user to navigate to a previous steps to alter any decisions they made in the process of designing the assay method and if all their decision are in line with their expectations they may select confirm storing their assay method via web service(s) to the cloud platform for future use in an experiment and on completion of the invocation of web service(s) the user interface would transition back to start at 922202.

In further embodiments, an assay method module may operate as follows. A first menu may be a design assay menu. Upon selection the design assay menu is relocated to the historical portion and a second menu is presented providing a user with an option to select a manual assay method or an automatic assay method.

Selecting manual assay method provides a third menu including recent assay methods and available assay methods as options.

Selecting recent assay method provides a third menu including names of recent assay methods. Selecting an assay name moves the assay to the historical portion and provides a new current assay design menu including "assay," "layout," "analysis method," and "confirm," menus. The assay menu provides, in sub-portions of the active portion, multiple sub-portions. A first sub-portion provides spot layout and lists of assays by spot assignment (i.e., test sites) in the selected method applied to an editable list of analytes. The first sub portion may include, test plate type on a horizontal wheel, e.g., 96 Wells 1 Small Spot, 96 Wells 1 Small Spot High Bind, 96 Wells 1 Small Spot Q, 96 Wells 1 Spot, 96 Wells 1 Spot High Bind, 96 Wells 1 Spot Q, 96 Wells 10 Spot, 96 Wells 10 Spot High Bind, 96 Wells 10 Spot Q, 96 Wells 10 Spot Q High Bind. If a 10-plex plate is chosen in the first sub-portion, then a middle sub-portion appears that lists 1-PLEX-10-PLEX. If a 10-plex plate is not chosen, then a right-side subportion appears that lists assays, which can be searchable depending on highlighted assay method or existence of unassigned spot position in first subportion. The layout menu provides a plate layout showing where sample types are located. The analysis menu provides a subsequent menu having subportions allowing a user to select from a first sub portion listing assays in the selected assay method and algorithm types for each assay in a second subportion. The confirm menu shows, in a first subportion a spot layout and list of assays by spot assignment in selected assay method and, in a second sub portion, assay method name, plate layout, and a confirm option.

Selecting available assay options provides a third menu showing multiple subportions. The first subportion presented the options of assays purchased from consumable manufacturer ("MSD Purchased"), available from consumable manufacturer ("MSD Catalog"), and usernames. The second subportion provides assay method types filtered by the highlighted item in first subportion: Bio-dosimetry, Custom Sandwich Immunoassay, Immunogenicity, PQ, Pharmacokinetic, S-PLEX, U-PLEX, U-PLEX Dev Pack, Utility, V-PLEX, where Utility is less than an entire assay protocol performed by an automated instrument; e.g., wash, add read buffer, read; or add read buffer, read. The third sub-portion provides assay methods filtered by highlighted item in first and second subportions. After selection of an assay method via this process, a new menu is provided according to the assay design menu as described above.

If, at the second menu, the user selects automated assay method, they are provided with a choice between recent assay methods and available assay methods, as described above. The only difference in the "available assay methods" flow as compared to the recent assay methods flow is in the protocol menu, described below.

Selecting recent assay methods provides a third menu including names of recent assay methods. Selecting an assay name moves the assay to the historical portion and provides a new current assay design menu including "assay," "layout," "analysis method," and "confirm," menus similar to those described above. The assay design menu also includes a protocol menu option.

The protocol menu option provides options for a coating menu, blocking, capture, detection, detection incubation, and secondary detection incubation. The coating menu provides options in a first subportion for Enable Coating, Wash Before Coating Step, Linker Volume, Capture Antibody Volume, Stop Solution Volume, Coating Species Volume, Volume of Diluent in Capture Blend, Coupled Antibody Volume in Blend, Coating Blend Dispensed Per Well, Coupling Incubation Duration, Stopper Incubation Duration, Coating Incubation Duration, with On/Off toggle or adapted to be editable to enter a number. The coating menu provides a second subportion that appears for editing numbers related to the first subportion. The blocking menu provides a first subportion for Enable Blocking, Wash Before Blocking Step, Blocking Volume, Blocking Incubation Duration, with On/Off toggle or adapted to be editable to enter a number. The blocking menu provides a second subportion that appears for editing numbers related to the first subportion. The capture menu provides a first subportion: Assay Volume, Wash Before Test Plate Incubation, Sample Incubation Duration, Test Plate Incubation Duration, with On/Off toggle or adapted to be editable to enter a number. The capture menu provides a second subportion that appears for editing numbers related to the first subportion. The detection menu provides a first subportion: Detect Volume, Detection Incubation Duration, with On/Off toggle or adapted to be editable to enter a number. The detection menu provides a second subportion that appears for editing numbers related to the first subportion. The detection incubation menu provides a first subportion: Wash Before Detection Step, Detection Species Volume, Detection Incubation Duration, with On/Off toggle or adapted to be editable to enter a number. The detection incubation menu provides a second subportion that appears for editing numbers related to the first subportion. The secondary detection incubation menu provides a first subportion including Enable Secondary Detection, Wash Before Secondary Detection Step, Secondary Detection Species Volume, Detection Incubation Duration, with On/Off toggle or adapted to be editable to enter a number. The secondary detection incubation menu provides a second subportion that appears for editing numbers related to the first subportion. The read buffer menu provides a first subportion: Read Buffer Volume, Read Buffer Incubation Duration, with On/Off toggle or adapted to be editable to enter a number. The read buffer menu provides a second subportion that appears for editing numbers related to the first subportion.

In FIG. 42B is an embodiment of a user experience flow through an assay method module focused on reviewing an assay method beginning with analytical user app at 422200 running on a user's computer with each step through a user interface numbered sequentially 1 through 'n' to represent the stepwise flow from begin (1) to end ('n') for a user as depicted in analytical user app at 421100 being labelled "1." as the first step. The experience flow of FIG. 42B may be facilitated by a MUI as discussed herein. At 422201 a user may select a user interface mechanism presenting one or more options including, but not limited to, module-specific functions, modules to select, and/or system functions being either a horizontal menu and/or toolbar, a vertical menu and/or toolbar, a scroll-wheel menu and/or toolbar, a dropdown menu and/or toolbar, a scroll-wheel menu and/or toolbar, a keyboard function, a voice-activated command, and/or any other like user interface mechanism to choose an option, choosing assay method module. On selection of assay method at 422201 the MUI transitions at 422202 to the start of the assay method module presenting a first menu including options at 422203 and at 422204 an option to design an assay method or review an assay method respectively. The illustrated workflow shows the results of a selection of 422204, to review an assay method, with the user in this case choosing to review at 422204.

On selection of review at 422204 a user is requested to choose an analysis method at 422206 from a next menu presenting options including recent assay methods at 422207 or available assay methods at 422208. The default may be recent assay method at 422207. The MUI may auto-transition to all assay methods at 422208, if recent at 422207 is empty as returned from a service request made via the cloud platform. On selection of recent assay methods at 422207, a user is presented a configurable amount, for example twenty five, of the most recently used assay methods at 422209 as returned from a service request made via the cloud platform. Alternatively, selection of available at 422208 presents to a user all assay methods at 422211 as returned from a service request made via the cloud platform. The assay methods may be organized by the source they are from, including, but not limited to, an overall catalog of available assay methods, purchased consumables associated with available assay methods, and by each username those who have created new assay methods, then the consumable family that organizes assay methods based on a common use model, and then assay method name, enabling a user to efficiently browse the various assay methods and to select the assay method to base their new assay method design. On selection of an assay method at either 422211 or 422209, the MUI transitions to 422213 to present the user a summary graphical view of the layout for a plate to be used in an experiment using the assay method's definition as returned from a service request made via the cloud platform. The display at 422213 may also be reached from the review assay method menu at 422204, where it will display a currently selected menu. Although this embodiment describes methods for performing assays and/or plate-based experiments, other experiments and tests are contemplated as well.

Figure 43A:
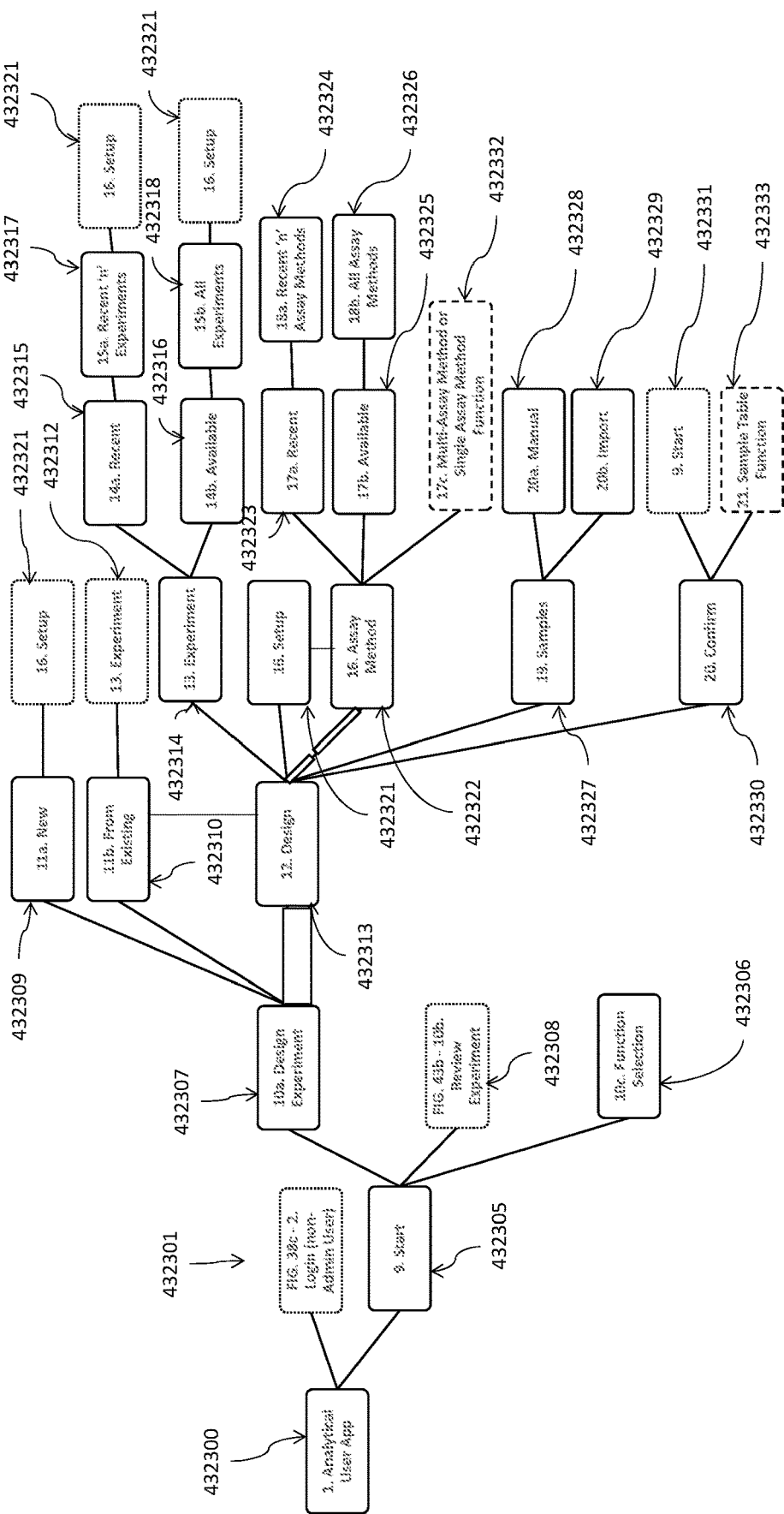
FIG. 43A illustrates the design flow for an experiment module in an analytical user app in an embodiment.

In FIG. 43A is an embodiment of a user experience flow through an experiment module focused on experiment design beginning with analytical user app at 432300 running on a user's computer with each step through a user interface numbered sequentially 1 through 'n' to represent the stepwise flow from begin (1) to end ('n') for a user as depicted in logical user app at 432300 being labelled "1." The user experience flow of FIG. 43A may be managed by a MUI as discussed herein. The experiment module may be implemented via a methodical user interface control system 1102 operating as part of or in conjunction with the analytical user app 432300. The experience flow of FIG. 43A may be facilitated via a MUI as described herein.

At 432301 a user is logging into the analytical user app 432300. After the login process the user interface transitions to start at 432305 since the experiment module is envisioned in this embodiment to be the default first module after a user logs in, where now the user has a menu of three options including either 1) design an experiment at 432307, 2) review an experiment at 432308, or 3) select a user interface mechanism at 432306. The user interface mechanism at 432306 permits a user to adjust a user interface by presenting one or more options including, but not limited to, module-specific functions, modules to select, and/or system functions being either a horizontal menu and/or toolbar, a vertical menu and/or toolbar, a scroll-wheel menu and/or toolbar, a dropdown menu and/or toolbar, a keyboard function, a voice-activated command, and/or any other like user interface mechanism to choose an option. The review experiment option at 432308 provides a workflow as discussed below with respect to FIG. 43B.

In choosing to design an experiment at 432307, the MUI transitions to a second (or next) menu with the user asked to choose to design at new experiment at 432309 or use a previous experiment at 432310 on which to base the new experiment.

On selection at 432309 of a new design, the MUI transitions to a design setup menu at 432321 (discussed further below).

On selection at 432310 of an existing design, the MUI transitions to design at 432313. The design menu at 432313 asks the user to choose an experiment at 432314 with options to select from recent experiments at 432315 or available experiments at 432316. The default is recent experiments at 432315 but the MUI may auto-transition to all experiments at 432318 if recent experiments at 432315 is empty as returned from a service request made via the cloud platform. At 432315 on selection of recent experiment, a user is presented a configurable amount, for example twenty five, of the most recently ran experiments at 432317 as returned from a service request made via the cloud platform. Alternatively, selection of available at 432316 presents to a user all experiments at 432318 as returned from a service request made via the cloud platform with the experiments organized by username and/or email address, date and time of creation, and experiment name, enabling a user to browse the various experiments and to select the experiment on which to base the new experiment.

On selection of an experiment at either 432317 or 432318 the MUI transitions back to the design menu at 432313 and auto-highlights design setup at 432321 as a next step. At 432321 a user is provided options to name an experiment starting with a unique default name provided by the system, for example but not limited to, a concatenation of username, date, and timestamp, that a user may edit, as well as choosing whether the experiment will be performed on a coordinated-operation instrument (also referred to as automation) or an individual-operation instrument(s) (also referred to as manual). On a user making their decisions at 432321 the user interface advances to assay method selection at 43232, which asks the user to choose an assay method with options to select from recent assay methods at 432323 or available assay methods at 432325. The default is recent at 432323, but the MUI may auto-transition to all assay methods at 432326 if recent at 432324 is empty as returned from a service request made via the cloud platform. At 432322 on selection of recent at 432323, a user is presented a configurable amount, for example twenty five, of the most recently used assay methods at 432324 as returned from a service request made via the cloud platform. Alternatively, selection of available at 432325 presents to a user all assay methods at 432326 as returned from a service request made via the cloud platform with the assay methods organized by the source being from but not limited to an overall catalog of available assay methods, purchased consumables associated with available assay methods, and by each username those who have created new assay methods, then the consumable family that organizes assay methods based on a common use model, and then assay method name, enabling a user to efficiently browse the various assay methods and to select the assay method to be used with the new experiment.

By default, an experiment may have assigned to it one assay method. But while choosing the assay method a user could select at 432306, the function selection (as used herein, the "function selection" menus of various embodiments refer to advanced context menus) to view an option to allow the experiment to have defined for it multiple assay methods that on selection initiates the action at 432332 to enable a user to select more than one assay method for an experiment and conversely toggle back to single assay method selection, where multiple assay method selection is used to broaden even further the assays to run against a collection of samples with the potential to limit the number of assay methods that may be selected and/or not limit the number of assay methods that may be selected dependent on operational constraints of available instruments or arbitrary limits a user may want to place on an experiment. Once a user has completed selecting the assay methods for the experiment, the user interface is transitioned to sample definition at 432327 where the user is presented with options either to enter the number of samples to test at 432328 with the system auto-generating sample identifiers from 1 to the number of samples the user has entered limited by the sample configuration in the selected assay method(s) or to import sample definition from an import file as provided by an external system at 432329. On manual sample definition at 432328 or import of samples at 432329, the user interface transitions to the final design step of confirming the experiment is ready to process at 432330. At 432330 a user is presented with the collection of one or more plates dependent on the number of samples being processed using the one or more selected assay methods, where each plate is assigned one assay method with an assigned set of samples to be processed on the respective plate, with a user being able to view the sample assignments to plates through a function at 432333 initiated through the function selection at 432306 and on completion returning at 432330. If a user selects one assay method for an experiment then the defined samples will result in one or more plates each with the same assay method where the samples are distributed from 1 to whatever the number defined or imported resulting in however many plate-assay method pairings are required to be able to process the total set of samples defined to create a run of plates-assay methods-samples, but the number of plate-assay method pairings could be limited by the type of experiment, automated or manual, being selected in setup at 432321 dependent on physical or arbitrary constraints placed on the system. If a user selects more than one assay method for an experiment then the defined samples will be limited to the least number of samples provided for in any of the selected assay methods where the samples are distributed from 1 to the least number of samples provided for in any of the selected assay methods on each plate that has for each plate-assay method pairing based on the selected assay methods of the experiment to create a run of plates-assay methods-samples. In either the single assay method or multiple assay method experiment, the samples to test could result in more than one run of plates-assay-methods-samples; such that, there could be no limit on the number of samples a user defined for an experiment where each run of plates-assay methods-samples would be repeated to cover the complete processing of the full set of samples defined. Once a user has established the designed experiment is as expected they would select the confirm function on the user interface at 432330 that on selection creates the experiment ready to be processed by a team through a service request made via the cloud platform and at 432331 the user interface transitions back to start at 432305. Setup components shown at 432311, 432312, 432319 and 432320 function similarly to 432321. In the alternative, the analytical user app can assist in performing other experiments in addition to or in place of the assay experiments and/or plate-based tests described herein.

Figure 43B:
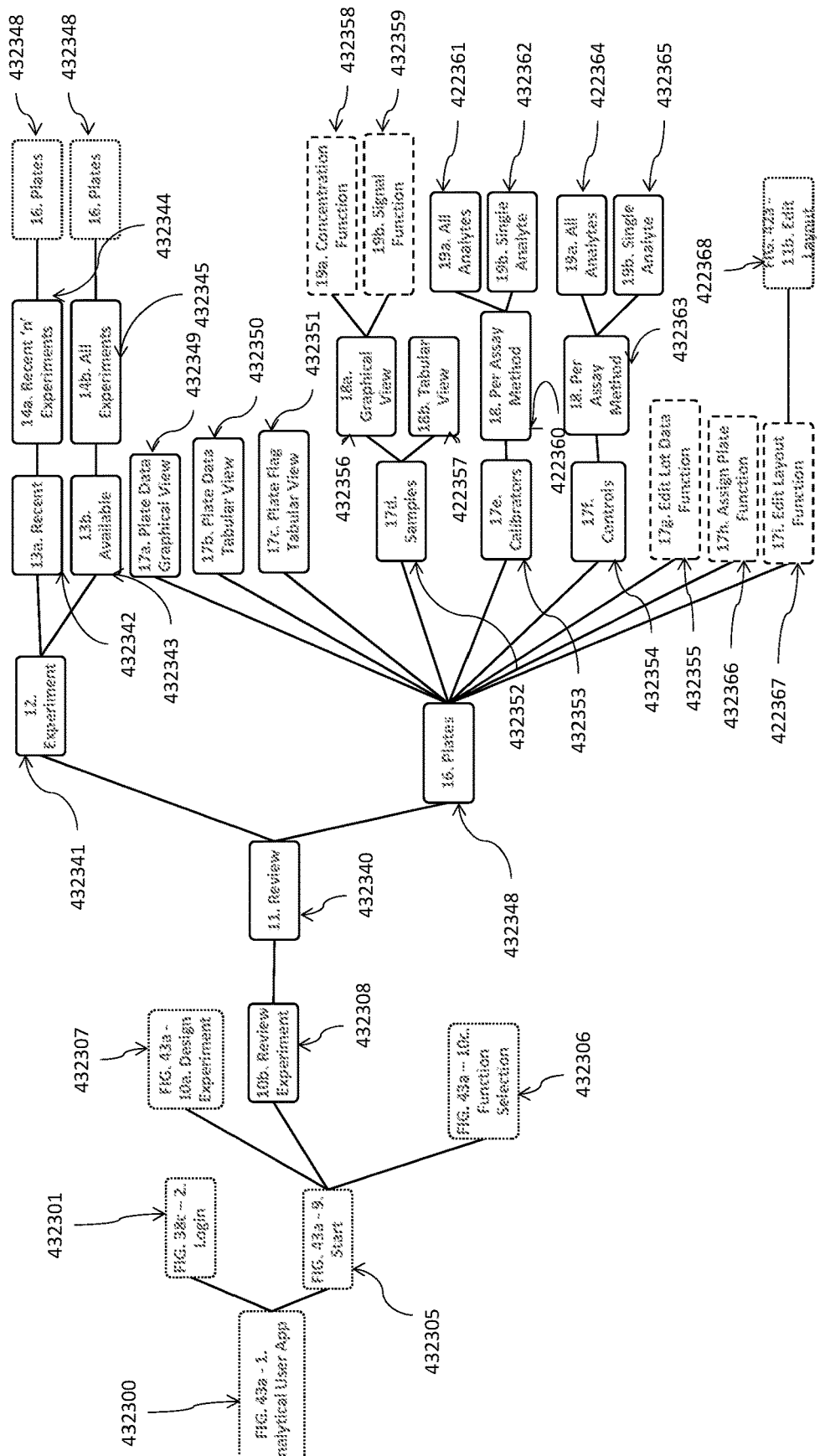
FIG. 43B illustrates the review flow for an experiment module in an analytical user app in an embodiment.

In FIG. 43B is an embodiment of a user experience flow through an experiment module focused on reviewing an experiment beginning with analytical user app at 432300 running on a user's computer with each step through a user interface numbered sequentially 1 through 'n' to represent the stepwise flow from begin (1) to end ('n') for a user as depicted in analytical user app at 432300 being labelled "1." as the first step. The experience flow of FIG. 43B may be facilitated by a MUI as discussed herein. At 432301 is a login user step. After the login process the user interface transitions to start at 432305 since the experiment module is envisioned in this embodiment to be the default first module after a user logs in, where now the user has three options either 1) design an experiment at 432307, 2) review an experiment at 432308, or 3) select a user interface mechanism at 432306. The user interface mechanism at 432306 presents one or more options including, but not limited to, module-specific functions, modules to select, and/or system functions being either a horizontal menu and/or toolbar, a vertical menu and/or toolbar, a scroll-wheel menu and/or toolbar, a dropdown menu and/or toolbar, a keyboard function, a voice-activated command, and/or any other like user interface mechanism to choose an option.

In choosing to review an experiment at 432308, the MUI transitions the application to 432340 and presents the user with a first menu permitting a user to select review of experiments at 432341 or of specific plates at 432348. Upon selecting experiments at 432341, a next menu permitting a user to select from recent experiments at 432342 or available experiments at 432343 is presented. The default may be recent experiments at 432342 but may auto-transition to all experiments at 432345 if recent experiments at 432344 is empty as returned from a service request made via the cloud platform.

At 432342, on selection of recent experiments, a user is presented with a configurable amount, for example twenty five, of the most recently ran experiments at 432344 as returned from a service request made via the cloud platform. Alternatively, selection of available at 432343 presents to a user all experiments at 432345 as returned from a service request made via the cloud platform. The experiments may be organized by username, date and time of creation, and experiment name, enabling a user to browse the various experiments and to select the experiment to view. On selection of an experiment either at 432344 or at 432345, the MUI transitions to review plates associated with the chosen experiment at 432348.

At 432348 a menu presents a collection of one or more plates in the order of the addition to the experiment and labeled with the assay method name assigned to the plate. Accessing the plates menu after selection of experiments serves as a filter to the plates menu, and only those plates corresponding with the selected experiment will be displayed. On selection of a plate at 432348 the MUI transitions to offer a next menu permitting a user to select from a plate data graphical view at 432349, a plate data tabular view at 432350, a plate flag tabular view at 432351, a sample menu at 432352, a calibrators menu at 432353, a controls menu at 432354, and execution menus for editing lot data function at 432355, assigning plate function at 432366, and editing layout function at 422367. Selection of 432349 causes the MUI to present the selected specific plate in the experiment with a heat map representation of signal or calculated concentration if available for all assays (or spots) in the assay method in each well of the plate, where a user may choose a particular assay to view narrowing down the data to just that one assay and a user may select a particular well to see the specific signal value for a sample in the selected well for the selected assay while being able to change the high and/or low signal or concentration range for the plate to alter the intensity of the heat map across all samples visible on the plate. In addition to viewing a heat map of a plate at 432349, a user has other options available for viewing plate data at 432350, at 432351, at 432352, at 432353, and at 432354. At 432350 a user is presented a well-by-well table view of the data presenting but not limited to sample identifier, assay, signal (log and linear), concentration (log and linear) if available, and statistics associated with the generated data. In embodiments, the columns presented in the table of data may include: Plate, Sample, Assay, Well, Spot, Dilution, Conc., Conc. Unit, Signal, Adj. Signal, Mean, Adj. Signal Mean, CV, Calc. Conc., Calc. Conc. Mean, Calc. Conc. CV, % Recovery, % Recovery Mean. Each of the data presentations at 43249-432354 may be presented in the active portion in three subportions. The first subportion may allow the user to select spots from a visual representation of a well. The second subportion may allow the user to select wells from a visual representation of a plate. The third subportion may provide data from the selected spot. At 432351 a user is optionally presented a table view of flags denoting abnormal events that may have occurred during processing of one or more plates potentially bringing the data's quality into question for a user, only available to a user if there was at least one flag generated for a plate. At 432352 a user may select a scatter plot at 432356 of sample signal or concentration, if available, for each assay on all of the plates and may select to switch viewing signal or concentration, if available, through a toggle function at 432358 and at 432359. At 432352 a user may also select to view the data in tabular form at 432357. At 432353 a user is presented calibration curve plots one assay method at a time with one plot for each assay in the assay method if the assay method is using an analysis method that produces sample concentrations with up to five plates visible on each plot providing a user interface mechanism to enable a user to change the five visible plates if there are more than five plates. The user may further select the option at 432360 to change the assay method for which to view the calibration curves and additionally select the option to drill down on a particular assay calibration curve plot at 432362 to expand that plot to see its one or more plates of visible data. Also provided is a mechanism to view a small table of signal and concentration data for one or more selected points on a curve including excluding calibrator points if a calibrator appears to have an abnormal response, as well as to select the group to view on each plate if the assay method for the viewed assay has defined for it more than one group on its plate layout. At 432354 a user is presented percent recovery plots of controls one assay method at a time with one plot for each assay in the assay method if the assay method is using an analysis method that produces sample concentrations with up to five plates visible on each plot providing a user interface mechanism to enable a user to change the five visible plates if there are more than five plates. The user is further given the option at 432363 to change the assay method for which to view the percent recovery plots and additionally providing the option to drill down on a particular assay percent recovery plot at 432365 to expand that plot to see its one or more plates of visible data, while also providing a mechanism to select the group to view on each plate if the assay method for the viewed assay has defined for it more than one group on its plate layout.

Execute menus provided at 432355 to edit provided lot-specific data associated with calibrators and/or controls, at 432356 to assign a plate manually in an experiment when the processing of an experiment cannot automatically assign processed plates to the experiment, and at 432357 to edit the layout for a specific plate being viewed in the case where a user needs to make a correction to a layout for an experiment. Supplemental functions not depicted in FIG. 43B include but are not limited to exporting various tables and/or charts for import into other software applications and copying various charts to be pasted into other software applications.

In an alternative, the analytical user app can assist in reviewing other experiments in addition to or in place of the assay experiments and/or plate-based tests described herein. Interface 12 at 432341 provides an interface that displays possible experiments associated with the analytical user app. Further, interface 14a at 432344, interface 16 at 432348 provides a visual representation of the plates associated with the experiments at interface 432344. Similarly, following interface 14b at 432345, interface 16 at 432348 provides a visual representation of the plates associated with the experiments at interface 432345. Interface 19a at 432361 and 432364 provide interfaces that display all analytes associated with a given assay method.

In embodiments, a reader module for running a designed experiment may be provided. The reader module may be adapted to allow a user to perform necessary functions, steps, and/or commands as they relate to the loading, reading, and unloading of plates, such as those used for ECL assays, although other experiments and/or assays are contemplated as well. In other embodiments, the Reader module relates to other equipment and/or instruments, such as medical equipment. By way of example, for medical equipment, the Reader module could be used for a Magnetic Resonance Imaging (MRI) device to assist doctors, other medical professionals, and/or technicians while using the machine. Other applications are contemplated as well.

Referring specifically to FIG. 43H, in certain embodiments, first portion 381821 can include a first menu of user-selectable choices including a Read choice and Review Recent Results choice (although other choices may also be included). The latter is explained in greater detail above with regard to the Experiment Module. In response to a selection of the Read command, a first portion or a second portion of the MUI display 206 is adapted to output a Play Button 432370 as shown, for example in FIG. 43C. The Play Button 432370 can be embodied as a graphical-based selectable input as shown in this figure, or it take other forms as well, including a non-graphical and/or text-based selection. When embodiment in a graphical selection, other geometric shapes may be employed in addition to the ones shown in this figure.

Figure 43D:
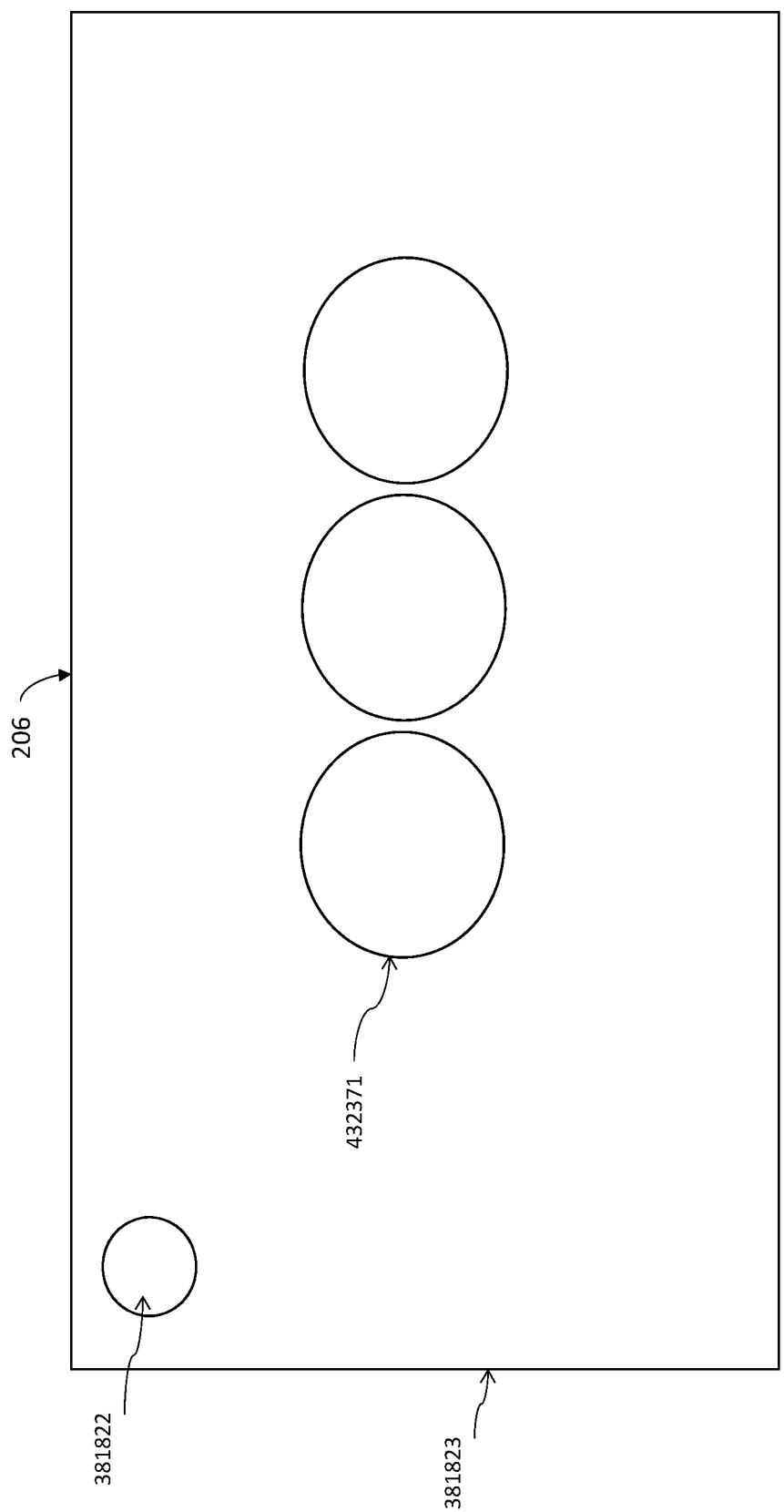

In response to a selection of the Play Button 432370, a plate reader is adapted to begin reading and/or analyzing one or more plates. The read process is described in greater detail herein in conjunction with one or more of the other modules described herein. As the one or more plates are read, the MUI display 206 is adapted to display a timer 432371 as shown in FIG. 43D. The timer 432371 is adapted to indicate, for example, in a visual representation one or more of: (a) the total amount of time to load the one or more plates; (b) the total amount of time to read the one or more plates; (c) the total amount of time to unload the one or more plates; (d) the time remaining to complete the loading of the one or more plates; (e) the time remaining to complete the reading of the one or more plates; and (f) the time remaining to complete the unloading of the one or more plates. In the embodiment shown in this figure, the timer includes three circles, each of which can provide a separate timer for the load, read, and unload processes, e.g., first, second, and third circles, respectively. In certain embodiments, the load process includes the time it takes a plate reader or other instrument to automatically load the plate to be read. Similarly, the unload process can include the time to automatically unload the plate after it has been read. Timers for these processes are not necessarily limited to automated plate-reading instruments but apply to manually fed instruments as well.

In some embodiments, the timer 432371 can toggle between a logo, e.g., a logo containing three circles, and a countdown timer wherein the perimeter of each circle be modified as time elapses to signify a countdown. For example, a completed circle can represent the beginning time and the perimeter forming the circle can be deleted in a clockwise or counterclockwise fashion to represent that time has elapsed. This can continue until the entire perimeter of the circle vanishes, representing that the entire timer has elapsed. In other examples, the perimeter lines forming the circle can fade vis-à-vis the unexpired portions of the timer as time elapses so as to illustrate that time has elapsed, while still maintaining the perimeter line of each circle. In other embodiments, rather than fading, the lines can be highlighted, and/or colored to signify how much time has elapsed, and how much time still remains for each of the load, read, and unload processes until they are complete. In other embodiments, other geometric shapes can be used for these times, either all the same, or one or more being of a different shape from the others. In some embodiments, fewer or greater than three of these geometric shapes can be utilized for the timer function.

Figure 43E:
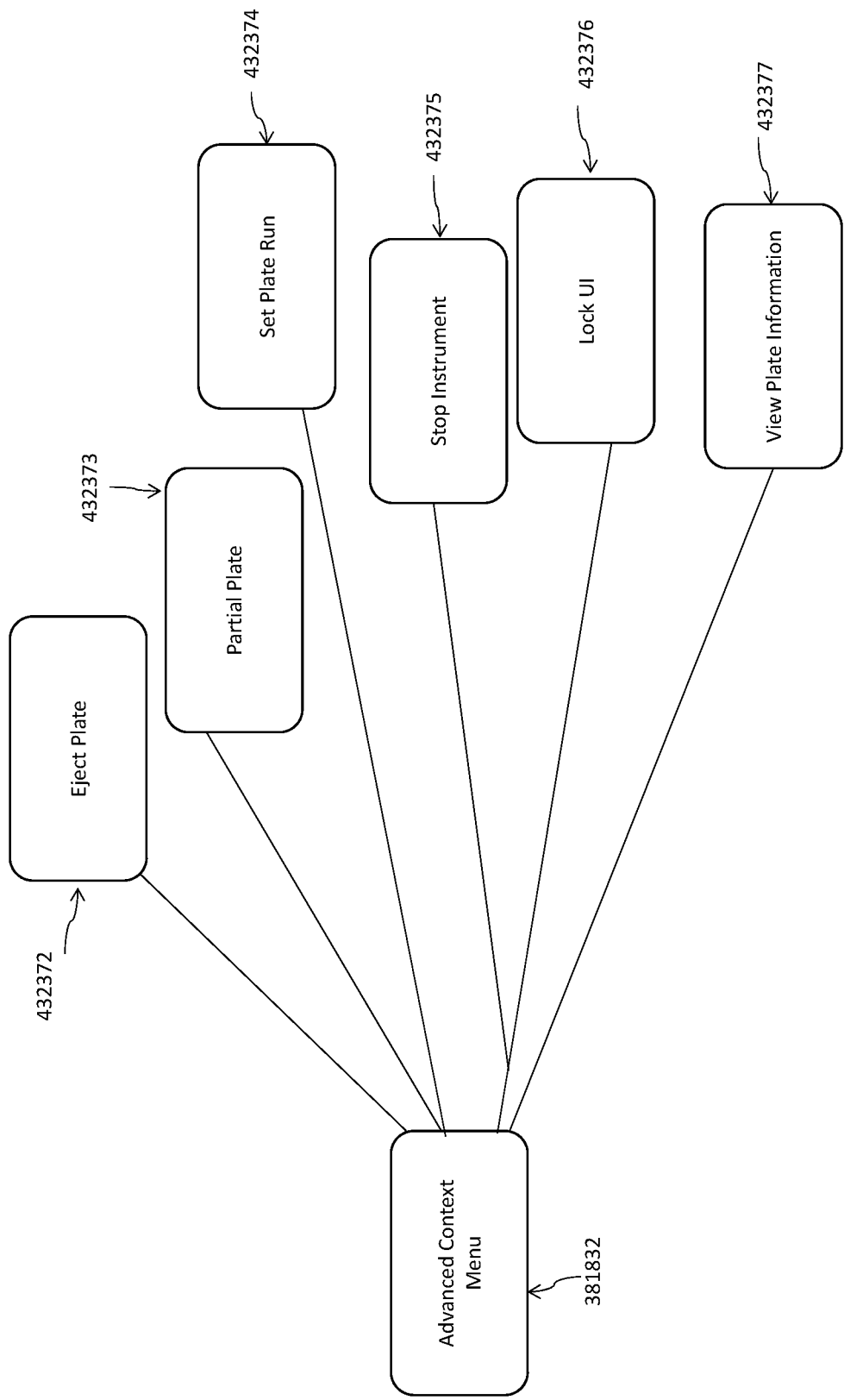
Figure 43F:
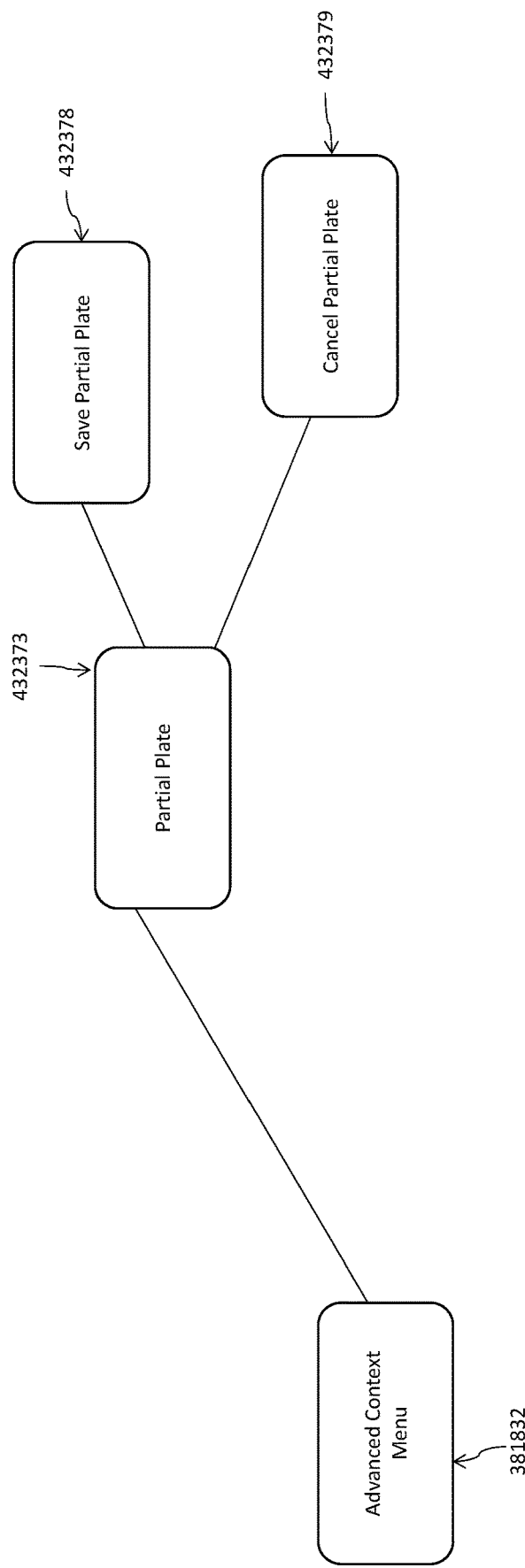
Figure 43G:
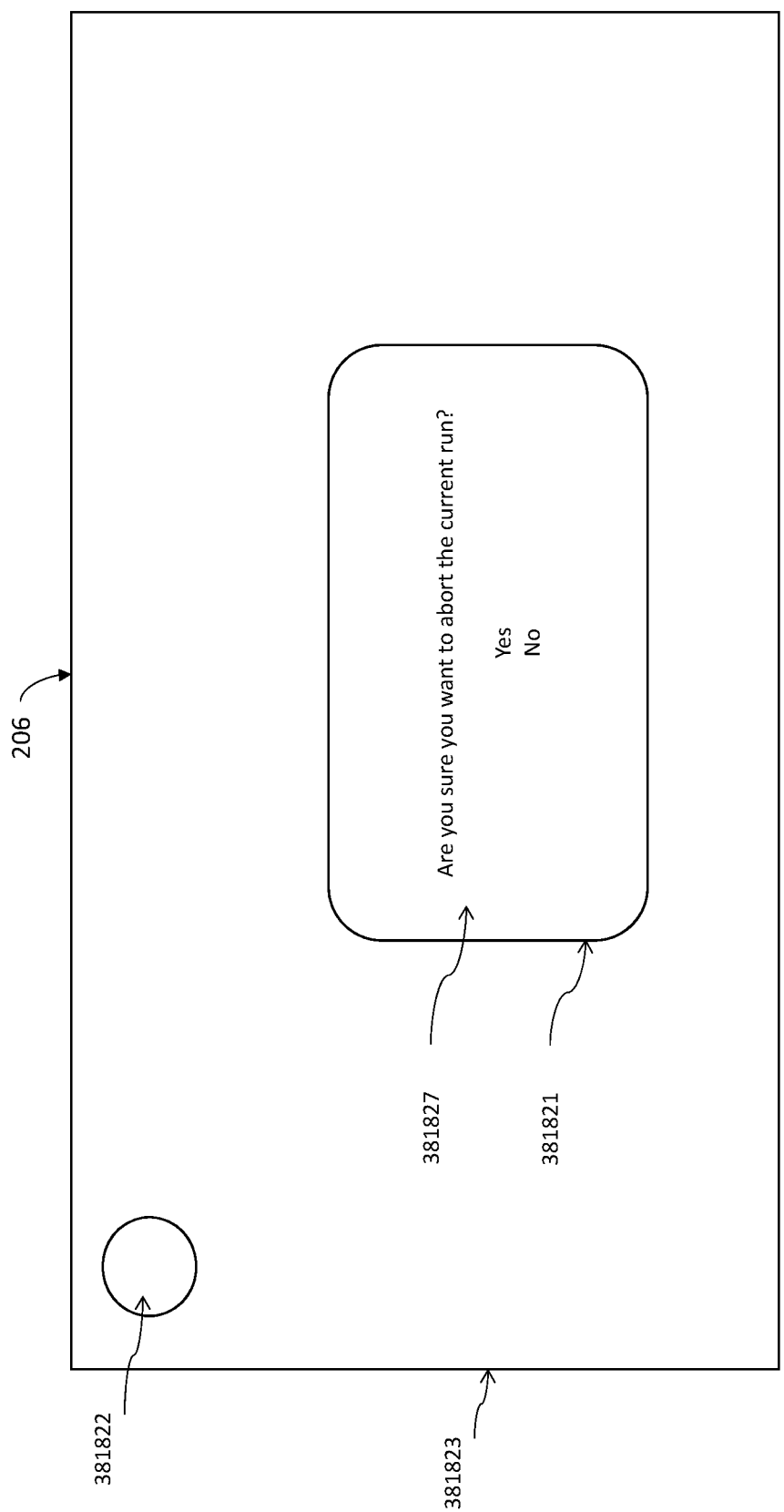

In one embodiment, as shown in FIG. 43E, the additional aspects and/or features of the Reader module can be accessed the advanced context selector 381822 as part of the advanced context menu 381832. In this example, the advanced context menu 381832 is adapted to be displayed in response to a selection of an advanced context selector 381822 (FIG. 39B) when outputted to the MUI display. When displayed, advanced context menu 381832 can include a plurality of commands and/or user-selectable choices arranged in a menu that may take the form of various configurations, as described in greater detail above in conjunction with the Audit Trail module.

The advanced context menu 381832 can include one or more commands and/or user-selectable choices. For example, for the embodiment depicted in FIG. 43E, the one or more command and/or user selectable choices can include eject plate 432372, partial plate 432373, set plate run 432374, stop instrument 432375, lock UI 432376, and view plate information 432377, although additional commands and/or user-selectable choices are contemplated as well.

In response to the eject plate choice 432372, the plate currently loaded into a plate-reading instrument is ejected. In one example, the plate is ejected automatically and fully from the plate-reading instrument. In the alternative, this eject choice can release the plate from the instrument, so that a user, such as a technical, lab manager, etc., can manually remove the plate from the plate reading instrument. In response to the partial plate choice 432373, the first portion (FIG. 43H, 381821) is adapted to receive bar code information as it relates a plate selected among one or more plates. For example, if the current plate does not contain a barcode, if the barcode itself is unreadable, or only a portion of it can be read, a user can manually input the barcode information to designate the plate that the reader module is currently working in conjunction with. This information can be inputted via a touchscreen, keyboard, or any other input manner as described herein. In other examples, the barcode could be inputted automatically with the aid of a barcode reader or the like. The first portion (FIG. 43H, 381821) is further adapted to display a user-selectable option for verifying the authenticity of the bar code information after it is received. When selected, the reader module can verify the inputted barcode against one or more of the databases, e.g., one or more of the databases described herein, of barcode information to determine if there is a match. If a match occurs, the plate can be verified. If no match occurs, the user can either try to input the barcode information again, e.g., in case of transcription error, or can elect to proceed with the unverified plate. Additionally, in response to the partial plate choice 432373, a graphical representation of the current plate can be displayed on the MUI display 206, either without regard to particular sectors, e.g., groups of wells, or on a sector basis by overlaying an outline defining one or more sectors of the plate. In further response to the partial plate choice 432373, the advanced context menu 381832 can include one or more additional commands and/or choices. For example, in the embodiment depicted in FIG. 43F, the menu can include a save partial plate choice 432378 and a cancel partial plate 432379, which can allow users to save the partial plate information or cancel the plate, e.g., terminate the current use of the plate, respectively.

In response to the set plate run choice 432374, the first portion (FIG. 43H, 381821) is adapted to receive a name for a plate run associated with a plate. For example, a user can enter, e.g., through an input device, e.g., touchscreen, keyboard etc., the name for the run associated with one or more plates that are to be read by the plate-reading instrument. In some embodiments, this information can already be encoded in the barcode, and thus, the run name will automatically populate. The run can be used for various reasons, for example to allow users to associate several plates together from a single experiment, to allow teams to more easily collaborate on experiments, assays, or analyses that involve one or more plates common to the team, etc.

In response to the stop instrument choice 432375, the first portion (FIG. 43H, 381821) is adapted to display a confirmation choice before issuing a stop instrument command. For the example shown in FIG. 43G, the first portion 381821 can include a confirmation choice 381827. This choice can be adapted to be displayed to provide one or more users with the ability to confirm whether they want to abort the current run of the plate. When presented with this confirmation choice 381827, the users can be presented with a choice as to whether they wish to abort the current run of a plate by issuing the stop instrument command, e.g., selecting "Yes" from this menu, or continuing the run by disregarding the stop instrument command, e.g., selecting "No" from the menu. These options are merely exemplary as other choices and/or command prompts are contemplated as well. If the stop instrument command is issued, the users can be automatically prompted on MUI display 206 with a menu of choice that are available in response to the Review Recent Results choices as described above, thus allowing the user to review the results of previously completed plates. In other words, in this example, by issuing the stop instrument command, the user will be directed automatically to Review Recent Results menu as described above. If the stop instrument command is disregarded, the timer 432371 (FIG. 43D) as described above can be re-displayed on the MUI display 206 throughout the remaining duration of the run in accordance with that feature as described above.

In response to the lock UI choice 432376, the MUI display 206 is adapted to be locked from user selections until receiving the current user's password. In this manner, input will be received from a user, whether it is through command and/or choice selections or other inputs, e.g., mouse clicks or scrolling, keyboard strokes, touchscreen inputs, etc., but those selects will not cause any modification to what is outputted to MUI display 206, nor will commands be received based on this user input, other than the password to unlock the MUI display 206. After this choice is selected, the MUI display 206 will remain locked throughout the duration of the plate run and will automatically unlock once the run is complete. In other embodiments, the MUI display 206 will remain locked until the current user's password is received. In response to the view plate information choice 432377, information that relates to one or more plates can be displayed. The information includes one or more of the plate run name, as described in greater detail above, plate barcode, e.g., the barcode provided by the plate manufacturer, long side customer barcode, e.g., a customer-specific barcode affixed to the long side of the plate, short side customer barcode, e.g., a customer-specific barcode affixed to the long side of the plate, plate type, e.g., single well, multi-well, assay time, coating type, etc., operator, e.g., user, team, account, etc., and read time, e.g., read time of one or more individual plates and/or total read time of the plates for a given plate run.

Figure 44:
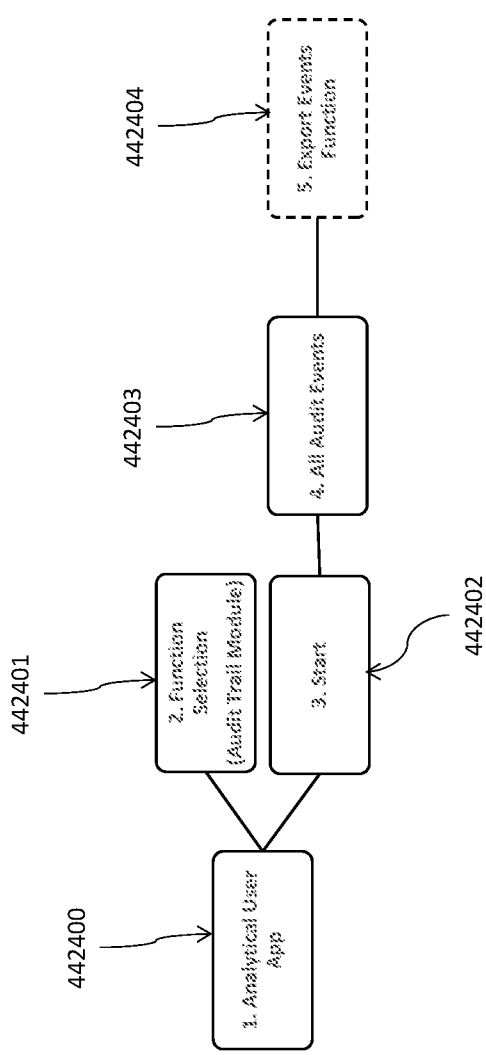
FIG. 44 illustrates the flow for an audit trail module in an analytical user app in an embodiment.

In FIG. 44 is an embodiment of a user experience flow through an audit trail module beginning with analytical user app at 442400 running on a user's computer with each step through a user interface numbered sequentially 1 through 'n' to represent the stepwise flow from begin (1) to end ('n') for a user as depicted in analytical user app at 442400 being labelled "1." as the first step. The user experience flow of FIG. 44 may be facilitated by a MUI as described herein. At 442401 a user may select a user interface mechanism presenting one or more options including but not limited to module-specific functions, modules to select, and/or system functions being either a horizontal menu and/or toolbar, a vertical menu and/or toolbar, a scroll-wheel menu and/or toolbar, a dropdown menu and/or toolbar, a keyboard function, a voice-activated command, and/or any other like user interface mechanism to choose an option. At 442402, a work flow starts and the MUI auto-transitions to all audit events at 442403 to present to a user a view of all events captured for a user's current team with each event including, but not limited to, username and/or email address of originator, date and timestamp, the source, and information pertaining the event as returned from a service request made via the cloud platform. This view at 442403 enables a user to sort the view in forward or reverse ordering by username, date and timestamp, source, or information about the event. At 442403 a user may use the function selection mechanism at 442401 or an export command in the menu provided at 442403 to export the entire collection of events at 442404 to a file format easily importable to other computer applications such as, without limitation, Excel, Word, and/or any other computer application, such as, CSV, tab-delimited text, JSON, XML, and/or any other format. At 442403 a user may use the function selection mechanism at 442401 to export the entire collection of events at 442404 to a computer operating system mechanism used for copying and pasting content from one computer application to another computer application often referred to as a clipboard.

Figure 45:
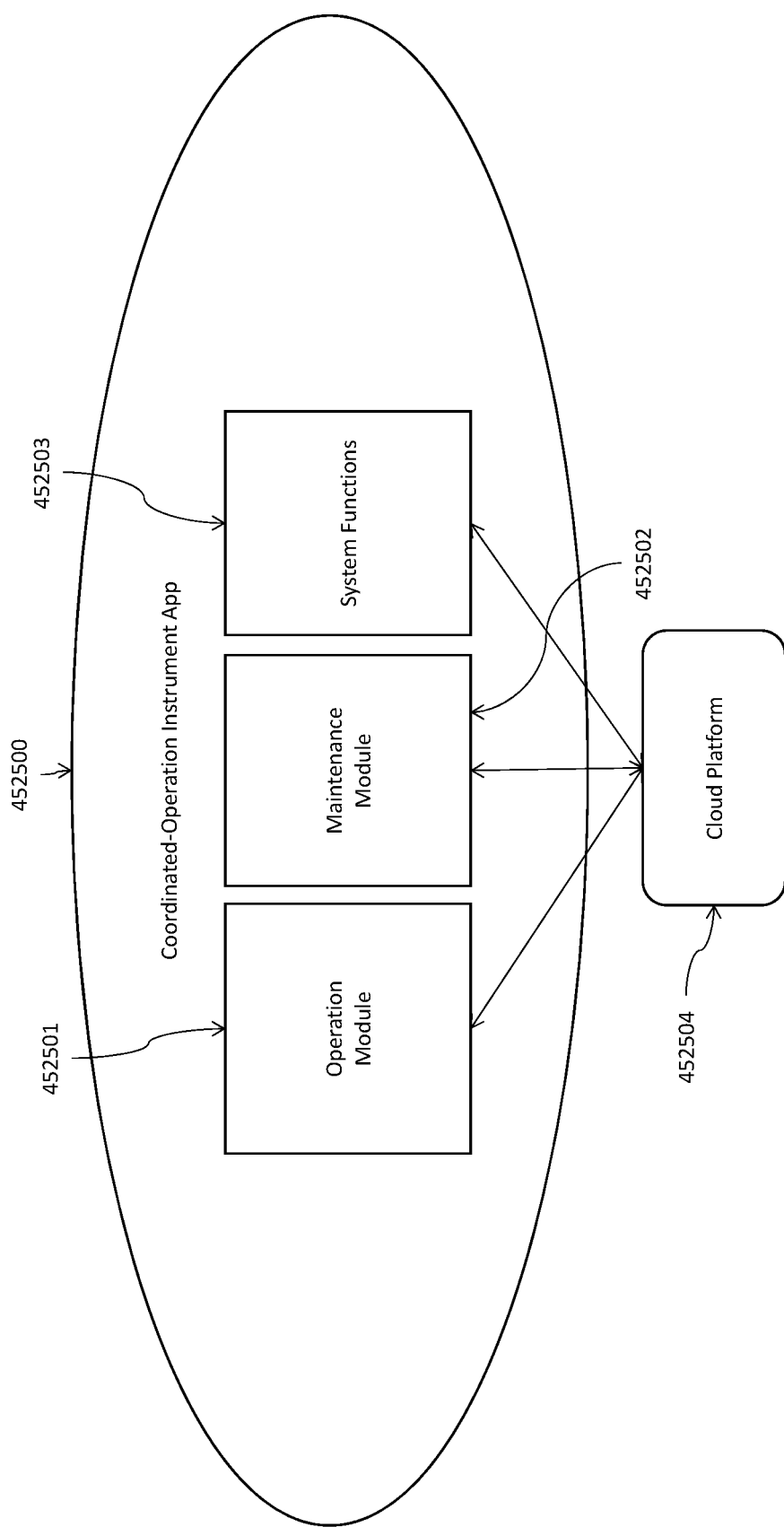
FIG. 45 illustrates the modules in a coordinated-operation instrument software application in an embodiment.

In FIG. 45 is an embodiment of software modules in a coordinated-operation instrument app 452500 forming the user interface experience for the use of a coordinated-operation instrument with each module using services provided by cloud platform 452504 to create, read, update, and/or delete any and all data relevant to each module's processing and commanding and controlling physical hardware integrated with, or separate from, the coordinated-operation instrument, as well as, any other services needed for each module's processing. Use of the coordinated-operation instrument app 452500 may be facilitated by a MUI as discussed herein. Accordingly, the coordinated-operation instrument app 452500 may include a methodical user interface control system 1102 or may operate in conjunction with a methodical user interface control system 1102. Operation module 452501 may be the active module by default when the coordinated-operation instrument app 452500 starts. Operation module providing the interface for executing experiments on an instrument to collect data for samples using assay methods defined in an experiment. Maintenance module 452502 provides the interface for executing maintenance functions on the instrument to ensure optimal operation of the instrument. A collection of system functions 452503 provides typical utilities in support of use of the coordinated-operation instrument such as, but not limited to, logging off, viewing help information, viewing user guide, viewing legal notices and/or documents, changing software configuration, changing user password, and/or other utilities. The collection of system function 452503 may be provided as a separate MUI module and/or a series of software protocols that operate alongside the other discussed MUI modules. A user can log into a coordinated-operation instrument app 452500 through system functions 452503 using services provided by cloud platform 452504. If authentication of a user by a login service on cloud platform 452504 returns that a user has more than one account and/or team, a user will be required to select the default account and/or team, but if a user does not belong to more than one account and/or team, the service on the cloud platform 452504 would auto-assign a user to the sole account and team for that user. On completing login, the user lands at start of the operation module and begins using the coordinated-operation instrument app as they need. In an alternative, the coordinated-operation instrument app 452500 can assist in performing other experiments in addition to or in place of the assay experiments described herein.

Figure 46:
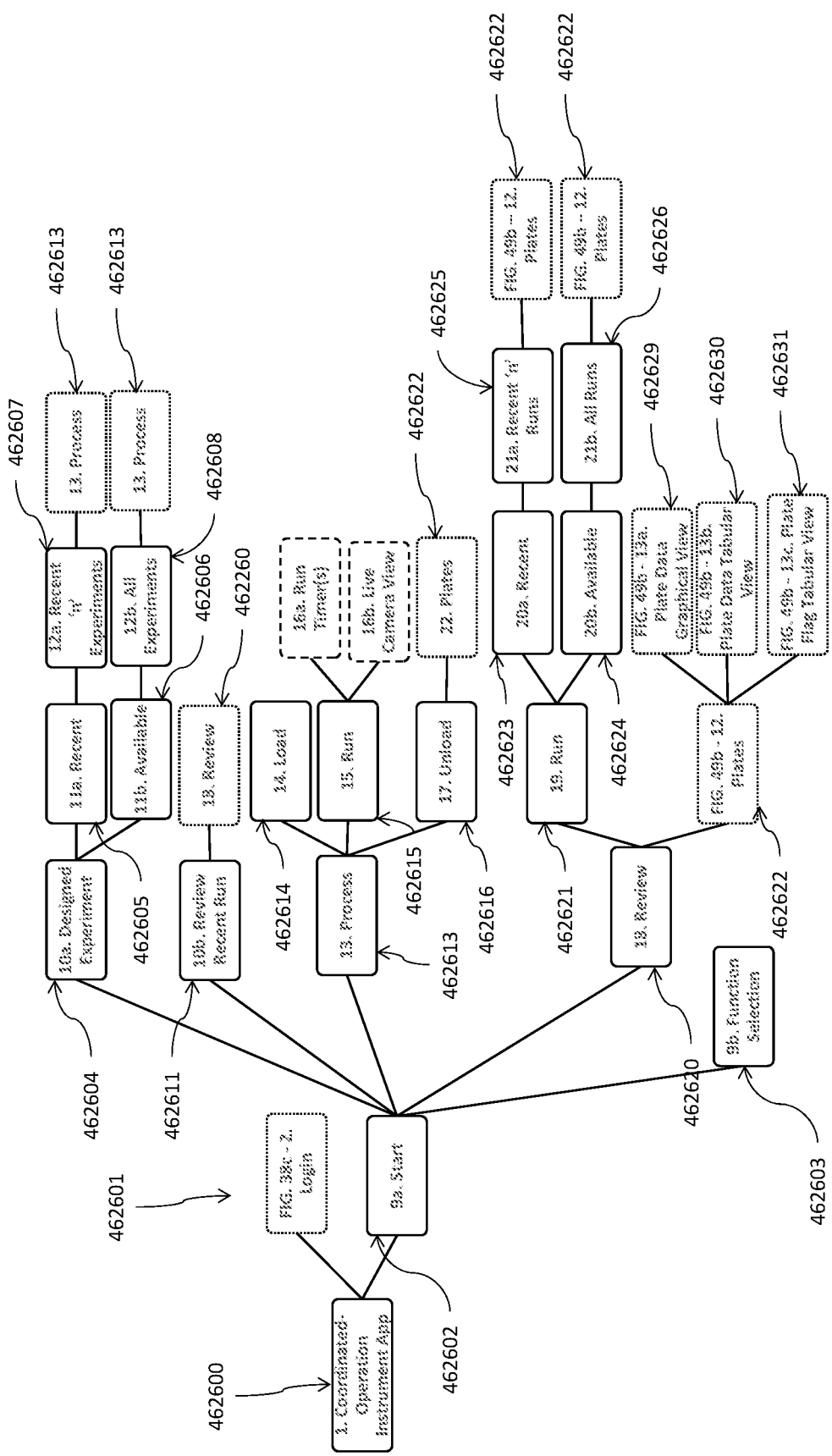
FIG. 46 illustrates the flow for an operation module in a coordinated-operation instrument app in an embodiment.

In FIG. 46 is an embodiment of a user experience flow through an operation module in the coordinated-operation instrument app at 462600 running on a instrument's computer with each step through a user interface numbered sequentially 1 through 'n' to represent the stepwise flow from begin (1) to end ('n') for a user as depicted in coordinated-operation instrument app at 462600 being labelled "1." The user experience flow of FIG. 46 may be facilitated via a MUI as discussed herein. At 462601 a user is logging into the coordinated-operation instrument app. After the login process the user interface transitions to start at 462602 and on login the MUI presents a menu of items including 1) selecting an experiment to run at 462604, 2) reviewing recent results of previous runs at 462611, 3) selecting a user interface mechanism at 462603, 4) processing a run at 462613, and 5) reviewing runs at 462620.

The user interface mechanism at 462603 presents one or more options including but not limited to module-specific functions, modules to select, and/or system functions being either a horizontal menu and/or toolbar, a vertical menu and/or toolbar, a scroll-wheel menu and/or toolbar, a drop-down menu and/or toolbar, a keyboard function, a voice-activated command, and/or any other like user interface mechanism to choose an option.

In choosing to select an experiment to run at 462604 the MUI presents a next menu of options to the user to select from recent experiments at 462605 or available experiments at 462606 with the default being recent at 462607. The MUI may auto-transition to all experiments at 462608 if recent at 462607 is empty as returned from a service request made via the cloud platform. At 462605 on selection of recent experiments a user is presented a configurable amount, for example twenty five, of the most recently designed experiments to run at 462607 as returned from a service request made via the cloud platform, although any other number of recently designed experiments is contemplated as well. Alternatively, selection of available at 462606 presents to a user all designed experiments ready to be run at 462608 as returned from a service request made via the cloud platform with the experiments organized by username, date and time of creation, and experiment name, enabling a user to browse the various experiments and to select the experiment to run.

On selecting an experiment to run either at 462607 or at 462608, the MUI transitions to process the experiment run that has just been selected at 462613 through the user interface leading a user through loading consumables and samples onto the appropriate locations on the instrument for the experiment's run at 462614 and on completing the load automatically transition to selecting to run the experiment at 462615. On selecting to run the experiment at 462615 the software initiates an automated inventory check of what was loaded by the user at 462614 through scanning of barcodes as appropriate presenting errors to the user to correct any issues that arise and on confirmation of 100% correctness of what was loaded, initiating the run and the automated execution of the experiment's assigned assay methods against the samples under test with one or more types of timers presenting the time remaining in the run while also enabling a user to see live video of the instrument running. On completion of the run the MUI presents instructions at 462616 for the user to unload the instrument leading the user through the process of removing consumables and samples from the instrument, as well as, emptying bulk containers used in the processing. On completion of the unload the MUI transitions to present to the user plate results at 462622 viewing the entire set of plates processed in the run at 462622 then choosing a plate to review in greater detail either at 462629, at 462630, and/or at 462631; and finally enabling a user to return to start at 462602 to perform another experiment run.

In an alternative to selecting an experiment to run at 462604, the user may choose to review recently ran experiments at 462611, cause the MUI to present a next menu of items to the user to select from runs at 462621 or plates at 462622. Upon selecting runs at 462621, a next menu provided by the MUI permits the user to select from recent ran experiments at 462623 or available ran experiments at 462624 with the default being recent at 462623. The MUI may auto-transition to available experiments at 462624 if recent at 462625 is empty as returned from a service request made via the cloud platform. At 462623 on selection of recent a user is presented a configurable amount, for example twenty five, of the most recently ran experiments to review at 462625 as returned from a service request made via the cloud platform. Alternatively, selection of available experiments at 462624 presents to a user all ran experiments ready to be reviewed at 462626 as returned from a service request made via the cloud platform with the experiments organized by username, date and time of creation, and experiment name, enabling a user to browse the various experiments and to select the experiment to review. On selecting an experiment to review either at 462625 or at 462626 the user interface transitions to present to the user plate results at 462622 viewing the entire set of plates processed in the run at 462622 then choosing a plate to review in greater detail either at 462629, at 462630, and/or at 462631. Although this embodiment describes methods for performing assays and/or plate-based tests, other experiments and tests are contemplated as well.

Figure 47:
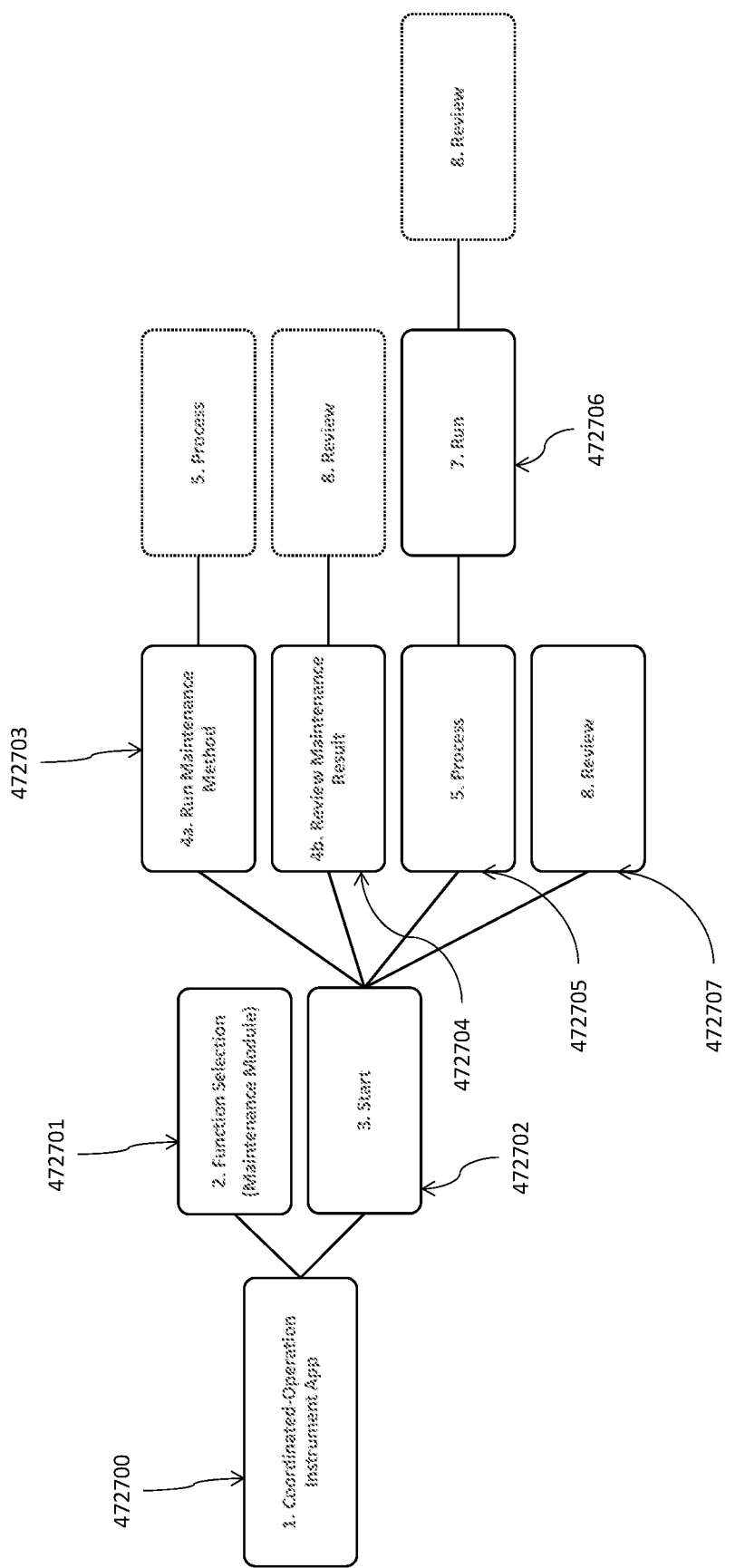
FIG. 47 illustrates the flow for a maintenance module in a coordinated-operation instrument app in an embodiment.

In FIG. 47 is an embodiment of a user experience flow through an maintenance module focused on maintaining an instrument beginning with coordinate-operation instrument app at 472700 running on a user's computer with each step through a user interface numbered sequentially 1 through 'n' to represent the stepwise flow from begin (1) to end ('n') for a user as depicted in coordinated-operation instrument app at 472700 being labelled "1." as the first step. The experience flow of FIG. 47 may be implemented via MUI as described herein. At 472701 a user may select a user interface mechanism presenting one or more options including but not limited to module-specific functions, modules to select, and/or system functions being either a horizontal menu and/or toolbar, a vertical menu and/or toolbar, a dropdown menu and/or toolbar, a keyboard function, a voice-activated command, and/or any other like user interface mechanism to choose an option, choosing maintenance module. On selection of maintenance module at 472701 the application transitions at 472702 to the start of the maintenance module and presents at 472703 an option to run a maintenance method or at 472704 an option review results of a previously ran maintenance method.

On selecting at 472703 a user is presented on the user interface the set of maintenance methods to run organized in a left set of top-level maintenance categories including but not limited to initializing the instrument, issuing a component command, and running a component test and associated with each item in the left set would be a right set of one or more maintenance methods pertinent to the instrument being maintained associated with the left maintenance category from which a user would select the maintenance method to perform. Once a maintenance method is selected at 472703 the software transitions to process the maintenance method at 472705 presenting the user a run button to initiate the processing and on tapping the run button the software initiates the robotic processing associated with the maintenance method presenting a user an hours:minutes:seconds countdown timer in various animations that a user could toggle through based on their preferences, as well as, an option to a live video to watch the robotic processing associated with the maintenance method. The maintenance method process menu at 472705 may be accessed via the start menu or may be auto-transitioned to after completion of the menu at 472703.

Once the maintenance method's robotic processing completes at 472706, the user interface transitions to 472707 for a user to review (also reachable via the start menu 472702) any results reported by the maintenance method presented in a table sorted by most recently run maintenance method showing the username of the person who ran the maintenance method, the name of the maintenance method, the date and time of completion of the maintenance method, and an optional result of the maintenance method if it reports a result. A user may select start at 472702 to return to the option of running another maintenance method at 472703 or reviewing maintenance results at 472704 or selecting a different module to switch to at 472701. On selecting reviewing maintenance results at 472704 the user interface is transitioned to 472707 to present to a user the previously disclosed maintenance method results table for FIG. 47.

Figure 48:
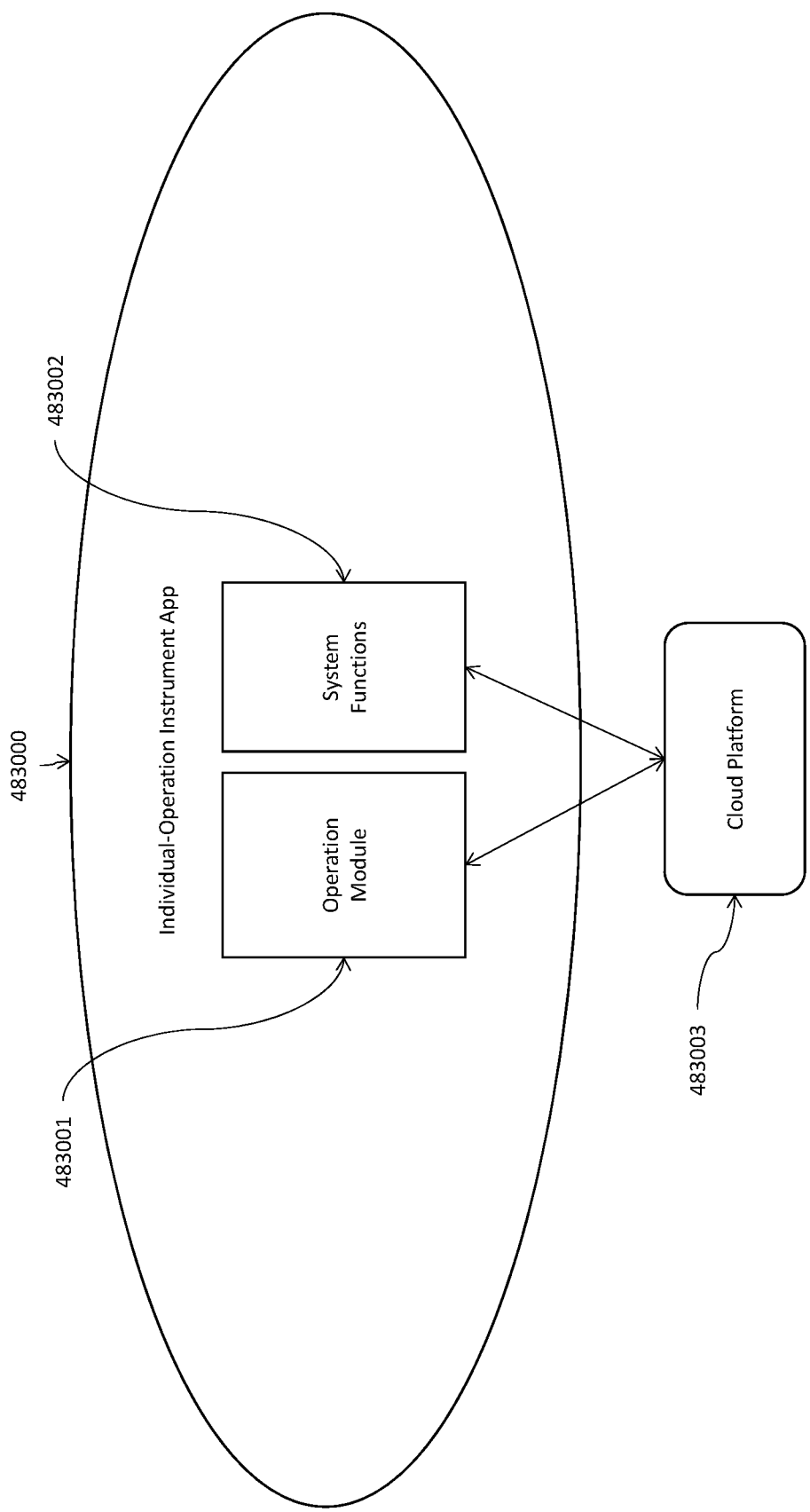
FIG. 48 illustrates the modules in an individual-operation instrument software application in an embodiment.

In FIG. 48 is an embodiment of software modules in an individual-operation instrument app 483000 forming the user interface experience for the use of an individual-operation instrument with each module using services provided by cloud platform 483003 to create, read, update, and/or delete any and all data relevant to each module's processing and commanding and controlling physical hardware integrated with, or separate from, the individual-operation instrument, as well as any other services needed for each module's processing. Operation module 483001 may be the active module by default when an individual-operation instrument app 483000 starts. Operation module 483001 provides the interface for executing an operation provided by the instrument in support of processing a defined assay method on samples for ultimate collection of data from the samples under test. 483002 Collection of system functions 483002 provides typical utilities in support of use of the individual-operation instrument such as, but not limited to, logging off, viewing help information, viewing user guide, viewing legal notices and/or documents, changing software configuration, changing user password, and/or other utilities. The collection of system function 483002 may be provided as a separate MUI module and/or a series of software protocols that operate alongside the other discussed MUI modules. As discussed above, the individual-operation instrument app 483000 may employ a MUI supplied by a methodical user interface control system 1102 for interface purposes. The operation module 483001 and the system functions 483002 may all employ a MUI for user interface purposes. A user will log into an individual-operation instrument app 483000 through system functions 483002 using services provided by cloud platform 483003. If authentication of a user by a login service on cloud platform 483003 returns that a user has more than one account and/or team, a user will be required to select the default account and/or team, but if a user does not belong to more than one account and/or team, the service on the cloud platform 483003 would auto-assign a user to the sole account and team for that user. On completing login, the user lands at start of the operation module 483001 and begins using the individual-operation instrument app 483000 as needed. In the alternative, the of software modules in an individual-operation instrument app 483000 can support other experiments in addition to or in place of the assay experiments described herein.

Figure 49A:
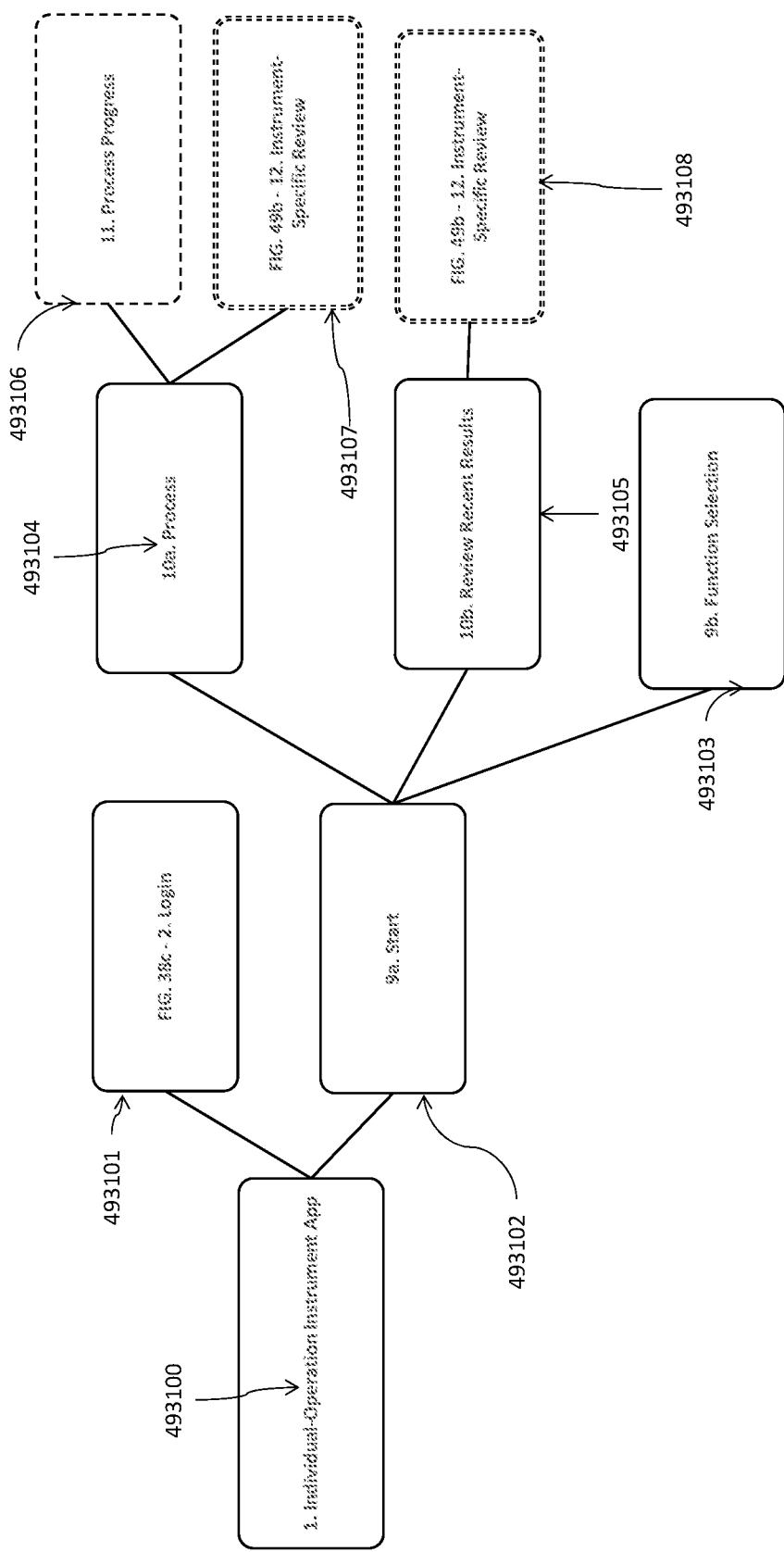
FIG. 49A illustrates the flow for an operation module in an individual-operation instrument app in an embodiment.

In FIG. 49A is an embodiment of a user experience flow through an operation module in the individual-operation instrument app at 493100 running on a instrument's computer with each step through a user interface numbered sequentially 1 through 'n' to represent the stepwise flow from begin (1) to end ('n') for a user as depicted in individual-operation instrument app at 493100 being labelled "1." The experience flow depicted in FIG. 49A may be implemented or facilitated by a MUI as discussed herein. At 493101 a user logs into the individual-operation instrument app 483000. After the login process the user interface transitions to start at 493102 and the user is presented with a first menu of items, including 1) perform the operation at 493104, 2) review recent results of previous performances of the operation at 493105, or 3) select a user interface mechanism at 493103. The user interface mechanism 493103 presents one or more options including, but not limited to, module-specific functions, modules to select, and/or system functions being either a horizontal menu and/or toolbar, a vertical menu and/or toolbar, a scroll-wheel menu and/or toolbar. a dropdown menu and/or toolbar, a keyboard function, a voice-activated command, and/or any other like user interface mechanism to choose an option.

On selection by a user to run a process at 493104 the MUI transitions to 493106 to prepare the instrument to execute the process. The MUI presents a progress indicator to keep the user apprised of progress and ultimate completion. The software may further provide a mechanism to perform the operation in a continuous mode, or repeat the operation on a new plate, if a user chooses to stack or batch plates up for processing. On completion of the operation over one or more plates, the data collected from the operation may be uploaded through services provided on the cloud platform to the user's team for review via the cloud as well as storing performance data gathered from the operation of the instrument for monitoring and support by the provider of the instrument, then the user interface would automatically transition to review at 493105 presenting instrument-specific results at 493107 of the one or more operations that just completed. Alternatively to performing the operation at 493104, the user could choose review at 493105 to cause the MUI to transit to present instrument-specific results at 493108 where the user is presented a maximum set of recent results that could be the last 'n' plates (e.g., 25) processed, the last 'n' days (e.g., 30), or any other desired configuration for presenting chronologically recent set of results provided by the instrument. In an alternative to performing the operation at 493104 or reviewing recent results at 493105, the user could choose one or more functions at 493103, including configuring the operation of the instrument for ultimate use. A user may perform the operation at 493104 time and time again, then review the results at 493105 to determine if the instrument performed as expected.

Figure 49B:
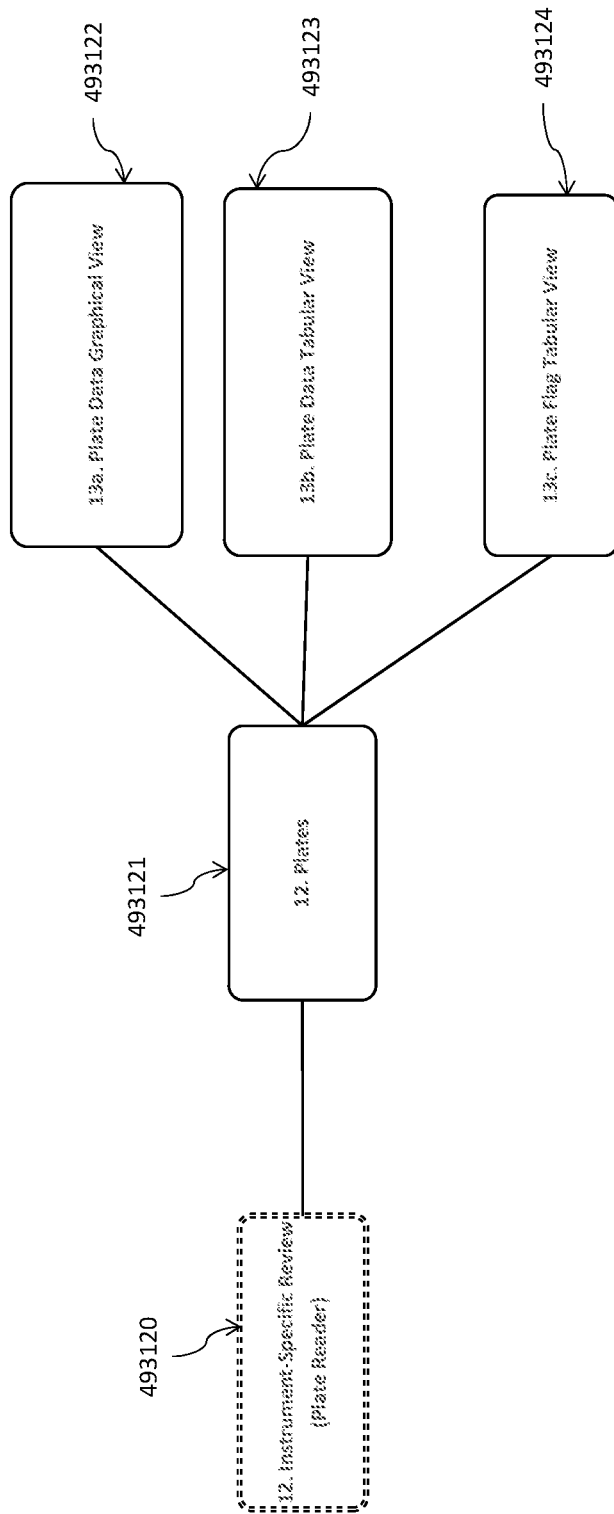
FIG. 49B illustrates the flow of results review in an operation module relating to a plate reader as an individual-operation instrument app in an embodiment.

FIG. 49B illustrates an embodiment of the flow of results review in an operation module 403120 specifically for a plate reader as an individual-operation instrument. The plates menu at 493121 is a collection of one or more plates in the order of operation execution and on selection of a plate at 493121 the MUI transitions to present options at 493122, at 493123, and at 493124. At 493122 a user is presented a specific plate in the experiment with a heat map representation of signal for all data locations in each well of the plate. A user may choose a particular data location to view across all wells of the plate narrowing down the data to just that one data location plus a user may select a particular well to see the specific signal value for a sample in the selected well while being able to change the high and/or low signal range for the plate to alter the intensity of the heat map across all samples visible on the plate. At 493123 a user is presented a well-by-well table view of the data presenting but not limited to sample identifier, data location, and signal. At 493124 a user is optionally presented a table view of flags denoting abnormal events that may have occurred during processing of a plate potentially bringing the data's quality into question for a user only available to a user if there was at least one flag generated for a plate. Although this embodiment describes plate-reader operations and/or applications, the methods described herein can be applied in the alternative to the review of other experiments and tests in the alternative.

Figure 50:
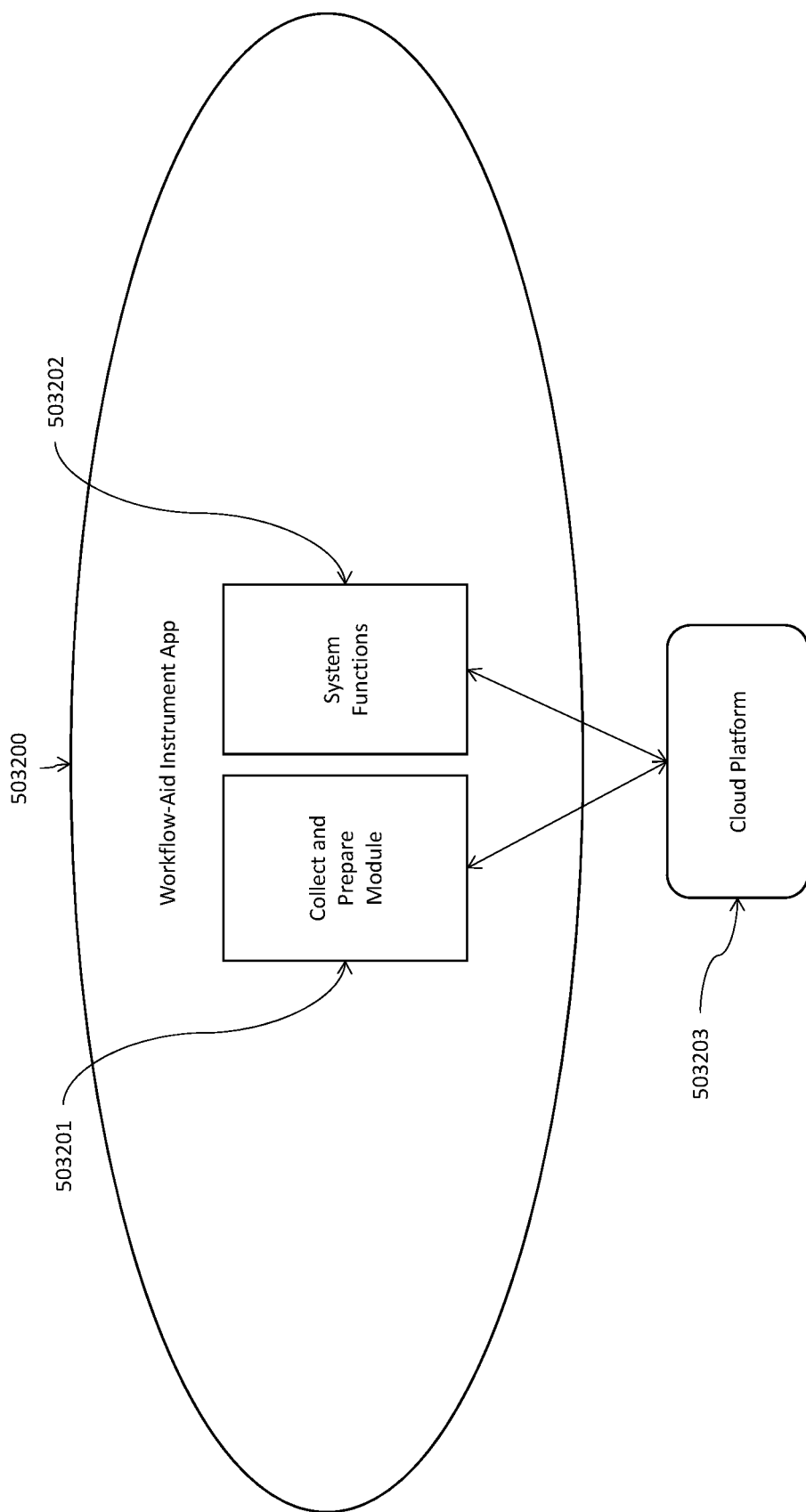
FIG. 50 illustrates the modules in a workflow-aid instrument software application in an embodiment.

In FIG. 50 is an embodiment of software modules in an workflow-aid instrument app at 503200 forming the user interface experience for the use of a workflow-aid instrument with each module using services provided by cloud platform at 503203 to create, read, update, and/or delete any and all data relevant to each module's processing and potentially commanding and controlling physical hardware integrated with the workflow-aid instrument, as well as, any other services needed for each module's processing, wherein, collect and prepare module at 503201 would be the active module by default when the workflow-aid instrument app at 503200 starts. The workflow-aid instrument app 502300 may employ or be implemented along with a MUI to provide user interfaces for the collect and prepare module 503201 and the system functions 503202. At 503201 is a collect and prepare module providing the interface for gathering constituent components stored in potentially different climate-controlled or room temperature environments to be used in processing one or more assays in a chosen experiment, for example but not limited to, kits, antibody sets, bulk solutions, plastic-ware such as tips and microtiter plates, and/or any other component required to be used in processing one or more assays in a chosen experiment; and preparing constituents components requiring pre-processing prior to being used in the processing of one or more assays defined for an experiment, for example, rehydrating lyophilized reagents, thawing frozen reagents, pretreating samples, and/or any other step required to prepare constituent components to be used in processing one or more assays in a chosen experiment. At 503202 is a collection of system functions providing typical utilities in support of use of the workflow-aid instrument such as but not limited to logging off, viewing help information, viewing user guide, viewing legal notices and/or documents, changing software configuration, changing user password, and/or other utilities. A user will log into a workflow-aid instrument app at 503200 through system functions at 503202 using services provided by cloud platform at 503203. If authentication of a user by a login service on cloud platform at 503203 returns that a user has more than one account and/or team, a user will be required to select the default account and/or team, but if a user does not belong to more than one account and/or team, the service on the cloud platform at 503203 would auto-assign a user to the sole account and team for that user. On completing login, the user lands at start of the collect and prepare module and begins using the workflow-aid instrument app as they require.

Figure 51:
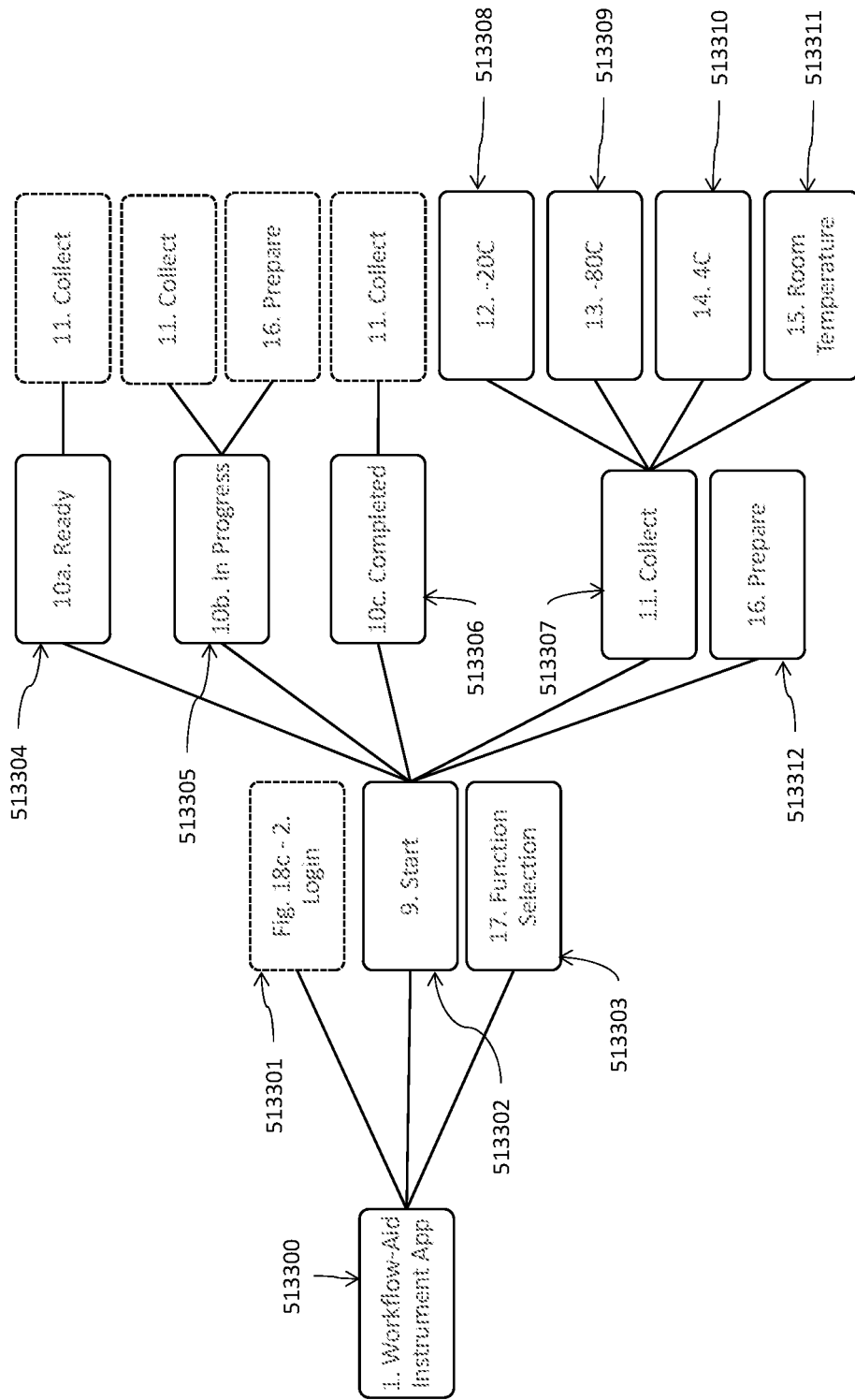
FIG. 51 illustrates the flow for a workflow-aid module in a workflow-aid instrument app in an embodiment.

In FIG. 51 is an embodiment of a user experience flow through a collect and prepare module in the workflow-aid instrument app at 513300 running on a instrument's computer with each step through a user interface numbered sequentially 1 through 'n' to represent the stepwise flow from begin (1) to end ('n') for a user as depicted in workflow-aid instrument app at 513300 being labelled "1." as the first step. The experience flow of FIG. 51 may be implemented via a MUI as discussed herein. At 513301 a user is logging into the workflow-aid instrument app. After the login process the user interface transitions to start at 513302 since the collect and prepare module is envisioned in this embodiment to be the default first module after a user logs in, where on login the user has four options either 1) select an experiment ready to begin collect and prepare at 513304, 2) select an in-progress experiment to continue collect and prepare at 513305, 3) select an experiment that was previously collected and prepared at 513306, or 4) select a user interface mechanism at 513303 presenting one or more options including but not limited to module-specific functions, modules to select, and/or system functions being either a horizontal menu and/or toolbar, a vertical menu and/or toolbar, a dropdown menu and/or toolbar, a keyboard function, a voice-activated command, and/or any other like user interface mechanism to choose an option. On selection by a user to begin an experiment ready to be collected and prepared at 513304 the user interface presents the set of experiments ready to be processed by calling a cloud service returning the available experiments and presenting the set of returned experiments, on user selection of a particular experiment transitioning to collect at 513307.

On transition by the MUI to 513307 the user is presented options to collect under various temperature storage modalities as required by the assay methods chosen for the experiment, in this embodiment but not limited to, −20 C at 513308, −80 C at 513309, 4 C at 513310, and at room temperature at 513311. The collect menu at 513307 is an example of a walk-through type execution menu, as described herein. Under each temperature zone the user will be presented a collection of assay methods each with one or more assay components to be collected from that temperature zone as returned by a call to a cloud service for the experiment being collected. The collection could be presented as a linear list to lead the user through the collection one item at a time requiring the user to check off each item as items are collected or a user could jump to the end of collection in a temperature by choosing to select a check-all control because they do not need to be led through collect. As a user works through the list of items to collect, they could be presented to the right of the list a photo or graphic representation of the item to be collected with a breakdown of its one or more constituent components if an item has one or more constituent components. To aid quick selection of an item the user could scan a barcode on the item that will automatically detect the item being collected and check it off in the list of items to be collected regardless of the item's position in the list. On checking off an item in the list a cloud service is called to store this information and the list automatically transitions to the next item to collect. Important to note a user could choose to jump around from one temperature zone to another as they wish, as well as, a function could be provided under function selection at 513303 to re-arrange the order of the temperature zones if a user wants a different order. A user may also be provided a function under function selection at 513303 (e.g., an advanced context menu) to print out the steps of collect if they prefer to have a paper copy, as well as, a function under function selection at 513303 to export the steps of collect to some $3^{rd}$ party software application. Once all items have been collected in a particular temperature zone a cloud service is called to update the experiment with its collection being completed and the user interface transitions to the next temperature zone continuing the process of collection until such time as the last item in the last temperature zone has been collected transitioning the user interface to prepare at 513312. The prepare menu at 513312 is an example of a walkthrough type execution menu.

On transition to prepare at 513312 the user is presented in this embodiment an aggregate list of the steps to be performed across all assay methods chosen for the experiment as returned by a call to a cloud service to retrieve the chosen assay methods for the experiment with the list ordered by the first step to last step defined for an assay method where assay methods sharing a common type of step in this embodiment would provide a sub-step selection for each common step type such that a user could perform the step for each assay method checking it off for each assay method or the user could check it off once for the step covering all associated assay methods. An alternative to the sub-step approach, but not intended to be limited to, would be a one-level list with one step for each step and assay method pairing. Regardless of how the steps are presented to a user, the one or more actions to be taken for the one active step to be performed by a user in this embodiment, but not intended to be limited to, would be presented to the right of the list of steps where the actions would be presented to a user as a video, one or more graphical representations, and/or text description with the intention this information helps a user properly perform the one or more actions of the step. As a user completes the actions of a step, whether for one assay method or many assay methods, they would check off the step causing a call to a cloud service to store the completed state for the step for all assay methods associated with that step.

Once all steps for all assay methods have been completed, denoted by checking off the step, prepare will be complete with the user asked via a modal dialog to confirm completion, where, positive confirmation of completion causes a call to a cloud service to update the state of the experiment to indicate it has been prepared and returning the user interface to start at 513302 with the experiment now ready to be processed; and negative confirmation of completion returns the user to the last performed step in prepare at 513312. A supplemental function available in any stage of collect and prepare under function selection at 513303 is the ability to display, export to $3^{rd}$ party software, and/or print the one or more sample input plates associated with an experiment.

Figure 52:
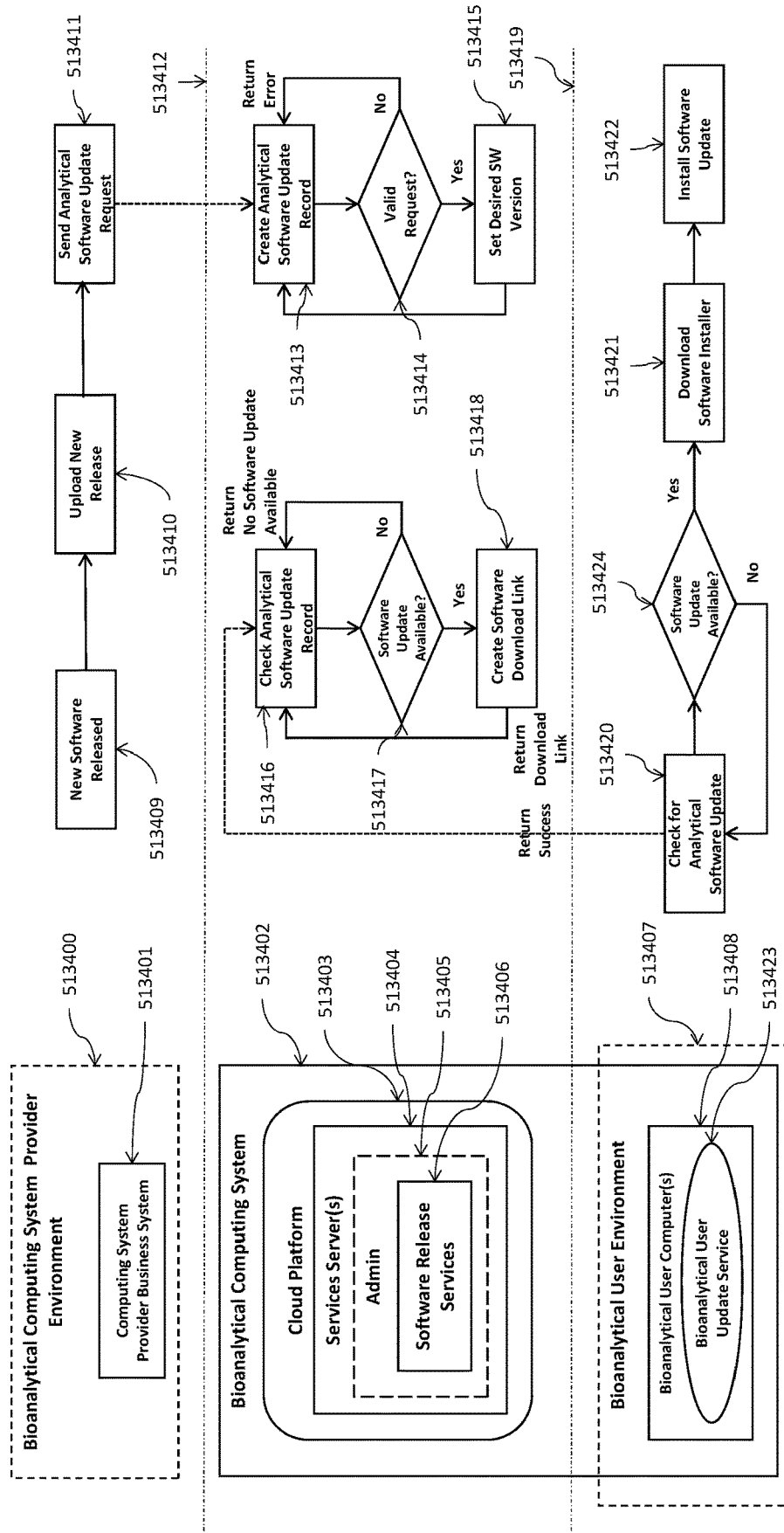
FIG. 52 is an embodiment of the computing flow of a software automatic update for analytical user computers.

In FIG. 52 is an embodiment of the computing flow of software automatic update for bioanalytical user computers at 513408 in the analytical computing system at 513402. The flow is represented in a "swim lane" diagram depicting independent computing systems operating concurrent to each other being computing system provider business system at 513401, cloud platform at 513403 with its software release services at 513406, and bioanalytical user computers at 513408 with its bioanalytical user update service at 513423 with processing swim lane for computing system provider business system at 513401 depicted above dotted line at 513412, processing swim lane for software release services depicted between dotted lines at 513412 and 513419, and processing swim lane for bioanalytical user update service at 513423 depicted below dotted line at 513419. The processing of computing system provider business system at 513400 is depicted as out of scope for the analytical computing system at 513402 with the dotted-line outline of analytical computing system provider environment at 513400 but in this embodiment software updates originate there at 513409 when a new release of software is produced for deployment with one or more files associated with the new release bundled at 513410 and pushed to cloud platform through file upload services inherent to the cloud platform then transitioning at 513411 to call a web service on the cloud platform at 513403 to request an auto-update of the software on various bioanalytical user computers at

513408. The processing of software release services at 513406 has two concurrent services, one service to create a software update record at 513413 provided for an outside agent to notify the analytical computing system at 513401 that an auto-software update is requested that in this embodiment occurs at 513411 and a second service for bioanalytical user computers to check for availability of an auto-software update at 513416. The service at 513413 receives a requesting to create the software update record, confirms at 513414 the request is a valid service request from an appropriately credentialed requester and if not valid the request is rejected and not processed, but if proper a new auto-software update is created for the version of software at 513415. The service at 513416 receives a request to check if there is an active auto-software update, confirms at 513417 the request is a valid service request from an appropriately credentialed requester and if not valid the request is rejected and not processed, but if valid the download link to the software update is returned to the requester. The processing of bioanalytical user update service at 513423 is a periodically executed service requesting availability of updates at 513420 via a web service call at 513416 and on receipt of a response checking the response at 513424 to either repeat the service request if not available or processing the software update if available at 513421 by downloading the software update via the download link provided by web service call at 513416 and on completion of the download executing the software install at 513422 and after completion of the install the bioanalytical user computer software is updated.

Figure 53:
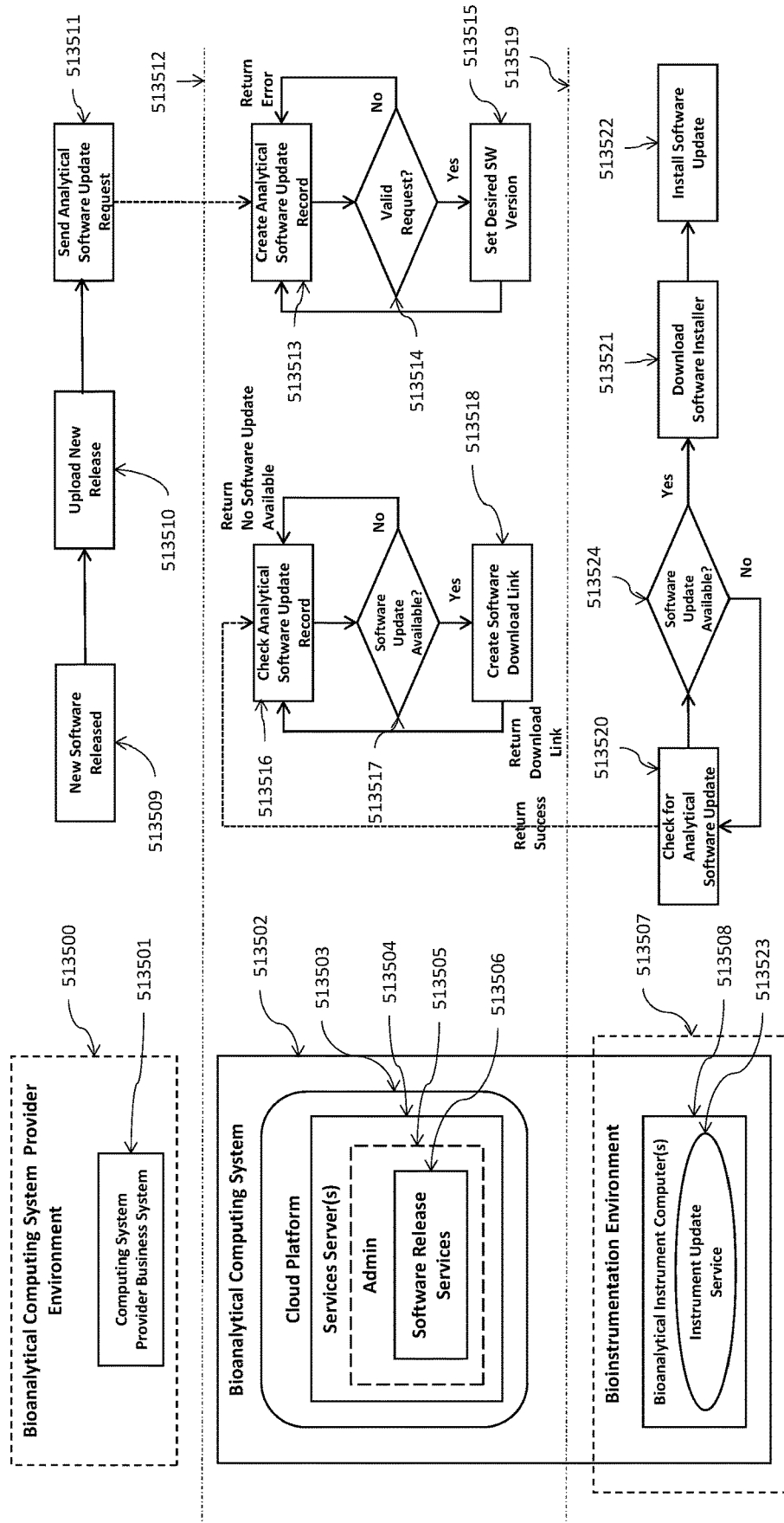
FIG. 53 is an embodiment of the computing flow of a software automatic update for analytical instrument computers.

In FIG. 53 is an embodiment of the computing flow of software automatic update for bioanalytical instrument computers in the analytical computing system at 513502. The term "bioanalytical instrument" is used in this context to represent any and all of the before-mentioned coordinated-operation instrument, individual-operation instrument, and/or workflow-aid instrument, generalized in FIG. 53 for simplicity of description since they operate the same in this regard. The flow is represented in a "swim lane" diagram depicting independent computing systems operating concurrent to each other being computing system provider business system at 513501, cloud platform at 513503 with its software release services at 513506, and bioanalytical instrument computers at 513508 with its instrument update service at 513523 with processing swim lane for computing system provider business system at 513501 depicted above dotted line at 513512, processing swim lane for software release services depicted between dotted lines at 513512 and 513519, and processing swim lane for instrument update service at 513523 depicted below dotted line at 513519. The processing of computing system provider business system at 513500 is depicted as out of scope for the analytical computing system at 513502 with the dotted-line outline of analytical computing system provider environment at 513500 but in this embodiment software updates originate there at 513509 when a new release of software is produced for deployment with one or more files associated with the new release bundled at 513510 and pushed to cloud platform through file upload services inherent to the cloud platform then transitioning at 513511 to call a web service on the cloud platform at 513503 to request an auto-update of the software on various bioanalytical instrument computers at 513508. The processing of software release services at 513506 has two concurrent services, one service to create a software update record at 513513 provided for an outside agent to notify the analytical computing system at 513501 that an auto-software update is requested that in this embodiment occurs at 513511 and a second service for bioanalytical instrument computers to check for availability of an auto-software update at 513516. The service at 513513 receives a requesting to create the software update record, confirms at 513514 the request is a valid service request from an appropriately credentialed requester and if not valid the request is rejected and not processed, but if proper a new auto-software update is created for the version of software at 513515. The service at 513516 receives a request to check if there is an active auto-software update, confirms at 513517 the request is a valid service request from an appropriately credentialed requester and if not valid the request is rejected and not processed, but if valid the download link to the software update is returned to the requester. The processing of instrument update service at 513523 is a periodically executed service requesting availability of updates at 513520 via a web service call at 513516 and on receipt of a response checking the response at 513524 to either repeat the service request if not available or processing the software update if available at 513521 by downloading the software update via the download link provided by web service call at 513516 and on completion of the download executing the software install at 513522 and after completion of the install the bioanalytical instrument computer software is updated.

The methods, techniques, and systems are described herein particularly with respect to instrumentation and bio-instrumentation. The methods, techniques, and systems, however, are not limited to such applications. MUIs as provided herein may be applied to any activity or process that may be structured according to a hierarchical process flow. MUIs as provided herein may be applied to processes in a variety of additional fields, including, for example, home and interior design, furniture assembly, cooking and meal design, travel planning, business planning, graphic design (e.g., business cards, invitations, crafts such as quilting, knitting, and sewing, web pages, etc.), financial planning, taxes, wills, video game design, video editing, media navigation (e.g., Netflix®, tv channel navigation), car purchase, home purchase, beer brewing, manufacturing, etc.

Figure 54:
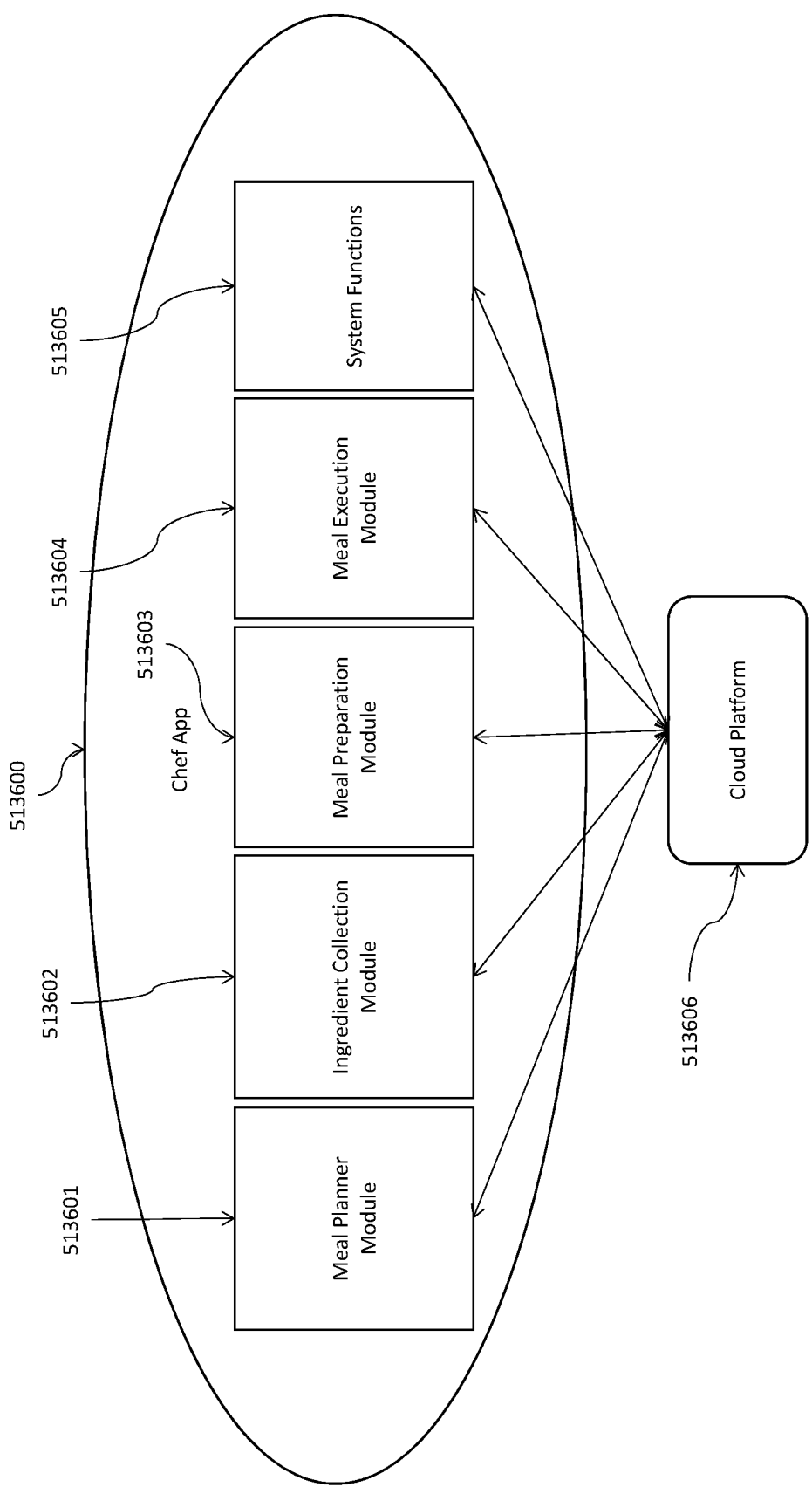
FIG. 54 is an embodiment of an example of a non-bioanalytical use of the disclosed architecture for software modules in a chef app.

In FIG. 54 is an embodiment of an example of a non-bioanalytical use of the disclosed architecture for software modules in an chef app at 513600 forming the primary user interface experience for creating a meal for one or more people with each module using services provided by cloud platform at 513606, assuming relevant chef-related services are available on cloud platform at 513606, to create, read, update, and/or delete any and all data relevant to each module's processing, as well as, any other services needed for each module's processing, wherein, meal planner module at 513601 would be the active module by default when the chef user app at 513600 starts, guiding a chef through the planning of the meal they wish to create. The chef app 513600 may be implemented in conjunction with a MUI to provide a user interface. At 513602 is an ingredient collection module providing the interface for guiding a chef and/or their designee through the purchasing and/or retrieval of all ingredients and/or anything required for the execution of the meal either used in meal preparation and/or used during eating the meal. At 513603 is a meal preparation module used to guide a chef and/or their designee through the steps of cooking the meal. At 513604 is a meal execution module used to guide a chef and/or their designee in setting the stage and mood for the meal as well as the timing of various courses of the meal. At 513605 is a collection of system functions providing typical utilities in support of use of the system such as but not limited to logging off, viewing help information, viewing user guide, viewing legal notices and/or documents, changing software configuration, changing user password, and/or other utilities. A user will log into the chef user app at 513600 through system functions at 513605 using services provided by cloud platform at 513606. On completing login, the user lands at start of the meal planner module at 513601 and begins using the chef user app at 513600 as they need. Only the meal planner module at 513601 will be further disclosed for the purpose of illustration of an example of a non-bioanalytical use.

Figure 55:
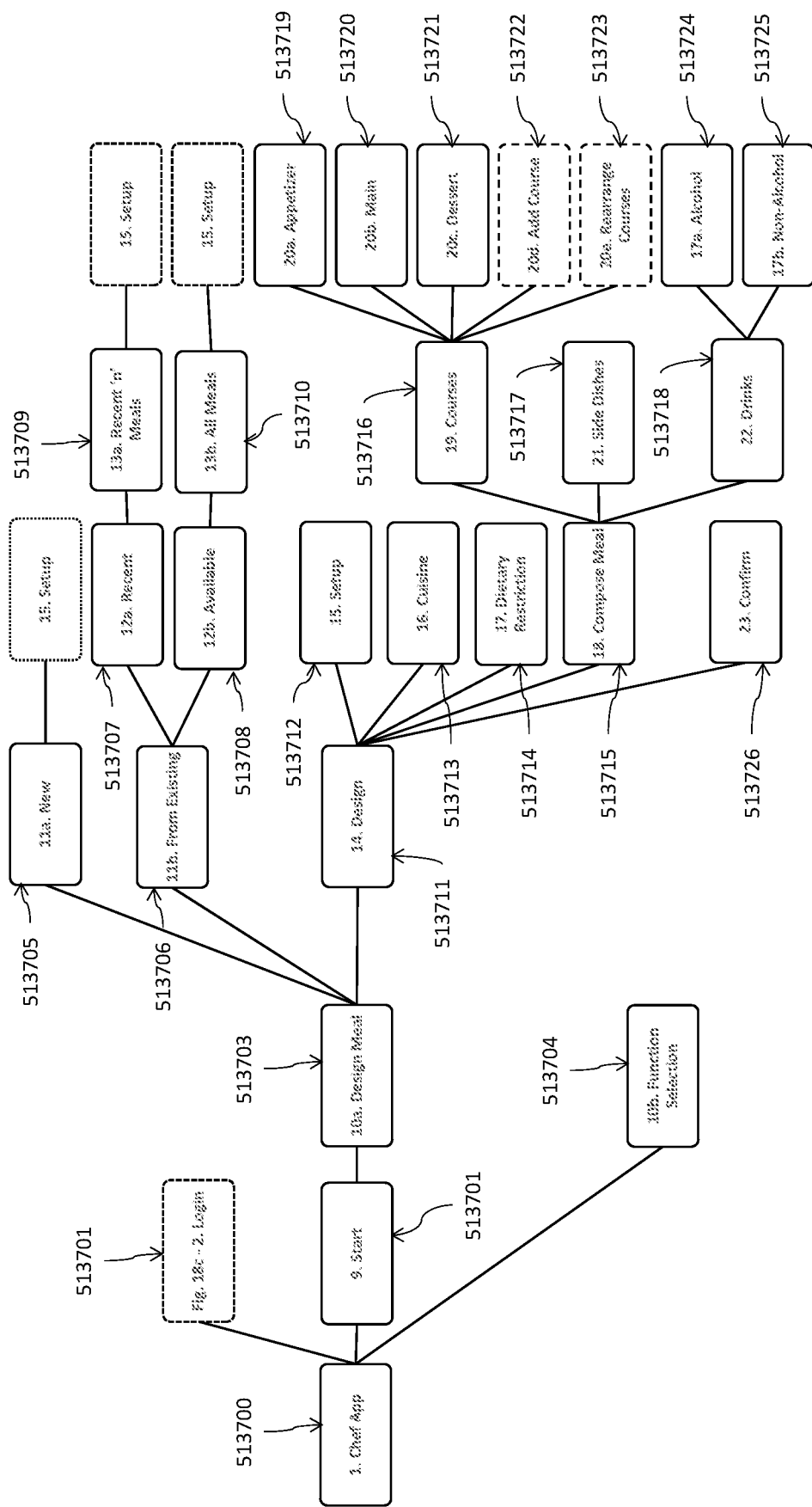
FIG. 55 is an embodiment of a user experience flow through a meal planner module beginning with chef app.

In FIG. 55 is an embodiment of a user experience flow through an meal planner module beginning with chef app at 513700 running on a user's computer with each step through a user interface numbered sequentially 1 through 'n' to represent the stepwise flow from begin (1) to end ('n') for a user as depicted in chef app at 513700 being labelled "1." as the first step. The user experience flow of FIG. 55 may be implemented via a MUI as described herein. After the login process the user interface transitions to start at 513701 since the meal planner module is envisioned in this embodiment to be the default first module after a user logs in with to options to design a meal at 513703 or at 513704 select a user interface mechanism presenting one or more options including but not limited to module-specific functions, modules to select, and/or system functions being either a horizontal menu and/or toolbar, a vertical menu and/or toolbar, a dropdown menu and/or toolbar, a keyboard function, a voice-activated command, and/or any other like user interface mechanism to choose an option. In this embodiment at 513703 a user is presented one option to design a meal plan with a user choosing to do so transitioning the user interface to a choice of creating a new meal plan from scratch at 513705 or creating a meal plan from a pre-existing meal plan at 513706, where choosing new at 513705 transitions the user interface directly to meal plan design setup at 513712 and choosing to base the new meal on a pre-existing meal plan at 513706 transitions the user interface to a choice of recent meal plans at 513707 or available meal plans at 513708 with the default being recent at 513707 but auto-transitioning to available at 513708 if recent at 513707 is empty as returned from a service request made via the cloud platform. At 513707 on selection of recent a user is presented a configurable amount, for example twenty five, of the most recently used meal plans at 513709 as returned from a service request made via the cloud platform. Alternatively, selection of available at 513708 presents to a user all meals at 513710 as returned from a service request made via the cloud platform with the meal plans organized by names of users creating meals plans and the name of the meal plans each user created, enabling a user to browse the various meal plans to select the meal plan of choice. On selection of a meal plan at either 513709 or 513710 the user interface transitions to meal plan design setup at 513712. At 513712 a user is presented a system-provided default name that a user may accept or edit but a plan must have a name; a number of diners for the meal with a default of 2 and a range of 1 to 10000; and an optional monetary budget with a default of no limit and accepting any monetary value; wherein on either accepting the defaults or editing one or more of the options, a user would then select cuisine at 513713 causing a service call on the cloud platform to store the decision made by the user for the options before transitioning the user interface. At 513713 a user is presented a two-part selection user interface mechanism showing on the left a cuisine origin and on the right cuisine options for the chosen origin, for example the left selection would be but not limited to American, European, Mexican, South American, Middle Eastern, Asian or Other, wherein the right selection for American would be but not limited to Southern, New England, Amish, or Southwestern; for European would be but not limited to French, Italian, German, Greek, Spanish, Portuguese, British Isles, or Scandinavian; for Mexican would be but not limited to Traditional or Tex-Mex; for South American would be but not limited to Peruvian or Brazilian; for Middle Eastern would be but not limited to Turkish, Lebanese, or Persian; for Asian would be but not limited to Chinese, Japanese, Thai, Vietnamese, Korean, or Indian; and Other would be but not limited to Caribbean or Name Your Own for a user provide their own cuisine style; and on user selection of a cuisine option the selection is saved via a service to the cloud platform and the user interface transitions to dietary restrictions at 513714. At 513714 a user is presented potential dietary restrictions in a scrollable outline format where at each level of the outline a user is enabled to click something as a restriction that on clicking will check-on the chosen restriction plus everything embedded underneath it in the outline, wherein the outline would be but not limited to:

Vegetarian;
Vegan;
Allergic (Tree nuts, Write in option);
Health (Lactose, Gluten, Write in option);
Religious;
Kosher (pork, shellfish), No dairy, meat okay, No meat, dairy okay, Pareve (no meat or dairy);
Halal, Write in option; and/or
Taste, Write in option.

After a user completes checking all restrictions they know of, they would choose compose meal at 513715 causing their selections to be stored via a web service to the cloud platform and therefore eliminating certain ingredients from meal preparation based on their selections before transitioning the user interface. At 513715 a user is presented three options for planning the meal being defining the courses at 513716, selecting side dishes at 513717, and/or selecting drinks at 513718. On selecting courses at 513716 a user is presented the three system-provided defaults in expected ultimate meal execution order of appetizer course at 513719, main course at 513720, and dessert course at 513721 but the user could alter the course selection and/or order by choosing function selection 513704 to see two functions options to add/remove a course at 513722 to either add one or more courses to the meal and/or remove one or more courses from the meal, as well as, a function to rearrange the courses of the meal for when executing the preparation and/or execution of the meal. At 513719 a user is presented a left-right selection control with the left side being types of dishes to be provided being but not limited to Soup, Salad, Finger Foods, Dips/Sauces, and Other for one or more user-provided choices, where when a preset option is clicked the user interface presents a collection of options set by the cuisine and dietary restrictions defined previously by the user with the options retrieved from web service(s) provided on the cloud platform from which the user may select one or more options. On completion of option selections and/or definitions at 513719 a user would select main course at 513720 with the software automatically storing the user's selections via web service(s) on the cloud platform before transitioning the user interface. At 513720 a user is presented a left-right selection control with the left side being types of dishes to be provided being but not limited to Poultry, Pork, Beef, Fish, Vegetarian, and Other for one or more user-provided choices, where when a preset option is clicked the user interface presents a collection of options set by the cuisine and dietary restrictions defined previously by the user with the options retrieved from web service(s) provided on the cloud platform from which the user may select one or more options. On completion of option selections and/or definitions at 513720 a user would select dessert course at 513721 with the software automatically storing the user's selections via web service(s) on the cloud platform before transitioning the user interface. At 513721 a user is presented a left-right selection control with the left side being types of desserts to be provided being but not limited to Cake, Cookies, Pie, Ice Cream, Pastry, and Other for one or more user-provided choices, where when a preset option is clicked the user interface presents a collection of options set by the cuisine and dietary restrictions defined previously by the user with the options retrieved from web service(s) provided on the cloud platform from which the user may select one or more options. On completion of option selections and/or definitions at 513721 a user would select the next course if one is available until the last course is defined then select side dishes at 513717 with the software automatically storing the user's selections via web service(s) on the cloud platform before transitioning the user interface. At 513717 a user is presented a left-right selection control with the left side being types of side dishes to be provided being but not limited to Bread, Starch, Vegetable, Dips/Sauces, and Other for one or more user-provided choices, where when a preset option is clicked the user interface presents a collection of options set by the cuisine and dietary restrictions defined previously by the user with the options retrieved from web service(s) provided on the cloud platform from which the user may select one or more options. On completion of option selections and/or definitions at 513717 a user would select drinks at 513718 with the software automatically storing the user's selections via web service(s) on the cloud platform before transitioning the user interface. At 513718 a user is presented a left-right selection control with the left side being types of drinks to be provided with sub-options of for alcohol at 513724 and non-alcohol at 513725 with options for alcohol being but not limited to Wine, Beer, Liquor, and Other for one or more user-provided choices and options for non-alcohol being Soda, Juice, Water, and Other for one or more user-provided choices, where when a preset option is clicked the user interface presents a collection of options set by the cuisine and dietary restrictions defined previously by the user with the options retrieved from web service(s) provided on the cloud platform from which the user may select one or more options, as well as, optionally associate each specific drink to a specific course if the user desires that specificity. On completion of option selections and/or definitions at 513718 a user would select confirm at 513726 because their meal is now defined with the software automatically storing the user's selections via web service(s) on the cloud platform before transitioning the user interface. At 513726 a user is presented a summary view of the meal they have planned to confirm they made all the right choices, enabling a user to navigate to a previous steps to alter any decisions they made in the process of planning the meal and if all their decision are in line with their expectations they would select confirm storing their meal plan via web service(s) to the cloud platform for future use and on completion of the invocation of web service(s) the user interface would transition back to start at 513702. At 513702 a user could choose a function selection user interface mechanism at 513704 seeing they are in a meal planner module and having three other modules available to them namely, an ingredient collection module, a meal preparation module, and a meal execution module helping them follow through on their new meal plan using one or more of these other modules In another example, in a cooking and meal design MUI module, a process flow may be structured as follows. A first menu may permit a user to select a type of meal, dinner, lunch, breakfast, formal, informal, etc., that is being prepared. Selection of a type of meal may lead to a next menu permitting a user to select a number of dishes to be prepared. A next menu may permit a user to select a cuisine style. A next menu may permit a user to select dish options, filtered by the cuisine style, for each dish. After completion of menu design, a recipe module may be selected. The recipe module may use a MUI as discussed herein to permit a user to quickly navigate between recipes of dishes selected for a menu. For example, a first menu may include each dish. A second menu may include options for ingredient lists and recipe steps. In this manner, a user might access the first menu in the historical portion to quickly jump between recipes while viewing navigating ingredients and steps of each individual recipe in the active portion of the MUI.

In another example, a cooking and meal design MUI module may operate as follows. A first menu may permit a user to select and define a plurality of meal parameters. For example, in a first menu, a user may select from menu items including cuisine selection, dietary restrictions, number of diners, meal design, wine pairing, and meal preparation.

Selecting the cuisine selection option permits a user access to a second menu of cuisine options, including, e.g., American, European, Mexican, Caribbean, South American, Middle Eastern, and Asian. Selecting from among the second menu options may lead to a third menu, for example, the American selection may lead to Southern, Southwestern, Texan, New England, Amish, Californian, etc., the European selection may lead to French, Italian, German, Greek, Spanish, Portuguese, British Isles, Scandinavian, etc., the South American selection may lead to Peruvian, Brazilian, etc., the Asian selection may lead to Chinese, Japanese, Vietnamese, Thai, Korean, Indian, etc. In embodiments, a user may select more than one cuisine option from the second menus that may provide a filter for other menus that a user may interact with.

Selecting the dietary restrictions option from the first menu permits a user to select from a second menu including options such as vegetarian, vegan, pescatarian, ovolacto vegetarian, allergies, health, religious, and taste. The vegetarian, vegan, pescatarian, and ovolacto vegetarian menus may be execution menus permitting the user to apply these restrictions as filters to meal choices and/or ingredients. The allergic and health menus lead to execution menus permitting a user to filter ingredients that should be restricted due to health or allergic reasons, such as tree nuts and shellfish (allergic), lactose and gluten (health). Both menus may further permit a user to write in additional options. The religious menu permits a user to access menus that filter based on religious dietary laws, such as Kosher or Halal restrictions. The Kosher menu selection offers a user execution menu including meat (filtering out all dairy options), pareve (filtering out all dairy and meat options), dairy (filtering out all meat options), Passover (filtering out all options including Chametz and/or Kitniyot). Executing any Kosher menu further serves to eliminate all non-Kosher ingredients, such as pork, shellfish, etc. The Halal menu selection offers a user an execution menu permitting the filtering of menu ingredients according to Halal restrictions. The taste menu is an execution menu permitting a user to filter out ingredient selections by diner taste.

The number of diners menu is an execution menu permitting a user to select a number of diners. Selecting the number of diners allows the module to modify recipe amounts to match the number of people eating. In embodiments, the number of diners menu may also allow a user to select options such as light, medium, and heavy as a further modifier on an amount of food to be prepared.

The meal design or meal composition selection offers a second menu of appetizer (which in turn offers a third menu of soup, salad, other), main course (which in turn offers a third menu of poultry, pork, beef, fish, vegetarian), side dishes (which in turn offers a third menu of bread, starch (rice, potatoes, other, etc.), and vegetable), and dessert. As the user drills down through these menus, they may reach additional menus providing menu items that correspond to the filters selected in the other second menus (cuisine, dietary restrictions, etc.). In embodiments, dishes may be eliminated according to the filters. In a further embodiment, dishes may include substitutes or eliminations based on the filters, e.g., oil for butter in a no-dairy dish. Each menu item leads to one or more recipe selection execution menus permitting the user to add the recipe to the final meal for preparation. The choices described here are by way of example only, and the meal composition submenu may include additional and/or different menus and hierarchy.

A wine pairing selection of the first menu offers a user second menu permitting selection of wines to match the selected dishes, e.g., by appetizer, main course, dessert, etc. After selecting a course to which a user will pair wines, execution menus may be provided for a user to actively select wines by varietal, style, label, and other features according to the selected dishes for that course.

The meal preparation selection of the first menu offers the user a combined walkthrough of meal preparation using the MUI menuing system. The walkthrough provides a series of second menu items including ingredient requirements, make-ahead dishes, and day-of dishes. The ingredient requirements selections provide a shopping list permitting a user to eliminate items they already have. The make-ahead dish menu and day-of dish menu are both similar and allow the user to select between integrated preparation and/or parallel preparation. The make-ahead dish menu offers a user access to preparation steps for all dishes and ingredients that may be prepared ahead of time, while the day-of dish menu provides a user access to preparation steps that are preferably not prepared ahead of time. The parallel preparation menu permits a user access to each selected recipe in its entirety. The integrated preparation menu permits a user access to the recipes in an integrated format. In the integrated preparation menu, a submenu is provided based on timing, e.g., 4 hours prior to meal-time, 3 hours prior to meal-time, 2 hours prior to meal-time, etc. For example, accessing the "4 hours prior" submenu provides the use with a list of tasks to complete 4 hours prior to the meal. The 3 hours prior submenu provides tasks for completion 3 hours prior to the meal, and so on. In this way, the multiple tasks from each recipe can be combined, for example, if the same ingredient needs chopping for more than one dish and integrated in the most efficient manner possible. In another embodiment, an integrated preparation submenu may be provided with menu items such as start main course, start appetizer, start side dish, complete main course, complete appetizer, complete side dish, etc. Accordingly, a chef's MUI module may permit a user to design a meal and then may provide a full integration of preparation steps In yet another example, a MUI as described herein may be implemented as an operating system or as an overlay to an operating system (OS). The MUI, as described herein, makes user interaction with any system or workflow more efficient by limiting exposure of items that are infrequently used. This design principle and the hierarchical menu flow may be applied, for example, to any aspect of an OS. For example, file tree navigation in Windows, Linux, Apple OS, etc., may be organized as a hierarchical menu tree as described herein, with lesser used options being limited from exposure and moved to a different menu, e.g., an advanced context menu. As discussed herein, lesser used options may refer to options not meeting the threshold percentage of usage frequency, e.g., 70%, 80%, 90%, or any other figure discussed herein. A user, therefore, would only see the file tree options that they interact with the most frequently unless they take steps to view other options. Apps on a mobile device operating system, iOS, Android, etc., may be arranged in the same way. Instead of being presented with multiple screens full of app icons, as is conventional, the system may categorize a user's app icons and present the apps to a user according to a hierarchical menu tree with limited exposure of lesser used apps.

In another example, the exposure limiting design principles discussed in accordance with the MUI may be applied to PUSH notifications. In the hierarchical menu trees, menu items that do not meet a threshold percentage of user interaction have their exposure limited. Similarly, push notifications to a user, e.g., alerts and notifications related to text messages, e-mails, app alerts, etc., may be limited based on user interaction. For example, the split of 90%/10% or 80%/20% or any other split discussed herein may be applied, where types of push notifications, as characterized, e.g., by sender, subject, recipients, etc., that a user interacts with most frequently are prioritized and other notifications are moved to an auxiliary menu. The push notifications that a user interacts with or accesses 90% of the time or 80% of the time, or any suitable number, may receive prioritized treatment, include vibration alerts, ring alerts, and immediate display. Other push notifications may be collected in a menu accessed only through direct user action.

In another example, a MUI as described herein may be employed for home design or remodeling. A first menu may permit a user to select a type of room, kitchen, bath, etc., to be remodeled or designed. A second menu may permit a user to select from multiple styles, modern, contemporary, traditional, etc., while a third menu may permit a user to begin selecting individual aspects of the room to be remodeled, i.e., in the case of a kitchen, cabinets, flooring, countertops, etc. In an example such as this, the MUI may interact and/or interface with more conventional design software to build and maintain a model of a user's design as they make selections and develop a design.

In yet another example, a MUI as described herein may be applied to media content navigation for selecting television programs or movies to watch. For example, a first menu may permit a user to select a category, e.g., genre, release date, popularity, starring actors/actresses, etc., by which they will browse media content. In some embodiments, each successive menu may provide similar options to the first menu, permitting the user to successively filter each next menu. In a MUI applied to media content, exclusion tables may be used, for example, as a content filter to ensure that certain viewers do not have access to inappropriate content. Limitation lists, as discussed herein, may be used to filter and alter menus according to a user's typical viewing habits.

Further embodiments include:

Embodiment 1 is a method of interactively navigating a user through a path of menu choices on a user interface in leading the user through a computer application, the method performed automatically by at least one hardware processor, the method comprising: displaying a current menu of choices on a first portion of a user interface display; allowing a user to select a menu item from the current menu of choices displayed on the first portion of the user interface display and to drill down through levels of menu choices based on selecting a menu item from a prior level of menu choices; displaying on a second portion of the user interface display, past selected and past unselected menu items of the drilled-down levels, wherein the past unselected menu items are displayed as selectable options; and allowing the user to jump to a different path of menu choices by allowing the user to select a past unselected menu item from a previously navigated menu level displayed on the second portion of the user interface display, wherein the first portion and the second portion are viewable concurrently on the user interface display.

Embodiment 2 is the method of embodiment 1, wherein responsive to detecting a selection of a menu item from the current menu of choices, relocating the current menu of choices to the second portion of the user interface display, and displaying on the first portion of the user interface display a next level of menu choices based on the selection of the menu item, wherein the relocated current menu of choices is shown on the second portion of the user interface display as the past selected and past unselected menu items of a past menu level, and the next level of menu choices is shown on the first portion as the current menu of choices.

Embodiment 3 is the method of embodiments 1 or 2, wherein the current menu of choices is displayed in first visual orientation on the first portion of the user interface display and the drilled-down levels of menu choices comprising the past selected and past unselected menu items are displayed on the second portion of the user interface display in second visual orientation.

Embodiment 4 is the method of embodiments 1 to 3, wherein the second visual orientation is substantially orthogonal to the first visual orientation.

Embodiment 5 is the method of embodiments 1 to 4, wherein the first visual orientation is a vertical orientation and the second visual orientation is a horizontal orientation.

Embodiment 6 is the method of embodiment 4 or 5, wherein the first visual orientation is a horizontal orientation and the second visual orientation is a vertical orientation.

Embodiment 7 is the method of embodiments 4 to 6, the drilled-down levels of menu choices relocated to the second portion are displayed as a stack of menu levels.

Embodiment 8 is the method of embodiments 3 to 7, wherein the current menu of choices is displayed as a graphical rotating wheel that rotates the choices in a direction of the first visual orientation.

Embodiment 9 is the method of embodiments 3 to 8, wherein a drilled-down level in the drilled-down levels of menu choices is displayed as a graphical rotating wheel that rotates choices of the drilled-down level in a direction of the second visual orientation.

Embodiment 10 is the method of embodiments 1 to 9, wherein the past selected menu items in the drilled-down levels displayed on the second portion of the user interface display are displayed highlighted relative to the past unselected menu items of the drilled-down levels displayed on the second portion of the user interface display.

Embodiment 11 is the method of embodiments 1 to 10, wherein the first portion and the second portion are displayed as a series of concentric circles.

Embodiment 12 is the method of embodiments 1 to 11, wherein the first portion and the second portion are displayed in a graphical decision tree configuration.

Embodiment 13 is the method of embodiments 1 to 12, wherein the first portion and the second portion are shifted to substantially center the first portion displaying the current menu of choices on the user interface display while fitting both the first portion and the second portion on the user interface display.

Embodiment 14 is a user interface system comprising: at least one hardware processor; and a memory device operatively coupled to the hardware processor, the hardware processor operable to retrieve from the memory device a current menu of choices and to display current menu of choices on a first portion of a user interface display, the hardware processor further operable to allow a user to select a menu item from the current menu of choices displayed on the first portion of the user interface display and to drill down through levels of menu choices based on selecting a menu item from a prior level of menu choices, the hardware processor displaying on a second portion of the user interface display, past selected and past unselected menu items of the drilled-down levels, wherein the past unselected menu items are displayed as selectable options, the hardware processor further operable to allow the user to jump to a different path of menu choices by allowing the user to select a past unselected menu item from a previously navigated menu level displayed on the second portion of the user interface display, wherein the first portion and the second portion are viewable concurrently on the user interface display.

Embodiment 15 is the system of embodiment 14, wherein responsive to detecting a selection of a menu item from the current menu of choices, the hardware processor relocating the current menu of choices to the second portion of the user interface display, and displaying on the first portion of the user interface display a next level of menu choices based on the selection of the menu item, wherein the relocated current menu of choices is shown on the second portion of the user interface display as the past selected and past unselected menu items of a past menu level, and the next level of menu choices is shown on the first portion as the current menu of choices.

Embodiment 16 is the system of embodiment 15, wherein the current menu of choices is displayed in first visual orientation on the first portion of the user interface display and the drilled-down levels of menu choices comprising the past selected and past unselected menu items are displayed on the second portion of the user interface display in second visual orientation.

Embodiment 17 is the system of embodiment 16, wherein the second visual orientation is substantially orthogonal to the first visual orientation.

Embodiment 18 is the system of embodiment 17, wherein the first visual orientation is a vertical orientation and the second visual orientation is a horizontal orientation.

Embodiment 19 is the system of embodiments 17 or 18, wherein the first visual orientation is a horizontal orientation and the second visual orientation is a vertical orientation.

Embodiment 20 is the system of embodiments 17 to 19, the drilled-down levels of menu choices relocated to the second portion are displayed as a stack of menu levels.

Embodiment 21 is the system of embodiments 16 to 20, wherein the current menu of choices is displayed as a graphical rotating wheel that rotates the choices in a direction of the first visual orientation.

Embodiment 22 is the system of embodiments 16 to 21, wherein a drilled-down level in the drilled-down levels of menu choices is displayed as a graphical rotating wheel that rotates choices of the drilled-down level in a direction of the second visual orientation.

Embodiment 23 is the system of embodiments 14 to 22, wherein the past selected menu items in the drilled-down levels displayed on the second portion of the user interface display are displayed highlighted relative to the past unselected menu items of the drilled-down levels displayed on the second portion of the user interface display.

Embodiment 24 is the system of embodiments 14 to 23, wherein the first portion and the second portion are displayed as a series of concentric circles.

Embodiment 25 is the system of embodiment 14 to 24, wherein the first portion and the second portion are displayed in a graphical decision tree configuration.

Embodiment 26 is the system of embodiment 14 to 25, wherein the first portion and the second portion are shifted to substantially center the first portion displaying the current menu of choices on the user interface display while fitting both the first portion and the second portion on the user interface display.

Embodiment 27 is a computer readable storage medium storing a program of instructions executable by a machine to perform a method of interactively navigating a user through a path of menu choices on a user interface in leading the user through a computer application, the method comprising: displaying a current menu of choices on a first portion of a user interface display; allowing a user to select a menu item from the current menu of choices displayed on the first portion of the user interface display and to drill down through levels of menu choices based on selecting a menu item from a prior level of menu choices; displaying on a second portion of the user interface display, past selected and past unselected menu items of the drilled-down levels, wherein the past unselected menu items are displayed as selectable options; allowing the user to jump to a different path of menu choices by allowing the user to select a past unselected menu item from a previously navigated menu level displayed on the second portion of the user interface display, wherein the first portion and the second portion are viewable concurrently on the user interface display.

Embodiment 28 is the computer readable storage medium of embodiment 27, wherein responsive to detecting a selection of a menu item from the current menu of choices, relocating the current menu of choices to the second portion of the user interface display, and displaying on the first portion of the user interface display a next level of menu choices based on the selection of the menu item, wherein the relocated current menu of choices is shown on the second portion of the user interface display as the past selected and past unselected menu items of a past menu level, and the next level of menu choices is shown on the first portion as the current menu of choices.

Embodiment 29 is the computer readable storage medium of embodiment 28, wherein the current menu of choices is displayed in first visual orientation on the first portion of the user interface display and the drilled-down levels of menu choices comprising the past selected and past unselected menu items are displayed on the second portion of the user interface display in second visual orientation.

Embodiment 30 is the computer readable storage medium of embodiment 29, wherein the second visual orientation is substantially orthogonal to the first visual orientation.

Embodiment 31 is the computer readable storage medium of embodiment 30, wherein the first visual orientation is a vertical orientation and the second visual orientation is a horizontal orientation.

Embodiment 32 is the computer readable storage medium of embodiments 30 to 31, wherein the first visual orientation is a horizontal orientation and the second visual orientation is a vertical orientation.

Embodiment 33 is the computer readable storage medium of embodiments 30 to 32, the drilled-down levels of menu choices relocated to the second portion are displayed as a stack of menu levels.

Embodiment 34 is the computer readable storage medium of embodiments 29 to 33, wherein the current menu of choices is displayed as a graphical rotating wheel that rotates the choices in a direction of the first visual orientation.

Embodiment 35 is the computer readable storage medium of embodiments 29 34, wherein a drilled-down level in the drilled-down levels of menu choices is displayed as a graphical rotating wheel that rotates choices of the drilled-down level in a direction of the second visual orientation.

Embodiment 36 is the computer readable storage medium of embodiments 27 to 35, wherein the past selected menu items in the drilled-down levels displayed on the second portion of the user interface display are displayed highlighted relative to the past unselected menu items of the drilled-down levels displayed on the second portion of the user interface display.

Embodiment 37 is the computer readable storage medium of embodiments 27 to 36, wherein the first portion and the second portion are displayed as a series of concentric circles.

Embodiment 38 is the computer readable storage medium of embodiments 27 to 37, wherein the first portion and the second portion are displayed in a graphical decision tree configuration.

Embodiment 39 is the computer readable storage medium of embodiments 27 to 38, wherein the first portion and the second portion are displayed in parallel in a same visual orientation.

Embodiment 40 is the computer readable storage medium of embodiments 27 to 39, wherein the first portion and the second portion are shifted to substantially center the first portion displaying the current menu of choices on the user interface display while fitting both the first portion and the second portion on the user interface display.

Embodiment 41 is the computer readable storage medium of embodiments 27 to 40, wherein the user interface navigates the user through an assay system while presenting a minimal number of menu choices the user needs to make for navigating through the assay system.

Embodiment 42 is the method of interactively navigating a user through a path of menu choices on a user interface in leading the user through a computer application, the method performed automatically by at least one hardware processor, the method comprising: displaying a current menu of choices on a first portion of a user interface display; allowing a user to select a menu item from the current menu of choices displayed on the first portion of the user interface display and to drill down through levels of menu choices based on selecting a menu item from a prior level of menu choices; and displaying on a second portion of the user interface display, past selected and past unselected menu items of the drilled-down levels, wherein the past unselected menu items are displayed as selectable options; wherein the first portion and the second portion are viewable concurrently on the user interface display; and wherein the graphical user interface maximizes black space by making a background of the user interface display black to thereby save storage and improve speed of presentation.

Embodiment 43 is the method of embodiment 42, wherein responsive to detecting a selection of a menu item from the current menu of choices, relocating the current menu of choices to the second portion of the user interface display, and displaying on the first portion of the user interface display a next level of menu choices based on the selection of the menu item, wherein the relocated current menu of choices is shown on the second portion of the user interface display as the past selected and past unselected menu items of a past menu level, and the next level of menu choices is shown on the first portion as the current menu of choices.

Embodiment 44 is the method of embodiment 42 or 43, wherein the current menu of choices is displayed in first visual orientation on the first portion of the user interface display and the drilled-down levels of menu choices comprising the past selected and past unselected menu items are displayed on the second portion of the user interface display in second visual orientation.

Embodiment 45 is the method of embodiment 43 or 44, wherein the second visual orientation is substantially orthogonal to the first visual orientation.

Embodiment 46 is the method of embodiments 44 or 45, wherein the first visual orientation is a vertical orientation and the second visual orientation is a horizontal orientation.

Embodiment 47 is the method of embodiments 44 to 46, wherein the first visual orientation is a horizontal orientation and the second visual orientation is a vertical orientation.

Embodiment 48 is the method of embodiments 44 to 47, the drilled-down levels of menu choices relocated to the second portion are displayed as a stack of menu levels.

Embodiment 49 is the method of embodiments 43 to 48, wherein the current menu of choices is displayed as a graphical rotating wheel that rotates the choices in a direction of the first visual orientation.

Embodiment 50 is the method of embodiments 42 to 49, wherein a drilled-down level in the drilled-down levels of menu choices is displayed as a graphical rotating wheel that rotates choices of the drilled-down level in a direction of the second visual orientation.

Embodiment 51 is the method of embodiments 42 to 50, wherein the past selected menu items in the drilled-down levels displayed on the second portion of the user interface display are displayed highlighted relative to the past unselected menu items of the drilled-down levels displayed on the second portion of the user interface display.

Embodiment 52 is the method of embodiments 42 to 51, wherein the first portion and the second portion are displayed as a series of concentric circles.

Embodiment 53 is the method of embodiments 42 to 52, wherein the first portion and the second portion are displayed in a graphical decision tree configuration.

Embodiment 54 is the method of embodiments 42 to 53, wherein the first portion and the second portion are shifted to substantially center the first portion displaying the current menu of choices on the user interface display while fitting both the first portion and the second portion on the user interface display.

Embodiment 55 is the method of embodiments 42 to 54, further comprising allowing the user to jump to a different path of menu choices by allowing the user to select a past unselected menu item from a previously navigated menu level displayed on the second portion of the user interface display.

Embodiment 56 is the method of interactively navigating a user through a path of menu choices on a user interface in leading the user through a computer application, the method performed automatically by at least one hardware processor, the method comprising: displaying a current menu of choices on a first portion of a user interface display; allowing a user to select a menu item from the current menu of choices displayed on the first portion of the user interface display and to drill down through levels of menu choices based on selecting a menu item from a prior level of menu choices; displaying on a second portion of the user interface display, past selected and past unselected menu items of the drilled-down levels, wherein the past unselected menu items are displayed as selectable options, wherein the first portion and the second portion are viewable concurrently on the user interface display, wherein at least the first portion includes a search function box, a sub-first area and a sub-second area, wherein the first portion is scrollable as a whole and shows the current menu of choices, wherein responsive the detecting an entry of a search term in the search function box, the first portion is bifurcated into the sub-first area and sub-second area that are scrollable individually.

Embodiment 57 is the method of embodiment 56, wherein the sub-second area displays a subset of the current menu choices that matches the search term.

Embodiment 58 is the method of embodiment 56 or 57, wherein the sub-second area displays the current menu of choices.

Embodiment 59 is the method of embodiments 56 to 58, wherein the sub-first area displays a recently chosen menu item.

Embodiment 60 is the method of embodiments 56 to 59, wherein the first portion is rendered on the user interface display as a graphical wheel.

Embodiment 61 is a method of interactively navigating a user through a path of menu choices on a user interface in leading the user through a computer application, the method performed automatically by at least one hardware processor, the method comprising: displaying a current menu of choices on a first portion of a user interface display; allowing a user to select a menu item from the current menu of choices displayed on the first portion of the user interface display and to drill down through levels of menu choices based on selecting a menu item from a prior level of menu choices; displaying on a second portion of the user interface display, past selected and past unselected menu items of the drilled-down levels, wherein the past unselected menu items are displayed as selectable options, wherein the first portion and the second portion are viewable concurrently on the user interface display, wherein the current menu of choices is displayed as a graphical rotating wheel that rotates the choices, wherein the graphical rotating wheel is rotatable from a first menu item in the current menu of choices to a last menu item in the current menu of choices, and the graphical rotating wheel is further rotatable from the last menu item to the first menu item, and the first menu item and the last menu item do not connect in the graphical rotating wheel's rotation.

Embodiment 62 is the method of embodiment 61, wherein the graphical rotating wheel is a vertical wheel that rotates vertically.

Embodiment 63 is the method of embodiment 61 or 62, wherein the graphical rotating wheel is a horizontal wheel that rotates horizontally.

Embodiment 64 is a method executed by at least one hardware processor for navigating a path of hierarchical menu levels outputted to a graphical user interface (GUI), the method comprising: providing a first command for a first menu of user-selectable choices to be displayed on a first portion of a user interface (UI) display; and providing a second command for a second menu of user-selectable choices to be displayed on the first portion of the UI display in response to a user's selection, wherein the second portion includes one or more of a past-selected and a past-unselected menu item of the hierarchical menu levels and is adapted to be concurrently viewed with the first portion.

Embodiment 65 is the method of embodiment 64 further comprising an advanced context menu, wherein the advanced context menu is adapted to be displayed in response to a selection of an advanced selector.

Embodiment 66 is the method of embodiment 65 or 64, wherein the advanced context menu includes one or more of the following user-selected choices: Export; Admin Console; Admin Audit Trail; Terms of Use; Privacy Policy; and Log out.

Embodiment 67 is the method of embodiments 64 to 66, wherein in response to a selection of Admin Audit Trail choice, the first portion is adapted to display audit information that includes one or more of the following: a timestamp, a user name and/or email address, module, record ID, type, message, category, code, and IP address of a user.

Embodiment 68 is the method of embodiment 67, wherein the audit information includes information relating to one or more of all users, accounts, and teams.

Embodiment 69 is the method of embodiment 67 or 68, wherein the audit information includes information relating to a particular team selected among previously added teams.

Embodiment 70 is the method of embodiment 69 further comprising providing a command to display an audit menu that includes the previously added teams in response to a selection of the Admin Audit Trail choice.

Embodiment 71 is the method of embodiment 67 embodiments 64 to 70, wherein the audit information is adapted to be exported to a user in response to a selection of the Export choice.

Embodiment 72 is the method of embodiments 64 to 72, wherein the second portion is adapted to display an audit menu for a user to select all audit information to be available for display, or to narrow the audit information to be displayed by one or more teams and/or instruments.

Embodiment 73 is the method of embodiments 66 to 72, wherein in response to a selection of Admin Audit Trail choice, the advanced context menu includes one or more of the following choices: Export and Copy to Clipboard.

Embodiment 74 is the method of embodiments 64 to 73, further comprising an advanced context menu, wherein the advanced context menu is adapted to be displayed in response to a selection of an advanced selector.

Embodiment 75 is the method of embodiments 64 to 74, wherein the first menu of user-selectable choices includes one or more of the following choices: Read; and Review Recent Results.

Embodiment 76 is the method of embodiment 75, wherein in response to a selection of the Read command, the second portion of the UI display is adapted to output a Play Button.

Embodiment 77 is the method of embodiment 76, wherein in response to a selection of the Play Button, a plate reader is adapted begin reading one or more plates.

Embodiment 78 is the method of embodiment 77, wherein in further response to the selection of the Play Button, the UI display is adapted to display a timer, wherein the timer is adapted to indicate one or more of: the total amount of time to load the one or more plates; the total amount of time to read the one or more plates; the total amount of time to unload the one or more plates; the time remaining to complete the loading of the one or more plates; the time remaining to complete the reading of the one or more plates; and the time remaining to complete the unloading of the one or more plates.

Embodiment 79 is the method of embodiments 74 to 78, wherein the advanced context menu includes one or more of the following user-selectable choices: Eject Plate; Partial Plate; Set Plate Run; Stop Instrument; Lock UI; and View Plate Information.

Embodiment 80 is the method of embodiment 79, wherein in response to a selection of the Partial Plate choice, the first portion is adapted to receive bar code information as it relates a plate selected among the one or more plates.

Embodiment 81 is the method of embodiment 80, wherein the first portion is further adapted to display a user-selectable option that, when selected, verifies the authenticity the received bar code information.

Embodiment 82 is the method of embodiment 79 to 81, wherein further in response to the Partial Plate choice, the advanced context menu includes one or more of the following choices: Save Partial Plate; and Cancel Partial Plate.

Embodiment 83 is the method of embodiment 79 to 83, wherein in response to a selection of the Set Plate Run choice, the first portion is adapted to receive a name for a plate run associated with a plate.

Embodiment 84 is the method of embodiment 79 to 84, wherein in response to a selection of the Stop Instrument choice, which the first portion is adapted to display a confirmation choice before issuing a stop instrument command.

Embodiment 85 is the method of embodiment 84, wherein the confirmation choice, when selected, is adapted to either abort the current run of a plate by issuing the stop instrument command or continuing the run by disregarding the stop instrument command.

Embodiment 86 is the method of embodiment 79 to 85, wherein in response to a selection of the Lock UI choice, the UI display is adapted to be locked from user selections until receiving the current user's password.

Embodiment 87 is the method of embodiment 79 to 86, wherein in response to a selection of the View Plate Information choice, the first portion is adapted to display Plate Information including one or more of the following: plate run name, plate barcode, long side customer barcode, short side customer barcode, plate type, operator, and read time.

Embodiment 88 is the method of embodiment 79 to 87, wherein in response to a selection of the Eject Plate choice, a plate is ejecting from a plate-reading instrument.

Embodiment 89 is the method of embodiment 64 to 88, wherein the first menu of user-selectable choices includes one or more of the following choices: Define Roles and Permissions; Add/Remove members; Assign Members to Roles; and Authorize and Inform Members.

Embodiment 90 is the method of embodiment 89, wherein the first portion includes two or more subsections of user-selectable choices from the second menu.

Embodiment 91 is the method of embodiment 90, wherein in response to a selection of Define Roles and Permissions, a first subsection of user-selectable choices includes one or more of the following choices: Lab Manager; Designer; Associate; Operator (Base); and Maintenance Tech (Base).

Embodiment 92 is the method of embodiment 91, wherein in response to a selection of one or more of: (a) Lab Manager; (b) Designer; or (c) Associate, a second subsection of user-selectable choices includes one or more of the following choices: Analysis Method; Assay Method; Experiment; Assay Engine; Audit Trail; Maintenance; Reader; and System.

Embodiment 93 is the method of embodiment 91 or 92, wherein in response to a selection of one or more of (a) Operator (Base) or (b) Maintenance Tech (Base), a second subsection of user-selectable choices includes one or more of the following choices: Assay Engine; Audit Trail; Maintenance; Reader; and System.

Embodiment 94 is the method of embodiment 91 to 93, wherein in response to a selection of Analysis Method, a third subsection of user-selectable choices includes a Run Analysis Method choice.

Embodiment 95 is the method of embodiment 91 to 94, wherein in response to a selection of Assay Method, a third subsection of user-selectable choices includes a Run Assay Method choice.

Embodiment 96 is the method of embodiment 91 to 95, wherein in response to a selection of Experiment, a third subsection of user-selectable choices includes one or more of the following choices: Create Experiment; Edit Layout; Exclude/Include Data Points; Export Data Table; Export Sample Result Table; and View Experiment.

Embodiment 97 is the method of one of embodiment 91 to 96, wherein in response to a selection of Assay Engine Method, a third subsection of user-selectable choices includes one or more of the following choices: Export Data Table; Modify Instrument Settings; Override Mesoscale Diagnostics Kit Lot Assignment; Retry Inventory Validation; Run Instrument; and Show ECL for Unverified Run.

Embodiment 98 is the method of one of embodiment 91 to 97, wherein in response to a selection of Audit Trail, a third subsection of user-selectable choices includes a View Audit Trail App choice.

Embodiment 99 is the method of one of embodiments 91 to 98, wherein in response to a selection of Maintenance, a third subsection of user-selectable choices includes one or more of the following choices: Run Maintenance; Run Maintenance Method; and View Maintenance Records.

Embodiment 100 is the method of one of embodiments 91 to 99, wherein in response to a selection of Reader, a third subsection of user-selectable choices includes one or more of the following choices: Manage Database; Modify Instrument Settings; and Run Instrument.

Embodiment 101 is the method of one of embodiments 91 to 100, wherein in response to a selection of System, a third subsection of user-selectable choices includes one or more of the following choices: Modify System Settings; and Unlock App Locked by Any User.

Embodiment 102 is the method of embodiments 90 to 102, wherein in response to a selection of the Add/Remove Members choice, the second menu of user-selectable choices includes previously added usernames and/or email addresses, further wherein one or more of the usernames and/or email addresses are adapted to be deleted from the second menu of user-selectable choices in response to a user's deletion input.

Embodiment 103 is the method of embodiment 102, wherein in further response to the selection of the Add/Remove Members choice, the second menu is adapted to receive new usernames and/or email addresses to add among the previously added usernames and/or email addresses.

Embodiment 104 is the method of embodiment 103, wherein in response to the user's deletion input, a confirmation screen is adapted to be displayed on the first portion of the user interface display, further wherein the confirmation screen is adapted to display user-selectable choices that include Cancel and OK.

Embodiment 105 is the method of embodiments 90 to 104, wherein in response to a selection of Assign Members to Roles, a first subsection of user-selectable choices includes previously added usernames and/or email addresses and the second subsection includes one or more of the following role-assignment choices: Lab Manager; Designer; Associate; Operator (Base); and Maintenance Tech (Base).

Embodiment 106 is the method of embodiment 105, wherein selections from the first- and second-subsections are adapted to create an association among one or more of the previously added usernames and/or email addresses with one or more of the role-assignment choices.

Embodiment 107 is the method of embodiment 106, wherein association among the one or more of the previously added usernames and/or email addresses with one or more of the role-assignment choices is adapted to be displayed on the UI in response to a selection of the Authorize and Inform Members choice.

Embodiment 108 is the method of embodiment 107, wherein in response to a selection of the Authorize and Inform Member choice, the first portion is adapted to display an Authorize and Email Install Instructions choice.

Embodiment 109 is the method of embodiment 108, wherein role-assignment information and/or instructions are adapted to be transmitted to the previously added email addresses in response to a selection of Authorize and Email Install Instructions choice.

Embodiment 110 is the method of embodiments 64 to 109, wherein the first menu of user-selectable choices includes one or more of the following choices: Prepare Teams; Define Administrators; and Manage Teams.

Embodiment 111 is the method of embodiment 110, wherein in response to a selection of Prepare Teams choice, the second menu of user-selectable choices includes one or more previously added teams.

Embodiment 112 is the method of embodiments 110 to 111, wherein in response to a selection of the Prepare Teams choice, the second menu of user-selectable choices is adapted to receive one or more new teams to add among the one or more previously added teams.

Embodiment 113 is the method of embodiments 110 to 112, wherein in response to a selection of the Prepare Teams choice, the second portion is adapted to display one or more of a number of available teams defined, a number of available seats assigned, a total number of available teams, and a total number of available seats.

Embodiment 114 is the of embodiments 110 to 113, wherein in response to a selection of Define Administrators choice, the second menu of user-selectable choices includes previously added usernames and/or email addresses, further wherein one or more of the usernames and/or email addresses are adapted to be deleted from the second menu of user-selectable choices in response to a user's deletion input.

Embodiment 115 is the method of embodiments 110 to 114, wherein further in response to a selection of the Define Administrators choice, the second menu of user-selectable choices is adapted to receive new usernames and/or email addresses to add among the previously added usernames and/or email addresses.

Embodiment 116 is the method of embodiments 111 to 115, wherein the second portion is adapted to display the one or more previously added teams as a menu of choices.

Embodiment 117 is the method of embodiment 116, wherein the previously added usernames and/or email addresses are associated with a particular team among the one or more previously added teams from the menu of choices.

Embodiment 118 is the method of embodiment 117, wherein in response to a selection of the Define Administrators choice, the first portion is adapted to display an Authorize and Email choice.

Embodiment 119 is the method of embodiment 118, wherein authorizations and/or team-assignment information are adapted to be transmitted to the previously added email addresses in response to a selection of the Authorize and Email Install Instructions choice.

Embodiment 120 is the method of embodiments 111 to 119, wherein the first menu of user-selectable choices identified in embodiment 89 are displayed in response to a selection of the Manage Teams choice:

Embodiment 121 is the method of embodiments 64 to 120 further comprising an advanced context menu, wherein the advanced context menu is adapted to be displayed in response to a selection of an advanced selector.

Embodiment 122 is the method of embodiment 121, wherein in response to a selection of Admin Audit Trail choice, the advanced context menu includes one or more of the following choices: Resend install instruction, Import, and Change Team Name, Change Account Name, Change Password Expiration.

Embodiment 123 is the method of embodiment 64 further comprising providing, by the at least one processor, a relocation command for the first menu to be relocated to the second portion of the UI display in response to the user's selection, wherein the second menu comprises a subsequent level of menu items for the user to select.

Embodiment 124 is the method of any of embodiments 64 or 123, wherein the subsequent level of menu items comprises one or more user-selectable menu items at least one hierarchical menu level lower than the first menu.

Embodiment 125 is the method of any of embodiments 64 or 123 to 124, wherein the subsequent level of menu items comprises one or more user-selectable menu items at more than one hierarchical menu level lower than the first menu.

Embodiment 126 is the method of any of embodiments 64 or 123 to 125, wherein the past-unselected menu item includes a previously navigated hierarchical menu level.

Embodiment 127 is the method of any of embodiments 64 or 123 to 126 wherein the first portion comprises an active portion, which includes one or more current, user-selectable menu items, and the second portion comprises a historical portion, which includes menu items previously made available to a user.

Embodiment 128 is the method of any of embodiments 64 or 123 to 127, wherein the first portion and the second portion are adapted to be displayed in a first visual orientation and a second visual orientation, respectively.

Embodiment 129 is the method of any of embodiments 64 or 123 to 128 wherein the second visual orientation is substantially orthogonal to the first visual orientation.

Embodiment 130 is the method of any of embodiments 64 or 123 to 129 wherein the first visual orientation is a vertical orientation and the second visual orientation is a horizontal orientation.

Embodiment 131 is the method of any of embodiments 64 or 123 to 130 wherein the first visual orientation is configured to provide one or more user-selectable menu items in one or more of a vertical, horizontal, or concentric orientation.

Embodiment 132 is the method of any of embodiments 64 or 123 to 131 wherein the second visual orientation is configured to provide user-selectable menu items in one or more of a vertical, horizontal, or concentric orientation.

Embodiment 133 is the method of any of embodiments 64 or 123 to 132 wherein a manner in which the menu items are adapted to be displayed is based on an attribute selected from one or more of: (a) being the selected menu item; (b) having a position in a list more central relative to other menu items in the list; (c) being available or unavailable to the user; (d) containing one or more characters typed by a user; and (e) being part of an advanced context menu.

Embodiment 134 is the method of any of embodiments 64 or 123 to 133 wherein the manner in which the menu items are adapted to be displayed includes one or both of: (a) emphasizing menu items that are one or more of: the selected menu item, positioned in a decision-making zone, or available to the user; and (b) deemphasizing menu items that are one or more of: not the selected menu item, positioned away from the decision-making zone, or unavailable to the user.

Embodiment 135 is the method of any of embodiments 64 or 123 to 134 wherein menu items are adapted to be emphasized by one or more of highlighting, bolding, making larger, underlining, or positioning on the UI display relative to other menu items.

Embodiment 136 is the method of any of embodiments 64 or 123 to 135, wherein menu items are adapted to be deemphasized by one or more of fading, making smaller, or positioning on the UI display relative to other menu items.

Embodiment 137 is the method of any of embodiments 64 or 123 to 136, wherein the decision-making zone is adapted to be displayed in a centrally located area.

Embodiment 138 is the method of any of embodiments 64 or 123 to 137 wherein the first and second menus are adapted to be displayed on a background, which is adapted to be displayed in a manner that contrasts with the first and second menus.

Embodiment 139 is the method of any of embodiments 64 or 123 to 138 wherein the second portion is adapted to be displayed across a smaller area than the first portion.

Embodiment 140 is the method of any of embodiments 64 or 123 to 139 wherein the first visual orientation is one or more of parallel, orthogonal, vertical, horizontal, and concentric to the second visual orientation.

Embodiment 141 is the method of any of embodiments 64 or 123 to 140 wherein the each of the providing steps is performed by the processor by executing a computer application stored on a machine.

Embodiment 142 is the method of any of embodiments 64 or 123 to 141 wherein the computer application comprises an application for manipulating, designing, performing, reviewing, measuring, or analyzing an experiment.

Embodiment 143 is the method of any of embodiments 64 or 123 to 142 wherein the experiment comprises one or more assays.

Embodiment 144 is the method of any of embodiments 64 or 123 to 143 wherein the experiment comprises one or more electrochemiluminescence assays.

Embodiment 145 is the method of any of embodiments 64 or 123 to 144 further comprising providing a limiting command to limit the total number of menu items to be displayed based on at least one of the following criteria: (a) frequency with which a user has previously selected the menu item while logged into his/her account; (b) frequency with which at least two users have previously selected the menu item while logged into an account; (c) frequency with which a user has previously selected the menu item while logged into an account associated with multiple accounts; (d) frequency with which at least two users have previously selected the menu item while logged into one or more accounts associated with multiple accounts; (e) frequency with which any users have previously selected the menu item while logged into any account; and (f) frequency with which any users have previously selected the menu item while logged into any account associated with multiple accounts.

Embodiment 146 is the method of any of embodiments 64 or 123 to 145, wherein the multiple accounts of elements (c), (d), and (f) are accounts associated with a team and the users are team members of the one or more team associated with the multiple accounts.

Embodiment 147 is the method of any of embodiments 64 or 123 to 146 further comprising providing an exclusion command to exclude menu items to be displayed based on at least one of the following criteria: (a) menu items designated as unavailable in a present module; (b) menu items designated as unavailable to a user; (c) menu items designated as unavailable to an aggregation of users; (d) menu items designated as unavailable to a particular machine storing the one or more copies of the computer application; and (e) menu items designated as unavailable to an aggregation of machines, each storing one or more copies of the computer application.

Embodiment 148 is the method of any of embodiments 64 or 123 to 147 wherein the frequency is determined over a defined time period.

Embodiment 149 is the method of any of embodiments 64 or 123 to 148 wherein the frequency is 50% or more.

Embodiment 150 is the method of any of embodiments 64 or 123 to 149 wherein the frequency is 80% or more.

Embodiment 151 is the method of any of embodiments 64 or 123 to 150, wherein the first and second menus are adapted to collectively display fewer than seven user-selectable menu items at any given point in time.

Embodiment 152 is the method of any of embodiments 64 or 123 to 151, wherein the background comprises pixels, wherein at least 75% of the pixels are monochromatic.

Embodiment 153 is the method of any of embodiments 64 or 123 to 152, wherein the background comprises pixels, wherein at least 75% of the pixels are black.

Embodiment 154 is the method of any of embodiments 64 or 123 to 153, further comprising providing a third command for a third menu of one or more user-selectable menu items to be displayed on a third portion of the UI display, wherein the third menu is adapted to be concurrently viewed with the first and second portions of the UI display.

Embodiment 155 is the method of any of embodiments 64 or 123 to 154 further comprising: providing a third command for a third menu of user-selectable menu items to be displayed on the first portion of the UI display in response to a user's selection from the second menu, wherein the one or more of a past-selected menu item and a past-unselected menu item of the hierarchical menu levels from the second menu is adapted to be displayed on the second portion and concurrently viewed with the first portion.

Embodiment 156 is the method of any of embodiments 64 or 123 to 155, wherein the second portion further comprises a submenu, wherein the submenu comprises one or more of a past-selected sub-menu item and a past-unselected sub-menu item selected among at least one lower hierarchical menu level of one or more of the first, second, and third menus.

Embodiment 157 is a system for navigating a path of hierarchical menu levels adapted for output to a graphical user interface (GUI), the system comprising at least one processor; a user input device; and a computer readable storage medium configured to store a computer application, wherein the at least one processor is configured to execute instructions of the computer application for providing a first command for a first menu of one or more user-selectable menu items to be displayed on a first portion of a user interface (UI) display, and providing a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in the first portion.

Embodiment 158 is a non-transitory computer readable medium having computer instructions stored thereon that, when executed by a processor, cause the processor to carry out a method for navigating a path of hierarchical menu levels adapted for output to a graphical user interface (GUI), the method comprising: providing a first command for a first menu of one or more user-selectable menu items to be displayed on a first portion of a user interface (UI) display; and providing a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in the first portion.

Embodiment 159 is the method of any of embodiments 64 or 124 to 156, further comprising an Advanced context menu, wherein the Advanced context menu is adapted to be displayed in response to a selection of an advanced selector.

Embodiment 160 is the method of any of embodiments 1-35 and embodiment 159, wherein the first menu comprises one or more of Design Assay Method and Review Assay Method.

Embodiment 161 is the method of embodiment 160, wherein the second menu is a submenu of Design Assay Method and comprises one or more of Manual Assay Method and Automated Assay Method in response to a selection of Design Assay Method.

Embodiment 162 is the method of embodiment 161, wherein the third menu comprises one or more name of recent assay methods in response to a selection of Manual Assay Methods or Automated Assay Methods.

Embodiment 163 is the method of embodiment 162, wherein the third menu includes one or more user-selectable choice selected from names of recent Assay Methods.

Embodiment 164 is the method of embodiments 160-163, further comprising providing a fourth command for a fourth menu of user-selectable items to be displayed on the first portion of the UI display in response to a user's selection from the third menu, wherein the one or more of a past-selected and a past-unselected menu item of the hierarchical menu levels from the first, second, and third menu is adapted to be displayed on the second portion and concurrently viewed with the first portion.

Embodiment 165 is the method of embodiment 164, wherein the second portion includes one or more of Recent and Available.

Embodiment 166 is the method of 164, wherein in response to a selection of a recent Assay Method, the second portion comprises one or more choices selected from Assay, Layout, Analysis Method, Protocol, and Confirm.

Embodiment 167 is the method of embodiment 166, wherein the fourth menu is a sub-menu of Assay and comprises one or more of a first subsection and a second subsection, wherein the first subsection comprises a spot layout and list of associated assays for the selected Assay Method and the second sub-section comprises a list of available assays for the selected Assay Method.

Embodiment 168 is the method of embodiment 166, wherein the fourth menu is a submenu of Layout and comprises a plate layout.

Embodiment 169 is the method of embodiment 166, wherein the fourth menu is a submenu of Analysis Method and comprises one or more of a first and a second subsection, wherein the first subsection comprises one or more of an assay of the selected Assay Method and its algorithm, and the second subsection comprises available algorithms when an algorithm in the first subsection is selected.

Embodiment 170 is the method of embodiment 166, wherein the fourth menu is a submenu of Protocol.

Embodiment 171 is the of embodiment 166, wherein the fourth menu is a submenu of Confirm and comprises one or more of a first subsection and a second subsection, wherein the first subsection comprises one or more of a spot layout and an associated list of assays in the selected Assay Method and the second subsection comprises one or more of a unique Assay method name, a plate layout, and Confirm.

Embodiment 172 is the method of embodiment 163, wherein the second portion comprises one or more of Recent and Available, and the in response to a selection of Available, the third menu is a submenu of Available and comprises one or more of a first, a second, and a third subsection, wherein the first subsection comprises one or more of MSD Purchased, MSD Catalog, and user name, the second subsection comprises one or more of available types of assay method filtered by the selection in the first subsection, and the third section comprises one or more of available assay methods filtered by the selections in the first and second subsections.

Embodiment 173 is the method of embodiment 172, wherein the second subsection comprises one or more assay method types selected from Custom, Immunogenicity, Pharmacokinetic, S-PLEX, U-PLEX, U-PLEX Development Pack, Utility, and V-PLEX.

Embodiment 174 is the method of embodiment 170, wherein the second portion comprises a further submenu of Protocol, wherein the further submenu comprises one or more of Blocking, Capture, Detection, and Read Buffer.

Embodiment 175 is the method of embodiment 174, wherein the third menu is a submenu of the Blocking, Capture, Detection, or Read Buffer submenu and comprises one or more user-selectable or user-nonselectable choices.

Embodiment 176 is the method of embodiment 175, wherein one or more of the choices in the third menu is user-selectable, and the user-selectable choices are adapted to be editable.

Embodiment 177 is the method of embodiments 174 or 175, wherein the third submenu is a submenu of the Blocking submenu and comprises one or more of Enable Blocking, Blocking Volume, and Blocking Incubation Duration.

Embodiment 178 is the method of embodiment 174 or 175, wherein the third submenu is a submenu of the Capture submenu and comprises Sample Incubation Duration.

Embodiment 179 is the method of embodiment 174 or 175, wherein the third submenu is a submenu of the Detection submenu and comprises Detection Incubation Duration.

Embodiment 180 is the method of embodiment 174 or 175, wherein the third submenu is a submenu of the Read Buffer submenu and comprises Read Buffer Incubation Duration.

Embodiment 181 method of embodiment 171, wherein the unique Assay method name is adapted to be edited to a second unique Assay method name.

Embodiment 182 is the method of any of embodiments 159-181, wherein in response to a selection of Review Assay Method, the second menu comprises one or more user-selectable choice selected from names of recent Assay Methods.

Embodiment 183 is the method of embodiment 64, wherein the second portion comprises one or more of Recent and Available.

Embodiment 184 is the method of embodiment 64, wherein in response to a selection of a recent Assay Method, the second portion comprises one or more of Assay Method and Definition, wherein the second menu is a submenu of Definition comprises one or more of a first and a second subsection.

Embodiment 185 is the method of embodiment 184, wherein the first subsection comprises one or more of an assay layout and one or more associated assays and the second subsection comprises one or more of an Assay Method name and a plate layout.

Embodiment 186 is the method of embodiment 64, wherein the second menu is a submenu of Available and comprises one or more of a first, a second, and a third subsection.

Embodiment 187 is the method of embodiment 186, wherein the first subsection comprises one or more of MSD Catalog and one or more user name, the second subsection comprises one or more of assay method type filtered by a selection in the first subsection, and the third subsection comprises one or more available assay methods filtered by a selection in the first and second subsections.

Embodiment 188 is the method of embodiment 187, wherein in response to a selection of an available assay method, the submenu comprises one or more of Assay Method and Definition, wherein the submenu for Definition comprises one or more of a first and a second subsection.

Embodiment 189 is the method of embodiment 64, wherein the first menu of user-selectable choices includes one or more of the following choices: designed experiment; and view Recent run.

Embodiment 190 is the method of any of embodiments 189, wherein in response to a selection of designed experiment, the second portion of the UI display is adapted to display one or more of the following choices: recent and available.

Embodiment 191 is the method of any of embodiments 189-190, wherein in response to a selection of designed experiment, the first portion of the UI display is adapted to display one or more experiments.

Embodiment 192 is the method of method of any of embodiments 189-191, wherein in response to a selection of available, the first portion of the UI display is adapted to display one or more a first-, second-, and third-subsection, wherein the first sub-section includes a user name, the second sub-section includes a date, and the third sub-section includes one or more experiment names.

Embodiment 193 is the method of any of embodiments 189-192, wherein in response to an experiment, the second portion includes one or more items selected from process, run, unload, and load components.

Embodiment 194 is the method of any of embodiments 189-193, wherein unload and load components are subsequent menus in response to a selection of the process item.

Embodiment 195 is the method of any of embodiments 189-194, wherein the first portion of the UI display is adapted to display one or more a first- and second-subsection, wherein the first sub-section includes one or more one or more instructions for loading one or more component of an experiment and one or more choice to check all items, each with an associated checkbox adapted to allow selection of that item.

Embodiment 196 is the method of any of embodiments 189-195, wherein the second-subsection includes a representation of the location for loading each component adapted to add a representation of and to highlight each component as an associated checkbox or the box for check all items is checked.

Embodiment 197 is the method of method of any of embodiments 189-196, wherein in response to a selection of the check all items checkbox or a selection of all associated checkboxes, the second-subsection includes a representation of the location for loading each component, the second portion of the UI display is adapted to output a Play Button.

Embodiment 198 is the method of any of embodiments 189-197, wherein in response to a selection of the Play Button, a run function is adapted to be performed.

Embodiment 199 is the method of any of embodiments 64 or 124-156, wherein the first menu comprises one or more of Design Experiment and Review Experiment.

Embodiment 200 is the method of embodiment 199 wherein the second menu comprises one or more of New and From Existing Experiment in response a selection of Design.

Embodiment 201 is the method of any of embodiments 199-200 wherein the third menu comprises one or more subsections in response to a selection of New.

Embodiment 202 is the method of any of embodiments 199-201, wherein the first subsection of the third menu comprises a first unique experiment name field and an experiment type field.

Embodiment 203 is the method of any of embodiments 199-202, wherein the experiment name field is adapted to allow manual entry of a second unique name and the experiment type field is adapted to be edited when clicked.

Embodiment 204 is the method of any of embodiments 199-203, wherein the second sub-section comprises Manual and Automation in response to a user clicking the experiment type.

Embodiment 205 is the method of any of embodiments 199-204, wherein the second portion includes one or more of Design Experiment, Setup, Assay Method, Samples, and Confirm in response to a selection of a unique experiment name and experiment type.

Embodiment 206 is the method of any of embodiments 199-205, wherein the second portion includes one or more of Design Experiment, Setup, Assay Method, Samples, and Confirm.

Embodiment 207 is the method of any of embodiments 199-206 further comprising providing a fourth command for a fourth menu of user-selectable items to be displayed on the first portion of the UI display in response to a user's selection from the third menu, wherein the one or more of a past-selected and a past-unselected menu item of the hierarchical menu levels from the first, second, and third menu is adapted to be displayed on the second portion and concurrently viewed with the first portion.

Embodiment 208 is the method of any of embodiments 199-207 wherein the second portion includes one or more of Recent and Available and both are subsequent menus of Assay Method.

Embodiment 209 is the method of any of embodiments 199-208 wherein the fourth menu includes one or more Recent assay method.

Embodiment 210 is the method of any of embodiments 199-209 wherein the first portion comprises one or more of a first, a second, and a third sub-section of the fourth menu.

Embodiment 211 is the method of any of embodiments 199-210 wherein the first sub-section includes one or more of MSD Purchased, MSD Catalog, and usernames.

Embodiment 212 is the method of any of embodiments 199-211 wherein the second sub-section includes one or more of Assay method types, filtered by the highlighted item in the first sub-section.

Embodiment 213 is the method of any of embodiments 199-212 wherein the third sub-section includes one or more available Assay Method filtered by the highlighted item in the first and second sub-sections.

Embodiment 214 is the method of any of embodiments 199-213 wherein the second portion further includes one or more of Manual and Import in response to a selection of an Assay Method, wherein Manual and Import are subsequent menus of Sample.

Embodiment 215 is the method of any of embodiments 199-214 wherein the Manual choice is configured to allow entry of a number of samples.

Embodiment 216 is the method of any of embodiments 199-215 wherein the Import choice is configured to allow entry of a document file path.

Embodiment 217 is the method of any of embodiments 199-216 wherein in response to a selection of a number of samples or a document file path, the third menu is a subsequent menu of Confirm and includes one or more of Experiment name, total sample number, plate layout, assay method name, and Confirm.

Embodiment 218 is the method of any of embodiments 199-217 wherein in response to a selection of From Existing Experiment, the third menu includes one or more of Recent and Available.

Embodiment 219 is the method of any of embodiments 199-218 wherein in response to a selection of Recent, the third menu includes a list of recent Experiments.

Embodiment 220 is the method of any of embodiments 199-219 wherein the third menu comprises a first, a second, and a third sub-section, wherein the first sub-section comprises one or more user names, the second sub-section comprises one or more Experiment dates filtered by highlighted user name, and the third sub-section comprises one or more names of existing Experiments filtered by highlighted user name and selected Experiment date, in response to a selection of Available.

Embodiment 221 is the method of any of embodiments 199-220 wherein in response to a selection of a name of a Recent or Available Experiment, the second portion comprises one or more of Design Experiment, Setup, Assay Method, Samples, and Confirm.

Embodiment 222 is the method of embodiment 199, wherein in response to a selection of Review Experiment, the second menu comprises one or more names of recent Experiments.

Embodiment 223 is the method of embodiment 222, the second portion comprises Recent and Available and the third menu is a subsequent menu of Recent.

Embodiment 224 is the method of embodiments 222 or 223, wherein the second menu comprises one or more of a first, a second, and a third subsection, wherein the first sub-section comprises one or more user names, the second sub-section comprises one or more Experiment dates filtered by highlighted user name, and the third sub-section comprises one or more names of existing Experiments filtered by highlighted user name and selected Experiment date, in response to a selection of Available.

Embodiment 225 is the method of embodiments 222 to 224, wherein the second portion comprises one or more of Experiment, Plates, Samples, Calibrators, Controls, and Data Table in response to a user's selection of a recent Experiment or Available Experiment.

Embodiment 226 is the method of embodiments 222 to 225 wherein the third menu of user-selectable choices is a subsequent menu of Plates and comprises one or more of Experiment name, total sample number, one or more plate representation, and an assay method name, wherein the one or more plate representation is adapted to be selected.

Embodiment 227 is the method of embodiments 222 to 226 further comprising providing a fourth command for a fourth menu of user-selectable items to be displayed on the first portion of the UI display in response to a user's selection of one of the one or more plate representation, wherein the one or more of a past-selected and a past-unselected menu item of the hierarchical menu levels from the first, second, and third menu is adapted to be displayed on the second portion and concurrently viewed with the first portion.

Embodiment 228 is the method of embodiments 222 to 227 wherein the second portion further comprises Heat Map and Data Table and the fourth menu is a subsequent menu of Heat Map and comprises one or more of a spot layout, a list of assays, a plate layout, and a graph, wherein the spots of the spot layout and wells of the plate layout are adapted to be highlighted by a user, wherein Heat Map and Data Table are subsequent menus of Plates.

Embodiment 229 is the method of embodiments 222 to 228 wherein in response to a highlighting of a spot, the graph populates with data for the selected spot over the entire plate, or wherein in response to a highlighting of a spot and a well, the graph populates with data for the highlighted spot in the highlighted well.

Embodiment 230 is the method of embodiments 222 to 229 wherein in response to a selection of one of the one or more patent representation, the third menu is a Table of Data for the selected plate and comprises one or more columns selected from Plate, Sample, Assay, Well, Spot, Dilution, Conc., Conc. Unit, Signal, Adj. Signal, Mean, Adj. Signal Mean, CV, Calc. Conc., Calc. Conc. Mean, Calc. Conc. CV, % Recovery, % Recovery Mean.

Embodiment 231 is the method of embodiments 222 to 230 wherein the third menu is a subsequent menu of Samples and comprises one or more graphs for Sample data, and the second portion comprises one or more of Graph and Table.

Embodiment 232 is the method of embodiments 222 to 231 wherein the third menu is a subsequent menu of Calibrators and comprises one or more graph for Calibrator data.

Embodiment 233 is the method of embodiments 222 to 232, wherein the third menu is a subsequent menu of Controls and comprises one or more graph for Control data.

Embodiment 234 is the method of embodiments 222 to 233 wherein the third menu is a subsequent menu of Data Table and comprises one or more tables for data for samples, calibrators (if any), and controls (if any).

Embodiment 235 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu;

Embodiment 236 is the method of embodiment 234, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion is an active portion of the UI display that is adapted to be consistently displayed within the same area of the UI display to optimize a user's focus while interacting with the UI display.

Embodiment 237 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device; and wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion includes between two to five sub-sections of one or more user-selectable menu items, wherein these menu items are divided among these subsections and the sub-sections are adapted to be displayed to create an association among the menu items from each of the respective sub-sections.

Embodiment 238 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an output in response to a received response, wherein the output is adapted to be transmitted to a device communicatively connected to the processor directing the device to perform a physical movement or undergo a physical transformation, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs.

Embodiment 239 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; and providing, by the at least one processor, a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the first portion comprises no more than a single menu of items at a given point in time, further wherein the first portion includes between two to five sub-sections of one or more user-selectable items, wherein these menu items are divided among these sub-sections and the sub-sections are adapted to be displayed to create an association among the items from each of the respective sub-sections.

Embodiment 240 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; providing, by the at least one processor, a dialog box adapted to be displayed on the foreground of the UI display to prompt a user for additional information or notify the user of an error, wherein the background of the dialog box is further adapted to match the background of the first and second portions of the UI display, further wherein one or more of text, graphics, photos, and videos displayed in the background of the first and second portions of the UI display are adapted to displayed out of focus when the dialog box is being displayed on the foreground of the UI display; providing, by the at least one processor, an output in response to a received response, wherein the output is adapted to be transmitted to a device communicatively connected to the processor directing the device to perform a physical movement or undergo a physical transformation; providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device; providing, by the at least one processor, a progress indicator adapted to be displayed on the UI display, wherein the progress indicator comprises a series of flickering pixels to indicate that the at least one processor is processing a received response and providing, by the at least one processor, an advanced context menu, wherein the advanced context menu is adapted to divided into a plurality of portions including one or more of the following: a top portion comprising items related to the currently active menu; a middle portion comprising items related to particular modules available to a user; and a bottom portion comprising global functions comprising one or more of login/logout functionality, user manuals and help, EULA information, and privacy policy information, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion is an active portion of the UI display that is adapted to be consistently displayed within the same area of the UI display to optimize a user's focus while interacting with the UI display, further wherein the second portion further comprises an indicator bar, further wherein one or more of the past-selected menu items are adapted to be visually aligned with the indicator bar to designate which menu items were previously selected throughout a user's traversal of the menu hierarchy, further wherein the second portion further comprises an indicator bar comprising a status indicator adapted to display one or more color-coded states, the states comprising red to indicate an error state and blue to indicate a non-error state, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the first portion comprises no more than a single menu of items at a given point in time, further wherein the first portion includes between two to five sub-sections of one or more user-selectable items, wherein the single menu of items is divided among these sub-sections and the sub-sections are adapted to be displayed to create an association among the items from each of the respective sub-sections, further wherein the first portion is adapted to display visually represented items to aid in a user's decision-making processes, wherein the visually represented item include one or more of: a video, a picture, a graph, a table, a chart, and a graphical representation of an object, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs, further wherein the at least one processor is adapted to provide an interface between and enable communications among: (a) users, accounts, or teams; and (b) non-human machines, wherein the interface and communications allow the one or more users, accounts, teams, and non-human machines to collaboratively solve one or more problems or sub-problems and notify one or more of each of the results derived from their collaboration.

Embodiment 241 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion is an active portion of the UI display that is adapted to be consistently displayed within the same area of the UI display to optimize a user's focus while interacting with the UI display.

Embodiment 242 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; and providing, by the at least one processor, a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the first portion comprises no more than a single menu of items at a given point in time.

Embodiment 243 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device; and wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion includes between two to five sub-sections of one or more user-selectable items, wherein the single menu of items is divided among these subsections and the sub-sections are adapted to be displayed to create an association among the items from each of the respective sub-sections.

Embodiment 244 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an output in response to a received response, wherein the output is adapted to be transmitted to a device communicatively connected to the processor directing the device to perform a physical movement or undergo a physical transformation, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment.

Embodiment 245 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; and providing, by the at least one processor, an advanced context menu, wherein the advanced context menu is adapted to divided into a plurality of portions including one or more of the following: a top portion comprising items related to the currently active menu; a middle portion comprising items related to particular modules available to a user; and a bottom portion comprising global functions comprising one or more of login/logout functionality, user manuals and help, EULA information, and privacy policy information, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the first portion is adapted to display visually represented items to aid in a user's decision-making processes, wherein the visually represented item include one or more of: a video, a picture, a graph, a table, a chart, and a graphical representation of an object.

Embodiment 246 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; and providing, by the at least one processor, a dialog box adapted to be displayed on the foreground of the UI display to prompt a user for additional information or notify the user of an error, wherein the background of the dialog box is further adapted to match the background of the first and second portions of the UI display, further wherein one or more of text, graphics, photos, and videos displayed in the background of the first and second portions of the UI display are adapted to displayed out of focus when the dialog box is being displayed on the foreground of the UI display, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion.

Embodiment 247 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu, wherein the first menu is adapted to be displayed on a second portion of the UI display and comprises one or more of a past-selected menu item and a past-unselected menu item of the hierarchical menu levels and is adapted to be concurrently viewed with the second menu in first portion. further wherein the first portion comprises no more than a single menu of items at a given point in time, further wherein the at least one processor is adapted to provide an interface between and enable communications among: (a) users, accounts, or teams; and (b) non-human machines, wherein the interface and communications allow the one or more users, accounts, teams, and non-human machines to collaboratively solve one or more problems or sub-problems and notify one or more of each of the results derived from their collaboration.

Embodiment 248 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; and providing, by the at least one processor, a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the first portion is an active portion of the UI display that is adapted to be consistently displayed within the same area of the UI display to optimize a user's focus while interacting with the UI display, further wherein the second portion further comprises an indicator bar, further wherein one or more of the past-selected menu items are adapted to be visually aligned with the indicator bar to designate which menu items were previously selected throughout a user's traversal of the menu hierarchy, further wherein the first portion comprises no more than a single menu of items at a given point in time.

Embodiment 249 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; and providing, by the at least one processor, a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the first portion is an active portion of the UI display that is adapted to be consistently displayed within the same area of the UI display to optimize a user's focus while interacting with the UI display, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to provide an interface between and enable communications among: (a) users, accounts, or teams; and (b) non-human machines, wherein the interface and communications allow the one or more users, accounts, teams, and non-human machines to collaboratively solve one or more problems or sub-problems and notify one or more of each of the results derived from their collaboration.

Embodiment 250 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; and providing, by the at least one processor, a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the first portion is an active portion of the UI display that is adapted to be consistently displayed within the same area of the UI display to optimize a user's focus while interacting with the UI display. further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs.

Embodiment 251 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an output in response to a received response, wherein the output is adapted to be transmitted to a device communicatively connected to the processor directing the device to perform a physical movement or undergo a physical transformation, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs.

Embodiment 252 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; and providing, by the at least one processor, a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the first portion comprises no more than a single menu of items at a given point in time, further wherein the first portion includes between two to five sub-sections of one or more user-selectable items, wherein the single menu of items is divided among these sub-sections and the sub-sections are adapted to be displayed to create an association among the items from each of the respective sub-sections.

Embodiment 253 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an output in response to a received response, wherein the output is adapted to be transmitted to a device communicatively connected to the processor directing the device to perform a physical movement or undergo a physical transformation; and providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion further comprises an indicator bar, further wherein one or more of the past-selected menu items are adapted to be visually aligned with the indicator bar to designate which menu items were previously selected throughout a user's traversal of the menu hierarchy.

Embodiment 254 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; and providing, by the at least one processor, a second command for a second menu of one or more user-selectable menu items to be displayed on the first portion of the UI display in response to a user's selection, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs, further wherein the at least one processor is adapted to provide an interface between and enable communications among: (a) users, accounts, or teams; and (b) non-human machines, wherein the interface and communications allow the one or more users, accounts, teams, and non-human machines to collaboratively solve one or more problems or sub-problems and notify one or more of each of the results derived from their collaboration.

Embodiment 255 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, a progress indicator adapted to be displayed on the UI display, wherein the progress indicator comprises a series of flickering pixels to indicate that the at least one processor is processing a received response, wherein the first menu is adapted to be displayed on a second portion of the UI display and comprises one or more of a past-selected menu item and a past-unselected menu item of the hierarchical menu levels and is adapted to be concurrently viewed with the second menu in first portion. further wherein the second portion further comprises an indicator bar, further wherein one or more of the past-selected menu items are adapted to be visually aligned with the indicator bar to designate which menu items were previously selected throughout a user's traversal of the menu hierarchy, further wherein the second portion further comprises an indicator bar comprising a status indicator adapted to display one or more color-coded states, the states comprising red to indicate an error state and blue to indicate a non-error state.

Embodiment 256 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion is an active portion of the UI display that is adapted to be consistently displayed within the same area of the UI display to optimize a user's focus while interacting with the UI display, further wherein the first portion comprises no more than a single menu of items at a given point in time.

Embodiment 257 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; and providing, by the at least one processor, a dialog box adapted to be displayed on the foreground of the UI display to prompt a user for additional information or notify the user of an error, wherein the background of the dialog box is further adapted to match the background of the first and second portions of the UI display, further wherein one or more of text, graphics, photos, and videos displayed in the background of the first and second portions of the UI display are adapted to displayed out of focus when the dialog box is being displayed on the foreground of the UI display, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion is an active portion of the UI display that is adapted to be consistently displayed within the same area of the UI display to optimize a user's focus while interacting with the UI display.

Embodiment 258 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion is an active portion of the UI display that is adapted to be consistently displayed within the same area of the UI display to optimize a user's focus while interacting with the UI display, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or subproblem to be solved; (c) a device; (d) a physical location; (e) a tool; (f) an instrument; or (g) equipment.

Embodiment 259 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, a dialog box adapted to be displayed on the foreground of the UI display to prompt a user for additional information or notify the user of an error, wherein the background of the dialog box is further adapted to match the background of the first and second portions of the UI display, further wherein one or more of text, graphics, photos, and videos displayed in the background of the first and second portions of the UI display are adapted to displayed out of focus when the dialog box is being displayed on the foreground of the UI display, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the first portion comprises no more than a single menu of items at a given point in time, further wherein the first portion includes between two to five sub-sections of one or more user-selectable items, wherein the single menu of items is divided among these sub-sections and the sub-sections are adapted to be displayed to create an association among the items from each of the respective sub-sections.

Embodiment 260 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion comprises no more than a single menu of items at a given point in time, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs.

Embodiment 261 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an output in response to a received response, wherein the output is adapted to be transmitted to a device communicatively connected to the processor directing the device to perform a physical movement or undergo a physical transformation; providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device; and providing, by the at least one processor, an advanced context menu, wherein the advanced context menu is adapted to divided into a plurality of portions including one or more of the following: a top portion comprising items related to the currently active menu; a middle portion comprising items related to particular modules available to a user; and a bottom portion comprising global functions comprising one or more of login/logout functionality, user manuals and help, EULA information, and privacy policy information, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment.

Embodiment 262 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; and providing, by the at least one processor, an advanced context menu, wherein the advanced context menu is adapted to divided into a plurality of portions including one or more of the following: a top portion comprising items related to the currently active menu; a middle portion comprising items related to particular modules available to a user; and a bottom portion comprising global functions comprising one or more of login/logout functionality, user manuals and help, EULA information, and privacy policy information, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion is an active portion of the UI display that is adapted to be consistently displayed within the same area of the UI display to optimize a user's focus while interacting with the UI display, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the first portion is adapted to display visually represented items to aid in a user's decision-making processes, wherein the visually represented item include one or more of: a video, a picture, a graph, a table, a chart, and a graphical representation of an object.

Embodiment 263 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; and providing, by the at least one processor, a dialog box adapted to be displayed on the foreground of the UI display to prompt a user for additional information or notify the user of an error, wherein the background of the dialog box is further adapted to match the background of the first and second portions of the UI display, further wherein one or more of text, graphics, photos, and videos displayed in the background of the first and second portions of the UI display are adapted to displayed out of focus when the dialog box is being displayed on the foreground of the UI display, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs.

Embodiment 264 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; and providing, by the at least one processor, a progress indicator adapted to be displayed on the UI display, wherein the progress indicator comprises a series of flickering pixels to indicate that the at least one processor is processing a received response, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion comprises no more than a single menu of items at a given point in time, further wherein the first portion is adapted to display visually represented items to aid in a user's decision-making processes, wherein the visually represented item include one or more of: a video, a picture, a graph, a table, a chart, and a graphical representation of an object, further wherein the at least one processor is adapted to provide an interface between and enable communications among: (a) users, accounts, or teams; and (b) non-human machines, wherein the interface and communications allow the one or more users, accounts, teams, and non-human machines to collaboratively solve one or more problems or sub-problems and notify one or more of each of the results derived from their collaboration.

Embodiment 265 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the first portion is an active portion of the UI display that is adapted to be consistently displayed within the same area of the UI display to optimize a user's focus while interacting with the UI display, further wherein the second portion further comprises an indicator bar, further wherein one or more of the past-selected menu items are adapted to be visually aligned with the indicator bar to designate which menu items were previously selected throughout a user's traversal of the menu hierarchy, further wherein the first portion comprises no more than a single menu of items at a given point in time, further wherein the first portion includes between two to five sub-sections of one or more user-selectable items, wherein the single menu of items is divided among these sub-sections and the sub-sections are adapted to be displayed to create an association among the items from each of the respective sub-sections, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs.

Embodiment 266 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; and providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the first portion is an active portion of the UI display that is adapted to be consistently displayed within the same area of the UI display to optimize a user's focus while interacting with the UI display, further wherein the first portion comprises no more than a single menu of items at a given point in time, further wherein the first portion includes between two to five sub-sections of one or more user-selectable items, wherein the single menu of items is divided among these sub-sections and the sub-sections are adapted to be displayed to create an association among the items from each of the respective sub-sections, further wherein the first portion is adapted to display visually represented items to aid in a user's decision-making processes, wherein the visually represented item include one or more of: a video, a picture, a graph, a table, a chart, and a graphical representation of an object, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to provide an interface between and enable communications among: (a) users, accounts, or teams; and (b) non-human machines, wherein the interface and communications allow the one or more users, accounts, teams, and non-human machines to collaboratively solve one or more problems or sub-problems and notify one or more of each of the results derived from their collaboration.

Embodiment 267 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an output in response to a received response, wherein the output is adapted to be transmitted to a device communicatively connected to the processor directing the device to perform a physical movement or undergo a physical transformation, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the first portion is an active portion of the UI display that is adapted to be consistently displayed within the same area of the UI display to optimize a user's focus while interacting with the UI display, further wherein the second portion further comprises an indicator bar comprising a status indicator adapted to display one or more color-coded states, the states comprising red to indicate an error state and blue to indicate a non-error state, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs.

Embodiment 268 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an output in response to a received response, wherein the output is adapted to be transmitted to a device communicatively connected to the processor directing the device to perform a physical movement or undergo a physical transformation; providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device; providing, by the at least one processor, a progress indicator adapted to be displayed on the UI display, wherein the progress indicator comprises a series of flickering pixels to indicate that the at least one processor is processing a received response; and providing, by the at least one processor, an advanced context menu, wherein the advanced context menu is adapted to be divided into a plurality of portions including one or more of the following: a top portion comprising items related to the currently active menu; a middle portion comprising items related to particular modules available to a user; and a bottom portion comprising global functions comprising one or more of login/logout functionality, user manuals and help, EULA information, and privacy policy information, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion is adapted to display at least one menu item from among one or more previously navigated menu levels and subsequent menu levels to provide a visual representation of: (1) a user's previous traversal of the menu hierarchy; and (2) future items that can be subsequently selected, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs, further wherein the at least one processor is adapted to provide an interface between and enable communications among: (a) users, accounts, or teams; and (b) non-human machines, wherein the interface and communications allow the one or more users, accounts, teams, and non-human machines to collaboratively solve one or more problems or sub-problems and notify one or more of each of the results derived from their collaboration.

Embodiment 269 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an advanced context menu adapted to be displayed in response to a selection of an advanced selector, wherein the first portion is adapted to display more than 50% of the available menu items from the menu currently displayed in the first portion based on or more of: (1) the most frequently used available menu items; (2) the importance to the outcome or user; (3) choices customarily made by the user; or (4) choices customarily made in an industry, further wherein the advanced context menu is adapted to display the remaining available items from that menu; providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device; and providing, by the at least one processor, a progress indicator adapted to be displayed on the UI display, wherein the progress indicator comprises a series of flickering pixels to indicate that the at least one processor is processing a received response, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the second portion further comprises an indicator bar, further wherein one or more of the past-selected menu items are adapted to be visually aligned with the indicator bar to designate which menu items were previously selected throughout a user's traversal of the menu hierarchy, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the first portion comprises no more than a single menu of items at a given point in time, further wherein the first portion includes between two to five sub-sections of one or more user-selectable items, wherein the single menu of items is divided among these sub-sections and the sub-sections are adapted to be displayed to create an association among the items from each of the respective sub-sections, further wherein the first portion is adapted to display visually represented items to aid in a user's decision-making processes, wherein the visually represented item include one or more of: a video, a picture, a graph, a table, a chart, and a graphical representation of an object.

Embodiment 270 is a method executed by at least one processor for navigating a path of hierarchical menu levels adapted for output to a graphical user interface (GUI), the method comprising: providing, by at least one processor, a first command for a first menu of one or more user-selectable menu items to be displayed on a first portion of a user interface (UI) display; providing, by the at least one processor, a second command for a second menu of one or more user-selectable menu items to be displayed on the first portion of the UI display in response to a user's selection; providing, by the at least one processor, an output in response to a received response, wherein the output is adapted to be transmitted to a device communicatively connected to the processor directing the device to perform a physical movement or undergo a physical transformation; and providing, by the at least one processor, a permissions command, wherein the permissions command is adapted to manage one or more of user's and team's levels of access, security, or control, wherein the levels of access are adapted to be assigned based on one or more of a role, user, team, account, instrument, equipment, or device, wherein the first menu is adapted to be displayed on a second portion of the UI display and comprises one or more of a past-selected menu item and a past-unselected menu item of the hierarchical menu levels and is adapted to be concurrently viewed with the second menu in first portion, further wherein the first portion is an active portion of the UI display that is adapted to be consistently displayed within the same area of the UI display to optimize a user's focus while interacting with the UI display, further wherein the second portion further comprises an indicator bar, further wherein one or more of the past-selected menu items are adapted to be visually aligned with the indicator bar to designate which menu items were previously selected throughout a user's traversal of the menu hierarchy, further wherein the second portion further comprises an indicator bar comprising a status indicator adapted to display one or more color-coded states, the states comprising red to indicate an error state and blue to indicate a non-error state, further wherein the second portion is adapted to display at least one menu item from one or more of previously navigated and subsequent menu levels, wherein the items among a single menu level are adapted to be displayed in a linear fashion and the previously navigated and subsequent menu levels are adapted to be displayed in a nested fashion, further wherein the at least one processor is adapted to receive benchmark inputs from one or more users, accounts, or teams, wherein an aggregation of the benchmark inputs is adapted to collaboratively solve one or more problems, either sequentially or in parallel, further wherein each of the benchmark inputs is adapted to be based on one or more of: (a) a module; (b) a problem or sub-problem to be solved; (c) a device; (d) a physical location; (e) a tool; (f) an instrument; or (g) equipment, further wherein the at least one processor is adapted to notify the one or more users, accounts, or teams, of the results derived from one or more of the received benchmark inputs.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The embodiments described above are illustrative examples and it should not be construed that the present invention is limited to these particular embodiments. It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the methods or processes). In addition, while certain features of embodiments hereof are described as being performed by a single module or unit for purposes of clarity, it should be understood that the features and functions described herein may be performed by any combination of units or modules. Thus, various changes and modifications may be affected by one skilled in the art without departing from the spirit or scope of the invention as defined in the appended claims.

What is claimed is:

1. A method executed by at least one processor for navigating a path of hierarchical menu levels outputted to a user interface (UI), the method comprising:
providing, by at least one processor, a first command for a first display of a first set of two or more user-selectable menu items to be displayed on a first portion of a user interface (UI) display;
providing, by the at least one processor, a relocation command for at least a portion of the first set of two or more user-selectable menu items to be relocated to a second portion of the UI display and removed from the first portion in response to a user selection of a user-selectable menu item from the first set of two or more user-selectable menu items;
providing, by the at least one processor, a second command to display a user-selectable navigation item in the second portion of the UI display with the at least a portion of the first set of two or more user-selectable menu items; and providing, by the at least one processor, a third command to provide a second display of a second set of two or more user-selectable items to be displayed on the first portion of the UI display in response to the user selection.

2. The method of claim 1, wherein in response to a selection of the user-selectable navigation item, an option to return to a previously presented menu is provided.

3. The method of claim 1, further comprising providing, by the at least one processor, a fourth command to provide a third display of user-selectable items to be displayed in the first portion in response to a second user selection from the second display.

4. The method of claim 1, wherein the first display includes one or more of: a read command; and a review recent results command.

5. The method of claim 4, further comprising, responsive to a selection of the read command, providing a third command to display a play button in the first portion of the UI display.

6. The method of claim 5, further comprising, responsive to a selection of the play button, providing a third command to a plate reader to begin reading one or more plates.

7. The method of claim 6, further comprising, further responsive to the selection of the play button, providing a display command to cause the UI display to display a timer, wherein the timer is adapted to indicate one or more of:
   a total amount of time to load the one or more plates;
   a total amount of time to read the one or more plates;
   a total amount of time to unload the one or more plates;
   a time remaining to complete the loading of the one or more plates;
   a time remaining to complete the reading of the one or more plates; and
   a time remaining to complete unloading of the one or more plates.

8. The method of claim 1, further comprising providing, by the at least one processor, a fourth command to display on the UI display an advanced context menu including one or more of user-selectable choices including:
   an eject plate choice;
   a partial plate choice;
   a set plate run choice;
   a stop instrument choice;
   a lock UI choice; and
   a view plate information choice.

9. The method of claim 8 further comprising adapting, responsive to a selection of the partial plate choice, the first portion to receive bar code information related to a plate selected among one or more plates.

10. The method of claim 9, further comprising adapting the first portion to display a user-selectable option that, when selected, verifies authenticity of the bar code information.

11. The method of claim 9, further comprising causing, responsive to the partial plate choice, the advanced context menu to further include one or more of user-selectable choices including:
   save partial plate; and
   cancel partial plate.

12. The method of claim 8, further comprising adapting, responsive to a selection of the set plate run choice, the first portion to receive a name for a plate run associated with a plate.

13. The method of claim 8, further comprising adapting, responsive to a selection of the stop instrument choice, the first portion to display a confirmation choice before issuing a stop instrument command.

14. The method of claim 13, further comprising, responsive to a selection of the confirmation choice, providing a stop instrument command to abort a current run of a plate.

15. The method of claim 8, further comprising, responsive to a selection of the lock UI choice, adapting the UI display to be locked from user selections until receiving a current user's password.

16. The method of claim 8, further comprising, responsive to a selection of the view plate information choice, adapting the first portion to display plate information including one or more of the following: plate run name, plate barcode, long side customer barcode, short side customer barcode, plate type, operator, and read time.

17. The method of claim 8, further comprising, responsive to a selection of the eject plate choice, providing an eject command to a plate-reading instrument.

18. The method of claim 1, wherein, in response to the user selection, the at least a portion of the first set of two or more user-selectable menu items adapted to be displayed on the second portion of the UI display comprises one or more of a past-selected menu item and a past-unselected menu item of the first set of two or more user-selectable menu items is adapted to be concurrently viewed in the second portion with the second set of two or more user-selectable items in the first portion.

19. The method of claim 1, further comprising adapting the second portion to display an indicator bar, wherein one or more of past-selected menu items are adapted to be visually aligned with the indicator bar to designate at least one menu item that was previously selected throughout a user's traversal of the path of hierarchical menu levels.

20. The method of claim 1, further comprising adapting the second portion to display an indicator bar comprising a status indicator adapted to display one or more color-coded states, the color-coded states comprising a first color indicate an error state and a second color to indicate a non-error state, wherein the first color and the second color are different.

21. The method of claim 20, wherein the first color is red.

22. The method of claim 20, wherein the second color is blue.

23. The method of claim 1, further comprising adapting the first portion to display visually represented items to aid in a user's decision-making processes, wherein the visually represented items include one or more of: a video, a picture, a graph, a table, a chart, and a graphical representation of an object.

24. The method of claim 23, wherein one or more of text, graphics, photos, and videos displayed in a background of the first or second portions of the UI display are adapted to displayed out of focus when a dialog box is being displayed on the foreground of the UI display.

25. The method of claim 1, further comprising:
   providing, by the at least one processor, a dialog box adapted to be displayed on a foreground of the UI display to prompt a user for additional information or notify the user of an error.

26. The method of claim 25, wherein a background of the dialog box is further adapted to match the background of the first and second portions of the UI display.

27. The method of claim 1, further comprising providing, by the at least one processor, an interface enabling communications among:
   (a) one or more users, accounts, or teams; and
   (b) non-human machines,
   wherein the interface and the communications allow the one or more users, accounts, teams, and non-human machines to collaboratively solve one or more problems or sub-problems and notify one or more of each of results derived from their collaboration.

28. The method of claim 1, further comprising providing, by the at least one processor, a progress indicator adapted to be displayed on the UI display, wherein the progress indicator comprises a series of flickering pixels to indicate that the at least one processor is processing a received response.

29. The method of claim 1, further comprising providing, by the at least one processor, an advanced context menu adapted for division into a plurality of portions including one or more of the following:
- a top portion comprising items related to a currently active menu;
- a middle portion comprising items related to particular modules available to a user; and
- a bottom portion comprising global functions comprising one or more of login/logout functionality, user manuals and help, EULA information, and privacy policy information.

30. The method of claim 1, wherein the first portion and the second portion do not overlap.

31. The method of claim 1, wherein the first portion is provided in a central location of the user interface and the second portion is provided at a top portion of the user interface.

* * * * *